United States Patent
Shokat et al.

(10) Patent No.: US 11,136,297 B2
(45) Date of Patent: Oct. 5, 2021

(54) COMPOSITIONS AND METHODS FOR TREATING CANCER

(71) Applicant: THE REGENTS OF THE UNIVERSITY OF CALIFORNIA, Oakland, CA (US)

(72) Inventors: Kevan M. Shokat, San Francisco, CA (US); Daniel Gentile, Darien, CT (US); Steven Moss, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/468,948

(22) PCT Filed: Dec. 15, 2017

(86) PCT No.: PCT/US2017/066839
§ 371 (c)(1),
(2) Date: Jun. 12, 2019

(87) PCT Pub. No.: WO2018/112420
PCT Pub. Date: Jun. 21, 2018

(65) Prior Publication Data
US 2020/0131135 A1    Apr. 30, 2020

Related U.S. Application Data

(60) Provisional application No. 62/434,971, filed on Dec. 15, 2016.

(51) Int. Cl.
| | | |
|---|---|---|
| C07D 231/14 | (2006.01) | |
| C12N 9/14 | (2006.01) | |
| C12N 9/96 | (2006.01) | |
| G01N 33/68 | (2006.01) | |

(52) U.S. Cl.
CPC .......... *C07D 231/14* (2013.01); *C12N 9/14* (2013.01); *C12N 9/96* (2013.01); *C12Y 306/05002* (2013.01); *G01N 33/68* (2013.01)

(58) Field of Classification Search
None
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,010,175 A | 4/1991 | Rutter et al. |
| 5,212,162 A | 5/1993 | Missel et al. |
| 5,288,514 A | 2/1994 | Ellman |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Köster |
| 5,777,324 A | 7/1998 | Hillenkamp |
| 5,858,659 A | 1/1999 | Sapolsky et al. |
| 5,919,626 A | 7/1999 | Shi et al. |
| 5,925,525 A | 7/1999 | Fodor et al. |
| 5,952,174 A | 9/1999 | Nikiforov et al. |
| 5,962,223 A | 10/1999 | Whiteley et al. |
| 6,017,696 A | 1/2000 | Heller |
| 6,043,031 A | 3/2000 | Köster et al. |
| 6,045,996 A | 4/2000 | Cronin et al. |
| 6,051,380 A | 4/2000 | Sosnowski et al. |
| 6,068,818 A | 5/2000 | Ackley et al. |
| 6,251,639 B1 | 6/2001 | Kurn |
| 2008/0064690 A1* | 3/2008 | Atkinson ............. C07D 417/12 514/227.8 |
| 2009/0298075 A1 | 12/2009 | Travers et al. |
| 2011/0319290 A1 | 12/2011 | Raymod et al. |
| 2015/0087628 A1 | 3/2015 | Ostrem et al. |
| 2016/0243223 A1 | 8/2016 | Hoey et al. |

FOREIGN PATENT DOCUMENTS

| | | |
|---|---|---|
| WO | WO-91/19735 A1 | 12/1991 |
| WO | WO-92/00091 A1 | 1/1992 |
| WO | WO-93/20242 A1 | 10/1993 |
| WO | WO-96/05309 A2 | 2/1996 |
| WO | WO-96/05309 A3 | 2/1996 |
| WO | WO-97/000271 A1 | 1/1997 |
| WO | WO-99/67641 A2 | 12/1999 |
| WO | WO-99/67641 A3 | 12/1999 |
| WO | WO-00/39587 A1 | 7/2000 |
| WO | WO-03/037274 A2 | 5/2003 |
| WO | WO-03/037274 A3 | 5/2003 |
| WO | WO-2008/058037 A1 | 5/2008 |
| WO | WO-2013/025939 A2 | 2/2013 |
| WO | WO-2013/025939 A9 | 2/2013 |
| WO | WO-2013/100672 A1 | 7/2013 |

(Continued)

OTHER PUBLICATIONS

Dewitt, S.H. et al. (Aug. 1, 1993). "Diversomers: An Approach to Nonpeptide, Nonoligomeric Chemical Diversity," *PNAS USA* 90(15):6909-6913.

Schubbert, S. et al. (Nov. 2007, e-published Sep. 17, 2007). "Biochemical and Functional Characterization of Germ Line KRAS Mutations," *Molecular and Cellular Biology* 27(22):7765-7770.

Ahmadian, M.R. et al. (Jun. 1999). "Guanosine triphosphatase stimulation of oncogenic Ras mutants," *PNAS USA* 96(12):7065-7070.

Capon, D.J .et al. (Aug. 11-17, 1983). "Activation of Ki-ras2 gene in human colon and lung carcinomas by two different point mutations," *Nature* 304(5926):507-513.

(Continued)

*Primary Examiner* — Joseph R Kosack

(74) *Attorney, Agent, or Firm* — Mintz, Levin, Cohn, Ferris, Glovsky and Popeo, P.C.; Kenneth E. Jenkins; Joohee Lee

(57) ABSTRACT

Disclosed herein, inter alia, are compositions and methods for modulating Ras and treating cancer.

20 Claims, 50 Drawing Sheets

Specification includes a Sequence Listing.

(56) References Cited

FOREIGN PATENT DOCUMENTS

| WO | WO-2013/155223 A1 | 10/2013 |
| WO | WO-2015/054572 A1 | 4/2015 |

OTHER PUBLICATIONS

Erlanson, D.A. et al. (2004). "Tethering: fragment-based drug discovery," *Annu Rev Biophys Biomol Struct* 33:199-223.

Forbes, S.A. et al. (Jan. 2011, e-published Oct. 15, 2010). "COSMIC: mining complete cancer genomes in the Catalogue of Somatic Mutations in Cancer," *Nucleic Acids Res* 39(Database issue):D945-950.

Hunter, J.C. et al. (Sep. 2015, e-published Jun. 2, 2015). "Biochemical and Structural Analysis of Common Cancer-Associated KRAS Mutations," *Mol Cancer Res* 13(9):1325-1335.

International Search Report dated Apr. 13, 2018, for PCT Application No. PCT/US2017/066839, filed Dec. 15, 2017, 6 pages.

John, J. et al. (Jun. 26, 1990). "Kinetics of interaction of nucleotides with nucleotide-free H-ras p21," *Biochemistry* 29(25):6058-6065.

Jones, S. et al. (Apr. 19, 2004). "Increased frequency of the k-ras G12C mutation in MYH polyposis colorectal adenomas," *Br J Cancer* 90(8):1591-1593.

Kraulis, P. et al. (Mar. 29, 1994). "Solution structure and dynamics of ras p21.GDP determined by heteronuclear three- and four-dimensional NMR spectroscopy," *Biochemistry* 33(12):3515-3531.

Lim, S.M. et al. (Jan. 3, 2014, e-published Nov. 20, 2013). "Therapeutic targeting of oncogenic K-Ras by a covalent catalytic site inhibitor," *Angew Chem Int Ed Engl* 53(1):199-204.

Lito, P. et al. (Feb. 5, 2016, e-published Jan. 14, 2016). "Allele-specific inhibitors inactivate mutant KRAS G12C by a trapping mechanism," *Science* 351(6273):604-608.

Maurer, T. et al. (Apr. 3, 2012, e-published Mar. 19, 2012). "Small-molecule ligands bind to a distinct pocket in Ras and inhibit SOS-mediated nucleotide exchange activity," *PNAS USA* 109(14):5299-5304.

McCormick, F. et al. (Mar. 2016, e-published Mar. 9, 2016). "K-Ras protein as a drug target," *J Mol Med* 94(3):253-258.

McGregor, L.M. et al. (Jun. 27, 2017, e-published Jun. 16, 2017). "Expanding the Scope of Electrophiles Capable of Targeting K-Ras Oncogenes," *Biochemistry* 56(25):3178-3183.

Milburn, M.V. et al. (Feb. 23, 1990). "Molecular switch for signal transduction: structural differences between active and inactive forms of protooncogenic ras proteins," *Science* 247(4945):939-945.

Ostrem, J.M. et al. (Nov. 28, 2013, e-published Nov. 20, 2013). "K-Ras(G12C) inhibitors allosterically control GTP affinity and effector interactions," *Nature* 503(7477):548-551.

Ostrem, J.M. et al. (Nov. 2016 e-published Jul. 29, 2016). "Direct small-molecule inhibitors of KRAS: from structural insights to mechanism-based design," *Nat Rev Drug Discov* 15(11):771-785.

Patgiri, A. et al. (Jul. 17, 2011). "An orthosteric inhibitor of the Ras-Sos interaction," *Nat Chem Biol* 7(9):585-587.

Patricelli, M.P. et al. (Mar. 2016, e-published Jan. 6, 2016). "Selective Inhibition of Oncogenic KRAS Output with Small Molecules Targeting the Inactive State," *Cancer Discov* 6(3):316-329.

PubChem CID 45285671 (May 13, 2010). 9 pages.

Shima, F. et al. (May 14, 2013, e-published Apr. 29, 2013). "In silico discovery of small-molecule Ras inhibitors that display antitumor activity by blocking the Ras-effector interaction," *PNAS USA* 110(2):8182-8187.

Spencer-Smith, R. et al. (Jan. 2017, e-published Nov. 7, 2016). "Inhibition of RAS function through targeting an allosteric regulatory site," 13(1):62-68.

Spoerner, M. et al. (Apr. 24, 2001). "Dynamic properties of the Ras switch I region and its importance for binding to effectors," *PNAS USA* 98(9):4944-4949.

Stephen, A.G. et al. (Mar. 17, 2014). "Dragging ras back in the ring," *Cancer Cell* 25(3):272-281.

Sun, Q. et al. (2012). "Discovery of small molecules that bind to K-Ras and inhibit Sos-mediated activation," *Angew Chem* 124:6244-6247.

Welsch, M.E. et al. (Feb. 2017). "Multivalent Small-Molecule Pan-RAS Inhibitors," *Cell* 168(5):878-889.

Written Opinion dated Apr. 13, 2018, for PCT Application No. PCT/US2017/066839, filed Dec. 15, 2017, 7 pages.

European Search Report dated Dec. 7, 2020, for EP Patent Application No. 17881029.7, 11 pages.

Partial Supplementary European Search Report dated Sep. 3, 2020, for EP Patent Application No. 17881029.7, 14 pages.

\* cited by examiner

The Ras-GTPase Effector Cycle

All cancers (2.8% G12C)　　　　Lung cancer (7.3% G12C)

KRas-G12C (GDP)

| H-Ras$^{M72C}$ Nucleotide State | βME$_{50}$ (95% Confidence) | ΔT$_{50}$ (95% Confidence) |
|---|---|---|
| DG01: | | |
| GDP | 2.53 mM (2.37 mM – 2.70 mM) | 2.65 °C (2.46 °C – 2.85 °C) |
| GppNHp | 1.10 mM (1.01 mM – 1.20 mM) | -2.39 °C (-2.65 °C – -2.14 °C) |
| DG02: | | |
| GDP | 1.43 mM (1.29 mM – 1.60 mM) | 2.36 °C (2.20 °C – 2.53 °C) |
| GppNHp | 1.08 mM (903 µM – 1.30 mM) | |

YM-254890

| H-Ras$^{M72C, Q61X}$ | ΔT$_{50}$ (95% Confidence) | ΔΔT$_{50}$ (95% Confidence) |
|---|---|---|
| DG-3-95A: | | |
| WT | 2.32 °C (2.18 °C – 2.47 °C) | 1.08 °C (.83 °C – 1.31 °C) |
| Lysine | 3.40 °C (3.30 °C – 3.49 °C) | |

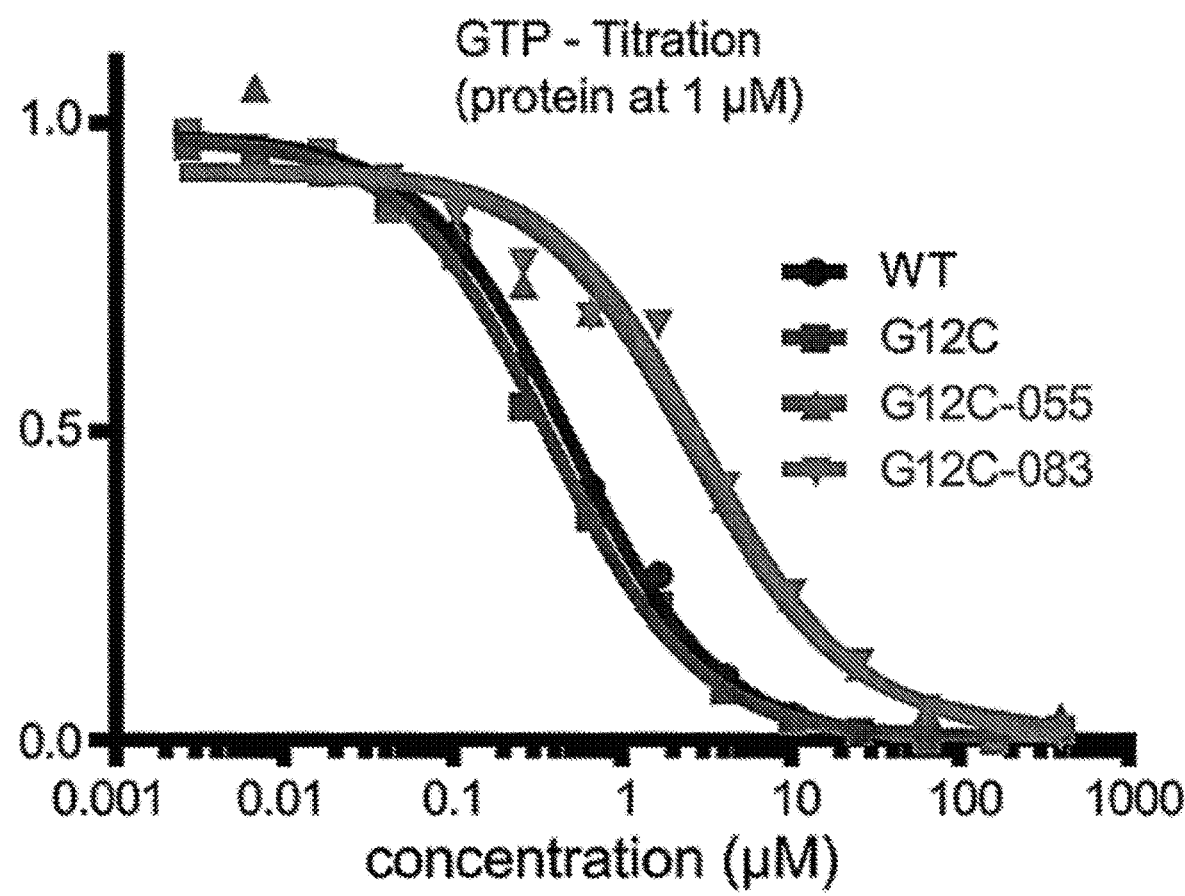

% Mod. G12C 12    100%

10    14%

17    0%

GDP State　　GTP State

C72/2C07
C12/Cmpd6

K-Ras^M72C • DG01 • GDP Structure

H-Ras^M72C • DG01 • GDP Structure

| 100 μM (25X) Drug, 24 hrs | GDP | GNP | 100 μM (25X) Drug, 24 hrs | GDP | GNP |
|---|---|---|---|---|---|
| | 35.17% (+/- 3.49%) | 9.78% (+/- 2.59%) | | 22.11% (+/- 1.63%) | 0.00% (+/- 0.00%) |
| | 30.38% (+/- 2.82%) | 7.29% (+/- 1.61%) | | 7.27% (+/- 2.02%) | 0.00% (+/- 0.00%) |
| | 66.52% (+/- 4.63%) | 23.27% (+/- 2.85%) | | 5.33% (+/- 8.80%) | 6.22% (+/- 1.39%) |
| | 100.00% (+/- 0.00%) | 100.00% (+/- 0.00%) | | 100.00% (0.00%) | 100.00% (0.00%) 2 Adducts |

Changes Between H-Ras(M72C) GppNHP and GppNHp 2C07

| 24 hr 100 µM | H-Ras(M72C) GDP | H-Ras(M72C) GppNHp |
|---|---|---|
|  1 | No Labeling | No Labeling |
|  2 | 66.5% (+/- 4.6%) | 23.3% (+/- 2.9%) |
|  3 | 100.0% (+/- 0.0%) | 100.0% (+/- 0.0%) |
|  4 | No Labeling | No Labeling |

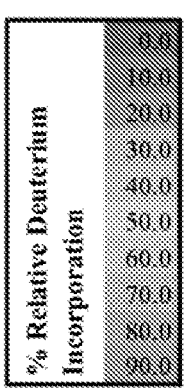

| S | E | Z | RT | Sequence | HRas-GppNHp 0.3 | SD | 3s | SD | 30s | SD | 300s | SD |
|---|---|---|---|---|---|---|---|---|---|---|---|---|
| 4 | 19 | 3 | 9.1 | YKLVVVGAGGVGKSAL | | 0.2 | | 0.2 | | 0.3 | | 0.8 |
| 5 | 19 | 3 | 8.0 | KLVVVGAGGVGKSAL | | 0.2 | | 0.4 | | 0.5 | | 1.4 |
| 7 | 19 | 2 | 7.6 | VVVGAGGVGKSAL | | 0.3 | | 0.5 | | 0.8 | | 1.3 |
| 7 | 20 | 1 | 7.1 | VVVGAGGVGKSALT | | 0.2 | | 0.2 | | 0.7 | | 1.7 |
| 7 | 20 | 2 | 7.1 | VVVGAGGVGKSALT | | 0.3 | | 0.3 | | 0.8 | | 1.1 |
| 23 | 31 | 1 | 8.1 | LIQNHFVDE | | 0.4 | | 0.8 | | 0.3 | | 1.6 |
| 23 | 31 | 2 | 8.1 | LIQNHFVDE | | 0.4 | | 0.7 | | 0.8 | | 1.5 |
| 24 | 31 | 1 | 6.8 | IQNHFVDE | | 0.9 | | 1.0 | | 0.5 | | 1.3 |
| 24 | 31 | 2 | 7.0 | IQNHFVDE | | 0.4 | | 0.9 | | 0.5 | | 1.1 |
| 24 | 37 | 2 | 9.7 | IQNHFVDEYDPTIE | | 1.2 | | 0.6 | | 0.5 | | 1.1 |
| 24 | 39 | 2 | 9.6 | IQNHFVDEYDPTIEDS | | 1.0 | | 0.7 | | 0.6 | | 1.5 |
| 27 | 39 | 2 | 9.0 | HFVDEYDPTIEDS | | 0.9 | | 0.6 | | 0.6 | | 2.0 |
| 29 | 39 | 1 | 8.2 | VDEYDPTIEDS | | 1.0 | | 0.9 | | 0.6 | | 1.2 |
| 32 | 37 | 1 | 7.2 | YDPTIE | | 2.0 | | 1.8 | | 0.6 | | 0.9 |
| 32 | 38 | 1 | 7.3 | YDPTIED | | 1.5 | | 1.4 | | 0.7 | | 1.6 |
| 32 | 39 | 1 | 7.1 | YDPTIEDS | | 1.4 | | 1.6 | | 0.8 | | 1.3 |
| 38 | 52 | 2 | 9.4 | DSYRKQVVIDGETCL | | 0.2 | | 0.6 | | 0.8 | | 1.9 |
| 38 | 52 | 3 | 9.4 | DSYRKQVVIDGETCL | | 0.4 | | 0.4 | | 0.7 | | 1.1 |
| 39 | 50 | 2 | 5.9 | SYRKQVVIDGET | | 0.3 | | 1.3 | | 0.8 | | 1.7 |
| 39 | 52 | 3 | 8.9 | SYRKQVVIDGETCL | | 0.3 | | 0.4 | | 0.6 | | 1.1 |
| 40 | 48 | 2 | 5.3 | YRKQVVIDG | | 0.4 | | 1.5 | | 0.6 | | 0.9 |
| 40 | 50 | 2 | 5.8 | YRKQVVIDGET | | 0.1 | | 0.5 | | 0.9 | | 1.2 |
| 40 | 52 | 2 | 8.8 | YRKQVVIDGETCL | | 0.3 | | 0.6 | | 0.6 | | 0.9 |
| 41 | 52 | 3 | 8.5 | RKQVVIDGETCL | | 0.1 | | 0.6 | | 1.1 | | 1.9 |
| 53 | 62 | 1 | 10.1 | LDILDTAGQE | | 0.7 | | 1.1 | | 1.4 | | 0.9 |
| 53 | 63 | 1 | 10.1 | LDILDTAGQEE | | 0.4 | | 0.9 | | 0.4 | | 1.4 |
| 53 | 64 | 1 | 11.0 | LDILDTAGQEEY | | 0.7 | | 0.8 | | 0.9 | | 1.6 |
| 57 | 63 | 1 | 3.4 | DTAGQEE | | 0.8 | | 2.5 | | 0.7 | | 1.2 |
| 57 | 64 | 1 | 5.9 | DTAGQEEY | | 0.7 | | 1.7 | | 0.8 | | 2.1 |
| 57 | 66 | 1 | 5.8 | DTAGQEEYSA | | 0.0 | | 1.3 | | 0.6 | | 2.5 |
| 57 | 67 | 1 | 8.8 | DTAGQEEYSAM | | 1.2 | | 0.7 | | 0.9 | | 1.8 |
| 64 | 71 | 2 | 6.9 | YSAMRDQY | | 1.3 | | 0.7 | | 0.6 | | 1.8 |
| 68 | 78 | 3 | 7.1 | RDQYCRTGEGF | | 0.5 | | 0.6 | | 0.6 | | 1.3 |
| 68 | 79 | 3 | 9.3 | RDQYCRTGEGFL | | 0.4 | | 0.6 | | 0.7 | | 1.0 |
| 72 | 78 | 1 | 6.2 | CRTGEGF | | 0.1 | | 0.7 | | 1.1 | | 1.3 |
| 72 | 79 | 2 | 9.3 | CRTGEGFL | | 0.2 | | 0.5 | | 0.5 | | 0.9 |
| 82 | 89 | 1 | 6.1 | FAINNTKS | | 0.9 | | 0.6 | | 0.9 | | 1.1 |
| 82 | 90 | 2 | 8.9 | FAINNTKSF | | 0.5 | | 0.4 | | 0.7 | | 0.9 |
| 82 | 91 | 2 | 8.8 | FAINNTKSFE | | 0.4 | | 0.7 | | 0.8 | | 1.3 |
| 82 | 95 | 3 | 8.7 | FAINNTKSFEDIHQ | | 0.3 | | 0.3 | | 0.6 | | 1.3 |
| 83 | 91 | 2 | 6.3 | AINNTKSFE | | 0.3 | | 0.2 | | 0.8 | | 1.6 |
| 83 | 95 | 2 | 7.1 | AINNTKSFEDIHQ | | 0.5 | | 0.4 | | 0.6 | | 1.1 |
| 90 | 95 | 1 | 6.1 | FEDIHQ | | 0.4 | | 0.4 | | 0.6 | | 2.2 |
| 90 | 113 | 5 | 9.7 | FEDIHQYREQIKRVKDSDDVPMVL | | 0.1 | | 0.5 | | 0.6 | | 1.3 |
| 91 | 113 | 3 | 9.1 | EDIHQYREQIKRVKDSDDVPMVL | | 0.2 | | 0.3 | | 0.5 | | 1.0 |
| 91 | 113 | 5 | 9.1 | EDIHQYREQIKRVKDSDDVPMVL | | 0.2 | | 0.4 | | 0.5 | | 1.0 |
| 92 | 113 | 4 | 9.1 | DIHQYREQIKRVKDSDDVPMVL | | 0.2 | | 0.4 | | 0.7 | | 1.0 |
| 96 | 113 | 3 | 8.5 | YREQIKRVKDSDDVPMVL | | 0.2 | | 0.4 | | 0.4 | | 0.8 |
| 96 | 113 | 5 | 8.5 | YREQIKRVKDSDDVPMVL | | 0.2 | | 0.3 | | 0.6 | | 1.0 |
| 97 | 113 | 4 | 8.3 | REQIKRVKDSDDVPMVL | | 0.0 | | 0.2 | | 0.7 | | 1.2 |
| 99 | 113 | 3 | 8.8 | QIKRVKDSDDVPMVL | | 0.2 | | 0.3 | | 0.6 | | 1.0 |
| 114 | 120 | 1 | 6.1 | VGNKCDL | | 0.1 | | 0.4 | | 1.1 | | 1.6 |
| 121 | 132 | 3 | 3.5 | AARTVESRQAQD | | 0.6 | | 1.6 | | 1.3 | | 1.9 |
| 121 | 133 | 3 | 5.5 | AARTVESRQAQDL | | 0.4 | | 1.2 | | 0.8 | | 2.0 |
| 121 | 136 | 4 | 5.0 | AARTVESRQAQDLARS | | 0.5 | | 1.1 | | 0.4 | | 2.0 |
| 127 | 133 | 2 | 4.9 | SRQAQDL | | 0.1 | | 0.3 | | 0.9 | | 1.5 |
| 133 | 144 | 2 | 10.5 | LARSYGIPYIET | | 0.1 | | 0.2 | | 0.4 | | 1.0 |
| 134 | 144 | 2 | 10.2 | ARSYGIPYIET | | 0.0 | | 0.1 | | 0.5 | | 1.1 |
| 134 | 146 | 2 | 10.1 | ARSYGIPYIETSA | | 0.1 | | 0.4 | | 1.0 | | 0.9 |
| 134 | 156 | 3 | 10.2 | ARSYGIPYIETSAKTRQGVEDAF | | 0.2 | | 0.2 | | 0.3 | | 0.9 |
| 137 | 144 | 1 | 11.1 | YGIPYIET | | 0.1 | | 0.0 | | 0.5 | | 1.0 |
| 145 | 153 | 2 | 3.2 | SAKTRQGVE | | 0.9 | | 0.6 | | 1.2 | | 1.7 |
| 145 | 155 | 2 | 3.7 | SAKTRQGVEDA | | 0.5 | | 0.6 | | 1.1 | | 2.0 |
| 145 | 156 | 2 | 3.3 | SAKTRQGVEDAF | | 0.2 | | 0.2 | | 0.9 | | 1.3 |
| 157 | 166 | 3 | 6.7 | YTLVREIRQH | | 0.2 | | 0.5 | | 0.3 | | 1.0 |
| 160 | 166 | 2 | 3.2 | VREIRQH | | 0.4 | | 1.4 | | 1.0 | | 1.7 |

FIG. 38D

| S | E | Z | RT | Sequence | HRas-2C87-GppNHp 0.3 | SD | 3s | SD | 30s | SD | 300s | SD |
|---|---|---|---|---|---|---|---|---|---|---|---|---|
| 4 | 19 | 3 | 9.1 | YKLVVVGAGGVGKSAL | | 0.1 | | 0.5 | | 0.2 | | 1.0 |
| 5 | 19 | 3 | 8.0 | KLVVVGAGGVGKSAL | | 0.3 | | 0.4 | | 0.3 | | 0.8 |
| 7 | 19 | 2 | 7.6 | VVVGAGGVGKSAL | | 0.4 | | 0.2 | | 0.2 | | 0.9 |
| 7 | 20 | 1 | 7.1 | VVVGAGGVGKSALT | | 0.4 | | 0.3 | | 0.2 | | 3.2 |
| 7 | 20 | 2 | 7.1 | VVVGAGGVGKSALT | | 0.3 | | 0.2 | | 0.2 | | 0.8 |
| 23 | 31 | 1 | 8.1 | LIQNHFVDE | | 1.5 | | 2.5 | | 0.4 | | 0.4 |
| 23 | 31 | 2 | 8.1 | LIQNHFVDE | | 0.4 | | 1.0 | | 0.3 | | 0.1 |
| 24 | 31 | 1 | 6.8 | IQNHFVDE | | 1.1 | | 0.9 | | 0.3 | | 0.2 |
| 24 | 31 | 2 | 7.0 | IQNHFVDE | | 1.0 | | 0.8 | | 0.2 | | 0.2 |
| 24 | 37 | 2 | 9.7 | IQNHFVDEYDPTIE | | 2.2 | | 2.7 | | 0.3 | | 1.1 |
| 24 | 39 | 2 | 9.6 | IQNHFVDEYDPTIEDS | | 1.9 | | 2.6 | | 0.3 | | 0.7 |
| 27 | 39 | 2 | 9.0 | HFVDEYDPTIEDS | | 1.6 | | 1.1 | | 0.7 | | 1.1 |
| 29 | 39 | 1 | 8.2 | VDEYDPTIEDS | | 1.9 | | 1.1 | | 0.1 | | 0.4 |
| 32 | 37 | 1 | 7.2 | YDPTIE | | 3.4 | | 2.5 | | 0.2 | | 0.1 |
| 32 | 38 | 1 | 7.3 | YDPTIED | | 3.3 | | 1.3 | | 0.4 | | 0.9 |
| 32 | 39 | 1 | 7.3 | YDPTIEDS | | 2.9 | | 1.2 | | 0.3 | | 0.7 |
| 38 | 52 | 2 | 9.4 | DSYRKQVVIDGETCL | | 0.8 | | 0.9 | | 0.4 | | 0.4 |
| 38 | 52 | 3 | 9.4 | DSYRKQVVIDGETCL | | 0.8 | | 0.9 | | 0.4 | | 0.4 |
| 39 | 50 | 2 | 8.9 | SYRKQVVIDGET | | 1.2 | | 1.1 | | 0.2 | | 1.2 |
| 39 | 52 | 3 | 8.9 | SYRKQVVIDGETCL | | 0.7 | | 0.8 | | 0.2 | | 0.1 |
| 40 | 48 | 2 | 5.3 | YRKQVVIDG | | 0.7 | | 1.5 | | 1.0 | | 1.3 |
| 40 | 50 | 2 | 5.8 | YRKQVVIDGET | | 1.2 | | 0.7 | | 0.4 | | 0.1 |
| 40 | 52 | 2 | 8.8 | YRKQVVIDGETCL | | 0.7 | | 0.7 | | 0.3 | | 0.2 |
| 41 | 52 | 3 | 8.5 | RKQVVIDGETCL | | 0.7 | | 0.9 | | 0.2 | | 0.3 |
| 53 | 62 | 1 | 10.1 | LDILDTAGQE | | 1.1 | | 1.8 | | 0.3 | | 0.4 |
| 53 | 63 | 1 | 10.1 | LDILDTAGQEE | | 1.3 | | 1.8 | | 0.6 | | 0.4 |
| 53 | 64 | 1 | 11.0 | LDILDTAGQEEY | | 1.1 | | 2.0 | | 0.5 | | 1.3 |
| 57 | 63 | 1 | 3.4 | DTAGQEE | | 2.0 | | 2.0 | | 0.9 | | 1.7 |
| 57 | 64 | 1 | 3.9 | DTAGQEEY | | 1.8 | | 1.1 | | 0.8 | | 1.3 |
| 57 | 66 | 1 | 5.8 | DTAGQEEYSA | | 2.8 | | 2.3 | | 1.9 | | 0.1 |
| 57 | 67 | 1 | 8.0 | DTAGQEEYSAM | | 2.9 | | 1.8 | | 0.4 | | 0.4 |
| 64 | 71 | 2 | 6.9 | YSAMRDQY | | 3.5 | | 0.7 | | 0.4 | | 0.5 |
| 68 | 78 | 3 | 7.1 | RDQYCRTGEGF | | 2.2 | | 2.3 | | 0.6 | | 0.1 |
| 68 | 79 | 3 | 9.3 | RDQYCRTGEGFL | | 1.2 | | 2.0 | | 0.6 | | 0.7 |
| 72 | 78 | 1 | 6.2 | CRTGEGF | | 1.2 | | 1.2 | | 1.9 | | 1.6 |
| 72 | 79 | 2 | 9.3 | CRTGEGFL | | 0.8 | | 1.4 | | 1.2 | | 1.6 |
| 82 | 89 | 1 | 6.1 | FAINNTKS | | 0.6 | | 0.6 | | 0.9 | | 1.2 |
| 82 | 90 | 2 | 8.9 | FAINNTKSF | | 0.2 | | 0.6 | | 0.6 | | 0.9 |
| 82 | 91 | 2 | 8.8 | FAINNTKSFE | | 0.1 | | 0.4 | | 0.2 | | 0.7 |
| 82 | 95 | 3 | 8.7 | FAINNTKSFEDIHQ | | 0.5 | | 0.7 | | 0.5 | | 0.2 |
| 83 | 91 | 2 | 6.3 | AINNTKSFE | | 0.8 | | 0.4 | | 0.2 | | 1.1 |
| 83 | 95 | 2 | 7.1 | AINNTKSFEDIHQ | | 0.7 | | 0.5 | | 0.4 | | 1.0 |
| 90 | 95 | 1 | 6.1 | FEDIHQ | | 1.1 | | 0.8 | | 0.3 | | 0.2 |
| 90 | 113 | 5 | 9.7 | FEDIHQYREQIKRVKDSDDVPMVL | | 0.2 | | 0.6 | | 0.4 | | 0.2 |
| 91 | 113 | 3 | 9.1 | EDIHQYREQIKRVKDSDDVPMVL | | 0.1 | | 0.5 | | 0.5 | | 0.7 |
| 91 | 113 | 5 | 9.1 | EDIHQYREQIKRVKDSDDVPMVL | | 0.1 | | 0.5 | | 0.4 | | 0.2 |
| 92 | 113 | 4 | 9.1 | DIHQYREQIKRVKDSDDVPMVL | | 0.2 | | 0.3 | | 0.5 | | 0.1 |
| 96 | 113 | 3 | 8.5 | YREQIKRVKDSDDVPMVL | | 0.1 | | 0.2 | | 0.3 | | 0.1 |
| 96 | 113 | 5 | 8.5 | YREQIKRVKDSDDVPMVL | | 0.1 | | 0.3 | | 0.2 | | 0.4 |
| 97 | 113 | 4 | 8.3 | REQIKRVKDSDDVPMVL | | 0.0 | | 0.5 | | 1.0 | | 0.9 |
| 99 | 113 | 3 | 8.8 | QIKRVKDSDDVPMVL | | 0.2 | | 0.3 | | 0.7 | | 0.1 |
| 114 | 120 | 1 | 6.1 | VGNKCDL | | 0.5 | | 0.5 | | 0.5 | | 1.0 |
| 121 | 132 | 3 | 3.5 | AARTVESRQAQD | | 1.7 | | 1.8 | | 0.6 | | 2.6 |
| 121 | 133 | 3 | 5.5 | AARTVESRQAQDL | | 1.1 | | 1.0 | | 0.3 | | 0.6 |
| 121 | 136 | 4 | 5.0 | AARTVESRQAQDLARS | | 1.3 | | 1.2 | | 0.1 | | 1.8 |
| 127 | 133 | 2 | 4.9 | SRQAQDL | | 0.5 | | 0.5 | | 0.2 | | 2.0 |
| 133 | 144 | 2 | 10.5 | LARSYGIPYIET | | 0.3 | | 0.1 | | 0.3 | | 0.8 |
| 134 | 144 | 2 | 10.2 | ARSYGIPYIET | | 0.3 | | 0.1 | | 0.7 | | 1.8 |
| 134 | 146 | 2 | 10.1 | ARSYGIPYIETSA | | 0.3 | | 0.1 | | 0.6 | | 0.7 |
| 134 | 156 | 3 | 10.2 | ARSYGIPYIETSAKTRQGVEDAF | | 0.1 | | 0.2 | | 0.5 | | 0.4 |
| 137 | 144 | 1 | 11.1 | YGIPYIET | | 0.4 | | 0.1 | | 0.5 | | 0.8 |
| 145 | 153 | 2 | 3.2 | SAKTRQGVE | | 1.0 | | 0.4 | | 0.5 | | 2.8 |
| 145 | 155 | 2 | 3.7 | SAKTRQGVEDA | | 0.7 | | 0.5 | | 0.6 | | 2.3 |
| 145 | 156 | 2 | 7.3 | SAKTRQGVEDAF | | 0.3 | | 0.2 | | 0.9 | | 5.7 |
| 157 | 166 | 3 | 6.7 | YTLVREIRQH | | 0.2 | | 0.7 | | 0.4 | | 0.5 |
| 160 | 166 | 2 | 3.2 | VREIRQH | | 0.6 | | 0.7 | | 0.5 | | 2.5 |

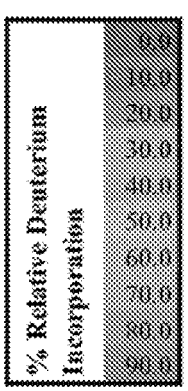

% Relative Deuterium Incorporation

COMPOSITIONS AND METHODS FOR TREATING CANCER

CROSS-REFERENCES TO RELATED APPLICATIONS

This application is the national stage filing under USC 371 of international application PCT/US17/66839, filed Dec. 15, 2017, which claims the benefit of U.S. Provisional Application No. 62/434,971, filed Dec. 15, 2016, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under R01 CA190408 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-595N01US_SequenceListing2_ST25.txt, created Dec. 18, 2019, 23,536 bytes, machine format IBM-PC, MS Windows operating system, is hereby incorporated by reference.

BACKGROUND

Ras proteins are small guanine nucleotide-binding proteins that act as molecular switches by cycling between active GTP-bound and inactive GDP-bound conformations. Ras signaling is regulated through a balance between activation by guanine nucleotide exchange factors (GEFs), most commonly son of sevenless (SOS), and inactivation by GTPase-activating proteins (GAPs) such as neurofibromin or p120GAP. The Ras proteins play a critical role in the regulation of cell proliferation, differentiation, and survival. Dysregulation of the Ras signaling pathway is almost invariably associated with disease. Hyper-activating somatic mutations in Ras are among the most common lesions found in human cancer. Most of these mutations have been shown to decrease the sensitivity of Ras to GAP stimulation and decrease its intrinsic GTPase activity, leading to an increase in the active GTP-bound population. Although mutation of any one of the three Ras isoforms (K-Ras, N-Ras, or H-Ras) has been shown to lead to oncogenic transformation, K-Ras mutations are by far the most common in human cancer. For example, K-Ras mutations are known to be often associated with pancreatic, colorectal and non-small-cell lung carcinomas. Similarly, H-Ras mutations are common in cancers such as papillary thyroid cancer, lung cancers and skin cancers. Finally, N-Ras mutations occur frequently in hepatocellular carcinoma.

Thus, there is a need in the art for effective Ras inhibitors and anticancer compounds. Described herein, inter alia, are solutions to these and other problems in the art.

BRIEF SUMMARY

Described herein, inter alia, is the use of novel compounds to target a Ras protein, including but not limited to chemically tractable oncogenic mutants such as K-RasG12C and method of designing such Ras modulators.

In an aspect is provided a compound (e.g., Switch 2—Binding Pocket binding compound) which is capable of binding an amino acid residue of a Ras protein (e.g., K-Ras, N-Ras, H-Ras, human K-Ras, human N-Ras and/or human H-Ras protein).

In an aspect is provided a compound having the formula:

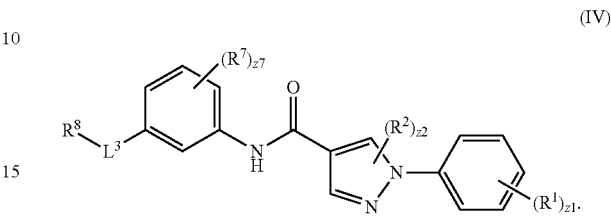

(IV)

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is independently halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is independently hydrogen, halogen, $-CX^8_3$, $-CHX^8_2$, $-CH_2X^8$, $-CN$, $-SO_{n8}R^{8D}$, $-SO_{v8}NR^{8A}R^{8B}$, $-C(O)R^{8C}$, $-C(O)OR^{8C}$, $-C(O)NR^{8A}R^{8B}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^3$ is a bond, $-N(H)-$, $-O-$, $-S-$, $-C(O)-$, $-C(O)N(H)-$, $-N(H)C(O)-$, $-N(H)C(O)NH-$, $-C(O)O-$, $-OC(O)-$, substituted or unsubstituted alkylene, or substituted or unsubstituted heteroalkylene. E is an electrophilic moiety. Each $R^{1A}$, $R^{1B}$, $R^{1C}$, $R^{1D}$, $R^{2A}$, $R^{2B}$, $R^{2C}$, $R^{2D}$, $R^{7A}$, $R^{7B}$, $R^{7C}$, $R^{7D}$, $R^{8A}$, $R^{8B}$, $R^{8C}$, and $R^{8D}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2.4}$ and $R^{2B}$ substituents bonded to the same nitrogen atom may optionally be joined to form a substituted or unsubstituted heterocycloalkyl or substituted or unsubstituted heteroaryl; $R^{7.4}$ and $R^{7B}$ substituents bonded to the same nitrogen atom may optionally be joined to form a substituted or unsubstituted heterocycloalkyl or substituted or unsubstituted heteroaryl; $R^{8.4}$ and $R^{8B}$ substituents bonded to the same nitrogen atom may optionally be joined to form a substituted or unsubstituted heterocycloalkyl or substituted or unsubstituted heteroaryl. z1 is an integer from 0 to 5. z2 is an integer from 0 to 3. z7 is an integer from 0 to 4. Each X, $X^1$, $X^2$, $X^7$, and $X^8$ is independently —F, —Cl, —Br, or —I. n1, n2, n7, and n8 are independently an integer from 0 to 4. m1, m2, m7, m8, v1, v2, v7, and v8 are independently 1 or 2.

In an aspect is provided a pharmaceutical composition including a pharmaceutically acceptable excipient and a compound as described herein.

In an aspect is provided a method of treating a disease in a patient in need of such treatment, the method including administering a therapeutically effective amount of a compound as described herein to the patient.

In an aspect is provided a method of modulating the activity of a Ras protein (e.g., K-Ras, H-Ras, N-Ras, human K-Ras, human H-Ras, or human N-Ras), the method including contacting the Ras protein (e.g., K-Ras, H-Ras, N-Ras, human K-Ras, human H-Ras, or human N-Ras) with an effective amount of a compound as described herein.

In an aspect is provided a method of modulating a Ras protein (e.g., K-Ras, H-Ras, N-Ras, human K-Ras, human H-Ras, or human N-Ras), the method including contacting the Ras protein (e.g., K-Ras, H-Ras, N-Ras, human K-Ras, human H-Ras, or human N-Ras) with an effective amount of a compound as described herein.

In an aspect is provided a Ras protein (e.g., K-Ras, H-Ras, N-Ras, human K-Ras, human H-Ras, or human N-Ras) covalently bound to a compound as described herein, wherein the compound is covalently bound to a cysteine residue of the Ras protein (e.g., K-Ras, H-Ras, N-Ras, human K-Ras, human H-Ras, or human N-Ras).

In an aspect is provided a Ras protein (e.g., K-Ras, H-Ras, N-Ras, human K-Ras, human H-Ras, or human N-Ras) non-covalently bound to a compound as described herein, wherein the compound is non-covalently bound to the Ras protein (e.g., K-Ras, H-Ras, N-Ras, human K-Ras, human H-Ras, or human N-Ras). Typical non-covalent interactions include electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like.

In an aspect is provided a method of identifying an inhibitor (e.g., a covalent or non-covalent inhibitor) of Ras protein (e.g., K-Ras, H-Ras, N-Ras, human K-Ras, human H-Ras, or human N-Ras) including: contacting a Ras protein (e.g., K-Ras, H-Ras, N-Ras, human K-Ras, human H-Ras, or human N-Ras) with a Ras (e.g., K-Ras, H-Ras, N-Ras, human K-Ras, human H-Ras, or human N-Ras) inhibitor test compound; allowing the Ras (e.g., K-Ras, H-Ras, N-Ras, human K-Ras, human H-Ras, or human N-Ras) inhibitor test compound to inhibit (e.g., covalently or non-covalently) the Ras protein (e.g., K-Ras, H-Ras, N-Ras, human K-Ras, human H-Ras, or human N-Ras); and detecting the level of inhibition of the Ras protein (e.g., K-Ras, H-Ras, N-Ras, human K-Ras, human H-Ras, or human N-Ras) thereby identifying an inhibitor (e.g., a covalent or non-covalent inhibitor) of a Ras protein (e.g., K-Ras, H-Ras, N-Ras, human K-Ras, human H-Ras, or human N-Ras).

In an aspect is provided a method of selectively modulating a Ras protein (e.g., K-Ras, H-Ras, N-Ras, human K-Ras, human H-Ras, or human N-Ras), the method including contacting the Ras protein (e.g., K-Ras, H-Ras, N-Ras, human K-Ras, human H-Ras, or human N-Ras) with a compound which contacts at least one amino acid residue forming a Switch 2 binding pocket of the Ras protein (e.g., K-Ras, H-Ras, N-Ras, human K-Ras, human H-Ras, or human N-Ras), wherein the at least one amino acid residue is selected from an amino acid corresponding to V9, C72, E63, Y64, R68, H94, Y96, and Q99 of the human K-Ras, and wherein the compound covalently reacts with an amino acid residue of the Ras protein (e.g., K-Ras, H-Ras, N-Ras, human K-Ras, human H-Ras, or human N-Ras).

BRIEF DESCRIPTION OF THE DRAWINGS

FIG. 1B shows G12 and G13.

FIG. 7A shows YM-254890 while FIG. 7B depicts the interaction of YM-254890 with the protein.

FIGS. 11A-11B. The compound binding disrupts K-Ras G12C binding to GTP and thereby blocks effector binding.

FIG. 12B depicts the chemical structures of compounds 12, 10, and 17.

FIG. 21A depicts the protein of H-Ras/GTP.

FIGS. 22A-22B. FIG. 22A depicts the chemical structures of compound 079 and 083.

FIG. 22B is a model of K-Ras inhibition by S-IIP inhibitors.

FIG. 23A: Top Left: K-Ras$^{M72C}$•GDP bound to DG01 (1.486 Å, R$_{Work}$: 0.1780, R$_{Free}$: 0.2073). Top Right: H-Ras$^{M72C}$•GDP bound to DG01 (1.570 Å, R$_{Work}$: 0.1623, R$_{Free}$: 0.1866), Bottom: Structure alignment of H and K-Ras$^{M72C}$ GDP structures bound to DG01.

FIG. 23B: Top: H-Ras$^{M72C}$ •GNP bound to DGO1 (2.200 Å, R$_{Work}$: 0.2109, R$_{Free}$: 0.2547), Bottom: Comparison of Mg$^{2+}$ coordination between the GDP state, the two GNP states (State 1 and 2), and the new GNP DG01 structure. FIG. 23B: H-Ras$^{M72C}$ •DG01 SNP Structure (top) with specific portions zoomed in to show contacts.

FIG. 26A: Surface and cartoon representation of the S-IIP formed by the binding of ARS-853 (5F2E). Residues of interest (Met 72 and Val 9) are marked and are proximal to the high affinity region of S-IIP's binding pocket where key polar contacts form between ARS-853 and Switch-II residues. FIG. 26B: βME50 values and percent labeling against various Ras constructs are reported for each tethering hit. FIG. 26C: Co-crystal structure of 2C07 and K-Ras (M72C) with GDP and Mg2+. Close-up surface representation of 2C07's binding site and FO-FC omit map (mesh 3 σ). Indicated residues are making hydrophobic contacts with 2C07. FIG. 26D: Differences between ARS-853 and 2C07 structures are mostly localized to Switch-II. Overlay of ARS-853's binding pose on the surface representation of the co-crystal structure of 2C07 and K-Ras(M72C).

FIG. 27A: Co-crystal structure of 2C07 and H-Ras(M72C) with GDP and Mg2+. FO-FC omit map (mesh 3 σ). FIG. 27B: Co-crystal structure of 2C07 and H-Ras(M72C) Chain C with GppNHp and Mg2+. FO-FC omit map (mesh 3 σ). FIG. 27C: Full cartoon structure comparison of 2C07 bound to both nucleotide states as well as a zoomed in view. 2C07 induces a disordering of Switch II and a drastic movement of Switch I away from the nucleotide. FIG. 27D: Distinct coordination states are representative of active (GppNHp State 2) and inactive forms of Ras (GDP and GppNHp State 1). 2C07 induces a new Mg 2+ coordination network that compromises nucleotide coordination and stability.

FIG. 28A: Change in % deuterium between H-Ras(M72C) GDP and H-Ras(M72C) GppNHp displayed on HRas GppNHP (5P21). FIG. 28B: Change in % deuterium between H-Ras(M72C) GDP and H-Ras (M72C) GDP 2C07 displayed on the H-Ras(M72C) GDP 2C07 crystal structure. FIG. 28C: Change in % deuterium between H-Ras(M72C) GppNHp and H-Ras(M72C) GppNHP 2C07 displayed on Chain C of the H-Ras(M72C) GppNHp 2C07 crystal structure. All reported differences are the highest % deuterium difference across a 300 sec time course and are assigned a color based on the corresponding legend. All regions indicated as either an increase or decrease were tested for significance by a two-tailed T-test and had a p value <0.05. The intensity key and legend in FIG. 28A may be used to understand the increase and decrease change in FIG. 28B and FIG. 28C.

FIG. 29A: Raf-1-RBD pull-down of H-Ras(M72C) GppNHP and H-Ras (M72C) 2C07 GppNHp at various concentrations of H-Ras shows 2C07 does not inhibit Raf binding. FIG. 29B: EDTA catalyed exchange and subsequent pull-down of H-Ras (M72C) GppNHp and H-Ras(M72C) GppNHp 2C07 by Raf-1-RBD demonstrates that 2C07 alters intrinsic Ras affinity for nucleotide towards GDP. FIG. 29C: SOS$^{cat}$ pull-down of H-Ras(M72C) GDP and H-Ras(M72C) GDP at various concentrations of H-Ras demonstrates that 2C07 inhibits SOS binding. FIG. 29D: Reconstruction of Ras cycle is achieved by inducing nucleotide exchange of 100 nM Ras by various concentrations of SOS$^{cat}$ for either 1 or 2 hours and subsequent pull-down by Raf-1-RBD. 2C07 inhibits activation of H-Ras by SOS$^{cat}$ and prevents pull-down by Raf-1-RBD.

In FIG. 33B) through FIG. 33D), normalized pull-down signals are shown below the blot. S. E. M for each signal, number of replicates, and a values for each comparative Standard T-Test are summarized herein (see Tables 33B, 33C, and 33D). Values that are significantly different ($\alpha \leq 0.05$) from one another are bolded. Comparative statistics were done for normalized pull-down signals between protein constructs of the same condition (i.e. in FIG. 33B) and FIG. 33C), column 1 for unlabeled and 1 for labeled protein, 2 for unlabeled and 2 for labeled, and so on were statistically compared, and in FIG. 33D) only the +SOS$^{cat}$ and +GppNHp lanes were compared across protein constructs). FIG. 33A) Cartoon representation of pull down protocol. Raf-1-RBD pull-down of H-Ras(M72C) GppNHp and H-Ras(M72C) 2C07 GppNHp at various concentrations of H-Ras demonstrate 2C07 does not inhibit Raf binding. Reported values are quantified pull-down signals normalized to input. FIG. 33B) Cartoon representation of pull down protocol. EDTA catalyzed exchange and subsequent pull down of H-Ras(M72C) GppNHp and H-Ras(M72C) GppNHp 2C07 by Raf-1-RBD demonstrates that 2C07 alters Ras nucleotide preference. FIG. 33C) Cartoon representation of pull down protocol. SOS$^{cat}$ pull-down of H-Ras(M72C) GDP at various concentrations of H-Ras demonstrates 2C07 inhibits SOS binding. FIG. 33D) Cartoon representation of pull down protocol. Ras activation is achieved by catalyzing nucleotide exchange by SOS$^{cat}$ and indirectly reading out activated Ras by subsequent pull down by Raf-1-RBD. 2C07 inhibits SOS$^{cat}$ catalyzed nucleotide exchange.

FIG. 34A) Covalent modification of H-Ras(M72C) bound to GDP and GppNHp monitored by whole protein LC/MS. FIG. 34B) Time-course of Compound 3 labeling of H-Ras(M72C) GDP and GppNHp monitored by whole protein LC/MS. FIG. 34C) Competition time course of Compound 3 labeling of H-Ras(M72C) GDP in the presence of varying concentrations of reversible Compound 4 with initial velocities, $V_0$(%/h), calculated per condition.

FIGS. 38A-38D. All HDX Peptide Data for Experiments Examining Changes in Dynamics Caused by the Interaction of 2C07 with H-Ras(M72C) in the GDP and GppNHp States. The residue start(S) and end(E) number, the charge state(Z), the retention time(RT), and the sequence are shown for every peptide. The relative level of HDX is colored according to the amount of deuterium incorporated on a continuum according to the key. The data presented are the average of three independent experiments with SD shown for each HDX value. The sequences are as follows, from top to bottom: YKLVVVGAGGVGKSAL (SEQ ID NO:7), KLVVVGAGGVGKSAL (SEQ ID NO:8), VVVGAGGVGKSAL (SEQ ID NO:9), VVVGAGGVGKSALT (SEQ ID NO:10), VVVGAGGVGKSALT (SEQ ID NO:10), LIQNHFVDE (SEQ ID NO: 11), LIQNHFVDE (SEQ ID NO: 11), IQNHFVDE (SEQ ID NO: 12), IQNHFVDE (SEQ ID NO: 12), IQNHFVDEYDPTIE (SEQ ID NO: 13), IQNHFVDEYDPTIEDS (SEQ ID NO: 14), HFVDEYDPTIEDS (SEQ ID NO: 15), VDEYDPTIEDS (SEQ ID NO:16), YDPTIE (SEQ ID NO:17), YDPTIED (SEQ ID NO:18), YDPTIEDS (SEQ ID NO: 19), DSYRKQVVIDGETCL (SEQ ID NO:20), DSYRKQVVIDGETCL (SEQ ID NO:20), SYRKQVVIDGET (SEQ ID NO:21), SYRKQVVIDGETCL (SEQ ID NO:22), YRKQVVIDG (SEQ ID NO:23), YRKQVVIDGET (SEQ ID NO:24), YRKQVVIDGETCL (SEQ ID NO:25), RKQVVIDGETCL (SEQ ID NO:26), LDILDTAGQE (SEQ ID NO:27), LDILDTAGQEE (SEQ ID NO:28), LDILDTAGQEEY (SEQ ID NO:29), DTAGQEE (SEQ ID NO:30), DTAGQEEY (SEQ ID NO:31), DTAGQEEYSA (SEQ ID NO:32), DTAGQEEYSAM (SEQ ID NO:33), YSAMRDQY (SEQ ID NO:34), RDQYCRTGEGF (SEQ ID NO:35), RDQYCRTGEGFL (SEQ ID NO:36), CRTGEGF (SEQ ID NO:37), CRTGEGFL (SEQ ID NO:38), FAINNTKS (SEQ ID NO:39), FAINNTKSF (SEQ ID NO:40), FAINNTKSFE (SEQ ID NO:41), FAINNTKSFEDIHQ (SEQ ID NO:42), AINNTKSFE (SEQ ID NO:43), AINNTKSFEDIHQ (SEQ ID NO:44), FEDIHQ (SEQ ID NO:45), FEDIHQYREQIKRVKDSDDVPMVL (SEQ ID NO:46), EDIHQYREQIKRVKDSDDVPMVL (SEQ ID NO:47), EDIHQYREQIKRVKDSDDVPMVL (SEQ ID NO:47), DIHQYREQIKRVKDSDDVPMVL (SEQ ID NO:48), YREQIKRVKDSDDVPMVL (SEQ ID NO:49), YREQIKRVKDSDDVPMVL (SEQ ID NO:49), REQIKRVKDSDDVPMVL (SEQ ID NO:50), QIKRVKDSDDVPMVL (SEQ ID NO:51), VGNKCDL (SEQ ID NO:52), AARTVESRQAQD (SEQ ID NO:53), AARTVESRQAQDL (SEQ ID NO:54), AARTVESRQAQDLARS (SEQ ID NO:55), SRQAQDL (SEQ ID NO:56), LARSYGIPYIET (SEQ ID NO:57), ARSYGIPYIET (SEQ ID NO:58), ARSYGIPYIETSA (SEQ ID NO:59), ARSYGIPYIETSAKTRQGVEDAF (SEQ ID NO:60), YGIPYIET (SEQ ID NO:61), SAKTRQGVE (SEQ ID NO:62), SAKTRQGVEDA (SEQ ID NO:63), SAKTRQGVEDAF (SEQ ID NO:64), YTLVREIRQH (SEQ ID NO:65), VREIRQH (SEQ ID NO:66).

FIG. 39A) Ras/Raf-1-RBD structure shows binding interactions are exclusive to switch-I. FIG. 39B) Overlay of 2C07 bound H-Ras(M72C) GppNHp with Ras/Raf-1-RBD structure shows compound disruption of switch-II is likely tolerated. FIG. 39C) Ras/PI3K-γ structure shows interactions occur between PI3K-γ and both switch regions. FIG. 39D) Overlay of 2C07 bound H-Ras(M72C) GppNHp with the Ras/PI3K-γ structure shows compound disruption of switch-II is not tolerated with significant clashes resulting between switch-II and PI3K-γ.

DETAILED DESCRIPTION

I. Definitions

Figure 1A:
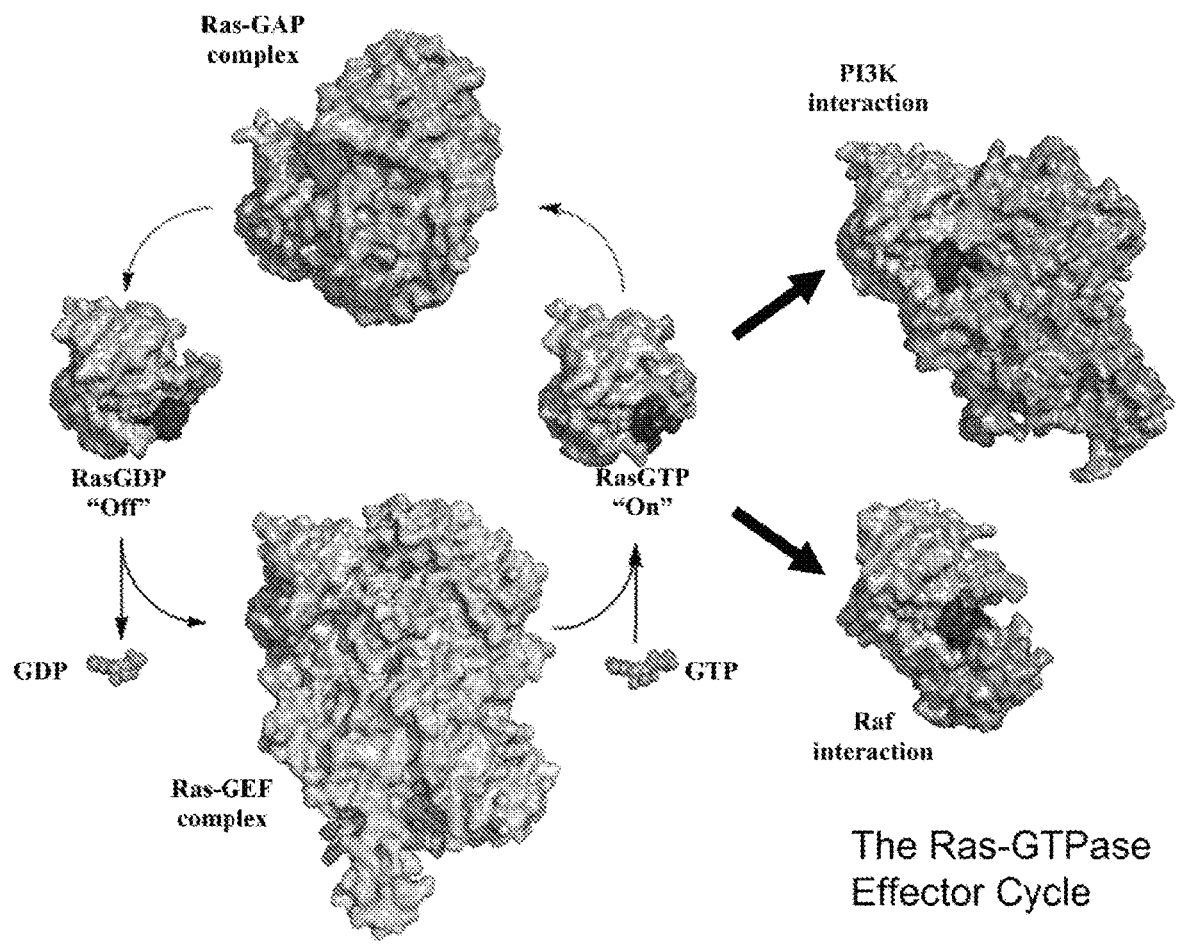
FIGS. 1A-1B. The Ras-GTPase Effector Cycle is depicted in FIG. 1A.
Figure 1B:
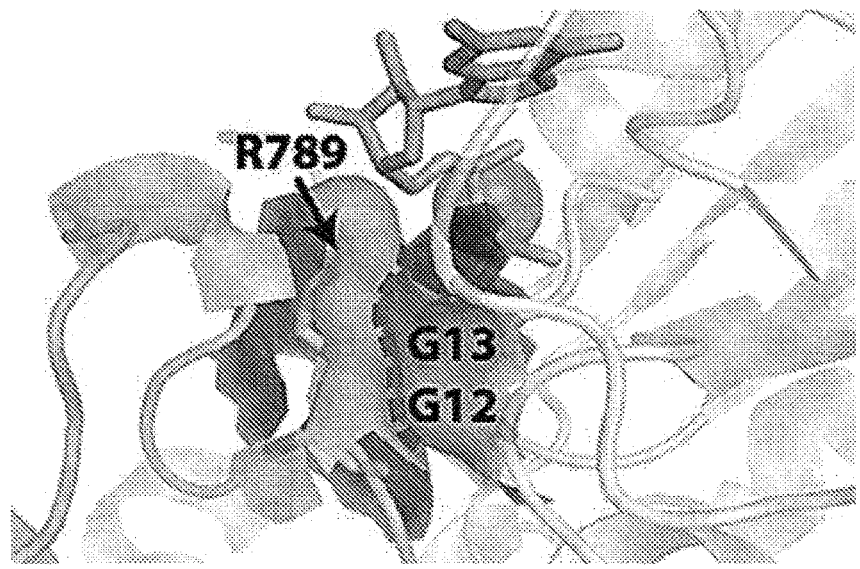
Figure 2:
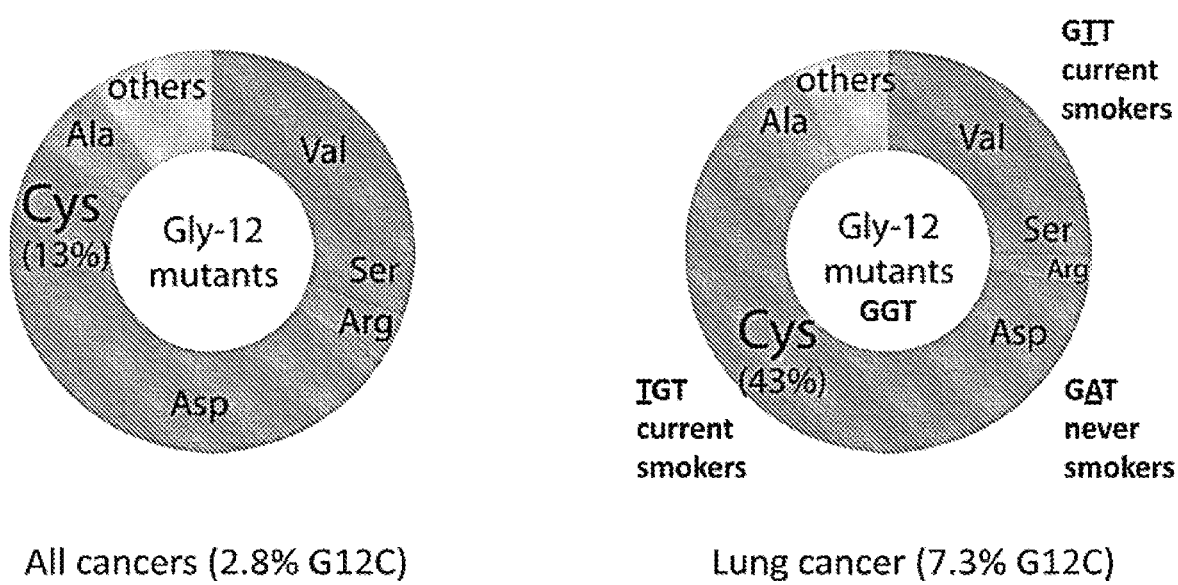
FIG. 2. G12C—A disease relevant cysteine provides a chemical opportunity to target K-Ras*.
Figure 3:
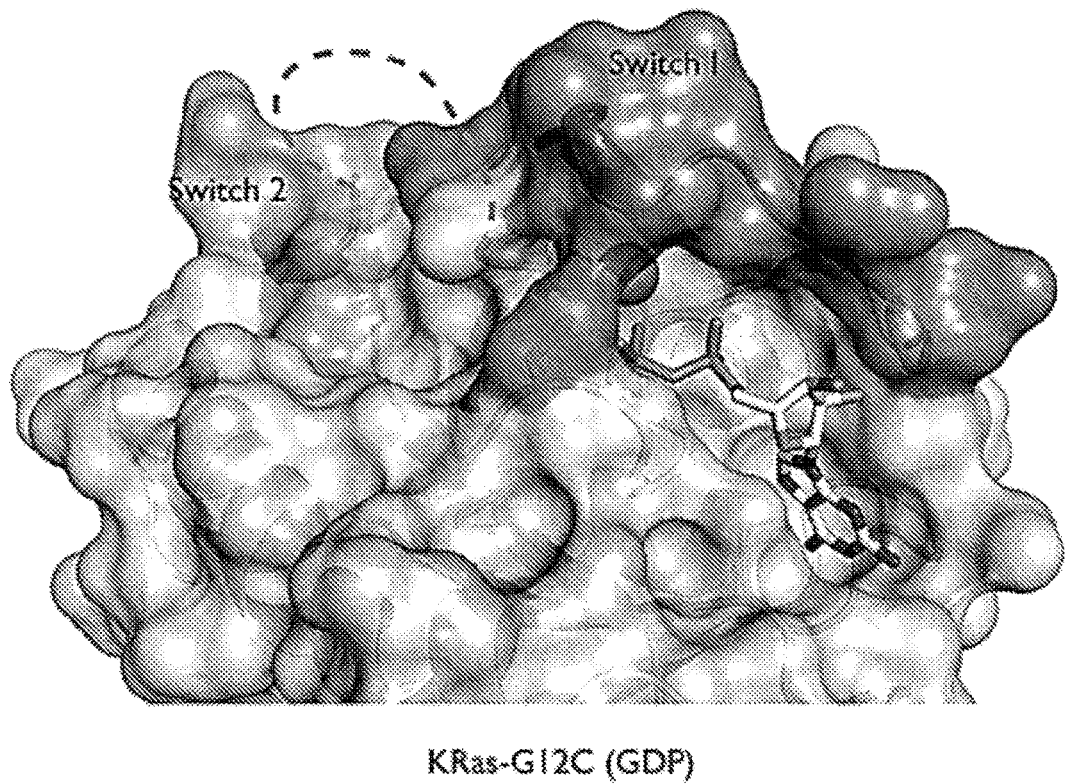
FIG. 3. KRas-G12C GDP showing the switch 2 and switch 1 binding pockets.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S, and wherein the nitrogen and sulfur atoms may optionally be oxidized, and the nitrogen heteroatom may optionally be quaternized). The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'- and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. In embodiments, a cycloalkyl is a spirocyclic cycloalkyl, wherein the spirocyclic rings are cycloalkyl rings. In embodiments, a cycloalkyl is a fused ring cycloalkyl, wherein the fused rings are cycloalkyl rings. In embodiments, a cycloalkyl is a bridged ring cycloalkyl, wherein the bridged rings are cycloalkyl rings. In embodiments, a cycloalkyl is monocyclic. In embodiments, a cycloalkyl is two rings. In embodiments, a cycloalkyl is three rings. In embodiments, a cycloalkyl is four rings. In embodiments, a cycloalkyl is five rings. In embodiments, a cycloalkyl is polycyclic. In embodiments, a heterocycloalkyl is a spirocyclic heterocycloalkyl, wherein the spirocyclic rings are one or more heterocycloalkyl rings and optionally one or more cycloalkyl rings. In embodiments, a heterocycloalkyl is a fused ring heterocycloalkyl, wherein the fused rings are one or more heterocycloalkyl rings and optionally one or more cycloalkyl rings. In embodiments, a heterocycloalkyl is a bridged ring heterocycloalkyl, wherein the bridged rings are one or more heterocycloalkyl rings and optionally one or more cycloalkyl rings. In embodiments, the rings of a spirocyclic, fused ring, or bridged ring heterocycloalkyl are heterocyclic rings. In embodiments, a heterocycloalkyl is monocyclic. In embodiments, a heterocycloalkyl is two rings. In embodiments, a heterocycloalkyl is three rings. In embodiments, a heterocycloalkyl is four rings. In embodiments, a heterocycloalkyl is five rings. In embodiments, a heterocycloalkyl is polycyclic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. In embodiments, an aryl is a fused ring aryl, wherein the fused rings are one or more aryl rings and optionally one or more cycloalkyl and/or heterocycloalkyl rings. In embodiments, an aryl is a bridged ring aryl, wherein the bridged rings are one or more aryl rings and optionally one or more cycloalkyl and/or heterocycloalkyl rings. In embodiments, the rings of a fused ring aryl or bridged ring aryl are aryl rings. In embodiments, an aryl is monocyclic. In embodiments, an aryl is two rings. In embodiments, an aryl is three rings. In embodiments, an aryl is four rings. In embodiments, an aryl is five rings. In embodiments, an aryl is polycyclic. In embodiments, a heteroaryl is a fused ring heteroaryl, wherein the fused rings are one or more heteroaryl rings and optionally one or more cycloalkyl, heterocycloalkyl, and/or aryl rings. In embodiments, a heteroaryl is a bridged ring heteroaryl, wherein the bridged rings are one or more heteroaryl rings and optionally one or more cycloalkyl, heterocycloalkyl, and/or aryl rings. In embodiments, the rings of a fused ring heteroaryl or bridged ring heteroaryl are heteroaryl rings. In embodiments, a heteroaryl is monocyclic. In embodiments, a heteroaryl is two rings. In embodiments, a heteroaryl is three rings. In embodiments, a heteroaryl is four rings. In embodiments, a heteroaryl is five rings. In embodiments, a heteroaryl is polycyclic. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⁓" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

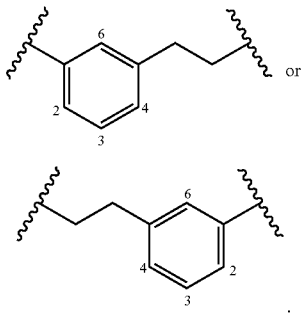

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_8$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings, bridged rings, or spirocyclic rings, a substituent depicted as associated with one member of the fused rings, bridged rings, or spirocyclic rings (a floating substituent on a single ring), may be a substituent on any of the fused rings, bridged rings, or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different bridged rings, or different spirocyclic rings, and each substituent may optionally be different. Where a point of attachment of a ring to the remainder of a molecule is not limited to a single atom (a floating substituent), the attachment point may be any atom of the ring and in the case of fused rings, bridged rings, or spirocyclic rings, any atom of any of the fused rings, bridged rings, or spirocyclic rings while obeying the rules of chemical valency. Where a ring, fused rings, bridged rings, or spirocyclic rings contain one or more ring heteroatoms and the ring, fused rings, bridged rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure and form a bridged ring structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C3-C8 cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCH Cl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$—C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)-for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl or unsubstituted 2 to 20 membered heteroalkyl," the group may contain one or more unsubstituted $C_1$-$C_{20}$ alkyls, and/or one or more unsubstituted 2 to 20 membered heteroalkyls. Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Where one or more moieties of a compound are substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the one or more moieties are each independently substituted with at least one substituent (e.g., a substituent group, a size-limited substituent group, or lower substituent group) and each substituents on each of the one or more moieties is optionally different. Additionally, where multiple substituents are present on a moiety, each substituent may be optionally differently.

Moreover, where a moiety is substituted with an R substituent, the moiety may be referred to as "R-substituted." Where a moiety is R-substituted, the moiety is substituted with at least one R substituent and each R substituent is optionally different. Where a particular R group is present in the description of a chemical genus, a Roman alphabetic symbol or number may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently. Alternatively, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently.

A "covalent cysteine modifier moiety" as used herein refers to a substituent that is capable of reacting with the sulfhydryl functional group of a cysteine amino acid (e.g. cysteine 12 or cysteine 13 of Ras (e.g., human Ras, human K-Ras, human H-Ras)) to form a covalent bond. Thus, the covalent cysteine modifier moiety is typically electrophilic.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "Ras modulator" refers to a compound (e.g. a compound described herein) that modulates the activity of Ras (e.g., human Ras (a human Ras modulator), human K-Ras (a human K-Ras modulator), human H-Ras (a human H-Ras modulator)) when compared to a control, such as absence of the compound or a compound with known inactivity.

A "Ras inhibitor" refers to a compound (e.g. a compound described herein) that reduces the activity of Ras (e.g., human Ras (a human Ras inhibitor), human K-Ras (a human K-Ras inhibitor), human H-Ras (a human H-Ras inhibitor)) when compared to a control, such as absence of the compound or a compound with known inactivity.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An amino acid residue in a protein "corresponds" to a given residue when it occupies the same essential structural position within the protein as the given residue. For example, a selected residue in a selected protein corresponds to Cys12 of human Ras (e.g., K-Ras or H-Ras) protein when the selected residue occupies the same essential spatial or other structural relationship as Cys12 in human Ras (e.g., K-Ras or H-Ras) protein. In some embodiments, where a selected protein is aligned for maximum homology with the human Ras (e.g., K-Ras or H-Ras) protein, the position in the aligned selected protein aligning with Cys12 is said to correspond to Cys12. Instead of a primary sequence alignment, a three dimensional structural alignment can also be used, e.g., where the structure of the selected protein is aligned for maximum correspondence with the human K-Ras protein and the overall structures compared. In this case, an amino acid that occupies the same essential position as Cys12 in the structural model is said to correspond to the Cys12 residue. An amino acid residue in a protein "corresponds" to a given residue when it occupies the same essential structural position within the protein as the given residue. For example, a selected residue in a selected protein corresponds to Cys13 of human Ras (e.g., K-Ras or H-Ras) protein when the selected residue occupies the same essential spatial or other structural relationship as Cys13 in human Ras (e.g., K-Ras or H-Ras) protein. In some embodiments, where a selected protein is aligned for maximum homology with the human Ras (e.g., K-Ras or H-Ras) protein, the position in the aligned selected protein aligning with Cys13 is said to correspond to Cys 13. Instead of a primary sequence alignment, a three dimensional structural alignment can also be used, e.g., where the structure of the selected protein is aligned for maximum correspondence with the human K-Ras protein and the overall structures compared. In this case, an amino acid that occupies the same essential position as Cys13 in the structural model is said to correspond to the Cys13 residue.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor contacts the target protein). In embodiments, inhibition refers to a reduction of activity of a target protein from an indirect interaction (e.g. an inhibitor contacts a protein that activates the target protein, thereby preventing target protein activation). A "Ras inhibitor" (e.g., human K-Ras inhibitor or human H-Ras inhibitor) is a compound that negatively affects (e.g. decreases) the activity or function of Ras (e.g., human K-Ras or human H-Ras) relative to the activity or function of Ras (e.g., human K-Ras or human H-Ras) in the absence of the inhibitor (e.g., wherein the Ras inhibitor contacts Ras).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient", "subject", or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the disclosure can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to 111In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, contacting of a Ras (e.g., human K-Ras or human H-Ras) protein with a compound as described herein may reduce the interactions between the Ras (e.g., human K-Ras or human H-Ras) protein and effectors or signaling pathway components, resulting in changes in cell growth, proliferation, or survival.

The compounds described herein can be used in combination with one another, with other active agents known to be useful in treating a disease associated with cells expressing a particular Ras, K-Ras, mutant K-Ras (e.g. cancer), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In therapeutic use for the treatment of cancer, compound utilized in the pharmaceutical compositions of the present disclosure may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present disclosure, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent.

The compounds of the disclosure can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

The compounds of the present disclosure can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present disclosure can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present disclosure can be administered transdermally. It is also envisioned that multiple routes of administration (e.g., intramuscular, oral, transdermal) can be used to administer the compounds of the disclosure. Accordingly, the present disclosure also provides pharmaceutical compositions comprising a pharmaceutically acceptable excipient and one or more compounds of the disclosure.

For preparing pharmaceutical compositions from the compounds of the present disclosure, pharmaceutically acceptable carriers can be either solid or liquid. Solid form preparations include powders, tablets, pills, capsules, cachets, suppositories, and dispersible granules. A solid carrier can be one or more substances, that may also act as diluents, flavoring agents, binders, preservatives, tablet disintegrating agents, or an encapsulating material.

In powders, the carrier is a finely divided solid in a mixture with the finely divided active component (e.g. a compound provided herein). In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the disclosure can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the disclosure are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the disclosure can also be incorporated into liposomes or administered via transdermal pumps or patches. Pharmaceutical admixtures suitable for use in the present disclosure are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component (e.g. compounds described herein) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the disclosure can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. a Ras, K-Ras, K-Ras G12C, K-Ras G12D, K-Ras G12V, K-Ras G13C, K-Ras G13D, a mutant K-Ras, an activated K-Ras), and/or reducing, eliminating, or slowing the progression of disease symptoms (e.g. cancer growth or metastasis). Determination of a therapeutically effective amount of a compound of the disclosure is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. lung cancer, NSCL cancer, colon cancer, colorectal cancer, breast cancer, pancreatic cancer, leukemia), kind of concurrent treatment, complications from the disease being treated or other health-related problems. Other therapeutic regimens or agents can be used in conjunction with the methods and compounds of Applicants' disclosure. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:

1520-1522 (1996) and U.S. Pat. No. 5,593,853). The methods above may be used to synthesize single molecular species.

An "effective amount" is an amount sufficient for a compound to accomplish a stated purpose relative to the absence of the compound (e.g. achieve the effect for which it is administered, treat a disease, reduce enzyme activity, increase enzyme activity, reduce signaling pathway, reduce one or more symptoms of a disease or condition (e.g. reduce GTPase activity in a cell, increase GTPase activity, reduce signaling pathway stimulated by GTP bound Ras (e.g. K-Ras), reduce the signaling pathway activity of Ras, reduce the signaling pathway activity of K-Ras, reduce the signaling pathway activity of K-Ras4A, reduce the signaling pathway activity of K-Ras4B, reduce the signaling pathway activity of H-Ras, reduce the signaling pathway activity of N-Ras, reduce the signaling pathway activity of K-Ras G12C, reduce the signaling pathway activity of K-Ras G12V, reduce the signaling pathway activity of K-Ras G13C, reduce the signaling pathway activity of K-Ras G13D, reduce the signaling pathway activity of K-Ras G12D, reduce the signaling pathway activity of a mutant K-Ras, increase the activity of Ras, increase the activity of K-Ras, increase the activity of K-Ras4A, increase the activity of K-Ras4B, increase the activity of H-Ras, increase the activity of N-Ras, increase the activity of K-Ras G12C, increase the activity of K-Ras G13C, increase the activity of K-Ras G12D, increase the activity of K-Ras G12V, increase the activity of K-Ras G13D, increase the activity of a mutant K-Ras, inhibit the binding of K-Ras to SOS, inhibit the binding of K-Ras to a GEF, inhibit nucleotide exchange). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist (e.g. disrupt the protein-protein interaction between K-Ras and a signaling pathway binding protein such as PI3K, disrupt the interaction of K-Ras and GEF, disrupt the interaction of K-Ras and SOS, disrupt the interaction of K-Ras with Raf). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g. GTPase activity, protein-protein interaction, signaling pathway) of a protein (e.g. Ras, K-Ras, mutant K-Ras, K-Ras G12C, K-Ras G12D, K-Ras G12V, K-Ras G13C, K-Ras G13D) in the absence of a compound as described herein.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" or "binding", which may be used interchangeably, may include allowing two species to react, interact, or physically touch, wherein the two species may be a compound as described herein and a protein or enzyme (e.g. Ras, K-Ras, H-Ras, N-Ras, K-Ras4A, K-Ras4B, mutant Ras, mutant K-Ras, K-Ras G12C, K-Ras G12V, K-Ras G13C, K-Ras G12D, K-Ras G13D). In some embodiments, the protein may be K-Ras. In some embodiments, the protein may be a mutant K-Ras (e.g. K-Ras G12C, K-Ras G12V, K-Ras G13C, K-Ras G12D, K-Ras G13D). In some embodiments, the protein may be K-Ras4A. In some embodiments, the protein may be K-Ras4B. In some embodiments, the protein may be human K-Ras. In some embodiments contacting or binding includes allowing a compound described herein to interact with a protein or enzyme that is involved in a signaling pathway. In some embodiments contacting or binding includes allowing a compound described herein to interact with a Switch 2—Binding Pocket. In some embodiments contacting or binding includes allowing a compound described herein to interact with a Switch 2 Groove.

As defined herein, the term "inhibition", "inhibit", "inhibiting" and the like in reference to a protein-inhibitor interaction means negatively affecting (e.g. decreasing) the activity or function of the protein (e.g. decreasing the signaling pathway stimulated by GTP bound Ras (e.g. K-Ras, K-Ras G12C, K-Ras G12V, K-Ras G13C, K-Ras G12D, K-Ras G13D), nucleotide exchange, effector protein binding, effector protein activation, guanine exchange factor (GEF) binding, SOS binding, GEF-facilitated nucleotide exchange, phosphate release, nucleotide release, nucleotide binding) relative to the activity or function of the protein in the absence of the inhibitor (e.g. mutant K-Ras inhibitor, activitated K-Ras inhibitor). In some embodiments inhibition refers to reduction of a disease or symptoms of disease. In some embodiments, inhibition refers to a reduction in the activity of a signal transduction pathway or signaling pathway (e.g. reduction of a pathway involving GTP bound Ras (e.g. K-Ras, K-Ras G12C, K-Ras G12V, K-Ras G13C, K-Ras G12D, K-Ras G13D), reduction of a pathway involving mutant K-Ras (e.g. K-Ras G12C, K-Ras G12V, K-Ras G13C, K-Ras G12D, K-Ras G13D)). Thus, inhibition includes, at least in part, partially or totally blocking stimulation, decreasing, preventing, or delaying activation, or inactivating, desensitizing, or down-regulating the signaling pathway or enzymatic activity or the amount of a protein (e.g. K-Ras, K-Ras G12C, K-Ras G12V, K-Ras G13C, K-Ras G12D, K-Ras G13D). In some embodiments, inhibition refers to inhibition of binding of Ras (K-Ras, K-Ras G12C, K-Ras G12V, K-Ras G13C, K-Ras G12D, K-Ras G13D) with signaling pathway binding partners (e.g. PI3K, SOS, Raf). In some embodiments, inhibition refers to inhibition of binding of Ras with a GEF (e.g. SOS).

The term "modulator" refers to a composition that increases or decreases the level of a target molecule or the function (e.g. GTPase activity, nucleotide exchange, effector protein binding, effector protein activation, guanine exchange factor (GEF) binding, SOS binding, GEF-facilitated nucleotide exchange, phosphate release, nucleotide release, nucleotide binding) of a target molecule or the physical state (e.g. Ras subcellular localization, Ras post-translational processing, Ras post-translational modifications) of the target of the molecule (e.g. a target may be K-Ras and the function may be to hydrolyze GTP or activate a signaling pathway that is activated by GTP bound K-Ras, binding of K-Ras with protein binding partners (e.g. PI3K, SOS, Raf)). In some embodiments, a GTPase modulator is a compound that reduces the activity of a GTPase in a cell. In some embodiments, a GTPase modulator is a compound that increases the activity of a GTPase in a cell. In some embodiments, a GTPase modulator is a compound that reduces the signaling pathway in a cell that is activated by the GTP bound form of Ras. In some embodiments, a GTPase modulator is a compound that increases the signaling pathway in a cell that is activated by the GTP bound form of Ras. In some embodiments, a K-Ras disease modulator is a compound that reduces the severity of one or more symptoms of a disease associated with K-Ras (e.g. cancer, metastatic cancer). A K-Ras modulator is a compound that increases or decreases the activity or function or level of activity or level of function of K-Ras or level of K-Ras or level of K-Ras in a particular physical state. A mutant K-Ras modulator is a compound that that increases or decreases the activity or function or level of activity or level of function of mutant K-Ras or level of mutant K-Ras or level of mutant K-Ras in a particular physical state. A K-Ras G12C modulator, K-Ras G12V modulator, K-Ras G12D modulator, K-Ras G13C modulator, or K-Ras G13D modulator is a compound that increases or decreases the activity or function or level of activity or level of function of that particular mutant K-Ras or level of that particular mutant K-Ras or level of that particular mutant K-Ras in a particular physical state. A K-Ras inhibitor is a compound that decreases the activity or function or level of activity or level of function of K-Ras or level of K-Ras or level of K-Ras in a particular physical state. A mutant K-Ras inhibitor is a compound that that decreases the activity or function or level of activity or level of function of mutant K-Ras or level of mutant K-Ras or level of mutant K-Ras in a particular physical state. A K-Ras G12C inhibitor, K-Ras G12V inhibitor, K-Ras G12D inhibitor, K-Ras G13C inhibitor, or K-Ras G13D inhibitor is a compound that decreases the activity or function or level of activity or level of function of that particular mutant K-Ras or level of that particular mutant K-Ras or level of that particular mutant K-Ras in a particular physical state. In some embodiments, a Ras (e.g., human K-Ras or human H-Ras) associated disease modulator is a compound that reduces the severity of one or more symptoms of a disease associated with Ras (e.g., human K-Ras or human H-Ras) (e.g. cancer). A Ras (e.g., human K-Ras or human H-Ras) modulator is a compound that increases or decreases the activity or function or level of activity or level of function of Ras (e.g., human K-Ras or human H-Ras).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Disease" or "condition" refer to a state of being or health status of a patient or subject capable of being treated with the compounds or methods provided herein. In some embodiments, the disease is a disease related to (e.g. caused by) a mutant Ras. In some embodiments, the disease is a disease related to (e.g. caused by) a mutant K-Ras (e.g. K-Ras G12C, G12V, G13C, G12D, or G13D) or aberrant K-Ras signaling pathway activity (e.g. lung cancer, breast cancer, colon cancer, colorectal cancer, pancreatic cancer, leukemia). Examples of diseases, disorders, or conditions include, but are not limited to cancer. Examples of diseases, disorders, or conditions include, but are not limited to MYH-associated polyposis. In some instances, "disease" or "condition" refers to cancer. In some instances, "disease" or "condition" refers to MYH-associated polyposis. In some further instances, "cancer" refers to human cancers and carcinomas, sarcomas, adenocarcinomas, lymphomas, leukemias, etc., including solid and lymphoid cancers, kidney, breast, lung (NSCLC), bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemia, lymphomas, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma *villosum*.

"Ras associated cancer" (also referred to herein as "Ras related cancer") refers to a cancer caused by aberrant Ras activity or signaling. A "cancer associated with aberrant K-Ras activity" (also referred to herein as "K-Ras related cancer") is a cancer caused by aberrant K-Ras activity or signaling (e.g. a mutant K-Ras). K-Ras related cancers may include lung cancer, non-small cell lung cancer, breast cancer, leukemia, pancreatic cancer, colon cancer, colorectal cancer. Other cancers that are associated with aberrant activity of one or more of Ras, K-Ras, H-Ras, N-Ras, mutant K-Ras (including K-Ras G12C, K-Ras G12V, K-Ras G13C, K-Ras G12D, K-Ras G13D mutants), mutant N-Ras, and mutant H-Ras are well known in the art and determining such cancers are within the skill of a person of skill in the art.

The term "administer (or administering) a Ras inhibitor" means administering a compound that inhibits the activity or level (e.g. amount) or level of a signaling pathway of one or more Ras proteins (e.g. a Ras inhibitor, K-Ras inhibitor, N-Ras inhibitor, H-Ras inhibitor, mutant K-Ras inhibitor, K-Ras G12C inhibitor, K-Ras G12V inhibitor, K-Ras G13C inhibitor, K-Ras G12D inhibitor, K-Ras G13D inhibitor) to a subject. Administration may include, without being limited by mechanism, allowing sufficient time for the Ras inhibitor to reduce the activity of one or more Ras proteins or for the Ras inhibitor to reduce one or more symptoms of a disease (e.g. cancer, wherein the Ras inhibitor may arrest the cell cycle, slow the cell cycle, reduce DNA replication, reduce cell replication, reduce cell growth, reduce metastasis, or cause cell death). The term "administer (or administering) a K-Ras inhibitor" means administering a compound that inhibits the activity or level (e.g. amount) or level of a signaling pathway of one or more K-Ras proteins (K-Ras, mutant K-Ras, K-Ras G12C, K-Ras G12V, K-Ras G12D, K-Ras G13C, K-Ras G13D). In embodiments, the administering does not include administration of any active agent other than the recited active agent.

The term "associated" or "associated with" in the context of a substance or substance activity or function associated with a disease (e.g. Ras (e.g., human K-Ras or human H-Ras) activity, a protein associated disease, a cancer associated with aberrant Ras activity, K-Ras associated cancer, mutant K-Ras associated cancer, activated K-Ras associated cancer, K-Ras G12C associated cancer, K-Ras G12V associated cancer, K-Ras G13C associated cancer, K-Ras G12D associated cancer, K-Ras G13D associated cancer) means that the disease (e.g. cancer) is caused by (in whole or in part), or a symptom of the disease is caused by (in whole or inpart) the substance or substance activity or function. For example, a cancer associated with aberrant Ras activity or function may be a cancer that results (entirely or partially) from aberrant Ras activity or function (e.g. enzyme activity, protein-protein binding, signaling pathway) or a cancer wherein a particular symptom of the disease is caused (entirely or partially) by aberrant Ras activity or function. As used herein, what is described as being associated with a disease, if a causative agent, could be a target for treatment of the disease. For example, a cancer associated with aberrant Ras activity or function or a Ras associated cancer, may be treated with a Ras modulator or Ras inhibitor, in the instance where increased Ras activity or function (e.g. signaling pathway activity) causes the cancer. For example, a cancer associated with K-Ras G12C may be a cancer that a subject with K-Ras G12C is at higher risk of developing as compared to a subject without K-Ras G12C. For example, a cancer associated with K-Ras G12V may be a cancer that a subject with K-Ras G12V is at higher risk of developing as compared to a subject without K-Ras G12V.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "electrophilic chemical moiety" is used in accordance with its plain ordinary chemical meaning and refers to a monovalent chemical group that is electrophilic.

The term "Ras" refers to one or more of the family of human Ras GTPase proteins (e.g. K-Ras, H-Ras, N-Ras). The term "K-Ras" refers to the nucleotide sequences or proteins of human K-Ras (e.g. human K-Ras4A (NP 203524.1), human K-Ras4B (NP_004976.2), or both K-Ras4A and K-Ras4B). The term "K-Ras" includes both the wild-type form of the nucleotide sequences or proteins as well as any mutants thereof. In some embodiments, "K-Ras" is wild-type K-Ras. In some embodiments, "K-Ras" is one or more mutant forms. The term "K-Ras" XYZ refers to a nucleotide sequence or protein of a mutant K-Ras wherein the Y numbered amino acid of K-Ras that has an X amino acid in the wildtype instead has a Z amino acid in the mutant (e.g. K-Ras G12C has a G in wildtype protein but a C in the K-Ras G12C mutant protein). In some embodiments K-Ras refers to K-Ras4A and K-Ras4B. In some embodiments, K-Ras refers to K-Ras4A. In some embodiments, K-Ras refers to K-Ras4B (e.g., NM_004985.4 or NP_004976.2). In some embodiments, K-Ras refers to the protein including (e.g., consisting of) the amino acid sequence below or including the sequence below with one or more mutations (e.g., G12C, G12V, or G13C):

```
                                          (SEQ ID NO: 1)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEK
```

In some embodiments, K-Ras refers to the protein including (e.g., consisting of) the amino acid sequence below or including (e.g., consisting of) the sequence below with one or more mutations (e.g., G12C, G12V, or G13C):

```
                                          (SEQ ID NO: 2)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEKMSKDGKKKKKKSKTKCVIM
```

```
                                          (SEQ ID NO: 3)
  1 mteyklvvvg aggvgksalt iqliqnhfvd eydptiedsy
    rkqvvidget clldildtag 61 qeeysamrdq ymrtgegflc vfainntksf edihhyreqi
    krvkdsedvp mvlvgnkcdl 121 psrtvdtkqa qdlarsygip fietsaktrq gvddafytlv
    reirkhkekm skdgkkkkkk 181 sktkcvim
```

The term "H-Ras" includes both the wild-type form of the nucleotide sequences or proteins as well as any mutants thereof. In some embodiments, "H-Ras" is wild-type H-Ras. In some embodiments, "H-Ras" is one or more mutant forms. The term "H-Ras" XYZ refers to a nucleotide sequence or protein of a mutant H-Ras wherein the Y numbered amino acid of H-Ras that has an X amino acid in the wildtype instead has a Z amino acid in the mutant (e.g. H-Ras G12C has a G in wildtype protein but a C in the H-Ras G12C mutant protein). In some embodiments, H-Ras refers to the protein NP_005334.1. In some embodiments, H-Ras refers to the protein including (e.g., consisting of) the amino acid sequence below or including (e.g., consisting of) the sequence below with one or more mutations (e.g., G12C, G12V, or G13C):

(SEQ ID NO: 4)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHQYREQI

KRVKDSDDVPMVLVGNKCDLAARTVESRQAQDLARSYGIPYIETSAKTRQ

GVEDAFYTLVREIRQH

In some embodiments, H-Ras refers to the protein including (e.g., consisting of) the amino acid sequence below or including (e.g., consisting of) the sequence below with one or more mutations (e.g., G12C, G12V, or G13C):

(SEQ ID NO: 5)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHQYREQI

KRVKDSDDVPMVLVGNKCDLAARTVESRQAQDLARSYGIPYIETSAKTRQ

GVEDAFYTLVREIRQHKLRKLNPPDESGPGCMSCKCVLS (SEQ ID NO: 6)
  1 mteyklvvvg aggvgksalt iqliqnhfvd eydptiedsy
    rkqvvidget clldildtag 61 qeeysamrdq ymrtgegflc vfainntksf edihqyreqi
    krvkdsddvp mvlvgnkcdl 121 aartvesrqa qdlarsygip yietsaktrq gvedafytlv
    reirqhklrk lnppdesgpg 181 cmsckcvls The term "Ras inhibitor test compound" as used herein refers to a compound that is being characterized in an assay for the ability to inhibit an activity, function, or level (e.g. amount) of a Ras protein. The term "K-Ras inhibitor test compound" as used herein refers to a compound that is being characterized in an assay for the ability to inhibit an activity, function, or level (e.g. amount) of K-Ras protein. A "Switch 2—Binding Pocket covalent inhibitor test compound" is a Ras inhibitor test compound that binds to a Ras Switch 2—Binding Pocket and is being tested for the ability to covalently inhibit an activity, function, or level (e.g. amount) of a Ras protein.

The terms "unsubstituted vinyl sulfone moiety", "unsubstituted vinyl sulfonamide moiety", "unsubstituted fluoro ($C_1$-$C_4$)alkylketone moiety", "unsubstituted chloro($C_1$-$C_4$) alkylketone moiety", "unsubstituted acrylamide moiety", "unsubstituted disulfide moiety", "unsubstituted thiol moiety", "unsubstituted phosphonate moiety", "unsubstituted aldehyde moiety", "unsubstituted enone moiety", "unsubstituted diazomethylketone moiety", "unsubstituted diazomethylamide moiety", "unsubstituted cyanocyclopropyl carboxamide moiety", "unsubstituted epoxide moiety", "unsubstituted epoxyketone moiety", "unsubstituted epoxyamide moiety", "unsubstituted aryl aldehyde moiety", "unsubstituted aryl dialdehyde moiety", "unsubstituted dialdehyde moiety", "unsubstituted nitrogen mustard moiety", "unsubstituted propargyl moiety", or "unsubstituted propargylamide moiety" are used according to their plain ordinary chemical meaning and refer to those monovalent chemical groups named having the lowest molecular weight for each such group while obeying the rules of chemical valency. A substituted form of one of the named groups may be substituted with one or more of any of the substituent groups described herein while obeying the rules of chemical valency.

"Switch 2," as used herein, refers to a protein domain of a Ras protein (e.g. K-Ras) formed at least in part by residues corresponding to residues 60-76 of K-Ras (e.g. K-Ras Switch 2 refers to residues 60-76 of K-Ras). A "Switch 2 Binding Region" is a region of a Ras protein (e.g. K-Ras) that is formed by amino acid residues that contact at least a portion of Switch 2 when Ras is bound to GTP. A "Switch 2—Binding Pocket" or "S2BP" or "switch-II pocket" or "S-IIP" is a cavity bound (the limits or boundaries of which are made), at least in part, by the amino acid residues that form Switch 2 and the Switch 2 Binding Region, which may also include adjacent (e.g., through space in the folded protein structure) amino acid residues (e.g., V9, E63, Y64, R68, M72, H94, Y96, and/or Q99; amino acids binding or contacting 2C07 in FIG. 18, 21A-B, 23A-B, 24, 26A-E, 27A-D, or 28A-C, A59, Y64, D69, R73, F78, K88, E91, D92, H94, H95, R97, R102, and/or V103; V7, V9, G10, P34, T58, A59, G60, Q61, E62, E63, Y64, R68, D69, Y71, M72, R73, F78, K88, E91, D92, H94, H95, Y96, R97, Q99, I100, R102, and/or V103; V7, V9, T58, A59, G60, E63, Y64, R68, D69, Y71, M72, R73, F78, K88, E91, D92, H94, H95, Y96, R97, Q99, I100, R102, and/or V103; or V9, A59, E63, Y64, R68, D69, M72, R73, F78, K88, E91, D92, H94, H95, Y96, R97, Q99, R102, and/or V103, or amino acids corresponding to such residues, wherein the numbering immediately above is K-Ras amino acid numbering). In some embodiments, a "Switch 2—Binding Pocket" or "S2BP" is a cavity, in the GDP bound form of Ras (e.g. K-Ras), bound (the limits or boundaries of which are made), at least in part, by the amino acid residues that form Switch 2 and the Switch 2 Binding Region which may also include adjacent (e.g., through space in the folded protein structure) amino acid residues (e.g., V9, E63, Y64, R68, M72, H94, Y96, and/or Q99; amino acids binding or contacting 2C07 in FIG. 18, 21A-B, 23A-B, 24, 26A-D, 27A-D, or 28A-C; V7, V9, G10, P34, T58, A59, G60, Q61, E62, E63, Y64, R68, D69, Y71, M72, R73, F78, K88, E91, D92, H94, H95, Y96, R97, Q99, I100, R102, and/or V103; V7, V9, T58, A59, G60, E63, Y64, R68, D69, Y71, M72, R73, F78, K88, E91, D92, H94, H95, Y96, R97, Q99, I100, R102, and/or V103, or amino acids corresponding thereto; A59, Y64, D69, R73, F78, K88, E91, D92, H94, H95, R97, R102, and/or V103, or amino acids corresponding thereto; V9, E63, Y64, R68, M72, H94, Y96, and/or Q99, or amino acids corresponding thereto; or V9, A59, E63, Y64, R68, D69, M72, R73, F78, K88, E91, D92, H94, H95, Y96, R97, Q99, R102, and/or V103, or amino acids corresponding thereto). In embodiments, a "Switch 2—Binding Pocket" or "S2BP" is a cavity, in the GTP bound form of Ras (e.g. K-Ras), bound (the limits or boundaries of which are made), at least in part, by the amino acid residues that form Switch 2 and the Switch 2 Binding Region, which may also include adjacent (e.g., through space in the folded protein structure) amino acid residues (e.g., V9, E63, Y64, R68, M72, H94, Y96, and/or Q99 of K-Ras or amino acid residues corresponding to V9, E63, Y64, R68, M72, H94, Y96, and/or Q99 of K-Ras; amino acids binding or contacting 2C07 in FIG. 18, 21A-B, 23A-B, 24, 26A-E, 27A-D, or 28A-C or amino acid residues corresponding to amino acids binding or contacting 2C07 in FIG. 18, 21A-B, 23A-B, 24, 26A-E, 27A-D, or 28A-C; V7, V9, G10, P34, T58, A59, G60, Q61, E62, E63, Y64, R68, D69, Y71, M72, R73, F78, K88, E91, D92, H94, H95, Y96, R97, Q99, I100, R102, or V103; V7, V9, T58, A59, G60, E63, Y64, R68, D69, Y71, M72, R73, F78, K88, E91, D92, H94, H95, Y96, R97, Q99, I100, R102, and/or V103, or amino acids corresponding thereto; A59, Y64, D69, R73, F78, K88, E91, D92, H94, H95, R97, R102, and/or V103, or amino acids corresponding thereto; V9, E63, Y64, R68, M72, H94, Y96, and/or Q99, or amino acids corresponding thereto; or V9, A59, E63, Y64, R68, D69, M72, R73, F78, K88, E91, D92, H94, H95, Y96, R97, Q99, R102, and/or V103, or amino acids corresponding thereto). In embodiments, the "Switch 2—Binding Pocket" or "S2BP" is a cavity bound (the limits or boundaries of which are made), at least in part, by the amino acid residues binding or contacting 2C07 in FIG. 18, 21A-B, 23A-B, 24, 26A-E, 27A-D, or 28A-C or amino acid residues corresponding to amino acids binding or contacting 2C07 in FIG. 18, 21A-B, 23A-B, 24, 26A-E, 27A-D, or 28A-C). In embodiments, the "Switch 2—Binding Pocket" or "S2BP" is a cavity bound (the limits or boundaries of which are made), at least in part, by the amino acid residues V9, E63, Y64, R68, M72, H94, Y96, and/or Q99 or amino acids corresponding thereto. In embodiments, the "Switch 2—Binding Pocket" or "S2BP" is a cavity bound (the limits or boundaries of which are made), at least in part, by the amino acid residues V7, V9, T58, A59, G60, E63, Y64, R68, D69, Y71, M72, R73, F78, K88, E91, D92, H94, H95, Y96, R97, Q99, I100, R102, and/or V103 (these amino acids may collectively be termed the "Switch 2 Groove") or amino acids corresponding thereto. In embodiments, the "Switch 2—Binding Pocket" or "S2BP" is a cavity bound (the limits or boundaries of which are made), at least in part, by the amino acid residues V7, V9, G10, P34, T58, A59, G60, Q61, E62, E63, Y64, R68, D69, Y71, M72, R73, F78, K88, E91, D92, H94, H95, Y96, R97, Q99, I100, R102, and/or V103 or amino acids corresponding thereto. In embodiments, the "Switch 2—Binding Pocket" or "S2BP" is a cavity bound (the limits or boundaries of which are made), at least in part, by the amino acid residues V9, A59, E63, Y64, R68, D69, M72, R73, F78, K88, E91, D92, H94, H95, Y96, R97, Q99, R102, and/or V103, or amino acids corresponding thereto. In embodiments, the "Switch 2—Binding Pocket" or "S2BP" is a cavity bound (the limits or boundaries of which are made), at least in part, by the amino acid residues A59, Y64, D69, R73, F78, K88, E91, D92, H94, H95, R97, R102, and/or V103 or amino acids corresponding thereto. In embodiments, the "Switch 2—Binding Pocket" or "S2BP" is a cavity bound (the limits or boundaries of which are made), at least in part, by the amino acid residues V9, E63, Y64, R68, M72, H94, Y96, and/or Q99 or amino acids corresponding thereto. In embodiments, the "Switch 2—Binding Pocket" or "S2BP" is a cavity bound (the limits or boundaries of which are made), by the amino acid residues V9, E63, Y64, R68, M72, H94, Y96, and/or Q99 of K-Ras or amino acids corresponding thereto. In embodiments, the "Switch 2—Binding Pocket" or "S2BP" is a cavity bound (the limits or boundaries of which are made), by the amino acid residues V7, V9, T58, A59, G60, E63, Y64, R68, D69, Y71, M72, R73, F78, K88, E91, D92, H94, H95, Y96, R97, Q99, I100, R102, and/or V103 of K-Ras or amino acids corresponding thereto. In embodiments, the "Switch 2—Binding Pocket" or "S2BP" is a cavity bound (the limits or boundaries of which are made), by the amino acid residues V7, V9, G10, P34, T58, A59, G60, Q61, E62, E63, Y64, R68, D69, Y71, M72, R73, F78, K88, E91, D92, H94, H95, Y96, R97, Q99, I100, R102, and/or V103 of K-Ras or amino acids corresponding thereto. In embodiments, the "Switch 2—Binding Pocket" or "S2BP" is a cavity bound (the limits or boundaries of which are made), by the amino acid residues V9, A59, E63, Y64, R68, D69, M72, R73, F78, K88, E91, D92, H94, H95, Y96, R97, Q99, R102, and/or V103 of K-Ras or amino acids corresponding thereto. In embodiments, the "Switch 2—Binding Pocket" or "S2BP" is a cavity bound (the limits or boundaries of which are made), by the amino acid residues A59, Y64, D69, R73, F78, K88, E91, D92, H94, H95, R97, R102, and/or V103 of K-Ras or amino acids corresponding thereto. In embodiments, the "Switch 2—Binding Pocket" or "S2BP" is a cavity bound (the limits or boundaries of which are made), by the amino acid residues V9, E63, Y64, R68, M72, H94, Y96, and/or Q99 of K-Ras or amino acids corresponding thereto. In embodiments, the "Switch 2—Binding Pocket" or "S2BP" is a cavity bound (the limits or boundaries of which are made), at least in part, by the amino acid residues corresponding to V9, E63, Y64, R68, M72, H94, Y96, and/or Q99 of K-Ras. In embodiments, the "Switch 2—Binding Pocket" or "S2BP" is a cavity bound (the limits or boundaries of which are made), at least in part, by the amino acid residues corresponding to V7, V9, T58, A59, G60, E63, Y64, R68, D69, Y71, M72, R73, F78, K88, E91, D92, H94, H95, Y96, R97, Q99, I100, R102, and/or V103 of K-Ras. In embodiments, the "Switch 2—Binding Pocket" or "S2BP" is a cavity bound (the limits or boundaries of which are made), at least in part, by the amino acid residues corresponding to V7, V9, G10, P34, T58, A59, G60, Q61, E62, E63, Y64, R68, D69, Y71, M72, R73, F78, K88, E91, D92, H94, H95, Y96, R97, Q99, I100, R102, and/or V103 of K-Ras. In embodiments, the "Switch 2—Binding Pocket" or "S2BP" is a cavity bound (the limits or boundaries of which are made), at least in part, by the amino acid residues corresponding to V9, A59, E63, Y64, R68, D69, M72, R73, F78, K88, E91, D92, H94, H95, Y96, R97, Q99, R102, and/or V103 of K-Ras. In embodiments, the "Switch 2—Binding Pocket" or "S2BP" is a cavity bound (the limits or boundaries of which are made), at least in part, by the amino acid residues corresponding to A59, Y64, D69, R73, F78, K88, E91, D92, H94, H95, R97, R102, and/or V103 of K-Ras. In embodiments, the "Switch 2—Binding Pocket" or "S2BP" is a cavity bound (the limits or boundaries of which are made), at least in part, by the amino acid residues corresponding to V9, E63, Y64, R68, M72, H94, Y96, and/or Q99 of K-Ras.

In some embodiments, the Switch 2—Binding Pocket is bound at least in part by one or more of V7, V9, G10, P34, T58, G60, Q61, E62, E63, Y64, R68, Y71, M72, H94, Y96, Q99, and/or I100 of K-Ras or equivalent residues in homologous, related (e.g. H-Ras, N-Ras), or mutant Ras proteins. In some embodiments, the Switch 2—Binding Pocket is bound at least in part by one or more of V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 of K-Ras or equivalent residues in homologous, related (e.g. H-Ras, N-Ras), or mutant Ras proteins. In some embodiments, the Switch 2—Binding Pocket is bound at least in part by one or more of V9, A59, E63, Y64, R68, D69, M72, R73, F78, K88, E91, D92, H94, H95, Y96, R97, Q99, R102, or V103 of K-Ras or equivalent residues in homologous, related (e.g. H-Ras, N-Ras), or mutant Ras proteins. In some embodiments, the Switch 2—Binding Pocket is bound at least in part by one or more of V9, E63, Y64, R68, M72, H94, Y96, and/or Q99 of K-Ras or equivalent residues in homologous, related (e.g. H-Ras, N-Ras), or mutant Ras proteins. In some embodiments, the Switch 2—Binding Pocket is bound at least in part by one or more of V7, V9, T58, A59, G60, E63, Y64, R68, D69, Y71, M72, R73, F78, K88, E91, D92, H94, H95, Y96, R97, Q99, I100, R102, or V103 of K-Ras or equivalent residues in homologous, related (e.g. H-Ras, N-Ras), or mutant Ras proteins. In some embodiments, the Switch 2—Binding Pocket is bound at least in part by one or more of V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 of K-Ras or equivalent residues in homologous, related (e.g. H-Ras, N-Ras), or mutant Ras proteins. In some embodiments, the Switch 2—Binding Pocket is bound at least in part by one or more of V9, A59, E63, Y64, R68, D69, M72, R73, F78, K88, E91, D92, H94, H95, Y96, R97, Q99, R102, and/or V103, of K-Ras or equivalent residues in homologous, related (e.g. H-Ras, N-Ras), or mutant Ras proteins. In some embodiments, the Switch 2—Binding Pocket is bound at least in part by one or more of A59, Y64, D69, R73, F78, K88, E91, D92, H94, H95, Y96, R97, R102, or V103 of K-Ras or equivalent residues in homologous, related (e.g. H-Ras, N-Ras), or mutant Ras proteins. In some embodiments, the Switch 2—Binding Pocket is bound at least in part by one or more of V9, E63, Y64, R68, M72, H94, Y96, or Q99 of K-Ras or equivalent residues in homologous, related (e.g. H-Ras, N-Ras), or mutant Ras proteins. A compound as described herein, which binds to amino acids that form or contacts amino acids that form the Switch 2—Binding Pocket is a "Switch 2—Binding Pocket binding compound" and a moiety of a compound that binds to amino acids that form or contacts amino acids that form the Switch 2—Binding Pocket is a "Switch 2—Binding Pocket binding moiety". A compound as described herein, which binds to amino acids that form or contacts amino acids that form the Switch 2 Groove is a "Switch 2 Groove binding compound" and a moiety of a compound that binds to amino acids that form or contacts amino acids that form the Switch 2 Groove is a "Switch 2 Groove binding moiety".

In some embodiments, a Switch 2—Binding Pocket binding compound or Switch 2—Binding Pocket binding moiety binds or contacts at least one amino acid that forms the Switch 2—Binding Pocket. In some embodiments, a Switch 2—Binding Pocket binding compound or Switch 2—Binding Pocket binding moiety binds or contacts multiple amino acids that form the Switch 2—Binding Pocket. In some embodiments, a Switch 2 Groove binding compound or Switch 2 Groove binding moiety binds or contacts at least one amino acid that forms the Switch 2 Groove. In some embodiments, a Switch 2 Groove binding compound or Switch 2 Groove binding moiety binds or contacts multiple amino acids that form the Switch 2 Groove.

In some embodiments, a Switch 2—Binding Pocket binding compound or Switch 2—Binding Pocket binding moiety binds or contacts at least one K-Ras amino acid selected from V7, V9, G10, P34, T58, G60, Q61, E62, E63, Y64, R68, Y71, M72, H94, Y96, Q99, and I100 or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, 13, 14, or 15) K-Ras amino acids selected from V7, V9, G10, P34, T58, G60, Q61, E62, E63, Y64, R68, Y71, M72, H94, Y96, Q99, and I100 or amino acids corresponding thereto. In some embodiments, a Switch 2—Binding Pocket binding compound or Switch 2—Binding Pocket binding moiety binds or contacts one K-Ras amino acid selected from V9, E63, Y64, R68, M72, H94, Y96, and Q99 or amino acids corresponding thereto. In some embodiments, a Switch 2—Binding Pocket binding compound or Switch 2—Binding Pocket binding moiety binds or contacts multiple (e.g., 2, 3, 4, 5, 6, 7, or 8) K-Ras amino acids selected from V9, E63, Y64, R68, M72, H94, Y96, and Q99 or amino acids corresponding thereto. In some embodiments, a Switch 2—Binding Pocket binding compound or Switch 2—Binding Pocket binding moiety binds or contacts at least one K-Ras amino acid selected from V7, V9, T58, A59, G60, E63, Y64, R68, D69, Y71, M72, R73, F78, K88, E91, D92, H94, H95, Y96, R97, Q99, I100, R102, and V103 or amino acids corresponding thereto. In some embodiments, a Switch 2—Binding Pocket binding compound or Switch 2—Binding Pocket binding moiety binds or contacts at least one K-Ras amino acid selected from V7, V9, G10, P34, T58, A59, G60, Q61, E62, E63, Y64, R68, D69, Y71, M72, R73, F78, K88, E91, D92, H94, H95, Y96, R97, Q99, I100, R102, and V103 or amino acids corresponding thereto. In some embodiments, a Switch 2—Binding Pocket binding compound or Switch 2—Binding Pocket binding moiety binds or contacts at least one K-Ras amino acid selected from V9, A59, E63, Y64, R68, D69, M72, R73, F78, K88, E91, D92, H94, H95, Y96, R97, Q99, R102, and V103, or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, 13, 14, 15, 16, 17, 18, 19, 20, 21, 22, 23, or 24) K-Ras amino acids selected from V7, V9, T58, A59, G60, E63, Y64, R68, D69, Y71, M72, R73, F78, K88, E91, D92, H94, H95, Y96, R97, Q99, I100, R102, and V103 or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, 13, 14, 15, 16, 17, 18, 19, 20, 21, 22, 23, 24, 25, 26, 27, or 28) K-Ras amino acids selected from V7, V9, G10, P34, T58, A59, G60, Q61, E62, E63, Y64, R68, D69, Y71, M72, R73, F78, K88, E91, D92, H94, H95, Y96, R97, Q99, I100, R102, and V103 or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, 13, 14, 15, 16, 17, 18, or 19) K-Ras amino acids selected from V9, A59, E63, Y64, R68, D69, M72, R73, F78, K88, E91, D92, H94, H95, Y96, R97, Q99, R102, and V103, or amino acids corresponding thereto. In some embodiments, a Switch 2—Binding Pocket binding compound or Switch 2—Binding Pocket binding moiety binds or contacts at least one K-Ras amino acid selected from A59, Y64, D69, R73, F78, K88, E91, D92, H94, H95, R97, R102, or V103 or amino acids corresponding thereto. In some embodiments, a Switch 2—Binding Pocket binding compound or Switch 2—Binding Pocket binding moiety binds or contacts multiple (e.g., 2, 3, 4, 5, 6, 7, 8, 9, 10, 11, 12, or 13) K-Ras amino acids selected from A59, Y64, D69, R73, F78, K88, E91, D92, H94, H95, R97, R102, or V103 or amino acids corresponding thereto.

In some embodiments, a Switch 2—Binding Pocket binding compound or Switch 2—Binding Pocket binding moiety binds or contacts at least one amino acid selected from amino acids in a mutant K-Ras, related Ras (H-Ras, N-Ras), or homolog of K-Ras corresponding to K-Ras residues V7, V9, G10, P34, T58, G60, Q61, E62, E63, Y64, R68, Y71, M72, H94, Y96, Q99, and I100 or amino acids corresponding thereto. In some embodiments, a Switch 2—Binding Pocket binding compound or Switch 2—Binding Pocket binding moiety binds or contacts multiple (e.g., 2, 3, 4, 5, 6, 7, 8, 9, 10, 11, 12, 13, 14, or 15) K-Ras amino acids selected from amino acids in a mutant K-Ras, related Ras (H-Ras, N-Ras), or homolog of K-Ras corresponding to K-Ras residues V7, V9, G10, P34, T58, G60, Q61, E62, E63, Y64, R68, Y71, M72, H94, Y96, Q99, and I100 or amino acids corresponding thereto. In some embodiments, a Switch 2—Binding Pocket binding compound or Switch 2—Binding Pocket binding moiety binds or contacts one amino acid selected from amino acids in a mutant K-Ras, related Ras (H-Ras, N-Ras), or homolog of K-Ras corresponding to K-Ras residues V9, E63, Y64, R68, M72, H94, Y96, and Q99 or amino acids corresponding thereto. In some embodiments, a Switch 2—Binding Pocket binding compound or Switch 2—Binding Pocket binding moiety binds or contacts multiple (e.g, 2, 3, 4, 5, 6, 7, or 8) K-Ras amino acids selected from amino acids in a mutant K-Ras, related Ras (H-Ras, N-Ras), or homolog of K-Ras corresponding to K-Ras residues V9, E63, Y64, R68, M72, H94, Y96, and Q99 or amino acids corresponding thereto. In some embodiments, a Switch 2—Binding Pocket binding compound or Switch 2—Binding Pocket binding moiety binds or contacts at least one amino acid selected from amino acids in a mutant K-Ras, related Ras (H-Ras, N-Ras), or homolog of K-Ras corresponding to K-Ras residues V7, V9, T58, A59, G60, E63, Y64, R68, D69, Y71, M72, R73, F78, K88, E91, D92, H94, H95, Y96, R97, Q99, I100, R102, or V103 or amino acids corresponding thereto. In some embodiments, a Switch 2—Binding Pocket binding compound or Switch 2—Binding Pocket binding moiety binds or contacts at least one amino acid selected from amino acids in a mutant K-Ras, related Ras (H-Ras, N-Ras), or homolog of K-Ras corresponding to K-Ras residues V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 or amino acids corresponding thereto. In some embodiments, a Switch 2—Binding Pocket binding compound or Switch 2—Binding Pocket binding moiety binds or contacts at least one amino acid selected from amino acids in a mutant K-Ras, related Ras (H-Ras, N-Ras), or homolog of K-Ras corresponding to K-Ras residues V9, A59, E63, Y64, R68, D69, M72, R73, F78, K88, E91, D92, H94, H95, Y96, R97, Q99, R102, or V103, or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, 13, 14, 15, 16, 17, 18, 19, 20, 21, 22, 23, or 24) K-Ras amino acids selected from amino acids in a mutant K-Ras, related Ras (H-Ras, N-Ras), or homolog of K-Ras corresponding to K-Ras residues V7, V9, T58, A59, G60, E63, Y64, R68, D69, Y71, M72, R73, F78, K88, E91, D92, H94, H95, Y96, R97, Q99, I100, R102, or V103 or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, 13, 14, 15, 16, 17, 18, 19, 20, 21, 22, 23, 24, 25, 26, 27, or 28) K-Ras amino acids selected from amino acids in a mutant K-Ras, related Ras (H-Ras, N-Ras), or homolog of K-Ras corresponding to K-Ras residues V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, 13, 14, 15, 16, 17, 18, or 19) K-Ras amino acids selected from amino acids in a mutant K-Ras, related Ras (H-Ras, N-Ras), or homolog of K-Ras corresponding to K-Ras residues V9, A59, E63, Y64, R68, D69, M72, R73, F78, K88, E91, D92, H94, H95, Y96, R97, Q99, R102, or V103, or amino acids corresponding thereto. In some embodiments, a Switch 2—Binding Pocket binding compound or Switch 2—Binding Pocket binding moiety binds or contacts at least one amino acid selected from amino acids in a mutant K-Ras, related Ras (H-Ras, N-Ras), or homolog of K-Ras corresponding to K-Ras residues A59, Y64, D69, R73, F78, K88, E91, D92, H94, H95, R97, R102, or V103 or amino acids corresponding thereto. In some embodiments, a Switch 2—Binding Pocket binding compound or Switch 2—Binding Pocket binding moiety binds or contacts multiple (e.g, 2, 3, 4, 5, 6, 7, 8, 9, 10, 11, 12, or 13) K-Ras amino acids selected from amino acids in a mutant K-Ras, related Ras (H-Ras, N-Ras), or homolog of K-Ras corresponding to K-Ras residues A59, Y64, D69, R73, F78, K88, E91, D92, H94, H95, R97, R102, or V103 or amino acids corresponding thereto.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

II. Compounds

In a first aspect is provided a compound (e.g., Switch 2—Binding Pocket binding compound, Switch 2 Groove binding compound) which is capable of binding an amino acid residue of a Ras protein (e.g., K-Ras, N-Ras, H-Ras, human K-Ras, human N-Ras and/or human H-Ras protein). In embodiments, the compound may contact a residue of a Ras protein Switch 2 binding pocket. In embodiments, the compound (e.g., Switch 2—Binding Pocket binding compound, Switch 2 Groove binding compound) is capable of binding a plurality of amino acid residues of a Ras protein (e.g., K-Ras, N-Ras, H-Ras, human K-Ras, human N-Ras and/or human H-Ras protein). In embodiments, the compound may contact a plurality of residues of a Ras protein Switch 2 binding pocket. In embodiments, the residue of the Switch 2 binding pocket that contacts the compound may be V7, V9, G10, P34, T58, G60, Q61, E62, E63, Y64, R68, Y71, M72, H94, Y96, Q99, or I100 or amino acids corresponding thereto. In embodiments, the residue of the Switch 2 binding pocket that contacts the compound may be V7, V9, T58, A59, G60, E63, Y64, R68, D69, Y71, M72, R73, F78, K88, E91, D92, H94, H95, Y96, R97, Q99, I100, R102, or V103 or amino acids corresponding thereto. In embodiments, the residue of the Switch 2 binding pocket that contacts the compound may be V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 or amino acids corresponding thereto. In embodiments, the residue of the Switch 2 binding pocket that contacts the compound may be V9, A59, E63, Y64, R68, D69, M72, R73, F78, K88, E91, D92, H94, H95, Y96, R97, Q99, R102, or V103, or amino acids corresponding thereto. In embodiments, the residue of the Switch 2 binding pocket that contacts the compound may be A59, Y64, D69, R73, F78, K88, E91, D92, H94, H95, R97, R102, or V103 or amino acids corresponding thereto. In embodiments, the residue of the Switch 2 binding pocket that contacts the compound may be V9, E63, Y64, R68, M72, H94, Y96, or Q99 or amino acids corresponding thereto. In embodiments, the residue of the Switch 2 binding pocket that contacts the compound may be V7, V9, G10, P34, T58, G60, Q61, E62, E63, R68, Y71, M72, Y96, Q99, or I100 or amino acids corresponding thereto. In embodiments, the residue of the Switch 2 binding pocket that contacts the compound may be V9, E63, Y64, R68, M72, H94, Y96, or Q99 or amino acids corresponding thereto. In some embodiments, the compound contacts at least one of V7, V9, T58, A59, G60, E63, Y64, R68, D69, Y71, M72, R73, F78, K88, E91, D92, H94, H95, Y96, R97, Q99, I100, R102, or V103 or amino acids corresponding thereto. In some embodiments, the compound contacts at least one of V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 or amino acids corresponding thereto. In some embodiments, the compound contacts at least one of V9, A59, E63, Y64, R68, D69, M72, R73, F78, K88, E91, D92, H94, H95, Y96, R97, Q99, R102, or V103, or amino acids corresponding thereto. In some embodiments, the compound contacts at least one of A59, Y64, D69, R73, F78, K88, E91, D92, H94, H95, R97, R102, or V103 or amino acids corresponding thereto. In some embodiments, the compound contacts at least one of V9, E63, Y64, R68, M72, H94, Y96, or Q99 or amino acids corresponding thereto. In some embodiments, the compound contacts at least one of V9, E63, Y64, R68, M72, H94, Y96, or Q99 or amino acids corresponding thereto. In some embodiments, the compound contacts at least one of Y64 and H94 or amino acids corresponding thereto. In some embodiments, the compound contacts at least one of G60, E62, or E63 or amino acids corresponding thereto. In embodiments, the compound is a Ras modulator (e.g., Ras inhibitor, K-Ras modulator, H-Ras modulator, K-Ras inhibitor, H-Ras inhibitor, human Ras modulator, human Ras inhibitor, human K-Ras modulator, human H-Ras modulator, human K-Ras inhibitor, or human H-Ras inhibitor). The amino acid numbering used above is human K-Ras amino acid numbering.

In some embodiments, the compound covalently reacts with an amino acid residue of the Ras protein to form a covalent bond (e.g. reversible or irreversible). For example the amino acid residue is a cysteine, aspartate, lysine, tyrosine or glutamate residue of the Ras protein. In some embodiments, the amino acid residue is a cysteine residue, for example a G12C or G13C residue of a K-Ras protein. In some embodiments, the amino acid residue is an aspartate residue, for example a G12D or G13D residue of a K-Ras protein.

In an aspect, is provided a novel Ras modulator (e.g., Ras inhibitor, K-Ras modulator, H-Ras modulator, K-Ras inhibitor, H-Ras inhibitor, human Ras modulator, human Ras inhibitor, human K-Ras modulator, human H-Ras modulator, human K-Ras inhibitor, or human H-Ras inhibitor). The Ras modulator may be a Switch 2—Binding Pocket binding compound or a compound described herein. The Ras modulator may be a Switch 2 Groove binding compound or a compound described herein. The Switch 2—Binding Pocket binding compounds of the present disclosure are compounds containing a Switch 2—Binding Pocket binding moiety. In embodiments, the compound may contact a residue of a Ras protein Switch 2 binding pocket. In embodiments, the residue of the Switch 2 binding pocket that contacts the compound may be V7, V9, T58, A59, G60, E63, Y64, R68, D69, Y71, M72, R73, F78, K88, E91, D92, H94, H95, Y96, R97, Q99, I100, R102, or V103 or amino acids corresponding thereto. In embodiments, the residue of the Switch 2 binding pocket that contacts the compound may be V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 or amino acids corresponding thereto. In embodiments, the residue of the Switch 2 binding pocket that contacts the compound may be V9, A59, E63, Y64, R68, D69, M72, R73, F78, K88, E91, D92, H94, H95, Y96, R97, Q99, R102, or V103, or amino acids corresponding thereto. In embodiments, the residue of the Switch 2 binding pocket that contacts the compound may be A59, Y64, D69, R73, F78, K88, E91, D92, H94, H95, R97, R102, or V103 or amino acids corresponding thereto. In embodiments, the residue of the Switch 2 binding pocket that contacts the compound may be V9, E63, Y64, R68, M72, H94, Y96, or Q99 or amino acids corresponding thereto. In embodiments, the residue of the Switch 2 binding pocket that contacts the compound may be V7, V9, G10, P34, T58, G60, Q61, E62, E63, Y64, R68, Y71, M72, H94, Y96, Q99, or I100 or amino acids corresponding thereto. In embodiments, the residue of the Switch 2 binding pocket that contacts the compound may be V7, V9, G10, P34, T58, G60, Q61, E62, E63, R68, Y71, M72, Y96, Q99, or I100 or amino acids corresponding thereto. In embodiments, the residue of the Switch 2 binding pocket that contacts the compound may be V9, E63, Y64, R68, M72, H94, Y96, or Q99 or amino acids corresponding thereto. In some embodiments, the compound contacts at least one of V9, E63, Y64, R68, M72, H94, Y96, or Q99 or amino acids corresponding thereto. In some embodiments, the compound contacts at least one of Y64 and H94 or amino acids corresponding thereto. In some embodiments, the compound contacts at least one of G60, E62, or E63 or amino acids corresponding thereto. In some embodiments, the compound contacts at least one of V7, V9, T58, A59, G60, E63, Y64, R68, D69, Y71, M72, R73, F78, K88, E91, D92, H94, H95, Y96, R97, Q99, I100, R102, or V103 or amino acids corresponding thereto. In some embodiments, the compound contacts at least one of V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 or amino acids corresponding thereto. In some embodiments, the compound contacts at least one of V9, A59, E63, Y64, R68, D69, M72, R73, F78, K88, E91, D92, H94, H95, Y96, R97, Q99, R102, or V103, or amino acids corresponding thereto. In some embodiments, the compound contacts at least one of A59, Y64, D69, R73, F78, K88, E91, D92, H94, H95, R97, R102, or V103 or amino acids corresponding thereto. In some embodiments, the compound contacts at least one of V9, E63, Y64, R68, M72, H94, Y96, or Q99 or amino acids corresponding thereto. The amino acid numbering used above is human K-Ras amino acid numbering.

The Switch 2—Binding Pocket binding moiety is a substituent which, upon contacting a Switch 2—Binding Pocket, fills space within the corresponding Switch 2—Binding Pocket. In some embodiments, the Switch 2—Binding Pocket binding moiety displaces at least one water molecule within the Switch 2—Binding Pocket. The Switch 2—Binding Pocket binding moiety may also contact one or more amino acids that from part of the Switch 2—Binding Pocket. A description of the Switch 2—Binding Pocket and methods of determining whether a substituent fills space within the Switch 2—Binding Pocket are set forth herein.

In an aspect is provided a compound having the formula:

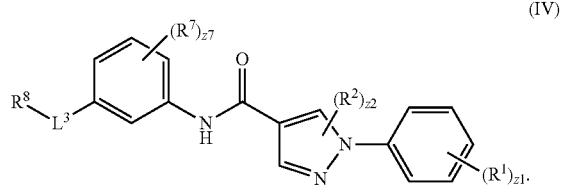

(IV)

$R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl$R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is independently halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —$C(O)$—$OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^7$ substituents may optionally be joined to form a substituted or unsubstituted cycloalkyl, substituted or unsubstituted heterocycloalkyl, substituted or unsubstituted aryl, or substituted or unsubstituted heteroaryl. $R^8$ is independently hydrogen, halogen, —$CX^8_3$, —$CHX^8_2$, —$CH_2X^8$, —$OCX^8_3$, —$OCH_2X^8$, —$OCHX^8_2$, —CN, —$SO_{n8}R^{8D}$, —$SO_{v8}NR^{8A}R^{8B}$, —$NHC(O)NR^{8A}R^{8B}$, —$N(O)_ms$, —$NR^{8A}R^{8B}$, —$C(O)R^{8C}$, —$C(O)$—$OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^3$ is a bond, —N(H)—, —O—, —S—, —C(O)—, —C(O)N(H)—, —N(H)C(O)—, —N(H)C(O)NH—, —C(O)O—, —OC(O)—, substituted or unsubstituted alkylene, or substituted or unsubstituted heteroalkylene. E is an electrophilic moiety.

Each $R^{1A}$, $R^{1B}$, $R^{1C}$, $R^{1D}$, $R^{2A}$, $R^{2B}$, $R^{2C}$, $R^{2D}$, $R^{7A}$, $R^{7B}$, $R^{7C}$, $R^{7D}$, $R^{8A}$, $R^{8B}$ $R^{8C}$, and $R^{8D}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{8A}$ and $R^{8B}$ substituents bonded to the same nitrogen atom may optionally be joined to form a substituted or unsubstituted heterocycloalkyl or substituted or unsubstituted heteroaryl. z1 is an integer from 0 to 5. z2 is an integer from 0 to 3. z7 is an integer from 0 to 4. Each X, $X^1$, $X^2$, $X^7$, and $X^8$ is independently $-F$, $-Cl$, $-Br$, or $-I$. n1, n2, n7, and n8 are independently an integer from 0 to 4. m1, m2, m7, m8, v1, v2, v7, and v8 are independently 1 or 2.

In embodiments, the compound has the formula:

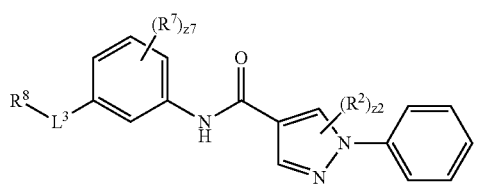

wherein $L^3$, z7, z2, $R^2$, and $R^8$ are as described herein, including embodiments. In embodiments, the compound has the formula:

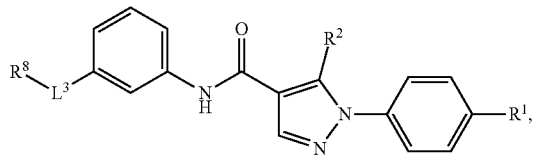

(IVa)

wherein $R^8$, $L^3$, $R^2$, and $R^1$ are as described herein, including embodiments.

In embodiments, the compound has the formula:

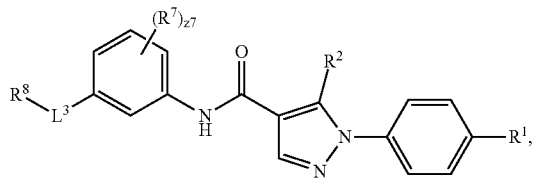

(IVb)

wherein $R^8$, $L^3$, $R^7$, z7, $R^2$, and $R^1$ are as described herein, including embodiments.

In embodiments, the compound has the formula:

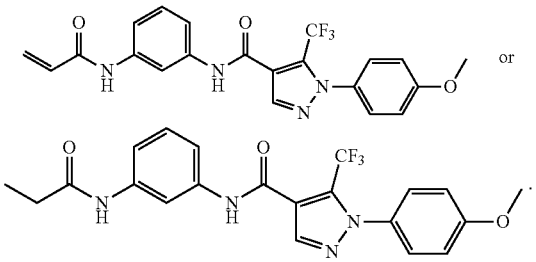

or

In embodiments, the compound has the formula:

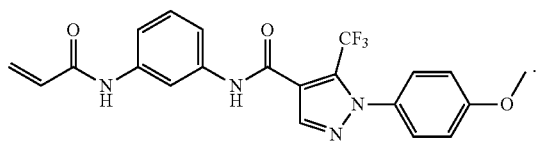 [SMILES: C=CC(=O)Nc1cccc(NC(=O)c2cnn(-c3ccc(OC)cc3)c2C(F)(F)F)c1]

In embodiments, the compound has the formula:

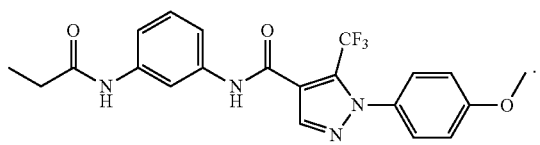 [SMILES: CCC(=O)Nc1cccc(NC(=O)c2cnn(-c3ccc(OC)cc3)c2C(F)(F)F)c1]

In embodiments, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^1$ is independently halogen, $-CX^1_3$, $-CHX^1_2$, $-CH_2X^1$, $-OCX^1_3$, $-OCH_2X^1$, $-OCHX^1_2$, substituted or unsubstituted alkyl, or substituted or unsubstituted heteroalkyl. In embodiments, $R^1$ is independently halogen, $-CX^1_3$, $-CHX^1_2$, $-CH_2X^1$, $-OCX^1_3$, $-OCH_2X^1$, $-OCHX^1_2$, substituted or unsubstituted ($C_1$-$C_4$) alkyl, or substituted or unsubstituted 2 to 4 membered heteroalkyl. In embodiments, $R^1$ is halogen, $-CH_3$, $-CH_2CH_3$, $-CX^1_3$, $-CHX^1_2$, $-CH_2X^1$, $-OCH_3$, $-OCX^1_3$, $-OCH_2X^1$, $-OCHX^1_2$, $-SCH_3$, $-SCX^1_3$, $-SCH_2X^1$, or $-SCHX^1_2$. In embodiments, $R^1$ is halogen, $-CH_3$, $-CH_2CH_3$, $-CF_3$, or $-OCH_3$. In embodiments, $R^1$ is $-CH_3$, $-CH_2CH_3$, or $-OCH_3$. In embodiments, $R^1$ is $-OCH_3$. In embodiments, $R^1$ is independently halogen, $-CX^1_3$, $-CHX^1_2$, $-CH_2X^1$, $-OCX^1_3$, $-OCH_2X^1$, $-OCHX^1_2$, $-CN$, substituted or unsubstituted alkyl, or substituted or unsubstituted heteroalkyl. In embodiments, $R^1$ is independently halogen, $-CX^1_3$, $-CHX^1_2$, $-CH_2X^1$, $-OCX^1_3$, $-OCH_2X^1$, $-OCHX^1_2$, $-CN$, substituted or unsubstituted ($C_1$-$C_4$) alkyl, or substituted or unsubstituted 2 to 4 membered heteroalkyl. In embodiments, $R^1$ is halogen, $-CH_3$, $-CH_2CH_3$, $-CX^1_3$, $-CHX^1_2$, $-CH_2X^1$, $-OCH_3$, $-OCX^1_3$, $-OCH_2X^1$, $-OCHX^1_2$, $-CN$, $-SCH_3$, $-SCX^1_3$, $-SCH_2X^1$, or $-SCHX^1_2$. In embodiments, $R^1$ is halogen, $-CN$, $-CH_3$, $-CF_3$, or $-OCH_3$. In embodiments, $R^1$ is halogen or $-CH_3$. In embodiments, $R^1$ is $-Cl$ or $-CH_3$. In embodiments, $R^1$ is $-CH_3$. In embodiments, $R^1$ is $-CH_3$ or $-CH_2CH_3$.

In embodiments, $R^1$ is independently halogen, $-CX^1_3$, $-CN$, $-OH$, $-NH_2$, $-SH$, $-OCX^1_3$, $-OCHX^1_2$, $-OCH_2X^1$, $-CHX^1_2$, $-CH_2X^1$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently halogen, $-CX^1_3$, $-CN$, $-OH$, $-NH_2$, $-SH$, $-OCX^1_3$, $-OCHX^1_2$, $-OCH_2X^1$, $-CHX^1_2$, $-CH_2X^1$, unsubstituted $C_1$-$C_4$ alkyl, or unsubstituted 2 to 4 membered heteroalkyl. In embodiments, $R^1$ is independently halogen. In embodiments, $R^1$ is independently $-CX^{13}$. In embodiments, $R^1$ is independently $-CHX^1_2$. In embodiments, $R^1$ is independently $-CH_2X^1$. In embodiments, $R^1$ is independently $-OCX^{13}$. In embodiments, $R^1$ is independently $-OCH_2X^1$. In embodiments, $R^1$ is independently $-OCHX^1_2$. In embodiments, $R^1$ is independently $-CN$. In embodiments, $R^1$ is independently $-SO_{n1}R^{1D}$. In embodiments, $R^1$ is independently $-SO_{v1}NR^{1A}R^{1B}$. In embodiments, $R^1$ is independently $-NHC(O)NR^{1A}R^{1B}$. In embodiments, $R^1$ is independently $-N(O)_{m1}$. In embodiments, $R^1$ is independently $-NR^{1A}R^{1B}$. In embodiments, $R^1$ is independently $-C(O)R^{1C}$. In embodiments, $R^1$ is independently $-C(O)-OR^{1C}$. In embodiments, $R^1$ is independently $-C(O)NR^{1A}R^{1B}$. In embodiments, $R^1$ is independently $-OR^{1D}$. In embodiments, $R^1$ is independently $-SR^{1D}$. In embodiments, $R^1$ is independently $-NR^{1A}SO_2R^{1D}$. In embodiments, $R^1$ is independently $-NR^{1A}C(O)R^{1C}$. In embodiments, $R^1$ is independently $-NR^{1A}C(O)OR^{1C}$. In embodiments, $R^1$ is independently $-NR^{1A}OR^{1C}$. In embodiments, $R^1$ is independently $-OH$. In embodiments, $R^1$ is independently $-NH_2$. In embodiments, $R^1$ is independently $-COOH$. In embodiments, $R^1$ is independently $-CONH_2$. In embodiments, $R^1$ is independently $-NO_2$. In embodiments, $R^1$ is independently $-SH$. In embodiments, $R^1$ is independently $-CF_3$. In embodiments, $R^1$ is independently $-CHF_2$. In embodiments, $R^1$ is independently $-CH_2F$. In embodiments, $R^1$ is independently $-OCF_3$. In embodiments, $R^1$ is independently $-OCH_2F$. In embodiments, $R^1$ is independently $-OCHF_2$. In embodiments, $R^1$ is independently $-OCH_3$. In embodiments, $R^1$ is independently $-OCH_2CH_3$. In embodiments, $R^1$ is independently $-OCH_2CH_2CH_3$. In embodiments, $R^1$ is independently $-OCH(CH_3)_2$. In embodiments, $R^1$ is independently $-OC(CH_3)_3$. In embodiments, $R^1$ is independently $-SCH_3$. In embodiments, $R^1$ is independently $-SCH_2CH_3$. In embodiments, $R^1$ is independently $-SCH_2CH_2CH_3$. In embodiments, $R^1$ is independently $-SCH(CH_3)_2$. In embodiments, $R^1$ is independently $-SC(CH_3)_3$. In embodiments, $R^1$ is independently $-CH_3$. In embodiments, $R^1$ is independently $-CH_2CH_3$. In embodiments, $R^1$ is independently $-CH_2CH_2CH_3$. In embodiments, $R^1$ is independently $-CH(CH_3)_2$. In embodiments, $R^1$ is independently $-C(CH_3)_3$. In embodiments, $R^1$ is independently $-F$. In embodiments, $R^1$ is independently $-Cl$. In embodiments, $R^1$ is independently $-Br$. In embodiments, $R^1$ is independently $-I$. In embodiments, $X^1$ is independently $-F$. In embodiments, $X^1$ is independently $-Cl$. In embodiments, $X^1$ is independently $-Br$. In embodiments, $X^1$ is independently $-I$.

In embodiments, $R^1$ is independently substituted or unsubstituted alkyl (e.g., $C_1$-$C_8$, $C_1$-$C_6$, $C_1$-$C_4$, or $C_1$-$C_2$). In embodiments, $R^1$ is independently substituted alkyl (e.g., $C_1$-$C_8$, $C_1$-$C_6$, $C_1$-$C_4$, or $C_1$-$C_2$). In embodiments, $R^1$ is independently unsubstituted alkyl (e.g., $C_1$-$C_8$, $C_1$-$C_6$, $C_1$-$C_4$, or $C_1$-$C_2$). In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted isopropyl. In embodiments, $R^1$ is independently unsubstituted tert-butyl. In embodiments, $R^1$ is independently substituted or unsubstituted heteroalkyl (e.g., 2 to 8 membered, 2 to 6 membered, 4 to 6 membered, 2 to 3 membered, or 4 to 5 membered). In embodiments, $R^1$ is independently substituted heteroalkyl (e.g., 2 to 8 membered, 2 to 6 membered, 4 to 6 membered, 2 to 3 membered, or 4 to 5 membered). In embodiments, $R^1$ is independently unsubstituted heteroalkyl (e.g., 2 to 8 membered, 2 to 6 membered, 4 to 6 membered, 2 to 3 membered, or 4 to 5 membered). In embodiments, $R^1$ is independently substituted or unsubstituted cycloalkyl (e.g., $C_3$-$C_8$, $C_3$-$C_6$, $C_4$-$C_6$, or $C_5$-$C_6$). In embodiments, $R^1$ is independently substituted cycloalkyl (e.g., $C_3$-$C_8$, $C_3$-$C_6$, $C_4$-$C_6$, or $C_5$-$C_6$). In embodiments, $R^1$ is independently unsubstituted cycloalkyl (e.g., $C_3$-$C_8$, $C_3$-$C_6$, $C_4$-$C_6$, or $C_5$-$C_6$). In embodiments, $R^1$ is independently substituted or unsubstituted heterocycloalkyl (e.g., 3 to 8 membered, 3 to 6 membered, 4 to 6 membered, 4 to 5 membered, or 5 to 6 membered). In embodiments, $R^1$ is independently substituted heterocycloalkyl (e.g., 3 to 8 membered, 3 to 6 membered, 4 to 6 membered, 4 to 5 membered, or 5 to 6 membered). In embodiments, $R^1$ is independently unsubstituted heterocycloalkyl (e.g., 3 to 8 membered, 3 to 6 membered, 4 to 6 membered, 4 to 5 membered, or 5 to 6 membered). In embodiments, $R^1$ is independently substituted or unsubstituted aryl (e.g., $C_6$-$C_{10}$ or phenyl). In embodiments, $R^1$ is independently substituted aryl (e.g., $C_6$-$C_{10}$ or phenyl). In embodiments, $R^1$ is independently unsubstituted aryl (e.g., $C_6$-$C_{10}$ or phenyl). In embodiments, $R^1$ is independently substituted or unsubstituted heteroaryl (e.g., 5 to 10 membered, 5 to 9 membered, or 5 to 6 membered). In embodiments, $R^1$ is independently substituted heteroaryl (e.g., 5 to 10 membered, 5 to 9 membered, or 5 to 6 membered). In embodiments, $R^1$ is independently unsubstituted heteroaryl (e.g., 5 to 10 membered, 5 to 9 membered, or 5 to 6 membered).

In embodiments, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_m$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, or substituted or unsubstituted heteroalkyl.

In embodiments, $R^1$ is independently $-OR^{1D}$, substituted or unsubstituted alkyl, or substituted or unsubstituted heteroalkyl. In embodiments, $R^1$ is independently $-OR^{1D}$, wherein $R^{1D}$ is substituted or unsubstituted alkyl. In embodiments, $R^1$ is independently $-OR^{1D}$, wherein $R^{1D}$ is substituted or unsubstituted $C_1$-$C_6$ alkyl. In embodiments, $R^1$ is independently $-OR^{1D}$, wherein $R^{1D}$ is substituted or unsubstituted $C_1$-$C_4$ alkyl. In embodiments, $R^1$ is independently —OR$^{1D}$, wherein R$^{1D}$ is unsubstituted C$_1$-C$_4$ alkyl. In embodiments, R$^1$ is independently —OCH$_3$.

In embodiments, R$^{1A}$ is independently hydrogen. In embodiments, R$^{1A}$ is independently —CX$^{1A}$$_3$. In embodiments, R$^{1A}$ is independently —CHX$^{1A}$$_2$. In embodiments, R$^{1A}$ is independently —CH$_2$X$^{1A}$. In embodiments, R$^{1A}$ is independently —CN. In embodiments, R$^{1A}$ is independently —COOH. In embodiments, R$^{1A}$ is independently —CONH$_2$. In embodiments, X$^{1A}$ is independently —F, —Cl, —Br, or —I.

In embodiments, R$^{1A}$ is independently substituted or unsubstituted alkyl (e.g., C$_1$-C$_8$, C$_1$-C$_6$, C$_1$-C$_4$, or C$_1$-C$_2$). In embodiments, R$^{1A}$ is independently substituted alkyl (e.g., C$_1$-C$_8$, C$_1$-C$_6$, C$_1$-C$_4$, or C$_1$-C$_2$). In embodiments, R$^{1A}$ is independently unsubstituted alkyl (e.g., C$_1$-C$_8$, C$_1$-C$_6$, C$_1$-C$_4$, or C$_1$-C$_2$). In embodiments, R$^{1A}$ is independently unsubstituted methyl. In embodiments, R$^{1A}$ is independently unsubstituted ethyl. In embodiments, R$^{1A}$ is independently unsubstituted propyl. In embodiments, R$^{1A}$ is independently unsubstituted isopropyl. In embodiments, R$^{1A}$ is independently unsubstituted tert-butyl. In embodiments, R$^{1A}$ is independently substituted or unsubstituted heteroalkyl (e.g., 2 to 8 membered, 2 to 6 membered, 4 to 6 membered, 2 to 3 membered, or 4 to 5 membered). In embodiments, R$^{1A}$ is independently substituted heteroalkyl (e.g., 2 to 8 membered, 2 to 6 membered, 4 to 6 membered, 2 to 3 membered, or 4 to 5 membered). In embodiments, R$^{1A}$ is independently unsubstituted heteroalkyl (e.g., 2 to 8 membered, 2 to 6 membered, 4 to 6 membered, 2 to 3 membered, or 4 to 5 membered). In embodiments, R$^{1A}$ is independently substituted or unsubstituted cycloalkyl (e.g., C$_3$-C$_8$, C$_3$-C$_6$, C$_4$-C$_6$, or C$_5$-C$_6$). In embodiments, R$^{1A}$ is independently substituted cycloalkyl (e.g., C$_3$-C$_6$, C$_3$-C$_6$, C$_4$-C$_6$, or C$_5$-C$_6$). In embodiments, R$^{1A}$ is independently unsubstituted cycloalkyl (e.g., C$_3$-C$_8$, C$_3$-C$_6$, C$_4$-C$_6$, or C$_5$-C$_6$). In embodiments, R$^{1A}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{1A}$ is independently substituted heterocycloalkyl (e.g., 3 to 8 membered, 3 to 6 membered, 4 to 6 membered, 4 to 5 membered, or 5 to 6 membered). In embodiments, R$^{1A}$ is independently unsubstituted heterocycloalkyl (e.g., 3 to 8 membered, 3 to 6 membered, 4 to 6 membered, 4 to 5 membered, or 5 to 6 membered). In embodiments, R$^{1A}$ is independently substituted or unsubstituted aryl (e.g., C$_6$-C$_{10}$ or phenyl). In embodiments, R$^{1A}$ is independently substituted aryl (e.g., C$_6$-C$_{10}$ or phenyl). In embodiments, R$^{1A}$ is independently unsubstituted aryl (e.g., C$_6$-C$_{10}$ or phenyl). In embodiments, R$^{1A}$ is independently substituted or unsubstituted heteroaryl (e.g., 5 to 10 membered, 5 to 9 membered, or 5 to 6 membered). In embodiments, R$^{1A}$ is independently substituted heteroaryl (e.g., 5 to 10 membered, 5 to 9 membered, or 5 to 6 membered). In embodiments, R$^{1A}$ is independently unsubstituted heteroaryl (e.g., 5 to 10 membered, 5 to 9 membered, or 5 to 6 membered).

In embodiments, R$^{1B}$ is independently hydrogen. In embodiments, R$^{1B}$ is independently —CX$^{1B}$$_3$. In embodiments, R$^{1B}$ is independently —CHX$^{1B}$$_2$. In embodiments, R$^{1B}$ is independently —CH$_2$X$^{1B}$. In embodiments, R$^{1B}$ is independently —CN. In embodiments, R$^{1B}$ is independently —COOH. In embodiments, R$^{1B}$ is independently —CONH$_2$. In embodiments, X$^{1B}$ is independently —F, —Cl, —Br, or —I.

In embodiments, R$^{1B}$ is independently substituted or unsubstituted alkyl (e.g., C$_1$-C$_8$, C$_1$-C$_6$, C$_1$-C$_4$, or C$_1$-C$_2$). In embodiments, R$^{1B}$ is independently substituted alkyl (e.g., C$_1$-C$_8$, C$_1$-C$_6$, C$_1$-C$_4$, or C$_1$-C$_2$). In embodiments, R$^{1B}$ is independently unsubstituted alkyl (e.g., C$_1$-C$_8$, C$_1$-C$_6$, C$_1$-C$_4$, or C$_1$-C$_2$). In embodiments, R$^{1B}$ is independently unsubstituted methyl. In embodiments, R$^{1B}$ is independently unsubstituted ethyl. In embodiments, R$^{1B}$ is independently unsubstituted propyl. In embodiments, R$^{1B}$ is independently unsubstituted isopropyl. In embodiments, R$^{1B}$ is independently unsubstituted tert-butyl. In embodiments, R$^{1B}$ is independently substituted or unsubstituted heteroalkyl (e.g., 2 to 8 membered, 2 to 6 membered, 4 to 6 membered, 2 to 3 membered, or 4 to 5 membered). In embodiments, R$^{1B}$ is independently substituted heteroalkyl (e.g., 2 to 8 membered, 2 to 6 membered, 4 to 6 membered, 2 to 3 membered, or 4 to 5 membered). In embodiments, R$^{1B}$ is independently unsubstituted heteroalkyl (e.g., 2 to 8 membered, 2 to 6 membered, 4 to 6 membered, 2 to 3 membered, or 4 to 5 membered). In embodiments, R$^{1B}$ is independently substituted or unsubstituted cycloalkyl (e.g., C$_3$-C$_8$, C$_3$-C$_6$, C$_4$-C$_6$, or C$_5$-C$_6$). In embodiments, R$^{1B}$ is independently substituted cycloalkyl (e.g., C$_3$-C$_8$, C$_3$-C$_6$, C$_4$-C$_6$, or C$_5$-C$_6$). In embodiments, R$^{1B}$ is independently unsubstituted cycloalkyl (e.g., C$_3$-C$_8$, C$_3$-C$_6$, C$_4$-C$_6$, or C$_5$-C$_6$). In embodiments, R$^{1B}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{1B}$ is independently substituted heterocycloalkyl (e.g., 3 to 8 membered, 3 to 6 membered, 4 to 6 membered, 4 to 5 membered, or 5 to 6 membered). In embodiments, R$^{1B}$ is independently unsubstituted heterocycloalkyl (e.g., 3 to 8 membered, 3 to 6 membered, 4 to 6 membered, 4 to 5 membered, or 5 to 6 membered). In embodiments, R$^{1B}$ is independently substituted or unsubstituted aryl (e.g., C$_6$-C$_{10}$ or phenyl). In embodiments, R$^{1B}$ is independently substituted aryl (e.g., C$_6$-C$_{10}$ or phenyl). In embodiments, R$^{1B}$ is independently unsubstituted aryl (e.g., C$_6$-C$_{10}$ or phenyl). In embodiments, R$^{1B}$ is independently substituted or unsubstituted heteroaryl (e.g., 5 to 10 membered, 5 to 9 membered, or 5 to 6 membered). In embodiments, R$^{1B}$ is independently substituted heteroaryl (e.g., 5 to 10 membered, 5 to 9 membered, or 5 to 6 membered). In embodiments, R$^{1B}$ is independently unsubstituted heteroaryl (e.g., 5 to 10 membered, 5 to 9 membered, or 5 to 6 membered).

In embodiments, R$^{1A}$ and R$^{1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, R$^{1A}$ and R$^{1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, R$^{1A}$ and R$^{1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, R$^{1A}$ and R$^{1B}$ substituents bonded to the same nitrogen atom may be joined to form a substituted or unsubstituted heteroaryl (e.g., 5 to 10 membered, 5 to 9 membered, or 5 to 6 membered). In embodiments, R$^{1A}$ and R$^{1B}$ substituents bonded to the same nitrogen atom may be joined to form a substituted heteroaryl (e.g., 5 to 10 membered, 5 to 9 membered, or 5 to 6 membered). In embodiments, R$^{1A}$ and R$^{1B}$ substituents bonded to the same nitrogen atom may be joined to form an unsubstituted heteroaryl (e.g., 5 to 10 membered, 5 to 9 membered, or 5 to 6 membered).

In embodiments, R$^{1C}$ is independently hydrogen. In embodiments, R$^{1C}$ is independently —CX$^{1C}$$_3$. In embodiments, $R^{1C}$ is independently —$CHX^{1C}{}_2$. In embodiments, $R^{1C}$ is independently —$CH_2X^{1C}$. In embodiments, $R^{1C}$ is independently —CN. In embodiments, $R^{1C}$ is independently —COOH. In embodiments, $R^{1C}$ is independently —$CONH_2$. In embodiments, $X^{1C}$ is independently —F, —Cl, —Br, or —I.

In embodiments, $R^{1C}$ is independently substituted or unsubstituted alkyl (e.g., $C_1$-$C_8$, $C_1$-$C_6$, $C_1$-$C_4$, or $C_1$-$C_2$). In embodiments, $R^{1C}$ is independently substituted alkyl (e.g., $C_1$-$C_8$, $C_1$-$C_6$, $C_1$-$C_4$, or $C_1$-$C_2$). In embodiments, $R^{1C}$ is independently unsubstituted alkyl (e.g., $C_1$-$C_8$, $C_1$-$C_6$, $C_1$-$C_4$, or $C_1$-$C_2$). In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl. In embodiments, $R^{1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted heteroalkyl (e.g., 2 to 8 membered, 2 to 6 membered, 4 to 6 membered, 2 to 3 membered, or 4 to 5 membered). In embodiments, $R^{1C}$ is independently unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted or unsubstituted cycloalkyl (e.g., $C_3$-$C_8$, $C_3$-$C_6$, $C_4$-$C_6$, or $C_5$-$C_6$). In embodiments, $R^{1C}$ is independently substituted cycloalkyl (e.g., $C_3$-$C_8$, $C_3$-$C_6$, $C_4$-$C_6$, or $C_5$-$C_6$). In embodiments, $R^{1C}$ is independently unsubstituted cycloalkyl (e.g., $C_3$-$C_8$, $C_3$-$C_6$, $C_4$-$C_6$, or $C_5$-$C_6$). In embodiments, $R^{1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted heterocycloalkyl (e.g., 3 to 8 membered, 3 to 6 membered, 4 to 6 membered, 4 to 5 membered, or 5 to 6 membered). In embodiments, $R^{1C}$ is independently unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted or unsubstituted aryl (e.g., $C_6$-$C_{10}$ or phenyl). In embodiments, $R^{1C}$ is independently substituted aryl (e.g., $C_6$-$C_{10}$ or phenyl). In embodiments, $R^{1C}$ is independently unsubstituted aryl (e.g., $C_6$-$C_{10}$ or phenyl). In embodiments, $R^{1C}$ is independently substituted or unsubstituted heteroaryl (e.g., 5 to 10 membered, 5 to 9 membered, or 5 to 6 membered). In embodiments, $R^{1C}$ is independently substituted heteroaryl (e.g., 5 to 10 membered, 5 to 9 membered, or 5 to 6 membered). In embodiments, $R^{1C}$ is independently unsubstituted heteroaryl (e.g., 5 to 10 membered, 5 to 9 membered, or 5 to 6 membered).

In embodiments, $R^{1D}$ is independently hydrogen. In embodiments, $R^{1D}$ is independently —$CX^{1D}{}_3$. In embodiments, $R^{1D}$ is independently —$CHX^{1D}{}_2$. In embodiments, $R^{1D}$ is independently —$CH_2X^{1D}$. In embodiments, $R^{1D}$ is independently —CN. In embodiments, $R^{1D}$ is independently —COOH. In embodiments, $R^{1D}$ is independently —$CONH_2$. In embodiments, $X^{1D}$ is independently —F, —Cl, —Br, or —I.

In embodiments, $R^{1D}$ is independently substituted or unsubstituted alkyl (e.g., $C_1$-$C_8$, $C_1$-$C_6$, $C_1$-$C_4$, or $C_1$-$C_2$). In embodiments, $R^{1D}$ is independently substituted alkyl (e.g., $C_1$-$C_8$, $C_1$-$C_6$, $C_1$-$C_4$, or $C_1$-$C_2$). In embodiments, $R^{1D}$ is independently unsubstituted alkyl (e.g., $C_1$-$C_8$, $C_1$-$C_6$, $C_1$-$C_4$, or $C_1$-$C_2$). In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl. In embodiments, $R^{1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted heteroalkyl (e.g., 2 to 8 membered, 2 to 6 membered, 4 to 6 membered, 2 to 3 membered, or 4 to 5 membered). In embodiments, $R^{1D}$ is independently unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted or unsubstituted cycloalkyl (e.g., $C_3$-$C_8$, $C_3$-$C_6$, $C_4$-$C_6$, or $C_5$-$C_6$). In embodiments, $R^{1D}$ is independently substituted cycloalkyl (e.g., $C_3$-$C_8$, $C_3$-$C_6$, $C_4$-$C_6$, or $C_5$-$C_6$). In embodiments, $R^{1D}$ is independently unsubstituted cycloalkyl (e.g., $C_3$-$C_8$, $C_3$-$C_6$, $C_4$-$C_6$, or $C_5$-$C_6$). In embodiments, $R^{1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted heterocycloalkyl (e.g., 3 to 8 membered, 3 to 6 membered, 4 to 6 membered, 4 to 5 membered, or 5 to 6 membered). In embodiments, $R^{1D}$ is independently unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted or unsubstituted aryl (e.g., $C_6$-$C_{10}$ or phenyl). In embodiments, $R^{1D}$ is independently substituted aryl (e.g., $C_6$-$C_{10}$ or phenyl). In embodiments, $R^{1D}$ is independently unsubstituted aryl (e.g., $C_6$-$C_{10}$ or phenyl). In embodiments, $R^{1D}$ is independently substituted or unsubstituted heteroaryl (e.g., 5 to 10 membered, 5 to 9 membered, or 5 to 6 membered). In embodiments, $R^{1D}$ is independently substituted heteroaryl (e.g., 5 to 10 membered, 5 to 9 membered, or 5 to 6 membered). In embodiments, $R^{1D}$ is independently unsubstituted heteroaryl (e.g., 5 to 10 membered, 5 to 9 membered, or 5 to 6 membered).

In embodiments, $R^1$ is independently halogen, —$CX^1{}_3$, —$CHX^1{}_2$, —$CH_2X^1$, —$OCX^1{}_3$, —$OCH_2X^1$, —$OCHX^1{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^1$ is independently halogen, —$CX^1{}_3$, —$CHX^1{}_2$, —$CH_2X^1$, —$OCX^1{}_3$, —$OCH_2X^1$, —$OCHX^1{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^1$ is independently —F, —Cl, —Br, or —I. In embodiments, $R^1$ is independently unsubstituted methyl. In embodiments, $R^1$ is independently unsubstituted ethyl.

$R^{20}$ is independently oxo,
halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{10}$ or phenyl), or $R^{21}$-substituted or unsubstituted heteroaryl (e.g., 5 to 10 membered, 5 to 9 membered, or 5 to 6 membered). In embodiments, $R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20}$ is independently —F, —Cl, —Br, or —I. In embodiments, $R^{20}$ is independently unsubstituted methyl. In embodiments, $R^{20}$ is independently unsubstituted ethyl.

$R^{21}$ is independently oxo,
halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{10}$ or phenyl), or $R^{22}$-substituted or unsubstituted heteroaryl (e.g., 5 to 10 membered, 5 to 9 membered, or 5 to 6 membered). In embodiments, $R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21}$ is independently —F, —Cl, —Br, or —I. In embodiments, $R^{21}$ is independently unsubstituted methyl. In embodiments, $R^{21}$ is independently unsubstituted ethyl.

$R^{22}$ is independently oxo,
halogen, —$CX^{22}_3$, —$CHX^{22}_2$, —$CH_2X^{22}$, —$OCX^{22}_3$, —$OCH_2X^{22}$, —$OCHX^{22}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22}$ is independently —F, —Cl, —Br, or —I. In embodiments, $R^{22}$ is independently unsubstituted methyl. In embodiments, $R^{22}$ is independently unsubstituted ethyl.

In embodiments, $R^{1A}$ is independently hydrogen, —$CX^{1A3}$, —$CHX^{1A2}$, —$CH_2X^{1A}$, —CN, —COOH, —$CONH_2$, $R^{20A}$-substituted or unsubstituted alkyl (e.g., $C_1$-$C_8$, $C_1$-$C_6$, $C_1$-$C_4$, or $C_1$-$C_2$), $R^{20A}$-substituted or unsubstituted heteroalkyl (e.g., 2 to 8 membered, 2 to 6 membered, 4 to 6 membered, 2 to 3 membered, or 4 to 5 membered), $R^{20A}$-substituted or unsubstituted cycloalkyl (e.g., $C_3$-$C_8$, $C_3$-$C_6$, $C_4$-$C_6$, or $C_5$-$C_6$), $R^{20A}$-substituted or unsubstituted heterocycloalkyl (e.g., 3 to 8 membered, 3 to 6 membered, 4 to 6 membered, 4 to 5 membered, or 5 to 6 membered), $R^{20A}$-substituted or unsubstituted aryl (e.g., $C_6$-$C_{10}$ or phenyl), or $R^{20A}$-substituted or unsubstituted heteroaryl (e.g., 5 to 10 membered, 5 to 9 membered, or 5 to 6 membered). In embodiments, $R^{1A}$ is independently hydrogen, —$CX^{1A3}$, —$CHX^{1A}_2$, —$CH_2X^{1A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1A}$ is independently —F, —Cl, —Br, or —I. In embodiments, $R^{1A}$ is independently hydrogen. In embodiments, $R^{1A}$ is independently unsubstituted methyl. In embodiments, $R^{1A}$ is independently unsubstituted ethyl.

In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered) or $R^{20A}$ substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form a $R^{20A}$ substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20A}$ is independently —F, —Cl, —Br, or —I. In embodiments, $R^{20A}$ is independently unsubstituted methyl. In embodiments, $R^{20A}$ is independently unsubstituted ethyl.

In embodiments, $R^{1B}$ is independently hydrogen, —$CX^{1B}_3$, —$CHX^{1B}_2$, —$CH_2X^{1B}$, —CN, —COOH, —$CONH_2$, $R^{20B}$-substituted or unsubstituted alkyl (e.g., $C_1$-$C_8$, $C_1$-$C_6$, $C_1$-$C_4$, or $C_1$-$C_2$), $R^{20B}$-substituted or unsubstituted heteroalkyl (e.g., 2 to 8 membered, 2 to 6 membered, 4 to 6 membered, 2 to 3 membered, or 4 to 5 membered), $R^{20B}$-substituted or unsubstituted cycloalkyl (e.g., $C_3$-$C_8$, $C_3$-$C_6$, $C_4$-$C_6$, or $C_5$-$C_6$), $R^{20B}$ substituted or unsubstituted heterocycloalkyl (e.g., 3 to 8 membered, 3 to 6 membered, 4 to 6 membered, 4 to 5 membered, or 5 to 6 membered), $R^{20B}$-substituted or unsubstituted aryl (e.g., $C_6$-$C_{10}$ or phenyl), or $R^{20B}$-substituted or unsubstituted heteroaryl (e.g., 5 to 10 membered, 5 to 9 membered, or 5 to 6 membered). In embodiments, $R^{1B}$ is independently hydrogen, —$CX^{1B}_3$, —$CHX^{1B}_2$, —$CH_2X^{1B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1B}$ is independently —F, —Cl, —Br, or —I. In embodiments, $R^{1B}$ is independently hydrogen. In embodiments, $R^{1B}$ is independently unsubstituted methyl. In embodiments, $R^{1B}$ is independently unsubstituted ethyl.

In embodiments, $R^{1A}$ and $R^{1B}$ substituents bonded to the same nitrogen atom may optionally be joined to form a $R^{20B}$-substituted or unsubstituted heterocycloalkyl (e.g., 3 to 8 membered, 3 to 6 membered, 4 to 6 membered, 4 to 5 membered, or 5 to 6 membered) or $R^{20B}$ substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, 4 to 5 membered, or 5 to 6 membered) or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form a $R^{20B}$ substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20B}$ is independently oxo, halogen, —$CX^{20B}_3$, —$CHX^{20B}_2$, —$CH_2X^{20B}$, —$OCX^{20B}_3$, —$OCH_2X^{20B}$, —$OCHX^{20B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20B}$ is independently —F, —Cl, —Br, or —I. In embodiments, $R^{20B}$ is independently unsubstituted methyl. In embodiments, $R^{20B}$ is independently unsubstituted ethyl.

In embodiments, $R^{1C}$ is independently hydrogen, —$CX^{1C}_3$, —$CHX^{1C}_2$, —$CH_2X^{1C}$, —CN, —COOH, —$CONH_2$, $R^{20C}$-substituted or unsubstituted alkyl (e.g., $C_1$-$C_8$, $C_1$-$C_6$, $C_1$-$C_4$, or $C_1$-$C_2$), $R^{20C}$-substituted or unsubstituted heteroalkyl (e.g., 2 to 8 membered, 2 to 6 membered, 4 to 6 membered, 2 to 3 membered, or 4 to 5 membered), $R^{20C}$-substituted or unsubstituted cycloalkyl (e.g., $C_3$-$C_8$, $C_3$-$C_6$, $C_4$-$C_6$, or $C_5$-$C_6$), $R^{20C}$ substituted or unsubstituted heterocycloalkyl (e.g., 3 to 8 membered, 3 to 6 membered, 4 to 6 membered, 4 to 5 membered, or 5 to 6 membered), $R^{20C}$-substituted or unsubstituted aryl (e.g., $C_6$-$C_{10}$ or phenyl), or $R^{20C}$-substituted or unsubstituted heteroaryl (e.g., 5 to 10 membered, 5 to 9 membered, or 5 to 6 membered). In embodiments, $R^{1C}$ is independently hydrogen, —$CX^{1C}_3$, —$CHX^{1C}_2$, —$CH_2X^{1C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1C}$ is independently —F, —Cl, —Br, or —I. In embodiments, $R^{1C}$ is independently hydrogen. In embodiments, $R^{1C}$ is independently unsubstituted methyl. In embodiments, $R^{1C}$ is independently unsubstituted ethyl.

$R^{20C}$ is independently oxo, halogen, —$CX^{20C}_3$, —$CHX^{20C}_2$, —$CH_2X^{20C}$, —$OCX^{20C}_3$, —$OCH_2X^{20}c$, —$OCHX^{20C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20C}$ is independently —F, —Cl, —Br, or —I. In embodiments, $R^{20C}$ is independently unsubstituted methyl. In embodiments, $R^{20C}$ is independently unsubstituted ethyl.

In embodiments, $R^{1D}$ is independently hydrogen, —$CX^{1D}_3$, —$CHX^{1D}_2$, —$CH_2X^{1D}$, —CN, —COOH, —$CONH_2$, $R^{20D}$-substituted or unsubstituted alkyl (e.g., $C_1$-$C_8$, $C_1$-$C_6$, $C_1$-$C_4$, or $C_1$-$C_2$), $R^{20D}$-substituted or unsubstituted heteroalkyl (e.g., 2 to 8 membered, 2 to 6 membered, 4 to 6 membered, 2 to 3 membered, or 4 to 5 membered), $R^{20D}$-substituted or unsubstituted cycloalkyl (e.g., $C_3$-$C_8$, $C_3$-$C_6$, $C_4$-$C_6$, or $C_5$-$C_6$), $R^{20D}$-substituted or unsubstituted heterocycloalkyl (e.g., 3 to 8 membered, 3 to 6 membered, 4 to 6 membered, 4 to 5 membered, or 5 to 6 membered), $R^{20D}$-substituted or unsubstituted aryl (e.g., $C_6$-$C_{10}$ or phenyl), or $R^{20D}$-substituted or unsubstituted heteroaryl (e.g., 5 to 10 membered, 5 to 9 membered, or 5 to 6 membered). In embodiments, $R^{1D}$ is independently hydrogen, —$CX^{1D}_3$, —$CHX^{1D}_2$, —$CH_2X^{1D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$—$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1D}$ is independently —F, —Cl, —Br, or —I. In embodiments, $R^{1D}$ is independently hydrogen. In embodiments, $R^{1D}$ is independently unsubstituted methyl. In embodiments, $R^{1D}$ is independently unsubstituted ethyl.

$R^{20D}$ is independently oxo, halogen, —$CX^{20D}_3$, —$CHX^{20D}_2$, —$CH_2X^{20D}$, —$OCX^{20D}_3$, —$OCH_2X^{20D}$, —$OCHX^{20D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20D}$ is independently —F, —Cl, —Br, or —I. In embodiments, $R^{20D}$ is independently unsubstituted methyl. In embodiments, $R^{20D}$ is independently unsubstituted ethyl.

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^2$ is independently halogen, —$CX^2_3$, —$CHX^2_2$, —$CH_2X^2$, —$OCX^2_3$, —$OCH_2X^2$, —$OCHX^2_2$, substituted or unsubstituted alkyl, or substituted or unsubstituted heteroalkyl. In embodiments, $R^2$ is independently halogen, —$CX^2_3$, —$CHX^2_2$, —$CH_2X^2$, —$OCX^2_3$, —$OCH_2X^2$, —$OCHX^2_2$, substituted or unsubstituted ($C_1$-$C_4$) alkyl, or substituted or unsubstituted 2 to 4 membered heteroalkyl. In embodiments, $R^2$ is halogen, —$CH_3$, —$CH_2CH_3$, —$CX^2_3$, —$CHX^2_2$, —$CH_2X^2$, —$OCH_3$, —$OCX^2_3$, —$OCH_2X^2$, —$OCHX^2_2$, —$SCH_3$—$SCX^2_3$, —$SCH_2X^2$, or —$SCHX^2_2$. In embodiments, $R^2$ is halogen, —$CH_3$, —$CH_2CH_3$, —$CF_3$, or —$OCH_3$. In embodiments, $R^2$ is —$CH_3$, —$CH_2CH_3$, or —$OCH_3$. In embodiments, $R^2$ is —$OCH_3$. In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, substituted or unsubstituted alkyl, or substituted or unsubstituted heteroalkyl. In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, substituted or unsubstituted ($C_1$-$C_4$) alkyl, or substituted or unsubstituted 2 to 4 membered heteroalkyl. In embodiments, $R^2$ is halogen, —$CH_3$, —$CH_2CH_3$, —$CX^2_3$, —$CHX^2_2$, —$CH_2X^2$, —$OCH_3$, —$OCX^2_3$, —$OCH_2X^2$, —$OCHX^2_2$, —CN, —$SCH_3$, —$SCX^2_3$, —$SCH_2X^2$, or —$SCHX^2_2$. In embodiments, $R^2$ is halogen, —CN, —$CH_3$, —$CF_3$, or —$OCH_3$. In embodiments, $R^2$ is halogen or —$CH_3$. In embodiments, $R^2$ is —$C_1$ or —$CH_3$. In embodiments, $R^2$ is —$CH_3$. In embodiments, $R^2$ is —$CH_3$ or —$CH_2CH_3$.

In embodiments, $R^2$ is independently halogen, —$CX^2_3$, —CN, —OH, —$NH_2$, —SH, —$OCX^2_3$, —$OCHX^2_2$, —$OCH_2X^2$, —$CHX^2_2$, —$CH_2X^2$, substituted or unsubstituted $C_1$-$C_4$ alkyl, or substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently halogen, —$CX^2_3$, —CN, —OH, —$NH_2$, —SH, —$OCX^2_3$, —$OCHX^2_2$, —$OCH_2X^2$, —$CHX^2_2$, —$CH_2X^2$, unsubstituted $C_1$-$C_4$ alkyl, or unsubstituted 2 to 4 membered heteroalkyl.

In embodiments, $R^2$ is independently halogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$OCX^2_3$. In embodiments, $R^2$ is independently —$OCH_2X^2$. In embodiments, $R^2$ is independently —$OCHX^2_2$. In embodiments, $R^2$ is independently —CN. In embodiments, $R^2$ is independently —$SO_{n2}R^{2D}$. In embodiments, $R^2$ is independently —$SO_{v2}NR^{2A}R^{2B}$. In embodiments, $R^2$ is independently —NHC(O)$NR^{2A}R^{2B}$. In embodiments, $R^2$ is independently —$N(O)_{m2}$. In embodiments, $R^2$ is independently —$NR^{2A}R^{2B}$. In embodiments, $R^2$ is independently —C(O)$R^{2C}$. In embodiments, $R^2$ is independently —C(O)—$OR^{2C}$. In embodiments, $R^2$ is independently —C(O)$NR^{2A}R^{2B}$. In embodiments, $R^2$ is independently —$OR^{2D}$. In embodiments, $R^2$ is independently —$SR^{2D}$. In embodiments, $R^2$ is independently —$NR^{2A}SO_2R^{2D}$. In embodiments, $R^2$ is independently —$NR^{2A}C(O)R^{2C}$. In embodiments, $R^2$ is independently —$NR^{2A}C(O)OR^{2C}$. In embodiments, $R^2$ is independently —$NR^{2A}OR^{2C}$. In embodiments, $R^2$ is independently —OH. In embodiments, $R^2$ is independently —$NH_2$. In embodiments, $R^2$ is independently —COOH. In embodiments, $R^2$ is independently —$CONH_2$. In embodiments, $R^2$ is independently —$NO_2$. In embodiments, $R^2$ is independently —SH. In embodiments, $R^2$ is independently —$CF_3$. In embodiments, $R^2$ is independently —$CHF_2$. In embodiments, $R^2$ is independently —$CH_2F$. In embodiments, $R^2$ is independently —$OCF_3$. In embodiments, $R^2$ is independently —$OCH_2F$. In embodiments, $R^2$ is independently —$OCHF_2$. In embodiments, $R^2$ is independently —$OCH_3$. In embodiments, $R^2$ is independently —$OCH_2CH_3$. In embodiments, $R^2$ is independently —$OCH_2CH_2CH_3$. In embodiments, $R^2$ is independently —$OCH(CH_3)_2$. In embodiments, $R^2$ is independently —$OC(CH_3)_3$. In embodiments, $R^2$ is independently —$SCH_3$. In embodiments, $R^2$ is independently —$SCH_2CH_3$. In embodiments, $R^2$ is independently —$SCH_2CH_2CH_3$. In embodiments, $R^2$ is independently —$SCH(CH_3)_2$. In embodiments, $R^2$ is independently —$SC(CH_3)_3$. In embodiments, $R^2$ is independently —$CH_3$. In embodiments, $R^2$ is independently —$CH_2CH_3$. In embodiments, $R^2$ is independently —$CH_2CH_2CH_3$. In embodiments, $R^2$ is independently —$CH(CH_3)_2$. In embodiments, $R^2$ is independently —$C(CH_3)_3$. In embodiments, $R^2$ is independently —F. In embodiments, $R^2$ is independently —Cl. In embodiments, $R^2$ is independently —Br. In embodiments, $R^2$ is independently —I. In embodiments, $X^2$ is independently —F. In embodiments, $X^2$ is independently —Cl. In embodiments, $X^2$ is independently —Br. In embodiments, $X^2$ is independently —I.

In embodiments, $R^2$ is independently substituted or unsubstituted alkyl (e.g., $C_1$-$C_8$, $C_1$-$C_6$, $C_1$-$C_4$, or $C_1$-$C_2$). In embodiments, $R^2$ is independently substituted alkyl (e.g., $C_1$-$C_8$, $C_1$-$C_6$, $C_1$-$C_4$, or $C_1$-$C_2$). In embodiments, $R^2$ is independently unsubstituted alkyl (e.g., $C_1$-$C_8$, $C_1$-$C_6$, $C_1$-$C_4$, or $C_1$-$C_2$). In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted isopropyl. In embodiments, $R^2$ is independently unsubstituted tert-butyl. In embodiments, $R^2$ is independently substituted or unsubstituted heteroalkyl (e.g., 2 to 8 membered, 2 to 6 membered, 4 to 6 membered, 2 to 3 membered, or 4 to 5 membered). In embodiments, $R^2$ is independently substituted heteroalkyl (e.g., 2 to 8 membered, 2 to 6 membered, 4 to 6 membered, 2 to 3 membered, or 4 to 5 membered). In embodiments, $R^2$ is independently unsubstituted heteroalkyl (e.g., 2 to 8 membered, 2 to 6 membered, 4 to 6 membered, 2 to 3 membered, or 4 to 5 membered). In embodiments, $R^2$ is independently substituted or unsubstituted cycloalkyl (e.g., $C_3$-$C_8$, $C_3$-$C_6$, $C_4$-$C_6$, or $C_5$-$C_6$). In embodiments, $R^2$ is independently substituted cycloalkyl (e.g., $C_3$-$C_8$, $C_3$-$C_6$, $C_4$-$C_6$, or $C_5$-$C_6$). In embodiments, $R^2$ is independently unsubstituted cycloalkyl (e.g., $C_3$-$C_8$, $C_3$-$C_6$, $C_4$-$C_6$, or $C_5$-$C_6$). In embodiments, $R^2$ is independently substituted or unsubstituted heterocycloalkyl (e.g., 3 to 8 membered, 3 to 6 membered, 4 to 6 membered, 4 to 5 membered, or 5 to 6 membered). In embodiments, $R^2$ is independently substituted heterocycloalkyl (e.g., 3 to 8 membered, 3 to 6 membered, 4 to 6 membered, 4 to 5 membered, or 5 to 6 membered). In embodiments, $R^2$ is independently unsubstituted heterocycloalkyl (e.g., 3 to 8 membered, 3 to 6 membered, 4 to 6 membered, 4 to 5 membered, or 5 to 6 membered). In embodiments, $R^2$ is independently substituted or unsubstituted aryl (e.g., $C_6$-$C_{10}$ or phenyl). In embodiments, $R^2$ is independently substituted aryl (e.g., $C_6$-$C_{10}$ or phenyl). In embodiments, $R^2$ is independently unsubstituted aryl (e.g., $C_6$-$C_{10}$ or phenyl). In embodiments, $R^2$ is independently substituted or unsubstituted heteroaryl (e.g., 5 to 10 membered, 5 to 9 membered, or 5 to 6 membered). In embodiments, $R^2$ is independently substituted heteroaryl (e.g., 5 to 10 membered, 5 to 9 membered, or 5 to 6 membered). In embodiments, $R^2$ is independently unsubstituted heteroaryl (e.g., 5 to 10 membered, 5 to 9 membered, or 5 to 6 membered).

In embodiments, $R^2$ is independently halogen, —$CX^2_3$, —$CHX^2_2$, —$CH_2X^2$, —$OCX^2_3$, —$OCH_2X^2$, —$OCHX^2_2$, substituted or unsubstituted alkyl, or substituted or unsubstituted heteroalkyl. In embodiments, $R^2$ is independently halogen, —$CX^2_3$, —$CHX^2_2$, or —$CH_2X^2$. In embodiments, $R^2$ is independently —$CX^2_3$. In embodiments, $R^2$ is independently —$CF_3$.

In embodiments, $R^{2A}$ is independently hydrogen. In embodiments, $R^{2A}$ is independently —$CX^{2A}_3$. In embodiments, $R^{2A}$ is independently —$CHX^{2A}_2$. In embodiments, $R^{2A}$ is independently —$CH_2X^{2A}$. In embodiments, $R^{2A}$ is independently —CN. In embodiments, $R^{2A}$ is independently —COOH. In embodiments, $R^{2A}$ is independently —$CONH_2$. In embodiments, $X^{2A}$ is independently —F, —Cl, —Br, or —I.

In embodiments, $R^{2A}$ is independently substituted or unsubstituted alkyl (e.g., $C_1$-$C_8$, $C_1$-$C_6$, $C_1$-$C_4$, or $C_1$-$C_2$). In embodiments, $R^{2A}$ is independently substituted alkyl (e.g., $C_1$-$C_8$, $C_1$-$C_6$, $C_1$-$C_4$, or $C_1$-$C_2$). In embodiments, $R^{2A}$ is independently unsubstituted alkyl (e.g., $C_1$-$C_8$, $C_1$-$C_6$, $C_1$-$C_4$, or $C_1$-$C_2$). In embodiments, $R^{2A}$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently unsubstituted isopropyl. In embodiments, $R^{2A}$ is independently unsubstituted tert-butyl. In embodiments, $R^{2A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2A}$ is independently substituted heteroalkyl (e.g., 2 to 8 membered, 2 to 6 membered, 4 to 6 membered, 2 to 3 membered, or 4 to 5 membered). In embodiments, $R^{2A}$ is independently unsubstituted heteroalkyl (e.g., 2 to 8 membered, 2 to 6 membered, 4 to 6 membered, 2 to 3 membered, or 4 to 5 membered). In embodiments, $R^{2A}$ is independently substituted or unsubstituted cycloalkyl (e.g., $C_3$-$C_8$, $C_3$-$C_6$, $C_4$-$C_6$, or $C_5$-$C_6$). In embodiments, $R^{2A}$ is independently substituted cycloalkyl (e.g., $C_3$-$C_8$, $C_3$-$C_6$, $C_4$-$C_6$, or $C_5$-$C_6$). In embodiments, $R^{2A}$ is independently unsubstituted cycloalkyl (e.g., $C_3$-$C_8$, $C_3$-$C_6$, $C_4$-$C_6$, or $C_5$-$C_6$). In embodiments, $R^{2A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted heterocycloalkyl (e.g., 3 to 8 membered, 3 to 6 membered, 4 to 6 membered, 4 to 5 membered, or 5 to 6 membered). In embodiments, $R^{2A}$ is independently unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted or unsubstituted aryl (e.g., $C_6$-$C_{10}$ or phenyl). In embodiments, $R^{2A}$ is independently substituted aryl (e.g., $C_6$-$C_{10}$ or phenyl). In embodiments, $R^{2A}$ is independently unsubstituted aryl (e.g., $C_6$-$C_{10}$ or phenyl). In embodiments, $R^{2A}$ is independently substituted or unsubstituted heteroaryl (e.g., 5 to 10 membered, 5 to 9 membered, or 5 to 6 membered). In embodiments, $R^{2A}$ is independently substituted heteroaryl (e.g., 5 to 10 membered, 5 to 9 membered, or 5 to 6 membered). In embodiments, $R^{2A}$ is independently unsubstituted heteroaryl (e.g., 5 to 10 membered, 5 to 9 membered, or 5 to 6 membered).

In embodiments, $R^{2B}$ is independently hydrogen. In embodiments, $R^{2B}$ is independently —$CX^{2B}_3$. In embodiments, $R^{2B}$ is independently —$CHX^{2B}_2$. In embodiments, $R^{2B}$ is independently —$CH_2X^{2B}$. In embodiments, $R^{2B}$ is independently —CN. In embodiments, $R^{2B}$ is independently —COOH. In embodiments, $R^{2B}$ is independently —$CONH_2$. In embodiments, $X^{2B}$ is independently —F, —Cl, —Br, or —I.

In embodiments, $R^{2B}$ is independently substituted or unsubstituted alkyl (e.g., $C_1$-$C_8$, $C_1$-$C_6$, $C_1$-$C_4$, or $C_1$-$C_2$). In embodiments, $R^{2B}$ is independently substituted alkyl (e.g., $C_1$-$C_8$, $C_1$-$C_6$, $C_1$-$C_4$, or $C_1$-$C_2$). In embodiments, $R^{2B}$ is independently unsubstituted alkyl (e.g., $C_1$-$C_8$, $C_1$-$C_6$, $C_1$-$C_4$, or $C_1$-$C_2$). In embodiments, $R^{2B}$ is independently unsubstituted methyl. In embodiments, $R^{2B}$ is independently unsubstituted ethyl. In embodiments, $R^{2B}$ is independently unsubstituted propyl. In embodiments, $R^{2B}$ is independently unsubstituted isopropyl. In embodiments, $R^{2B}$ is independently unsubstituted tert-butyl. In embodiments, $R^{2B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted heteroalkyl (e.g., 2 to 8 membered, 2 to 6 membered, 4 to 6 membered, 2 to 3 membered, or 4 to 5 membered). In embodiments, $R^{2B}$ is independently unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted or unsubstituted cycloalkyl (e.g., $C_3$-$C_8$, $C_3$-$C_6$, $C_4$-$C_6$, or $C_5$-$C_6$). In embodiments, $R^{2B}$ is independently substituted cycloalkyl (e.g., $C_3$-$C_8$, $C_3$-$C_6$, $C_4$-$C_6$, or $C_5$-$C_6$). In embodiments, $R^{2B}$ is independently unsubstituted cycloalkyl (e.g., $C_3$-$C_8$, $C_3$-$C_6$, $C_4$-$C_6$, or $C_5$-$C_6$). In embodiments, $R^{2B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted heterocycloalkyl (e.g., 3 to 8 membered, 3 to 6 membered, 4 to 6 membered, 4 to 5 membered, or 5 to 6 membered). In embodiments, $R^{2B}$ is independently unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted or unsubstituted aryl (e.g., $C_6$-$C_{10}$ or phenyl). In embodiments, $R^{2B}$ is independently substituted aryl (e.g., $C_6$-$C_{10}$ or phenyl). In embodiments, $R^{2B}$ is independently unsubstituted aryl (e.g., $C_6$-$C_{10}$ or phenyl). In embodiments, $R^{2B}$ is independently substituted or unsubstituted heteroaryl (e.g., 5 to 10 membered, 5 to 9 membered, or 5 to 6 membered). In embodiments, $R^{2B}$ is independently substituted heteroaryl (e.g., 5 to 10 membered, 5 to 9 membered, or 5 to 6 membered). In embodiments, $R^{2B}$ is independently unsubstituted heteroaryl (e.g., 5 to 10 membered, 5 to 9 membered, or 5 to 6 membered).

In embodiments, $R^{2A}$ and $R^{2B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form a substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may be joined to form a substituted heteroaryl (e.g., 5 to 10 membered, 5 to 9 membered, or 5 to 6 membered). In embodiments, $R^{2A}$ and $R^{2B}$ substituents bonded to the same nitrogen atom may be joined to form an unsubstituted heteroaryl (e.g., 5 to 10 membered, 5 to 9 membered, or 5 to 6 membered).

In embodiments, $R^{2C}$ is independently hydrogen. In embodiments, $R^{2C}$ is independently —$CX^{2C}_3$. In embodiments, $R^{2C}$ is independently —$CHX^{2C}_2$. In embodiments, $R^{2C}$ is independently —$CH_2X^{2C}$. In embodiments, $R^{2C}$ is independently —CN. In embodiments, $R^{2C}$ is independently —COOH. In embodiments, $R^{2C}$ is independently —$CONH_2$. In embodiments, $X^{2C}$ is independently —F, —Cl, —Br, or —I.

In embodiments, $R^{2C}$ is independently substituted or unsubstituted alkyl (e.g., $C_1$-$C_8$, $C_1$-$C_6$, $C_1$-$C_4$, or $C_1$-$C_2$). In embodiments, $R^{2C}$ is independently substituted alkyl (e.g., $C_1$-$C_8$, $C_1$-$C_6$, $C_1$-$C_4$, or $C_1$-$C_2$). In embodiments, $R^{2C}$ is independently unsubstituted alkyl (e.g., $C_1$-$C_8$, $C_1$-$C_6$, $C_1$-$C_4$, or $C_1$-$C_2$). In embodiments, $R^{2C}$ is independently unsubstituted methyl. In embodiments, $R^{2C}$ is independently unsubstituted ethyl. In embodiments, $R^{2C}$ is independently unsubstituted propyl. In embodiments, $R^{2C}$ is independently unsubstituted isopropyl. In embodiments, $R^{2C}$ is independently unsubstituted tert-butyl. In embodiments, $R^{2C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted heteroalkyl (e.g., 2 to 8 membered, 2 to 6 membered, 4 to 6 membered, 2 to 3 membered, or 4 to 5 membered). In embodiments, $R^{2C}$ is independently unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted or unsubstituted cycloalkyl (e.g., $C_3$-$C_8$, $C_3$-$C_6$, $C_4$-$C_6$, or $C_5$-$C_6$). In embodiments, $R^{2C}$ is independently substituted cycloalkyl (e.g., $C_3$-$C_8$, $C_3$-$C_6$, $C_4$-$C_6$, or $C_5$-$C_6$). In embodiments, $R^{2C}$ is independently unsubstituted cycloalkyl (e.g., $C_3$-$C_8$, $C_3$-$C_6$, $C_4$-$C_6$, or $C_5$-$C_6$). In embodiments, $R^{2C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted heterocycloalkyl (e.g., 3 to 8 membered, 3 to 6 membered, 4 to 6 membered, 4 to 5 membered, or 5 to 6 membered). In embodiments, $R^{2C}$ is independently unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted or unsubstituted aryl (e.g., $C_6$-$C_{10}$ or phenyl). In embodiments, $R^{2C}$ is independently substituted aryl (e.g., $C_6$-$C_{10}$ or phenyl). In embodiments, $R^{2C}$ is independently unsubstituted aryl (e.g., $C_6$-$C_{10}$ or phenyl). In embodiments, $R^{2C}$ is independently substituted or unsubstituted heteroaryl (e.g., 5 to 10 membered, 5 to 9 membered, or 5 to 6 membered). In embodiments, $R^{2C}$ is independently substituted heteroaryl (e.g., 5 to 10 membered, 5 to 9 membered, or 5 to 6 membered). In embodiments, $R^{2C}$ is independently unsubstituted heteroaryl (e.g., 5 to 10 membered, 5 to 9 membered, or 5 to 6 membered).

In embodiments, $R^{2D}$ is independently hydrogen. In embodiments, $R^{2D}$ is independently —$CX^{2D}_3$. In embodiments, $R^{2D}$ is independently —$CHX^{2D}_2$. In embodiments, $R^{2D}$ is independently —$CH_2X^{2D}$. In embodiments, $R^{2D}$ is independently —CN. In embodiments, $R^{2D}$ is independently —COOH. In embodiments, $R^{2D}$ is independently —$CONH_2$. In embodiments, $X^{2D}$ is independently —F, —Cl, —Br, or —I.

In embodiments, $R^{2D}$ is independently substituted or unsubstituted alkyl (e.g., $C_1$-$C_8$, $C_1$-$C_6$, $C_1$-$C_4$, or $C_1$-$C_2$). In embodiments, $R^{2D}$ is independently substituted alkyl (e.g., $C_1$-$C_8$, $C_1$-$C_6$, $C_1$-$C_4$, or $C_1$-$C_2$). In embodiments, $R^{2D}$ is independently unsubstituted alkyl (e.g., $C_1$-$C_8$, $C_1$-$C_6$, $C_1$-$C_4$, or $C_1$-$C_2$). In embodiments, $R^{2D}$ is independently unsubstituted methyl. In embodiments, $R^{2D}$ is independently unsubstituted ethyl. In embodiments, $R^{2D}$ is independently unsubstituted propyl. In embodiments, $R^{2D}$ is independently unsubstituted isopropyl. In embodiments, $R^{2D}$ is independently unsubstituted tert-butyl. In embodiments, $R^{2D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted heteroalkyl (e.g., 2 to 8 membered, 2 to 6 membered, 4 to 6 membered, 2 to 3 membered, or 4 to 5 membered). In embodiments, $R^{2D}$ is independently unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted or unsubstituted cycloalkyl (e.g., $C_3$-$C_8$, $C_3$-$C_6$, $C_4$-$C_6$, or $C_5$-$C_6$). In embodiments, $R^{2D}$ is independently substituted cycloalkyl (e.g., $C_3$-$C_8$, $C_3$-$C_6$, $C_4$-$C_6$, or $C_5$-$C_6$). In embodiments, $R^{2D}$ is independently unsubstituted cycloalkyl (e.g., $C_3$-$C_8$, $C_3$-$C_6$, $C_4$-$C_6$, or $C_5$-$C_6$). In embodiments, $R^{2D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted heterocycloalkyl (e.g., 3 to 8 membered, 3 to 6 membered, 4 to 6 membered, 4 to 5 membered, or 5 to 6 membered). In embodiments, $R^{2D}$ is independently unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted or unsubstituted aryl (e.g., $C_6$-$C_{10}$ or phenyl). In embodiments, $R^{2D}$ is independently substituted aryl (e.g., $C_6$-$C_{10}$ or phenyl). In embodiments, $R^{2D}$ is independently unsubstituted aryl (e.g., $C_6$-$C_{10}$ or phenyl). In embodiments, $R^{2D}$ is independently substituted or unsubstituted heteroaryl (e.g., 5 to 10 membered, 5 to 9 membered, or 5 to 6 membered). In embodiments, $R^{2D}$ is independently substituted heteroaryl (e.g., 5 to 10 membered, 5 to 9 membered, or 5 to 6 membered). In embodiments, $R^{2D}$ is independently unsubstituted heteroaryl (e.g., 5 to 10 membered, 5 to 9 membered, or 5 to 6 membered).

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{23}$-substituted or unsubstituted alkyl (e.g., $C_1$-$C_8$, $C_1$-$C_6$, $C_1$-$C_4$, or $C_1$-$C_2$), $R^{23}$-substituted or unsubstituted heteroalkyl (e.g., 2 to 8 membered, 2 to 6 membered, 4 to 6 membered, 2 to 3 membered, or 4 to 5 membered), $R^{23}$-substituted or unsubstituted cycloalkyl (e.g., $C_3$-$C_8$, $C_3$-$C_6$, $C_4$-$C_6$, or $C_5$-$C_6$), $R^{23}$-substituted or unsubstituted heterocycloalkyl (e.g., 3 to 8 membered, 3 to 6 membered, 4 to 6 membered, 4 to 5 membered, or 5 to 6 membered), $R^{23}$-substituted or unsubstituted aryl (e.g., $C_6$-$C_{10}$ or phenyl), or $R^{23}$-substituted or unsubstituted heteroaryl (e.g., 5 to 10 membered, 5 to 9 membered, or 5 to 6 membered). In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^2$ is independently —F, —Cl, —Br, or —I. In embodiments, $R^2$ is independently unsubstituted methyl. In embodiments, $R^2$ is independently unsubstituted ethyl.

$R^{23}$ is independently oxo, halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered). In embodiments, $R^{23}$ is independently oxo, halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23}$ is independently —F, —Cl, —Br, or —I. In embodiments, $R^{23}$ is independently unsubstituted methyl. In embodiments, $R^{23}$ is independently unsubstituted ethyl.

$R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 8 membered, 3 to 6 membered, 4 to 6 membered, 4 to 5 membered, or 5 to 6 membered), $R^{25}$-substituted or unsubstituted aryl (e.g., $C_6$-$C_{10}$ or phenyl), or $R^{25}$-substituted or unsubstituted heteroaryl (e.g., 5 to 10 membered, 5 to 9 membered, or 5 to 6 membered). In embodiments, $R^{24}$ is independently oxo, halogen, —$CX^{24}{}_3$, —$CHX^{24}{}_2$, —$CH_2X^{24}$, —$OCX^{24}{}_3$, —$OCH_2X^{24}$, —$OCHX^{24}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24}$ is independently —F, —Cl, —Br, or —I. In embodiments, $R^{24}$ is independently unsubstituted methyl. In embodiments, $R^{24}$ is independently unsubstituted ethyl.

$R^{25}$ is independently oxo, halogen, —$CX^{25}{}_3$, —$CHX^{25}{}_2$, —$CH_2X^{25}$, —$OCX^{25}{}_3$, —$OCH_2X^{25}$, —$OCHX^{25}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25}$ is independently —F, —Cl, —Br, or —I. In embodiments, $R^{25}$ is independently unsubstituted methyl. In embodiments, $R^{25}$ is independently unsubstituted ethyl.

In embodiments, $R^{2A}$ is independently hydrogen, —$CX^{2A}{}_3$, —$CHX^{2A}{}_2$, —$CH_2X^{2A}$, —CN, —COOH, —$CONH_2$, $R^{23A}$-substituted or unsubstituted alkyl (e.g., $C_1$-$C_8$, $C_1$-$C_6$, $C_1$-$C_4$, or $C_1$-$C_2$), $R^{23A}$-substituted or unsubstituted heteroalkyl (e.g., 2 to 8 membered, 2 to 6 membered, 4 to 6 membered, 2 to 3 membered, or 4 to 5 membered), $R^{23A}$-substituted or unsubstituted cycloalkyl (e.g., $C_3$-$C_8$, $C_3$-$C_6$, $C_4$-$C_6$, or $C_5$-$C_6$), $R^{23A}$-substituted or unsubstituted heterocycloalkyl (e.g., 3 to 8 membered, 3 to 6 membered, 4 to 6 membered, 4 to 5 membered, or 5 to 6 membered), $R^{23A}$-substituted or unsubstituted aryl (e.g., $C_6$-$C_{10}$ or phenyl), or $R^{23A}$-substituted or unsubstituted heteroaryl (e.g., 5 to 10 membered, 5 to 9 membered, or 5 to 6 membered). In embodiments, $R^{2A}$ is independently hydrogen, —$CX^{2A}{}_3$, —$CHX^{2A}{}_2$, —$CH_2X^{2A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2A}$ is independently —F, —Cl, —Br, or —I. In embodiments, $R^{2A}$ is independently hydrogen. In embodiments, $R^{2A}$ is independently unsubstituted methyl. In embodiments, $R^{2A}$ is independently unsubstituted ethyl.

In embodiments, $R^{2A}$ and $R^{2B}$ substituents bonded to the same nitrogen atom may optionally be joined to form a $R^{23A}$-substituted or unsubstituted heterocycloalkyl (e.g., 3 to 8 membered, 3 to 6 membered, 4 to 6 membered, 4 to 5 membered, or 5 to 6 membered) or $R^{23A}$-substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form a $R^{23A}$ substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{23A}$ is independently oxo, halogen, —$CX^{23A}{}_3$, —$CHX^{23A}{}_2$, —$CH_2X^{23A}$, —$OCX^{23A}{}_3$, —$OCH_2X^{23A}$, —$OCHX^{23A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23A}$ is independently —F, —Cl, —Br, or —I. In embodiments, $R^{23A}$ is independently unsubstituted methyl. In embodiments, $R^{23A}$ is independently unsubstituted ethyl.

In embodiments, $R^{2B}$ is independently hydrogen, —$CX^{2B}{}_3$, —$CHX^{2B}{}_2$, —$CH_2X^{2B}$, —CN, —COOH, —$CONH_2$, $R^{23B}$-substituted or unsubstituted alkyl (e.g., $C_1$-$C_8$, $C_1$-$C_6$, $C_1$-$C_4$, or $C_1$-$C_2$), $R^{23B}$-substituted or unsubstituted heteroalkyl (e.g., 2 to 8 membered, 2 to 6 membered, 4 to 6 membered, 2 to 3 membered, or 4 to 5 membered), $R^{23B}$-substituted or unsubstituted cycloalkyl (e.g., $C_3$-$C_8$, $C_3$-$C_6$, $C_4$-$C_6$, or $C_5$-$C_6$), $R^{23B}$-substituted or unsubstituted heterocycloalkyl (e.g., 3 to 8 membered, 3 to 6 membered, 4 to 6 membered, 4 to 5 membered, or 5 to 6 membered), $R^{23B}$-substituted or unsubstituted aryl (e.g., $C_6$-$C_{10}$ or phenyl), or $R^{23B}$-substituted or unsubstituted heteroaryl (e.g., 5 to 10 membered, 5 to 9 membered, or 5 to 6 membered). In embodiments, $R^{2B}$ is independently hydrogen, —$CX^{2B}{}_3$, —$CHX^{2B}{}_2$, —$CH_2X^{2B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2B}$ is independently —F, —Cl, —Br, or —I. In embodiments, $R^{2B}$ is independently hydrogen. In embodiments, $R^{2B}$ is independently unsubstituted methyl. In embodiments, $R^{2B}$ is independently unsubstituted ethyl.

In embodiments, $R^{2A}$ and $R^{2B}$ substituents bonded to the same nitrogen atom may optionally be joined to form a $R^{23B}$-substituted or unsubstituted heterocycloalkyl (e.g., 3 to 8 membered, 3 to 6 membered, 4 to 6 membered, 4 to 5 membered, or 5 to 6 membered) or $R^{23B}$ substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form a $R^{23B}$ substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{23B}$ is independently oxo, halogen, $-CX^{23B}_3$, $-CHX^{23B}_2$, $-CH_2X^{23B}$, $-OCX^{23B}_3$, $-OCH_2X^{23B}$, $-OCHX^{23B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23B}$ is independently $-F$, $-Cl$, $-Br$, or $-I$. In embodiments, $R^{23B}$ is independently unsubstituted methyl. In embodiments, $R^{23B}$ is independently unsubstituted ethyl.

In embodiments, $R^{2C}$ is independently hydrogen, $-CX^{2C}_3$, $-CHX^{2C}_2$, $-CH_2X^{2C}$, $-CN$, $-COOH$, $-CONH_2$, $R^{23C}$-substituted or unsubstituted alkyl (e.g., $C_1$-$C_8$, $C_1$-$C_6$, $C_1$-$C_4$, or $C_1$-$C_2$), $R^{23C}$-substituted or unsubstituted heteroalkyl (e.g., 2 to 8 membered, 2 to 6 membered, 4 to 6 membered, 2 to 3 membered, or 4 to 5 membered), $R^{23C}$-substituted or unsubstituted cycloalkyl (e.g., $C_3$-$C_8$, $C_3$-$C_6$, $C_4$-$C_6$, or $C_5$-$C_6$), $R^{23C}$-substituted or unsubstituted heterocycloalkyl (e.g., 3 to 8 membered, 3 to 6 membered, 4 to 6 membered, 4 to 5 membered, or 5 to 6 membered), $R^{23C}$-substituted or unsubstituted aryl (e.g., $C_6$-$C_{10}$ or phenyl), or $R^{23C}$-substituted or unsubstituted heteroaryl (e.g., 5 to 10 membered, 5 to 9 membered, or 5 to 6 membered). In embodiments, $R^{2C}$ is independently hydrogen, $-CX^{2C}_3$, $-CHX^{2C}_2$, $-CH_2X^{2C}$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2C}$ is independently $-F$, $-Cl$, $-Br$, or $-I$. In embodiments, $R^{2C}$ is independently hydrogen. In embodiments, $R^{2C}$ is independently unsubstituted methyl. In embodiments, $R^{2C}$ is independently unsubstituted ethyl.

$R^{23C}$ is independently oxo, halogen, $-CX^{23C}_3$, $-CHX^{23C}_2$, $-CH_2X^{23C}$, $-OCX^{23C}_3$, $-OCH_2X^{23C}$, $-OCHX^{23C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23C}$ is independently $-F$, $-Cl$, $-Br$, or $-I$. In embodiments, $R^{23C}$ is independently unsubstituted methyl. In embodiments, $R^{23C}$ is independently unsubstituted ethyl.

In embodiments, $R^{2D}$ is independently hydrogen, $-CX^{2D}_3$, $-CHX^{2D}_2$, $-CH_2X^{2D}$, $-CN$, $-COOH$, $-CONH_2$, $R^{23D}$-substituted or unsubstituted alkyl (e.g., $C_1$-$C_8$, $C_1$-$C_6$, $C_1$-$C_4$, or $C_1$-$C_2$), $R^{23D}$-substituted or unsubstituted heteroalkyl (e.g., 2 to 8 membered, 2 to 6 membered, 4 to 6 membered, 2 to 3 membered, or 4 to 5 membered), $R^{23D}$-substituted or unsubstituted cycloalkyl (e.g., $C_3$-$C_8$, $C_3$-$C_6$, $C_4$-$C_6$, or $C_5$-$C_6$), $R^{23D}$-substituted or unsubstituted heterocycloalkyl (e.g., 3 to 8 membered, 3 to 6 membered, 4 to 6 membered, 4 to 5 membered, or 5 to 6 membered), $R^{23D}$-substituted or unsubstituted aryl (e.g., $C_6$-$C_{10}$ or phenyl), or $R^{23D}$-substituted or unsubstituted heteroaryl (e.g., 5 to 10 membered, 5 to 9 membered, or 5 to 6 membered). In embodiments, $R^{2D}$ is independently hydrogen, $-CX^{2D}_3$, $-CHX^{2D}_2$, $-CH_2X^{2D}$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2D}$ is independently $-F$, $-Cl$, $-Br$, or $-I$. In embodiments, $R^{2D}$ is independently hydrogen. In embodiments, $R^{2D}$ is independently unsubstituted methyl. In embodiments, $R^{2D}$ is independently unsubstituted ethyl.

$R^{23D}$ is independently oxo, halogen, $-CX^{23D}_3$, $-CHX^{23D}_2$, $-CH_2X^{23D}$, $-OCX^{23D}_3$, $-OCH_2X^{23D}$, $-OCHX^{23D}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23D}$ is independently $-F$, —Cl, —Br, or —I. In embodiments, $R^{23D}$ is independently unsubstituted methyl. In embodiments, $R^{23D}$ is independently unsubstituted ethyl.

$L^3$ is a bond, —N(H)—, —O—, —S—, —C(O)—, —C(O)N(H)—, —N(H)C(O)—, —N(H)C(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), or substituted or unsubstituted heteroalkylene (e.g., 2 to 8 membered, 2 to 6 membered, 4 to 6 membered, 2 to 3 membered, or 4 to 5 membered). In embodiments, $L^3$ is a bond, —N(H)—, —O—, —S—, —C(O)—, —C(O)N(H)—, —N(H)C(O)—, —N(H)C(O)NH—, —C(O)O—, —OC(O)—, unsubstituted alkylene, or unsubstituted heteroalkylene. In embodiments, $L^3$ is a bond, —C(O)—, —C(O)N(CH$_3$)—, —N(CH$_3$)—, or —NH—. In embodiments, $L^3$ is a bond. In embodiments, $L^3$ is —O—. In embodiments, $L^3$ is —S—. In embodiments, $L^3$ is —C(O)—. In embodiments, $L^3$ is —NH—. In embodiments, $L^3$ is —C(O)NH—. In embodiments, $L^3$ is —NHC(O)—. In embodiments, $L^3$ is —N(CH$_3$)—. In embodiments, $L^3$ is —C(O)N(CH$_3$)—. In embodiments, $L^3$ is —N(CH$_2$CH$_3$)—. In embodiments, $L^3$ is —C(O)N(CH$_2$CH$_3$)—. In embodiments, $L^3$ is —N(H)C(O)NH—.

In embodiments, $L^3$ is independently substituted or unsubstituted alkylene (e.g., $C_1$-$C_8$, $C_1$-$C_6$, $C_1$-$C_4$, or $C_1$-$C_2$). In embodiments, $L^3$ is independently substituted alkylene (e.g., $C_1$-$C_8$, $C_1$-$C_6$, $C_1$-$C_4$, or $C_1$-$C_2$). In embodiments, $L^3$ is independently unsubstituted alkylene (e.g., $C_1$-$C_8$, $C_1$-$C_6$, $C_1$-$C_4$, or $C_1$-$C_2$). In embodiments, $L^3$ is independently unsubstituted methylene. In embodiments, $L^3$ is independently unsubstituted ethylene. In embodiments, $L^3$ is independently unsubstituted propylene. In embodiments, $L^3$ is independently unsubstituted isopropylene. In embodiments, $L^3$ is independently unsubstituted tert-butylene. In embodiments, $L^3$ is independently substituted or unsubstituted heteroalkylene (e.g., 2 to 8 membered, 2 to 6 membered, 4 to 6 membered, 2 to 3 membered, or 4 to 5 membered). In embodiments, $L^3$ is independently substituted heteroalkylene (e.g., 2 to 8 membered, 2 to 6 membered, 4 to 6 membered, 2 to 3 membered, or 4 to 5 membered). In embodiments, $L^3$ is independently unsubstituted heteroalkylene (e.g., 2 to 8 membered, 2 to 6 membered, 4 to 6 membered, 2 to 3 membered, or 4 to 5 membered).

In embodiments, $L^3$ is independently bond, —N(H)—, —O—, —S—, —C(O)—, —C(O)N(H)—, —N(H)C(O)—, —N(H)C(O)NH—, —C(O)O—, —OC(O)—, $R^{44}$-substituted or unsubstituted alkylene (e.g., $C_1$-$C_8$, $C_1$-$C_6$, $C_1$-$C_4$, or $C_1$-$C_2$), or $R^{44}$-substituted or unsubstituted heteroalkylene (e.g., 2 to 8 membered, 2 to 6 membered, 4 to 6 membered, 2 to 3 membered, or 4 to 5 membered). In embodiments, $L^3$ is independently bond, —N(H)—, —O—, —S—, —C(O)—, —C(O)N(H)—, —N(H)C(O)—, —N(H)C(O)NH—, —C(O)O—, —OC(O)—, unsubstituted alkylene (e.g., $C_1$-$C_8$, $C_1$-$C_6$, $C_1$-$C_4$, or $C_1$-$C_2$), or unsubstituted heteroalkylene (e.g., 2 to 8 membered, 2 to 6 membered, 4 to 6 membered, 2 to 3 membered, or 4 to 5 membered).

In embodiments, $L^3$ is independently a bond, —N(H)—, —C(O)N(H)—, —N(H)C(O)—, —N(H)C(O)NH—, —NHC(O)N(H)—, —C(O)O—, —OC(O)—, substituted or unsubstituted alkylene, or substituted or unsubstituted heteroalkylene. In embodiments, $L^3$ is independently —N(H)—, —C(O)N(H)—, or —N(H)C(O)—. In embodiments, $L^3$ is independently —N(H)—.

$R^{44}$ is independently oxo, halogen, —CX$^{44}_3$, —CHX$^{44}_2$, —CH$_2$X$^{44}$, —OCX$^{44}_3$, —OCH$_2$X$^{44}$, —OCHX$^{44}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{45}$-substituted or unsubstituted alkyl (e.g., $C_1$-$C_8$, $C_1$-$C_6$, $C_1$-$C_4$, or $C_1$-$C_2$), $R^{45}$-substituted or unsubstituted heteroalkyl (e.g., 2 to 8 membered, 2 to 6 membered, 4 to 6 membered, 2 to 3 membered, or 4 to 5 membered), $R^{45}$-substituted or unsubstituted cycloalkyl (e.g., $C_3$-$C_8$, $C_3$-$C_6$, $C_4$-$C_6$, or $C_5$-$C_6$), $R^{45}$-substituted or unsubstituted heterocycloalkyl (e.g., 3 to 8 membered, 3 to 6 membered, 4 to 6 membered, 4 to 5 membered, or 5 to 6 membered), $R^{45}$-substituted or unsubstituted aryl (e.g., $C_6$-$C_{10}$ or phenyl), or $R^{45}$-substituted or unsubstituted heteroaryl (e.g., 5 to 10 membered, 5 to 9 membered, or 5 to 6 membered). In embodiments, $R^{44}$ is independently oxo, halogen, —CX$^{44}_3$, —CHX$^{44}_2$, —CH$_2$X$^{44}$, —OCX$^{44}_3$, —OCH$_2$X$^{44}$, —OCHX$^{44}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{44}$ is independently —F, —Cl, —Br, or —I. In embodiments, $R^{44}$ is independently unsubstituted methyl. In embodiments, $R^{44}$ is independently unsubstituted ethyl.

$R^{45}$ is independently oxo, halogen, —CX$^{45}_3$, —CHX$^{45}_2$, —CH$_2$X$^{45}$, —OCX$^{45}_3$, —OCH$_2$X$^{45}$, —OCHX$^{45}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{46}$-substituted or unsubstituted alkyl (e.g., $C_1$-$C_8$, $C_1$-$C_6$, $C_1$-$C_4$, or $C_1$-$C_2$), $R^{46}$-substituted or unsubstituted heteroalkyl (e.g., 2 to 8 membered, 2 to 6 membered, 4 to 6 membered, 2 to 3 membered, or 4 to 5 membered), $R^{46}$-substituted or unsubstituted cycloalkyl (e.g., $C_3$-$C_8$, $C_3$-$C_6$, $C_4$-$C_6$, or $C_5$-$C_6$), $R^{46}$-substituted or unsubstituted heterocycloalkyl (e.g., 3 to 8 membered, 3 to 6 membered, 4 to 6 membered, 4 to 5 membered, or 5 to 6 membered), $R^{46}$-substituted or unsubstituted aryl (e.g., $C_6$-$C_{10}$ or phenyl), or $R^{46}$-substituted or unsubstituted heteroaryl (e.g., 5 to 10 membered, 5 to 9 membered, or 5 to 6 membered). In embodiments, $R^{45}$ is independently oxo, halogen, —CX$^{45}_3$, —CHX$^{45}_2$, —CH$_2$X$^{45}$, —OCX$^{45}_3$, —OCH$_2$X$^{45}$, —OCHX$^{45}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{45}$ is independently —F, —Cl, —Br, or —I. In embodiments, $R^{45}$ is independently unsubstituted methyl. In embodiments, $R^{45}$ is independently unsubstituted ethyl.

$R^{46}$ is independently oxo, halogen, $-CX^{46}_3$, $-CHX^{46}_2$, $-CH_2X^{46}$, $-OCX^{46}_3$, $-OCH_2X^{46}$, $-OCHX^{46}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{46}$ is independently $-F$, $-Cl$, $-Br$, or $-I$. In embodiments, $R^{46}$ is independently unsubstituted methyl. In embodiments, $R^{46}$ is independently unsubstituted ethyl.

In embodiments, $R^7$ is independently halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^7$ is independently halogen, $-CX^7_3$, $-CHX^7_2$, $-CH_2X^7$, $-OCX^7_3$, $-OCH_2X^7$, $-OCHX^7_2$, substituted or unsubstituted alkyl, or substituted or unsubstituted heteroalkyl. In embodiments, $R^7$ is independently halogen, $-CX^7_3$, $-CHX^7_2$, $-CH_2X^7$, $-OCX^7_3$, $-OCH_2X^7$, $-OCHX^7_2$, substituted or unsubstituted ($C_1$-$C_4$) alkyl, or substituted or unsubstituted 2 to 4 membered heteroalkyl. In embodiments, $R^7$ is independently halogen, $-CH_3$, $-CH_2CH_3$, $-CX^7_3$, $-CHX^7_2$, $-CH_2X^7$, $-OCH_3$, $-OCX^7_3$, $-OCH_2X^7$, $-OCHX^7_2$, $-SCH_3$, $-SCX^7_3$, $-SCH_2X^7$, or $-SCHX^7_2$. In embodiments, $R^7$ is independently halogen, $-CH_3$, $-CH_2CH_3$, $-CF_3$, or $-OCH_3$. In embodiments, $R^7$ is independently $-CH_3$, $-CH_2CH_3$, or $-OCH_3$. In embodiments, $R^7$ is independently $-OCH_3$. In embodiments, $R^7$ is independently halogen, $-CX^7_3$, $-CHX^7_2$, $-CH_2X^7$, $-OCX^7_3$, $-OCH_2X^7$, $-OCHX^7_2$, $-CN$, substituted or unsubstituted alkyl, or substituted or unsubstituted heteroalkyl. In embodiments, $R^7$ is independently halogen, $-CX^7_3$, $-CHX^7_2$, $-CH_2X^7$, $-OCX^7_3$, $-OCH_2X^7$, $-OCHX^7_2$, $-CN$, substituted or unsubstituted ($C_1$-$C_4$) alkyl, or substituted or unsubstituted 2 to 4 membered heteroalkyl. In embodiments, $R^7$ is independently halogen, $-CH_3$, $-CH_2CH_3$, $-CX^7_3$, $-CHX^7_2$, $-CH_2X^7$, $-OCH_3$, $-OCX^7_3$, $-OCH_2X^7$, $-OCHX^7_2$, $-CN$, $-SCH_3$, $-SCX^7_3$, $-SCH_2X^7$, or $-SCHX^7_2$. In embodiments, $R^7$ is independently halogen, $-CN$, $-CH_3$, $-CF_3$, or $-OCH_3$. In embodiments, $R^7$ is independently halogen or $-CH_3$. In embodiments, $R^7$ is independently $-Cl$ or $-CH_3$. In embodiments, $R^7$ is independently $-CH_3$. In embodiments, $R^7$ is independently $-Cl$. In embodiments, $R^7$ is independently $-F$. In embodiments, $R^7$ is independently $-Br$. In embodiments, $R^7$ is independently $-I$. In embodiments, $R^7$ is independently $-CH_3$ or $-CH_2CH_3$. In embodiments, $X^7$ is independently $-Cl$. In embodiments, $X^7$ is independently $-F$. In embodiments, $X^7$ is independently $-Br$. In embodiments, $X^7$ is independently $-I$.

In embodiments, $R^7$ is independently halogen, $-CX^7_3$, $-CN$, $-OH$, $-NH_2$, $-SH$, $-OCX^7_3$, $-OCHX^7_2$, $-OCH_2X^7$, $-CHX^7_2$, $-CH_2X^7$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^7$ is independently halogen, $-CX^7_3$, $-CN$, $-OH$, $-NH_2$, $-SH$, $-OCX^7_3$, $-OCHX^7_2$, $-OCH_2X^7$, $-CHX^7_2$, $-CH_2X^7$, unsubstituted $C_1$-$C_4$ alkyl, or unsubstituted 2 to 4 membered heteroalkyl.

In embodiments, $R^7$ is independently halogen. In embodiments, $R^7$ is independently $-CX^7_3$. In embodiments, $R^7$ is independently $-CHX^7_2$. In embodiments, $R^7$ is independently $-CH_2X^7$. In embodiments, $R^7$ is independently $-OCX^7_3$. In embodiments, $R^7$ is independently $-OCH_2X^7$. In embodiments, $R^7$ is independently $-OCHX^7_2$. In embodiments, $R^7$ is independently $-CN$. In embodiments, $R^7$ is independently $-SO_{n7}R^{7D}$. In embodiments, $R^7$ is independently $-SO_{v7}NR^{7A}R^{7B}$. In embodiments, $R^7$ is independently $-NHC(O)NR^{7A}R^{7B}$. In embodiments, $R^7$ is independently $-N(O)_{m7}$. In embodiments, $R^7$ is independently $-NR^{7A}R^{7B}$. In embodiments, $R^7$ is independently $-C(O)R^{7C}$. In embodiments, $R^7$ is independently $-C(O)-OR^{7C}$. In embodiments, $R^7$ is independently $-C(O)NR^{7A}R^{7B}$. In embodiments, $R^7$ is independently $-OR^{7D}$. In embodiments, $R^7$ is independently $-SR^{7D}$. In embodiments, $R^7$ is independently $-NR^{7A}SO_2R^{7D}$. In embodiments, $R^7$ is independently $-NR^{7A}C(O)R^{7C}$. In embodiments, $R^7$ is independently $-NR^{7A}C(O)OR^{7C}$. In embodiments, $R^7$ is independently $-NR^{7A}OR^{7C}$. In embodiments, $R^7$ is independently $-OH$. In embodiments, $R^7$ is independently $-NH_2$. In embodiments, $R^7$ is independently $-COOH$. In embodiments, $R^7$ is independently $-CONH_2$. In embodiments, $R^7$ is independently $-NO_2$. In embodiments, $R^7$ is independently $-SH$. In embodiments, $R^7$ is independently $-CF_3$. In embodiments, $R^7$ is independently $-CHF_2$. In embodiments, $R^7$ is independently $-CH_2F$. In embodiments, $R^7$ is independently $-OCF_3$. In embodiments, $R^7$ is independently $-OCH_2F$. In embodiments, $R^7$ is independently $-OCHF_2$. In embodiments, $R^7$ is independently $-OCH_3$. In embodiments, $R^7$ is independently $-OCH_2CH_3$. In embodiments, $R^7$ is independently $-OCH_2CH_2CH_3$. In embodiments, $R^7$ is independently $-OCH(CH_3)_2$. In embodiments, $R^7$ is independently $-OC(CH_3)_3$. In embodiments, $R^7$ is independently $-SCH_3$. In embodiments, $R^7$ is independently $-SCH_2CH_3$. In embodiments, $R^7$ is independently $-SCH_2CH_2CH_3$. In embodiments, $R^7$ is independently $-SCH(CH_3)_2$. In embodiments, $R^7$ is independently $-SC(CH_3)_3$. In embodiments, $R^7$ is independently $-CH_3$. In embodiments, $R^7$ is independently $-CH_2CH_3$. In embodiments, $R^7$ is independently $-CH_2CH_2CH_3$. In embodiments, $R^7$ is independently $-CH(CH_3)_2$. In embodiments, $R^7$ is independently $-C(CH_3)_3$. In embodiments, $R^7$ is independently $-F$. In embodiments, $R^7$ is independently $-Cl$. In embodiments, $R^7$ is independently $-Br$. In embodiments, $R^7$ is independently $-I$.

In embodiments, $R^7$ is independently substituted or unsubstituted alkyl (e.g., $C_1$-$C_8$, $C_1$-$C_6$, $C_1$-$C_4$, or $C_1$-$C_2$). In embodiments, $R^7$ is independently substituted alkyl (e.g., $C_1$-$C_8$, $C_1$-$C_6$, $C_1$-$C_4$, or $C_1$-$C_2$). In embodiments, $R^7$ is independently unsubstituted alkyl (e.g., $C_1$-$C_8$, $C_1$-$C_6$, $C_1$-$C_4$, or $C_1$-$C_2$). In embodiments, $R^7$ is independently unsubstituted methyl. In embodiments, $R^7$ is independently unsubstituted ethyl. In embodiments, $R^7$ is independently unsubstituted propyl. In embodiments, $R^7$ is independently unsubstituted isopropyl. In embodiments, $R^7$ is independently unsubstituted tert-butyl. In embodiments, $R^7$ is independently substituted or unsubstituted heteroalkyl (e.g., 2 to 8 membered, 2 to 6 membered, 4 to 6 membered, 2 to 3 membered, or 4 to 5 membered). In embodiments, $R^7$ is independently substituted heteroalkyl (e.g., 2 to 8 membered, 2 to 6 membered, 4 to 6 membered, 2 to 3 membered, or 4 to 5 membered). In embodiments, $R^7$ is independently unsubstituted heteroalkyl (e.g., 2 to 8 membered, 2 to 6 membered, 4 to 6 membered, 2 to 3 membered, or 4 to 5 membered). In embodiments, $R^7$ is independently substituted or unsubstituted cycloalkyl (e.g., $C_3$-$C_8$, $C_3$-$C_6$, $C_4$-$C_6$, or $C_5$-$C_6$). In embodiments, $R^7$ is independently substituted cycloalkyl (e.g., $C_3$-$C_8$, $C_3$-$C_6$, $C_4$-$C_6$, or $C_5$-$C_6$). In embodiments, $R^7$ is independently unsubstituted cycloalkyl (e.g., $C_3$-$C_8$, $C_3$-$C_6$, $C_4$-$C_6$, or $C_5$-$C_6$). In embodiments, $R^7$ is independently substituted or unsubstituted heterocycloalkyl (e.g., 3 to 8 membered, 3 to 6 membered, 4 to 6 membered, 4 to 5 membered, or 5 to 6 membered). In embodiments, $R^7$ is independently substituted heterocycloalkyl (e.g., 3 to 8 membered, 3 to 6 membered, 4 to 6 membered, 4 to 5 membered, or 5 to 6 membered). In embodiments, R' is independently unsubstituted heterocycloalkyl (e.g., 3 to 8 membered, 3 to 6 membered, 4 to 6 membered, 4 to 5 membered, or 5 to 6 membered). In embodiments, $R^7$ is independently substituted or unsubstituted aryl (e.g., $C_6$-$C_{10}$ or phenyl). In embodiments, $R^7$ is independently substituted aryl (e.g., $C_6$-$C_{10}$ or phenyl). In embodiments, $R^7$ is independently unsubstituted aryl (e.g., $C_6$-$C_{10}$ or phenyl). In embodiments, $R^7$ is independently substituted or unsubstituted heteroaryl (e.g., 5 to 10 membered, 5 to 9 membered, or 5 to 6 membered). In embodiments, $R^7$ is independently substituted heteroaryl (e.g., 5 to 10 membered, 5 to 9 membered, or 5 to 6 membered). In embodiments, $R^7$ is independently unsubstituted heteroaryl (e.g., 5 to 10 membered, 5 to 9 membered, or 5 to 6 membered).

In embodiments, $R^7$ is independently halogen, —$CX^7_3$, —$CHX^7_2$, —$CH_2X^7$, —$OCX^7_3$, —$OCH_2X^7$, —$OCHX^7_2$, —CN, substituted or unsubstituted alkyl, or substituted or unsubstituted heteroalkyl. In embodiments, $R^7$ is independently halogen, —$CX^7_3$, —$CHX^7_2$, —$CH_2X^7$, —$OCX^7_3$, —$OCH_2X^7$, or —$OCHX^7_2$. In embodiments, $R^7$ is independently halogen. In embodiments, $R^7$ is independently —Cl.

In embodiments, $R^{7A}$ is independently hydrogen. In embodiments, $R^{7A}$ is independently —$CX^{7A}_3$. In embodiments, $R^{7A}$ is independently —$CHX^{7A}_2$. In embodiments, $R^{7A}$ is independently —$CH_2X^{7A}$. In embodiments, $R^{7A}$ is independently —CN. In embodiments, $R^{7A}$ is independently —COOH. In embodiments, $R^{7A}$ is independently —$CONH_2$. In embodiments, $X^{7A}$ is independently —F, —Cl, —Br, or —I.

In embodiments, $R^{7A}$ is independently substituted or unsubstituted alkyl (e.g., $C_1$-$C_8$, $C_1$-$C_6$, $C_1$-$C_4$, or $C_1$-$C_2$). In embodiments, $R^{7A}$ is independently substituted alkyl (e.g., $C_1$-$C_8$, $C_1$-$C_6$, $C_1$-$C_4$, or $C_1$-$C_2$). In embodiments, $R^{7A}$ is independently unsubstituted alkyl (e.g., $C_1$-$C_8$, $C_1$-$C_6$, $C_1$-$C_4$, or $C_1$-$C_2$). In embodiments, $R^{7A}$ is independently unsubstituted methyl. In embodiments, $R^{7A}$ is independently unsubstituted ethyl. In embodiments, $R^{7A}$ is independently unsubstituted propyl. In embodiments, $R^{7A}$ is independently unsubstituted isopropyl. In embodiments, $R^{7A}$ is independently unsubstituted tert-butyl. In embodiments, $R^{7A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{7A}$ is independently substituted heteroalkyl (e.g., 2 to 8 membered, 2 to 6 membered, 4 to 6 membered, 2 to 3 membered, or 4 to 5 membered). In embodiments, $R^{7A}$ is independently unsubstituted heteroalkyl (e.g., 2 to 8 membered, 2 to 6 membered, 4 to 6 membered, 2 to 3 membered, or 4 to 5 membered). In embodiments, $R^{7A}$ is independently substituted or unsubstituted cycloalkyl (e.g., $C_3$-$C_8$, $C_3$-$C_6$, $C_4$-$C_6$, or $C_5$-$C_6$). In embodiments, $R^{7A}$ is independently substituted cycloalkyl (e.g., $C_3$-$C_8$, $C_3$-$C_6$, $C_4$-$C_6$, or $C_5$-$C_6$). In embodiments, $R^{7A}$ is independently unsubstituted cycloalkyl (e.g., $C_3$-$C_8$, $C_3$-$C_6$, $C_4$-$C_6$, or $C_5$-$C_6$). In embodiments, $R^{7A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ is independently substituted heterocycloalkyl (e.g., 3 to 8 membered, 3 to 6 membered, 4 to 6 membered, 4 to 5 membered, or 5 to 6 membered). In embodiments, $R^{7A}$ is independently unsubstituted heterocycloalkyl (e.g., 3 to 8 membered, 3 to 6 membered, 4 to 6 membered, 4 to 5 membered, or 5 to 6 membered). In embodiments, $R^{7A}$ is independently substituted or unsubstituted aryl (e.g., $C_6$-$C_{10}$ or phenyl). In embodiments, $R^{7A}$ is independently substituted aryl (e.g., $C_6$-$C_{10}$ or phenyl). In embodiments, $R^{7A}$ is independently unsubstituted aryl (e.g., $C_6$-$C_{10}$ or phenyl). In embodiments, $R^{7A}$ is independently substituted or unsubstituted heteroaryl (e.g., 5 to 10 membered, 5 to 9 membered, or 5 to 6 membered). In embodiments, $R^{7A}$ is independently substituted heteroaryl (e.g., 5 to 10 membered, 5 to 9 membered, or 5 to 6 membered). In embodiments, $R^{7A}$ is independently unsubstituted heteroaryl (e.g., 5 to 10 membered, 5 to 9 membered, or 5 to 6 membered).

In embodiments, $R^{7B}$ is independently hydrogen. In embodiments, $R^{7B}$ is independently —$CX^{7B}_3$. In embodiments, $R^{7B}$ is independently —$CHX^{7B}_2$. In embodiments, $R^{7B}$ is independently —$CH_2X^{7B}$. In embodiments, $R^{7B}$ is independently —CN. In embodiments, $R^{7B}$ is independently —COOH. In embodiments, $R^{7B}$ is independently —$CONH_2$. In embodiments, $X^{7B}$ is independently —F, —Cl, —Br, or —I.

In embodiments, $R^{7B}$ is independently substituted or unsubstituted alkyl (e.g., $C_1$-$C_8$, $C_1$-$C_6$, $C_1$-$C_4$, or $C_1$-$C_2$). In embodiments, $R^{7B}$ is independently substituted alkyl (e.g., $C_1$-$C_8$, $C_1$-$C_6$, $C_1$-$C_4$, or $C_1$-$C_2$). In embodiments, $R^{7B}$ is independently unsubstituted alkyl (e.g., $C_1$-$C_8$, $C_1$-$C_6$, $C_1$-$C_4$, or $C_1$-$C_2$). In embodiments, $R^{7B}$ is independently unsubstituted methyl. In embodiments, $R^{7B}$ is independently unsubstituted ethyl. In embodiments, $R^{7B}$ is independently unsubstituted propyl. In embodiments, $R^{7B}$ is independently unsubstituted isopropyl. In embodiments, $R^{7B}$ is independently unsubstituted tert-butyl. In embodiments, $R^{7B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{7B}$ is independently substituted heteroalkyl (e.g., 2 to 8 membered, 2 to 6 membered, 4 to 6 membered, 2 to 3 membered, or 4 to 5 membered). In embodiments, $R^{7B}$ is independently unsubstituted heteroalkyl (e.g., 2 to 8 membered, 2 to 6 membered, 4 to 6 membered, 2 to 3 membered, or 4 to 5 membered). In embodiments, $R^{7B}$ is independently substituted or unsubstituted cycloalkyl (e.g., $C_3$-$C_8$, $C_3$-$C_6$, $C_4$-$C_6$, or $C_5$-$C_6$). In embodiments, $R^{7B}$ is independently substituted cycloalkyl (e.g., $C_3$-$C_8$, $C_3$-$C_6$, $C_4$-$C_6$, or $C_5$-$C_6$). In embodiments, $R^{7B}$ is independently unsubstituted cycloalkyl (e.g., $C_3$-$C_8$, $C_3$-$C_6$, $C_4$-$C_6$, or $C_5$-$C_6$). In embodiments, $R^{7B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{7B}$ is independently substituted heterocycloalkyl (e.g., 3 to 8 membered, 3 to 6 membered, 4 to 6 membered, 4 to 5 membered, or 5 to 6 membered). In embodiments, $R^{7B}$ is independently unsubstituted heterocycloalkyl (e.g., 3 to 8 membered, 3 to 6 membered, 4 to 6 membered, 4 to 5 membered, or 5 to 6 membered). In embodiments, $R^{7B}$ is independently substituted or unsubstituted aryl (e.g., $C_6$-$C_{10}$ or phenyl). In embodiments, $R^{7B}$ is independently substituted aryl (e.g., $C_6$-$C_{10}$ or phenyl). In embodiments, $R^{7B}$ is independently unsubstituted aryl (e.g., $C_6$-$C_{10}$ or phenyl). In embodiments, $R^{7B}$ is independently substituted or unsubstituted heteroaryl (e.g., 5 to 10 membered, 5 to 9 membered, or 5 to 6 membered). In embodiments, $R^{7B}$ is independently substituted heteroaryl (e.g., 5 to 10 membered, 5 to 9 membered, or 5 to 6 membered). In embodiments, $R^{7B}$ is independently unsubstituted heteroaryl (e.g., 5 to 10 membered, 5 to 9 membered, or 5 to 6 membered).

In embodiments, $R^{7A}$ and $R^{7B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{7A}$ and $R^{7B}$ substituents bonded to the same nitrogen atom may be joined to form a substituted or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may be joined to form a substituted heteroaryl (e.g., 5 to 10 membered, 5 to 9 membered, or 5 to 6 membered). In embodiments, $R^{7A}$ and $R^{7B}$ substituents bonded to the same nitrogen atom may be joined to form an unsubstituted heteroaryl (e.g., 5 to 10 membered, 5 to 9 membered, or 5 to 6 membered).

In embodiments, $R^{7C}$ is independently hydrogen. In embodiments, $R^{7C}$ is independently —$CX^{7C}_3$. In embodiments, $R^{7C}$ is independently —$CHX^{7C}_2$. In embodiments, $R^{7C}$ is independently —$CH_2X^{7C}$. In embodiments, $R^{7C}$ is independently —CN. In embodiments, $R^{7C}$ is independently —COOH. In embodiments, $R^{7C}$ is independently —$CONH_2$. In embodiments, $X^{7C}$ is independently —F, —Cl, —Br, or —I.

In embodiments, $R^{7C}$ is independently substituted or unsubstituted alkyl (e.g., $C_1$-$C_8$, $C_1$-$C_6$, $C_1$-$C_4$, or $C_1$-$C_2$). In embodiments, $R^{7C}$ is independently substituted alkyl (e.g., $C_1$-$C_8$, $C_1$-$C_6$, $C_1$-$C_4$, or $C_1$-$C_2$). In embodiments, $R^{7C}$ is independently unsubstituted alkyl (e.g., $C_1$-$C_8$, $C_1$-$C_6$, $C_1$-$C_4$, or $C_1$-$C_2$). In embodiments, $R^{7C}$ is independently unsubstituted methyl. In embodiments, $R^{7C}$ is independently unsubstituted ethyl. In embodiments, $R^{7C}$ is independently unsubstituted propyl. In embodiments, $R^{7C}$ is independently unsubstituted isopropyl. In embodiments, $R^{7C}$ is independently unsubstituted tert-butyl. In embodiments, $R^{7C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{7C}$ is independently substituted heteroalkyl (e.g., 2 to 8 membered, 2 to 6 membered, 4 to 6 membered, 2 to 3 membered, or 4 to 5 membered). In embodiments, $R^{7C}$ is independently unsubstituted heteroalkyl (e.g., 2 to 8 membered, 2 to 6 membered, 4 to 6 membered, 2 to 3 membered, or 4 to 5 membered). In embodiments, $R^{7C}$ is independently substituted or unsubstituted cycloalkyl (e.g., $C_3$-$C_8$, $C_3$-$C_6$, $C_4$-$C_6$, or $C_5$-$C_6$). In embodiments, $R^{7C}$ is independently substituted cycloalkyl (e.g., $C_3$-$C_8$, $C_3$-$C_6$, $C_4$-$C_6$, or $C_5$-$C_6$). In embodiments, $R^{7C}$ is independently unsubstituted cycloalkyl (e.g., $C_3$-$C_8$, $C_3$-$C_6$, $C_4$-$C_6$, or $C_5$-$C_6$). In embodiments, $R^{7C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{7C}$ is independently substituted heterocycloalkyl (e.g., 3 to 8 membered, 3 to 6 membered, 4 to 6 membered, 4 to 5 membered, or 5 to 6 membered). In embodiments, $R^{7C}$ is independently unsubstituted heterocycloalkyl (e.g., 3 to 8 membered, 3 to 6 membered, 4 to 6 membered, 4 to 5 membered, or 5 to 6 membered). In embodiments, $R^{7C}$ is independently substituted or unsubstituted aryl (e.g., $C_6$-$C_{10}$ or phenyl). In embodiments, $R^{7C}$ is independently substituted aryl (e.g., $C_6$-$C_{10}$ or phenyl). In embodiments, $R^{7C}$ is independently unsubstituted aryl (e.g., $C_6$-$C_{10}$ or phenyl). In embodiments, $R^{7C}$ is independently substituted or unsubstituted heteroaryl (e.g., 5 to 10 membered, 5 to 9 membered, or 5 to 6 membered). In embodiments, $R^{7C}$ is independently substituted heteroaryl (e.g., 5 to 10 membered, 5 to 9 membered, or 5 to 6 membered). In embodiments, $R^{7C}$ is independently unsubstituted heteroaryl (e.g., 5 to 10 membered, 5 to 9 membered, or 5 to 6 membered).

In embodiments, $R^{7D}$ is independently hydrogen. In embodiments, $R^{7D}$ is independently —$CX^{7D}_3$. In embodiments, $R^{7D}$ is independently —$CHX^{7D}_2$. In embodiments, $R^{7D}$ is independently —$CH_2X^{7D}$. In embodiments, $R^{7D}$ is independently —CN. In embodiments, $R^{7D}$ is independently —COOH. In embodiments, $R^{7D}$ is independently —$CONH_2$. In embodiments, $X^{7D}$ is independently —F, —Cl, —Br, or —I.

In embodiments, $R^{7D}$ is independently substituted or unsubstituted alkyl (e.g., $C_1$-$C_8$, $C_1$-$C_6$, $C_1$-$C_4$, or $C_1$-$C_2$). In embodiments, $R^{7D}$ is independently substituted alkyl (e.g., $C_1$-$C_8$, $C_1$-$C_6$, $C_1$-$C_4$, or $C_1$-$C_2$). In embodiments, $R^{7D}$ is independently unsubstituted alkyl (e.g., $C_1$-$C_8$, $C_1$-$C_6$, $C_1$-$C_4$, or $C_1$-$C_2$). In embodiments, $R^{7D}$ is independently unsubstituted methyl. In embodiments, $R^{7D}$ is independently unsubstituted ethyl. In embodiments, $R^{7D}$ is independently unsubstituted propyl. In embodiments, $R^{7D}$ is independently unsubstituted isopropyl. In embodiments, $R^{7D}$ is independently unsubstituted tert-butyl. In embodiments, $R^{7D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{7D}$ is independently substituted heteroalkyl (e.g., 2 to 8 membered, 2 to 6 membered, 4 to 6 membered, 2 to 3 membered, or 4 to 5 membered). In embodiments, $R^{7D}$ is independently unsubstituted heteroalkyl (e.g., 2 to 8 membered, 2 to 6 membered, 4 to 6 membered, 2 to 3 membered, or 4 to 5 membered). In embodiments, $R^{7D}$ is independently substituted or unsubstituted cycloalkyl (e.g., $C_3$-$C_8$, $C_3$-$C_6$, $C_4$-$C_6$, or $C_5$-$C_6$). In embodiments, $R^{7D}$ is independently substituted cycloalkyl (e.g., $C_3$-$C_8$, $C_3$-$C_6$, $C_4$-$C_6$, or $C_5$-$C_6$). In embodiments, $R^{7D}$ is independently unsubstituted cycloalkyl (e.g., $C_3$-$C_8$, $C_3$-$C_6$, $C_4$-$C_6$, or $C_5$-$C_6$). In embodiments, $R^{7D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{7D}$ is independently substituted heterocycloalkyl (e.g., 3 to 8 membered, 3 to 6 membered, 4 to 6 membered, 4 to 5 membered, or 5 to 6 membered). In embodiments, $R^{7D}$ is independently unsubstituted heterocycloalkyl (e.g., 3 to 8 membered, 3 to 6 membered, 4 to 6 membered, 4 to 5 membered, or 5 to 6 membered). In embodiments, $R^{7D}$ is independently substituted or unsubstituted aryl (e.g., $C_6$-$C_{10}$ or phenyl). In embodiments, $R^{7D}$ is independently substituted aryl (e.g., $C_6$-$C_{10}$ or phenyl). In embodiments, $R^{7D}$ is independently unsubstituted aryl (e.g., $C_6$-$C_{10}$ or phenyl). In embodiments, $R^{7D}$ is independently substituted or unsubstituted heteroaryl (e.g., 5 to 10 membered, 5 to 9 membered, or 5 to 6 membered). In embodiments, $R^{7D}$ is independently substituted heteroaryl (e.g., 5 to 10 membered, 5 to 9 membered, or 5 to 6 membered). In embodiments, $R^{7D}$ is independently unsubstituted heteroaryl (e.g., 5 to 10 membered, 5 to 9 membered, or 5 to 6 membered).

In embodiments, $R^7$ is independently halogen, —$CX^7_3$, —$CHX^7_2$, —$CH_2X^7$, —$OCX^7_3$, —$OCH_2X^7$, —$OCHX^7_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{38}$-substituted or unsubstituted alkyl (e.g., $C_1$-$C_8$, $C_1$-$C_6$, $C_1$-$C_4$, or $C_1$-$C_2$), $R^{38}$-substituted or unsubstituted heteroalkyl (e.g., 2 to 8 membered, 2 to 6 membered, 4 to 6 membered, 2 to 3 membered, or 4 to 5 membered), $R^{38}$-substituted or unsubstituted cycloalkyl (e.g., $C_3$-$C_8$, $C_3$-$C_6$, $C_4$-$C_6$, or $C_5$-$C_6$), $R^{38}$-substituted or unsubstituted heterocycloalkyl (e.g., 3 to 8 membered, 3 to 6 membered, 4 to 6 membered, 4 to 5 membered, or 5 to 6 membered), $R^{38}$-substituted or unsubstituted aryl (e.g., $C_6$-$C_{10}$ or phenyl), or $R^{38}$-substituted or unsubstituted heteroaryl (e.g., 5 to 10 membered, 5 to 9 membered, or 5 to 6 membered). In embodiments, $R^7$ is independently halogen, —$CX^7_3$, —$CHX^7_2$, —$CH_2X^7$, —$OCX^7_3$, —$OCH_2X^7$, —$OCHX^7_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^7$ is independently —F, —Cl, —Br, or —I. In embodiments, $R^7$ is independently unsubstituted methyl. In embodiments, $R^7$ is independently unsubstituted ethyl.

$R^{38}$ is independently oxo,
halogen, —$CX^{38}_3$, —$CHX^{38}_2$, —$CH_2X^{38}$, —$OCX^{38}_3$, —$OCH_2X^{38}$, —$OCHX^{38}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 8 membered, 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered). In embodiments, $R^{38}$ is independently oxo,
halogen, —$CX^{38}_3$, —$CHX^{38}_2$, —$CH_2X^{38}$, —$OCX^{38}_3$, —$OCH_2X^{38}$, —$OCHX^{38}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38}$ is independently —F, —Cl, —Br, or —I. In embodiments, $R^{38}$ is independently unsubstituted methyl. In embodiments, $R^{38}$ is independently unsubstituted ethyl.

$R^{39}$ is independently oxo,
halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 8 membered, 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered). In embodiments, $R^{39}$ is independently oxo,
halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{39}$ is independently —F, —Cl, —Br, or —I. In embodiments, $R^{39}$ is independently unsubstituted methyl. In embodiments, $R^{39}$ is independently unsubstituted ethyl.

$R^{40}$ is independently oxo,
halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{40}$ is independently —F, —Cl, —Br, or —I. In embodiments, $R^{40}$ is independently unsubstituted methyl. In embodiments, $R^{40}$ is independently unsubstituted ethyl.

In embodiments, $R^{7A}$ is independently
hydrogen, —$CX^{7A}_3$, —$CHX^{7A}_2$, —$CH_2X^{7A}$, —CN, —COOH, —$CONH_2$, $R^{38A}$-substituted or unsubstituted alkyl (e.g., $C_1$-$C_8$, $C_1$-$C_6$, $C_1$-$C_4$, or $C_1$-$C_2$), $R^{38A}$-substituted or unsubstituted heteroalkyl (e.g., 2 to 8 membered, 2 to 6 membered, 4 to 6 membered, 2 to 3 membered, or 4 to 5 membered), $R^{38A}$-substituted or unsubstituted cycloalkyl (e.g., $C_3$-$C_8$, $C_3$-$C_6$, $C_4$-$C_6$, or $C_5$-$C_6$), $R^{38A}$-substituted or unsubstituted heterocycloalkyl (e.g., 3 to 8 membered, 3 to 6 membered, 4 to 6 membered, 4 to 5 membered, or 5 to 6 membered), $R^{38A}$-substituted or unsubstituted aryl (e.g., $C_6$-$C_{10}$ or phenyl), or $R^{38A}$-substituted or unsubstituted heteroaryl (e.g., 5 to 10 membered, 5 to 9 membered, or 5 to 6 membered). In embodiments, $R^{7A}$ is independently
hydrogen, —$CX^{7A}_3$, —$CHX^{7A}_2$, —$CH_2X^{7A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7A}$ is independently —F, —Cl, —Br, or —I. In embodiments, $R^{7A}$ is independently hydrogen. In embodiments, $R^{7A}$ is independently unsubstituted methyl. In embodiments, $R^{7A}$ is independently unsubstituted ethyl.

In embodiments, $R^{7A}$ and $R^{7B}$ substituents bonded to the same nitrogen atom may optionally be joined to form a $R^{38A}$-substituted or unsubstituted heterocycloalkyl (e.g., 3 to 8 membered, 3 to 6 membered, 4 to 6 membered, 4 to 5 membered, or 5 to 6 membered) or $R^{38A}$-substituted or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form a $R^{38A}$ substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{38A}$ is independently oxo,
halogen, —$CX^{38A}_3$, —$CHX^{38A}_2$, —$CH_2X^{38A}$, —$OCX^{38A}_3$, —$OCH_2X^{38A}$, —$OCHX^{38A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38A}$ is independently —F, —Cl, —Br, or —I. In embodiments, $R^{38A}$ is independently unsubstituted methyl. In embodiments, $R^{38A}$ is independently unsubstituted ethyl.

In embodiments, $R^{7B}$ is independently
hydrogen, —$CX^{7B}_3$, —$CHX^{7B}_2$, —$CH_2X^{7B}$, —CN, —COOH, —$CONH_2$, $R^{38B}$-substituted or unsubstituted alkyl (e.g., $C_1$-$C_8$, $C_1$-$C_6$, $C_1$-$C_4$, or $C_1$-$C_2$), $R^{38B}$-substituted or unsubstituted heteroalkyl (e.g., 2 to 8 membered, 2 to 6 membered, 4 to 6 membered, 2 to 3 membered, or 4 to 5 membered), $R^{38B}$-substituted or unsubstituted cycloalkyl (e.g., $C_3$-$C_8$, $C_3$-$C_6$, $C_4$-$C_6$, or $C_5$-$C_6$), $R^{38B}$-substituted or unsubstituted heterocycloalkyl (e.g., 3 to 8 membered, 3 to 6 membered, 4 to 6 membered, 4 to 5 membered, or 5 to 6 membered), $R^{38B}$-substituted or unsubstituted aryl (e.g., $C_6$-$C_{10}$ or phenyl), or $R^{38B}$-substituted or unsubstituted heteroaryl (e.g., 5 to 10 membered, 5 to 9 membered, or 5 to 6 membered). In embodiments, $R^{7B}$ is independently
hydrogen, —$CX^{7B}_3$, —$CHX^{7B}_2$, —$CH_2X^{7B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7B}$ is independently —F, —Cl, —Br, or —I. In embodiments, $R^{7B}$ is independently hydrogen. In embodiments, $R^{7B}$ is independently unsubstituted methyl. In embodiments, $R^{7B}$ is independently unsubstituted ethyl.

In embodiments, $R^{7A}$ and $R^{7B}$ substituents bonded to the same nitrogen atom may optionally be joined to form a $R^{38B}$-substituted or unsubstituted heterocycloalkyl (e.g., 3 to 8 membered, 3 to 6 membered, 4 to 6 membered, 4 to 5 membered, or 5 to 6 membered) or $R^{38B}$ substituted or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{7A}$ and $R^{7B}$ substituents bonded to the same nitrogen atom may optionally be joined to form a $R^{38B}$ substituted or unsubstituted heterocycloalkyl (e.g., 3 to 8 membered, 3 to 6 membered, 4 to 6 membered, 4 to 5 membered, or 5 to 6 membered). In embodiments, $R^{7A}$ and $R^{7B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{38B}$ is independently oxo,
halogen, —$CX^{38B}_3$, —$CHX^{38B}_2$, —$CH_2X^{38}B$, —$OCX^{38B}_3$, —$OCH_2X^{38B}$, —$OCHX^{38B}_2$, —CN, —OH, —$NH_2$, —C OOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38B}$ is independently —F, —Cl, —Br, or —I. In embodiments, $R^{38B}$ is independently unsubstituted methyl. In embodiments, $R^{38B}$ is independently unsubstituted ethyl.

In embodiments, $R^{7C}$ is independently hydrogen, —$CX^{7C}_3$, —$CHX^{7C}_2$, —$CH_2X^{7C}$, —CN, —COOH, —$CONH_2$, $R^{38C}$-substituted or unsubstituted alkyl (e.g., $C_1$-$C_8$, $C_1$-$C_6$, $C_1$-$C_4$, or $C_1$-$C_2$), $R^{38C}$-substituted or unsubstituted heteroalkyl (e.g., 2 to 8 membered, 2 to 6 membered, 4 to 6 membered, 2 to 3 membered, or 4 to 5 membered), $R^{38C}$-substituted or unsubstituted cycloalkyl (e.g., $C_3$-$C_8$, $C_3$-$C_6$, $C_4$-$C_6$, or $C_5$-$C_6$), $R^{38C}$-substituted or unsubstituted heterocycloalkyl (e.g., 3 to 8 membered, 3 to 6 membered, 4 to 6 membered, 4 to 5 membered, or 5 to 6 membered), $R^{38C}$-substituted or unsubstituted aryl (e.g., $C_6$-$C_{10}$ or phenyl), or $R^{38C}$-substituted or unsubstituted heteroaryl (e.g., 5 to 10 membered, 5 to 9 membered, or 5 to 6 membered). In embodiments, $R^{7C}$ is independently hydrogen, —$CX^{7C}_3$, —$CHX^{7C}_2$, —$CH_2X^{7C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7C}$ is independently —F, —Cl, —Br, or —I. In embodiments, $R^{7C}$ is independently hydrogen. In embodiments, $R^{7C}$ is independently unsubstituted methyl. In embodiments, $R^{7C}$ is independently unsubstituted ethyl.

$R^{38C}$ is independently oxo, halogen, —$CX^{38C}_3$, —$CHX^{38C}_2$, —$CH_2X^{38C}$, —$OCX^{38C}_3$, —$OCH_2X^{38C}$, —$OCHX^{38C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38C}$ is independently —F, —Cl, —Br, or —I. In embodiments, $R^{38C}$ is independently unsubstituted methyl. In embodiments, $R^{38C}$ is independently unsubstituted ethyl.

In embodiments, $R^{7D}$ is independently hydrogen, —$CX^{7D}_3$, —$CHX^{7D}_2$, —$CH_2X^{7D}$, —CN, —COOH, —$CONH_2$, $R^{38D}$-substituted or unsubstituted alkyl (e.g., $C_1$-$C_8$, $C_1$-$C_6$, $C_1$-$C_4$, or $C_1$-$C_2$), $R^{38D}$-substituted or unsubstituted heteroalkyl (e.g., 2 to 8 membered, 2 to 6 membered, 4 to 6 membered, 2 to 3 membered, or 4 to 5 membered), $R^{38D}$-substituted or unsubstituted cycloalkyl (e.g., $C_3$-$C_8$, $C_3$-$C_6$, $C_4$-$C_6$, or $C_5$-$C_6$), $R^{38D}$-substituted or unsubstituted heterocycloalkyl (e.g., 3 to 8 membered, 3 to 6 membered, 4 to 6 membered, 4 to 5 membered, or 5 to 6 membered), $R^{38D}$-substituted or unsubstituted aryl (e.g., $C_6$-$C_{10}$ or phenyl), or $R^{38D}$-substituted or unsubstituted heteroaryl (e.g., 5 to 10 membered, 5 to 9 membered, or 5 to 6 membered). In embodiments, $R^{7D}$ is independently hydrogen, —$CX^{7D}_3$, —$CHX^{7D}_2$, —$CH_2X^{7D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7D}$ is independently —F, —Cl, —Br, or —I. In embodiments, $R^{7D}$ is independently hydrogen. In embodiments, $R^{7D}$ is independently unsubstituted methyl. In embodiments, $R^{7D}$ is independently unsubstituted ethyl.

$R^{38D}$ is independently oxo, halogen, —$CX^{38D}_3$, —$CHX^{38D}_2$, —$CH_2X^{38}D$, —$OCX^{38D}_3$, —$OCH_2X^{38}D$, —$OCHX^{38D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38D}$ is independently —F, —Cl, —Br, or —I. In embodiments, $R^{38D}$ is independently unsubstituted methyl. In embodiments, $R^{38D}$ is independently unsubstituted ethyl.

In embodiments, $R^8$ is independently hydrogen, halogen, —$CX^8_3$, —$CHX^8_2$, —$CH_2X^8$, —$OCX^8_3$, —$OCH_2X^8$, —$OCHX^8_2$, —CN, —$SO_{n8}R^{8D}$, —$SO_{v8}NR^{8A}R^{8B}$, —NHC(O)$NR^{8A}R^{8B}$, —$N(O)_{m8}$, —$NR^{8A}R^{8B}$, —$C(O)R^{8C}$, —C(O)—$OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^8$ is independently hydrogen, halogen, —$CX^8_3$, —$CHX^8_2$, —$CH_2X^8$, —$OCX^8_3$, —$OCH_2X^8$, —$OCHX^8_2$, substituted or unsubstituted alkyl, or substituted or unsubstituted heteroalkyl. In embodiments, $R^8$ is independently hydrogen, halogen, —$CX^8_3$, —$CHX^8_2$, —$CH_2X^8$, —$OCX^8_3$, —$OCH_2X^8$, —$OCHX^8_2$, substituted or unsubstituted ($C_1$-$C_4$) alkyl, or substituted or unsubstituted 2 to 4 membered heteroalkyl. In embodiments, $R^8$ is hydrogen, halogen, —$CH_3$, —$CH_2CH_3$, —$CX^8_3$, —$CHX^8_2$, —$CH_2X^8$, —$OCH_3$, —$OCX^8_3$, —$OCH_2X^8$, —$OCHX^8_2$, —$SCH_3$, —$SCX^8_3$, —$SCH_2X^8$, or —$SCHX^8_2$. In embodiments, $R^8$ is hydrogen, halogen, —$CH_3$, —$CH_2CH_3$, —$CF_3$, or —$OCH_3$. In embodiments, $R^8$ is —$CH_3$, —$CH_2CH_3$, or —OCH$_3$. In embodiments, R$^8$ is —OCH$_3$. In embodiments, R$^8$ is independently hydrogen, halogen, —CX$^8_3$, —CHX$^8_2$, —CH$_2$X$^8$, —OCX$^8_3$, —OCH$_2$X$^8$, —OCHX$^8_2$, —CN, substituted or unsubstituted alkyl, or substituted or unsubstituted heteroalkyl. In embodiments, R$^8$ is independently hydrogen, halogen, —CX$^8_3$, —CHX$^8_2$, —CH$_2$X$^8$, —OCX$^8_3$, —OCH$_2$X$^8$, —OCHX$^8_2$, —CN, substituted or unsubstituted (C$_1$-C$_4$) alkyl, or substituted or unsubstituted 2 to 4 membered heteroalkyl. In embodiments, R$^8$ is hydrogen, halogen, —CH$_3$, —CH$_2$CH$_3$, —CX$^8_3$, —CHX$^8_2$, —CH$_2$X$^8$, —OCH$_3$, —OCX$^8_3$, —OCH$_2$X$^8$, —OCHX$^8_2$, —CN, —SCH$_3$, —SCX$^8_3$, —SCH$_2$X$^8$, or —SCHX$^8_2$. In embodiments, R$^8$ is hydrogen, halogen, —CN, —CH$_3$, —CF$_3$, or —OCH$_3$. In embodiments, R$^8$ is halogen or —CH$_3$. In embodiments, R$^8$ is —C$_1$ or —CH$_3$. In embodiments, R$^8$ is —CH$_3$. In embodiments, R$^8$ is hydrogen. In embodiments, R$^8$ is —CH$_3$ or —CH$_2$CH$_3$. In embodiments, R$^8$ is —C(O)R$^{8C}$. In embodiments, R$^8$ is —C(O)CH$_3$. In embodiments, R$^8$ is —C(O)CH$_2$CH$_3$. In embodiments, R$^8$ is —C(O)CH$_2$CH$_2$CH$_3$. In embodiments, R$^8$ is —C(O)CH(CH$_3$)$_2$. In embodiments, R$^8$ is —C(O)C(CH$_3$)$_3$. In embodiments, R$^8$ is —C(O)CH$_2$CH$_2$CH$_2$CH$_3$. In embodiments, R$^8$ is —NHC(O)CH$_3$. In embodiments, R$^8$ is —NHC(O)CH$_2$CH$_3$. In embodiments, R$^8$ is —NHC(O)CH$_2$CH$_2$CH$_3$. In embodiments, R$^8$ is —NHC(O)CH(CH$_3$)$_2$. In embodiments, R$^8$ is —NHC(O)C(CH$_3$)$_3$. In embodiments, R$^8$ is —NHC(O)CH$_2$CH$_2$CH$_2$CH$_3$.

In embodiments, R$^8$ is independently hydrogen, halogen, —CX$^8_3$, —CN, —OH, —NH$_2$, —SH, —OCX$^8_3$, —OCHX$^8_2$, —OCH$_2$X$^8$, —CHX$^8_2$, —CH$_2$X$^8$, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, R$^8$ is independently hydrogen, halogen, —CX$^8_3$, —CN, —OH, —NH$_2$, —SH, —OCX$^8_3$, —OCHX$^8_2$, —OCH$_2$X$^8$, —CHX$^8_2$, —CH$_2$X$^8$, unsubstituted C$_1$-C$_4$ alkyl, or unsubstituted 2 to 4 membered heteroalkyl.

In embodiments, R$^8$ is independently hydrogen. In embodiments, R$^8$ is independently halogen. In embodiments, R$^8$ is independently —CX$^8_3$. In embodiments, R$^8$ is independently —CHX$^8_2$. In embodiments, R$^8$ is independently —CH$_2$X$^8$. In embodiments, R$^8$ is independently —OCX$^8_3$. In embodiments, R$^8$ is independently —OCH$_2$X$^8$. In embodiments, R$^8$ is independently —OCHX$^8_2$. In embodiments, R$^8$ is independently —CN. In embodiments, R$^8$ is independently —SO$_{n8}$R$^{8D}$. In embodiments, R$^8$ is independently —SO$_{v8}$NR$^{8A}$R$^{8B}$. In embodiments, R$^8$ is independently —NHC(O)NR$^{8A}$R$^{8B}$. In embodiments, R$^8$ is independently —N(O)$_m$s. In embodiments, R$^8$ is independently —NR$^{8A}$R$^{8B}$. In embodiments, R$^8$ is independently —C(O)R$^{8C}$. In embodiments, R$^8$ is independently —C(O)—OR$^{8C}$. In embodiments, R$^8$ is independently —C(O)NR$^{8A}$R$^{8B}$. In embodiments, R$^8$ is independently —OR$^{8D}$. In embodiments, R$^8$ is independently —SR$^{8D}$. In embodiments, R$^8$ is independently —NR$^{8A}$SO$_2$R$^{8D}$. In embodiments, R$^8$ is independently —NR$^{8A}$C(O)R$^{8C}$. In embodiments, R$^8$ is independently —NR$^{8A}$C(O)OR$^{8C}$. In embodiments, R$^8$ is independently —NR$^{8A}$OR$^{8C}$. In embodiments, R$^8$ is independently —OH. In embodiments, R$^8$ is independently —NH$_2$. In embodiments, R$^8$ is independently —COOH. In embodiments, R$^8$ is independently —CONH$_2$. In embodiments, R$^8$ is independently —NO$_2$. In embodiments, R$^8$ is independently —SH. In embodiments, R$^8$ is independently —CF$_3$. In embodiments, R$^8$ is independently —CHF$_2$. In embodiments, R$^8$ is independently —CH$_2$F. In embodiments, R$^8$ is independently —OCF$_3$. In embodiments, R$^8$ is independently —OCH$_2$F. In embodiments, R$^8$ is independently —OCHF$_2$. In embodiments, R$^8$ is independently —OCH$_3$. In embodiments, R$^8$ is independently —OCH$_2$CH$_3$. In embodiments, R$^8$ is independently —OCH$_2$CH$_2$CH$_3$. In embodiments, R$^8$ is independently —OCH(CH$_3$)$_2$. In embodiments, R$^8$ is independently —OC(CH$_3$)$_3$. In embodiments, R$^8$ is independently —SCH$_3$. In embodiments, R$^8$ is independently —SCH$_2$CH$_3$. In embodiments, R$^8$ is independently —SCH$_2$CH$_2$CH$_3$. In embodiments, R$^8$ is independently —SCH(CH$_3$)$_2$. In embodiments, R$^8$ is independently —SC(CH$_3$)$_3$. In embodiments, R$^8$ is independently —CH$_3$. In embodiments, R$^8$ is independently —CH$_2$CH$_3$. In embodiments, R$^8$ is independently —CH$_2$CH$_2$CH$_3$. In embodiments, R$^8$ is independently —CH(CH$_3$)$_2$. In embodiments, R$^8$ is independently —C(CH$_3$)$_3$. In embodiments, R$^8$ is independently —F. In embodiments, R$^8$ is independently —Cl. In embodiments, R$^8$ is independently —Br. In embodiments, R$^8$ is independently —I. In embodiments, X$^8$ is independently —F. In embodiments, X$^8$ is independently —Cl. In embodiments, X$^8$ is independently —Br. In embodiments, X$^8$ is independently —I.

In embodiments, R$^8$ is independently substituted or unsubstituted alkyl (e.g., C$_1$-C$_8$, C$_1$-C$_6$, C$_1$-C$_4$, or C$_1$-C$_2$). In embodiments, R$^8$ is independently substituted alkyl (e.g., C$_1$-C$_8$, C$_1$-C$_6$, C$_1$-C$_4$, or C$_1$-C$_2$). In embodiments, R$^8$ is independently unsubstituted alkyl (e.g., C$_1$-C$_8$, C$_1$-C$_6$, C$_1$-C$_4$, or C$_1$-C$_2$). In embodiments, R$^8$ is independently unsubstituted methyl. In embodiments, R$^8$ is independently unsubstituted ethyl. In embodiments, R$^8$ is independently unsubstituted propyl. In embodiments, R$^8$ is independently unsubstituted isopropyl. In embodiments, R$^8$ is independently unsubstituted tert-butyl. In embodiments, R$^8$ is independently substituted or unsubstituted heteroalkyl (e.g., 2 to 8 membered, 2 to 6 membered, 4 to 6 membered, 2 to 3 membered, or 4 to 5 membered). In embodiments, R$^8$ is independently substituted heteroalkyl (e.g., 2 to 8 membered, 2 to 6 membered, 4 to 6 membered, 2 to 3 membered, or 4 to 5 membered). In embodiments, R$^8$ is independently unsubstituted heteroalkyl (e.g., 2 to 8 membered, 2 to 6 membered, 4 to 6 membered, 2 to 3 membered, or 4 to 5 membered). In embodiments, R$^8$ is independently substituted or unsubstituted cycloalkyl (e.g., C$_3$-C$_8$, C$_3$-C$_6$, C$_4$-C$_6$, or C$_5$-C$_6$). In embodiments, R$^8$ is independently substituted cycloalkyl (e.g., C$_3$-C$_8$, C$_3$-C$_6$, C$_4$-C$_6$, or C$_5$-C$_6$). In embodiments, R$^8$ is independently unsubstituted cycloalkyl (e.g., C$_3$-C$_8$, C$_3$-C$_6$, C$_4$-C$_6$, or C$_5$-C$_6$). In embodiments, R$^8$ is independently substituted or unsubstituted heterocycloalkyl (e.g., 3 to 8 membered, 3 to 6 membered, 4 to 6 membered, 4 to 5 membered, or 5 to 6 membered). In embodiments, R$^8$ is independently substituted heterocycloalkyl (e.g., 3 to 8 membered, 3 to 6 membered, 4 to 6 membered, 4 to 5 membered, or 5 to 6 membered). In embodiments, R$^8$ is independently unsubstituted heterocycloalkyl (e.g., 3 to 8 membered, 3 to 6 membered, 4 to 6 membered, 4 to 5 membered, or 5 to 6 membered). In embodiments, R$^8$ is independently substituted or unsubstituted aryl (e.g., C$_6$-C$_{10}$ or phenyl). In embodiments, R$^8$ is independently substituted aryl (e.g., C$_6$-C$_{10}$ or phenyl). In embodiments, R$^8$ is independently unsubstituted aryl (e.g., C$_6$-C$_{10}$ or phenyl). In embodiments, R$^8$ is independently substituted or unsubstituted heteroaryl (e.g., 5 to 10 membered, 5 to 9 membered, or 5 to 6 membered). In embodiments, R$^8$ is independently substituted heteroaryl (e.g., 5 to 10 membered, 5 to 9 membered, or 5 to 6 membered). In embodiments, R$^8$ is independently unsubstituted heteroaryl (e.g., 5 to 10 membered, 5 to 9 membered, or 5 to 6 membered).

In embodiments, $R^8$ is independently hydrogen, halogen, $-SO_{n8}R^{8D}$, $-SO_{v8}NR^{8A}R^{8B}$, $-C(O)R^{8C}$, $-C(O)OR^{8C}$, $-C(O)NR^{8A}R^{8B}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^8$ is independently hydrogen, $-SO_2R^{8D}$, $-SO_2NR^{8A}R^{8B}$, $-C(O)R^{8C}$, $-C(O)OR^{8C}$, $-C(O)NR^{8A}R^{8B}$, substituted or unsubstituted alkyl, or substituted or unsubstituted heteroalkyl. In embodiments, $R^8$ is independently $-C(O)R^{8C}$ or $-C(O)OR^{8C}$, wherein $R^{8C}$ is substituted or unsubstituted alkyl, substituted or unsubstituted heteroalkyl. In embodiments, $R^8$ is independently $-C(O)R^{8C}$, wherein $R^{8C}$ is substituted or unsubstituted $C_1$-$C_6$ alkyl. In embodiments, $R^8$ is

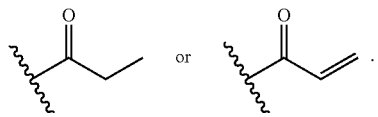

In embodiments, $R^8$ is

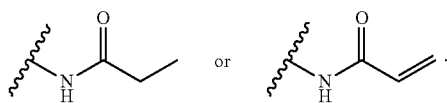

In embodiments, $R^8$ is independently E.

In embodiments, $R^{8A}$ is independently hydrogen. In embodiments, $R^{8A}$ is independently $-CX^{8A}_3$. In embodiments, $R^{8A}$ is independently $-CHX^{8A}_2$. In embodiments, $R^{8A}$ is independently $-CH_2X^{8A}$. In embodiments, $R^{8A}$ is independently $-CN$. In embodiments, $R^{8A}$ is independently $-COOH$. In embodiments, $R^{8A}$ is independently $-CONH_2$. In embodiments, $X^{8A}$ is independently $-F$, $-Cl$, $-Br$, or $-I$.

In embodiments, $R^{8A}$ is independently substituted or unsubstituted alkyl (e.g., $C_1$-$C_8$, $C_1$-$C_6$, $C_1$-$C_4$, or $C_1$-$C_2$). In embodiments, $R^{8A}$ is independently substituted alkyl (e.g., $C_1$-$C_8$, $C_1$-$C_6$, $C_1$-$C_4$, or $C_1$-$C_2$). In embodiments, $R^{8A}$ is independently unsubstituted alkyl (e.g., $C_1$-$C_8$, $C_1$-$C_6$, $C_1$-$C_4$, or $C_1$-$C_2$). In embodiments, $R^{8A}$ is independently unsubstituted methyl. In embodiments, $R^{8A}$ is independently unsubstituted ethyl. In embodiments, $R^{8A}$ is independently unsubstituted propyl. In embodiments, $R^{8A}$ is independently unsubstituted isopropyl. In embodiments, $R^{8A}$ is independently unsubstituted tert-butyl. In embodiments, $R^{8A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{8A}$ is independently substituted heteroalkyl (e.g., 2 to 8 membered, 2 to 6 membered, 4 to 6 membered, 2 to 3 membered, or 4 to 5 membered). In embodiments, $R^{8A}$ is independently unsubstituted heteroalkyl (e.g., 2 to 8 membered, 2 to 6 membered, 4 to 6 membered, 2 to 3 membered, or 4 to 5 membered). In embodiments, $R^{8A}$ is independently substituted or unsubstituted cycloalkyl (e.g., $C_3$-$C_8$, $C_3$-$C_6$, $C_4$-$C_6$, or $C_5$-$C_6$). In embodiments, $R^{8A}$ is independently substituted cycloalkyl (e.g., $C_3$-$C_8$, $C_3$-$C_6$, $C_4$-$C_6$, or $C_5$-$C_6$). In embodiments, $R^{8A}$ is independently unsubstituted cycloalkyl (e.g., $C_3$-$C_8$, $C_3$-$C_6$, $C_4$-$C_6$, or $C_5$-$C_6$). In embodiments, $R^{8A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{8A}$ is independently substituted heterocycloalkyl (e.g., 3 to 8 membered, 3 to 6 membered, 4 to 6 membered, 4 to 5 membered, or 5 to 6 membered). In embodiments, $R^{8A}$ is independently unsubstituted heterocycloalkyl (e.g., 3 to 8 membered, 3 to 6 membered, 4 to 6 membered, 4 to 5 membered, or 5 to 6 membered). In embodiments, $R^{8A}$ is independently substituted or unsubstituted aryl (e.g., $C_6$-$C_{10}$ or phenyl). In embodiments, $R^{8A}$ is independently substituted aryl (e.g., $C_6$-$C_{10}$ or phenyl). In embodiments, $R^{8A}$ is independently unsubstituted aryl (e.g., $C_6$-$C_{10}$ or phenyl). In embodiments, $R^{8A}$ is independently substituted or unsubstituted heteroaryl (e.g., 5 to 10 membered, 5 to 9 membered, or 5 to 6 membered). In embodiments, $R^{8A}$ is independently substituted heteroaryl (e.g., 5 to 10 membered, 5 to 9 membered, or 5 to 6 membered). In embodiments, $R^{8A}$ is independently unsubstituted heteroaryl (e.g., 5 to 10 membered, 5 to 9 membered, or 5 to 6 membered).

In embodiments, $R^{8B}$ is independently hydrogen. In embodiments, $R^{8B}$ is independently $-CX^{8B}_3$. In embodiments, $R^{8B}$ is independently $-CHX^{8B}_2$. In embodiments, $R^{8B}$ is independently $-CH_2X^{8B}$. In embodiments, $R^{8B}$ is independently $-CN$. In embodiments, $R^{8B}$ is independently $-COOH$. In embodiments, $R^{8B}$ is independently $-CONH_2$. In embodiments, $X^{8B}$ is independently $-F$, $-Cl$, $-Br$, or $-I$.

In embodiments, $R^{8B}$ is independently substituted or unsubstituted alkyl (e.g., $C_1$-$C_8$, $C_1$-$C_6$, $C_1$-$C_4$, or $C_1$-$C_2$). In embodiments, $R^{8B}$ is independently substituted alkyl (e.g., $C_1$-$C_8$, $C_1$-$C_6$, $C_1$-$C_4$, or $C_1$-$C_2$). In embodiments, $R^{8B}$ is independently unsubstituted alkyl (e.g., $C_1$-$C_8$, $C_1$-$C_6$, $C_1$-$C_4$, or $C_1$-$C_2$). In embodiments, $R^{8B}$ is independently unsubstituted methyl. In embodiments, $R^{8B}$ is independently unsubstituted ethyl. In embodiments, $R^{8B}$ is independently unsubstituted propyl. In embodiments, $R^{8B}$ is independently unsubstituted isopropyl. In embodiments, $R^{8B}$ is independently unsubstituted tert-butyl. In embodiments, $R^{8B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{8B}$ is independently substituted heteroalkyl (e.g., 2 to 8 membered, 2 to 6 membered, 4 to 6 membered, 2 to 3 membered, or 4 to 5 membered). In embodiments, $R^{8B}$ is independently unsubstituted heteroalkyl (e.g., 2 to 8 membered, 2 to 6 membered, 4 to 6 membered, 2 to 3 membered, or 4 to 5 membered). In embodiments, $R^{8B}$ is independently substituted or unsubstituted cycloalkyl (e.g., $C_3$-$C_8$, $C_3$-$C_6$, $C_4$-$C_6$, or $C_5$-$C_6$). In embodiments, $R^{8B}$ is independently substituted cycloalkyl (e.g., $C_3$-$C_8$, $C_3$-$C_6$, $C_4$-$C_6$, or $C_5$-$C_6$). In embodiments, $R^{8B}$ is independently unsubstituted cycloalkyl (e.g., $C_3$-$C_8$, $C_3$-$C_6$, $C_4$-$C_6$, or $C_5$-$C_6$). In embodiments, $R^{8B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{8B}$ is independently substituted heterocycloalkyl (e.g., 3 to 8 membered, 3 to 6 membered, 4 to 6 membered, 4 to 5 membered, or 5 to 6 membered). In embodiments, $R^{8B}$ is independently unsubstituted heterocycloalkyl (e.g., 3 to 8 membered, 3 to 6 membered, 4 to 6 membered, 4 to 5 membered, or 5 to 6 membered). In embodiments, $R^{8B}$ is independently substituted or unsubstituted aryl (e.g., $C_6$-$C_{10}$ or phenyl). In embodiments, $R^{8B}$ is independently substituted aryl (e.g., $C_6$-$C_{10}$ or phenyl). In embodiments, $R^{8B}$ is independently unsubstituted aryl (e.g., $C_6$-$C_{10}$ or phenyl). In embodiments, $R^{8B}$ is independently substituted or unsubstituted heteroaryl (e.g., 5 to 10 membered, 5 to 9 membered, or 5 to 6 membered). In embodiments, $R^{8B}$ is independently substituted heteroaryl (e.g., 5 to 10 membered, 5 to 9 membered, or 5 to 6 membered). In embodiments, $R^{8B}$ is independently unsubstituted heteroaryl (e.g., 5 to 10 membered, 5 to 9 membered, or 5 to 6 membered).

In embodiments, $R^{8A}$ and $R^{8B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{8A}$ and $R^{8B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{8A}$ and $R^{8B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{8A}$ and $R^{8B}$ substituents bonded to the same nitrogen atom may be joined to form a substituted or unsubstituted heteroaryl (e.g., 5 to 10 membered, 5 to 9 membered, or 5 to 6 membered). In embodiments, $R^{8A}$ and $R^{8B}$ substituents bonded to the same nitrogen atom may be joined to form a substituted heteroaryl (e.g., 5 to 10 membered, 5 to 9 membered, or 5 to 6 membered). In embodiments, $R^{8A}$ and $R^{8B}$ substituents bonded to the same nitrogen atom may be joined to form an unsubstituted heteroaryl (e.g., 5 to 10 membered, 5 to 9 membered, or 5 to 6 membered).

In embodiments, $R^{8C}$ is independently hydrogen. In embodiments, $R^{8C}$ is independently —$CX^{8C}_3$. In embodiments, $R^{8C}$ is independently —$CHX^{8C}_2$. In embodiments, $R^{8C}$ is independently —$CH_2X^{8C}$. In embodiments, $R^{8C}$ is independently —CN. In embodiments, $R^{8C}$ is independently —COOH. In embodiments, $R^{8C}$ is independently —$CONH_2$. In embodiments, $X^{8C}$ is independently —F, —Cl, —Br, or —I.

In embodiments, $R^{8C}$ is independently substituted or unsubstituted alkyl (e.g., $C_1$-$C_8$, $C_1$-$C_6$, $C_1$-$C_4$, or $C_1$-$C_2$). In embodiments, $R^{8C}$ is independently substituted alkyl (e.g., $C_1$-$C_8$, $C_1$-$C_6$, $C_1$-$C_4$, or $C_1$-$C_2$). In embodiments, $R^{8C}$ is independently unsubstituted alkyl (e.g., $C_1$-$C_8$, $C_1$-$C_6$, $C_1$-$C_4$, or $C_1$-$C_2$). In embodiments, $R^{8C}$ is independently unsubstituted methyl. In embodiments, $R^{8C}$ is independently unsubstituted ethyl. In embodiments, $R^{8C}$ is independently unsubstituted propyl. In embodiments, $R^{8C}$ is independently unsubstituted isopropyl. In embodiments, $R^{8C}$ is independently unsubstituted tert-butyl. In embodiments, $R^{8C}$ is independently unsubstituted pentyl. In embodiments, $R^{8C}$ is independently unsubstituted hexyl. In embodiments, $R^{8C}$ is independently unsubstituted heptyl. In embodiments, $R^{8C}$ is independently unsubstituted octyl. In embodiments, $R^{8C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{8C}$ is independently substituted heteroalkyl (e.g., 2 to 8 membered, 2 to 6 membered, 4 to 6 membered, 2 to 3 membered, or 4 to 5 membered). In embodiments, $R^{8C}$ is independently unsubstituted heteroalkyl (e.g., 2 to 8 membered, 2 to 6 membered, 4 to 6 membered, 2 to 3 membered, or 4 to 5 membered). In embodiments, $R^{8C}$ is independently substituted or unsubstituted cycloalkyl (e.g., $C_3$-$C_8$, $C_3$-$C_6$, $C_4$-$C_6$, or $C_5$-$C_6$). In embodiments, $R^{8C}$ is independently substituted cycloalkyl (e.g., $C_3$-$C_8$, $C_3$-$C_6$, $C_4$-$C_6$, or $C_5$-$C_6$). In embodiments, $R^{8C}$ is independently unsubstituted cycloalkyl (e.g., $C_3$-$C_8$, $C_3$-$C_6$, $C_4$-$C_6$, or $C_5$-$C_6$). In embodiments, $R^{8C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{8C}$ is independently substituted heterocycloalkyl (e.g., 3 to 8 membered, 3 to 6 membered, 4 to 6 membered, 4 to 5 membered, or 5 to 6 membered). In embodiments, $R^{8C}$ is independently unsubstituted heterocycloalkyl (e.g., 3 to 8 membered, 3 to 6 membered, 4 to 6 membered, 4 to 5 membered, or 5 to 6 membered). In embodiments, $R^{8C}$ is independently substituted or unsubstituted aryl (e.g., $C_6$-$C_{10}$ or phenyl). In embodiments, $R^{8C}$ is independently substituted aryl (e.g., $C_6$-$C_{10}$ or phenyl). In embodiments, $R^{8C}$ is independently unsubstituted aryl (e.g., $C_6$-$C_{10}$ or phenyl). In embodiments, $R^{8C}$ is independently substituted or unsubstituted heteroaryl (e.g., 5 to 10 membered, 5 to 9 membered, or 5 to 6 membered). In embodiments, $R^{8C}$ is independently substituted heteroaryl (e.g., 5 to 10 membered, 5 to 9 membered, or 5 to 6 membered). In embodiments, $R^{8C}$ is independently unsubstituted heteroaryl (e.g., 5 to 10 membered, 5 to 9 membered, or 5 to 6 membered).

In embodiments, $R^{8D}$ is independently hydrogen. In embodiments, $R^{8D}$ is independently —$CX^{8D}_3$. In embodiments, $R^{8D}$ is independently —$CHX^{8D}_2$. In embodiments, $R^{8D}$ is independently —$CH_2X^{8D}$. In embodiments, $R^{8D}$ is independently —CN. In embodiments, $R^{8D}$ is independently —COOH. In embodiments, $R^{8D}$ is independently —$CONH_2$. In embodiments, $X^{8D}$ is independently —F, —Cl, —Br, or —I.

In embodiments, $R^{8D}$ is independently substituted or unsubstituted alkyl (e.g., $C_1$-$C_8$, $C_1$-$C_6$, $C_1$-$C_4$, or $C_1$-$C_2$). In embodiments, $R^{8D}$ is independently substituted alkyl (e.g., $C_1$-$C_8$, $C_1$-$C_6$, $C_1$-$C_4$, or $C_1$-$C_2$). In embodiments, $R^{8D}$ is independently unsubstituted alkyl (e.g., $C_1$-$C_8$, $C_1$-$C_6$, $C_1$-$C_4$, or $C_1$-$C_2$). In embodiments, $R^{8D}$ is independently unsubstituted methyl. In embodiments, $R^{8D}$ is independently unsubstituted ethyl. In embodiments, $R^{8D}$ is independently unsubstituted propyl. In embodiments, $R^{8D}$ is independently unsubstituted isopropyl. In embodiments, $R^{8D}$ is independently unsubstituted tert-butyl. In embodiments, $R^{8D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{8D}$ is independently substituted heteroalkyl (e.g., 2 to 8 membered, 2 to 6 membered, 4 to 6 membered, 2 to 3 membered, or 4 to 5 membered). In embodiments, $R^{8D}$ is independently unsubstituted heteroalkyl (e.g., 2 to 8 membered, 2 to 6 membered, 4 to 6 membered, 2 to 3 membered, or 4 to 5 membered). In embodiments, $R^{8D}$ is independently substituted or unsubstituted cycloalkyl (e.g., $C_3$-$C_8$, $C_3$-$C_6$, $C_4$-$C_6$, or $C_5$-$C_6$). In embodiments, $R^{8D}$ is independently substituted cycloalkyl (e.g., $C_3$-$C_8$, $C_3$-$C_6$, $C_4$-$C_6$, or $C_5$-$C_6$). In embodiments, $R^{8D}$ is independently unsubstituted cycloalkyl (e.g., $C_3$-$C_8$, $C_3$-$C_6$, $C_4$-$C_6$, or $C_5$-$C_6$). In embodiments, $R^{8D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{8D}$ is independently substituted heterocycloalkyl (e.g., 3 to 8 membered, 3 to 6 membered, 4 to 6 membered, 4 to 5 membered, or 5 to 6 membered). In embodiments, $R^{8D}$ is independently unsubstituted heterocycloalkyl (e.g., 3 to 8 membered, 3 to 6 membered, 4 to 6 membered, 4 to 5 membered, or 5 to 6 membered). In embodiments, $R^{8D}$ is independently substituted or unsubstituted aryl (e.g., $C_6$-$C_{10}$ or phenyl). In embodiments, $R^{8D}$ is independently substituted aryl (e.g., $C_6$-$C_{10}$ or phenyl). In embodiments, $R^{8D}$ is independently unsubstituted aryl (e.g., $C_6$-$C_{10}$ or phenyl). In embodiments, $R^{8D}$ is independently substituted or unsubstituted heteroaryl (e.g., 5 to 10 membered, 5 to 9 membered, or 5 to 6 membered). In embodiments, $R^{8D}$ is independently substituted heteroaryl (e.g., 5 to 10 membered, 5 to 9 membered, or 5 to 6 membered). In embodiments, $R^{8D}$ is independently unsubstituted heteroaryl (e.g., 5 to 10 membered, 5 to 9 membered, or 5 to 6 membered).

In embodiments, $R^8$ is independently hydrogen, halogen, $-CX^8_3$, $-CHX^8_2$, $-CH_2X^8$, $-OCX^8_3$, $-OCH_2X^8$, $-OCHX^8_2$, $-CN$, $-OH$, $-NH_2$, $-COOH$, $-CO\ NH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{41}$-substituted or unsubstituted alkyl (e.g., $C_1$-$C_8$, $C_1$-$C_6$, $C_1$-$C_4$, or $C_1$-$C_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., $C_3$-$C_8$, $C_3$-$C_6$, $C_4$-$C_6$, or $C_5$-$C_6$), $R^{41}$-substituted or unsubstituted heterocycloalkyl (e.g., 3 to 8 membered, 3 to 6 membered, 4 to 6 membered, 4 to 5 membered, or 5 to 6 membered), $R^{41}$-substituted or unsubstituted aryl (e.g., $C_6$-$C_{10}$ or phenyl), or $R^{41}$-substituted or unsubstituted heteroaryl (e.g., 5 to 10 membered, 5 to 9 membered, or 5 to 6 membered). In embodiments, $R^8$ is independently hydrogen, halogen, $-CX^8_3$, $-CHX^8_2$, $-CH_2X^8$, $-OCX^8_3$, $-OCH_2X^8$, $-OCHX^8_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^8$ is independently $-F$, $-Cl$, $-Br$, or $-I$. In embodiments, $R^8$ is independently hydrogen. In embodiments, $R^8$ is independently unsubstituted methyl. In embodiments, $R^8$ is independently unsubstituted ethyl.

$R^{41}$ is independently oxo,
halogen, $-CX^{41}_3$, $-CHX^{41}_2$, $-CH_2X^{41}$, $-OCX^{41}_3$, $-OCH_2X^{41}$, $-OCHX^{41}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{42}$-substituted or unsubstituted alkyl (e.g., $C_1$-$C_8$, $C_1$-$C_6$, $C_1$-$C_4$, or $C_1$-$C_2$), $R^{42}$-substituted or unsubstituted heteroalkyl (e.g., 2 to 8 membered, 2 to 6 membered, 4 to 6 membered, 2 to 3 membered, or 4 to 5 membered), $R^{42}$-substituted or unsubstituted cycloalkyl (e.g., $C_3$-$C_8$, $C_3$-$C_6$, $C_4$-$C_6$, or $C_5$-$C_6$), $R^{42}$-substituted or unsubstituted heterocycloalkyl (e.g., 3 to 8 membered, 3 to 6 membered, 4 to 6 membered, 4 to 5 membered, or 5 to 6 membered), $R^{42}$-substituted or unsubstituted aryl (e.g., $C_6$-$C_{10}$ or phenyl), or $R^{42}$-substituted or unsubstituted heteroaryl (e.g., 5 to 10 membered, 5 to 9 membered, or 5 to 6 membered). In embodiments, $R^{41}$ is independently oxo,
halogen, $-CX^{41}_3$, $-CHX^{41}_2$, $-CH_2X^{41}$, $-OCX^{41}_3$, $-OCH_2X^{41}$, $-OCHX^{41}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41}$ is independently $-F$, $-Cl$, $-Br$, or $-I$. In embodiments, $R^{41}$ is independently unsubstituted methyl. In embodiments, $R^{41}$ is independently unsubstituted ethyl.

$R^{42}$ is independently oxo,
halogen, $-CX^{42}_3$, $-CHX^{42}_2$, $-CH_2X^{42}$, $-OCX^{42}_3$, $-OCH_2X^{42}$, $-OCHX^{42}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{43}$-substituted or unsubstituted alkyl (e.g., $C_1$-$C_8$, $C_1$-$C_6$, $C_1$-$C_4$, or $C_1$-$C_2$), $R^{43}$-substituted or unsubstituted heteroalkyl (e.g., 2 to 8 membered, 2 to 6 membered, 4 to 6 membered, 2 to 3 membered, or 4 to 5 membered), $R^{43}$-substituted or unsubstituted cycloalkyl (e.g., $C_3$-$C_8$, $C_3$-$C_6$, $C_4$-$C_6$, or $C_5$-$C_6$), $R^{43}$-substituted or unsubstituted heterocycloalkyl (e.g., 3 to 8 membered, 3 to 6 membered, 4 to 6 membered, 4 to 5 membered, or 5 to 6 membered), $R^{43}$-substituted or unsubstituted aryl (e.g., $C_6$-$C_{10}$ or phenyl), or $R^{43}$-substituted or unsubstituted heteroaryl (e.g., 5 to 10 membered, 5 to 9 membered, or 5 to 6 membered). In embodiments, $R^{42}$ is independently oxo,
halogen, $-CX^{42}_3$, $-CHX^{42}_2$, $-CH_2X^{42}$, $-OCX^{42}_3$, $-OCH_2X^4_2$, $-OCHX^{42}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{42}$ is independently $-F$, $-Cl$, $-Br$, or $-I$. In embodiments, $R^{42}$ is independently unsubstituted methyl. In embodiments, $R^{42}$ is independently unsubstituted ethyl.

$R^{43}$ is independently oxo,
halogen, $-CX^{43}_3$, $-CHX^{43}_2$, $-CH_2X^{43}$, $-OCX^{43}_3$, $-OCH_2X^{43}$, $-OCHX^{43}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{43}$ is independently $-F$, $-Cl$, $-Br$, or $-I$. In embodiments, $R^{43}$ is independently unsubstituted methyl. In embodiments, $R^{43}$ is independently unsubstituted ethyl.

In embodiments, $R^{8A}$ is independently hydrogen, $-CX^{8A}_3$, $-CHX^{8A}_2$, $-CH_2X^{8A}$, $-CN$, $-COOH$, $-CONH_2$, $R^{41A}$-substituted or unsubstituted alkyl (e.g., $C_1$-$C_8$, $C_1$-$C_6$, $C_1$-$C_4$, or $C_1$-$C_2$), $R^{41A}$-substituted or unsubstituted heteroalkyl (e.g., 2 to 8 membered, 2 to 6 membered, 4 to 6 membered, 2 to 3 membered, or 4 to 5 membered), $R^{41A}$-substituted or unsubstituted cycloalkyl (e.g., $C_3$-$C_8$, $C_3$-$C_6$, $C_4$-$C_6$, or $C_5$-$C_6$), $R^{41A}$-substituted or unsubstituted heterocycloalkyl (e.g., 3 to 8 membered, 3 to 6 membered, 4 to 6 membered, 4 to 5 membered, or 5 to 6 membered), $R^{41A}$-substituted or unsubstituted aryl (e.g., $C_6$-$C_{10}$ or phenyl), or $R^{41A}$-substituted or unsubstituted heteroaryl (e.g., 5 to 10 membered, 5 to 9 membered, or 5 to 6 membered). In embodiments, $R^{8A}$ is independently hydrogen, —$CX^{8A}_3$, —$CHX^{8A}_2$, —$CH_2X^{8A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{8A}$ is independently —F, —Cl, —Br, or —I. In embodiments, $R^{8A}$ is independently hydrogen. In embodiments, $R^{8A}$ is independently unsubstituted methyl. In embodiments, $R^{8A}$ is independently unsubstituted ethyl.

In embodiments, $R^{8A}$ and $R^{8B}$ substituents bonded to the same nitrogen atom may optionally be joined to form a $R^{41A}$-substituted or unsubstituted heterocycloalkyl (e.g., 3 to 8 membered, 3 to 6 membered, 4 to 6 membered, 4 to 5 membered, or 5 to 6 membered) or $R^{41A}$-substituted or unsubstituted heteroaryl (e.g., 5 to 10 membered, 5 to 9 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{8A}$ and $R^{8B}$ substituents bonded to the same nitrogen atom may optionally be joined to form a $R^{41A}$-substituted or unsubstituted heterocycloalkyl (e.g., 3 to 8 membered, 3 to 6 membered, 4 to 6 membered, 4 to 5 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{41A}$ is independently oxo, halogen, —$CX^{41A}_3$, —$CHX^{41A}_2$, —$CH_2X^{41A}$, —$OCX^{41A}_3$, —$OCH_2X^{41A}$, —$OCHX^{41A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41A}$ is independently —F, —Cl, —Br, or —I. In embodiments, $R^{41A}$ is independently unsubstituted methyl. In embodiments, $R^{41A}$ is independently unsubstituted ethyl.

In embodiments, $R^{8B}$ is independently
hydrogen, —$CX^{8B}_3$, —$CHX^{8B}_2$, —$CH_2X^{8B}$, —CN, —COOH, —$CONH_2$, $R^{41B}$-substituted or unsubstituted alkyl (e.g., $C_1$-$C_8$, $C_1$-$C_6$, $C_1$-$C_4$, or $C_1$-$C_2$), $R^{41B}$-substituted or unsubstituted heteroalkyl (e.g., 2 to 8 membered, 2 to 6 membered, 4 to 6 membered, 2 to 3 membered, or 4 to 5 membered), $R^{41B}$-substituted or unsubstituted cycloalkyl (e.g., $C_3$-$C_8$, $C_3$-$C_6$, $C_4$-$C_6$, or $C_5$-$C_6$), $R^{41B}$-substituted or unsubstituted heterocycloalkyl (e.g., 3 to 8 membered, 3 to 6 membered, 4 to 6 membered, 4 to 5 membered, or 5 to 6 membered), $R^{41B}$-substituted or unsubstituted aryl (e.g., $C_6$-$C_{10}$ or phenyl), or $R^{41B}$-substituted or unsubstituted heteroaryl (e.g., 5 to 10 membered, 5 to 9 membered, or 5 to 6 membered). In embodiments, $R^{8B}$ is independently hydrogen, —$CX^{8B}_3$, —$CHX^{8B}_2$, —$CH_2X^{8B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{8B}$ is independently —F, —Cl, —Br, or —I. In embodiments, $R^{8B}$ is independently hydrogen. In embodiments, $R^{8B}$ is independently unsubstituted methyl. In embodiments, $R^{8B}$ is independently unsubstituted ethyl.

In embodiments, $R^{8A}$ and $R^{8B}$ substituents bonded to the same nitrogen atom may optionally be joined to form a $R^{41B}$-substituted or unsubstituted heterocycloalkyl (e.g., 3 to 8 membered, 3 to 6 membered, 4 to 6 membered, 4 to 5 membered, or 5 to 6 membered) or $R^{41B}$ substituted or unsubstituted heteroaryl (e.g., 5 to 10 membered, 5 to 9 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{8A}$ and $R^{8B}$ substituents bonded to the same nitrogen atom may optionally be joined to form a $R^{41B}$ substituted or unsubstituted heterocycloalkyl (e.g., 3 to 8 membered, 4 to 6 membered, 4 to 5 membered, or 5 to 6 membered). In embodiments, $R^{8A}$ and $R^{8B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{41B}$ is independently oxo, halogen, —$CX^{41B}_3$, —$CHX^{41B}_2$, —$CH_2X^{41B}$, —$OCX^{41B}_3$, —$OCH_2X^{41B}$, —$OCHX^{41B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41B}$ is independently —F, —Cl, —Br, or —I. In embodiments, $R^{41B}$ is independently unsubstituted methyl. In embodiments, $R^{41B}$ is independently unsubstituted ethyl.

In embodiments, $R^{8C}$ is independently hydrogen, —$CX^{8C}_3$, —$CHX^{8C}_2$, —$CH_2X^{8C}$, —CN, —COOH, —$CONH_2$, $R^{41C}$-substituted or unsubstituted alkyl (e.g., $C_1$-$C_8$, $C_1$-$C_6$, $C_1$-$C_4$, or $C_1$-$C_2$), $R^{41C}$-substituted or unsubstituted heteroalkyl (e.g., 2 to 8 membered, 2 to 6 membered, 4 to 6 membered, 2 to 3 membered, or 4 to 5 membered), $R^{41C}$-substituted or unsubstituted cycloalkyl (e.g., $C_3$-$C_8$, $C_3$-$C_6$, $C_4$-$C_6$, or $C_5$-$C_6$), $R^{41C}$-substituted or unsubstituted heterocycloalkyl (e.g., 3 to 8 membered, 3 to 6 membered, 4 to 6 membered, 4 to 5 membered, or 5 to 6 membered), $R^{41C}$-substituted or unsubstituted aryl (e.g., $C_6$-$C_{10}$ or phenyl), or $R^{41C}$-substituted or unsubstituted heteroaryl (e.g., 5 to 10 membered, 5 to 9 membered, or 5 to 6 membered). In embodiments, $R^{8C}$ is independently hydrogen, —$CX^{8C}_3$, —$CHX^{8C}_2$, —$CH_2X^{8C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{8C}$ is independently —F, —Cl, —Br, or —I. In embodiments, $R^{8C}$ is independently hydrogen. In embodiments, $R^{8C}$ is independently unsubstituted methyl. In embodiments, $R^{8C}$ is independently unsubstituted ethyl.

$R^{41C}$ is independently oxo, halogen, —$CX^{41C}_3$, —$CHX^{41C}_2$, —$CH_2X^{41C}$, —$OCX^{41C}_3$, —$OCH_2X^{41c}$, —$OCHX^{41C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41C}$ is independently —F, —Cl, —Br, or —I. In embodiments, $R^{41C}$ is independently unsubstituted methyl. In embodiments, $R^{41C}$ is independently unsubstituted ethyl.

In embodiments, $R^{8D}$ is independently hydrogen, —$CX^{8D}_3$, —$CHX^{8D}_2$, —$CH_2X^{8D}$, —CN, —COOH, —$CONH_2$, $R^{41D}$-substituted or unsubstituted alkyl (e.g., $C_1$-$C_8$, $C_1$-$C_6$, $C_1$-$C_4$, or $C_1$-$C_2$), $R^{41D}$-substituted or unsubstituted heteroalkyl (e.g., 2 to 8 membered, 2 to 6 membered, 4 to 6 membered, 2 to 3 membered, or 4 to 5 membered), $R^{41D}$-substituted or unsubstituted cycloalkyl (e.g., $C_3$-$C_8$, $C_3$-$C_6$, $C_4$-$C_6$, or $C_5$-$C_6$), $R^{41D}$-substituted or unsubstituted heterocycloalkyl (e.g., 3 to 8 membered, 3 to 6 membered, 4 to 6 membered, 4 to 5 membered, or 5 to 6 membered), $R^{41D}$-substituted or unsubstituted aryl (e.g., $C_6$-$C_{10}$ or phenyl), or $R^{41D}$-substituted or unsubstituted heteroaryl (e.g., 5 to 10 membered, 5 to 9 membered, or 5 to 6 membered). In embodiments, $R^{8D}$ is independently hydrogen, —$CX^{8D}_3$, —$CHX^{8D}_2$, —$CH_2X^{8D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{8D}$ is independently —F, —Cl, —Br, or —I. In embodiments, $R^{8D}$ is independently hydrogen. In embodiments, $R^{8D}$ is independently unsubstituted methyl. In embodiments, $R^{8D}$ is independently unsubstituted ethyl.

$R^{41D}$ is independently oxo, halogen, —$CX^{41D}_3$, —$CHX^{41D}_2$, —$CH_2X^{41D}$, —$OCX^{41D}_3$, —$OCH_2X^{41D}$, —$OCHX^{41D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41D}$ is independently —F, —Cl, —Br, or —I. In embodiments, $R^{41D}$ is independently unsubstituted methyl. In embodiments, $R^{41D}$ is independently unsubstituted ethyl. n1 may independently be 0. n1 may independently be 1. n1 may independently be 2. n1 may independently be 3. n1 may independently be 4. n2 may independently be 0. n2 may independently be 1. n2 may independently be 2. n2 may independently be 3. n2 may independently be 4. n7 may independently be 0. n7 may independently be 1. n7 may independently be 2. n7 may independently be 3. n7 may independently be 4. n8 may independently be 0. n8 may independently be 1. n8 may independently be 2. n8 may independently be 3. n8 may independently be 4. v1 may independently be 1. v1 may independently be 2. v2 may independently be 1. v2 may independently be 2. v7 may independently be 1. v7 may independently be 2. v8 may independently be 1. v8 may independently be 2. m1 may independently be 1. m1 may independently be 2. m2 may independently be 1. m2 may independently be 2. m7 may independently be 1. m7 may independently be 2. m8 may independently be 1. m8 may independently be 2.

z1 may independently be 0. z1 may independently be 1. z1 may independently be 2. z1 may independently be 3. z1 may independently be 4. z1 may independently be 5. z2 may independently be 0. z2 may independently be 1. z2 may independently be 2. z7 may independently be 0. z7 may independently be 1. z7 may independently be 2. z7 may independently be 3. z7 may independently be 4. In embodiments, z1, z2, and z7 are 0. In embodiments, z2 and z7 are 0.

Each X, $X^1$, $X^2$, $X^7$, and $X^8$ is independently —F, —Cl, —Br, or —I. $X^1$ may independently be —F. $X^1$ may independently be —Cl. $X^1$ may independently be —Br. $X^1$ may independently be —I. $X^2$ may independently be —F. $X^2$ may independently be —Cl. $X^2$ may independently be —Br. $X^2$ may independently be —I. $X^7$ may independently be —F. $X^7$ may independently be —Cl. $X^7$ may independently be —Br. $X^7$ may independently be —I. $X^8$ may independently be —F. $X^8$ may independently be —Cl. $X^8$ may independently be —Br. $X^8$ may independently be —I.

Figures 24, 25:
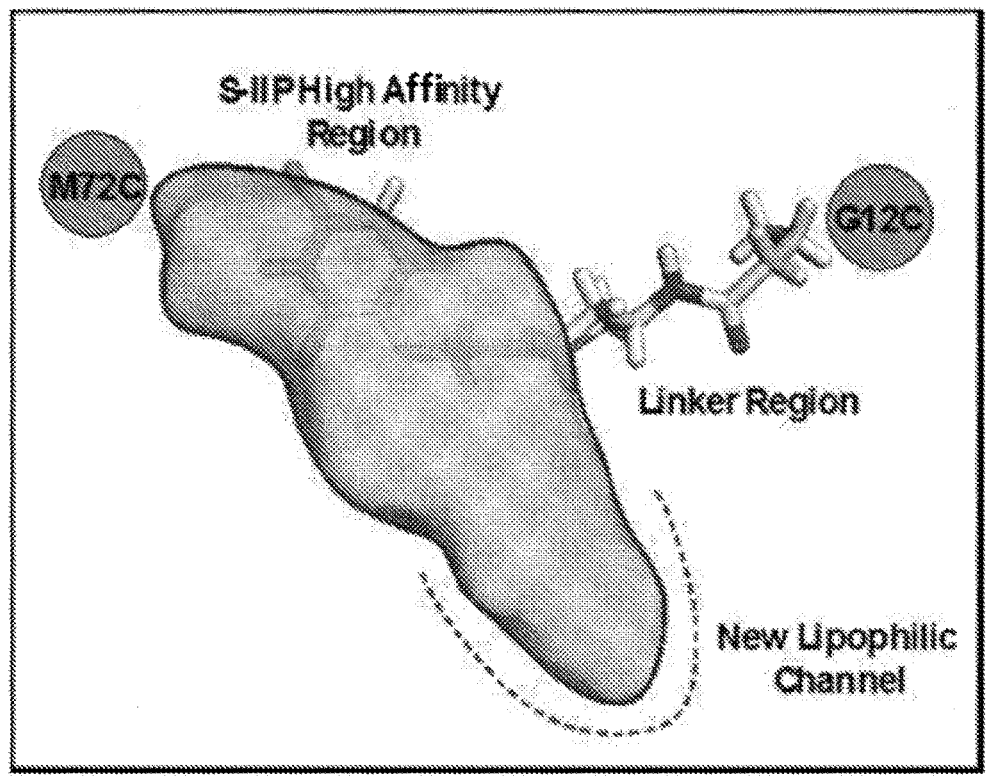
FIG. 24. Overlay of H-Ras$^{M72C}$ •GDP structure with 4LUC (H-Ras$^{G12C}$•GDP bound to tethering compound 6 shows directions for SAR.
FIG. 25. Preliminary SAR results demonstrate improved binding to the S-IIP high affinity region and engagement with C72 with a variety of electrophilic moieties. DG01/2 represents a compound moiety (e.g., a compound described herein).
Figure 26A:
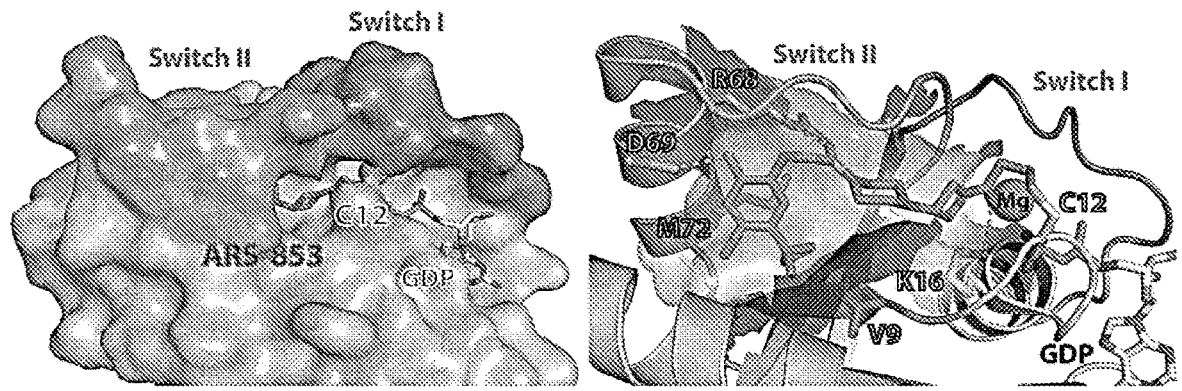
FIGS. 26A-26D. Tethering at Cys 72 Yields New S-IIP Binder.
Figure 26B:
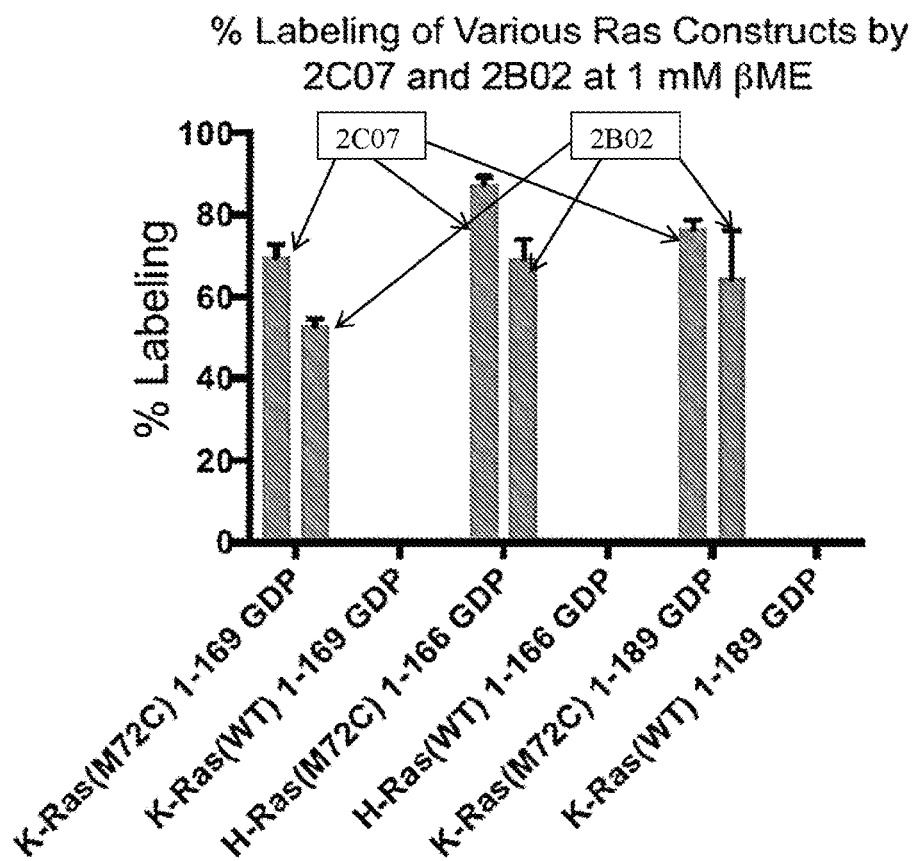
Figure 26C:
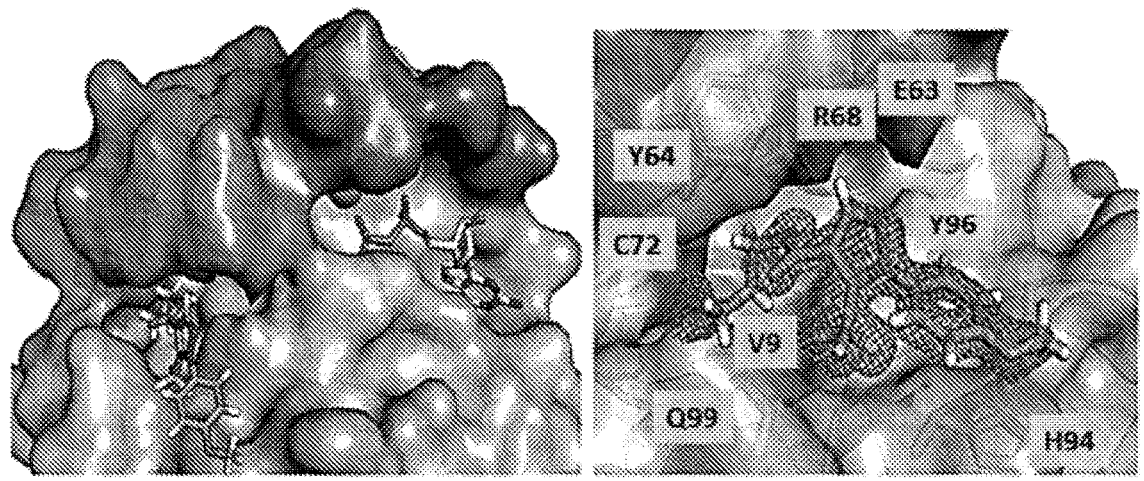
Figure 26D:
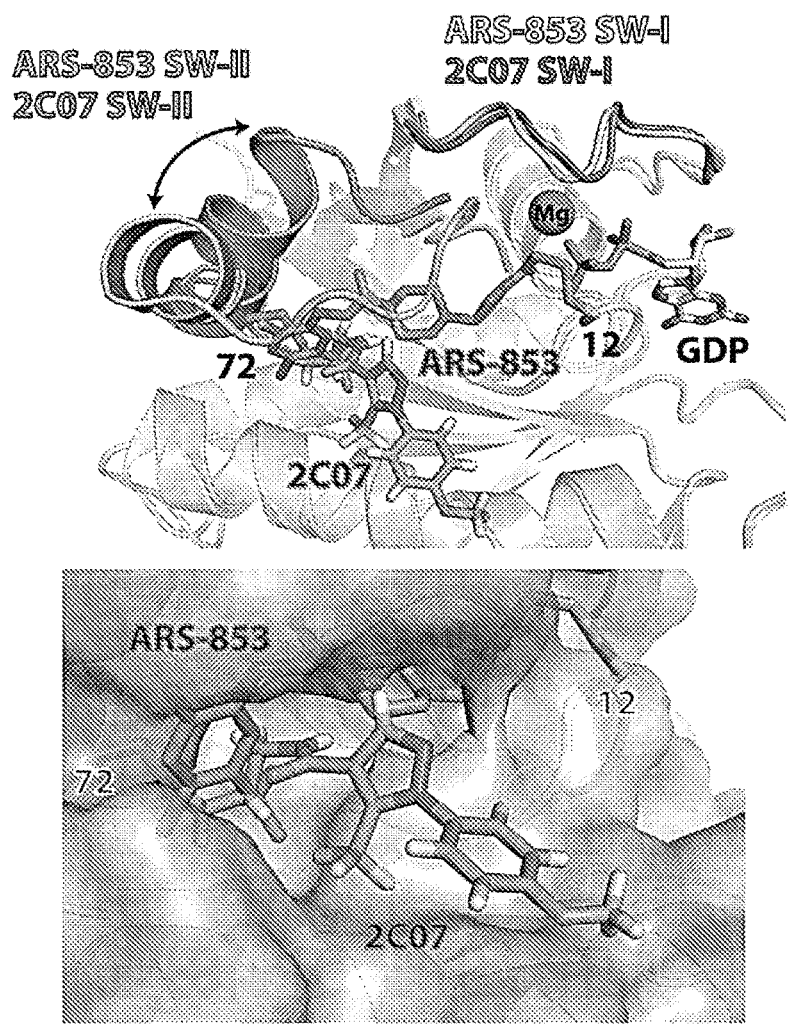
Figure 27A:
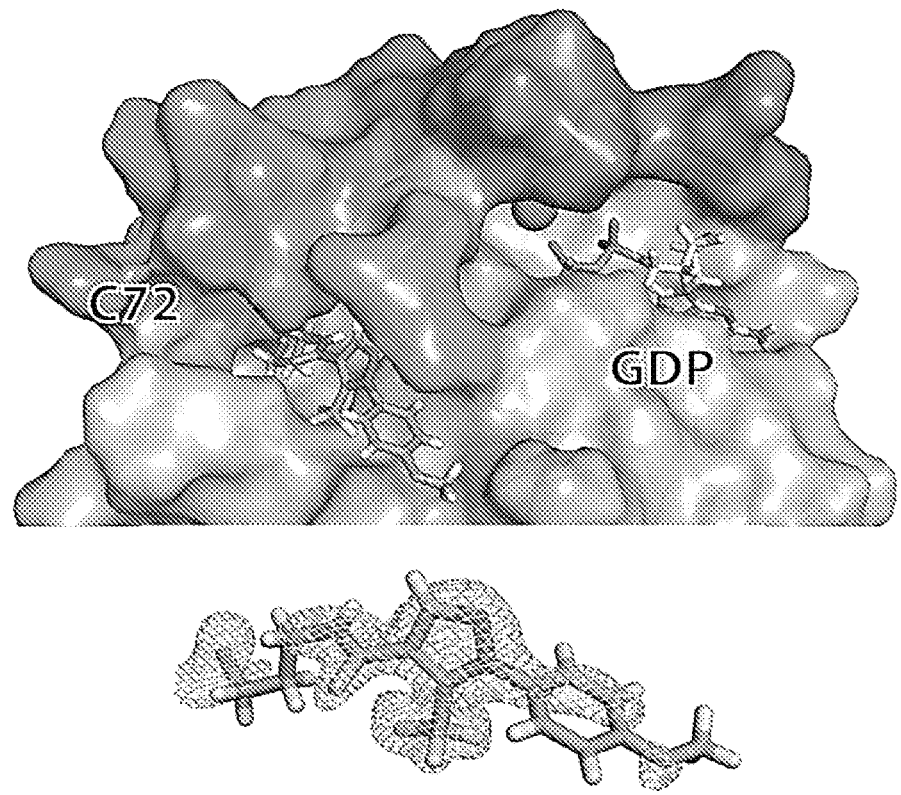
FIGS. 27A-27D. Compound 2C07 Binds and Engages With the S-IIP in Both Nucleotide States Disrupting Mg2+ Coordination in the GTP State.
Figure 27B:
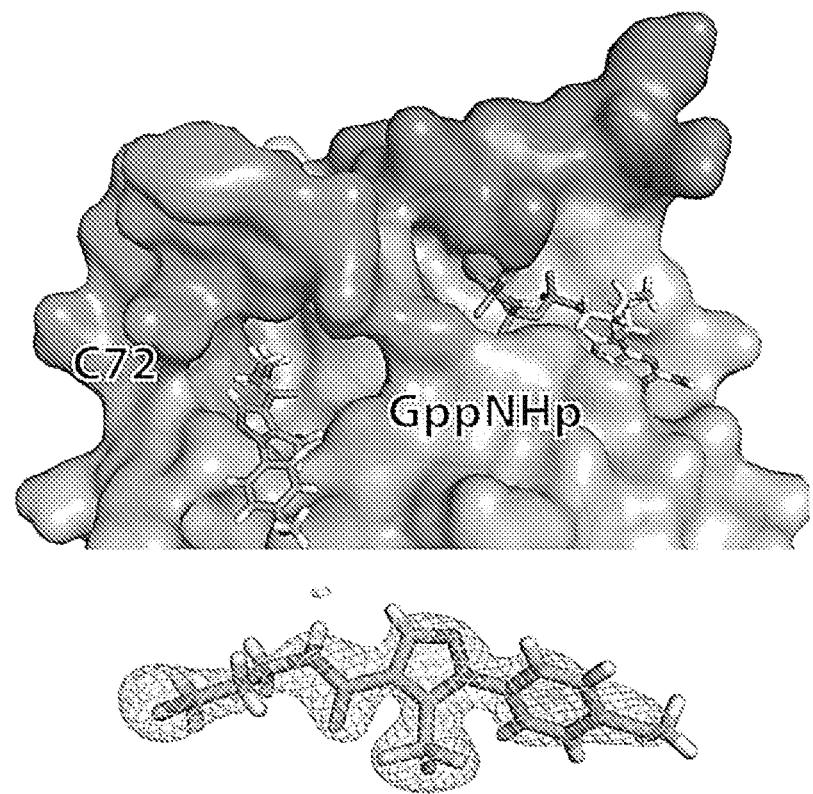
Figure 27C:
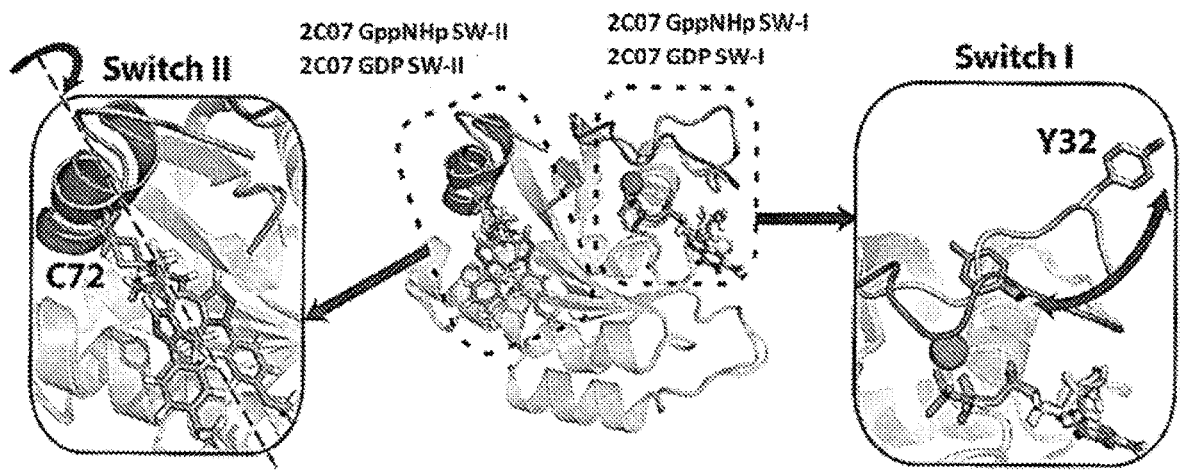
Figure 27D:
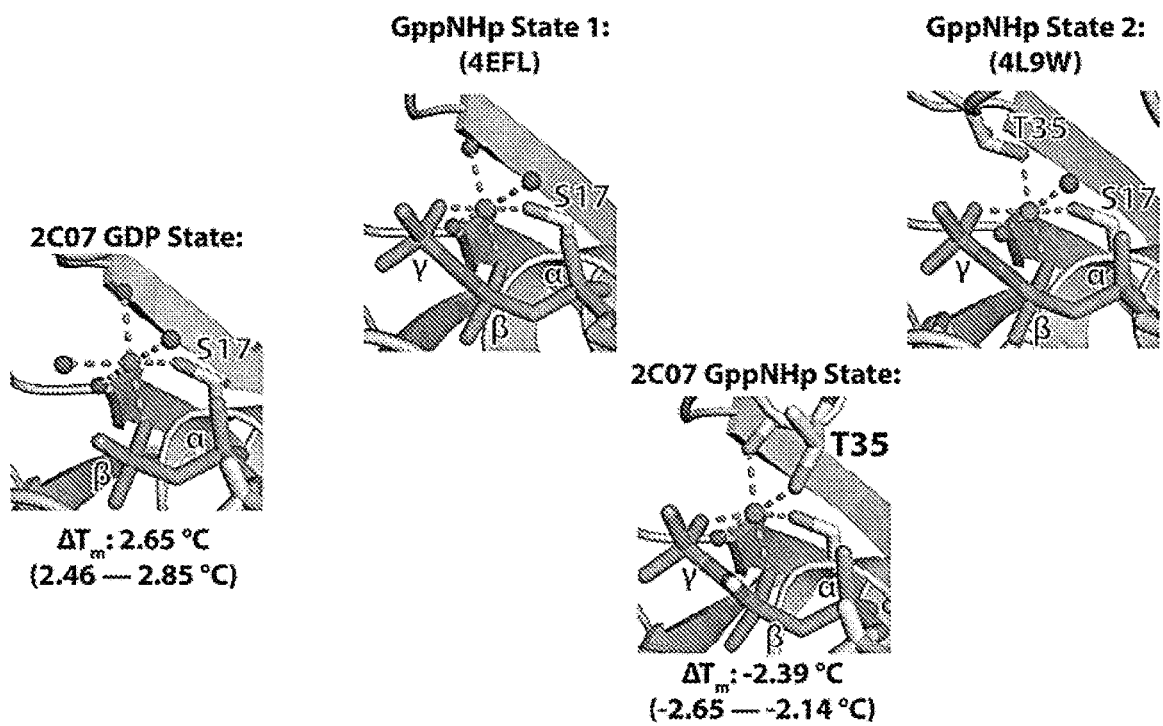
Figure 28A:
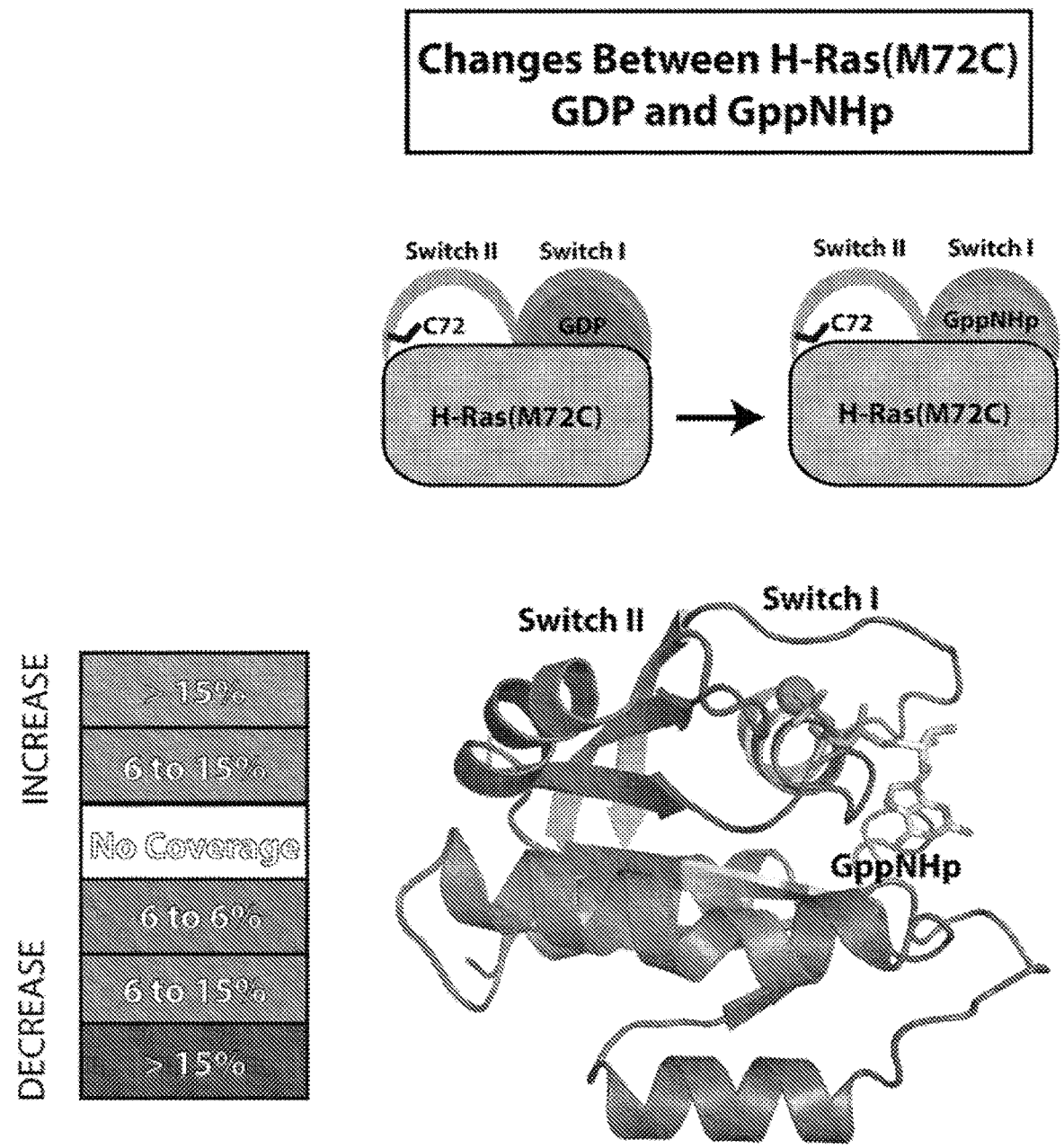
FIGS. 28A-28C. Hydrogen Deuterium Exchange (HDX) Supports 2C07 Crystallographic Binding Pose in Both Nucleotide States.
Figure 28B:
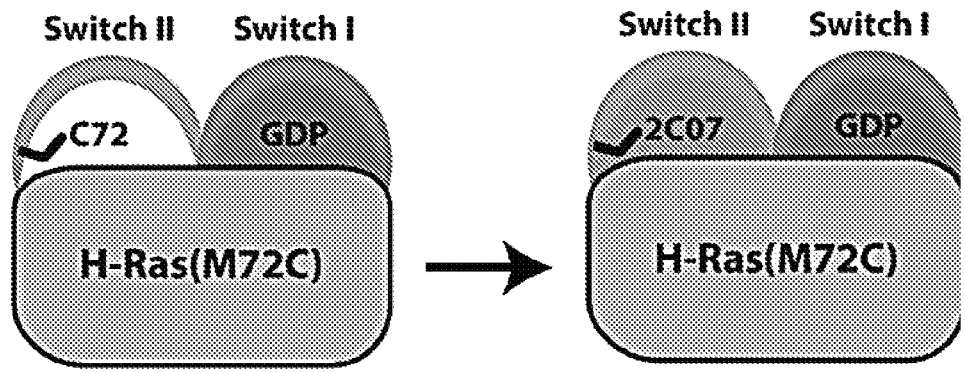
Figure 28B:
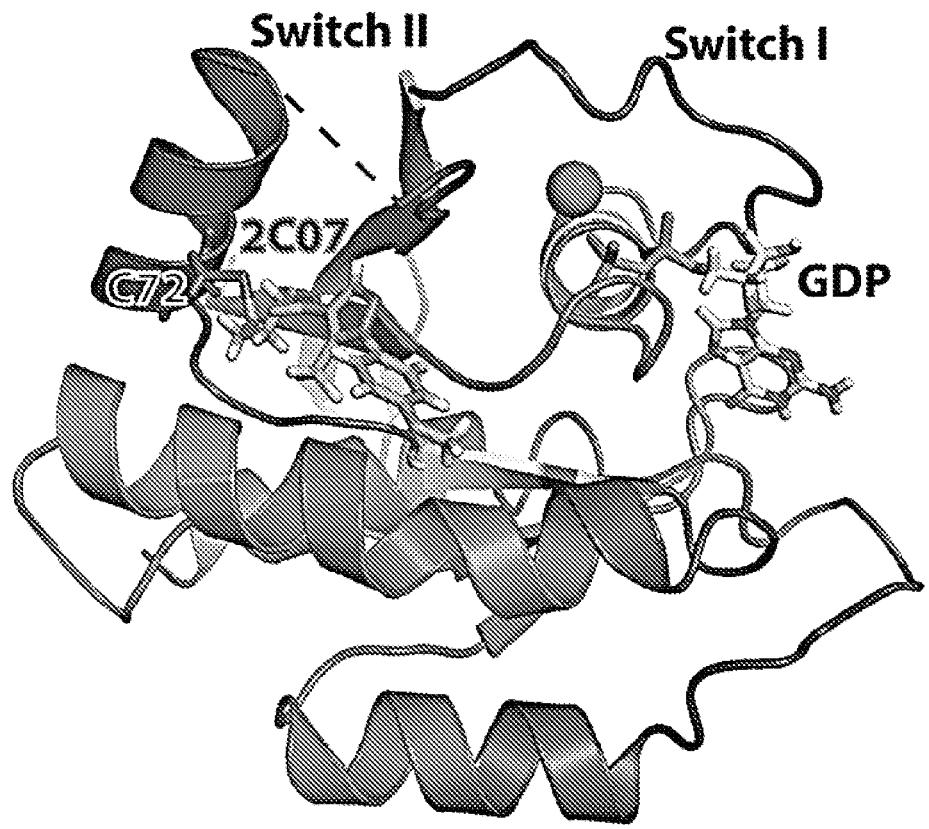
Figure 28C:
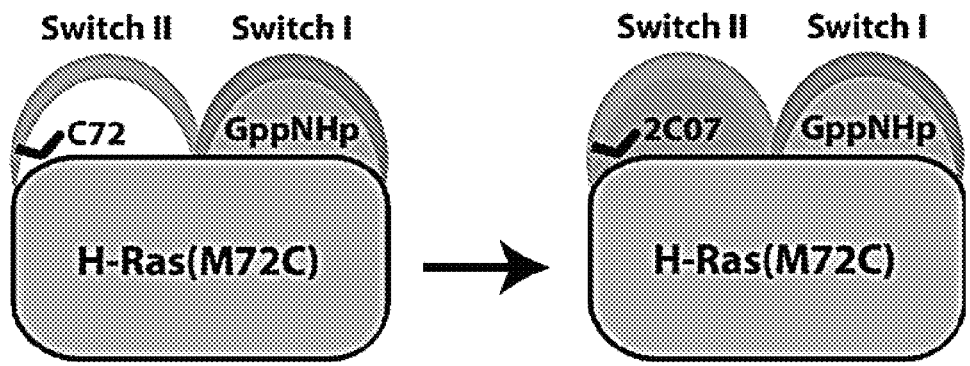
Figure 28C:
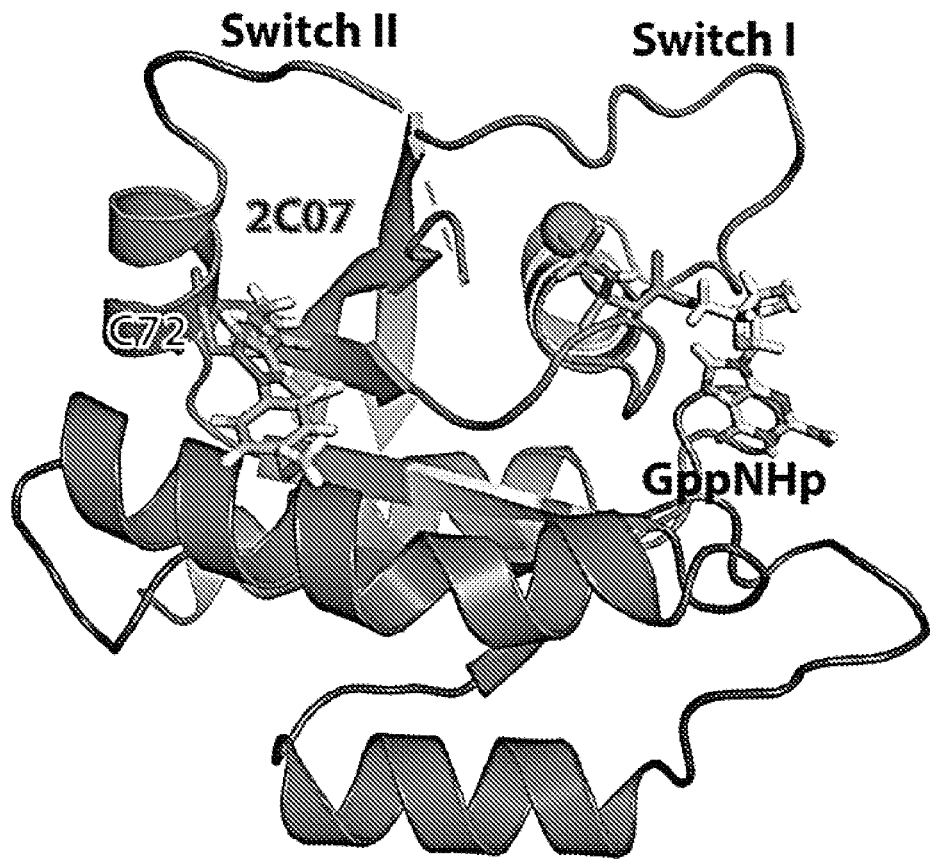
Figure 29A:
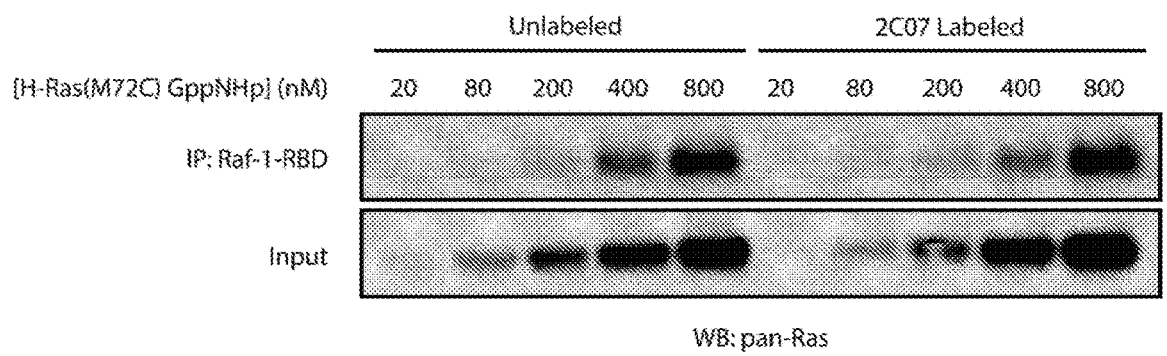
FIGS. 29A-29D. Pull-down Studies Show 2C07 Binding Preserves H-Ras(M72C) Binding to Raf, Shifts Intrinsic Nucleotide Preference Towards the Inactive GDP State, and Prevents SOS Binding and Activation.
Figure 29B:
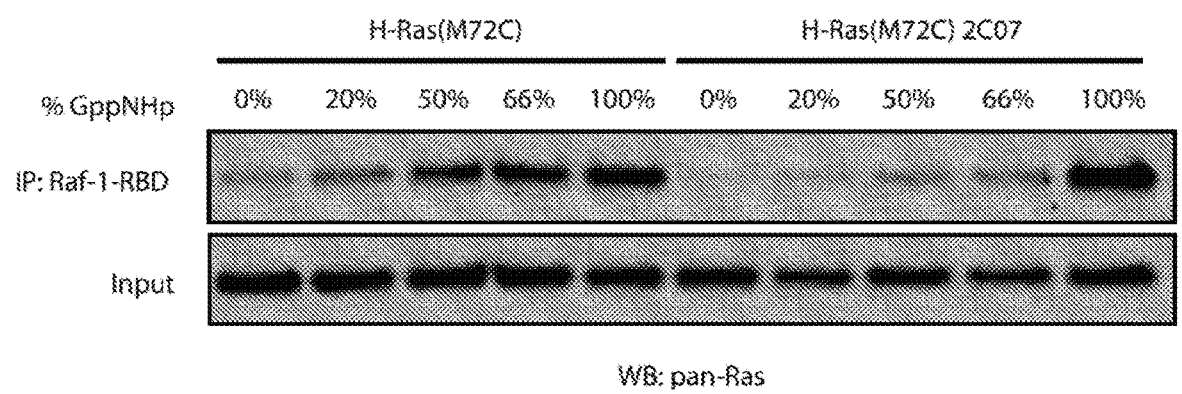
Figure 29C:
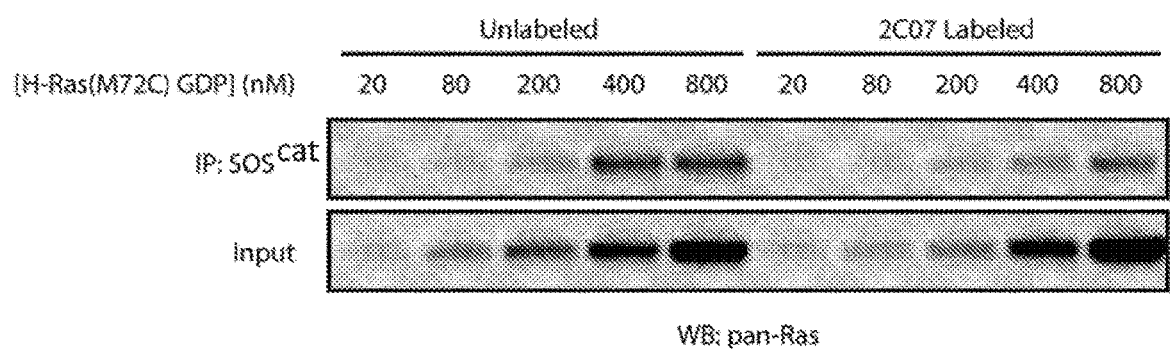
Figure 29D:
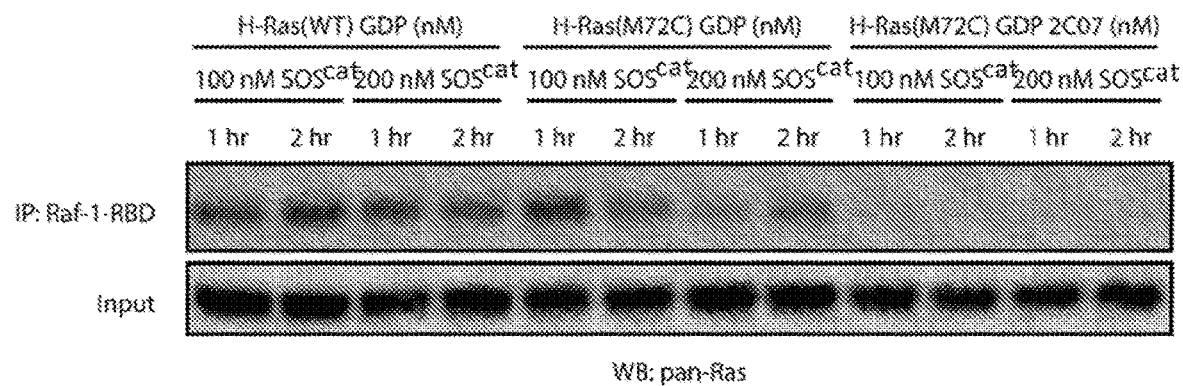
Figure 30:
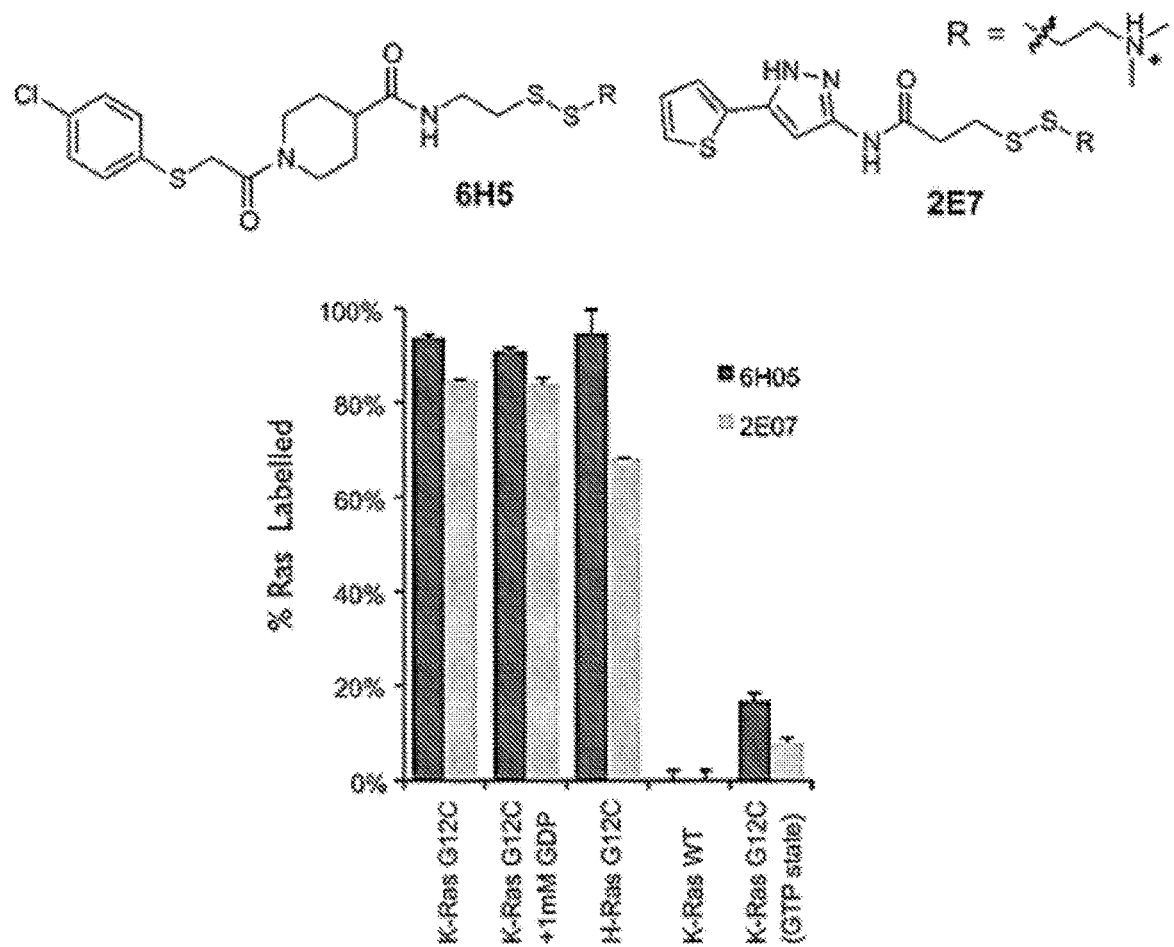
FIG. 30. Tethering screen hits 6H5 and 2E7 and their activity.

In embodiments, E is a covalent cysteine modifier moiety (e.g., as described in FIG. 25, wherein E is the moiety attached to DG01 or DG02).

In embodiments, E is

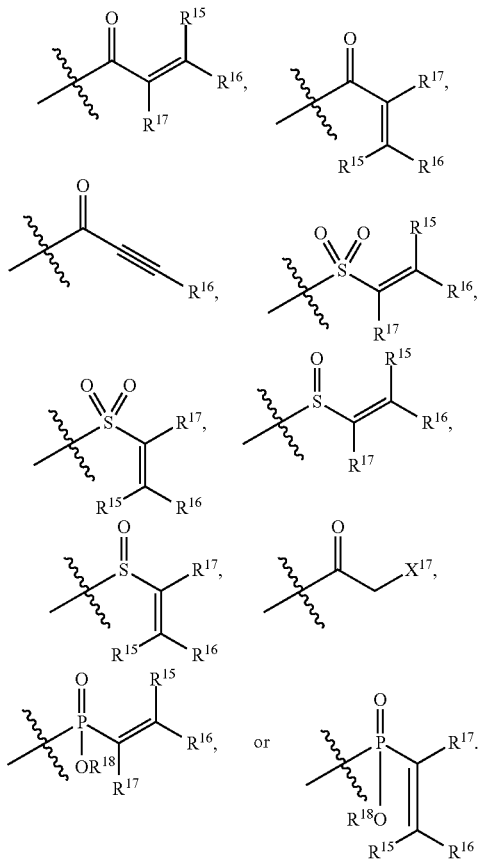

Each X, $X^{15}$, $X^{16}$, $X^{17}$ and $X^{18}$ is independently —F, —Cl, —Br, or —I.

The symbols n15, n16, n17, v15, v16, and v17, are independently an integer from 0 to 4.

The symbols m15, m16, and m17 are independently 1 or 2.

In embodiments, E is

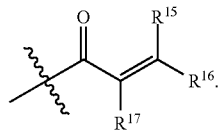

In embodiments, $R^{15}$ is hydrogen; $R^{16}$ is hydrogen; and $R^{17}$ is hydrogen.

$R^{15}$ is independently hydrogen, halogen, —$CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —$NHC=(O)NHNR^{15A}R^{15B}$, —$NHC(O)NR^{15A}R^{15B}$, —$N(O)_{m5}$, —$NR^{15A}R^{15B}$, —$C(O)R^{15C}$, —$C(O)$—$OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$OCX^{15}_3$, —$OCHX^{15}_2$, —$OCH_2X^{15}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{16}$ is independently hydrogen, halogen, —$CX^{16}_3$, —$CHX^{16}_2$, —$CH_2X^{16}$, —CN, —$SO_{n16}R_{16}R^{16D}$, —$SO_{v16}NR^{16A}R^{16B}$, —$NHNR^{16A}R^{16B}$, —$ONR^{16A}R^{16B}$, —$NHC=(O)NHNR^{16A}R^{16B}$, —$NHC(O)NR^{16A}R^{16B}$, —$N(O)_{m16}$, —$NR^{16A}R^{16B}$, —$C(O)R^{16C}$, —$C(O)$—$OR^{16C}$, —$C(O)NR^{16A}R^{16B}$, —$OR^{16D}$, —$NR^{16A}SO_2R^{16D}$, —$NR^{16A}C(O)R^{16C}$, —$NR^{16A}C(O)OR^{16C}$, —$NR^{16A}OR^{16C}$, —$OCX^{16}_3$, —$OCHX^{16}_2$, —$OCH_2X^{16}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{17}$ is independently hydrogen, halogen, —$CX^{17}_3$, —$CHX^{17}_2$, —$CH_2X^{17}$, —CN, —$SO_{n17}R^{17D}$, —$SO_{v17}NR^{17A}R^{17B}$, —$NHNR^{17A}R^{17B}$, —$ONR^{17A}R^{17B}$, —$NHC=(O)NHNR^{17A}R^{17B}$, —$NHC(O)NR^{17A}R^{17B}$, —$N(O)_{m17}$, —$NR^{17A}R^{17B}$, —$C(O)R^{17C}$, —$C(O)$—$OR^{17C}$, —$C(O)NR^{17A}R^{17B}$, —$OR^{17D}$, —$NR^{17A}SO_2R^{17D}$, —$NR^{17A}C(O)R^{17C}$, —$NR^{17A}C(O)OR^{17C}$, —$NR^{17A}OR^{17C}$, —$OCX^{17}_3$, —$OCHX^{17}_2$, —$OCH_2X^{17}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{18}$ is independently hydrogen, —$CX^{18}_3$, —$CHX^{18}_2$, —$CH_2X^{18}$, —$C(O)R^{18C}$, —$C(O)OR^{18C}$, —$C(O)NR^{18A}R^{18B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

Each $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, is independently hydrogen, —$CX_3$, —CN, —COOH, —$CONH_2$, —$CHX_2$, —$CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); $R^{15A}$ and $R^{15B}$ substituents bonded to the same nitrogen atom may optionally be joined to form a substituted or unsubstituted heterocycloalkyl (e.g., 2 to 8 membered, 2 to 6 membered, 4 to 6 membered, 2 to 3 membered, or 4 to 5 membered) or substituted or unsubstituted heteroaryl (e.g., 5 to 10 membered, 5 to 9 membered, or 5 to 6 membered); $R^{16A}$ and $R^{16B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{17A}$ and $R^{17B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{18A}$ and $R^{18B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered). Each X, $X^{15}$, $X^{16}$, $X^{17}$ and $X^{18}$ is independently —F, —Cl, —Br, or —I. The symbols n15, n16, n17, v15, v16, and v17, are each independently an integer from 0 to 4. The symbols m15, m16, and m17 are independently 1 or 2.

In embodiments, E is:

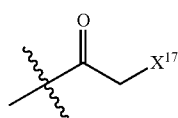

and $X^{17}$ is —Cl. In embodiments, E is:

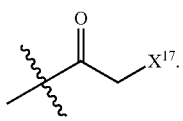

In embodiments, $X^{17}$ is —Cl.

In embodiments, E is:

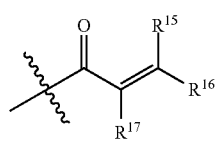

and $R^{15}$, $R^{16}$, and $R^{17}$ are independently hydrogen. In embodiments, E is:

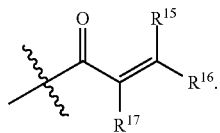

In embodiments, $R^{15}$, $R^{16}$, and $R^{17}$ are independently hydrogen.

In embodiments, E is:

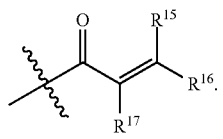

In embodiments, E is:

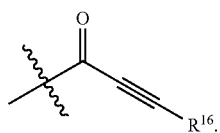

In embodiments, E is:

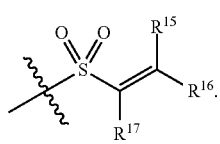

In embodiments, E is:

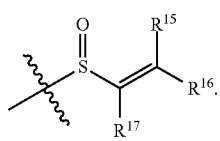

In embodiments, E is:

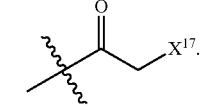

In embodiments, E is:

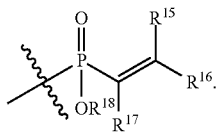

In embodiments, E is:

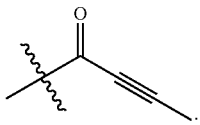 [SMILES: *C(=O)C#CC]

In embodiments, E is:

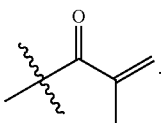 [SMILES: *C(=O)C(=C)C]

In embodiments, E is:

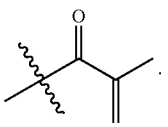

In embodiments, E is:

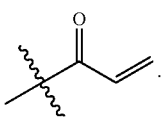 [SMILES: *C(=O)C=C]

In embodiments, E is:

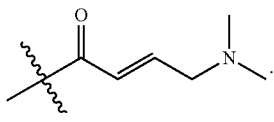 [SMILES: *C(=O)/C=C/CN(C)C]

In embodiments, E is

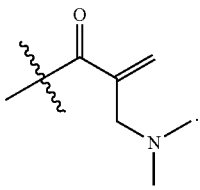 [SMILES: *C(=O)C(=C)CN(C)C]

X may independently be —F. X may independently be —Cl. X may independently be —Br. X may independently be —I. $X^{15}$ may independently be —F. $X^{15}$ may independently be —Cl. $X^{15}$ may independently be —Br. $X^{15}$ may independently be —I. $X^{16}$ may independently be —F. $X^{16}$ may independently be —Cl. $X^{16}$ may independently be —Br. $X^{16}$ may independently be —I. $X^{17}$ may independently be —F. $X^{17}$ may independently be —Cl. $X^{17}$ may independently be —Br. $X^{17}$ may independently be —I. $X^{18}$ may independently be —F. $X^{18}$ may independently be —Cl. $X^{18}$ may independently be —Br. $X^{18}$ may independently be —I. n15 may independently be 0. n15 may independently be 1. n15 may independently be 2. n15 may independently be 3. n15 may independently be 4. n16 may independently be 0. n16 may independently be 1. n16 may independently be 2. n16 may independently be 3. n16 may independently be 4. n17 may independently be 0. n17 may independently be 1. n17 may independently be 2. n17 may independently be 3. n17 may independently be 4. v15 may independently be 0. v15 may independently be 1. v15 may independently be 2. v15 may independently be 3. v15 may independently be 4. v16 may independently be 0. v16 may independently be 1. v16 may independently be 2. v16 may independently be 3. v16 may independently be 4. v17 may independently be 0. v17 may independently be 1. v17 may independently be 2. v17 may independently be 3. v17 may independently be 4. m15 may independently be 1. m15 may independently be 2. m16 may independently be 1. m16 may independently be 2. m17 may independently be 1. m17 may independently be 2.

In embodiments, $R^{15}$ is hydrogen. In embodiments, $R^{15}$ is halogen. In embodiments, $R^{15}$ is —$CX^{15}_3$. In embodiments, $R^{15}$ is —$CHX^{15}_2$. In embodiments, $R^{15}$ is —$CH_2X^{15}$. In embodiments, $R^{15}$ is —CN. In embodiments, $R^{15}$ is —$SO_{n15}R^{15D}$. In embodiments, $R^{15}$ is —$SO_{v15}NR^{15A}R^{15B}$. In embodiments, $R^{15}$ is —$NHNR^{15A}R^{15B}$. In embodiments, $R^{15}$ is —$ONR^{15A}R^{15B}$. In embodiments, $R^{15}$ is —NHC=(O)$NHNR^{15A}R^{15B}$. In embodiments, $R^{15}$ is —NHC(O)$NR^{15A}R^{15B}$. In embodiments, $R^{15}$ is —$N(O)_{m15}$. In embodiments, $R^{15}$ is —$NR^{15A}R^{15B}$. In embodiments, $R^{15}$ is —C(O)$R^{15C}$. In embodiments, $R^{15}$ is —C(O)—$OR^{15C}$. In embodiments, $R^{15}$ is —C(O)$NR^{15A}R^{15B}$. In embodiments, $R^{15}$ is —$OR^{15D}$. In embodiments, $R^{15}$ is —$NR^{15A}SO_2R^{15D}$. In embodiments, $R^{15}$ is —$NR^{15A}C(O)R^{15C}$. In embodiments, $R^{15}$ is —$NR^{15A}C(O)OR^{15C}$. In embodiments, $R^{15}$ is —$NR^{15A}OR^{15C}$. In embodiments, $R^{15}$ is —$OCX^{15}_3$. In embodiments, $R^{15}$ is —$OCHX^{15}_2$. In embodiments, $R^{15}$ is —$OCH_2X^{15}$. In embodiments, $R^{15}$ is independently —OH. In embodiments, $R^{15}$ is independently —$NH_2$. In embodiments, $R^{15}$ is independently —COOH. In embodiments, $R^{15}$ is independently —$CONH_2$. In embodiments, $R^{15}$ is independently —$NO_2$. In embodiments, $R^{15}$ is independently —SH. In embodiments, $R^{15}$ is independently —$CF_3$. In embodiments, $R^{15}$ is independently —$CHF_2$. In embodiments, $R^{15}$ is independently —$CH_2F$. In embodiments, $R^{15}$ is independently —$OCF_3$. In embodiments, $R^{15}$ is independently —$OCH_2F$. In embodiments, $R^{15}$ is independently —$OCHF_2$. In embodiments, $R^{15}$ is independently —$OCH_3$. In embodiments, $R^{15}$ is independently —$OCH_2CH_3$. In embodiments, $R^{15}$ is independently —$OCH_2CH_2CH_3$. In embodiments, $R^{15}$ is independently —$OCH(CH_3)_2$. In embodiments, $R^{15}$ is independently —$OC(CH_3)_3$. In embodiments, $R^{15}$ is independently —$SCH_3$. In embodiments, $R^{15}$ is independently —$SCH_2CH_3$. In embodiments, $R^{15}$ is independently —$SCH_2CH_2CH_3$. In embodiments, $R^{15}$ is independently —$SCH(CH_3)_2$. In embodiments, $R^{15}$ is independently —$SC(CH_3)_3$. In embodiments, $R^{15}$ is independently —$CH_3$. In embodiments, $R^{15}$ is independently —$CH_2CH_3$. In embodiments, $R^{15}$ is independently —CH$_2$CH$_2$CH$_3$. In embodiments, R$^{15}$ is independently —CH(CH$_3$)$_2$. In embodiments, R$^{15}$ is independently —C(CH$_3$)$_3$. In embodiments, R$^{15}$ is independently —F. In embodiments, R$^{15}$ is independently —Cl. In embodiments, R$^{15}$ is independently —Br. In embodiments, R$^{15}$ is independently —I.

In embodiments, R$^{15}$ is independently substituted or unsubstituted alkyl (e.g., C$_1$-C$_8$, C$_1$-C$_6$, C$_1$-C$_4$, or C$_1$-C$_2$). In embodiments, R$^{15}$ is independently substituted alkyl (e.g., C$_1$-C$_8$, C$_1$-C$_6$, C$_1$-C$_4$, or C$_1$-C$_2$). In embodiments, R$^{15}$ is independently unsubstituted alkyl (e.g., C$_1$-C$_8$, C$_1$-C$_6$, C$_1$-C$_4$, or C$_1$-C$_2$). In embodiments, R$^{15}$ is independently unsubstituted methyl. In embodiments, R$^{15}$ is independently unsubstituted ethyl. In embodiments, R$^{15}$ is independently unsubstituted propyl. In embodiments, R$^{15}$ is independently unsubstituted isopropyl. In embodiments, R$^{15}$ is independently unsubstituted tert-butyl. In embodiments, R$^{15}$ is independently substituted or unsubstituted heteroalkyl (e.g., 2 to 8 membered, 2 to 6 membered, 4 to 6 membered, 2 to 3 membered, or 4 to 5 membered). In embodiments, R$^{15}$ is independently substituted heteroalkyl (e.g., 2 to 8 membered, 2 to 6 membered, 4 to 6 membered, 2 to 3 membered, or 4 to 5 membered). In embodiments, R$^{15}$ is independently unsubstituted heteroalkyl (e.g., 2 to 8 membered, 2 to 6 membered, 4 to 6 membered, 2 to 3 membered, or 4 to 5 membered). In embodiments, R$^{15}$ is independently substituted or unsubstituted cycloalkyl (e.g., C$_3$-C$_8$, C$_3$-C$_6$, C$_4$-C$_6$, or C$_5$-C$_6$). In embodiments, R$^{15}$ is independently substituted cycloalkyl (e.g., C$_3$-C$_8$, C$_3$-C$_6$, C$_4$-C$_6$, or C$_5$-C$_6$). In embodiments, R$^{15}$ is independently unsubstituted cycloalkyl (e.g., C$_3$-C$_8$, C$_3$-C$_6$, C$_4$-C$_6$, or C$_5$-C$_6$). In embodiments, R$^{15}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{15}$ is independently substituted heterocycloalkyl (e.g., 3 to 8 membered, 3 to 6 membered, 4 to 6 membered, 4 to 5 membered, or 5 to 6 membered). In embodiments, R$^{15}$ is independently unsubstituted heterocycloalkyl (e.g., 3 to 8 membered, 3 to 6 membered, 4 to 6 membered, 4 to 5 membered, or 5 to 6 membered). In embodiments, R$^{15}$ is independently substituted or unsubstituted aryl (e.g., C$_6$-C$_{10}$ or phenyl). In embodiments, R$^{15}$ is independently substituted aryl (e.g., C$_6$-C$_{10}$ or phenyl). In embodiments, R$^{15}$ is independently unsubstituted aryl (e.g., C$_6$-C$_{10}$ or phenyl). In embodiments, R$^{15}$ is independently substituted or unsubstituted heteroaryl (e.g., 5 to 10 membered, 5 to 9 membered, or 5 to 6 membered). In embodiments, R$^{15}$ is independently substituted heteroaryl (e.g., 5 to 10 membered, 5 to 9 membered, or 5 to 6 membered). In embodiments, R$^{15}$ is independently unsubstituted heteroaryl (e.g., 5 to 10 membered, 5 to 9 membered, or 5 to 6 membered).

In embodiments, R$^{15A}$ is independently hydrogen. In embodiments, R$^{15A}$ is independently —CX$^{15A}$$_3$. In embodiments, R$^{15A}$ is independently —CHX$^{15A}$$_2$. In embodiments, R$^{15A}$ is independently —CH$_2$X$^{15A}$. In embodiments, R$^{15A}$ is independently —CN. In embodiments, R$^{15A}$ is independently —COOH. In embodiments, R$^{15A}$ is independently —CONH$_2$. In embodiments, X$^{15A}$ is independently —F, —Cl, —Br, or —I.

In embodiments, R$^{15A}$ is independently substituted or unsubstituted alkyl (e.g., C$_1$-C$_8$, C$_1$-C$_6$, C$_1$-C$_4$, or C$_1$-C$_2$). In embodiments, R$^{15A}$ is independently substituted alkyl (e.g., C$_1$-C$_8$, C$_1$-C$_6$, C$_1$-C$_4$, or C$_1$-C$_2$). In embodiments, R$^{15A}$ is independently unsubstituted alkyl (e.g., C$_1$-C$_8$, C$_1$-C$_6$, C$_1$-C$_4$, or C$_1$-C$_2$). In embodiments, R$^{15A}$ is independently unsubstituted methyl. In embodiments, R$^{15A}$ is independently unsubstituted ethyl. In embodiments, R$^{15A}$ is independently unsubstituted propyl. In embodiments, R$^{15A}$ is independently unsubstituted isopropyl. In embodiments, R$^{15A}$ is independently unsubstituted tert-butyl. In embodiments, R$^{15A}$ is independently substituted or unsubstituted heteroalkyl (e.g., 2 to 8 membered, 2 to 6 membered, 4 to 6 membered, 2 to 3 membered, or 4 to 5 membered). In embodiments, R$^{15A}$ is independently substituted heteroalkyl (e.g., 2 to 8 membered, 2 to 6 membered, 4 to 6 membered, 2 to 3 membered, or 4 to 5 membered). In embodiments, R$^{15A}$ is independently unsubstituted heteroalkyl (e.g., 2 to 8 membered, 2 to 6 membered, 4 to 6 membered, 2 to 3 membered, or 4 to 5 membered). In embodiments, R$^{15A}$ is independently substituted or unsubstituted cycloalkyl (e.g., C$_3$-C$_8$, C$_3$-C$_6$, C$_4$-C$_6$, or C$_5$-C$_6$). In embodiments, R$^{15A}$ is independently substituted cycloalkyl (e.g., C$_3$-C$_8$, C$_3$-C$_6$, C$_4$-C$_6$, or C$_5$-C$_6$). In embodiments, R$^{15A}$ is independently unsubstituted cycloalkyl (e.g., C$_3$-C$_8$, C$_3$-C$_6$, C$_4$-C$_6$, or C$_5$-C$_6$). In embodiments, R$^{15A}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{15A}$ is independently substituted heterocycloalkyl (e.g., 3 to 8 membered, 3 to 6 membered, 4 to 6 membered, 4 to 5 membered, or 5 to 6 membered). In embodiments, R$^{15A}$ is independently unsubstituted heterocycloalkyl (e.g., 3 to 8 membered, 4 to 6 membered, 4 to 5 membered, or 5 to 6 membered). In embodiments, R$^{15A}$ is independently substituted or unsubstituted aryl (e.g., C$_6$-C$_{10}$ or phenyl). In embodiments, R$^{15A}$ is independently substituted aryl (e.g., C$_6$-C$_{10}$ or phenyl). In embodiments, R$^{15A}$ is independently unsubstituted aryl (e.g., C$_6$-C$_{10}$ or phenyl). In embodiments, R$^{15A}$ is independently substituted or unsubstituted heteroaryl (e.g., 5 to 10 membered, 5 to 9 membered, or 5 to 6 membered). In embodiments, R$^{15A}$ is independently substituted heteroaryl (e.g., 5 to 10 membered, 5 to 9 membered, or 5 to 6 membered). In embodiments, R$^{15A}$ is independently unsubstituted heteroaryl (e.g., 5 to 10 membered, 5 to 9 membered, or 5 to 6 membered).

In embodiments, R$^{15B}$ is independently hydrogen. In embodiments, R$^{15B}$ is independently —CX$^{15B}$$_3$. In embodiments, R$^{15B}$ is independently —CHX$^{15B}$$_2$. In embodiments, R$^{15B}$ is independently —CH$_2$X$^{15B}$. In embodiments, R$^{15B}$ is independently —CN. In embodiments, R$^{15B}$ is independently —COOH. In embodiments, R$^{15B}$ is independently —CONH$_2$. In embodiments, X$^{15B}$ is independently —F, —Cl, —Br, or —I.

In embodiments, R$^{15B}$ is independently substituted or unsubstituted alkyl (e.g., C$_1$-C$_8$, C$_1$-C$_6$, C$_1$-C$_4$, or C$_1$-C$_2$). In embodiments, R$^{15B}$ is independently substituted alkyl (e.g., C$_1$-C$_8$, C$_1$-C$_6$, C$_1$-C$_4$, or C$_1$-C$_2$). In embodiments, R$^{15B}$ is independently unsubstituted alkyl (e.g., C$_1$-C$_8$, C$_1$-C$_6$, C$_1$-C$_4$, or C$_1$-C$_2$). In embodiments, R$^{15B}$ is independently unsubstituted methyl. In embodiments, R$^{15B}$ is independently unsubstituted ethyl. In embodiments, R$^{15B}$ is independently unsubstituted propyl. In embodiments, R$^{15B}$ is independently unsubstituted isopropyl. In embodiments, R$^{15B}$ is independently unsubstituted tert-butyl. In embodiments, R$^{15B}$ is independently substituted or unsubstituted heteroalkyl (e.g., 2 to 8 membered, 2 to 6 membered, 4 to 6 membered, 2 to 3 membered, or 4 to 5 membered). In embodiments, R$^{15B}$ is independently substituted heteroalkyl (e.g., 2 to 8 membered, 2 to 6 membered, 4 to 6 membered, 2 to 3 membered, or 4 to 5 membered). In embodiments, R$^{15B}$ is independently unsubstituted heteroalkyl (e.g., 2 to 8 membered, 2 to 6 membered, 4 to 6 membered, 2 to 3 membered, or 4 to 5 membered). In embodiments, R$^{15B}$ is independently substituted or unsubstituted cycloalkyl (e.g., $C_3$-$C_8$, $C_3$-$C_6$, $C_4$-$C_6$, or $C_5$-$C_6$). In embodiments, $R^{15B}$ is independently substituted cycloalkyl (e.g., $C_3$-$C_8$, $C_3$-$C_6$, $C_4$-$C_6$, or $C_5$-$C_6$). In embodiments, $R^{15B}$ is independently unsubstituted cycloalkyl (e.g., $C_3$-$C_8$, $C_3$-$C_6$, $C_4$-$C_6$, or $C_5$-$C_6$). In embodiments, $R^{15B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15B}$ is independently substituted heterocycloalkyl (e.g., 3 to 8 membered, 3 to 6 membered, 4 to 6 membered, 4 to 5 membered, or 5 to 6 membered). In embodiments, $R^{15B}$ is independently unsubstituted heterocycloalkyl (e.g., 3 to 8 membered, 3 to 6 membered, 4 to 6 membered, 4 to 5 membered, or 5 to 6 membered). In embodiments, $R^{15B}$ is independently substituted or unsubstituted aryl (e.g., $C_6$-$C_{10}$ or phenyl). In embodiments, $R^{15B}$ is independently substituted aryl (e.g., $C_6$-$C_{10}$ or phenyl). In embodiments, $R^{15B}$ is independently unsubstituted aryl (e.g., $C_6$-$C_{10}$ or phenyl). In embodiments, $R^{15B}$ is independently substituted or unsubstituted heteroaryl (e.g., 5 to 10 membered, 5 to 9 membered, or 5 to 6 membered). In embodiments, $R^{15B}$ is independently substituted heteroaryl (e.g., 5 to 10 membered, 5 to 9 membered, or 5 to 6 membered). In embodiments, $R^{15B}$ is independently unsubstituted heteroaryl (e.g., 5 to 10 membered, 5 to 9 membered, or 5 to 6 membered).

In embodiments, $R^{15A}$ and $R^{15B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{15A}$ and $R^{15B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{15A}$ and $R^{15B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{15A}$ and $R^{15B}$ substituents bonded to the same nitrogen atom may be joined to form a substituted or unsubstituted heteroaryl (e.g., 5 to 10 membered, 5 to 9 membered, or 5 to 6 membered). In embodiments, $R^{15A}$ and $R^{15B}$ substituents bonded to the same nitrogen atom may be joined to form a substituted heteroaryl (e.g., 5 to 10 membered, 5 to 9 membered, or 5 to 6 membered). In embodiments, $R^{15A}$ and $R^{15B}$ substituents bonded to the same nitrogen atom may be joined to form an unsubstituted heteroaryl (e.g., 5 to 10 membered, 5 to 9 membered, or 5 to 6 membered).

In embodiments, $R^{15C}$ is independently hydrogen. In embodiments, $R^{15C}$ is independently —$CX^{15C}_3$. In embodiments, $R^{15C}$ is independently —$CHX^{15C}_2$. In embodiments, $R^{15C}$ is independently —$CH_2X^{15C}$. In embodiments, $R^{15C}$ is independently —CN. In embodiments, $R^{15C}$ is independently —COOH. In embodiments, $R^{15C}$ is independently —$CONH_2$. In embodiments, $X^{15C}$ is independently —F, —Cl, —Br, or —I.

In embodiments, $R^{15C}$ is independently substituted or unsubstituted alkyl (e.g., $C_1$-$C_8$, $C_1$-$C_6$, $C_1$-$C_4$, or $C_1$-$C_2$). In embodiments, $R^{15C}$ is independently substituted alkyl (e.g., $C_1$-$C_8$, $C_1$-$C_6$, $C_1$-$C_4$, or $C_1$-$C_2$). In embodiments, $R^{15C}$ is independently unsubstituted alkyl (e.g., $C_1$-$C_8$, $C_1$-$C_6$, $C_1$-$C_4$, or $C_1$-$C_2$). In embodiments, $R^{15C}$ is independently unsubstituted methyl. In embodiments, $R^{15C}$ is independently unsubstituted ethyl. In embodiments, $R^{15C}$ is independently unsubstituted propyl. In embodiments, $R^{15C}$ is independently unsubstituted isopropyl. In embodiments, $R^{15C}$ is independently unsubstituted tert-butyl. In embodiments, $R^{15C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{15C}$ is independently substituted heteroalkyl (e.g., 2 to 8 membered, 2 to 6 membered, 4 to 6 membered, 2 to 3 membered, or 4 to 5 membered). In embodiments, $R^{15C}$ is independently unsubstituted heteroalkyl (e.g., 2 to 8 membered, 2 to 6 membered, 4 to 6 membered, 2 to 3 membered, or 4 to 5 membered). In embodiments, $R^{15C}$ is independently substituted or unsubstituted cycloalkyl (e.g., $C_3$-$C_8$, $C_3$-$C_6$, $C_4$-$C_6$, or $C_5$-$C_6$). In embodiments, $R^{15C}$ is independently substituted cycloalkyl (e.g., $C_3$-$C_8$, $C_3$-$C_6$, $C_4$-$C_6$, or $C_5$-$C_6$). In embodiments, $R^{15C}$ is independently unsubstituted cycloalkyl (e.g., $C_3$-$C_8$, $C_3$-$C_6$, $C_4$-$C_6$, or $C_5$-$C_6$). In embodiments, $R^{15C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15C}$ is independently substituted heterocycloalkyl (e.g., 3 to 8 membered, 3 to 6 membered, 4 to 6 membered, 4 to 5 membered, or 5 to 6 membered). In embodiments, $R^{15C}$ is independently unsubstituted heterocycloalkyl (e.g., 3 to 8 membered, 3 to 6 membered, 4 to 6 membered, 4 to 5 membered, or 5 to 6 membered). In embodiments, $R^{15C}$ is independently substituted or unsubstituted aryl (e.g., $C_6$-$C_{10}$ or phenyl). In embodiments, $R^{15C}$ is independently substituted aryl (e.g., $C_6$-$C_{10}$ or phenyl). In embodiments, $R^{15C}$ is independently unsubstituted aryl (e.g., $C_6$-$C_{10}$ or phenyl). In embodiments, $R^{15C}$ is independently substituted or unsubstituted heteroaryl (e.g., 5 to 10 membered, 5 to 9 membered, or 5 to 6 membered). In embodiments, $R^{15C}$ is independently substituted heteroaryl (e.g., 5 to 10 membered, 5 to 9 membered, or 5 to 6 membered). In embodiments, $R^{15C}$ is independently unsubstituted heteroaryl (e.g., 5 to 10 membered, 5 to 9 membered, or 5 to 6 membered).

In embodiments, $R^{15D}$ is independently hydrogen. In embodiments, $R^{15D}$ is independently —$CX^{15D}_3$. In embodiments, $R^{15D}$ is independently —$CHX^{15D}_2$. In embodiments, $R^{15D}$ is independently —$CH_2X^{15D}$. In embodiments, $R^{15D}$ is independently —CN. In embodiments, $R^{15D}$ is independently —COOH. In embodiments, $R^{15D}$ is independently —$CONH_2$. In embodiments, $X^{15D}$ is independently —F, —Cl, —Br, or —I.

In embodiments, $R^{15D}$ is independently substituted or unsubstituted alkyl (e.g., $C_1$-$C_8$, $C_1$-$C_6$, $C_1$-$C_4$, or $C_1$-$C_2$). In embodiments, $R^{15D}$ is independently substituted alkyl (e.g., $C_1$-$C_8$, $C_1$-$C_6$, $C_1$-$C_4$, or $C_1$-$C_2$). In embodiments, $R^{15D}$ is independently unsubstituted alkyl (e.g., $C_1$-$C_8$, $C_1$-$C_6$, $C_1$-$C_4$, or $C_1$-$C_2$). In embodiments, $R^{15D}$ is independently unsubstituted methyl. In embodiments, $R^{15D}$ is independently unsubstituted ethyl. In embodiments, $R^{15D}$ is independently unsubstituted propyl. In embodiments, $R^{15D}$ is independently unsubstituted isopropyl. In embodiments, $R^{15D}$ is independently unsubstituted tert-butyl. In embodiments, $R^{15D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{15D}$ is independently substituted heteroalkyl (e.g., 2 to 8 membered, 2 to 6 membered, 4 to 6 membered, 2 to 3 membered, or 4 to 5 membered). In embodiments, $R^{15D}$ is independently unsubstituted heteroalkyl (e.g., 2 to 8 membered, 2 to 6 membered, 4 to 6 membered, 2 to 3 membered, or 4 to 5 membered). In embodiments, $R^{15D}$ is independently substituted or unsubstituted cycloalkyl (e.g., $C_3$-$C_8$, $C_3$-$C_6$, $C_4$-$C_6$, or $C_5$-$C_6$). In embodiments, $R^{15D}$ is independently substituted cycloalkyl (e.g., $C_3$-$C_8$, $C_3$-$C_6$, $C_4$-$C_6$, or $C_5$-$C_6$). In embodiments, $R^{15D}$ is independently unsubstituted cycloalkyl (e.g., $C_3$-$C_8$, $C_3$-$C_6$, $C_4$-$C_6$, or $C_5$-$C_6$). In embodiments, $R^{15D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{15D}$ is independently substituted heterocycloalkyl (e.g., 3 to 8 membered, 3 to 6 membered, 4 to 6 membered, 4 to 5 membered, or 5 to 6 membered). In embodiments, $R^{15D}$ is independently unsubstituted heterocycloalkyl (e.g., 3 to 8 membered, 3 to 6 membered, 4 to 6 membered, 4 to 5 membered, or 5 to 6 membered). In embodiments, $R^{15D}$ is independently substituted or unsubstituted aryl (e.g., $C_6$-$C_{10}$ or phenyl). In embodiments, $R^{15D}$ is independently substituted aryl (e.g., $C_6$-$C_{10}$ or phenyl). In embodiments, $R^{15D}$ is independently unsubstituted aryl (e.g., $C_6$-$C_{10}$ or phenyl). In embodiments, $R^{15D}$ is independently substituted or unsubstituted heteroaryl (e.g., 5 to 10 membered, 5 to 9 membered, or 5 to 6 membered). In embodiments, $R^{15D}$ is independently substituted heteroaryl (e.g., 5 to 10 membered, 5 to 9 membered, or 5 to 6 membered). In embodiments, $R^{15D}$ is independently unsubstituted heteroaryl (e.g., 5 to 10 membered, 5 to 9 membered, or 5 to 6 membered).

In embodiments, $R^{15}$ is independently hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{72}$-substituted or unsubstituted alkyl (e.g., $C_1$-$C_8$, $C_1$-$C_6$, $C_1$-$C_4$, or $C_1$-$C_2$), $R^{72}$-substituted or unsubstituted heteroalkyl (e.g., 2 to 8 membered, 2 to 6 membered, 4 to 6 membered, 2 to 3 membered, or 4 to 5 membered), $R^{72}$-substituted or unsubstituted cycloalkyl (e.g., $C_3$-$C_8$, $C_3$-$C_6$, $C_4$-$C_6$, or $C_5$-$C_6$), $R^{72}$-substituted or unsubstituted heterocycloalkyl (e.g., 3 to 8 membered, 3 to 6 membered, 4 to 6 membered, 4 to 5 membered, or 5 to 6 membered), $R^{72}$-substituted or unsubstituted aryl (e.g., $C_6$-$C_{10}$ or phenyl), or $R^{72}$-substituted or unsubstituted heteroaryl (e.g., 5 to 10 membered, 5 to 9 membered, or 5 to 6 membered). In embodiments, $R^{15}$ is independently hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15}$ is independently —F, —Cl, —Br, or —I. In embodiments, $R^{15}$ is independently hydrogen. In embodiments, $R^{15}$ is independently unsubstituted methyl. In embodiments, $R^{15}$ is independently unsubstituted ethyl.

$R^{72}$ is independently oxo, halogen, —$CX^{72}_3$, —$CHX^{72}_2$, —$CH_2X^{72}$, —$OCX^{72}_3$, —$OCH_2X^{72}$, —$OCHX^{72}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{73}$-substituted or unsubstituted alkyl (e.g., $C_1$-$C_8$, $C_1$-$C_6$, $C_1$-$C_4$, or $C_1$-$C_2$), $R^{73}$-substituted or unsubstituted heteroalkyl (e.g., 2 to 8 membered, 2 to 6 membered, 4 to 6 membered, 2 to 3 membered, or 4 to 5 membered), $R^{73}$-substituted or unsubstituted cycloalkyl (e.g., $C_3$-$C_8$, $C_3$-$C_6$, $C_4$-$C_6$, or $C_5$-$C_6$), $R^{73}$-substituted or unsubstituted heterocycloalkyl (e.g., 3 to 8 membered, 3 to 6 membered, 4 to 6 membered, 4 to 5 membered, or 5 to 6 membered), $R^{73}$-substituted or unsubstituted aryl (e.g., $C_6$-$C_{10}$ or phenyl), or $R^{73}$-substituted or unsubstituted heteroaryl (e.g., 5 to 10 membered, 5 to 9 membered, or 5 to 6 membered). In embodiments, $R^{72}$ is independently oxo, halogen, —$CX^{72}_3$, —$CHX^{72}_2$, —$CH_2X^{72}$, —$OCX^{72}_3$, —$OCH_2X^{72}$, —$OCHX^{72}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{72}$ is independently —F, —Cl, —Br, or —I. In embodiments, $R^{72}$ is independently unsubstituted methyl. In embodiments, $R^{72}$ is independently unsubstituted ethyl.

$R^{73}$ is independently oxo, halogen, —$CX^{73}_3$, —$CHX^{73}_2$, —$CH_2X^{73}$, —$OCX^{73}_3$, —$OCH_2X^{73}$, —$OCHX^{73}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{74}$-substituted or unsubstituted alkyl (e.g., $C_1$-$C_8$, $C_1$-$C_6$, $C_1$-$C_4$, or $C_1$-$C_2$), $R^{74}$-substituted or unsubstituted heteroalkyl (e.g., 2 to 8 membered, 2 to 6 membered, 4 to 6 membered, 2 to 3 membered, or 4 to 5 membered), $R^{74}$-substituted or unsubstituted cycloalkyl (e.g., $C_3$-$C_8$, $C_3$-$C_6$, $C_4$-$C_6$, or $C_5$-$C_6$), $R^{74}$-substituted or unsubstituted heterocycloalkyl (e.g., 3 to 8 membered, 3 to 6 membered, 4 to 6 membered, 4 to 5 membered, or 5 to 6 membered), $R^{74}$-substituted or unsubstituted aryl (e.g., $C_6$-$C_{10}$ or phenyl), or $R^{74}$-substituted or unsubstituted heteroaryl (e.g., 5 to 10 membered, 5 to 9 membered, or 5 to 6 membered). In embodiments, $R^{73}$ is independently oxo, halogen, —$CX^{73}_3$, —$CHX^{73}_2$, —$CH_2X^{73}$, —$OCX^{73}_3$, —$OCH_2X^{73}$, —$OCHX^{73}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{73}$ is independently —F, —Cl, —Br, or —I. In embodiments, $R^{73}$ is independently unsubstituted methyl. In embodiments, $R^{73}$ is independently unsubstituted ethyl.

$R^{74}$ is independently oxo, halogen, —$CX^{74}_3$, —$CHX^{74}_2$, —$CH_2X^{74}$, —$OCX^{74}_3$, —$OCH_2X^{74}$, —$OCHX^{74}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)

NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{74}$ is independently —F, —Cl, —Br, or —I. In embodiments, R$^{74}$ is independently unsubstituted methyl. In embodiments, R$^{74}$ is independently unsubstituted ethyl.

In embodiments, R$^{16}$ is hydrogen. In embodiments, R$^{16}$ is halogen. In embodiments, R$^{16}$ is —CX$^{16}_3$. In embodiments, R$^{16}$ is —CHX$^{16}_2$. In embodiments, R$^{16}$ is —CH$_2$X$^{16}$. In embodiments, R$^{16}$ is —CN. In embodiments, R$^{16}$ is —SO$_{n16}$R$^{16D}$. In embodiments, R$^{16}$ is —SO$_{v16}$NR$^{16A}$R$^{16B}$. In embodiments, R$^{16}$ is —NHNR$^{16A}$R$^{16B}$. In embodiments, R$^{16}$ is —ONR$^{16A}$R$^{16B}$. In embodiments, R$^{16}$ is —NHC=(O)NHNR$^{16A}$R$^{16B}$. In embodiments, R$^{16}$ is —NHC(O)NR$^{16A}$R$^{16B}$. In embodiments, R$^{16}$ is —N(O)$_{m16}$. In embodiments, R$^{16}$ is —NR$^{16A}$R$^{16B}$. In embodiments, R$^{16}$ is —C(O)R$^{16C}$. In embodiments, R$^{16}$ is —C(O)—OR$^{16C}$. In embodiments, R$^{16}$ is —C(O)NR$^{16A}$R$^{16B}$. In embodiments, R$^{16}$ is —OR$^{16D}$. In embodiments, R$^{16}$ is —NR$^{16A}$SO$_2$R$^{16D}$. In embodiments, R$^{16}$ is —NR$^{16A}$C(O)R$^{16C}$. In embodiments, R$^{16}$ is —NR$^{16A}$C(O)OR$^{16C}$. In embodiments, R$^{16}$ is —NR$^{16A}$OR$^{16C}$. In embodiments, R$^{16}$ is —OCX$^{16}_3$. In embodiments, R$^{16}$ is —OCHX$^{16}_2$. In embodiments, R$^{16}$ is independently —OH. In embodiments, R$^{16}$ is independently —NH$_2$. In embodiments, R$^{16}$ is independently —COOH. In embodiments, R$^{16}$ is independently —CONH$_2$. In embodiments, R$^{16}$ is independently —NO$_2$. In embodiments, R$^{16}$ is independently —SH. In embodiments, R$^{16}$ is independently —CF$_3$. In embodiments, R$^{16}$ is independently —CHF$_2$. In embodiments, R$^{16}$ is independently —CH$_2$F. In embodiments, R$^{16}$ is independently —OCF$_3$. In embodiments, R$^{16}$ is independently —OCH$_2$F. In embodiments, R$^{16}$ is independently —OCHF$_2$. In embodiments, R$^{16}$ is independently —OCH$_3$. In embodiments, R$^{16}$ is independently —OCH$_2$CH$_3$. In embodiments, R$^{16}$ is independently —OCH$_2$CH$_2$CH$_3$. In embodiments, R$^{16}$ is independently —OCH(CH$_3$)$_2$. In embodiments, R$^{16}$ is independently —OC(CH$_3$)$_3$. In embodiments, R$^{16}$ is independently —SCH$_3$. In embodiments, R$^{16}$ is independently —SCH$_2$CH$_3$. In embodiments, R$^{16}$ is independently —SCH$_2$CH$_2$CH$_3$. In embodiments, R$^{16}$ is independently —SCH(CH$_3$)$_2$. In embodiments, R$^{16}$ is independently —SC(CH$_3$)$_3$. In embodiments, R$^{16}$ is independently —CH$_3$. In embodiments, R$^{16}$ is independently —CH$_2$CH$_3$. In embodiments, R$^{16}$ is independently —CH$_2$CH$_2$CH$_3$. In embodiments, R$^{16}$ is independently —CH(CH$_3$)$_2$. In embodiments, R$^{16}$ is independently —C(CH$_3$)$_3$. In embodiments, R$^{16}$ is independently —F. In embodiments, R$^{16}$ is independently —Cl. In embodiments, R$^{16}$ is independently —Br. In embodiments, R$^{16}$ is independently —I.

In embodiments, R$^{16}$ is independently substituted or unsubstituted alkyl (e.g., C$_1$-C$_8$, C$_1$-C$_6$, C$_1$-C$_4$, or C$_1$-C$_2$). In embodiments, R$^{16}$ is independently substituted alkyl (e.g., C$_1$-C$_8$, C$_1$-C$_6$, C$_1$-C$_4$, or C$_1$-C$_2$). In embodiments, R$^{16}$ is independently unsubstituted alkyl (e.g., C$_1$-C$_8$, C$_1$-C$_6$, C$_1$-C$_4$, or C$_1$-C$_2$). In embodiments, R$^{16}$ is independently unsubstituted methyl. In embodiments, R$^{16}$ is independently unsubstituted ethyl. In embodiments, R$^{16}$ is independently unsubstituted propyl. In embodiments, R$^{16}$ is independently unsubstituted isopropyl. In embodiments, R$^{16}$ is independently unsubstituted tert-butyl. In embodiments, R$^{16}$ is independently substituted or unsubstituted heteroalkyl (e.g., 2 to 8 membered, 2 to 6 membered, 4 to 6 membered, 2 to 3 membered, or 4 to 5 membered). In embodiments, R$^{16}$ is independently substituted heteroalkyl (e.g., 2 to 8 membered, 2 to 6 membered, 4 to 6 membered, 2 to 3 membered, or 4 to 5 membered). In embodiments, R$^{16}$ is independently unsubstituted heteroalkyl (e.g., 2 to 8 membered, 2 to 6 membered, 4 to 6 membered, 2 to 3 membered, or 4 to 5 membered). In embodiments, R$^{16}$ is independently substituted or unsubstituted cycloalkyl (e.g., C$_3$-C$_8$, C$_3$-C$_6$, C$_4$-C$_6$, or C$_5$-C$_6$). In embodiments, R$^{16}$ is independently substituted cycloalkyl (e.g., C$_3$-C$_8$, C$_3$-C$_6$, C$_4$-C$_6$, or C$_5$-C$_6$). In embodiments, R$^{16}$ is independently unsubstituted cycloalkyl (e.g., C$_3$-C$_8$, C$_3$-C$_6$, C$_4$-C$_6$, or C$_5$-C$_6$). In embodiments, R$^{16}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{16}$ is independently substituted heterocycloalkyl (e.g., 3 to 8 membered, 3 to 6 membered, 4 to 6 membered, 4 to 5 membered, or 5 to 6 membered). In embodiments, R$^{16}$ is independently unsubstituted heterocycloalkyl (e.g., 3 to 8 membered, 3 to 6 membered, 4 to 6 membered, 4 to 5 membered, or 5 to 6 membered). In embodiments, R$^{16}$ is independently substituted or unsubstituted aryl (e.g., C$_6$-C$_{10}$ or phenyl). In embodiments, R$^{16}$ is independently substituted aryl (e.g., C$_6$-C$_{10}$ or phenyl). In embodiments, R$^{16}$ is independently unsubstituted aryl (e.g., C$_6$-C$_{10}$ or phenyl). In embodiments, R$^{16}$ is independently substituted or unsubstituted heteroaryl (e.g., 5 to 10 membered, 5 to 9 membered, or 5 to 6 membered). In embodiments, R$^{16}$ is independently substituted heteroaryl (e.g., 5 to 10 membered, 5 to 9 membered, or 5 to 6 membered). In embodiments, R$^{16}$ is independently unsubstituted heteroaryl (e.g., 5 to 10 membered, 5 to 9 membered, or 5 to 6 membered).

In embodiments, R$^{16A}$ is independently hydrogen. In embodiments, R$^{16A}$ is independently —CX$^{16A}_3$. In embodiments, R$^{16A}$ is independently —CHX$^{16A}_2$. In embodiments, R$^{16A}$ is independently —CH$_2$X$^{16A}$. In embodiments, R$^{16A}$ is independently —CN. In embodiments, R$^{16A}$ is independently —COOH. In embodiments, R$^{16A}$ is independently —CONH$_2$. In embodiments, X$^{16A}$ is independently —F, —Cl, —Br, or —I.

In embodiments, R$^{16A}$ is independently substituted or unsubstituted alkyl (e.g., C$_1$-C$_8$, C$_1$-C$_6$, C$_1$-C$_4$, or C$_1$-C$_2$). In embodiments, R$^{16A}$ is independently substituted alkyl (e.g., C$_1$-C$_8$, C$_1$-C$_6$, C$_1$-C$_4$, or C$_1$-C$_2$). In embodiments, R$^{16A}$ is independently unsubstituted alkyl (e.g., C$_1$-C$_8$, C$_1$-C$_6$, C$_1$-C$_4$, or C$_1$-C$_2$). In embodiments, R$^{16A}$ is independently unsubstituted methyl. In embodiments, R$^{16A}$ is independently unsubstituted ethyl. In embodiments, R$^{16A}$ is independently unsubstituted propyl. In embodiments, R$^{16A}$ is independently unsubstituted isopropyl. In embodiments, R$^{16A}$ is independently unsubstituted tert-butyl. In embodiments, R$^{16A}$ is independently substituted or unsubstituted heteroalkyl (e.g., 2 to 8 membered, 2 to 6 membered, 4 to 6 membered, 2 to 3 membered, or 4 to 5 membered). In embodiments, R$^{16A}$ is independently substituted heteroalkyl (e.g., 2 to 8 membered, 2 to 6 membered, 4 to 6 membered, 2 to 3 membered, or 4 to 5 membered). In embodiments, R$^{16A}$ is independently unsubstituted heteroalkyl (e.g., 2 to 8 membered, 2 to 6 membered, 4 to 6 membered, 2 to 3 membered, or 4 to 5 membered). In embodiments, R$^{16A}$ is independently substituted or unsubstituted cycloalkyl (e.g., C$_3$-C$_8$, C$_3$-C$_6$, C$_4$-C$_6$, or C$_5$-C$_6$). In embodiments, R$^{16A}$ is independently substituted cycloalkyl (e.g., C$_3$-C$_8$, C$_3$-C$_6$, C$_4$-C$_6$, or C$_5$-C$_6$). In embodiments, R$^{16A}$ is independently unsubstituted cycloalkyl (e.g., $C_3$-$C_8$, $C_3$-$C_6$, $C_4$-$C_6$, or $C_5$-$C_6$). In embodiments, $R^{16A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16A}$ is independently substituted heterocycloalkyl (e.g., 3 to 8 membered, 3 to 6 membered, 4 to 6 membered, 4 to 5 membered, or 5 to 6 membered). In embodiments, $R^{16A}$ is independently unsubstituted heterocycloalkyl (e.g., 3 to 8 membered, 3 to 6 membered, 4 to 6 membered, 4 to 5 membered, or 5 to 6 membered). In embodiments, $R^{16A}$ is independently substituted or unsubstituted aryl (e.g., $C_6$-$C_{10}$ or phenyl). In embodiments, $R^{16A}$ is independently substituted aryl (e.g., $C_6$-$C_{10}$ or phenyl). In embodiments, $R^{16A}$ is independently unsubstituted aryl (e.g., $C_6$-$C_{10}$ or phenyl). In embodiments, $R^{16A}$ is independently substituted or unsubstituted heteroaryl (e.g., 5 to 10 membered, 5 to 9 membered, or 5 to 6 membered). In embodiments, $R^{16A}$ is independently substituted heteroaryl (e.g., 5 to 10 membered, 5 to 9 membered, or 5 to 6 membered). In embodiments, $R^{16A}$ is independently unsubstituted heteroaryl (e.g., 5 to 10 membered, 5 to 9 membered, or 5 to 6 membered).

In embodiments, $R^{16B}$ is independently hydrogen. In embodiments, $R^{16B}$ is independently —$CX^{16B}_3$. In embodiments, $R^{16B}$ is independently —$CHX^{16B}_2$. In embodiments, $R^{16B}$ is independently —$CH_2X^{16B}$. In embodiments, $R^{16B}$ is independently —CN. In embodiments, $R^{16B}$ is independently —COOH. In embodiments, $R^{16B}$ is independently —$CONH_2$. In embodiments, $X^{16B}$ is independently —F, —Cl, —Br, or —I.

In embodiments, $R^{16B}$ is independently substituted or unsubstituted alkyl (e.g., $C_1$-$C_8$, $C_1$-$C_6$, $C_1$-$C_4$, or $C_1$-$C_2$). In embodiments, $R^{16B}$ is independently substituted alkyl (e.g., $C_1$-$C_8$, $C_1$-$C_6$, $C_1$-$C_4$, or $C_1$-$C_2$). In embodiments, $R^{16B}$ is independently unsubstituted alkyl (e.g., $C_1$-$C_8$, $C_1$-$C_6$, $C_1$-$C_4$, or $C_1$-$C_2$). In embodiments, $R^{16B}$ is independently unsubstituted methyl. In embodiments, $R^{16B}$ is independently unsubstituted ethyl. In embodiments, $R^{16B}$ is independently unsubstituted propyl. In embodiments, $R^{16B}$ is independently unsubstituted isopropyl. In embodiments, $R^{16B}$ is independently unsubstituted tert-butyl. In embodiments, $R^{16B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16B}$ is independently substituted heteroalkyl (e.g., 2 to 8 membered, 2 to 6 membered, 4 to 6 membered, 2 to 3 membered, or 4 to 5 membered). In embodiments, $R^{16B}$ is independently unsubstituted heteroalkyl (e.g., 2 to 8 membered, 2 to 6 membered, 4 to 6 membered, 2 to 3 membered, or 4 to 5 membered). In embodiments, $R^{16B}$ is independently substituted or unsubstituted cycloalkyl (e.g., $C_3$-$C_8$, $C_3$-$C_6$, $C_4$-$C_6$, or $C_5$-$C_6$). In embodiments, $R^{16B}$ is independently substituted cycloalkyl (e.g., $C_3$-$C_8$, $C_3$-$C_6$, $C_4$-$C_6$, or $C_5$-$C_6$). In embodiments, $R^{16B}$ is independently unsubstituted cycloalkyl (e.g., $C_3$-$C_8$, $C_3$-$C_6$, $C_4$-$C_6$, or $C_5$-$C_6$). In embodiments, $R^{16B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16B}$ is independently substituted heterocycloalkyl (e.g., 3 to 8 membered, 3 to 6 membered, 4 to 6 membered, 4 to 5 membered, or 5 to 6 membered). In embodiments, $R^{16B}$ is independently unsubstituted heterocycloalkyl (e.g., 3 to 8 membered, 3 to 6 membered, 4 to 6 membered, 4 to 5 membered, or 5 to 6 membered). In embodiments, $R^{16B}$ is independently substituted or unsubstituted aryl (e.g., $C_6$-$C_{10}$ or phenyl). In embodiments, $R^{16B}$ is independently substituted aryl (e.g., $C_6$-$C_{10}$ or phenyl). In embodiments, $R^{16B}$ is independently unsubstituted aryl (e.g., $C_6$-$C_{10}$ or phenyl). In embodiments, $R^{16B}$ is independently substituted or unsubstituted heteroaryl (e.g., 5 to 10 membered, 5 to 9 membered, or 5 to 6 membered). In embodiments, $R^{16B}$ is independently substituted heteroaryl (e.g., 5 to 10 membered, 5 to 9 membered, or 5 to 6 membered). In embodiments, $R^{16B}$ is independently unsubstituted heteroaryl (e.g., 5 to 10 membered, 5 to 9 membered, or 5 to 6 membered).

In embodiments, $R^{16A}$ and $R^{16B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{16A}$ and $R^{16B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{16A}$ and $R^{16B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered). In embodiments, $R^{16A}$ and $R^{16B}$ substituents bonded to the same nitrogen atom may be joined to form a substituted or unsubstituted heteroaryl (e.g., 5 to 10 membered, 5 to 9 membered, or 5 to 6 membered). In embodiments, $R^{16A}$ and $R^{16B}$ substituents bonded to the same nitrogen atom may be joined to form a substituted heteroaryl (e.g., 5 to 10 membered, 5 to 9 membered, or 5 to 6 membered). In embodiments, $R^{16A}$ and $R^{16B}$ substituents bonded to the same nitrogen atom may be joined to form an unsubstituted heteroaryl (e.g., 5 to 10 membered, 5 to 9 membered, or 5 to 6 membered).

In embodiments, $R^{16C}$ is independently hydrogen. In embodiments, $R^{16C}$ is independently —$CX^{16C}_3$. In embodiments, $R^{16C}$ is independently —$CHX^{16C}_2$. In embodiments, $R^{16C}$ is independently —$CH_2X^{16C}$. In embodiments, $R^{16C}$ is independently —CN. In embodiments, $R^{16C}$ is independently —COOH. In embodiments, $R^{16C}$ is independently —$CONH_2$. In embodiments, $X^{16C}$ is independently —F, —Cl, —Br, or —I.

In embodiments, $R^{16C}$ is independently substituted or unsubstituted alkyl (e.g., $C_1$-$C_8$, $C_1$-$C_6$, $C_1$-$C_4$, or $C_1$-$C_2$). In embodiments, $R^{16C}$ is independently substituted alkyl (e.g., $C_1$-$C_8$, $C_1$-$C_6$, $C_1$-$C_4$, or $C_1$-$C_2$). In embodiments, $R^{16C}$ is independently unsubstituted alkyl (e.g., $C_1$-$C_8$, $C_1$-$C_6$, $C_1$-$C_4$, or $C_1$-$C_2$). In embodiments, $R^{16C}$ is independently unsubstituted methyl. In embodiments, $R^{16C}$ is independently unsubstituted ethyl. In embodiments, $R^{16C}$ is independently unsubstituted propyl. In embodiments, $R^{16C}$ is independently unsubstituted isopropyl. In embodiments, $R^{16C}$ is independently unsubstituted tert-butyl. In embodiments, $R^{16C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16C}$ is independently substituted heteroalkyl (e.g., 2 to 8 membered, 2 to 6 membered, 4 to 6 membered, 2 to 3 membered, or 4 to 5 membered). In embodiments, $R^{16C}$ is independently unsubstituted heteroalkyl (e.g., 2 to 8 membered, 2 to 6 membered, 4 to 6 membered, 2 to 3 membered, or 4 to 5 membered). In embodiments, $R^{16C}$ is independently substituted or unsubstituted cycloalkyl (e.g., $C_3$-$C_8$, $C_3$-$C_6$, $C_4$-$C_6$, or $C_5$-$C_6$). In embodiments, $R^{16C}$ is independently substituted cycloalkyl (e.g., $C_3$-$C_8$, $C_3$-$C_6$, $C_4$-$C_6$, or $C_5$-$C_6$). In embodiments, $R^{16C}$ is independently unsubstituted cycloalkyl (e.g., $C_3$-$C_8$, $C_3$-$C_6$, $C_4$-$C_6$, or $C_5$-$C_6$). In embodiments, $R^{16C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16C}$ is independently substituted heterocycloalkyl (e.g., 3 to 8 membered, 3 to 6 membered, 4 to 6 membered, 4 to 5 membered, or 5 to 6 membered). In embodiments, $R^{16C}$ is independently unsubstituted heterocycloalkyl (e.g., 3 to 8 membered, 3 to 6 membered, 4 to 6 membered, 4 to 5 membered, or 5 to 6 membered). In embodiments, $R^{16C}$ is independently substituted or unsubstituted aryl (e.g., $C_6$-$C_{10}$ or phenyl). In embodiments, $R^{16C}$ is independently substituted aryl (e.g., $C_6$-$C_{10}$ or phenyl). In embodiments, $R^{16C}$ is independently unsubstituted aryl (e.g., $C_6$-$C_{10}$ or phenyl). In embodiments, $R^{16C}$ is independently substituted or unsubstituted heteroaryl (e.g., 5 to 10 membered, 5 to 9 membered, or 5 to 6 membered). In embodiments, $R^{16C}$ is independently substituted heteroaryl (e.g., 5 to 10 membered, 5 to 9 membered, or 5 to 6 membered). In embodiments, $R^{16C}$ is independently unsubstituted heteroaryl (e.g., 5 to 10 membered, 5 to 9 membered, or 5 to 6 membered).

In embodiments, $R^{16D}$ is independently hydrogen. In embodiments, $R^{16D}$ is independently —$CX^{16D}_3$. In embodiments, $R^{16D}$ is independently —$CHX^{16D}_2$. In embodiments, $R^{16D}$ is independently —$CH_2X^{16D}$. In embodiments, $R^{16D}$ is independently —CN. In embodiments, $R^{16D}$ is independently —COOH. In embodiments, $R^{16D}$ is independently —$CONH_2$. In embodiments, $X^{16D}$ is independently —F, —Cl, —Br, or —I.

In embodiments, $R^{16D}$ is independently substituted or unsubstituted alkyl (e.g., $C_1$-$C_8$, $C_1$-$C_6$, $C_1$-$C_4$, or $C_1$-$C_2$). In embodiments, $R^{16D}$ is independently substituted alkyl (e.g., $C_1$-$C_8$, $C_1$-$C_6$, $C_1$-$C_4$, or $C_1$-$C_2$). In embodiments, $R^{16D}$ is independently unsubstituted alkyl (e.g., $C_1$-$C_8$, $C_1$-$C_6$, $C_1$-$C_4$, or $C_1$-$C_2$). In embodiments, $R^{16D}$ is independently unsubstituted methyl. In embodiments, $R^{16D}$ is independently unsubstituted ethyl. In embodiments, $R^{16D}$ is independently unsubstituted propyl. In embodiments, $R^{16D}$ is independently unsubstituted isopropyl. In embodiments, $R^{16D}$ is independently unsubstituted tert-butyl. In embodiments, $R^{16D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{16D}$ is independently substituted heteroalkyl (e.g., 2 to 8 membered, 2 to 6 membered, 4 to 6 membered, 2 to 3 membered, or 4 to 5 membered). In embodiments, $R^{16D}$ is independently unsubstituted heteroalkyl (e.g., 2 to 8 membered, 2 to 6 membered, 4 to 6 membered, 2 to 3 membered, or 4 to 5 membered). In embodiments, $R^{16D}$ is independently substituted or unsubstituted cycloalkyl (e.g., $C_3$-$C_8$, $C_3$-$C_6$, $C_4$-$C_6$, or $C_5$-$C_6$). In embodiments, $R^{16D}$ is independently substituted cycloalkyl (e.g., $C_3$-$C_8$, $C_3$-$C_6$, $C_4$-$C_6$, or $C_5$-$C_6$). In embodiments, $R^{16D}$ is independently unsubstituted cycloalkyl (e.g., $C_3$-$C_8$, $C_3$-$C_6$, $C_4$-$C_6$, or $C_5$-$C_6$). In embodiments, $R^{16D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{16D}$ is independently substituted heterocycloalkyl (e.g., 3 to 8 membered, 3 to 6 membered, 4 to 6 membered, 4 to 5 membered, or 5 to 6 membered). In embodiments, $R^{16D}$ is independently unsubstituted heterocycloalkyl (e.g., 3 to 8 membered, 3 to 6 membered, 4 to 6 membered, 4 to 5 membered, or 5 to 6 membered). In embodiments, $R^{16D}$ is independently substituted or unsubstituted aryl (e.g., $C_6$-$C_{10}$ or phenyl). In embodiments, $R^{16D}$ is independently substituted aryl (e.g., $C_6$-$C_{10}$ or phenyl). In embodiments, $R^{16D}$ is independently unsubstituted aryl (e.g., $C_6$-$C_{10}$ or phenyl). In embodiments, $R^{16D}$ is independently substituted or unsubstituted heteroaryl (e.g., 5 to 10 membered, 5 to 9 membered, or 5 to 6 membered). In embodiments, $R^{16D}$ is independently substituted heteroaryl (e.g., 5 to 10 membered, 5 to 9 membered, or 5 to 6 membered). In embodiments, $R^{16D}$ is independently unsubstituted heteroaryl (e.g., 5 to 10 membered, 5 to 9 membered, or 5 to 6 membered).

In embodiments, $R^{16}$ is independently hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{75}$-substituted or unsubstituted alkyl (e.g., $C_1$-$C_8$, $C_1$-$C_6$, $C_1$-$C_4$, or $C_1$-$C_2$), $R^{75}$-substituted or unsubstituted heteroalkyl (e.g., 2 to 8 membered, 2 to 6 membered, 4 to 6 membered, 2 to 3 membered, or 4 to 5 membered), $R^{75}$-substituted or unsubstituted cycloalkyl (e.g., $C_3$-$C_8$, $C_3$-$C_6$, $C_4$-$C_6$, or $C_5$-$C_6$), $R^{75}$-substituted or unsubstituted heterocycloalkyl (e.g., 3 to 8 membered, 3 to 6 membered, 4 to 6 membered, 4 to 5 membered, or 5 to 6 membered), $R^{75}$-substituted or unsubstituted aryl (e.g., $C_6$-$C_{10}$ or phenyl), or $R^{75}$-substituted or unsubstituted heteroaryl (e.g., 5 to 10 membered, 5 to 9 membered, or 5 to 6 membered). In embodiments, $R^{16}$ is independently hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{16}$ is independently —F, —Cl, —Br, or —I. In embodiments, $R^{16}$ is independently hydrogen. In embodiments, $R^{16}$ is independently unsubstituted methyl. In embodiments, $R^{16}$ is independently unsubstituted ethyl.

$R^{75}$ is independently oxo, halogen, —$CX^{75}_3$, —$CHX^{75}_2$, —$CH_2X^{75}$, —$OCX^{75}_3$, —$OCH_2X^{75}$, —$OCHX^{75}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{76}$-substituted or unsubstituted alkyl (e.g., $C_1$-$C_8$, $C_1$-$C_6$, $C_1$-$C_4$, or $C_1$-$C_2$), $R^{76}$-substituted or unsubstituted heteroalkyl (e.g., 2 to 8 membered, 2 to 6 membered, 4 to 6 membered, 2 to 3 membered, or 4 to 5 membered), $R^{76}$-substituted or unsubstituted cycloalkyl (e.g., $C_3$-$C_8$, $C_3$-$C_6$, $C_4$-$C_6$, or $C_5$-$C_6$), $R^{76}$-substituted or unsubstituted heterocycloalkyl (e.g., 3 to 8 membered, 3 to 6 membered, 4 to 6 membered, 4 to 5 membered, or 5 to 6 membered), $R^{76}$-substituted or unsubstituted aryl (e.g., $C_6$-$C_{10}$ or phenyl), or $R^{76}$-substituted or unsubstituted heteroaryl (e.g., 5 to 10 membered, 5 to 9 membered, or 5 to 6 membered). In embodiments, $R^{75}$ is independently oxo, halogen, —$CX^{75}_3$, —$CHX^{75}_2$, —$CH_2X^{75}$, —$OCX^{75}_3$, —$OCH_2X^{75}$, —$OCHX^{75}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{75}$ is independently —F, —Cl, —Br, or —I. In embodiments, $R^{75}$ is independently unsubstituted methyl. In embodiments, $R^{75}$ is independently unsubstituted ethyl.

$R^{76}$ is independently oxo, halogen, —$CX^{76}_3$, —$CHX^{76}_2$, —$CH_2X^{76}$, —$OCX^{76}_3$, —$OCH_2X^{76}$, —$OCHX^{76}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{77}$-substituted or unsubstituted alkyl (e.g., $C_1$-$C_8$, $C_1$-$C_6$, $C_1$-$C_4$, or $C_1$-$C_2$), $R^{77}$-substituted or unsubstituted heteroalkyl (e.g., 2 to 8 membered, 2 to 6 membered, 4 to 6 membered, 2 to 3 membered, or 4 to 5 membered), $R^{77}$-substituted or unsubstituted cycloalkyl (e.g., $C_3$-$C_8$, $C_3$-$C_6$, $C_4$-$C_6$, or $C_5$-$C_6$), $R^{77}$-substituted or unsubstituted heterocycloalkyl (e.g., 3 to 8 membered, 3 to 6 membered, 4 to 6 membered, 4 to 5 membered, or 5 to 6 membered), $R^{77}$-substituted or unsubstituted aryl (e.g., $C_6$-$C_{10}$ or phenyl), or $R^{77}$-substituted or unsubstituted heteroaryl (e.g., 5 to 10 membered, 5 to 9 membered, or 5 to 6 membered). In embodiments, $R^{76}$ is independently oxo, halogen, —$CX^{76}_3$, —$CHX^{76}_2$, —$CH_2X^{76}$, —$OCX^{76}_3$, —$OCH_2X^{76}$, —$OCHX^{76}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{76}$ is independently —F, —Cl, —Br, or —I. In embodiments, $R^{76}$ is independently unsubstituted methyl. In embodiments, $R^{76}$ is independently unsubstituted ethyl.

$R^{77}$ is independently oxo, halogen, —$CX^{77}_3$, —$CHX^{77}_2$, —$CH_2X^{77}$, —$OCX^{77}_3$, —$OCH_2X^{77}$, —$OCHX^{77}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{77}$ is independently —F, —Cl, —Br, or —I. In embodiments, $R^{77}$ is independently unsubstituted methyl. In embodiments, $R^{77}$ is independently unsubstituted ethyl.

In embodiments, $R^{17}$ is hydrogen. In embodiments, $R^{17}$ is halogen. In embodiments, $R^{17}$ is —$CX^{17}_3$. In embodiments, $R^{17}$ is —$CHX^{17}_2$. In embodiments, $R^{17}$ is —$CH_2X^{17}$. In embodiments, $R^{17}$ is —CN. In embodiments, $R^{17}$ is —$SO_{n17}R^{17D}$. In embodiments, $R^{17}$ is —$SO_{v17}NR^{17A}R^{17B}$. In embodiments, $R^{17}$ is —$NHNR^{17A}R^{17B}$. In embodiments, $R^{17}$ is —$ONR^{17A}R^{17B}$. In embodiments, $R^{17}$ is —NHC=(O)$NHNR^{17A}R^{17B}$. In embodiments, $R^{17}$ is —NHC(O)$NR^{17A}R^{17B}$. In embodiments, $R^{17}$ is —N(O)$_{m17}$. In embodiments, $R^{17}$ is —$NR^{17A}R^{17B}$. In embodiments, $R^{17}$ is —C(O)$R^{17C}$. In embodiments, $R^{17}$ is —C(O)—$OR^{17C}$. In embodiments, $R^{17}$ is —C(O)$NR^{17A}R^{17B}$. In embodiments, $R^{17}$ is —$OR^{17D}$. In embodiments, $R^{17}$ is —$NR^{17A}SO_2R^{17D}$. In embodiments, $R^{17}$ is —$NR^{17A}C(O)R^{17C}$. In embodiments, $R^{17}$ is —$NR^{17A}C(O)OR^{17C}$. In embodiments, $R^{17}$ is —$NR^{17A}OR^{17C}$. In embodiments, $R^{17}$ is —$OCX^{17}_3$. In embodiments, $R^{17}$ is —$OCHX^{17}_2$. In embodiments, $R^{17}$ is independently —OH. In embodiments, $R^{17}$ is independently —$NH_2$. In embodiments, $R^{17}$ is independently —COOH. In embodiments, $R^{17}$ is independently —$CONH_2$. In embodiments, $R^{17}$ is independently —$NO_2$. In embodiments, $R^{17}$ is independently —SH. In embodiments, $R^{17}$ is independently —$CF_3$. In embodiments, $R^{17}$ is independently —$CHF_2$. In embodiments, $R^{17}$ is independently —$CH_2F$. In embodiments, $R^{17}$ is independently —$OCF_3$. In embodiments, $R^{17}$ is independently —$OCH_2F$. In embodiments, $R^{17}$ is independently —$OCHF_2$. In embodiments, $R^{17}$ is independently —$OCH_3$. In embodiments, $R^{17}$ is independently —$OCH_2CH_3$. In embodiments, $R^{17}$ is independently —$OCH_2CH_2CH_3$. In embodiments, $R^{17}$ is independently —$OCH(CH_3)_2$. In embodiments, $R^{17}$ is independently —$OC(CH_3)_3$. In embodiments, $R^{17}$ is independently —$SCH_3$. In embodiments, $R^{17}$ is independently —$SCH_2CH_3$. In embodiments, $R^{17}$ is independently —$SCH_2CH_2CH_3$. In embodiments, $R^{17}$ is independently —$SCH(CH_3)_2$. In embodiments, $R^{17}$ is independently —$SC(CH_3)_3$. In embodiments, $R^{17}$ is independently —$CH_3$. In embodiments, $R^{17}$ is independently —$CH_2CH_3$. In embodiments, $R^{17}$ is independently —$CH_2CH_2CH_3$. In embodiments, $R^{17}$ is independently —$CH(CH_3)_2$. In embodiments, $R^{17}$ is independently —$C(CH_3)_3$. In embodiments, $R^{17}$ is independently —F. In embodiments, $R^{17}$ is independently —Cl. In embodiments, $R^{17}$ is independently —Br. In embodiments, $R^{17}$ is independently —I.

In embodiments, $R^{17}$ is independently substituted or unsubstituted alkyl (e.g., $C_1$-$C_8$, $C_1$-$C_6$, $C_1$-$C_4$, or $C_1$-$C_2$). In embodiments, $R^{17}$ is independently substituted alkyl (e.g., $C_1$-$C_8$, $C_1$-$C_6$, $C_1$-$C_4$, or $C_1$-$C_2$). In embodiments, $R^{17}$ is independently unsubstituted alkyl (e.g., $C_1$-$C_8$, $C_1$-$C_6$, $C_1$-$C_4$, or $C_1$-$C_2$). In embodiments, $R^{17}$ is independently unsubstituted methyl. In embodiments, $R^{17}$ is independently unsubstituted ethyl. In embodiments, $R^{17}$ is independently unsubstituted propyl. In embodiments, $R^{17}$ is independently unsubstituted isopropyl. In embodiments, $R^{17}$ is independently unsubstituted tert-butyl. In embodiments, $R^{17}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17}$ is independently substituted heteroalkyl (e.g., 2 to 8 membered, 2 to 6 membered, 4 to 6 membered, 2 to 3 membered, or 4 to 5 membered). In embodiments, $R^{17}$ is independently unsubstituted heteroalkyl (e.g., 2 to 8 membered, 2 to 6 membered, 4 to 6 membered, 2 to 3 membered, or 4 to 5 membered). In embodiments, $R^{17}$ is independently substituted or unsubstituted cycloalkyl (e.g., $C_3$-$C_8$, $C_3$-$C_6$, $C_4$-$C_6$, or $C_5$-$C_6$). In embodiments, $R^{17}$ is independently substituted cycloalkyl (e.g., $C_3$-$C_8$, $C_3$—$C_6$, $C_4$-$C_6$, or $C_5$-$C_6$). In embodiments, $R^{17}$ is independently unsubstituted cycloalkyl (e.g., $C_3$-$C_8$, $C_3$-$C_6$, $C_4$-$C_6$, or $C_5$-$C_6$). In embodiments, $R^{17}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17}$ is independently substituted heterocycloalkyl (e.g., 3 to 8 membered, 3 to 6 membered, 4 to 6 membered, 4 to 5 membered, or 5 to 6 membered). In embodiments, $R^{17}$ is independently unsubstituted heterocycloalkyl (e.g., 3 to 8 membered, 3 to 6 membered, 4 to 6 membered, 4 to 5 membered, or 5 to 6 membered). In embodiments, $R^{17}$ is independently substituted or unsubstituted aryl (e.g., $C_6$-$C_{10}$ or phenyl). In embodiments, $R^{17}$ is independently substituted aryl (e.g., $C_6$-$C_{10}$ or phenyl). In embodiments, $R^{17}$ is independently unsubstituted aryl (e.g., $C_6$-$C_{10}$ or phenyl). In embodiments, $R^{17}$ is independently substituted or unsubstituted heteroaryl (e.g., 5 to 10 membered, 5 to 9 membered, or 5 to 6 membered). In embodiments, $R^{17}$ is independently substituted heteroaryl (e.g., 5 to 10 membered, 5 to 9 membered, or 5 to 6 membered). In embodiments, $R^{17}$ is independently unsubstituted heteroaryl (e.g., 5 to 10 membered, 5 to 9 membered, or 5 to 6 membered).

In embodiments, $R^{17A}$ is independently hydrogen. In embodiments, $R^{17A}$ is independently —$CX^{17A}_3$. In embodiments, $R^{17A}$ is independently —$CHX^{17A}_2$. In embodiments, $R^{17A}$ is independently —$CH_2X^{17A}$. In embodiments, $R^{17A}$ is independently —CN. In embodiments, $R^{17A}$ is independently —COOH. In embodiments, $R^{17A}$ is independently —$CONH_2$. In embodiments, $X^{17A}$ is independently —F, —Cl, —Br, or —I.

In embodiments, $R^{17A}$ is independently substituted or unsubstituted alkyl (e.g., $C_1$-$C_8$, $C_1$-$C_6$, $C_1$-$C_4$, or $C_1$-$C_2$). In embodiments, $R^{17A}$ is independently substituted alkyl (e.g., $C_1$-$C_8$, $C_1$-$C_6$, $C_1$-$C_4$, or $C_1$-$C_2$). In embodiments, $R^{17A}$ is independently unsubstituted alkyl (e.g., $C_1$-$C_8$, $C_1$-$C_6$, $C_1$-$C_4$, or $C_1$-$C_2$). In embodiments, $R^{17A}$ is independently unsubstituted methyl. In embodiments, $R^{17A}$ is independently unsubstituted ethyl. In embodiments, $R^{17A}$ is independently unsubstituted propyl. In embodiments, $R^{17A}$ is independently unsubstituted isopropyl. In embodiments, $R^{17A}$ is independently unsubstituted tert-butyl. In embodiments, $R^{17A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17A}$ is independently substituted heteroalkyl (e.g., 2 to 8 membered, 2 to 6 membered, 4 to 6 membered, 2 to 3 membered, or 4 to 5 membered). In embodiments, $R^{17A}$ is independently unsubstituted heteroalkyl (e.g., 2 to 8 membered, 2 to 6 membered, 4 to 6 membered, 2 to 3 membered, or 4 to 5 membered). In embodiments, $R^{17A}$ is independently substituted or unsubstituted cycloalkyl (e.g., $C_3$-$C_8$, $C_3$-$C_6$, $C_4$-$C_6$, or $C_5$-$C_6$). In embodiments, $R^{17A}$ is independently substituted cycloalkyl (e.g., $C_3$-$C_8$, $C_3$-$C_6$, $C_4$-$C_6$, or $C_5$-$C_6$). In embodiments, $R^{17A}$ is independently unsubstituted cycloalkyl (e.g., $C_3$-$C_8$, $C_3$-$C_6$, $C_4$-$C_6$, or $C_5$-$C_6$). In embodiments, $R^{17A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17A}$ is independently substituted heterocycloalkyl (e.g., 3 to 8 membered, 3 to 6 membered, 4 to 6 membered, 4 to 5 membered, or 5 to 6 membered). In embodiments, $R^{17A}$ is independently unsubstituted heterocycloalkyl (e.g., 3 to 8 membered, 3 to 6 membered, 4 to 6 membered, 4 to 5 membered, or 5 to 6 membered). In embodiments, $R^{17A}$ is independently substituted or unsubstituted aryl (e.g., $C_6$-$C_{10}$ or phenyl). In embodiments, $R^{17A}$ is independently substituted aryl (e.g., $C_6$-$C_{10}$ or phenyl). In embodiments, $R^{17A}$ is independently unsubstituted aryl (e.g., $C_6$-$C_{10}$ or phenyl). In embodiments, $R^{17A}$ is independently substituted or unsubstituted heteroaryl (e.g., 5 to 10 membered, 5 to 9 membered, or 5 to 6 membered). In embodiments, $R^{17A}$ is independently substituted heteroaryl (e.g., 5 to 10 membered, 5 to 9 membered, or 5 to 6 membered). In embodiments, $R^{17A}$ is independently unsubstituted heteroaryl (e.g., 5 to 10 membered, 5 to 9 membered, or 5 to 6 membered).

In embodiments, $R^{17B}$ is independently hydrogen. In embodiments, $R^{17B}$ is independently —$CX^{17B}_3$. In embodiments, $R^{17B}$ is independently —$CHX^{17B}_2$. In embodiments, $R^{17B}$ is independently —$CH_2X^{17B}$. In embodiments, $R^{17B}$ is independently —CN. In embodiments, $R^{17B}$ is independently —COOH. In embodiments, $R^{17B}$ is independently —$CONH_2$. In embodiments, $X^{17B}$ is independently —F, —Cl, —Br, or —I.

In embodiments, $R^{17B}$ is independently substituted or unsubstituted alkyl (e.g., $C_1$-$C_8$, $C_1$-$C_6$, $C_1$-$C_4$, or $C_1$-$C_2$). In embodiments, $R^{17B}$ is independently substituted alkyl (e.g., $C_1$-$C_8$, $C_1$-$C_6$, $C_1$-$C_4$, or $C_1$-$C_2$). In embodiments, $R^{17B}$ is independently unsubstituted alkyl (e.g., $C_1$-$C_8$, $C_1$-$C_6$, $C_1$-$C_4$, or $C_1$-$C_2$). In embodiments, $R^{17B}$ is independently unsubstituted methyl. In embodiments, $R^{17B}$ is independently unsubstituted ethyl. In embodiments, $R^{17B}$ is independently unsubstituted propyl. In embodiments, $R^{17B}$ is independently unsubstituted isopropyl. In embodiments, $R^{17B}$ is independently unsubstituted tert-butyl. In embodiments, $R^{17B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17B}$ is independently substituted heteroalkyl (e.g., 2 to 8 membered, 2 to 6 membered, 4 to 6 membered, 2 to 3 membered, or 4 to 5 membered). In embodiments, $R^{17B}$ is independently unsubstituted heteroalkyl (e.g., 2 to 8 membered, 2 to 6 membered, 4 to 6 membered, 2 to 3 membered, or 4 to 5 membered). In embodiments, $R^{17B}$ is independently substituted or unsubstituted cycloalkyl (e.g., $C_3$-$C_8$, $C_3$-$C_6$, $C_4$-$C_6$, or $C_5$-$C_6$). In embodiments, $R^{17B}$ is independently substituted cycloalkyl (e.g., $C_3$-$C_8$, $C_3$-$C_6$, $C_4$-$C_6$, or $C_5$-$C_6$). In embodiments, $R^{17B}$ is independently unsubstituted cycloalkyl (e.g., $C_3$-$C_8$, $C_3$-$C_6$, $C_4$-$C_6$, or $C_5$-$C_6$). In embodiments, $R^{17B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17B}$ is independently substituted heterocycloalkyl (e.g., 3 to 8 membered, 3 to 6 membered, 4 to 6 membered, 4 to 5 membered, or 5 to 6 membered). In embodiments, $R^{17B}$ is independently unsubstituted heterocycloalkyl (e.g., 3 to 8 membered, 3 to 6 membered, 4 to 6 membered, 4 to 5 membered, or 5 to 6 membered). In embodiments, $R^{17B}$ is independently substituted or unsubstituted aryl (e.g., $C_6$-$C_{10}$ or phenyl). In embodiments, $R^{17B}$ is independently substituted aryl (e.g., $C_6$-$C_{10}$ or phenyl). In embodiments, $R^{17B}$ is independently unsubstituted aryl (e.g., $C_6$-$C_{10}$ or phenyl). In embodiments, $R^{17B}$ is independently substituted or unsubstituted heteroaryl (e.g., 5 to 10 membered, 5 to 9 membered, or 5 to 6 membered). In embodiments, $R^{17B}$ is independently substituted heteroaryl (e.g., 5 to 10 membered, 5 to 9 membered, or 5 to 6 membered). In embodiments, $R^{17B}$ is independently unsubstituted heteroaryl (e.g., 5 to 10 membered, 5 to 9 membered, or 5 to 6 membered).

In embodiments, $R^{17A}$ and $R^{17B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{17A}$ and $R^{17B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{17A}$ and $R^{17B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{17A}$ and $R^{17B}$ substituents bonded to the same nitrogen atom may be joined to form a substituted or unsubstituted heteroaryl (e.g., 5 to 10 membered, 5 to 9 membered, or 5 to 6 membered). In embodiments, $R^{17A}$ and $R^{17B}$ substituents bonded to the same nitrogen atom may be joined to form a substituted heteroaryl (e.g., 5 to 10 membered, 5 to 9 membered, or 5 to 6 membered). In embodiments, $R^{17A}$ and $R^{17B}$ substituents bonded to the same nitrogen atom may be joined to form an unsubstituted heteroaryl (e.g., 5 to 10 membered, 5 to 9 membered, or 5 to 6 membered).

In embodiments, $R^{17C}$ is independently hydrogen. In embodiments, $R^{17C}$ is independently —$CX^{17C}_3$. In embodiments, $R^{17C}$ is independently —$CHX^{17C}_2$. In embodiments, $R^{17C}$ is independently —$CH_2X^{17C}$. In embodiments, $R^{17C}$ is independently —CN. In embodiments, $R^{17C}$ is independently —COOH. In embodiments, $R^{17C}$ is independently —$CONH_2$. In embodiments, $X^{17C}$ is independently —F, —Cl, —Br, or —I.

In embodiments, $R^{17C}$ is independently substituted or unsubstituted alkyl (e.g., $C_1$-$C_8$, $C_1$-$C_6$, $C_1$-$C_4$, or $C_1$-$C_2$). In embodiments, $R^{17C}$ is independently substituted alkyl (e.g., $C_1$-$C_8$, $C_1$-$C_6$, $C_1$-$C_4$, or $C_1$-$C_2$). In embodiments, $R^{17C}$ is independently unsubstituted alkyl (e.g., $C_1$-$C_8$, $C_1$-$C_6$, $C_1$-$C_4$, or $C_1$-$C_2$). In embodiments, $R^{17C}$ is independently unsubstituted methyl. In embodiments, $R^{17C}$ is independently unsubstituted ethyl. In embodiments, $R^{17C}$ is independently unsubstituted propyl. In embodiments, $R^{17C}$ is independently unsubstituted isopropyl. In embodiments, $R^{17C}$ is independently unsubstituted tert-butyl. In embodiments, $R^{17C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17C}$ is independently substituted heteroalkyl (e.g., 2 to 8 membered, 2 to 6 membered, 4 to 6 membered, 2 to 3 membered, or 4 to 5 membered). In embodiments, $R^{17C}$ is independently unsubstituted heteroalkyl (e.g., 2 to 8 membered, 2 to 6 membered, 4 to 6 membered, 2 to 3 membered, or 4 to 5 membered). In embodiments, $R^{17C}$ is independently substituted or unsubstituted cycloalkyl (e.g., $C_3$-$C_8$, $C_3$-$C_6$, $C_4$-$C_6$, or $C_5$-$C_6$). In embodiments, $R^{17C}$ is independently substituted cycloalkyl (e.g., $C_3$-$C_8$, $C_3$-$C_6$, $C_4$-$C_6$, or $C_5$-$C_6$). In embodiments, $R^{17C}$ is independently unsubstituted cycloalkyl (e.g., $C_3$-$C_8$, $C_3$-$C_6$, $C_4$-$C_6$, or $C_5$-$C_6$). In embodiments, $R^{17C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17C}$ is independently substituted heterocycloalkyl (e.g., 3 to 8 membered, 3 to 6 membered, 4 to 6 membered, 4 to 5 membered, or 5 to 6 membered). In embodiments, $R^{17C}$ is independently unsubstituted heterocycloalkyl (e.g., 3 to 8 membered, 3 to 6 membered, 4 to 6 membered, 4 to 5 membered, or 5 to 6 membered). In embodiments, $R^{17C}$ is independently substituted or unsubstituted aryl (e.g., $C_6$-$C_{10}$ or phenyl). In embodiments, $R^{17C}$ is independently substituted aryl (e.g., $C_6$-$C_{10}$ or phenyl). In embodiments, $R^{17C}$ is independently unsubstituted aryl (e.g., $C_6$-$C_{10}$ or phenyl). In embodiments, $R^{17C}$ is independently substituted or unsubstituted heteroaryl (e.g., 5 to 10 membered, 5 to 9 membered, or 5 to 6 membered). In embodiments, $R^{17C}$ is independently substituted heteroaryl (e.g., 5 to 10 membered, 5 to 9 membered, or 5 to 6 membered). In embodiments, $R^{17C}$ is independently unsubstituted heteroaryl (e.g., 5 to 10 membered, 5 to 9 membered, or 5 to 6 membered).

In embodiments, $R^{17D}$ is independently hydrogen. In embodiments, $R^{17D}$ is independently —$CX^{17D}_3$. In embodiments, $R^{17D}$ is independently —$CHX^{17D}_2$. In embodiments, $R^{17D}$ is independently —$CH_2X^{17D}$. In embodiments, $R^{17D}$ is independently —CN. In embodiments, $R^{17D}$ is independently —COOH. In embodiments, $R^{17D}$ is independently —$CONH_2$. In embodiments, $X^{17D}$ is independently —F, —Cl, —Br, or —I.

In embodiments, $R^{17D}$ is independently substituted or unsubstituted alkyl (e.g., $C_1$-$C_8$, $C_1$-$C_6$, $C_1$-$C_4$, or $C_1$-$C_2$). In embodiments, $R^{17D}$ is independently substituted alkyl (e.g., $C_1$-$C_8$, $C_1$-$C_6$, $C_1$-$C_4$, or $C_1$-$C_2$). In embodiments, $R^{17D}$ is independently unsubstituted alkyl (e.g., $C_1$-$C_8$, $C_1$-$C_6$, $C_1$-$C_4$, or $C_1$-$C_2$). In embodiments, $R^{17D}$ is independently unsubstituted methyl. In embodiments, $R^{17D}$ is independently unsubstituted ethyl. In embodiments, $R^{17D}$ is independently unsubstituted propyl. In embodiments, $R^{17D}$ is independently unsubstituted isopropyl. In embodiments, $R^{17D}$ is independently unsubstituted tert-butyl. In embodiments, $R^{17D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{17D}$ is independently substituted heteroalkyl (e.g., 2 to 8 membered, 2 to 6 membered, 4 to 6 membered, 2 to 3 membered, or 4 to 5 membered). In embodiments, $R^{17D}$ is independently unsubstituted heteroalkyl (e.g., 2 to 8 membered, 2 to 6 membered, 4 to 6 membered, 2 to 3 membered, or 4 to 5 membered). In embodiments, $R^{17D}$ is independently substituted or unsubstituted cycloalkyl (e.g., $C_3$-$C_8$, $C_3$-$C_6$, $C_4$-$C_6$, or $C_5$-$C_6$). In embodiments, $R^{17D}$ is independently substituted cycloalkyl (e.g., $C_3$-$C_8$, $C_3$-$C_6$, $C_4$-$C_6$, or $C_5$-$C_6$). In embodiments, $R^{17D}$ is independently unsubstituted cycloalkyl (e.g., $C_3$-$C_8$, $C_3$-$C_6$, $C_4$-$C_6$, or $C_5$-$C_6$). In embodiments, $R^{17D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{17D}$ is independently substituted heterocycloalkyl (e.g., 3 to 8 membered, 3 to 6 membered, 4 to 6 membered, 4 to 5 membered, or 5 to 6 membered). In embodiments, $R^{17D}$ is independently unsubstituted heterocycloalkyl (e.g., 3 to 8 membered, 3 to 6 membered, 4 to 6 membered, 4 to 5 membered, or 5 to 6 membered). In embodiments, $R^{17D}$ is independently substituted or unsubstituted aryl (e.g., $C_6$-$C_{10}$ or phenyl). In embodiments, $R^{17D}$ is independently substituted aryl (e.g., $C_6$-$C_{10}$ or phenyl). In embodiments, $R^{17D}$ is independently unsubstituted aryl (e.g., $C_6$-$C_{10}$ or phenyl). In embodiments, $R^{17D}$ is independently substituted or unsubstituted heteroaryl (e.g., 5 to 10 membered, 5 to 9 membered, or 5 to 6 membered). In embodiments, $R^{17D}$ is independently substituted heteroaryl (e.g., 5 to 10 membered, 5 to 9 membered, or 5 to 6 membered). In embodiments, $R^{17D}$ is independently unsubstituted heteroaryl (e.g., 5 to 10 membered, 5 to 9 membered, or 5 to 6 membered).

In embodiments, $R^{17}$ is independently hydrogen, halogen, —$CX^{17}_3$, —$CHX^{17}_2$, —$CH_2X^{17}$, —$OCX^{17}_3$, —$OCH_2X^{17}$, —$OCHX^{17}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O) NH$_2$, —NHSO$_2$H, —NHC=(O)H, —NHC(O)—OH, —NHOH, $R^{78}$-substituted or unsubstituted alkyl (e.g., $C_1$-$C_8$, $C_1$-$C_6$, $C_1$-$C_4$, or $C_1$-$C_2$), $R^{78}$-substituted or unsubstituted heteroalkyl (e.g., 2 to 8 membered, 2 to 6 membered, 4 to 6 membered, 2 to 3 membered, or 4 to 5 membered), $R^{78}$-substituted or unsubstituted cycloalkyl (e.g., $C_3$-$C_8$, $C_3$-$C_6$, $C_4$-$C_6$, or $C_5$-$C_6$), $R^{78}$-substituted or unsubstituted heterocycloalkyl (e.g., 3 to 8 membered, 3 to 6 membered, 4 to 6 membered, 4 to 5 membered, or 5 to 6 membered), $R^{78}$-substituted or unsubstituted aryl (e.g., $C_6$-$C_{10}$ or phenyl), or $R^{78}$-substituted or unsubstituted heteroaryl (e.g., 5 to 10 membered, 5 to 9 membered, or 5 to 6 membered). In embodiments, $R^{17}$ is independently hydrogen, halogen, —$CX^{17}_3$, —$CHX^{17}_2$, —$CH_2X^{17}$, —$OCX^{17}_3$, —$OCH_2X^{17}$, —$OCHX^{17}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17}$ is independently —F, —Cl, —Br, or —I. In embodiments, $R^{17}$ is independently hydrogen. In embodiments, $R^{17}$ is independently unsubstituted methyl. In embodiments, $R^{17}$ is independently unsubstituted ethyl.

$R^{78}$ is independently oxo, halogen, —$CX^{78}_3$, —$CHX^{78}_2$, —$CH_2X^{78}$, —$OCX^{78}_3$, —$OCH_2X^{78}$, —$OCHX^{78}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{79}$-substituted or unsubstituted alkyl (e.g., $C_1$-$C_8$, $C_1$-$C_6$, $C_1$-$C_4$, or $C_1$-$C_2$), $R^{79}$-substituted or unsubstituted heteroalkyl (e.g., 2 to 8 membered, 2 to 6 membered, 4 to 6 membered, 2 to 3 membered, or 4 to 5 membered), $R^{79}$-substituted or unsubstituted cycloalkyl (e.g., $C_3$-$C_8$, $C_3$-$C_6$, $C_4$-$C_6$, or $C_5$-$C_6$), $R^{79}$-substituted or unsubstituted heterocycloalkyl (e.g., 3 to 8 membered, 3 to 6 membered, 4 to 6 membered, 4 to 5 membered, or 5 to 6 membered), $R^{79}$-substituted or unsubstituted aryl (e.g., $C_6$-$C_{10}$ or phenyl), or $R^{79}$-substituted or unsubstituted heteroaryl (e.g., 5 to 10 membered, 5 to 9 membered, or 5 to 6 membered). In embodiments, $R^{78}$ is independently oxo, halogen, —$CX^{78}_3$, —$CHX^{78}_2$, —$CH_2X^{78}$, —$OCX^{78}_3$, —$OCH_2X^{78}$, —$OCHX^{78}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{78}$ is independently —F, —Cl, —Br, or —I. In embodiments, $R^{78}$ is independently unsubstituted methyl. In embodiments, $R^{78}$ is independently unsubstituted ethyl.

$R^{79}$ is independently oxo, halogen, —$CX^{79}_3$, —$CHX^{79}_2$, —$CH_2X^{79}$, —$OCX^{79}_3$, —$OCH_2X^{79}$, —$OCHX^{79}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{80}$-substituted or unsubstituted alkyl (e.g., $C_1$-$C_8$, $C_1$-$C_6$, $C_1$-$C_4$, or $C_1$-$C_2$), $R^{80}$-substituted or unsubstituted heteroalkyl (e.g., 2 to 8 membered, 2 to 6 membered, 4 to 6 membered, 2 to 3 membered, or 4 to 5 membered), $R^{80}$-substituted or unsubstituted cycloalkyl (e.g., $C_3$-$C_8$, $C_3$-$C_6$, $C_4$-$C_6$, or $C_5$-$C_6$), $R^{80}$-substituted or unsubstituted heterocycloalkyl (e.g., 3 to 8 membered, 3 to 6 membered, 4 to 6 membered, 4 to 5 membered, or 5 to 6 membered), $R^{80}$-substituted or unsubstituted aryl (e.g., $C_6$-$C_{10}$ or phenyl), or $R^{80}$-substituted or unsubstituted heteroaryl (e.g., 5 to 10 membered, 5 to 9 membered, or 5 to 6 membered). In embodiments, $R^{79}$ is independently oxo, halogen, —$CX^{79}_3$, —$CHX^{79}_2$, —$CH_2X^{79}$, —$OCX^{79}_3$, —$OCH_2X^{79}$, —$OCHX^{79}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{79}$ is independently —F, —Cl, —Br, or —I. In embodiments, $R^{79}$ is independently unsubstituted methyl. In embodiments, $R^{79}$ is independently unsubstituted ethyl.

$R^{80}$ is independently oxo, halogen, —$CX^{80}_3$, —$CHX^{80}_2$, —$CH_2X^{80}$, —$OCX^{80}_3$, —$OCH_2X^{80}$, —$OCHX^{80}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{80}$ is independently —F, —Cl, —Br, or —I. In embodiments, $R^{80}$ is independently unsubstituted methyl. In embodiments, $R^{80}$ is independently unsubstituted ethyl.

In embodiments, $R^{18}$ is hydrogen. In embodiments, $R^{18}$ is halogen. In embodiments, $R^{18}$ is —$CX^{18}_3$. In embodiments, $R^{18}$ is —$CHX^{18}_2$. In embodiments, $R^{18}$ is —$CH_2X^{18}$. In embodiments, $R^{18}$ is —CN. In embodiments, $R^{18}$ is —$SO_{n18}R^{18D}$. In embodiments, $R^{18}$ is —$SO_{v15}NR^{18A}R^{18B}$. In embodiments, $R^{18}$ is —$NHNR^{18A}R^{18B}$. In embodiments, $R^{18}$ is —$ONR^{18A}R^{18B}$. In embodiments, $R^{18}$ is —NHC=(O)$NHNR^{18A}R^{18B}$. In embodiments, $R^{18}$ is —NHC(O) $NR^{18A}R^{18B}$. In embodiments, $R^{18}$ is —$N(O)_{m18}$. In embodiments, $R^{18}$ is —$NR^{18A}R^{18B}$. In embodiments, $R^{18}$ is —C(O)$R^{18C}$. In embodiments, $R^{18}$ is —C(O)—$OR^{18C}$. In embodiments, $R^{18}$ is —C(O)$NR^{18A}R^{18B}$. In embodiments, $R^{18}$ is —$OR^{18D}$. In embodiments, $R^{18}$ is —$NR^{18A}SO_2R^{18D}$. In embodiments, $R^{18}$ is —$NR^{18A}C(O)R^{18C}$. In embodiments, $R^8$ is —$NR^{18A}C(O)OR^{18C}$. In embodiments, $R^{18}$ is —$NR^{18A}OR^{18C}$. In embodiments, $R^{18}$ is —$OCX^{18}_3$. In embodiments, $R^{18}$ is —$OCHX^{18}_2$. In embodiments, $R^{18}$ is independently —OH. In embodiments, $R^{18}$ is independently —NH$_2$. In embodiments, R$^{18}$ is independently —COOH. In embodiments, R$^{18}$ is independently —CONH$_2$. In embodiments, R$^{18}$ is independently —NO$_2$. In embodiments, R$^8$ is independently —SH. In embodiments, R$^{18}$ is independently —CF$_3$. In embodiments, R$^{18}$ is independently —CHF$_2$. In embodiments, R$^{18}$ is independently —CH$_2$F. In embodiments, R$^8$ is independently —OCF$_3$. In embodiments, R$^{18}$ is independently —OCH$_2$F. In embodiments, R$^{18}$ is independently —OCHF$_2$. In embodiments, R$^{18}$ is independently —OCH$_3$. In embodiments, R$^{18}$ is independently —OCH$_2$CH$_3$. In embodiments, R$^{18}$ is independently —OCH$_2$CH$_2$CH$_3$. In embodiments, R$^{18}$ is independently —OCH(CH$_3$)$_2$. In embodiments, R$^{18}$ is independently —OC(CH$_3$)$_3$. In embodiments, R$^{18}$ is independently —SCH$_3$. In embodiments, R$^{18}$ is independently —SCH$_2$CH$_3$. In embodiments, R$^{18}$ is independently —SCH$_2$CH$_2$CH$_3$. In embodiments, R$^{18}$ is independently —SCH(CH$_3$)$_2$. In embodiments, R$^{18}$ is independently —SC(CH$_3$)$_3$. In embodiments, R$^{18}$ is independently —CH$_3$. In embodiments, R$^{18}$ is independently —CH$_2$CH$_3$. In embodiments, R$^{18}$ is independently —CH$_2$CH$_2$CH$_3$. In embodiments, R$^{18}$ is independently —CH(CH$_3$)$_2$. In embodiments, R$^{18}$ is independently —C(CH$_3$)$_3$. In embodiments, R$^{18}$ is independently —F. In embodiments, R$^{18}$ is independently —Cl. In embodiments, R$^{18}$ is independently —Br. In embodiments, R$^{18}$ is independently —I.

In embodiments, R$^{18}$ is independently substituted or unsubstituted alkyl (e.g., C$_1$-C$_8$, C$_1$-C$_6$, C$_1$-C$_4$, or C$_1$-C$_2$). In embodiments, R$^{18}$ is independently substituted alkyl (e.g., C$_1$-C$_8$, C$_1$-C$_6$, C$_1$-C$_4$, or C$_1$-C$_2$). In embodiments, R$^{18}$ is independently unsubstituted alkyl (e.g., C$_1$-C$_8$, C$_1$-C$_6$, C$_1$-C$_4$, or C$_1$-C$_2$). In embodiments, R$^{18}$ is independently unsubstituted methyl. In embodiments, R$^{18}$ is independently unsubstituted ethyl. In embodiments, R$^{18}$ is independently unsubstituted propyl. In embodiments, R$^{18}$ is independently unsubstituted isopropyl. In embodiments, R$^{18}$ is independently unsubstituted tert-butyl. In embodiments, R$^{18}$ is independently substituted or unsubstituted heteroalkyl (e.g., 2 to 8 membered, 2 to 6 membered, 4 to 6 membered, 2 to 3 membered, or 4 to 5 membered). In embodiments, R$^{18}$ is independently substituted heteroalkyl (e.g., 2 to 8 membered, 2 to 6 membered, 4 to 6 membered, 2 to 3 membered, or 4 to 5 membered). In embodiments, R$^{18}$ is independently unsubstituted heteroalkyl (e.g., 2 to 8 membered, 2 to 6 membered, 4 to 6 membered, 2 to 3 membered, or 4 to 5 membered). In embodiments, R$^{18}$ is independently substituted or unsubstituted cycloalkyl (e.g., C$_3$-C$_8$, C$_3$-C$_6$, C$_4$-C$_6$, or C$_5$-C$_6$). In embodiments, R$^{18}$ is independently substituted cycloalkyl (e.g., C$_3$-C$_8$, C$_3$-C$_6$, C$_4$-C$_6$, or C$_5$-C$_6$). In embodiments, R$^{18}$ is independently unsubstituted cycloalkyl (e.g., C$_3$-C$_8$, C$_3$-C$_6$, C$_4$-C$_6$, or C$_5$-C$_6$). In embodiments, R$^{18}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{18}$ is independently substituted heterocycloalkyl (e.g., 3 to 8 membered, 3 to 6 membered, 4 to 6 membered, 4 to 5 membered, or 5 to 6 membered). In embodiments, R$^{18}$ is independently unsubstituted heterocycloalkyl (e.g., 3 to 8 membered, 3 to 6 membered, 4 to 6 membered, 4 to 5 membered, or 5 to 6 membered). In embodiments, R$^{18}$ is independently substituted or unsubstituted aryl (e.g., C$_6$-C$_{10}$ or phenyl). In embodiments, R$^{18}$ is independently substituted aryl (e.g., C$_6$-C$_{10}$ or phenyl). In embodiments, R$^{18}$ is independently unsubstituted aryl (e.g., C$_6$-C$_{10}$ or phenyl). In embodiments, R$^{18}$ is independently substituted or unsubstituted heteroaryl (e.g., 5 to 10 membered, 5 to 9 membered, or 5 to 6 membered). In embodiments, R$^{18}$ is independently substituted heteroaryl (e.g., 5 to 10 membered, 5 to 9 membered, or 5 to 6 membered). In embodiments, R$^{18}$ is independently unsubstituted heteroaryl (e.g., 5 to 10 membered, 5 to 9 membered, or 5 to 6 membered).

In embodiments, R$^{18A}$ is independently hydrogen. In embodiments, R$^{18A}$ is independently —CX$^{18A}$$_3$. In embodiments, R$^{18A}$ is independently —CHX$^{18A}$$_2$. In embodiments, R$^{18A}$ is independently —CH$_2$X$^{18A}$. In embodiments, R$^{18A}$ is independently —CN. In embodiments, R$^{18A}$ is independently —COOH. In embodiments, R$^{18A}$ is independently —CONH$_2$. In embodiments, X$^{18A}$ is independently —F, —Cl, —Br, or —I.

In embodiments, R$^{18A}$ is independently substituted or unsubstituted alkyl (e.g., C$_1$-C$_8$, C$_1$-C$_6$, C$_1$-C$_4$, or C$_1$-C$_2$). In embodiments, R$^{18A}$ is independently substituted alkyl (e.g., C$_1$-C$_8$, C$_1$-C$_6$, C$_1$-C$_4$, or C$_1$-C$_2$). In embodiments, R$^{18A}$ is independently unsubstituted alkyl (e.g., C$_1$-C$_8$, C$_1$-C$_6$, C$_1$-C$_4$, or C$_1$-C$_2$). In embodiments, R$^{18A}$ is independently unsubstituted methyl. In embodiments, R$^{18A}$ is independently unsubstituted ethyl. In embodiments, R$^{18A}$ is independently unsubstituted propyl. In embodiments, R$^{18A}$ is independently unsubstituted isopropyl. In embodiments, R$^{18A}$ is independently unsubstituted tert-butyl. In embodiments, R$^{18A}$ is independently substituted or unsubstituted heteroalkyl (e.g., 2 to 8 membered, 2 to 6 membered, 4 to 6 membered, 2 to 3 membered, or 4 to 5 membered). In embodiments, R$^{18A}$ is independently substituted heteroalkyl (e.g., 2 to 8 membered, 2 to 6 membered, 4 to 6 membered, 2 to 3 membered, or 4 to 5 membered). In embodiments, R$^{18A}$ is independently unsubstituted heteroalkyl (e.g., 2 to 8 membered, 2 to 6 membered, 4 to 6 membered, 2 to 3 membered, or 4 to 5 membered). In embodiments, R$^{18A}$ is independently substituted or unsubstituted cycloalkyl (e.g., C$_3$-C$_8$, C$_3$-C$_6$, C$_4$-C$_6$, or C$_5$-C$_6$). In embodiments, R$^{18A}$ is independently substituted cycloalkyl (e.g., C$_3$-C$_8$, C$_3$-C$_6$, C$_4$-C$_6$, or C$_5$-C$_6$). In embodiments, R$^{18A}$ is independently unsubstituted cycloalkyl (e.g., C$_3$-C$_8$, C$_3$-C$_6$, C$_4$-C$_6$, or C$_5$-C$_6$). In embodiments, R$^{18A}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{18A}$ is independently substituted heterocycloalkyl (e.g., 3 to 8 membered, 3 to 6 membered, 4 to 6 membered, 4 to 5 membered, or 5 to 6 membered). In embodiments, R$^{18A}$ is independently unsubstituted heterocycloalkyl (e.g., 3 to 8 membered, 3 to 6 membered, 4 to 6 membered, 4 to 5 membered, or 5 to 6 membered). In embodiments, R$^{18A}$ is independently substituted or unsubstituted aryl (e.g., C$_6$-C$_{10}$ or phenyl). In embodiments, R$^{18A}$ is independently substituted aryl (e.g., C$_6$-C$_{10}$ or phenyl). In embodiments, R$^{18A}$ is independently unsubstituted aryl (e.g., C$_6$-C$_{10}$ or phenyl). In embodiments, R$^{18A}$ is independently substituted or unsubstituted heteroaryl (e.g., 5 to 10 membered, 5 to 9 membered, or 5 to 6 membered). In embodiments, R$^{18A}$ is independently substituted heteroaryl (e.g., 5 to 10 membered, 5 to 9 membered, or 5 to 6 membered). In embodiments, R$^{18A}$ is independently unsubstituted heteroaryl (e.g., 5 to 10 membered, 5 to 9 membered, or 5 to 6 membered).

In embodiments, R$^{18B}$ is independently hydrogen. In embodiments, R$^{18B}$ is independently —CX$^{18B}$$_3$. In embodiments, R$^{18B}$ is independently —CHX$^{18B}$$_2$. In embodiments, R$^{18B}$ is independently —CH$_2$X$^{18B}$. In embodiments, R$^{18B}$ is independently —CN. In embodiments, R$^{18B}$ is independently —COOH. In embodiments, R$^{18B}$ is independently —CONH$_2$. In embodiments, X$^{18B}$ is independently —F, —Cl, —Br, or —I.

In embodiments, $R^{18B}$ is independently substituted or unsubstituted alkyl (e.g., $C_1$-$C_8$, $C_1$-$C_6$, $C_1$-$C_4$, or $C_1$-$C_2$). In embodiments, $R^{18B}$ is independently substituted alkyl (e.g., $C_1$-$C_8$, $C_1$-$C_6$, $C_1$-$C_4$, or $C_1$-$C_2$). In embodiments, $R^{18B}$ is independently unsubstituted alkyl (e.g., $C_1$-$C_8$, $C_1$-$C_6$, $C_1$-$C_4$, or $C_1$-$C_2$). In embodiments, $R^{18B}$ is independently unsubstituted methyl. In embodiments, $R^{18B}$ is independently unsubstituted ethyl. In embodiments, $R^{18B}$ is independently unsubstituted propyl. In embodiments, $R^{18B}$ is independently unsubstituted isopropyl. In embodiments, $R^{18B}$ is independently unsubstituted tert-butyl. In embodiments, $R^{18B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18B}$ is independently substituted heteroalkyl (e.g., 2 to 8 membered, 2 to 6 membered, 4 to 6 membered, 2 to 3 membered, or 4 to 5 membered). In embodiments, $R^{18B}$ is independently unsubstituted heteroalkyl (e.g., 2 to 8 membered, 2 to 6 membered, 4 to 6 membered, 2 to 3 membered, or 4 to 5 membered). In embodiments, $R^{18B}$ is independently substituted or unsubstituted cycloalkyl (e.g., $C_3$-$C_8$, $C_3$-$C_6$, $C_4$-$C_6$, or $C_5$-$C_6$). In embodiments, $R^{18B}$ is independently substituted cycloalkyl (e.g., $C_3$-$C_8$, $C_3$-$C_6$, $C_4$-$C_6$, or $C_5$-$C_6$). In embodiments, $R^{18B}$ is independently unsubstituted cycloalkyl (e.g., $C_3$-$C_8$, $C_3$-$C_6$, $C_4$-$C_6$, or $C_5$-$C_6$). In embodiments, $R^{18B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18B}$ is independently substituted heterocycloalkyl (e.g., 3 to 8 membered, 3 to 6 membered, 4 to 6 membered, 4 to 5 membered, or 5 to 6 membered). In embodiments, $R^{18B}$ is independently unsubstituted heterocycloalkyl (e.g., 3 to 8 membered, 3 to 6 membered, 4 to 6 membered, 4 to 5 membered, or 5 to 6 membered). In embodiments, $R^{18B}$ is independently substituted or unsubstituted aryl (e.g., $C_6$-$C_{10}$ or phenyl). In embodiments, $R^{18B}$ is independently substituted aryl (e.g., $C_6$-$C_{10}$ or phenyl). In embodiments, $R^{18B}$ is independently unsubstituted aryl (e.g., $C_6$-$C_{10}$ or phenyl). In embodiments, $R^{18B}$ is independently substituted or unsubstituted heteroaryl (e.g., 5 to 10 membered, 5 to 9 membered, or 5 to 6 membered). In embodiments, $R^{18B}$ is independently substituted heteroaryl (e.g., 5 to 10 membered, 5 to 9 membered, or 5 to 6 membered). In embodiments, $R^{18B}$ is independently unsubstituted heteroaryl (e.g., 5 to 10 membered, 5 to 9 membered, or 5 to 6 membered).

In embodiments, $R^{18A}$ and $R^{18B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{18A}$ and $R^{18B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{18A}$ and $R^{18B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{18A}$ and $R^{18B}$ substituents bonded to the same nitrogen atom may be joined to form a substituted or unsubstituted heteroaryl (e.g., 5 to 10 membered, 5 to 9 membered, or 5 to 6 membered). In embodiments, $R^{18A}$ and $R^{18B}$ substituents bonded to the same nitrogen atom may be joined to form a substituted heteroaryl (e.g., 5 to 10 membered, 5 to 9 membered, or 5 to 6 membered). In embodiments, $R^{18A}$ and $R^{18B}$ substituents bonded to the same nitrogen atom may be joined to form an unsubstituted heteroaryl (e.g., 5 to 10 membered, 5 to 9 membered, or 5 to 6 membered).

In embodiments, $R^{18C}$ is independently hydrogen. In embodiments, $R^{18C}$ is independently —$CX^{18C}_3$. In embodiments, $R^{18C}$ is independently —$CHX^{18C}_2$. In embodiments, $R^{18C}$ is independently —$CH_2X^{18C}$. In embodiments, $R^{18C}$ is independently —CN. In embodiments, $R^{18C}$ is independently —COOH. In embodiments, $R^{18C}$ is independently —$CONH_2$. In embodiments, $X^{18C}$ is independently —F, —Cl, —Br, or —I.

In embodiments, $R^{18C}$ is independently substituted or unsubstituted alkyl (e.g., $C_1$-$C_8$, $C_1$-$C_6$, $C_1$-$C_4$, or $C_1$-$C_2$). In embodiments, $R^{18C}$ is independently substituted alkyl (e.g., $C_1$-$C_8$, $C_1$-$C_6$, $C_1$-$C_4$, or $C_1$-$C_2$). In embodiments, $R^{18C}$ is independently unsubstituted alkyl (e.g., $C_1$-$C_8$, $C_1$-$C_6$, $C_1$-$C_4$, or $C_1$-$C_2$). In embodiments, $R^{18C}$ is independently unsubstituted methyl. In embodiments, $R^{18C}$ is independently unsubstituted ethyl. In embodiments, $R^{18C}$ is independently unsubstituted propyl. In embodiments, $R^{18C}$ is independently unsubstituted isopropyl. In embodiments, $R^{18C}$ is independently unsubstituted tert-butyl. In embodiments, $R^{18C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18C}$ is independently substituted heteroalkyl (e.g., 2 to 8 membered, 2 to 6 membered, 4 to 6 membered, 2 to 3 membered, or 4 to 5 membered). In embodiments, $R^{18C}$ is independently unsubstituted heteroalkyl (e.g., 2 to 8 membered, 2 to 6 membered, 4 to 6 membered, 2 to 3 membered, or 4 to 5 membered). In embodiments, $R^{18C}$ is independently substituted or unsubstituted cycloalkyl (e.g., $C_3$-$C_8$, $C_3$-$C_6$, $C_4$-$C_6$, or $C_5$-$C_6$). In embodiments, $R^{18C}$ is independently substituted cycloalkyl (e.g., $C_3$-$C_8$, $C_3$-$C_6$, $C_4$-$C_6$, or $C_5$-$C_6$). In embodiments, $R^{18C}$ is independently unsubstituted cycloalkyl (e.g., $C_3$-$C_8$, $C_3$-$C_6$, $C_4$-$C_6$, or $C_5$-$C_6$). In embodiments, $R^{18C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18C}$ is independently substituted heterocycloalkyl (e.g., 3 to 8 membered, 3 to 6 membered, 4 to 6 membered, 4 to 5 membered, or 5 to 6 membered). In embodiments, $R^{18C}$ is independently unsubstituted heterocycloalkyl (e.g., 3 to 8 membered, 3 to 6 membered, 4 to 6 membered, 4 to 5 membered, or 5 to 6 membered). In embodiments, $R^{18C}$ is independently substituted or unsubstituted aryl (e.g., $C_6$-$C_{10}$ or phenyl). In embodiments, $R^{18C}$ is independently substituted aryl (e.g., $C_6$-$C_{10}$ or phenyl). In embodiments, $R^{18C}$ is independently unsubstituted aryl (e.g., $C_6$-$C_{10}$ or phenyl). In embodiments, $R^{18C}$ is independently substituted or unsubstituted heteroaryl (e.g., 5 to 10 membered, 5 to 9 membered, or 5 to 6 membered). In embodiments, $R^{18C}$ is independently substituted heteroaryl (e.g., 5 to 10 membered, 5 to 9 membered, or 5 to 6 membered). In embodiments, $R^{18C}$ is independently unsubstituted heteroaryl (e.g., 5 to 10 membered, 5 to 9 membered, or 5 to 6 membered).

In embodiments, $R^{18D}$ is independently hydrogen. In embodiments, $R^{18D}$ is independently —$CX^{18D}_3$. In embodiments, $R^{18D}$ is independently —$CHX^{18D}_2$. In embodiments, $R^{18D}$ is independently —$CH_2X^{18D}$. In embodiments, $R^{18D}$ is independently —CN. In embodiments, $R^{18D}$ is independently —COOH. In embodiments, $R^{18D}$ is independently —$CONH_2$. In embodiments, $X^{18}D$ is independently —F, —Cl, —Br, or —I.

In embodiments, $R^{18D}$ is independently substituted or unsubstituted alkyl (e.g., $C_1$-$C_8$, $C_1$-$C_6$, $C_1$-$C_4$, or $C_1$-$C_2$). In embodiments, $R^{18D}$ is independently substituted alkyl (e.g., $C_1$-$C_8$, $C_1$-$C_6$, $C_1$-$C_4$, or $C_1$-$C_2$). In embodiments, $R^{18D}$ is independently unsubstituted alkyl (e.g., $C_1$-$C_8$, $C_1$-$C_6$, $C_1$-$C_4$, or $C_1$-$C_2$). In embodiments, $R^{18D}$ is independently unsubstituted methyl. In embodiments, $R^{18D}$ is independently unsubstituted ethyl. In embodiments, $R^{18D}$ is independently unsubstituted propyl. In embodiments, $R^{18D}$ is independently unsubstituted isopropyl. In embodiments, $R^{18D}$ is independently unsubstituted tert-butyl. In embodiments, $R^{18D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{18D}$ is independently substituted heteroalkyl (e.g., 2 to 8 membered, 2 to 6 membered, 4 to 6 membered, 2 to 3 membered, or 4 to 5 membered). In embodiments, $R^{18D}$ is independently unsubstituted heteroalkyl (e.g., 2 to 8 membered, 2 to 6 membered, 4 to 6 membered, 2 to 3 membered, or 4 to 5 membered). In embodiments, $R^{18D}$ is independently substituted or unsubstituted cycloalkyl (e.g., $C_3$-$C_8$, $C_3$-$C_6$, $C_4$-$C_6$, or $C_5$-$C_6$). In embodiments, $R^{18D}$ is independently substituted cycloalkyl (e.g., $C_3$-$C_8$, $C_3$-$C_6$, $C_4$-$C_6$, or $C_5$-$C_6$). In embodiments, $R^{18D}$ is independently unsubstituted cycloalkyl (e.g., $C_3$-$C_8$, $C_3$-$C_6$, $C_4$-$C_6$, or $C_5$-$C_6$). In embodiments, $R^{18D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{18D}$ is independently substituted heterocycloalkyl (e.g., 3 to 8 membered, 3 to 6 membered, 4 to 6 membered, 4 to 5 membered, or 5 to 6 membered). In embodiments, $R^{18D}$ is independently unsubstituted heterocycloalkyl (e.g., 3 to 8 membered, 3 to 6 membered, 4 to 6 membered, 4 to 5 membered, or 5 to 6 membered). In embodiments, $R^{18D}$ is independently substituted or unsubstituted aryl (e.g., $C_6$-$C_{10}$ or phenyl). In embodiments, $R^{18D}$ is independently substituted aryl (e.g., $C_6$-$C_{10}$ or phenyl). In embodiments, $R^{18D}$ is independently unsubstituted aryl (e.g., $C_6$-$C_{10}$ or phenyl). In embodiments, $R^{18D}$ is independently substituted or unsubstituted heteroaryl (e.g., 5 to 10 membered, 5 to 9 membered, or 5 to 6 membered). In embodiments, $R^{18D}$ is independently substituted heteroaryl (e.g., 5 to 10 membered, 5 to 9 membered, or 5 to 6 membered). In embodiments, $R^{18D}$ is independently unsubstituted heteroaryl (e.g., 5 to 10 membered, 5 to 9 membered, or 5 to 6 membered).

In embodiments, $R^{18}$ is independently hydrogen, halogen, —$CX^{18}_3$, —$CHX^{18}_2$, —$CH_2X^{18}$, —$OCX^{18}_3$, —$OCH_2X^{18}$, —$OCHX^{18}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{81}$-substituted or unsubstituted alkyl (e.g., $C_1$-$C_8$, $C_1$-$C_6$, $C_1$-$C_4$, or $C_1$-$C_2$), $R^{81}$-substituted or unsubstituted heteroalkyl (e.g., 2 to 8 membered, 2 to 6 membered, 4 to 6 membered, 2 to 3 membered, or 4 to 5 membered), $R^{81}$-substituted or unsubstituted cycloalkyl (e.g., $C_3$-$C_8$, $C_3$-$C_6$, $C_4$-$C_6$, or $C_5$-$C_6$), $R^{81}$-substituted or unsubstituted heterocycloalkyl (e.g., 3 to 8 membered, 3 to 6 membered, 4 to 6 membered, 4 to 5 membered, or 5 to 6 membered), $R^{81}$-substituted or unsubstituted aryl (e.g., $C_6$-$C_{10}$ or phenyl), or $R^{81}$-substituted or unsubstituted heteroaryl (e.g., 5 to 10 membered, 5 to 9 membered, or 5 to 6 membered). In embodiments, $R^{18}$ is independently hydrogen, halogen, —$CX^{18}_3$, —$CHX^{18}_2$, —$CH_2X^{18}$, —$OCX^{18}_3$, —$OCH_2X^{18}$, —$OCHX^{18}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{18}$ is independently —F, —Cl, —Br, or —I. In embodiments, $R^{18}$ is independently hydrogen. In embodiments, $R^{18}$ is independently unsubstituted methyl. In embodiments, $R^{18}$ is independently unsubstituted ethyl.

$R^{81}$ is independently oxo, halogen, —$CX^{81}_3$, —$CHX^{81}_2$, —$CH_2X^{81}$, —$OCX^{81}_3$, —$OCH_2X^{81}$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{82}$-substituted or unsubstituted alkyl (e.g., $C_1$-$C_8$, $C_1$-$C_6$, $C_1$-$C_4$, or $C_1$-$C_2$), $R^{82}$-substituted or unsubstituted heteroalkyl (e.g., 2 to 8 membered, 2 to 6 membered, 4 to 6 membered, 2 to 3 membered, or 4 to 5 membered), $R^{82}$-substituted or unsubstituted cycloalkyl (e.g., $C_3$-$C_8$, $C_3$-$C_6$, $C_4$-$C_6$, or $C_5$-$C_6$), $R^{82}$-substituted or unsubstituted heterocycloalkyl (e.g., 3 to 8 membered, 3 to 6 membered, 4 to 6 membered, 4 to 5 membered, or 5 to 6 membered), $R^{82}$-substituted or unsubstituted aryl (e.g., $C_6$-$C_{10}$ or phenyl), or $R^{82}$-substituted or unsubstituted heteroaryl (e.g., 5 to 10 membered, 5 to 9 membered, or 5 to 6 membered). In embodiments, $R^{81}$ is independently oxo, halogen, —$CX^{81}_3$, —$CHX^1_2$, —$CH_2X^{81}$, —$OCX^{81}_3$, —$OCH_2X^{81}$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{81}$ is independently —F, —Cl, —Br, or —I. In embodiments, $R^{81}$ is independently unsubstituted methyl. In embodiments, $R^{81}$ is independently unsubstituted ethyl.

$R^{82}$ is independently oxo, halogen, —$CX^{82}_3$, —$CHX^{82}_2$, —$CH_2X^{82}$, —$OCX^{82}_3$, —$OCH_2X^{82}$, —$OCHX^{82}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{83}$-substituted or unsubstituted alkyl (e.g., $C_1$-$C_8$, $C_1$-$C_6$, $C_1$-$C_4$, or $C_1$-$C_2$), $R^{83}$-substituted or unsubstituted heteroalkyl (e.g., 2 to 8 membered, 2 to 6 membered, 4 to 6 membered, 2 to 3 membered, or 4 to 5 membered), $R^{83}$-substituted or unsubstituted cycloalkyl (e.g., $C_3$-$C_8$, $C_3$-$C_6$, $C_4$-$C_6$, or $C_5$-$C_6$), $R^{83}$-substituted or unsubstituted heterocycloalkyl (e.g., 3 to 8 membered, 3 to 6 membered, 4 to 6 membered, 4 to 5 membered, or 5 to 6 membered), $R^{83}$-substituted or unsubstituted aryl (e.g., $C_6$-$C_{10}$ or phenyl), or $R^{83}$-substituted or unsubstituted heteroaryl (e.g., 5 to 10 membered, 5 to 9 membered, or 5 to 6 membered). In embodiments, $R^{82}$ is independently oxo, halogen, —CX$^{82}_3$, —CHX$^{82}_2$, —CH$_2$X$^{82}$, —OCX$^{82}_3$, —OCH$_2$X$^{82}$, —OCHX$^{82}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{82}$ is independently —F, —Cl, —Br, or —I. In embodiments, R$^{82}$ is independently unsubstituted methyl. In embodiments, R$^{82}$ is independently unsubstituted ethyl.

R$^{83}$ is independently oxo, halogen, —CX$^{83}_3$, —CHX$^{83}_2$, —CH$_2$X$^{83}$, —OCX$^{83}_3$, —OCH$_2$X$^{83}$, —OCHX$^{83}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{83}$ is independently —F, —Cl, —Br, or —I. In embodiments, R$^{83}$ is independently unsubstituted methyl. In embodiments, R$^{83}$ is independently unsubstituted ethyl.

In embodiments, R$^{15}$, R$^{16}$, R$^{17}$, and R$^{18}$ are hydrogen.

In embodiments, E is:

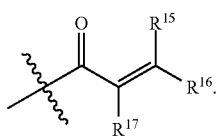

In embodiments, E is:

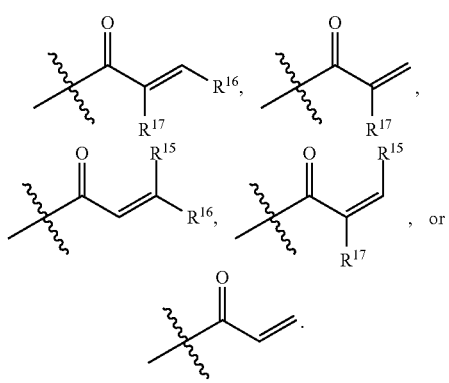

In embodiments, E is:

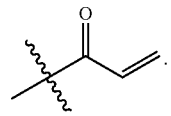 [SMILES: *C(=O)C=C]

In embodiments, E is:

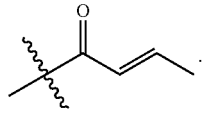

In embodiments, E is:

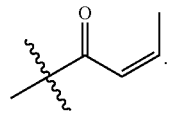 [SMILES: *C(=O)/C=C\C]

In embodiments, E is:

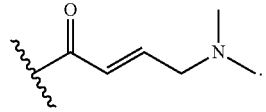 [SMILES: *C(=O)/C=C/CN(C)C]

In embodiments, E is:

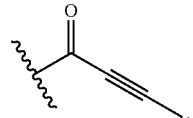 [SMILES: *C(=O)C#CC]

In embodiments, E is —C(O)CH=CH$_2$, —C(O)CH=CHCH$_2$N(CH$_3$)$_2$, —C(O)C(=CH$_2$)CH$_2$N(CH$_3$)$_2$, —C(O)C≡CCH$_3$, —C(O)C(=CH$_2$)CH$_3$.

In embodiments, the compound has the formula:

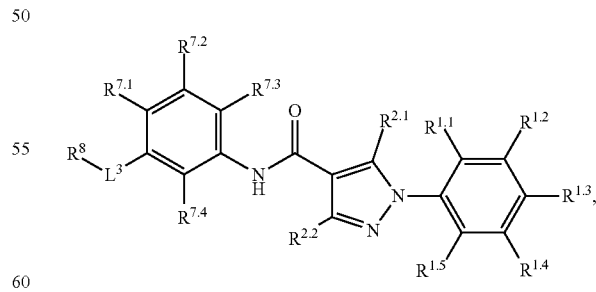

wherein L$^3$ and R$^8$ are as described herein, including embodiments. R$^{1.1}$, R$^{1.2}$, R$^{1.3}$, R$^{1.4}$, and R$^{1.5}$ are each independently hydrogen or R$^1$ at a fixed position on the attached ring. R$^{1.1}$, R$^{1.2}$, R$^{1.3}$, R$^{1.4}$, and R$^{1.5}$ may independently be any substituent of R$^1$ described herein, including in any aspect, embodiment, example, figure, or claim. R$^{2.1}$ and R$^{2.2}$ are each independently hydrogen or $R^2$ at a fixed position on the attached ring. $R^{2.1}$ and $R^{2.2}$ may independently be any substituent of $R^2$ described herein, including in any aspect, embodiment, example, figure, or claim. $R^{7.1}$, $R^{7.2}$, $R^{7.3}$, and $R^{7.4}$ are each independently hydrogen or $R^7$ at a fixed position on the attached ring. $R^{7.1}$, $R^{7.2}$, $R^{7.3}$, and $R^{7.4}$ may independently be any substituent of $R^7$ described herein, including in any aspect, embodiment, example, figure, or claim.

In embodiments, the compound has the formula:

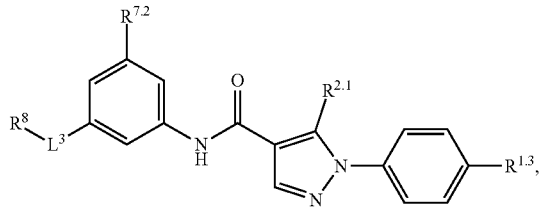

wherein $R^{1.3}$, $R^{2.1}$, $R^{7.2}$, $L^3$ and $R^8$ are as described herein, including embodiments.

$R^{1.1}$, $R^{1.2}$, $R^{1.3}$, $R^{1.4}$, and $R^{1.5}$ are each independently hydrogen, halogen, $-CX^1{}_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{1.1}$, $R^{1.2}$, $R^{1.3}$, $R^{1.4}$, and $R^{1.5}$ are each independently hydrogen, halogen, $-CX^1{}_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{1.1}$, $R^{1.2}$, $R^{1.3}$, $R^{1.4}$, and $R^{1.5}$ are each independently hydrogen, halogen, $-CX^1{}_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, or $-NR^{1A}OR^{1C}$. In embodiments, $R^{1.1}$, $R^{1.2}$, $R^{1.3}$, $R^{1.4}$ and $R^{1.5}$ are each independently hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{1.1}$ is independently hydrogen. In embodiments, $R^{1.1}$ is independently halogen. In embodiments, $R^{1.1}$, is $-CF_3$. In embodiments, $R^{1.1}$, is $-CCl_3$. In embodiments, $R^{1.1}$, is $-CBr_3$. In embodiments, $R^{1.1}$, is $-CI_3$. In embodiments, $R^{1.1}$, is $-CHF_2$. In embodiments, $R^{1.1}$, is $-CHBr_2$. In embodiments, $R^{1.1}$, is $-CHCl_2$. In embodiments, $R^{1.1}$, is $-CHI_2$. In embodiments, $R^{1.1}$, is $-CH_2F$. In embodiments, $R^{1.1}$, is $-CH_2Cl$. In embodiments, $R^{1.1}$, is $-CH_2Br$. In embodiments, $R^{1.1}$, is $-CH_2I$. In embodiments, $R^{1.1}$, is $-OCF_3$. In embodiments, $R^{1.1}$, is $-OCCl_3$. In embodiments, $R^{1.1}$, is $-OCBr_3$. In embodiments, $R^{1.1}$, is $-OCI_3$. In embodiments, $R^{1.1}$, is $-OCHF_2$. In embodiments, $R^{1.1}$, is $-OCHBr_2$. In embodiments, $R^{1.1}$, is $-OCHCl_2$. In embodiments, $R^{1.1}$, is $-OCHI_2$. In embodiments, $R^{1.1}$, is $-OCH_2F$. In embodiments, $R^{1.1}$, is $-OCH_2Cl$. In embodiments, $R^{1.1}$, is $-OCH_2Br$. In embodiments, $R^{1.1}$, is $-OCH_2I$. In embodiments, $R^{1.1}$, is $-CN$. In embodiments, $R^{1.1}$, is $-SO_{n1}R^{1D}$. In embodiments, $R^{1.1}$, is $-SO_{v1}NR^{1A}R^{1B}$. In embodiments, $R^1$, is $-NHC(O)NR^{1A}R^{1B}$. In embodiments, $R^{1.1}$, is $-N(O)_{m1}$. In embodiments, $R^{1.1}$, is $-NR^{1A}R^{1B}$. In embodiments, $R^{1.1}$, is $-C(O)R^{1C}$. In embodiments, $R^{1.1}$, is $-C(O)-OR^{1C}$. In embodiments, $R^{1.1}$, is $-C(O)NR^{1A}R^{1B}$. In embodiments, $R^{1.1}$, is $-OR^{1D}$. In embodiments, $R^{1.1}$, is $-NR^{1A}SO_2R^{1D}$. In embodiments, $R^{1.1}$, is $-NR^{1A}C(O)R^{1C}$. In embodiments, $R^{1.1}$, is $-NR^{1A}C(O)OR^{1C}$. In embodiments, $R^{1.1}$, is $-NR^{1A}OR^{1C}$. In embodiments, $R^{1.1}$, is $-SO_2H$. In embodiments, $R^{1.1}$, is $-SO_2NH_2$. In embodiments, $R^{1.1}$, is $-NHC(O)NH_2$. In embodiments, $R^{1.1}$, is $-N(O)_2$. In embodiments, $R^{1.1}$, is $-NH_2$. In embodiments, $R^{1.1}$, is $-C(O)H$. In embodiments, $R^{1.1}$, is $-C(O)-OH$. In embodiments, $R^{1.1}$, is $-C(O)NH_2$. In embodiments, $R^{1.1}$, is $-OH$. In embodiments, $R^{1.1}$, is $-NHSO_2H$. In embodiments, $R^{1.1}$, is $-NHC(O)H$. In embodiments, $R^{1.1}$, is $-NHC(O)OH$. In embodiments, $R^{1.1}$, is $-NHOH$. In embodiments, $R^{1.1}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{1.1}$ is substituted or unsubstituted alkyl (e.g., $C_1$-$C_8$ alkyl, $C_1$-$C_6$ alkyl, or $C_1$-$C_4$ alkyl). In embodiments, $R^{1.1}$ is substituted alkyl (e.g., $C_1$-$C_8$ alkyl, $C_1$-$C_6$ alkyl, or $C_1$-$C_4$ alkyl). In embodiments, R1 is an unsubstituted alkyl (e.g., $C_1$-$C_8$ alkyl, $C_1$-$C_6$ alkyl, or $C_1$-$C_4$ alkyl). In embodiments, $R^{1.1}$ is substituted or unsubstituted heteroalkyl (e.g., 2 to 8 membered heteroalkyl, 2 to 6 membered heteroalkyl, or 2 to 4 membered heteroalkyl). In embodiments, $R^{1.1}$ is substituted heteroalkyl (e.g., 2 to 8 membered heteroalkyl, 2 to 6 membered heteroalkyl, or 2 to 4 membered heteroalkyl). In embodiments, $R^{1.1}$ is an unsubstituted heteroalkyl (e.g., 2 to 8 membered heteroalkyl, 2 to 6 membered heteroalkyl, or 2 to 4 membered heteroalkyl). In embodiments, $R^{1.1}$ is —$OCH_3$. In embodiments, $R^{1.1}$ is —$OCH_2CH_3$. In embodiments, $R^{1.1}$ is —$OR^{1D}$, wherein $R^{1D}$ is hydrogen, substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered).

In embodiments, $R^{1.2}$ is independently hydrogen. In embodiments, $R^{1.2}$ is independently halogen. In embodiments, $R^{1.2}$, is —$CF_3$. In embodiments, $R^{1.2}$, is —$CCl_3$. In embodiments, $R^{1.2}$, is —$CBr_3$. In embodiments, $R^{1.2}$, is —$CI_3$. In embodiments, $R^{1.2}$, is —$CHF_2$. In embodiments, $R^{1.2}$, is —$CHBr_2$. In embodiments, $R^{1.2}$, is —$CHCl_2$. In embodiments, $R^{1.2}$, is —$CHI_2$. In embodiments, $R^{1.2}$, is —$CH_2F$. In embodiments, $R^{1.2}$, is —$CH_2Cl$. In embodiments, $R^{1.2}$, is —$CH_2Br$. In embodiments, $R^{1.2}$, is —$CH_2I$. In embodiments, $R^{1.2}$, is —$OCF_3$. In embodiments, $R^{1.2}$, is —$OCCl_3$. In embodiments, $R^{1.2}$, is —$OCBr_3$. In embodiments, $R^{1.2}$, is —$OCI_3$. In embodiments, $R^{1.2}$, is —$OCHF_2$. In embodiments, $R^{1.2}$, is —$OCHBr_2$. In embodiments, $R^{1.2}$, is —$OCHCl_2$. In embodiments, $R^{1.2}$, is —$OCHI_2$. In embodiments, $R^{1.2}$, is —$OCH_2F$. In embodiments, $R^{1.2}$, is —$OCH_2Cl$. In embodiments, $R^{1.2}$, is —$OCH_2Br$. In embodiments, $R^{1.2}$, is —$OCH_2I$. In embodiments, $R^{1.2}$, is —CN. In embodiments, $R^{1.2}$, is —$SO_{n1}R^{1D}$. In embodiments, $R^{1.2}$, is —$SO_{v1}NR^{1A}R^{1B}$. In embodiments, $R^{1.2}$, is —NHC(O)$NR^{1A}R^{1B}$. In embodiments, $R^{1.2}$, is —$N(O)_{m1}$. In embodiments, $R^{1.2}$, is —$NR^{1A}R^{1B}$. In embodiments, $R^{1.2}$, is —C(O)$R^{1C}$. In embodiments, $R^{1.2}$, is —C(O)—$OR^{1C}$. In embodiments, $R^{1.2}$, is —C(O)$NR^{1A}R^{1B}$. In embodiments, $R^{1.2}$, is —$OR^{1D}$. In embodiments, $R^{1.2}$, is —$NR^{1A}SO_2R^{1D}$. In embodiments, $R^{1.2}$, is —$NR^{1A}C(O)R^{1C}$. In embodiments, $R^{1.2}$, is —$NR^{1A}C(O)OR^{1C}$. In embodiments, $R^{1.2}$, is —$NR^{1A}OR^{1C}$. In embodiments, $R^{1.2}$, is —$SO_2H$. In embodiments, $R^{1.2}$, is —$SO_2NH_2$. In embodiments, $R^{1.2}$, is —$NHC(O)NH_2$. In embodiments, $R^{1.2}$, is —$N(O)_2$. In embodiments, $R^{1.2}$, is —$NH_2$. In embodiments, $R^{1.2}$, is —C(O)H. In embodiments, $R^{1.2}$, is —C(O)—OH. In embodiments, $R^{1.2}$, is —C(O)$NH_2$. In embodiments, $R^{1.2}$, is —OH. In embodiments, $R^{1.2}$, is —$NHSO_2H$. In embodiments, $R^{1.2}$, is —NHC(O)H. In embodiments, $R^{1.2}$, is —NHC(O)OH. In embodiments, $R^{1.2}$, is —NHOH. In embodiments, $R^{1.2}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{1.2}$ is substituted or unsubstituted alkyl (e.g., $C_1$-$C_8$ alkyl, $C_1$-$C_6$ alkyl, or $C_1$-$C_4$ alkyl). In embodiments, $R^{1.2}$ is substituted alkyl (e.g., $C_1$-$C_8$ alkyl, $C_1$-$C_6$ alkyl, or $C_1$-$C_4$ alkyl). In embodiments, $R^{1.2}$ is an unsubstituted alkyl (e.g., $C_1$-$C_8$ alkyl, $C_1$-$C_6$ alkyl, or $C_1$-$C_4$ alkyl). In embodiments, $R^{1.2}$ is substituted or unsubstituted heteroalkyl (e.g., 2 to 8 membered heteroalkyl, 2 to 6 membered heteroalkyl, or 2 to 4 membered heteroalkyl). In embodiments, $R^{1.2}$ is substituted heteroalkyl (e.g., 2 to 8 membered heteroalkyl, 2 to 6 membered heteroalkyl, or 2 to 4 membered heteroalkyl). In embodiments, $R^{1.2}$ is an unsubstituted heteroalkyl (e.g., 2 to 8 membered heteroalkyl, 2 to 6 membered heteroalkyl, or 2 to 4 membered heteroalkyl). In embodiments, $R^{1.2}$ is —$OCH_3$. In embodiments, $R^{1.2}$ is —$OCH_2CH_3$. In embodiments, $R^{1.2}$ is —$OR^{1D}$, wherein $R^{1D}$ is hydrogen, substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered).

In embodiments, $R^{1.3}$ is independently hydrogen. In embodiments, $R^{1.3}$ is independently halogen. In embodiments, $R^{1.3}$, is —$CF_3$. In embodiments, $R^{1.3}$, is —$CCl_3$. In embodiments, $R^{1.3}$, is —$CBr_3$. In embodiments, $R^{1.3}$, is —$CI_3$. In embodiments, $R^{1.3}$, is —$CHF_2$. In embodiments, $R^{1.3}$, is —$CHBr_2$. In embodiments, $R^{1.3}$, is —$CHCl_2$. In embodiments, $R^{1.3}$, is —$CHI_2$. In embodiments, $R^{1.3}$, is —$CH_2F$. In embodiments, $R^{1.3}$, is —$CH_2Cl$. In embodiments, $R^{1.3}$, is —$CH_2Br$. In embodiments, $R^{1.3}$, is —$CH_2I$. In embodiments, $R^{1.3}$, is —$OCF_3$. In embodiments, $R^{1.3}$, is —$OCCl_3$. In embodiments, $R^{1.3}$, is —$OCBr_3$. In embodiments, $R^{1.3}$, is —$OCI_3$. In embodiments, $R^{1.3}$, is —$OCHF_2$. In embodiments, $R^{1.3}$, is —$OCHBr_2$. In embodiments, $R^{1.3}$, is —$OCHCl_2$. In embodiments, $R^{1.3}$, is —$OCHI_2$. In embodiments, $R^{1.3}$, is —$OCH_2F$. In embodiments, $R^{1.3}$, is —$OCH_2Cl$. In embodiments, $R^{1.3}$, is —$OCH_2Br$. In embodiments, $R^{1.3}$, is —$OCH_2I$. In embodiments, $R^{1.3}$, is —CN. In embodiments, $R^{1.3}$, is —$SO_{n1}R^{1D}$. In embodiments, $R^{1.3}$ is —$SO_{v1}NR^{1A}R^{1B}$. In embodiments, $R^{1.3}$ is —NHC(O)$NR^{1A}R^{1B}$. In embodiments, $R^{1.3}$, is —$N(O)_{m1}$. In embodiments, $R^{1.3}$, is —$NR^{1A}R^{1B}$. In embodiments, $R^{1.3}$, is —C(O)$R^{1C}$. In embodiments, $R^{1.3}$, is —C(O)—$OR^{1C}$. In embodiments, $R^{1.3}$, is —C(O)$NR^{1A}R^{1B}$. In embodiments, $R^{1.3}$, is —$OR^{1D}$. In embodiments, $R^{1.3}$, is —$NR^{1A}SO_2R^{1D}$. In embodiments, $R^{1.3}$, is —$NR^{1A}C(O)R^{1C}$. In embodiments, $R^{1.3}$, is —$NR^{1A}C(O)OR^{1C}$. In embodiments, $R^{1.3}$, is —$NR^{1A}OR^{1C}$. In embodiments, $R^{1.3}$, is —$SO_2H$. In embodiments, $R^{1.3}$, is —$SO_2NH_2$. In embodiments, $R^{1.3}$, is —$NHC(O)NH_2$. In embodiments, $R^{1.3}$, is —$N(O)_2$. In embodiments, $R^{1.3}$, is —$NH_2$. In embodiments, $R^{1.3}$, is —C(O)H. In embodiments, $R^{1.3}$, is —C(O)—OH. In embodiments, $R^{1.3}$, is —C(O)$NH_2$. In embodiments, $R^{1.3}$, is —OH. In embodiments, $R^{1.3}$, is —$NHSO_2H$. In embodiments, $R^{1.3}$ is —NHC(O)H. In embodiments, $R^{1.3}$, is —NHC(O)OH. In embodiments, $R^{1.3}$, is —NHOH. In embodiments, $R^{1.3}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{1.3}$ is substituted or unsubstituted alkyl (e.g., $C_1$-$C_8$ alkyl, $C_1$-$C_6$ alkyl, or $C_1$-$C_4$ alkyl). In embodiments, $R^{1.3}$ is substituted alkyl (e.g., $C_1$-$C_8$ alkyl, $C_1$-$C_6$ alkyl, or $C_1$-$C_4$ alkyl). In embodiments, $R^{1.3}$ is an unsubstituted alkyl (e.g., $C_1$-$C_8$ alkyl, $C_1$-$C_6$ alkyl, or $C_1$-$C_4$ alkyl). In embodiments, $R^{1.3}$ is substituted or unsubstituted heteroalkyl (e.g., 2 to 8 membered heteroalkyl, 2 to 6 membered heteroalkyl, or 2 to 4 membered heteroalkyl). In embodiments, $R^{1.3}$ is substituted heteroalkyl (e.g., 2 to 8 membered heteroalkyl, 2 to 6 membered heteroalkyl, or 2 to 4 membered heteroalkyl). In embodiments, $R^{1.3}$ is an unsubstituted heteroalkyl (e.g., 2 to 8 membered heteroalkyl, or 2 to 4 membered heteroalkyl). In embodiments, $R^{1.3}$ is —$OCH_3$. In embodiments, $R^{1.3}$ is —$OCH_2CH_3$. In embodiments, $R^{1.3}$ is —$OR^{1D}$, wherein $R^{1D}$ is hydrogen, substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered).

In embodiments, $R^{1.4}$ is independently hydrogen. In embodiments, $R^{1.4}$ is independently halogen. In embodiments, $R^{1.4}$, is —$CF_3$. In embodiments, $R^{1.4}$, is —$CCl_3$. In embodiments, $R^{1.4}$, is —$CBr_3$. In embodiments, $R^{1.4}$, is —$CI_3$. In embodiments, $R^{1.4}$, is —$CHF_2$. In embodiments, $R^{1.4}$, is —$CHBr_2$. In embodiments, $R^{1.4}$, is —$CHCl_2$. In embodiments, $R^{1.4}$, is —$CHI_2$. In embodiments, $R^{1.4}$, is —$CH_2F$. In embodiments, $R^{1.4}$, is —$CH_2Cl$. In embodiments, $R^{1.4}$, is —$CH_2Br$. In embodiments, $R^{1.4}$, is —$CH_2I$. In embodiments, $R^{1.4}$, is —$OCF_3$. In embodiments, $R^{1.4}$, is —$OCCl_3$. In embodiments, $R^{1.4}$, is —$OCBr_3$. In embodiments, $R^{1.4}$, is —$OCI_3$. In embodiments, $R^{1.4}$, is —$OCHF_2$. In embodiments, $R^{14}$, is —$OCHBr_2$. In embodiments, $R^{1.4}$, is —$OCHCl_2$. In embodiments, $R^{1.4}$, is —$OCHI_2$. In embodiments, $R^{1.4}$, is —$OCH_2F$. In embodiments, $R^{1.4}$, is —$OCH_2Cl$. In embodiments, $R^{1.4}$, is —$OCH_2Br$. In embodiments, $R^{1.4}$, is —$OCH_2I$. In embodiments, $R^{1.4}$, is —CN. In embodiments, $R^{1.4}$, is —$SO_{n1}R^{1D}$. In embodiments, $R^{1.4}$, is —$SO_{v1}NR^{1A}R^{1B}$. In embodiments, $R^{14}$, is —NHC(O)$NR^{1A}R^{1B}$. In embodiments, $R^{1.4}$, is —N(O)$_{m1}$. In embodiments, $R^{1.4}$, is —$NR^{1A}R^{1B}$. In embodiments, $R^{1.4}$, is —C(O)$R^{1C}$. In embodiments, $R^{1.4}$, is —C(O)—$OR^{1C}$. In embodiments, $R^{1.4}$ is —C(O)$NR^{1A}R^{1B}$. In embodiments, $R^{1.4}$, is —$OR^{1D}$. In embodiments, $R^{1.4}$, is —$NR^{1A}SO_2R^{1D}$. In embodiments, $R^{1.4}$, is —$NR^{1A}C(O)R^{1C}$. In embodiments, $R^{1.4}$, is —$NR^{1A}C(O)OR^{1C}$. In embodiments, $R^{1.4}$, is —$NR^{1A}OR^{1C}$. In embodiments, $R^{1.4}$, is —$SO_2H$. In embodiments, $R^{1.4}$, is —$SO_2NH_2$. In embodiments, $R^{1.4}$, is —NHC(O)$NH_2$. In embodiments, $R^{1.4}$, is —N(O)$_2$. In embodiments, $R^{1.4}$, is —$NH_2$. In embodiments, $R^{1.4}$, is —C(O)H. In embodiments, $R^{1.4}$, is —C(O)—OH. In embodiments, $R^{1.4}$, is —C(O)$NH_2$. In embodiments, $R^{1.4}$, is —OH. In embodiments, $R^{1.4}$, is —$NHSO_2H$. In embodiments, $R^{1.4}$, is —NHC(O)H. In embodiments, $R^{1.4}$, is —NHC(O)OH. In embodiments, $R^{1.4}$, is —NHOH. In embodiments, $R^{1.4}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{1.4}$ is substituted or unsubstituted alkyl (e.g., $C_1$-$C_8$ alkyl, $C_1$-$C_6$ alkyl, or $C_1$-$C_4$ alkyl). In embodiments, $R^{1.4}$ is substituted alkyl (e.g., $C_1$-$C_8$ alkyl, $C_1$-$C_6$ alkyl, or $C_1$-$C_4$ alkyl). In embodiments, $R^{1.4}$ is an unsubstituted alkyl (e.g., $C_1$-$C_8$ alkyl, $C_1$-$C_6$ alkyl, or $C_1$-$C_4$ alkyl). In embodiments, $R^{1.4}$ is substituted or unsubstituted heteroalkyl (e.g., 2 to 8 membered heteroalkyl, 2 to 6 membered heteroalkyl, or 2 to 4 membered heteroalkyl). In embodiments, $R^{1.4}$ is substituted heteroalkyl (e.g., 2 to 8 membered heteroalkyl, 2 to 6 membered heteroalkyl, or 2 to 4 membered heteroalkyl). In embodiments, $R^{1.4}$ is an unsubstituted heteroalkyl (e.g., 2 to 8 membered heteroalkyl, 2 to 6 membered heteroalkyl, or 2 to 4 membered heteroalkyl). In embodiments, $R^{1.4}$ is —$OCH_3$. In embodiments, $R^{1.4}$ is —$OCH_2CH_3$. In embodiments, $R^{1.4}$ is —$OR^{1D}$, wherein $R^{1D}$ is hydrogen, substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered).

In embodiments, $R^{1.5}$ is independently hydrogen. In embodiments, $R^{1.5}$ is independently halogen. In embodiments, $R^{1.5}$, is —$CF_3$. In embodiments, $R^{1.5}$, is —$CCl_3$. In embodiments, $R^{1.5}$, is —$CBr_3$. In embodiments, $R^{1.5}$, is —$CI_3$. In embodiments, $R^{1.5}$, is —$CHF_2$. In embodiments, $R^{1.5}$, is —$CHBr_2$. In embodiments, $R^{1.5}$, is —$CHCl_2$. In embodiments, $R^{1.5}$, is —$CHI_2$. In embodiments, $R^{1.5}$, is —$CH_2F$. In embodiments, $R^{1.5}$, is —$CH_2Cl$. In embodiments, $R^{1.5}$, is —$CH_2Br$. In embodiments, $R^{1.5}$, is —$CH_2I$. In embodiments, $R^{1.5}$, is —$OCF_3$. In embodiments, $R^{1.5}$, is —$OCCl_3$. In embodiments, $R^{1.5}$, is —$OCBr_3$. In embodiments, $R^{1.5}$, is —$OCI_3$. In embodiments, $R^{1.5}$, is —$OCHF_2$. In embodiments, $R^{1.5}$, is —$OCHBr_2$. In embodiments, $R^{1.5}$, is —$OCHCl_2$. In embodiments, $R^{1.5}$, is —$OCHI_2$. In embodiments, $R^{1.5}$, is —$OCH_2F$. In embodiments, $R^{1.5}$, is —$OCH_2Cl$. In embodiments, $R^{1.5}$, is —$OCH_2Br$. In embodiments, $R^{1.5}$, is —$OCH_2I$. In embodiments, $R^{1.5}$, is —CN. In embodiments, $R^{1.5}$, is —$SO_{n1}R^{1D}$. In embodiments, $R^{1.5}$, is —$SO_{v1}NR^{1A}R^{1B}$. In embodiments, $R^{1.5}$, is —NHC(O)$NR^{1A}R^{1B}$. In embodiments, $R^{1.5}$, is —N(O)$_{m1}$. In embodiments, $R^{1.5}$, is —$NR^{1A}R^{1B}$. In embodiments, $R^{1.5}$, is —C(O)$R^{1C}$. In embodiments, $R^{1.5}$, is —C(O)—$OR^{1C}$. In embodiments, $R^{1.5}$ is —C(O)$NR^{1A}R^{1B}$. In embodiments, $R^{1.5}$, is —$OR^{1D}$. In embodiments, $R^{1.5}$, is —$NR^{1A}SO_2R^{1D}$. In embodiments, $R^{1.5}$, is —$NR^{1A}C(O)R^{1C}$. In embodiments, $R^{1.5}$, is —$NR^{1A}C(O)OR^{1C}$. In embodiments, $R^{1.5}$, is —$NR^{1A}OR^{1C}$. In embodiments, $R^{1.5}$, is —$SO_2H$. In embodiments, $R^{1.5}$, is —$SO_2NH_2$. In embodiments, $R^{1.5}$, is —NHC(O)$NH_2$. In embodiments, $R^{1.5}$, is —N(O)$_2$. In embodiments, $R^{1.5}$, is —$NH_2$. In embodiments, $R^{1.5}$, is —C(O)H. In embodiments, $R^{1.5}$, is —C(O)—OH. In embodiments, $R^{1.5}$, is —C(O)$NH_2$. In embodiments, $R^{1.5}$, is —OH. In embodiments, $R^{1.5}$, is —$NHSO_2H$. In embodiments, $R^{1.5}$, is —NHC(O)H. In embodiments, $R^{1.5}$, is —NHC(O)OH. In embodiments, $R^{1.5}$, is —NHOH. In embodiments, $R^{1.5}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$—C, $C_3$-$C_6$, $C_4$-$C_6$, or $C_5$-$C_6$), or substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{1.5}$ is substituted or unsubstituted alkyl (e.g., $C_1$-$C_8$ alkyl, $C_1$-$C_6$ alkyl, or $C_1$-$C_4$ alkyl). In embodiments, $R^{1.5}$ is substituted alkyl (e.g., $C_1$-$C_8$ alkyl, $C_1$-$C_6$ alkyl, or $C_1$-$C_4$ alkyl). In embodiments, $R^{1.5}$ is an unsubstituted alkyl (e.g., $C_1$-$C_8$ alkyl, $C_1$-$C_6$ alkyl, or $C_1$-$C_4$ alkyl). In embodiments, $R^{1.5}$ is substituted or unsubstituted heteroalkyl (e.g., 2 to 8 membered heteroalkyl, 2 to 6 membered heteroalkyl, or 2 to 4 membered heteroalkyl). In embodiments, $R^{1.5}$ is substituted heteroalkyl (e.g., 2 to 8 membered heteroalkyl, 2 to 6 membered heteroalkyl, or 2 to 4 membered heteroalkyl). In embodiments, $R^{1.5}$ is an unsubstituted heteroalkyl (e.g., 2 to 8 membered heteroalkyl, 2 to 6 membered heteroalkyl, or 2 to 4 membered heteroalkyl). In embodiments, $R^{1.5}$ is —$OCH_3$. In embodiments, $R^{1.5}$ is —$OCH_2CH_3$. In embodiments, $R^{1.5}$ is —$OR^{1D}$, wherein $R^{1D}$ is hydrogen, substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered).

In embodiments, $R^{2.1}$ and $R^{2.2}$ are each independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{2.1}$ and $R^{2.2}$ are each independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, or $-NR^{2A}OR^{2C}$. In embodiments, $R^{2.1}$ and $R^{2.2}$ are each independently hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{2.1}$ is independently hydrogen. In embodiments, $R^{2.1}$ is halogen. In embodiments, $R^{2.1}$, is $-CF_3$. In embodiments, $R^{2.1}$, is $-CCl_3$. In embodiments, $R^{2.1}$, is $-CBr_3$. In embodiments, $R^{2.1}$, is $-CI_3$. In embodiments, $R^{2.1}$, is $-CHF_2$. In embodiments, $R^{2.1}$, is $-CHBr_2$. In embodiments, $R^{2.1}$, is $-CHCl_2$. In embodiments, $R^{2.1}$, is $-CHI_2$. In embodiments, $R^{2.1}$, is $-CH_2F$. In embodiments, $R^{2.1}$, is $-CH_2Cl$. In embodiments, $R^{2.1}$, is $-CH_2Br$. In embodiments, $R^{2.1}$, is $-CH_2I$. In embodiments, $R^{2.1}$, is $-OCF_3$. In embodiments, $R^{2.1}$, is $-OCCl_3$. In embodiments, $R^{2.1}$, is $-OCBr_3$. In embodiments, $R^{2.1}$, is $-OCI_3$. In embodiments, $R^{2.1}$, is $-OCHF_2$. In embodiments, $R^{2.1}$, is $-OCHBr_2$. In embodiments, $R^{2.1}$, is $-OCHCl_2$. In embodiments, $R^{2.1}$, is $-OCHI_2$. In embodiments, $R^{2.1}$, is $-OCH_2F$. In embodiments, $R^{2.1}$, is $-OCH_2Cl$. In embodiments, $R^{2.1}$, is $-OCH_2Br$. In embodiments, $R^{2.1}$, is $-OCH_2I$. In embodiments, $R^{2.1}$, is $-CN$. In embodiments, $R^{2.1}$, is $-SO_{n2}R^{2D}$. In embodiments, $R^{2.1}$, is $-SO_2NR^{2A}R^{2B}$. In embodiments, $R^{2.1}$, is $-NHC(O)NR^{2A}R^{2B}$. In embodiments, $R^{2.1}$, is $-N(O)_{m2}$. In embodiments, $R^{2.1}$, is $-NR^{2A}R^{2B}$. In embodiments, $R^{2.1}$, is $-C(O)R^{2C}$. In embodiments, $R^{2.1}$, is $-C(O)-OR^{2C}$. In embodiments, $R^{2.1}$, is $-C(O)NR^{2A}R^{2B}$. In embodiments, $R^{2.1}$, is $-OR^{2D}$. In embodiments, $R^{2.1}$, is $-NR^{2A}SO_2R^{2D}$. In embodiments, $R^{2.1}$, is $-NR^{2A}C(O)R^{2C}$. In embodiments, $R^{2.1}$, is $-NR^{2A}C(O)OR^{2C}$. In embodiments, $R^{2.1}$, is $-NR^{2A}OR^{2C}$. In embodiments, $R^{2.1}$, is $-SO_2H$. In embodiments, $R^{2.1}$, is $-SO_2NH_2$. In embodiments, $R^{2.1}$, is $-NHC(O)NH_2$. In embodiments, $R^{2.1}$, is $-N(O)_2$. In embodiments, $R^{2.1}$, is $-NH_2$. In embodiments, $R^{2.1}$, is $-C(O)H$. In embodiments, $R^{2.1}$, is $-C(O)-OH$. In embodiments, $R^{2.1}$, is $-C(O)NH_2$. In embodiments, $R^{2.1}$, is $-OH$. In embodiments, $R^{2.1}$, is $-NHSO_2H$. In embodiments, $R^{2.1}$, is $-NHC(O)H$. In embodiments, $R^{2.1}$, is $-NHC(O)OH$. In embodiments, $R^{2.1}$, is $-NHOH$. In embodiments, $R^{2.1}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{2.1}$ is substituted or unsubstituted alkyl (e.g., $C_1$-$C_8$ alkyl, $C_1$-$C_6$ alkyl, or $C_1$-$C_4$ alkyl). In embodiments, $R^{2.1}$ is substituted alkyl (e.g., $C_1$-$C_8$ alkyl, $C_1$-$C_6$ alkyl, or $C_1$-$C_4$ alkyl). In embodiments, $R^{2.1}$ is an unsubstituted alkyl (e.g., $C_1$-$C_8$ alkyl, $C_1$-$C_6$ alkyl, or $C_1$-$C_4$ alkyl). In embodiments, $R^{2.1}$ is substituted or unsubstituted heteroalkyl (e.g., 2 to 8 membered heteroalkyl, 2 to 6 membered heteroalkyl, or 2 to 4 membered heteroalkyl). In embodiments, $R^{2.1}$ is substituted heteroalkyl (e.g., 2 to 8 membered heteroalkyl, 2 to 6 membered heteroalkyl, or 2 to 4 membered heteroalkyl). In embodiments, $R^{2.1}$ is an unsubstituted heteroalkyl (e.g., 2 to 8 membered heteroalkyl, 2 to 6 membered heteroalkyl, or 2 to 4 membered heteroalkyl). In embodiments, $R^{2.1}$ is $-OCH_3$. In embodiments, $R^{2.1}$ is $-OCH_2CH_3$. In embodiments, $R^{2.1}$ is $-OR^{2D}$, wherein $R^{2D}$ is hydrogen, substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered).

In embodiments, $R^{2.2}$ is independently hydrogen. In embodiments, $R^{2.2}$ is halogen. In embodiments, $R^{2.2}$, is $-CF_3$. In embodiments, $R^{2.2}$, is $-CCl_3$. In embodiments, $R^{2.2}$, is $-CBr_3$. In embodiments, $R^{2.2}$, is $-CI_3$. In embodiments, $R^{2.2}$, is $-CHF_2$. In embodiments, $R^{2.2}$, is $-CHBr_2$. In embodiments, $R^{2.2}$, is $-CHCl_2$. In embodiments, $R^{2.2}$, is $-CHI_2$. In embodiments, $R^{2.2}$, is $-CH_2F$. In embodiments, $R^{2.2}$, is $-CH_2Cl$. In embodiments, $R^{2.2}$, is $-CH_2Br$. In embodiments, $R^{2.2}$, is $-CH_2I$. In embodiments, $R^{2.2}$, is $-OCF_3$. In embodiments, $R^{2.2}$, is $-OCCl_3$. In embodiments, $R^{2.2}$, is $-OCBr_3$. In embodiments, $R^{2.2}$, is $-OCI_3$. In embodiments, $R^{2.2}$, is $-OCHF_2$. In embodiments, $R^{2.2}$, is $-OCHBr_2$. In embodiments, $R^{2.2}$, is $-OCHCl_2$. In embodiments, $R^{2.2}$, is $-OCHI_2$. In embodiments, $R^{2.2}$, is $-OCH_2F$. In embodiments, $R^{2.2}$, is $-OCH_2Cl$. In embodiments, $R^{2.2}$, is $-OCH_2Br$. In embodiments, $R^{2.2}$, is $-OCH_2I$. In embodiments, $R^{2.2}$, is $-CN$. In embodiments, $R^{2.2}$, is $-SO_{n2}R^{2D}$. In embodiments, $R^{2.2}$, is $-SO_{v2}NR^{2A}R^{2B}$. In embodiments, $R^{2.2}$, is $-NHC(O)NR^{2A}R^{2B}$. In embodiments, $R^{2.2}$, is $-N(O)_{m2}$. In embodiments, $R^{2.2}$, is $-NR^{2A}R^{2B}$. In embodiments, $R^{2.2}$, is $-C(O)R^{2C}$. In embodiments, $R^{2.2}$, is $-C(O)-OR^{2C}$. In embodiments, $R^{2.2}$, is $-C(O)NR^{2A}R^{2B}$. In embodiments, $R^{2.2}$, is $-OR^{2D}$. In embodiments, $R^{2.2}$, is $-NR^{2A}SO_2R^{2D}$. In embodiments, $R^{2.2}$, is $-NR^{2A}C(O)R^{2C}$. In embodiments, $R^{2.2}$, is $-NR^{2A}C(O)OR^{2C}$. In embodiments, $R^{2.2}$, is $-NR^{2A}OR^{2C}$. In embodiments, $R^{2.2}$, is $-SO_2H$. In embodiments, $R^{2.2}$, is $-SO_2NH_2$. In embodiments, $R^{2.2}$, is $-NHC(O)NH_2$. In embodiments, $R^{2.2}$, is $-N(O)_2$. In embodiments, $R^{2.2}$, is $-NH_2$. In embodiments, $R^{2.2}$, is $-C(O)H$. In embodiments, $R^{2.2}$, is $-C(O)-OH$. In embodiments, $R^{2.2}$, is $-C(O)NH_2$. In embodiments, $R^{2.2}$, is $-OH$. In embodiments, $R^{2.2}$, is $-NHSO_2H$. In embodiments, $R^{2.2}$, is $-NHC(O)H$. In embodiments, $R^{2.2}$, is —NHC(O)OH. In embodiments, $R^{2.2}$, is —NHOH. In embodiments, $R^{22}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$—C, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{2.2}$ is substituted or unsubstituted alkyl (e.g., $C_1$-$C_8$ alkyl, $C_1$-$C_6$ alkyl, or $C_1$-$C_4$ alkyl). In embodiments, $R^{22}$ is substituted alkyl (e.g., $C_1$-$C_8$ alkyl, $C_1$-$C_6$ alkyl, or $C_1$-$C_4$ alkyl). In embodiments, $R^{2.2}$ is an unsubstituted alkyl (e.g., $C_1$-$C_8$ alkyl, $C_1$-$C_6$ alkyl, or $C_1$-$C_4$ alkyl). In embodiments, $R^{2.2}$ is substituted or unsubstituted heteroalkyl (e.g., 2 to 8 membered heteroalkyl, 2 to 6 membered heteroalkyl, or 2 to 4 membered heteroalkyl). In embodiments, $R^{2.2}$ is substituted heteroalkyl (e.g., 2 to 8 membered heteroalkyl, 2 to 6 membered heteroalkyl, or 2 to 4 membered heteroalkyl). In embodiments, $R^{2.2}$ is an unsubstituted heteroalkyl (e.g., 2 to 8 membered heteroalkyl, 2 to 6 membered heteroalkyl, or 2 to 4 membered heteroalkyl). In embodiments, $R^{2.2}$ is —$OCH_3$. In embodiments, $R^{2.2}$ is —$OCH_2CH_3$. In embodiments, $R^{2.2}$ is —$OR^{2D}$, wherein $R^{2D}$ is hydrogen, substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered).

In embodiments, $R^{7.1}$, $R^{7.2}$, $R^{7.3}$, and $R^{7.4}$ are each independently hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —$N(O)_{m7}$, —$NR^{7A}R^{7B}$, —C(O)$R^{7C}$, —C(O)—$OR^{7C}$, —C(O)$NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{7.1}$, $R^{7.2}$, $R^{7.3}$, and $R^{7.4}$ are each hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —$N(O)_{m7}$, —$NR^{7A}R^{7B}$, —C(O)$R^{7C}$, —C(O)—$OR^{7C}$, —C(O)$NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, or —$NR^{7A}OR^{7C}$. In embodiments, $R^{7.1}$, $R^{7.2}$, $R^{7.3}$, and $R^{7.4}$ are each independently hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —$N(O)_{m7}$, —$NR^{7A}R^{7B}$, —C(O)$R^{7C}$, —C(O)—$OR^{7C}$, —C(O)$NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7.1}$ is independently hydrogen. In embodiments, $R^{7.1}$ is halogen. In embodiments, $R^{7.1}$ is —F. In embodiments, $R^{7.1}$ is —Cl. In embodiments, $R^{7.1}$ is —Br. In embodiments, $R^{7.1}$ is —I. In embodiments, $R^{7.1}$, is —$CF_3$. In embodiments, $R^{7.1}$, is —$CCl_3$. In embodiments, $R^{7.1}$, is —$CBr_3$. In embodiments, $R^{7.1}$, is —$CI_3$. In embodiments, $R^{7.1}$, is —$CHF_2$. In embodiments, $R^{7.1}$, is —$CHBr_2$. In embodiments, $R^{7.1}$, is —$CHCl_2$. In embodiments, $R^{7.1}$, is —$CHI_2$. In embodiments, $R^{7.1}$, is —$CH_2F$. In embodiments, $R^{7.1}$, is —$CH_2Cl$. In embodiments, $R^{7.1}$, is —$CH_2Br$. In embodiments, $R^{7.1}$, is —$CH_2I$. In embodiments, $R^{7.1}$, is —$OCF_3$. In embodiments, $R^{7.1}$, is —$OCCl_3$. In embodiments, $R^{7.1}$, is —$OCBr_3$. In embodiments, $R^{7.1}$, is —$OCI_3$. In embodiments, $R^{7.1}$, is —$OCHF_2$. In embodiments, $R^{7.1}$, is —$OCHBr_2$. In embodiments, $R^{7.1}$, is —$OCHCl_2$. In embodiments, $R^{7.1}$, is —$OCHI_2$. In embodiments, $R^{7.1}$, is —$OCH_2F$. In embodiments, $R^{7.1}$, is —$OCH_2Cl$. In embodiments, $R^{7.1}$, is —$OCH_2Br$. In embodiments, $R^{7.1}$, is —$OCH_2I$. In embodiments, $R^{7.1}$, is —CN. In embodiments, $R^{7.1}$, is —$SO_{n2}R^{7D}$. In embodiments, $R^{7.1}$, is —$SO_{v2}NR^{7A}R^{7B}$. In embodiments, R71, is —NHC(O)$NR^{7A}R^{7B}$. In embodiments, $R^{7.1}$, is —$N(O)_{m2}$. In embodiments, $R^{7.1}$, is —$NR^{7A}R^{7B}$. In embodiments, $R^{7.1}$, is —C(O)$R^{7C}$. In embodiments, $R^{7.1}$, is —C(O)—$OR^{7C}$. In embodiments, $R^{7.1}$, is —C(O)$NR^{7A}R^{7B}$. In embodiments, $R^{7.1}$, is —$OR^{7D}$. In embodiments, $R^{7.1}$, is —$NR^{7A}SO_2R^{7D}$. In embodiments, $R^{7.1}$, is —$NR^{7A}C(O)R^{7C}$. In embodiments, $R^{7.1}$, is —$NR^{7A}C(O)OR^{7C}$. In embodiments, $R^{7.1}$, is —$NR^{7A}OR^{7C}$. In embodiments, $R^{7.1}$, is —$SO_2H$. In embodiments, $R^{7.1}$, is —$SO_2NH_2$. In embodiments, $R^{7.1}$, is —$NHC(O)NH_2$. In embodiments, $R^{7.1}$, is —$N(O)_2$. In embodiments, $R^{7.1}$, is —$NH_2$. In embodiments, $R^{7.1}$, is —C(O)H. In embodiments, $R^{7.1}$, is —C(O)—OH. In embodiments, $R^{7.1}$, is —C(O)$NH_2$. In embodiments, $R^{7.1}$, is —OH. In embodiments, $R^{7.1}$, is —$NHSO_2H$. In embodiments, $R^{7.1}$, is —NHC(O)H. In embodiments, $R^{7.1}$, is —NHC(O)OH. In embodiments, $R^{7.1}$, is —NHOH. In embodiments, $R^{7.1}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7.1}$ is substituted or unsubstituted alkyl (e.g., $C_1$-$C_8$ alkyl, $C_1$-$C_6$ alkyl, or $C_1$-$C_4$ alkyl). In embodiments, $R^{7.1}$ is substituted alkyl (e.g., $C_1$-$C_8$ alkyl, $C_1$-$C_6$ alkyl, or $C_1$-$C_4$ alkyl). In embodiments, $R^{7.1}$ is an unsubstituted alkyl (e.g., $C_1$-$C_8$ alkyl, $C_1$-$C_6$ alkyl, or $C_1$-$C_4$ alkyl). In embodiments, $R^{7.1}$ is substituted or unsubstituted heteroalkyl (e.g., 2 to 8 membered heteroalkyl, 2 to 6 membered heteroalkyl, or 2 to 4 membered heteroalkyl). In embodiments, $R^{7.1}$ is substituted heteroalkyl (e.g., 2 to 8 membered heteroalkyl, 2 to 6 membered heteroalkyl, or 2 to 4 membered heteroalkyl). In embodiments, $R^{7.1}$ is an unsubstituted heteroalkyl (e.g., 2 to 8 membered heteroalkyl, 2 to 6 membered heteroalkyl, or 2 to 4 membered heteroalkyl).

In embodiments, $R^{7.2}$ is independently hydrogen. In embodiments, $R^{7.2}$ is halogen. In embodiments, $R^{7.2}$ is —F. In embodiments, $R^{7.2}$ is —Cl. In embodiments, $R^{7.2}$ is —Br. In embodiments, $R^{7.2}$ is —I. In embodiments, $R^{7.2}$, is —$CF_3$. In embodiments, $R^{7.2}$, is —$CCl_3$. In embodiments, $R^{7.2}$, is —$CBr_3$. In embodiments, $R^{7.2}$, is —$CI_3$. In embodiments, $R^{7.2}$, is —$CHF_2$. In embodiments, $R^{7.2}$, is —$CHBr_2$. In embodiments, $R^{7.2}$, is —$CHCl_2$. In embodiments, $R^{7.2}$, is —$CHI_2$. In embodiments, $R^{7.2}$, is —$CH_2F$. In embodiments, $R^{7.2}$, is —$CH_2Cl$. In embodiments, $R^{7.2}$, is —$CH_2Br$. In embodiments, $R^{7.2}$, is —$CH_2I$. In embodiments, $R^{7.2}$, is —$OCF_3$. In embodiments, $R^{7.2}$, is —$OCCl_3$. In embodiments, $R^{7.2}$, is —$OCBr_3$. In embodiments, $R^{7.2}$, is —$OCI_3$. In embodiments, $R^{7.2}$, is —$OCHF_2$. In embodiments, $R^{7.2}$, is —$OCHBr_2$. In embodiments, $R^{7.2}$, is —$OCHCl_2$. In embodiments, $R^{7.2}$, is —$OCHI_2$. In embodiments, $R^{7.2}$, is —$OCH_2F$. In embodiments, $R^{7.2}$, is —$OCH_2Cl$. In embodiments, $R^{7.2}$, is —$OCH_2Br$. In embodiments, $R^{7.2}$, is —$OCH_2I$. In embodiments, $R^{7.2}$, is —CN. In embodiments, $R^{7.2}$, is —$SO_2R^{7D}$. In embodiments, $R^{7.2}$, is —$SO_{v2}NR^{7A}R^{7B}$. In embodiments, $R^{7.2}$, is —NHC(O)NR$^{7A}$R$^{7B}$. In embodiments, $R^{7.2}$, is —$N(O)_{m2}$. In embodiments, $R^{7.2}$, is —$NR^{7A}R^{7B}$. In embodiments, $R^{7.2}$, is —C(O)R$^{7C}$. In embodiments, $R^{7.2}$, is —C(O)—OR$^{7C}$. In embodiments, $R^{7.2}$, is —C(O)NR$^{7A}$R$^{7B}$. In embodiments, $R^{7.2}$, is —OR$^{7D}$. In embodiments, $R^{7.2}$, is —NR$^{7A}$SO$_2$R$^{7D}$. In embodiments, $R^{7.2}$, is —NR$^{7A}$C(O)R$^{7C}$. In embodiments, $R^{7.2}$, is —NR$^{7A}$C(O)OR$^{7C}$. In embodiments, $R^{7.2}$, is —NR$^{7A}$OR$^{7C}$. In embodiments, $R^{7.2}$, is —$SO_2H$. In embodiments, $R^{7.2}$, is —$SO_2NH_2$. In embodiments, $R^{7.2}$, is —$NHC(O)NH_2$. In embodiments, $R^{7.2}$, is —$N(O)_2$. In embodiments, $R^{7.2}$, is —$NH_2$. In embodiments, $R^{7.2}$, is —C(O)H. In embodiments, $R^{7.2}$, is —C(O)—OH. In embodiments, $R^{7.2}$, is —C(O)NH$_2$. In embodiments, $R^{7.2}$, is —OH. In embodiments, $R^{7.2}$, is —NHSO$_2$H. In embodiments, $R^{7.2}$, is —NHC(O)H. In embodiments, $R^{7.2}$, is —NHC(O)OH. In embodiments, $R^{7.2}$, is —NHOH. In embodiments, $R^{7.2}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7.2}$ is substituted or unsubstituted alkyl (e.g., $C_1$-$C_8$ alkyl, $C_1$-$C_6$ alkyl, or $C_1$-$C_4$ alkyl). In embodiments, $R^{7.2}$ is substituted alkyl (e.g., $C_1$-$C_8$ alkyl, $C_1$-$C_6$ alkyl, or $C_1$-$C_4$ alkyl). In embodiments, $R^{7.2}$ is an unsubstituted alkyl (e.g., $C_1$-$C_8$ alkyl, $C_1$-$C_6$ alkyl, or $C_1$-$C_4$ alkyl). In embodiments, $R^{7.2}$ is substituted or unsubstituted heteroalkyl (e.g., 2 to 8 membered heteroalkyl, 2 to 6 membered heteroalkyl, or 2 to 4 membered heteroalkyl). In embodiments, $R^{7.2}$ is substituted heteroalkyl (e.g., 2 to 8 membered heteroalkyl, 2 to 6 membered heteroalkyl, or 2 to 4 membered heteroalkyl). In embodiments, $R^{7.2}$ is an unsubstituted heteroalkyl (e.g., 2 to 8 membered heteroalkyl, 2 to 6 membered heteroalkyl, or 2 to 4 membered heteroalkyl).

In embodiments, $R^{7.3}$ is independently hydrogen. In embodiments, $R^{7.3}$ is halogen. In embodiments, $R^{7.3}$ is —F. In embodiments, $R^{7.3}$ is —Cl. In embodiments, $R^{7.3}$ is —Br. In embodiments, $R^{7.3}$ is —I. In embodiments, $R^{7.3}$ is —$CF_3$. In embodiments, $R^{7.3}$, is —$CCl_3$. In embodiments, $R^{7.3}$, is —$CBr_3$. In embodiments, $R^{7.3}$, is —$CI_3$. In embodiments, $R^{7.3}$, is —$CHF_2$. In embodiments, $R^{7.3}$, is —$CHBr_2$. In embodiments, $R^{7.3}$, is —$CHCl_2$. In embodiments, $R^{7.3}$, is —$CHI_2$. In embodiments, $R^{7.3}$, is —$CH_2F$. In embodiments, $R^{7.3}$, is —$CH_2Cl$. In embodiments, $R^{7.3}$, is —$CH_2Br$. In embodiments, $R^{7.3}$, is —$CH_2I$. In embodiments, $R^{7.3}$, is —$OCF_3$. In embodiments, $R^{7.3}$, is —$OCCl_3$. In embodiments, $R^{7.3}$, is —$OCBr_3$. In embodiments, $R^{7.3}$, is —$OCI_3$. In embodiments, $R^{7.3}$, is —$OCHF_2$. In embodiments, $R^{7.3}$, is —$OCHBr_2$. In embodiments, $R^{7.3}$, is —$OCHCl_2$. In embodiments, $R^{7.3}$, is —$OCHI_2$. In embodiments, $R^{7.3}$, is —$OCH_2F$. In embodiments, $R^{7.3}$, is —$OCH_2Cl$. In embodiments, $R^{7.3}$, is —$OCH_2Br$. In embodiments, $R^{7.3}$, is —$OCH_2I$. In embodiments, $R^{7.3}$, is —CN. In embodiments, $R^{7.3}$, is —$SO_{n2}R^{7D}$. In embodiments, R7.3, is —$SO_{v2}NR^{7A}R^{7B}$. In embodiments, $R^{7.3}$, is —NHC(O)NR$^{7A}$R$^{7B}$. In embodiments, $R^{7.3}$, is —$N(O)_{m2}$. In embodiments, $R^{7.3}$, is —NR$^{7A}$R$^{7B}$. In embodiments, $R^{7.3}$, is —C(O)R$^{7C}$. In embodiments, $R^{7.3}$, is —C(O)—OR$^{7C}$. In embodiments, $R^{7.3}$, is —C(O)NR$^{7A}$R$^{7B}$. In embodiments, $R^{7.3}$, is —OR$^{7D}$. In embodiments, $R^{7.3}$, is —NR$^{7A}$SO$_2$R$^{7D}$. In embodiments, $R^{7.3}$, is —NR$^{7A}$C(O)R$^{7C}$. In embodiments, $R^{7.3}$, is —NR$^{7A}$C(O)OR$^{7C}$. In embodiments, $R^{7.3}$, is —NR$^{7A}$OR$^{7C}$. In embodiments, $R^{7.3}$, is —$SO_2H$. In embodiments, $R^{7.3}$, is —$SO_2NH_2$. In embodiments, $R^{7.3}$, is —$NHC(O)NH_2$. In embodiments, $R^{7.3}$, is —$N(O)_2$. In embodiments, $R^{7.3}$, is —$NH_2$. In embodiments, $R^{7.3}$, is —C(O)H. In embodiments, $R^{7.3}$, is —C(O)—OH. In embodiments, $R^{7.3}$, is —C(O)NH$_2$. In embodiments, $R^{7.3}$, is —OH. In embodiments, $R^{7.3}$, is —NHSO$_2$H. In embodiments, $R^{7.3}$ is —NHC(O)H. In embodiments, $R^{7.3}$, is —NHC(O)OH. In embodiments, $R^{7.3}$, is —NHOH. In embodiments, $R^{73}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7.3}$ is substituted or unsubstituted alkyl (e.g., $C_1$-$C_8$ alkyl, $C_1$-$C_6$ alkyl, or $C_1$-$C_4$ alkyl). In embodiments, $R^{7.3}$ is substituted alkyl (e.g., $C_1$-$C_8$ alkyl, $C_1$-$C_6$ alkyl, or $C_1$-$C_4$ alkyl). In embodiments, $R^{7.3}$ is an unsubstituted alkyl (e.g., $C_1$-$C_8$ alkyl, $C_1$-$C_6$ alkyl, or $C_1$-$C_4$ alkyl). In embodiments, $R^{7.3}$ is substituted or unsubstituted heteroalkyl (e.g., 2 to 8 membered heteroalkyl, 2 to 6 membered heteroalkyl, or 2 to 4 membered heteroalkyl). In embodiments, $R^{7.3}$ is substituted heteroalkyl (e.g., 2 to 8 membered heteroalkyl, 2 to 6 membered heteroalkyl, or 2 to 4 membered heteroalkyl). In embodiments, $R^{73}$ is an unsubstituted heteroalkyl (e.g., 2 to 8 membered heteroalkyl, 2 to 6 membered heteroalkyl, or 2 to 4 membered heteroalkyl).

In embodiments, $R^{7.4}$ is independently hydrogen. In embodiments, $R^{7.4}$ is halogen. In embodiments, $R^{7.4}$ is —F. In embodiments, $R^{7.4}$ is —Cl. In embodiments, $R^{7.4}$ is —Br. In embodiments, $R^{7.4}$ is —I. In embodiments, $R^{7.4}$, is —$CF_3$. In embodiments, $R^{7.4}$, is —$CCl_3$. In embodiments, $R^{7.4}$, is —$CBr_3$. In embodiments, $R^{7.4}$, is —$CI_3$. In embodiments, $R^{7.4}$, is —$CHF_2$. In embodiments, $R^{7.4}$, is —$CHBr_2$. In embodiments, $R^{7.4}$, is —$CHCl_2$. In embodiments, $R^{7.4}$, is —$CH_2F$. In embodiments, $R^{7.4}$, is —$CH_2Cl$. In embodiments, $R^{7.4}$, is —$CH_2Br$. In embodiments, $R^{7.4}$, is —$CH_2I$. In embodiments, $R^{7.4}$, is —$OCF_3$. In embodiments, $R^{7.4}$, is —$OCCl_3$. In embodiments, $R^{7.4}$, is —OCBr$_3$. In embodiments, $R^{7.4}$, is —OCI$_3$. In embodiments, $R^{7.4}$, is —OCHF$_2$. In embodiments, $R^{7.4}$, is —OCHBr$_2$. In embodiments, $R^{7.4}$, is —OCHCl$_2$. In embodiments, $R^{7.4}$, is —OCHI$_2$. In embodiments, $R^{7.4}$, is —OCH$_2$F. In embodiments, $R^{7.4}$, is —OCH$_2$Cl. In embodiments, $R^{7.4}$, is —OCH$_2$Br. In embodiments, $R^{7.4}$, is —OCH$_2$I. In embodiments, $R^{7.4}$, is —CN. In embodiments, $R^{7.4}$, is —SO$_2$R$^{7D}$. In embodiments, $R^{7.4}$, is —SO$_{v2}$NR$^{7A}$R$^{7B}$. In embodiments, $R^{7.4}$, is —NHC(O)NR$^{7A}$R$^{7B}$. In embodiments, $R^{7.4}$, is —N(O)$_{m2}$. In embodiments, $R^{7.4}$, is —NR$^{7A}$R$^{7B}$. In embodiments, $R^{7.4}$, is —C(O)R$^{7C}$. In embodiments, $R^{7.1}$, is —C(O)—OR$^{7C}$. In embodiments, $R^{7.4}$, is —C(O)NR$^{7A}$R$^{7B}$. In embodiments, $R^{7.4}$, is —OR$^{7D}$. In embodiments, $R^{7.4}$, is —NR$^{7A}$SO$_2$R$^{7D}$. In embodiments, $R^{7.4}$, is —NR$^{7A}$C(O)R$^{7C}$. In embodiments, $R^{7.4}$, is —NR$^{7A}$C(O)OR$^{7C}$. In embodiments, $R^{7.4}$, is —NR$^{7A}$OR$^{7C}$. In embodiments, $R^{7.4}$, is —SO$_2$H. In embodiments, $R^{7.4}$, is —SO$_2$NH$_2$. In embodiments, $R^{7.4}$, is —NHC(O)NH$_2$. In embodiments, $R^{7.4}$, is —N(O)$_2$. In embodiments, $R^{7.4}$, is —NH$_2$. In embodiments, $R^{7.4}$, is —C(O)H. In embodiments, $R^{7.4}$, is —C(O)—OH. In embodiments, $R^{7.4}$, is —C(O)NH$_2$. In embodiments, $R^{7.4}$, is —OH. In embodiments, $R^{7.4}$, is —NHSO$_2$H. In embodiments, $R^{7.4}$, is —NHC(O)H. In embodiments, $R^{7.4}$, is —NHC(O)OH. In embodiments, $R^{7.4}$, is —NHOH. In embodiments, $R^{7.4}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7.4}$ is substituted or unsubstituted alkyl (e.g., $C_1$-$C_8$ alkyl, $C_1$-$C_6$ alkyl, or $C_1$-$C_4$ alkyl). In embodiments, $R^{7.4}$ is substituted alkyl (e.g., $C_1$-$C_8$ alkyl, $C_1$-$C_6$ alkyl, or $C_1$-$C_4$ alkyl). In embodiments, $R^{7.4}$ is an unsubstituted alkyl (e.g., $C_1$-$C_8$ alkyl, $C_1$-$C_6$ alkyl, or $C_1$-$C_4$ alkyl). In embodiments, $R^{7.4}$ is substituted or unsubstituted heteroalkyl (e.g., 2 to 8 membered heteroalkyl, 2 to 6 membered heteroalkyl, or 2 to 4 membered heteroalkyl). In embodiments, $R^{7.4}$ is substituted heteroalkyl (e.g., 2 to 8 membered heteroalkyl, 2 to 6 membered heteroalkyl, or 2 to 4 membered heteroalkyl). In embodiments, $R^{7.4}$ is an unsubstituted heteroalkyl (e.g., 2 to 8 membered heteroalkyl, 2 to 6 membered heteroalkyl, or 2 to 4 membered heteroalkyl).

In embodiments, $L^3$ is —NH—, $R^1$ is unsubstituted $C_1$-$C_4$ alkoxy, $R^2$ is —CX$^2_3$, and $R^8$ is hydrogen or E. In embodiments, $L^3$ is —NH, $R^1$ is unsubstituted $C_1$-$C_4$ alkoxy, $R^7$ is halogen, $R^2$ is —CX$^2_3$, and $R^8$ is hydrogen, E, or —C(O)-(unsubstituted alkyl).

In embodiments, the compound has the formula:

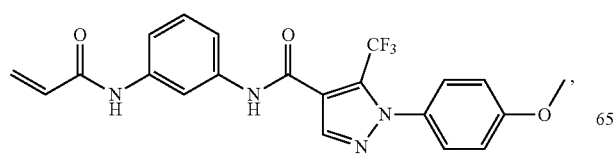

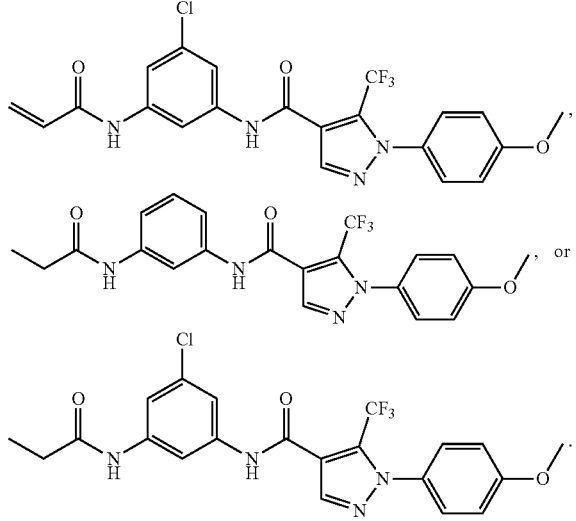

In embodiments, the compound has the formula:

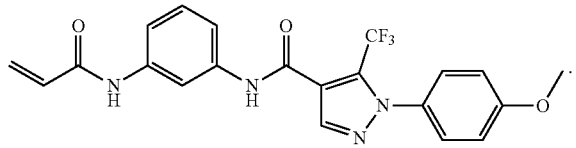 [SMILES: C=CC(=O)Nc1cccc(NC(=O)c2cnn(-c3ccc(OC)cc3)c2C(F)(F)F)c1]

In embodiments, the compound has the formula:

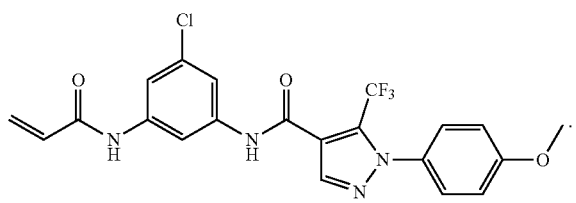 [SMILES: C=CC(=O)Nc1cc(Cl)cc(NC(=O)c2cnn(-c3ccc(OC)cc3)c2C(F)(F)F)c1]

In embodiments, the compound has the formula:

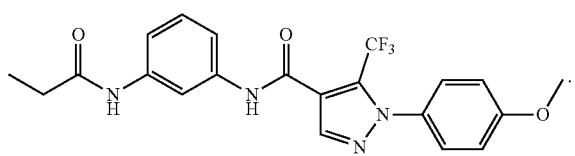 [SMILES: CCC(=O)Nc1cccc(NC(=O)c2cnn(-c3ccc(OC)cc3)c2C(F)(F)F)c1]

In embodiments, the compound has the formula:

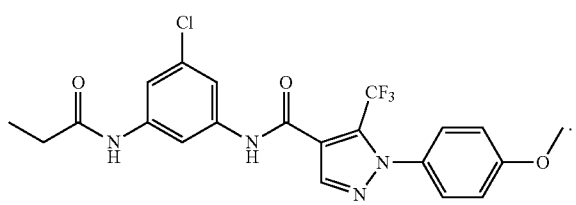

In an aspect is provided a compound having the formula:

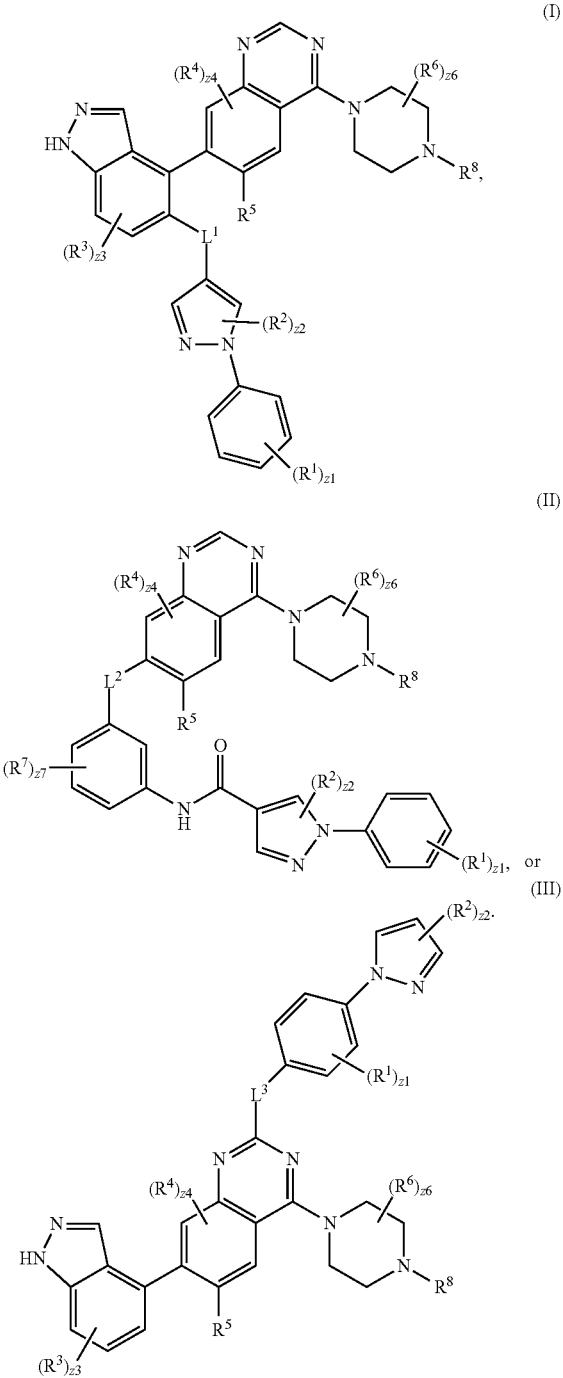

R¹ is independently halogen, —CX¹₃, —CHX¹₂, —CH₂X¹, —OCX¹₃, —OCH₂X¹, —OCHX¹₂, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$—C, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, R¹ is independently halogen, —CX¹₃, —CHX¹₂, —CH₂X¹, —OCX¹₃, —OCH₂X¹, —OCHX¹₂, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, R¹ is independently halogen, —CX¹₃, —CHX¹₂, —CH₂X¹, —OCX¹₃, —OCH₂X¹, —OCHX¹₂, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, unsubstituted alkyl, unsubstituted heteroalkyl, unsubstituted cycloalkyl, unsubstituted heterocycloalkyl, unsubstituted aryl, or unsubstituted heteroaryl.

R² is independently halogen, —CX²₃, —CHX²₂, —CH₂X², —OCX²₃, —OCH₂X², —OCHX²₂, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO₂R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, R² is independently halogen, —CX²₃, —CHX²₂, —CH₂X², —OCX²₃, —OCH₂X², —OCHX²₂, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO₂R$^{2D}$, —NR$^{2A}$C(O)R$^{2C}$, —NR$^{2A}$C(O)OR$^{2C}$, —NR$^{2A}$OR$^{2C}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, unsubstituted alkyl, unsubstituted heteroalkyl, unsubstituted cycloalkyl, unsubstituted heterocycloalkyl, unsubstituted aryl, or unsubstituted heteroaryl.

$R^3$ is independently halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^3$ is independently halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^3$ is independently halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, unsubstituted alkyl, unsubstituted heteroalkyl, unsubstituted cycloalkyl, unsubstituted heterocycloalkyl, unsubstituted aryl, or unsubstituted heteroaryl.

$R^4$ is independently halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^4$ is independently halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^4$ is independently halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, unsubstituted alkyl, unsubstituted heteroalkyl, unsubstituted cycloalkyl, unsubstituted heterocycloalkyl, unsubstituted aryl, or unsubstituted heteroaryl.

$R^5$ is independently hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n8}R^{5D}$, $-SO_{v8}NR^{5A}R^{5B}$, $-NHC(O)NR^{5A}R^{5B}$, $-N(O)_{m8}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^5$ is independently hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n5}R^{5D}$, $-SO_{v8}NR^{5A}R^{5B}$, $-NHC(O)NR^{5A}R^{5B}$, $-N(O)_{m8}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^5$ is independently hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n8}R^{5D}$, $-SO_{v5}NR^{5A}R^{5B}$, $-NHC(O)NR^{5A}R^{5B}$, $-N(O)_{m5}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, unsubstituted alkyl, unsubstituted heteroalkyl, unsubstituted cycloalkyl, unsubstituted heterocycloalkyl, unsubstituted aryl, or unsubstituted heteroaryl.

$R^6$ is independently halogen, $-CX^6_3$, $-CHX^6_2$, $-CH_2X^6$, $-OCX^6_3$, $-OCH_2X^6$, $-OCHX^6_2$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^6$ is independently halogen, $-CX^6_3$, $-CHX^6_2$, $-CH_2X^6$, $-OCX^6_3$, $-OCH_2X^6$, $-OCHX^6_2$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^6$ is independently halogen, $-CX^6_3$, $-CHX^6_2$, $-CH_2X^6$, $-OCX^6_3$, $-OCH_2X^6$, $-OCHX^6_2$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, unsubstituted alkyl, unsubstituted heteroalkyl, unsubstituted cycloalkyl, unsubstituted heterocycloalkyl, unsubstituted aryl, or unsubstituted heteroaryl.

$R^7$ is independently halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^7$ is independently halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^7$ is independently halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, unsubstituted alkyl, unsubstituted heteroalkyl, unsubstituted cycloalkyl, unsubstituted heterocycloalkyl, unsubstituted aryl, or unsubstituted heteroaryl.

$R^8$ is independently hydrogen, halogen, $-CX^8_3$, $-CHX^8_2$, $-CH_2X^8$, $-CN$, $-SO_{n8}R^{8D}$, $-SO_{v8}NR^{8A}R^{8B}$, $-C(O)R^{8C}$, $-C(O)OR^{8C}$, $-C(O)NR^{8A}R^{8B}$, E, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^8$ is independently hydrogen, halogen, $-CX^8_3$, $-CHX^8_2$, $-CH_2X^8$, $-CN$, $-SO_{n8}R^{8D}$, $-SO_{v8}NR^{8A}R^{8B}$, $-C(O)R^{8C}$, $-C(O)OR^{8C}$, $-C(O)NR^{8A}R^{8B}$, E, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^8$ is independently hydrogen, halogen, —$CX^8_3$, —$CHX^8_2$, —$CH_2X^8$, —CN, —$SO_{n8}R^{8D}$, —$SO_{v8}NR^{8A}R^{8B}$, —$C(O)R^{8C}$, —$C(O)OR^{8C}$, —$C(O)NR^{8A}R^{8B}$, E, unsubstituted alkyl, unsubstituted heteroalkyl, unsubstituted cycloalkyl, unsubstituted heterocycloalkyl, unsubstituted aryl, or unsubstituted heteroaryl.

$L^1$ is a
bond, —N(H)—, —O—, —S—, —C(O)—, —C(O)N(H)—, —N(H)C(O)—, —N(H)C(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), or substituted or unsubstituted heteroalkylene (e.g., 2 to 8 membered, 2 to 6 membered, 4 to 6 membered, 2 to 3 membered, or 4 to 5 membered). In embodiments, $L^1$ is a bond, —N(H)—, —O—, —S—, —C(O)—, —C(O)N(H)—, —N(H)C(O)—, —N(H)C(O)NH—, —C(O)O—, —OC(O)—, substituted (e.g., substituted with a substituent group, a size-limited substituent group, or lower substituent group) or unsubstituted alkylene, or substituted (e.g., substituted with a substituent group, a size-limited substituent group, or lower substituent group) or unsubstituted heteroalkylene.

In embodiments, $L^1$ is a
bond, —N(H)—, —O—, —S—, —C(O)—, —C(O)N(H)—, —N(H)C(O)—, —N(H)C(O)NH—, —C(O)O—, —OC(O)—, unsubstituted alkylene, or unsubstituted heteroalkylene.

$L^2$ is a
bond, —N(H)—, —O—, —S—, —C(O)—, —C(O)N(H)—, —N(H)C(O)—, —N(H)C(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), or substituted or unsubstituted heteroalkylene (e.g., 2 to 8 membered, 2 to 6 membered, 4 to 6 membered, 2 to 3 membered, or 4 to 5 membered).

In embodiments, $L^2$ is a
bond, —N(H)—, —O—, —S—, —C(O)—, —C(O)N(H)—, —N(H)C(O)—, —N(H)C(O)NH—, —C(O)O—, —OC(O)—, substituted (e.g., substituted with a substituent group, a size-limited substituent group, or lower substituent group) or unsubstituted alkylene, or substituted (e.g., substituted with a substituent group, a size-limited substituent group, or lower substituent group) or unsubstituted heteroalkylene. In embodiments, $L^2$ is a
bond, —N(H)—, —O—, —S—, —C(O)—, —C(O)N(H)—, —N(H)C(O)—, —N(H)C(O)NH—, —C(O)O—, —OC(O)—, unsubstituted alkylene, or unsubstituted heteroalkylene.

$L^3$ is a
bond, —N(H)—, —O—, —S—, —C(O)—, —C(O)N(H)—, —N(H)C(O)—, —N(H)C(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), or substituted or unsubstituted heteroalkylene (e.g., 2 to 8 membered, 2 to 6 membered, 4 to 6 membered, 2 to 3 membered, or 4 to 5 membered). In embodiments, $L^3$ is a bond, —N(H)—, —O—, —S—, —C(O)—, —C(O)N(H)—, —N(H)C(O)—, —N(H)C(O)NH—, —C(O)O—, —OC(O)—, substituted (e.g., substituted with a substituent group, a size-limited substituent group, or lower substituent group) or unsubstituted alkylene, or substituted (e.g., substituted with a substituent group, a size-limited substituent group, or lower substituent group) or unsubstituted heteroalkylene. In embodiments, $L^3$ is a bond, —N(H)—, —O—, —S—, —C(O)—, —C(O)N(H)—, —N(H)C(O)—, —N(H)C(O) NH—, —C(O)O—, —OC(O)—, unsubstituted alkylene, or unsubstituted heteroalkylene.

E is an electrophilic moiety.

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{8C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, and $R^{8D}$ is independently hydrogen, —$CX_3$, —CN, —COOH, —$CONH_2$, —$CHX_2$, —$CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{8C}$, $R^{5D}$, $R^{6A}$, $R^{6B}$, $R^{6C}$, $R^{6D}$, $R^{7A}$, $R^{7B}$, $R^{7C}R^{7D}$, $R^{8A}$, $R^{8B}$, $R^{8C}$, and $R^{8D}$ is independently hydrogen, —$CX_3$, —CN, —COOH, —$CONH_2$, —$CHX_2$, —$CH_2X$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, and $R^{8D}$ is independently hydrogen, —$CX_3$, —CN, —COOH, —$CONH_2$, —$CHX_2$, —$CH_2X$, unsubstituted alkyl, unsubstituted heteroalkyl, unsubstituted cycloalkyl, unsubstituted heterocycloalkyl, unsubstituted aryl, or unsubstituted heteroaryl.

$R^{1A}$ and $R^{1B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{2A}$ and $R^{2B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{3A}$ and $R^{3B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{4A}$ and $R^{4B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{5A}$ and $R^{5B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{6A}$ and $R^{6B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{7A}$ and $R^{7B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{8A}$ and $R^{8B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

z1 is an integer from 0 to 5. z2 is an integer from 0 to 3. z3 is an integer from 0 to 5. z4 is an integer from 0 to 2. z6 is an integer from 0 to 8. z7 is an integer from 0 to 4. In embodiments, z1, z2, z3, z4, z6, and z7 are 0. In embodiments, z2, z3, z4, z6, and z7 are 0.

Each X, $X^1$, $X^2$, $X^3$, $X^4$, $X^5$, $X^6$, $X^7$, and $X^8$ is independently —F, —Cl, —Br, or —I.

n1, n2, n3, n4, n5, n6, n7, and n8 are independently an integer from 0 to 4.

m1, m2, m3, m4, m5, m6, m7, m8, v1, v2, v3, v4, v5, v6, v7, and v8 are independently 1 or 2.

In embodiments, E is a covalent cysteine modifier moiety. In embodiments, E is

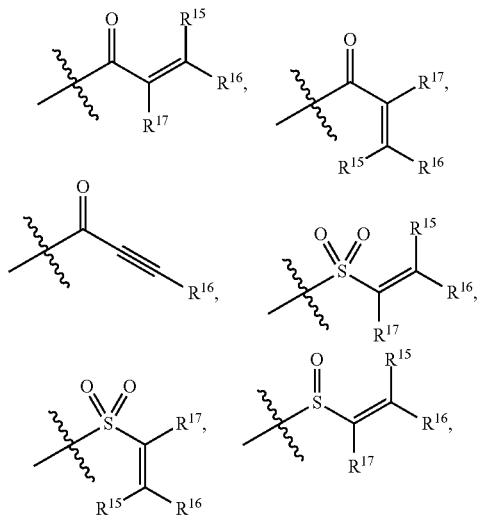

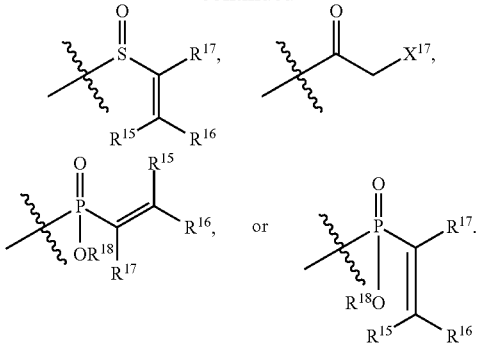

$R^{15}$ is independently hydrogen, halogen, —$CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —$NHC=(O)NHNR^{15A}R^{15B}$, —$NHC(O)NR^{15A}R^{15B}$, —$N(O)_{m15}$, —$NR^{15A}R^{15B}$, —$C(O)R^{15C}$, —$C(O)$—$OR^{15}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$OCX^{15}_3$, —$OCHX^{15}_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{15}$ is independently hydrogen, halogen, —$CX^{15}_3$, —$CHX^{15}_2$, —$CH_2X^{15}$, —CN, —$SO_{n15}R^{8D}$, —$SO_{v15}NR^{15A}R^{15B}$, —$NHNR^{15A}R^{15B}$, —$ONR^{15A}R^{15B}$, —$NHC=(O)NHNR^{15A}R^{15B}$, —$NHC(O)NR^{15A}R^{15B}$, —$N(O)_{m15}$, —$NR^{15A}R^{15B}$, —$C(O)R^{15C}$, —$C(O)$—$OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$OCX^5_3$, —$OCHX^{15}_2$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{15}$ is independently hydrogen, halogen, —$CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —$NHC=(O)NHNR^{15A}R^{15B}$, —$NHC(O)NR^{15A}R^{15B}$, —$N(O)_{m8}$, —$NR^{15A}R^{15B}$, —$C(O)R^{15C}$, —$C(O)$—$OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$OCX^5_3$, —$OCHX^{15}_2$, unsubstituted alkyl, unsubstituted heteroalkyl, unsubstituted cycloalkyl, unsubstituted heterocycloalkyl, unsubstituted aryl, or unsubstituted heteroaryl.

$R^{16}$ is independently hydrogen, halogen, $-CX^{16}_3$, $-CHX^{16}_2$, $-CH_2X^{16}$, $-CN$, $-SO_{n16}R^{16}R^{6D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, $-OCX^{16}_3$, $-OCHX^{16}_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{16}$ is independently hydrogen, halogen, $-CX^{16}_3$, $-CHX^{16}_2$, $-CH_2X^{16}$, $-CN$, $-SO_{n16}R^{16}R^{6D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, $-OCX^{16}_3$, $-OCHX^{16}_2$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{16}$ is independently hydrogen, halogen, $-CX^{16}_3$, $-CHX^{16}_2$, $-CH_2X^{16}$, $-CN$, $-SO_{n16}R^{16}R^{6D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, $-OCX^{16}_3$, $-OCHX^{16}_2$, unsubstituted alkyl, unsubstituted heteroalkyl, unsubstituted cycloalkyl, unsubstituted heterocycloalkyl, unsubstituted aryl, or unsubstituted heteroaryl.

$R^{17}$ is independently hydrogen, halogen, $-CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, $-OCX^{17}_3$, $-OCHX^{17}_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{17}$ is independently hydrogen, halogen, $-CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, $-OCX^{17}_3$, $-OCHX^{17}_2$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{17}$ is independently hydrogen, halogen, $-CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, $-OCX^{17}_3$, $-OCHX^{17}_2$, unsubstituted alkyl, unsubstituted heteroalkyl, unsubstituted cycloalkyl, unsubstituted heterocycloalkyl, unsubstituted aryl, or unsubstituted heteroaryl.

$R^{18}$ is independently hydrogen, $-CX^{18}_3$, $-CHX^{18}_2$, $-CH_2X^{18}$, $-C(O)R^{18C}$, $-C(O)OR^{18C}$, $-C(O)NR^{18A}R^{18B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{18}$ is independently hydrogen, $-CX^{18}_3$, $-CHX^{18}_2$, $-CH_2X^{18}$, $-C(O)R^{18C}$, $-C(O)OR^{18C}$, $-C(O)NR^{18A}R^{18B}$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{18}$ is independently hydrogen, $-CX^{18}_3$, $-CHX^{18}_2$, $-CH_2X^{18}$, $-C(O)R^{18C}$, $-C(O)OR^{18C}$, $-C(O)NR^{18A}R^{18B}$, unsubstituted alkyl, unsubstituted heteroalkyl, unsubstituted cycloalkyl, unsubstituted heterocycloalkyl, unsubstituted aryl, or unsubstituted heteroaryl.

$R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, are independently hydrogen, —$CX_3$, —CN, —COOH, —$CONH_2$, —$CHX_2$, —$CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $R^{15A}$ and $R^{15B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{16A}$ and $R^{16B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{17A}$ and $R^{17B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{18A}$ and $R^{18B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, are independently
hydrogen, —$CX_3$, —CN, —COOH, —$CONH_2$, —$CHX_2$, —$CH_2X$, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$ are independently hydrogen, —$CX_3$, —CN, —COOH, —$CONH_2$, —$CHX_2$, —$CH_2X$, unsubstituted alkyl, unsubstituted heteroalkyl, unsubstituted cycloalkyl, unsubstituted heterocycloalkyl, unsubstituted aryl, or unsubstituted heteroaryl.

Each X, $X^{15}$, $X^{16}$, $X^{17}$ and $X^{18}$ is independently —F, —Cl, —Br, or —I.

The symbols n15, n16, n17, v15, v16, and v17, are independently an integer from 0 to 4.

The symbols m15, m16, and m17 are independently 1 or 2.

In embodiments, E is:

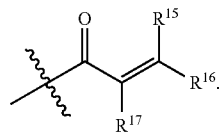

In embodiments, $R^{15}$ is hydrogen; $R^{16}$ is hydrogen; and $R^{17}$ is hydrogen.

In embodiments, the compound has the formula:

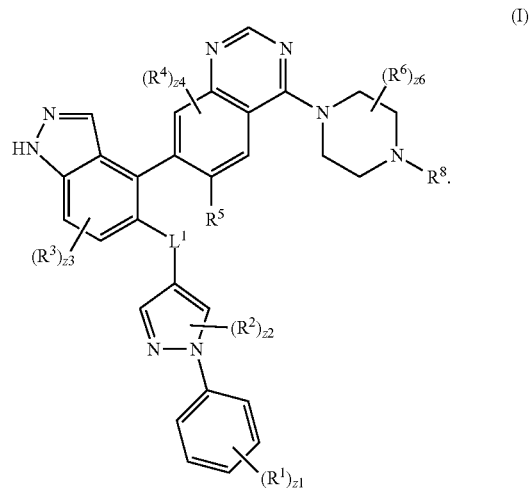

(I)

$R^1$, $R^2$, $R^3$, $R^4$, $R^5$, $R^6$, $R^8$, z1, z2, z3, z4, z6, and $L^1$ are as described herein.

In embodiments, the compound has the formula:

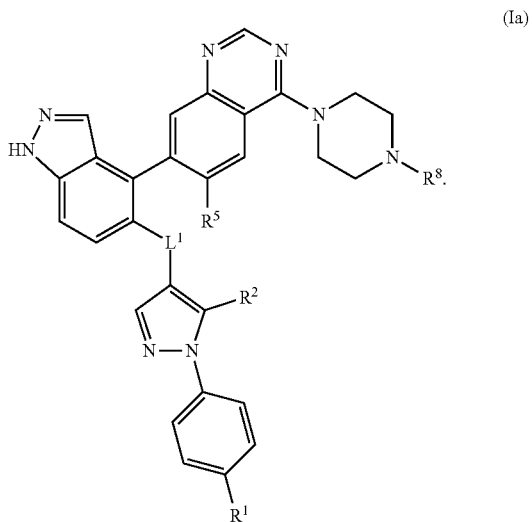

(Ia)

$R^1$, $R^2$, $R^5$, $R^8$, and $L^1$ are as described herein.

In embodiments, $L^1$ is —N(H)C(O)—, —$OCH_2$—, or —$NHCH_2CH_2CH_2$—. In embodiments, $R^1$ is unsubstituted $C_1$-$C_4$ alkoxy. In embodiments, $R^2$ is —$CX^2{}_3$. In embodiments, $R^5$ is halogen. In embodiments, $R^8$ is independently hydrogen or E.

In embodiments, the compound has the formula:

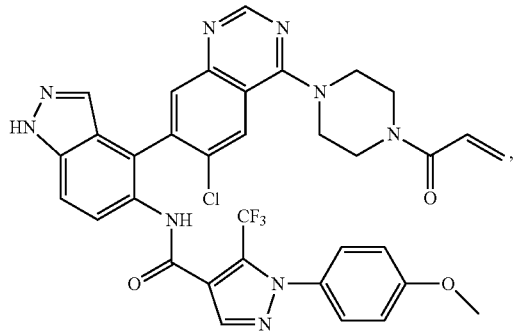

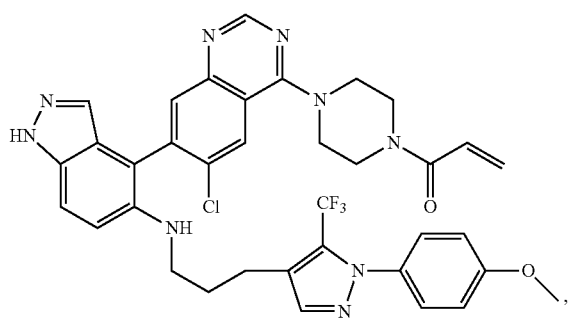

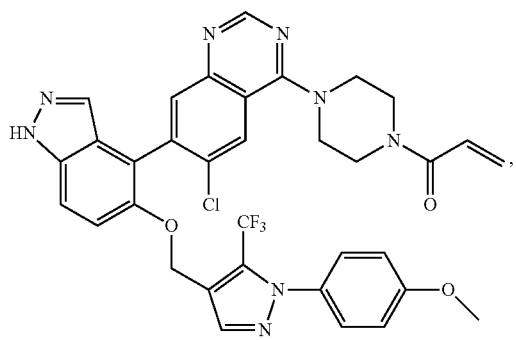

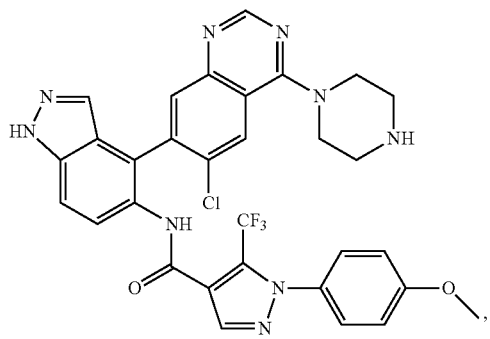

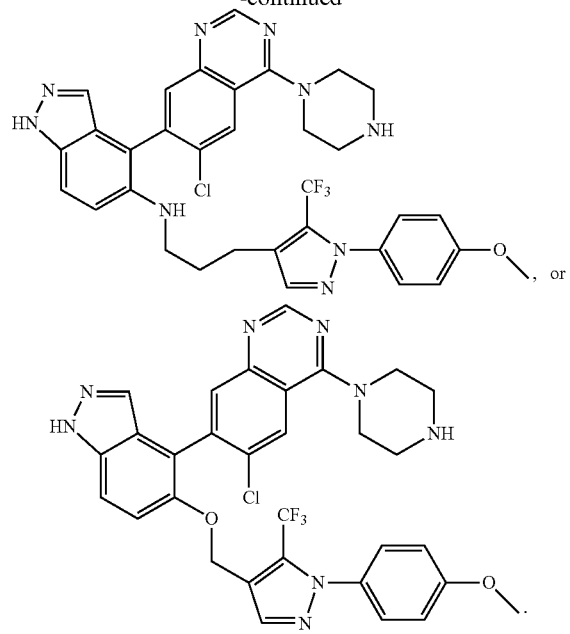

In embodiments, the compound has the formula:

(II)

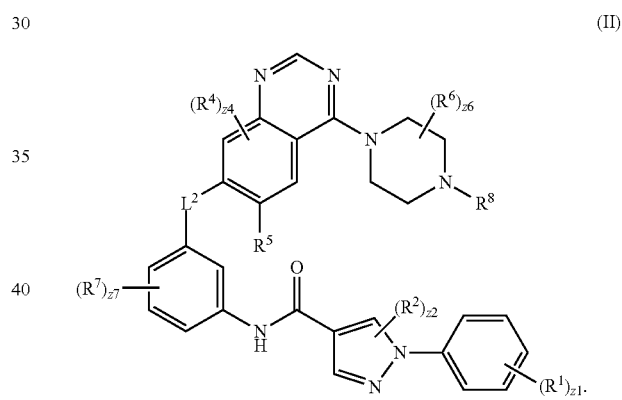

$R^1$, $R^2$, $R^4$, $R^5$, $R^6$, $R^7$, $R^8$, z1, z2, z4, z6, z7, and $L^2$ are as described herein.

In embodiments, the compound has the formula:

(IIa)

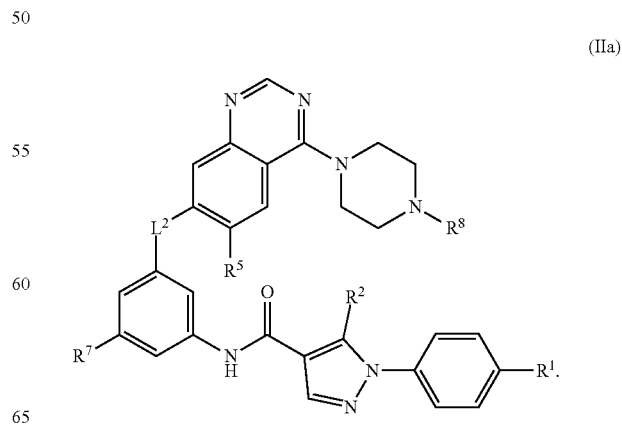

$R^1$, $R^2$, $R^5$, $R^7$, $R^8$, and $L^2$ are as described herein.

In embodiments, L² is —O—, —OCH₂—, —CH₂—, or —CH₂CH₂—. In embodiments, R¹ is unsubstituted $C_1$-$C_4$ alkoxy. In embodiments, R² is —CX²₃. In embodiments, R⁵ is halogen. In embodiments, R⁷ is —NHC(O)CH₂CH₃. In embodiments, R⁸ is hydrogen or E.
In embodiments, the compound has the formula:
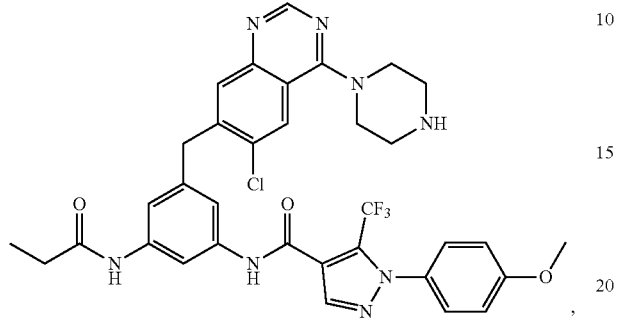
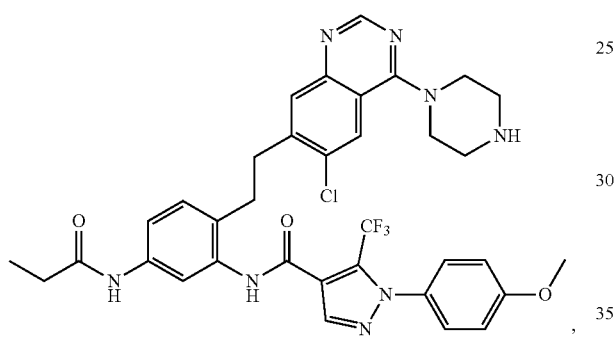
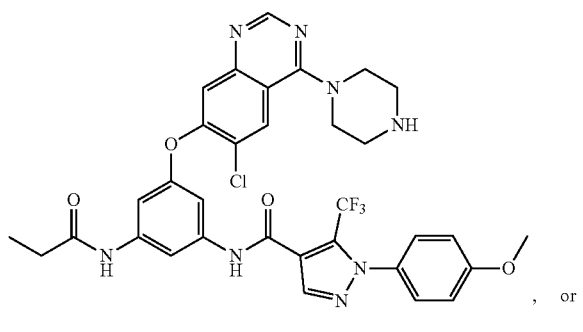
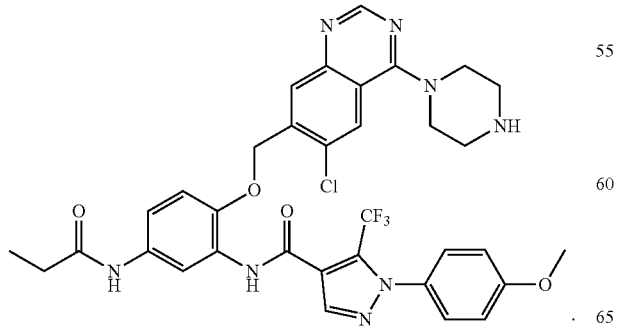
In embodiments, the compound has the formula:
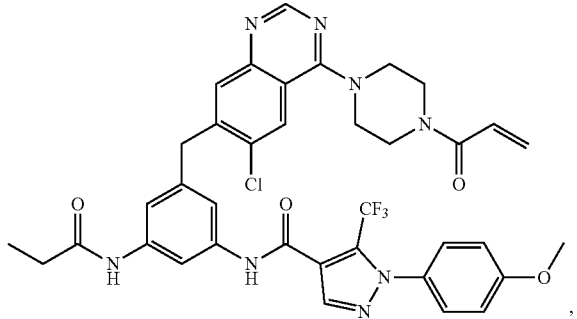
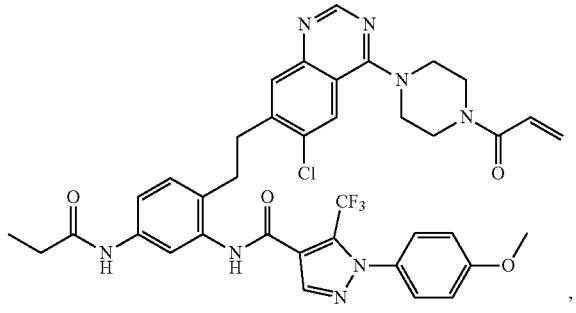
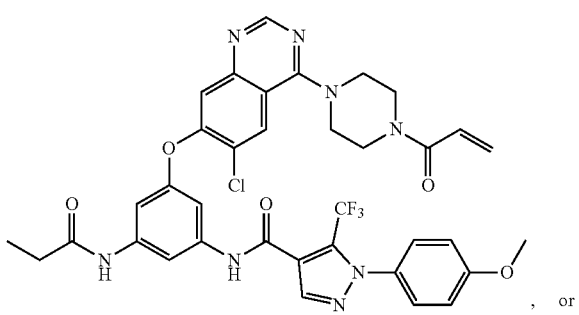
, or
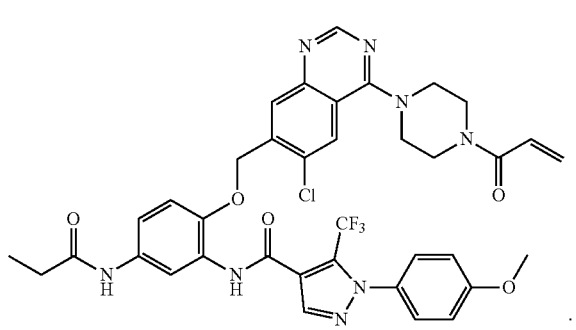
, or In embodiments, the compound has the formula:

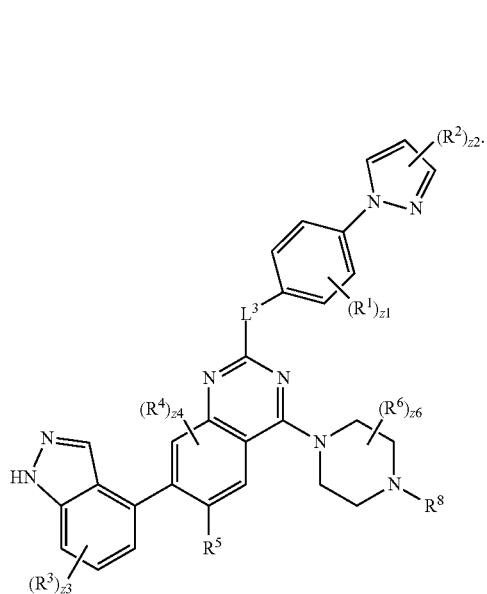

$R^1$, $R^2$, $R^3$, $R^4$, $R^5$, $R^6$, $R^8$, z1, z2, z3, z4, z6, and $L^3$ are as described herein.

In embodiments, the compound has the formula:

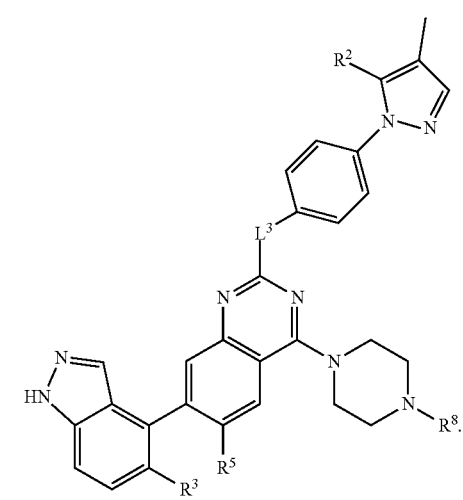

$R^2$, $R^3$, $R^5$, $R^8$, and $L^3$ are as described herein.
In embodiments, $L^3$ is —OCH$_2$CH$_2$NH—. In embodiments, $R^2$ is —CX$^2{}_3$. In embodiments, $R^3$ is unsubstituted $C_1$-$C_4$ alkyl. In embodiments, $R^5$ is halogen. In embodiments, $R^8$ is hydrogen or E.

In embodiments, the compound has the formula:

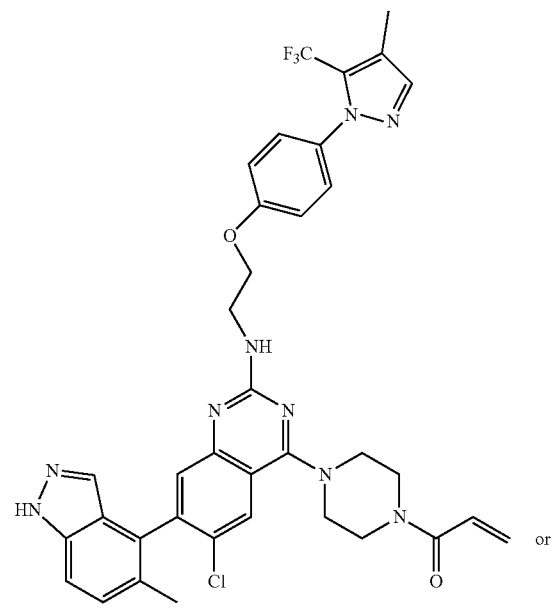

or

In embodiments, the compound has the formula:

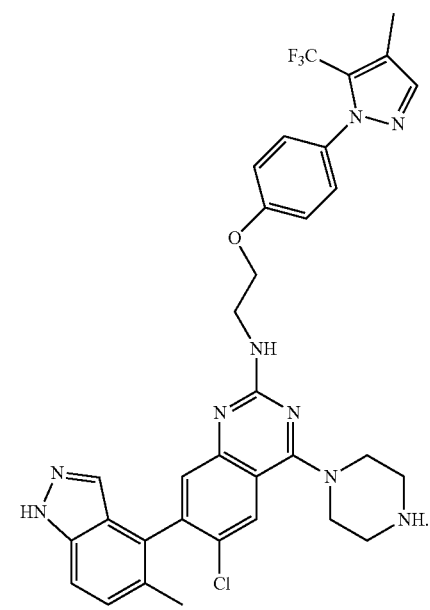

In embodiments, the compound has the formula:

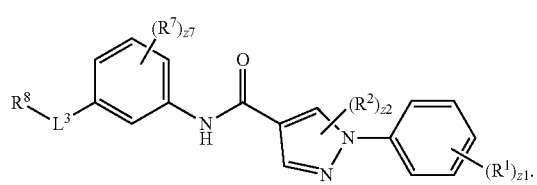

$R^1$, $R^2$, $R^7$, $R^8$, z1, z2, z7, and $L^3$ are as described herein.

In embodiments, the compound has the formula:

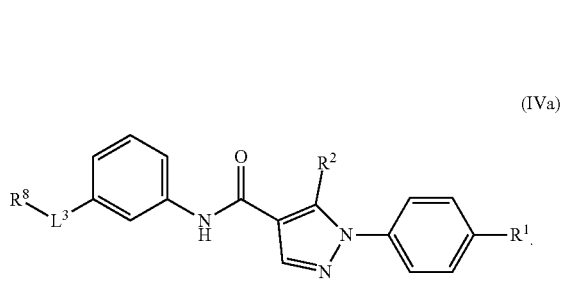
(IVa)

$R^1$, $R^2$, $R^8$, and $L^3$ are as described herein.

In embodiments, $L^3$ is —NH—. In embodiments, $R^1$ is unsubstituted $C_1$-$C_4$ alkoxy. In embodiments, $R^2$ is —$CX^2_3$. In embodiments, $R^8$ is hydrogen or E In embodiments, the compound has the formula:

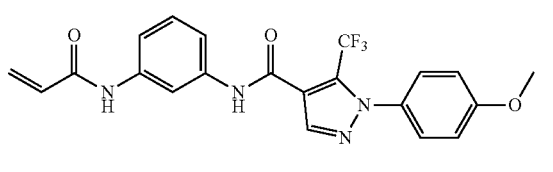

or

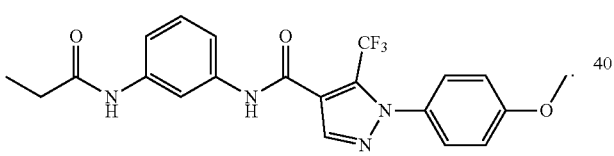

In an aspect is provided a compound having the formula:

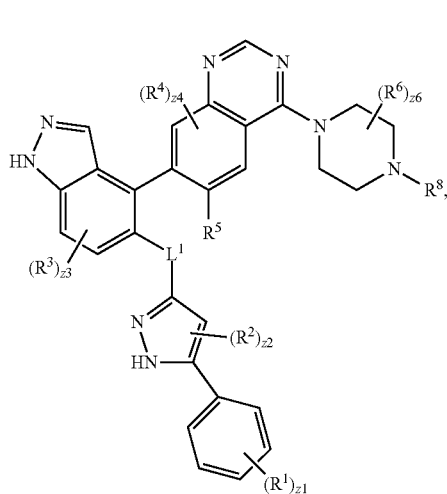
(Ib)

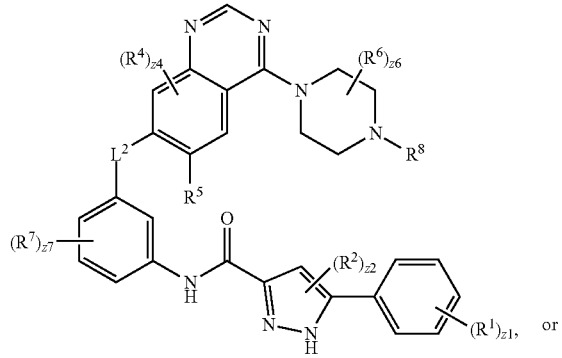
(IIb)

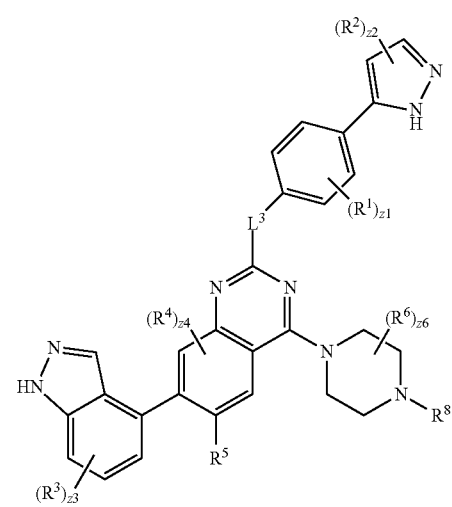
(IIIb)

$R^1$, $R^2$, $R^3$, $R^4$, $R^5$, $R^6$, $R^7$, $R^8$, z1, z2, z3, z4, z6, z7, $L^1$, $L^2$, and $L^3$ are as described herein. In embodiments, $R^1$ is halogen. In embodiments, $R^1$ is —Br. In embodiments, z2, z3, z4, z6, and z7 are 0.

In an aspect is provided a compound having the formula:

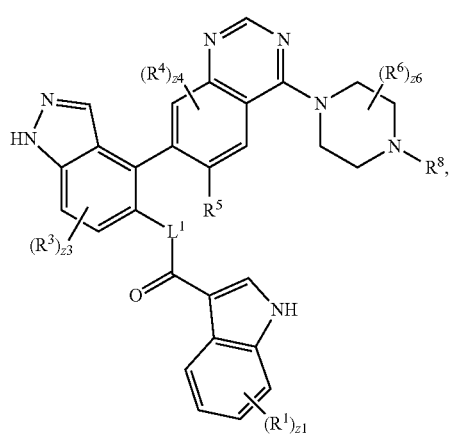
(Ic)

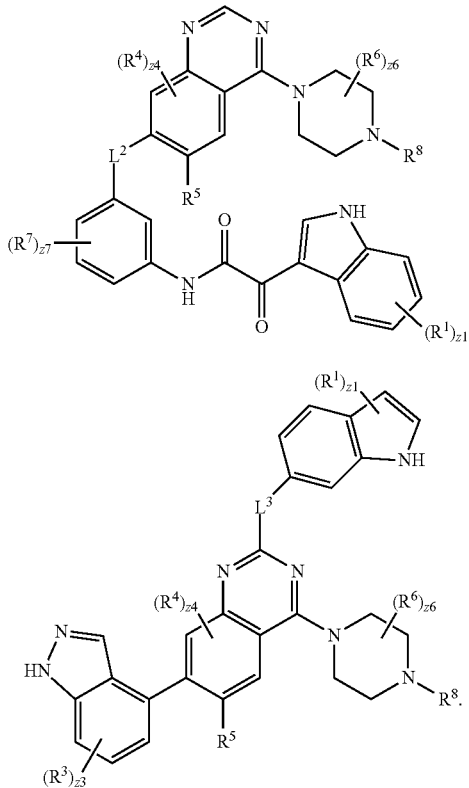

$R^1$, $R^3$, $R^4$, $R^5$, $R^6$, $R^7$, $R^8$, z1, z2, z3, z4, z6, z7, $L^1$, $L^2$, and $L^3$ are as described herein. In embodiments, $R^1$ is —C(O) (unsubstituted $C_1$-$C_4$ alkyl). In embodiments, z3, z4, z6, and z7 are 0.

Figure 17A:
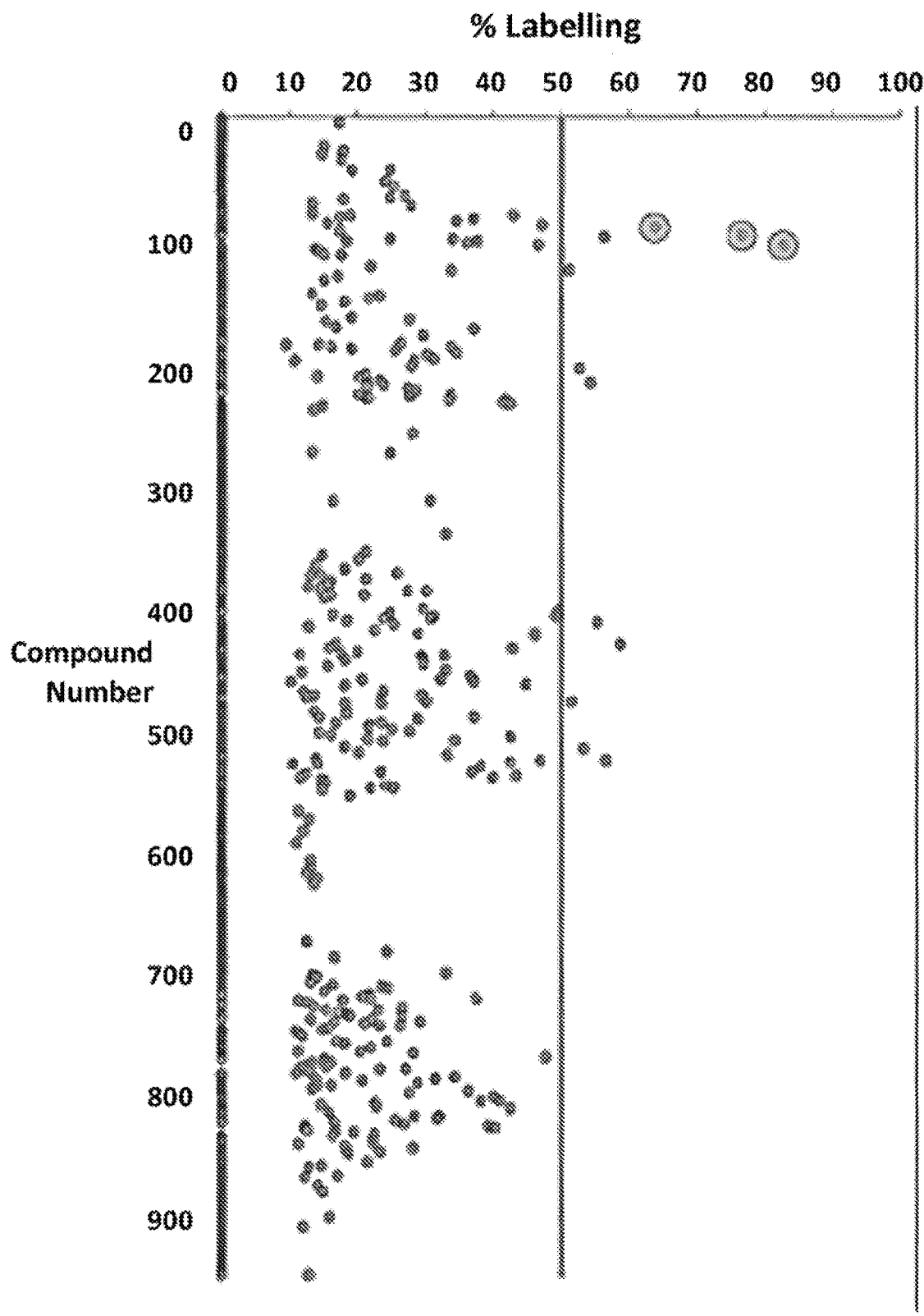
FIGS. 17A-17B. Tethering screen results for K-Ras$^{M72C}$. Percent labeling at 1 mM βME Vs. Compound Number. Compounds are represented by a dot, and the line marks the 50% modification threshold for hit ID. Large dots are the top three hits shown in FIG. 17B. Three fragments from the tethering screen are shown in FIG. 17B, 2C07, 2B09, and 2B02 and their percent modification.
Figure 17B:
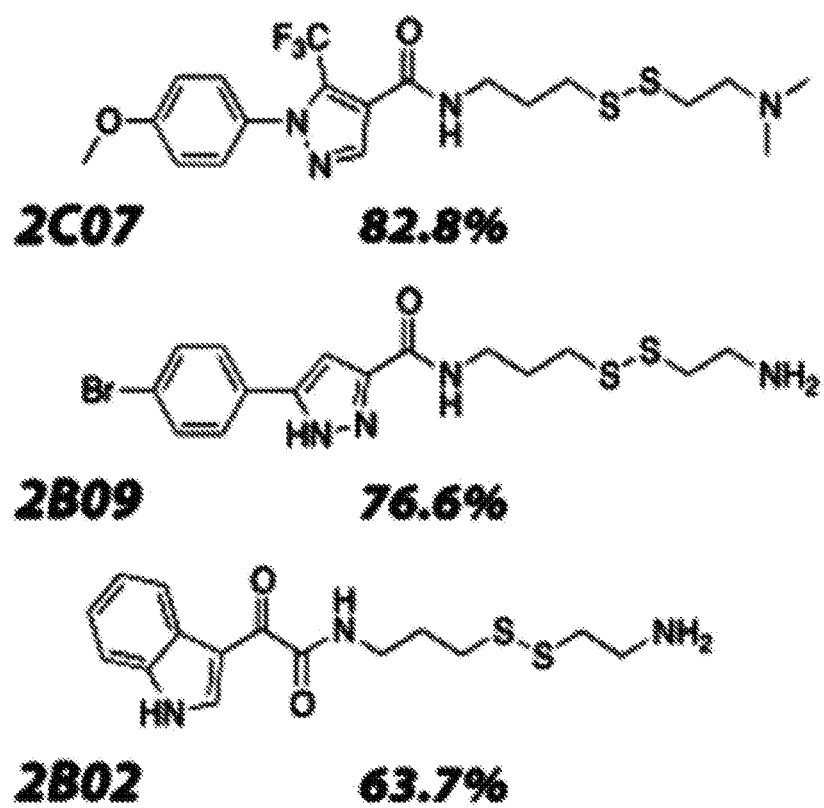
Figure 18:
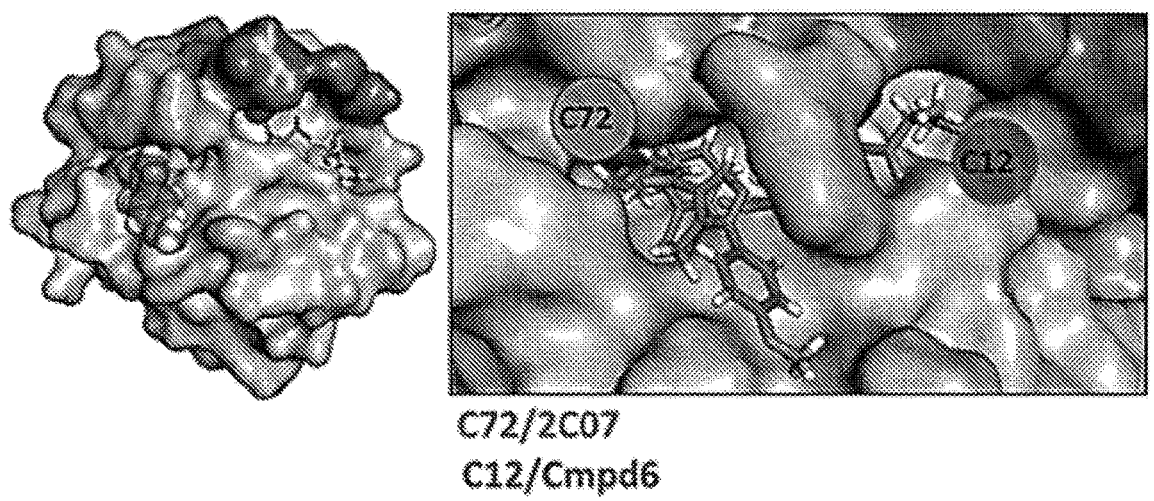
FIG. 18. Rendering of the protein showing that compound 2C07 occupies half of the switch II pocket and a new lipophilic channel.
Figure 19:
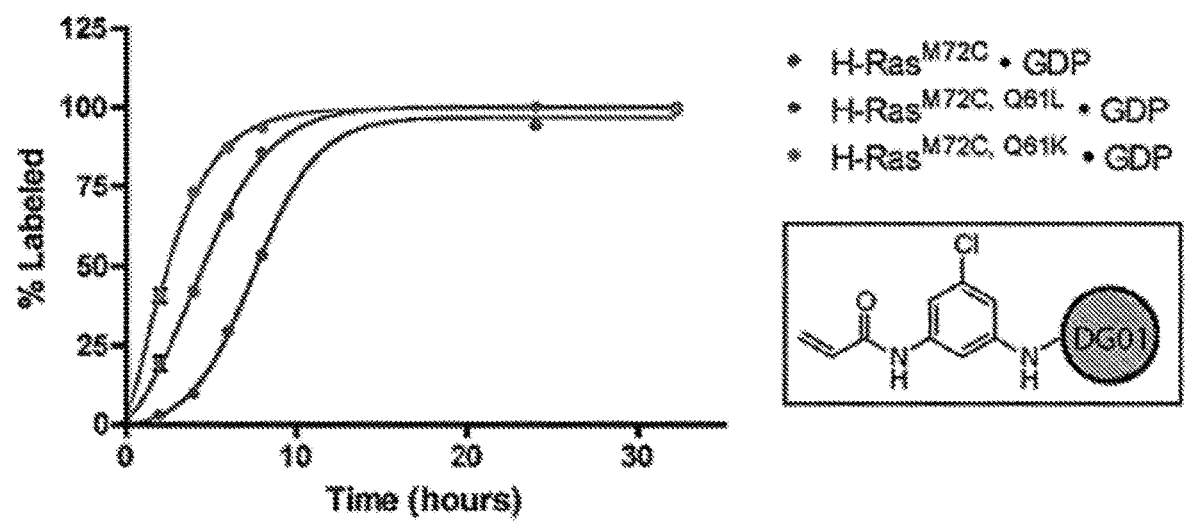
FIG. 19. DG-3-95A (also referred to as compound 3 in FIG. 34A) labeling kinetics at 20 μM (5×) drug. The kinetic curves demonstrate that DG-3-95A labeling is effected by the presence of other oncogenic mutations at position 61 in both the GDP and GNP states. Contacting deep in the switch II pocket accesses a new pocket which is influenced by Q61 mutations.
Figure 20:
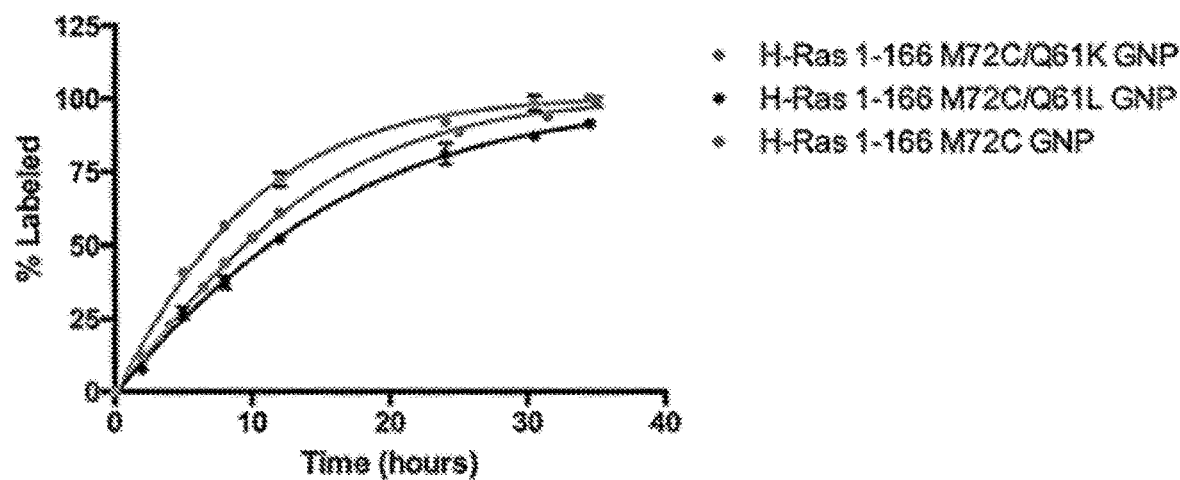
FIG. 20. The switch II pocket is accessible in the GTP bound state. DG-3-95A (also referred to as compound 3 in FIG. 34A) labeling kinetics at 20 μM (5×) drug. The kinetic curves demonstrate that DG-3-95A labeling is effected by the presence of other oncogenic mutations at position 61 in both the GDP and GNP states. Contacting deep in the switch II pocket accesses a new pocket which is influenced by Q61 mutations.
Figure 21A:
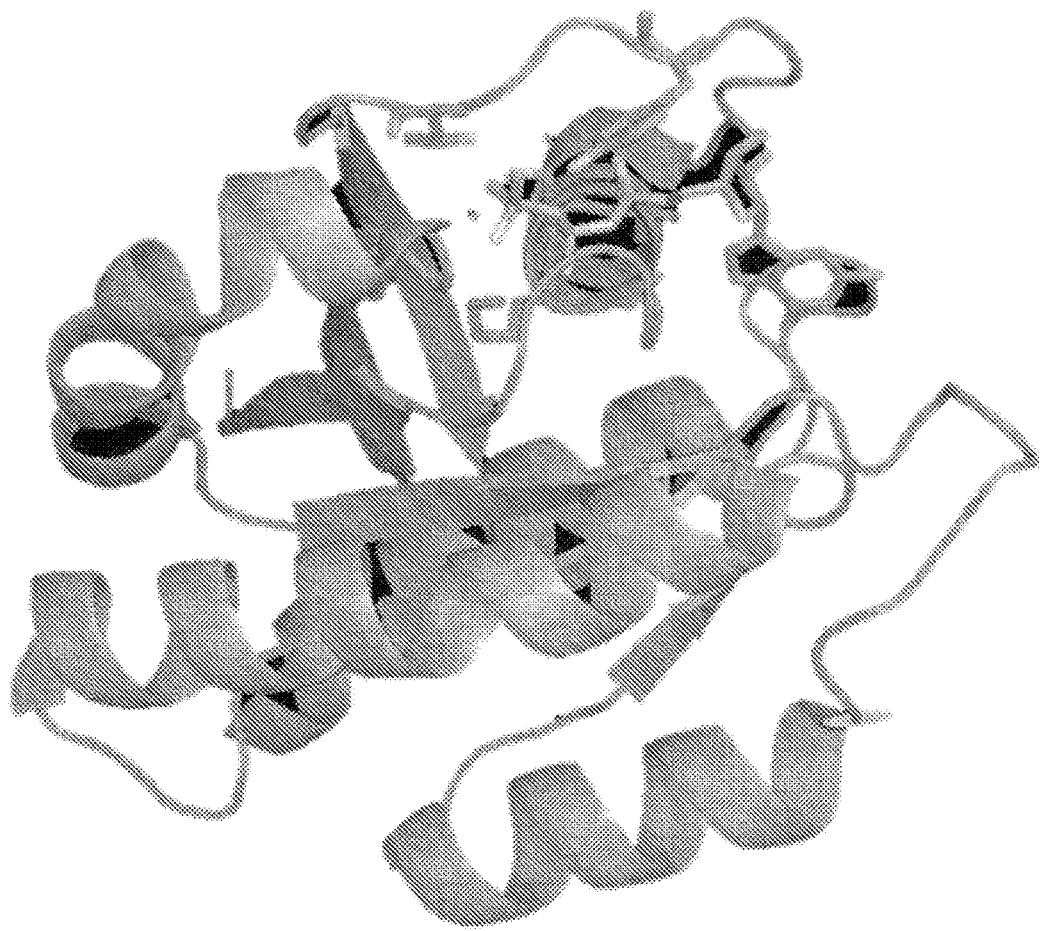
FIGS. 21A-21B.
Figure 21B:
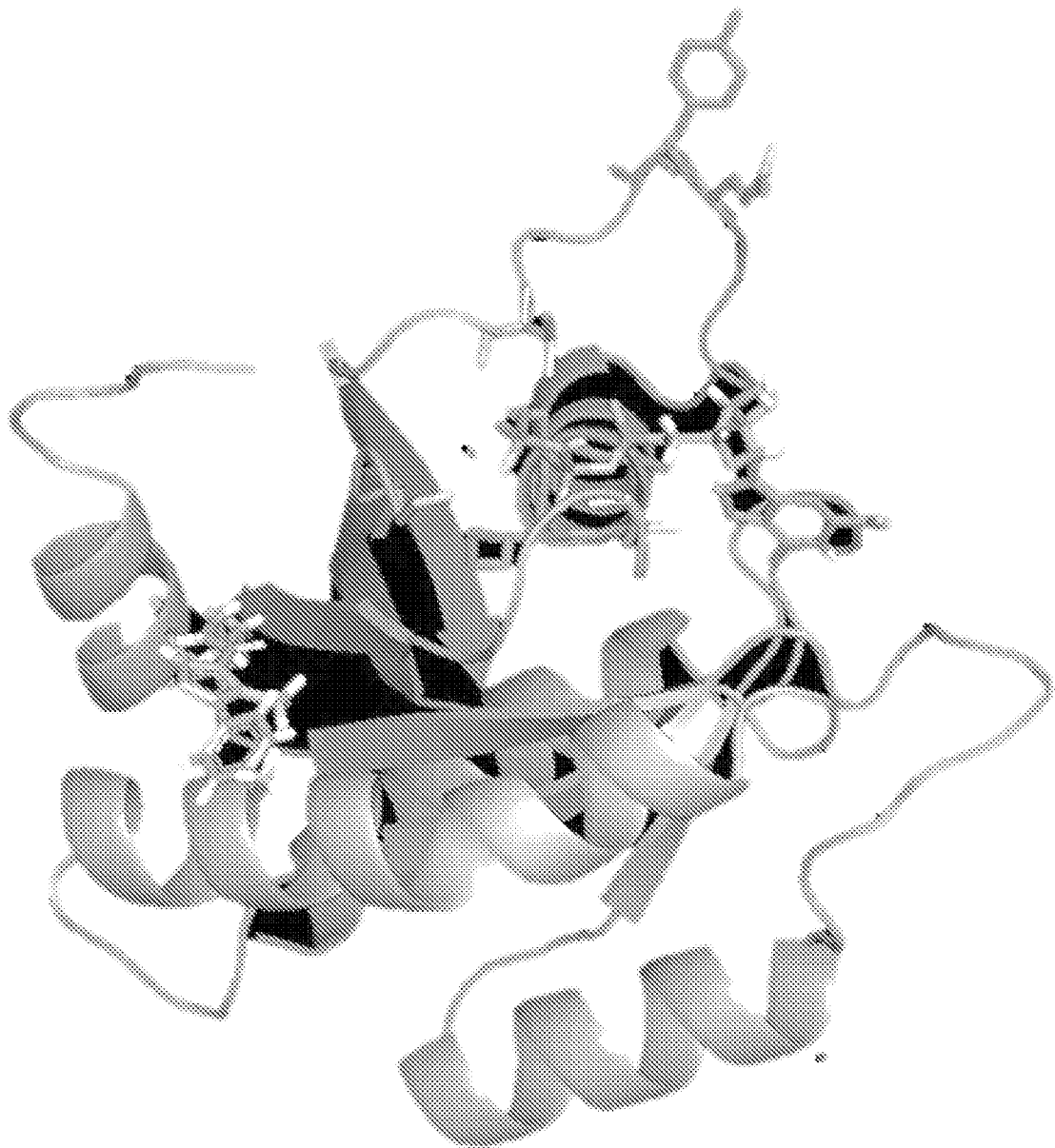
Figure 22A:
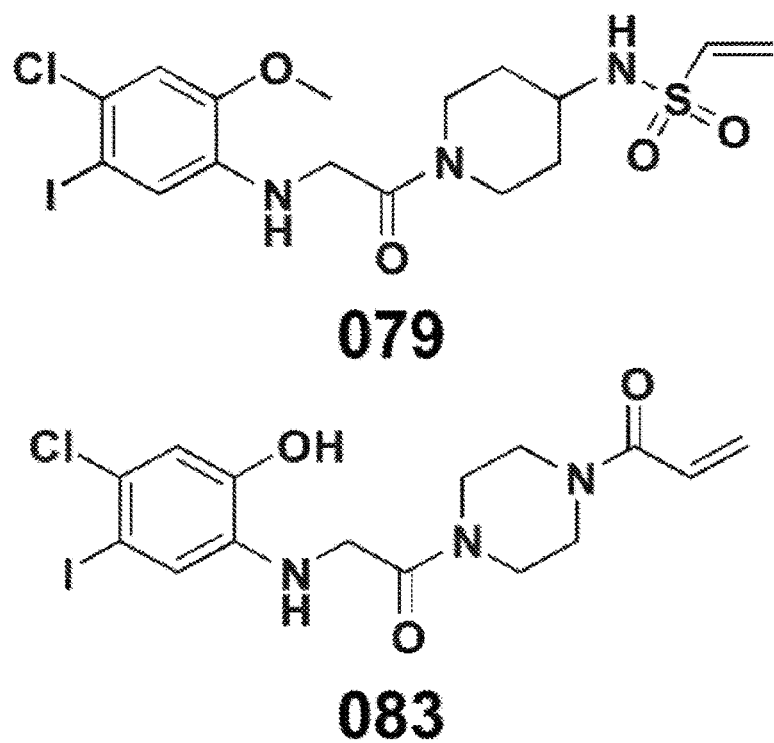
Figure 22B:
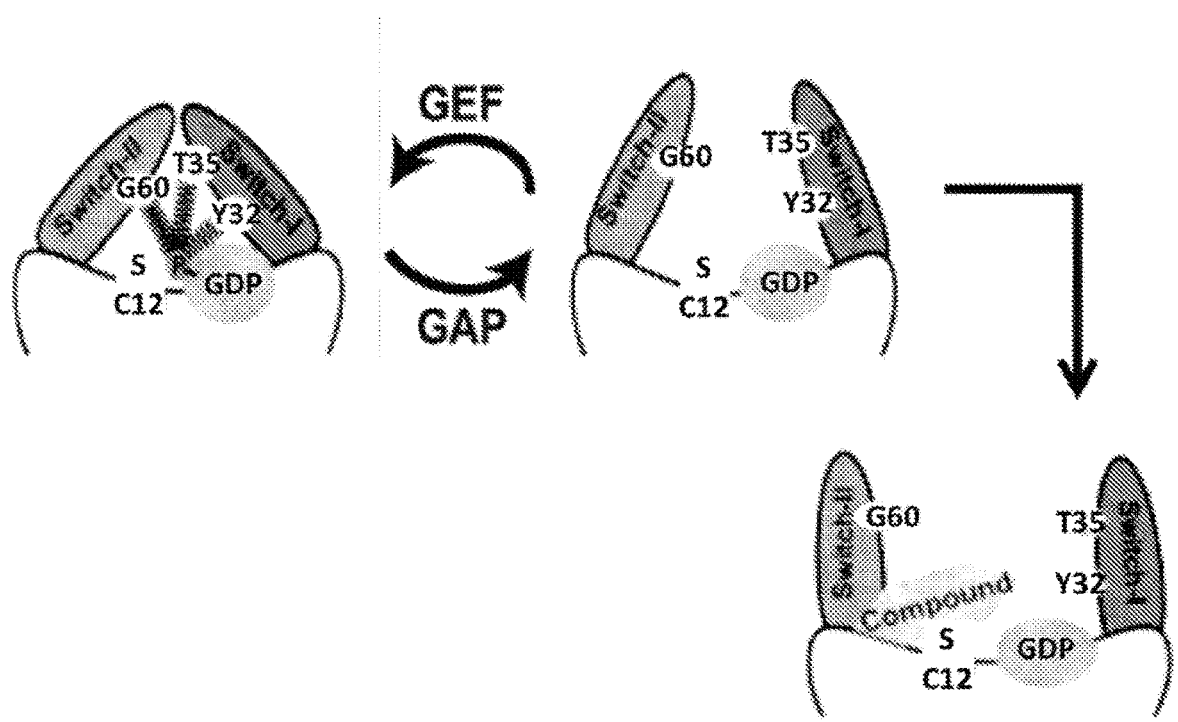
FIG. 22B depicts the protein of H-Ras-switch-2 binder/GTP.
Figure 23A:
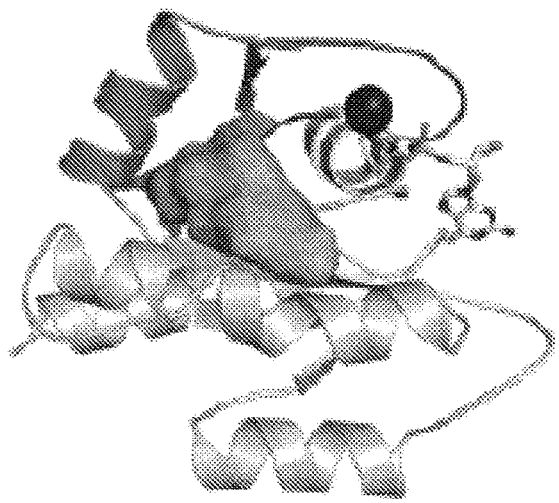
FIGS. 23A-23B.
Figure 23A:
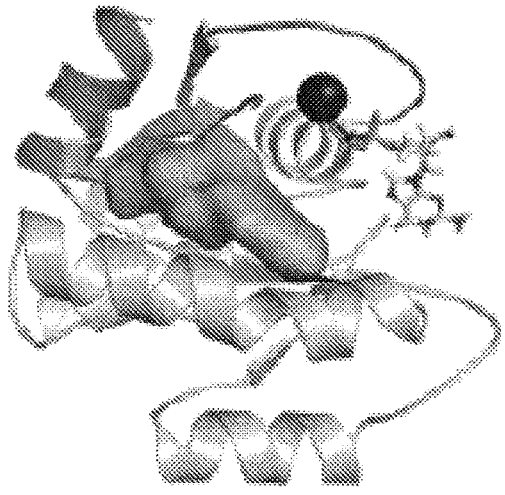
Figure 23A:
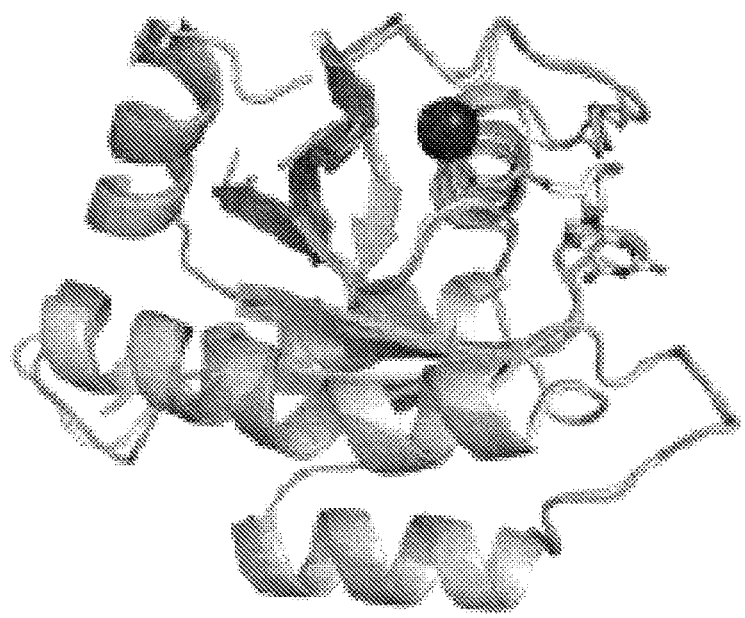
Figure 23B:
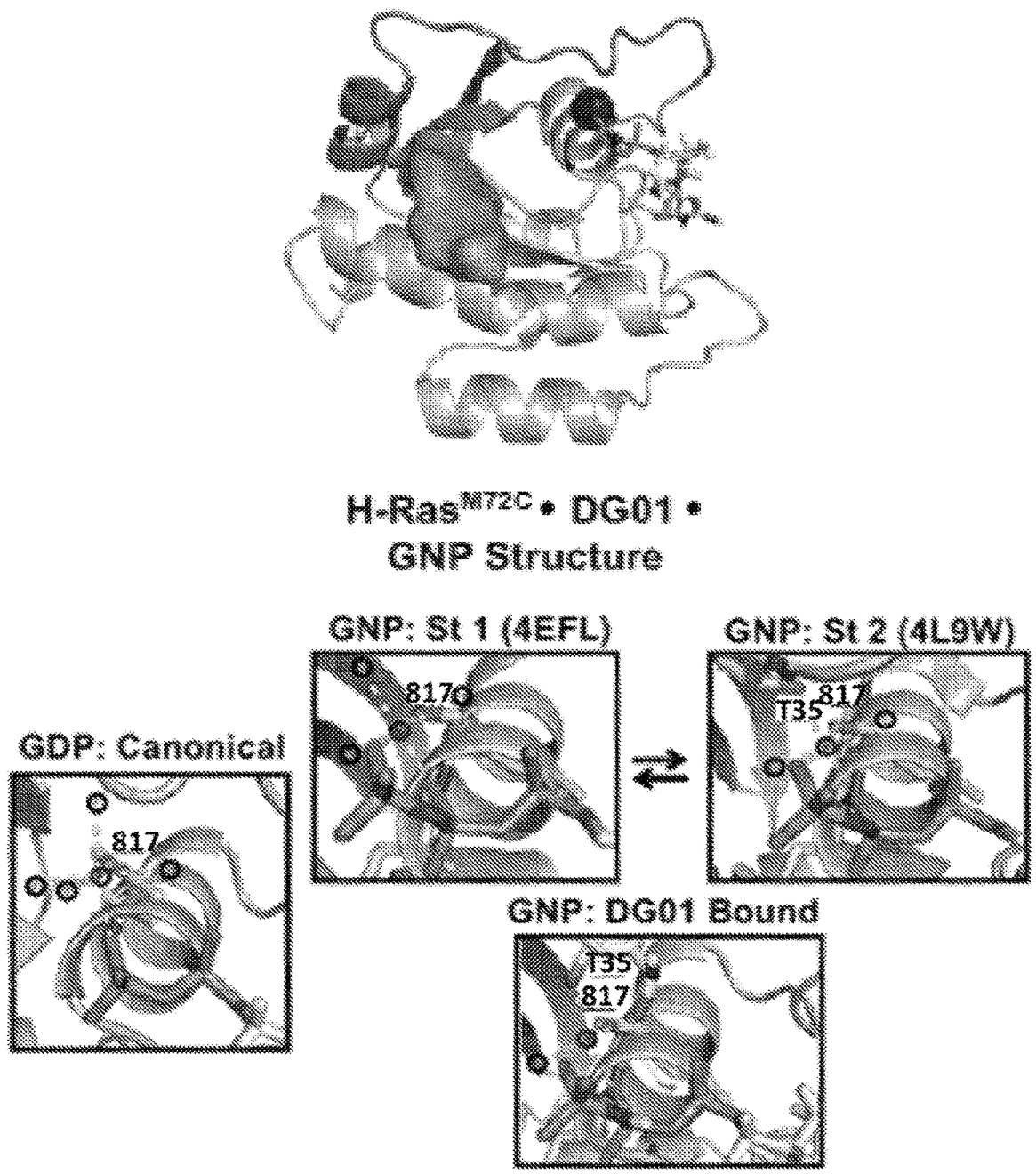

In an aspect is provided a compound including 1) a portion of compound 2C07, 2B09, or 2B02 (FIG. 17B), which does not include —$CH_2CH_2CH_2SSCH_2CH_2N(CH_3)_2$ or —$CH_2CH_2CH_2SSCH_2CH_2NH_2$, and 2) a portion of a compound described in WO2015/054572, which is incorporated herein by reference in its entirety for any purpose; a portion of a compound described in WO2013/155223, which is incorporated herein by reference in its entirety for any purpose; or a portion of compound ARS-853, wherein ARS-853 has the formula:

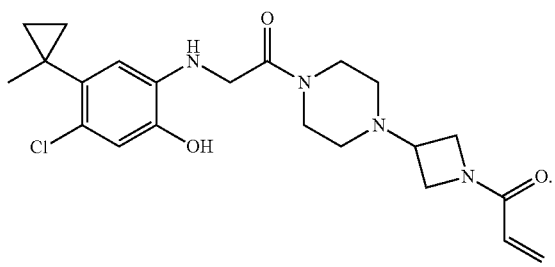 [SMILES: C=CC(=O)N1CC(N2CCN(C(=O)CNc3cc(C4(C)CC4)c(Cl)cc3O)CC2)C1]

Figure 6:
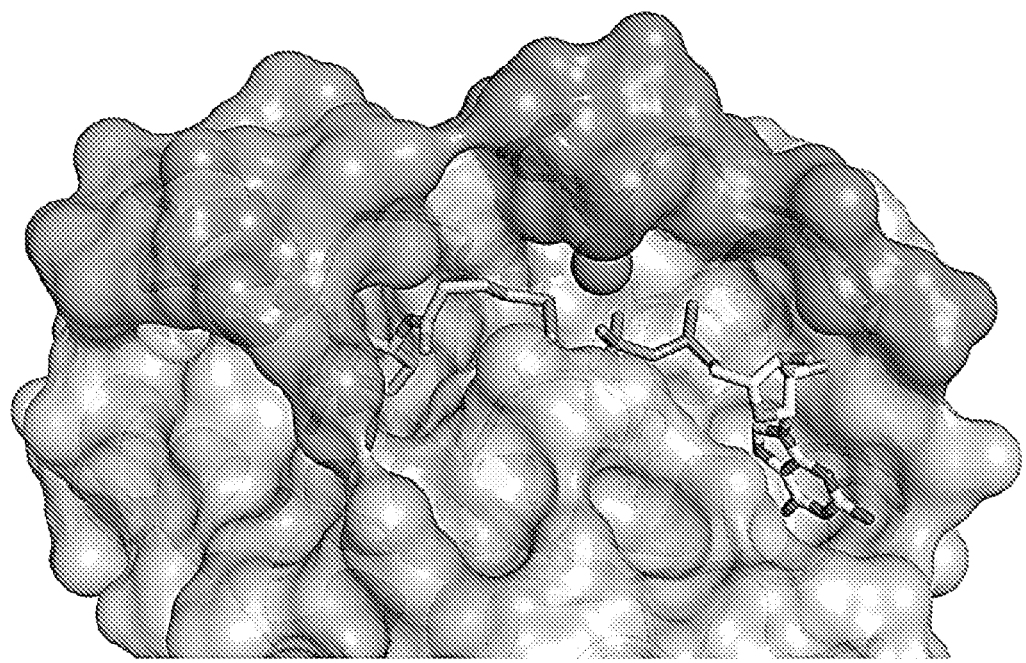
FIG. 6. iRAS148 binds behind Switch II.
Figure 7A:
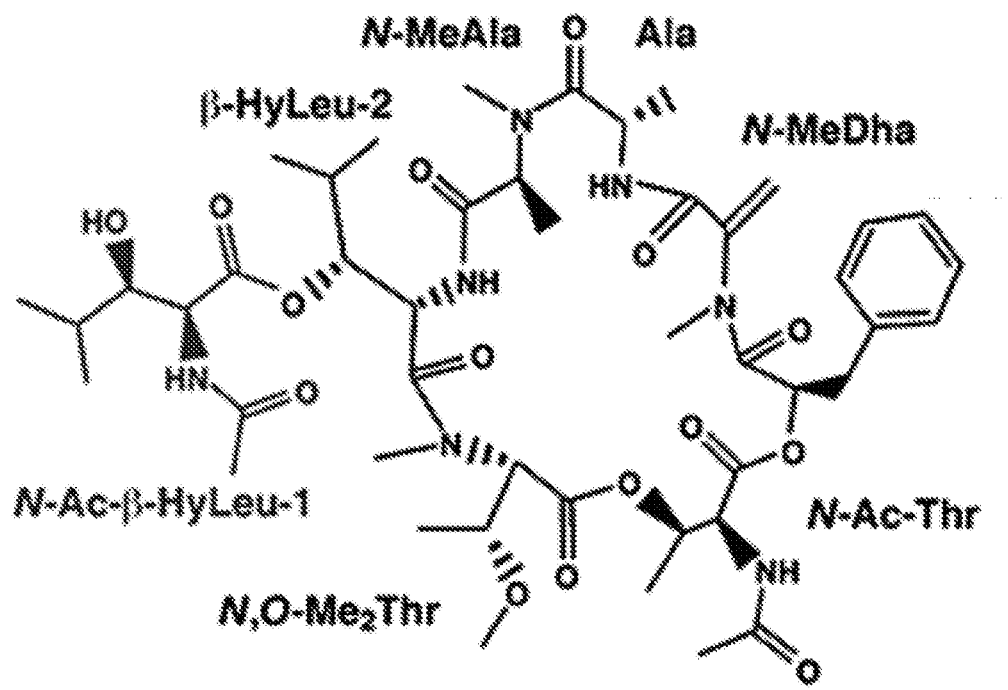
FIGS. 7A-7B. The natural product inhibitory of a GTPase (Gq).
Figure 7B:
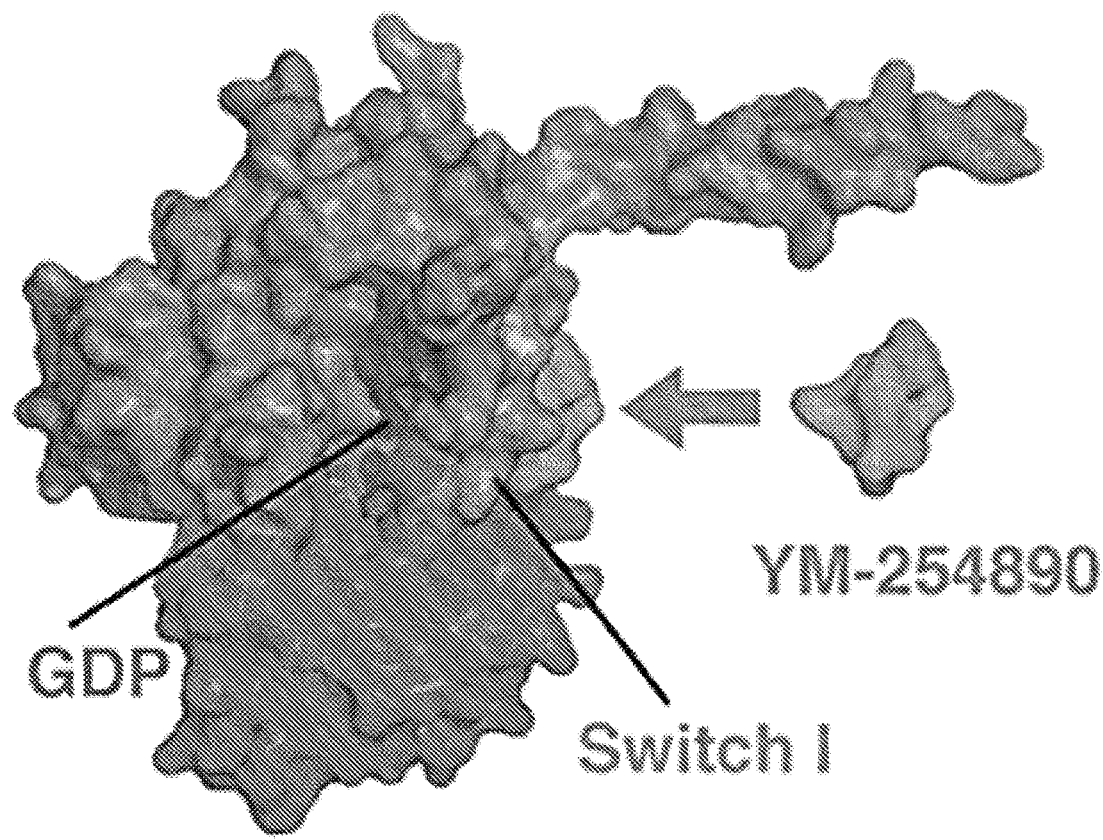
Figure 7B:
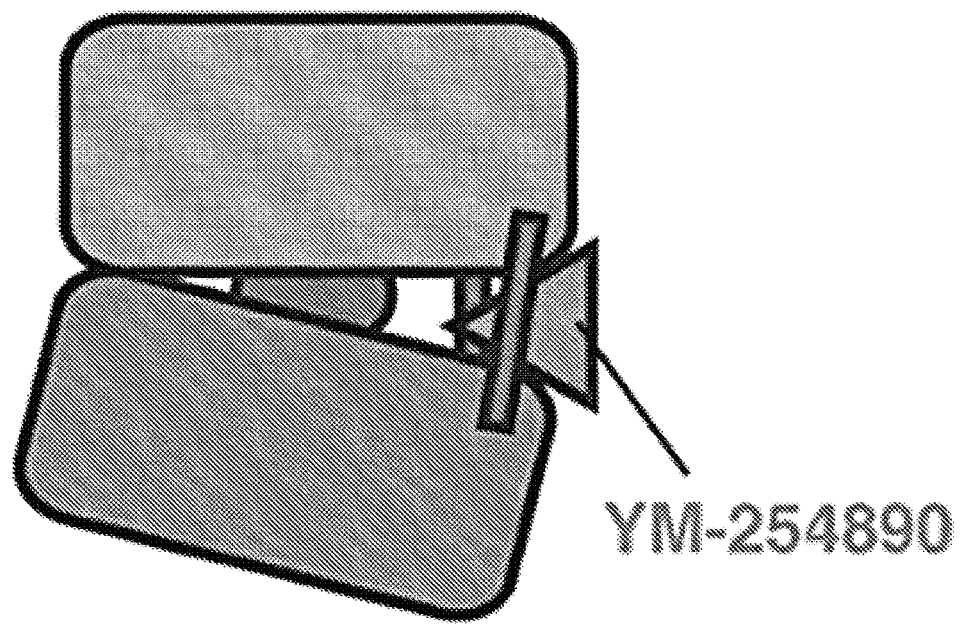
Figure 8:
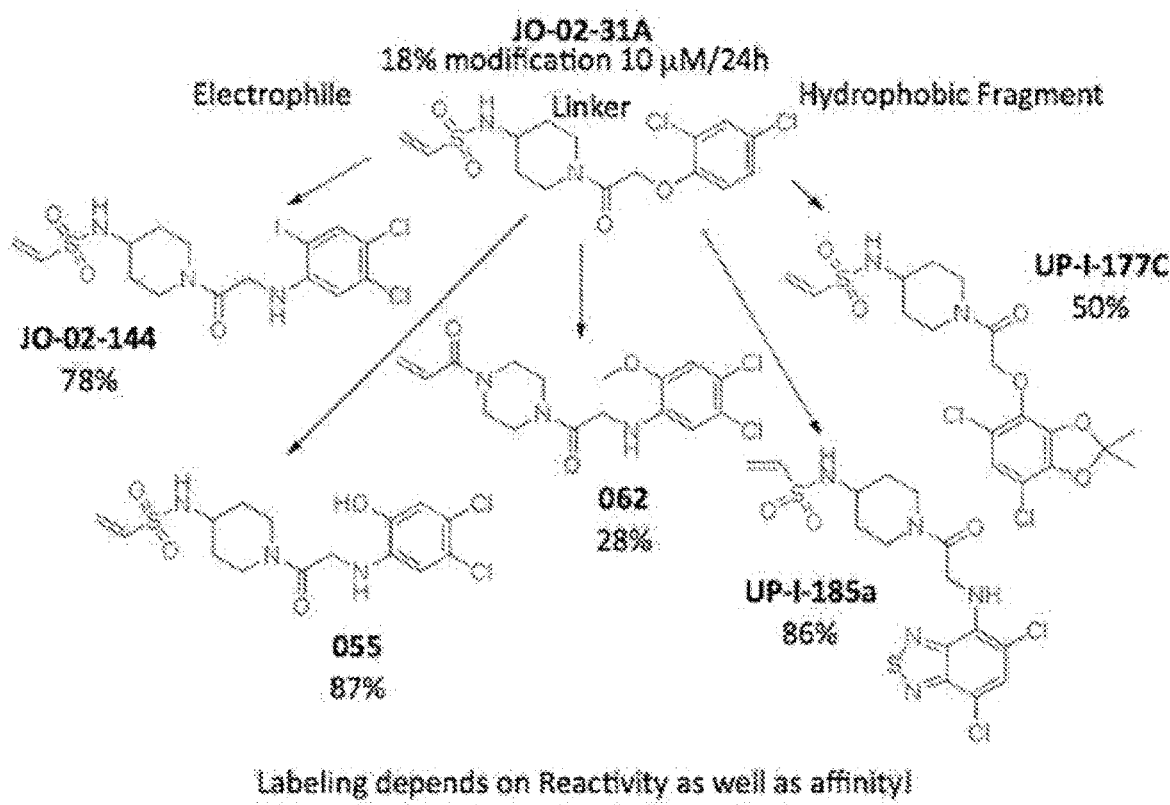
FIG. 8. The optimization of the reversible binding element and the cysteine reactive group.
Figures 9, 10:
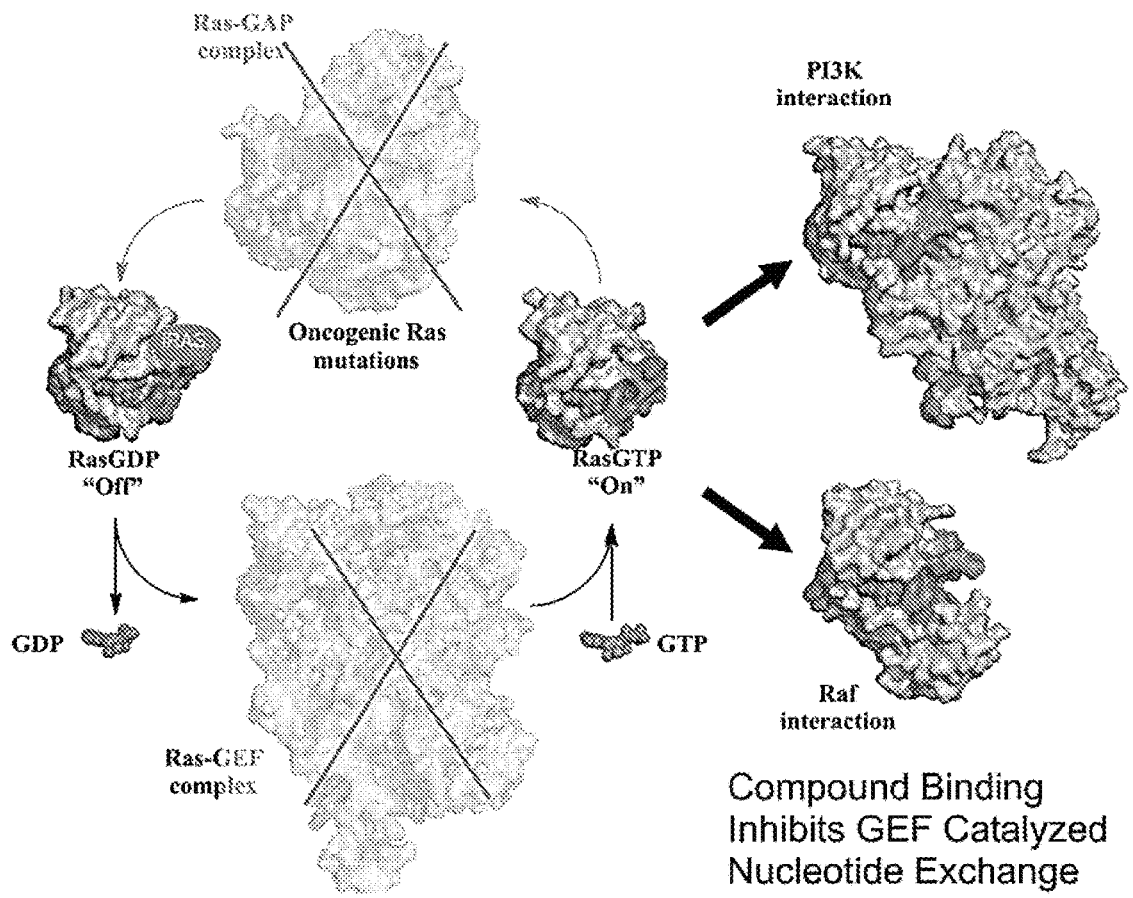
FIG. 9. Effects of the compound binding of the Ras-GTPase Effector cycle. When the compound binds, it inhibits GEF catalyzed nucleotide exchange.
FIG. 10. Increased labeling kinetics correlates with a larger stabilization by thermofluor indicating the potential for K61-specific interactions with DG-3-95A.
Figure 11A:
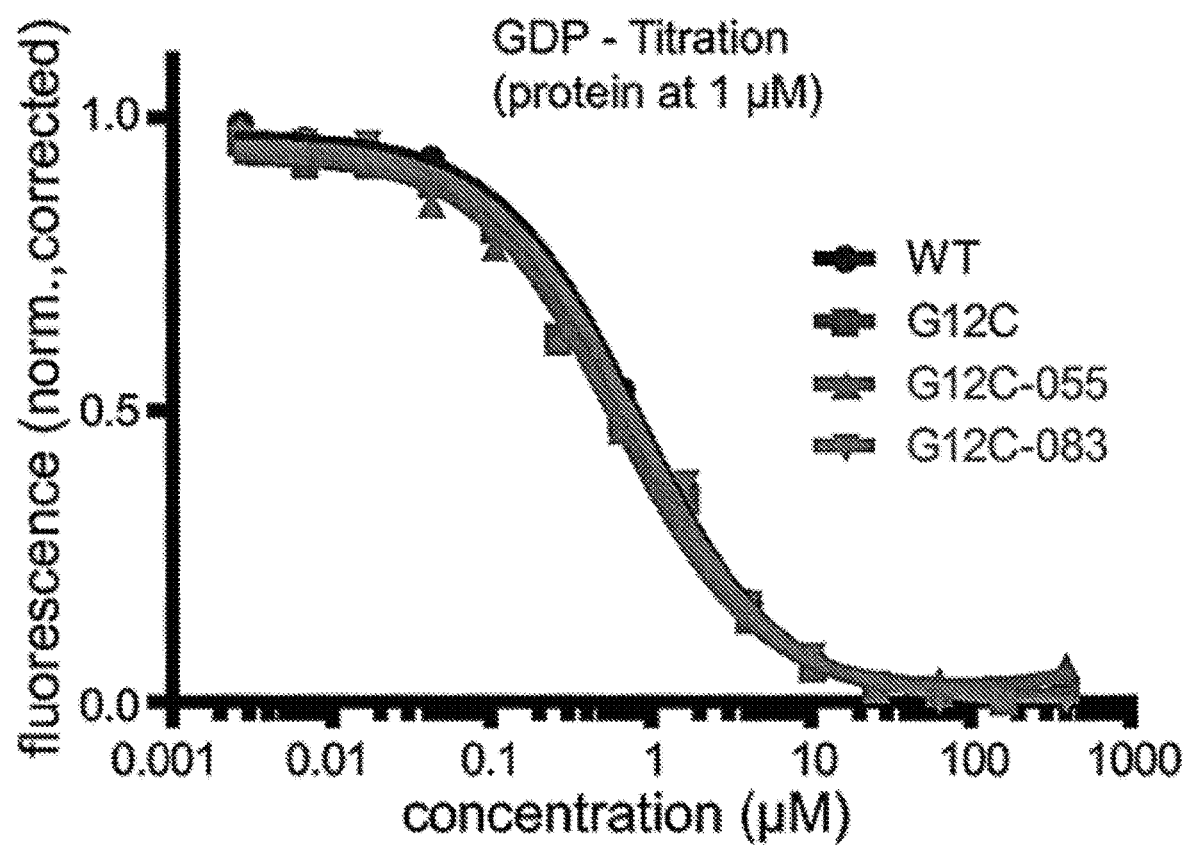
Figure 12A:
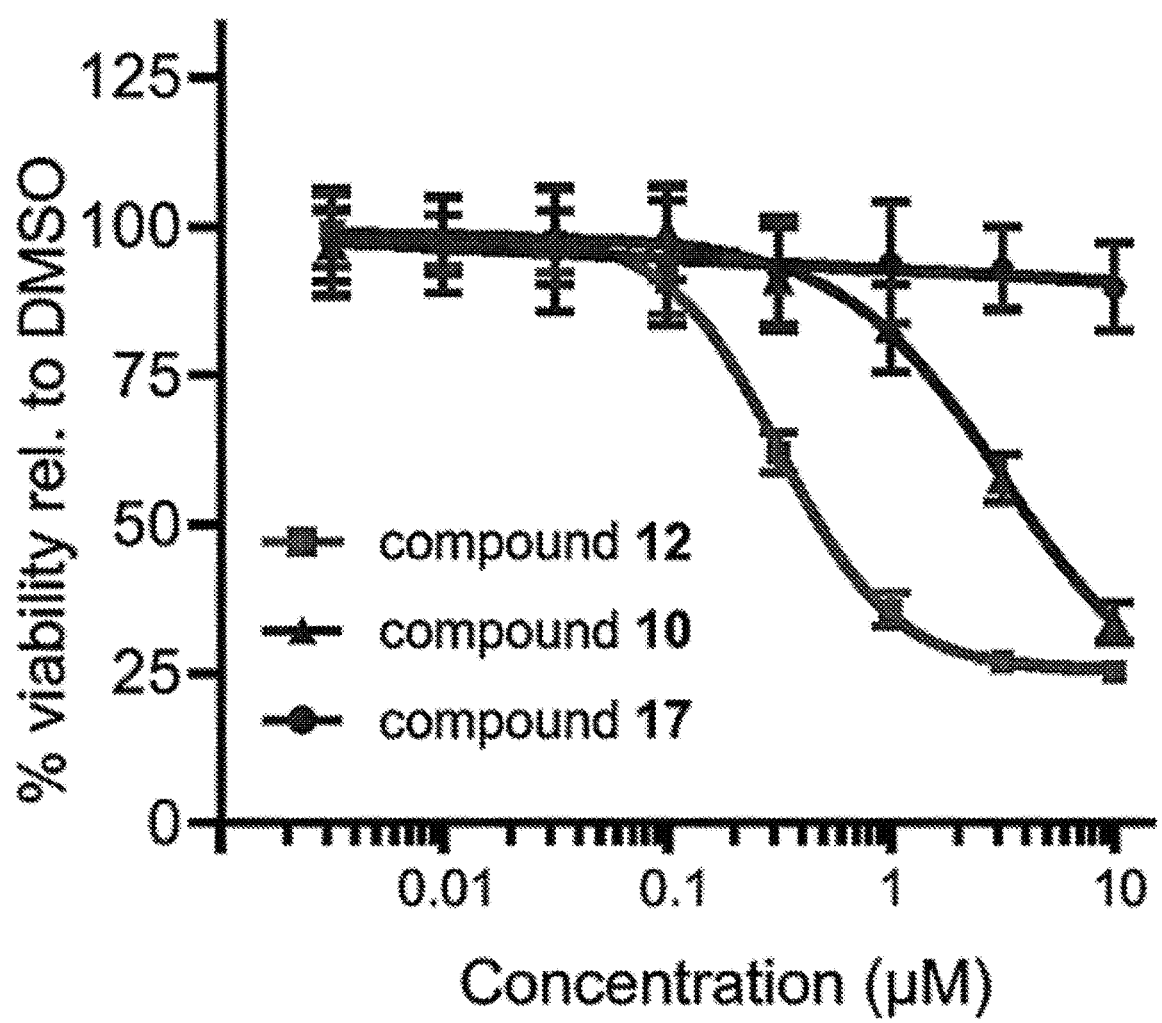
FIGS. 12A-12B. Correlation between biochemical and cellular potency.
Figure 12B:
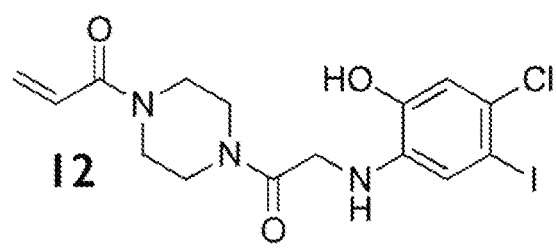
Figure 12B:
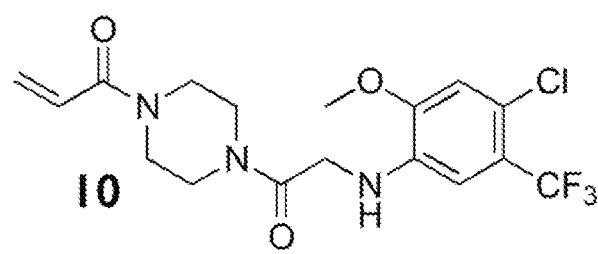
Figure 12B:
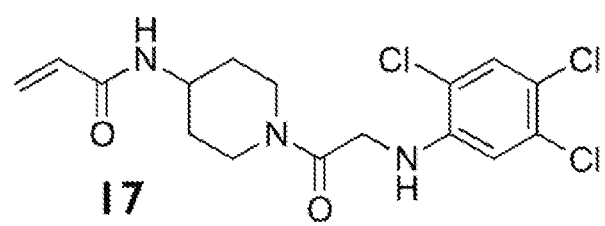
Figure 13:
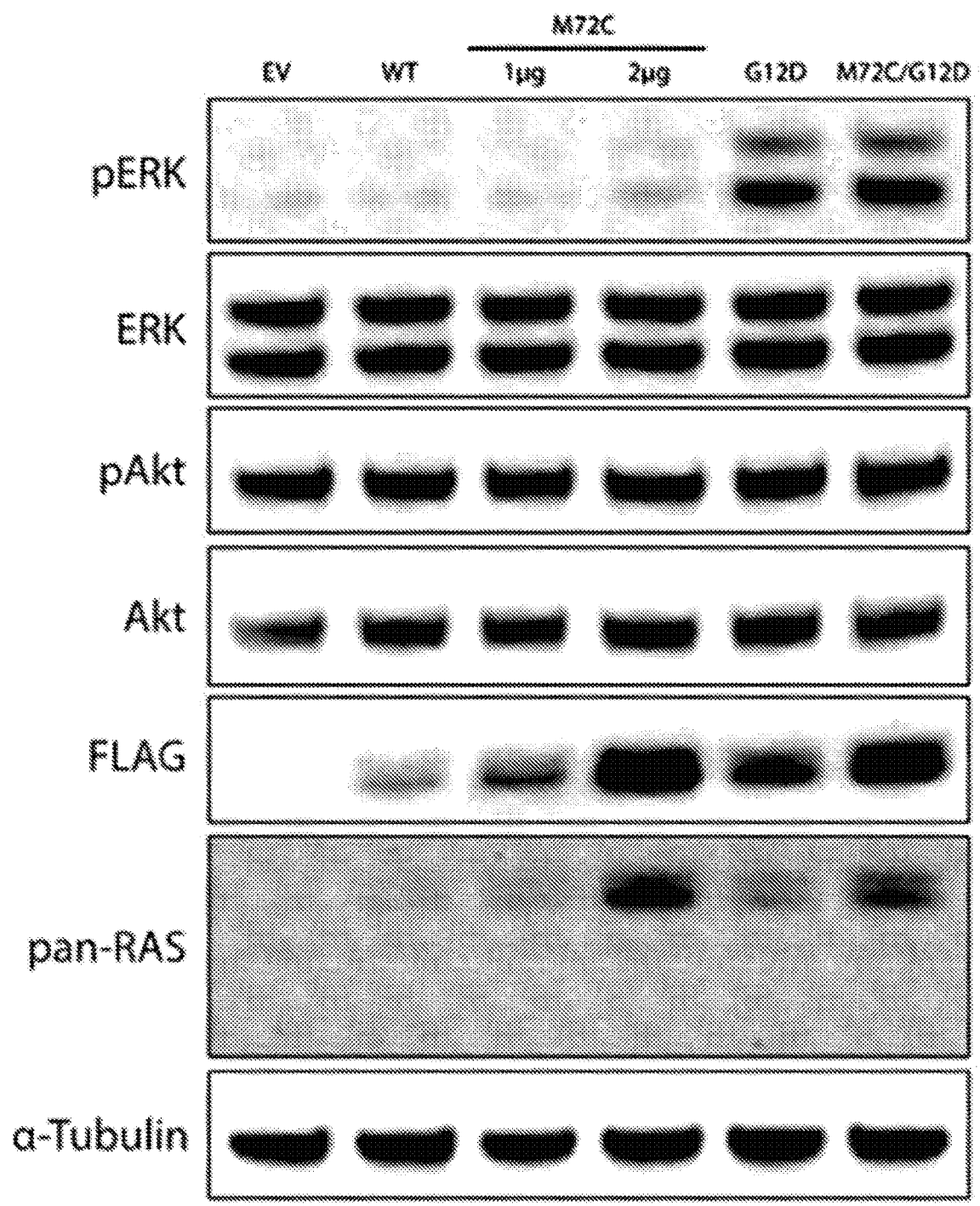
FIG. 13. This blot shows the transient transfection of HEK 293s with various FLAG K-Ras constructs. This experiment indicates that M72C is a silent mutation that has no significant effect on MAPK signaling. It also does not interfere with known oncogenic mutations and their increased flux through the MAPK pathway (i.e. G12D). Preliminary data suggests that M72C is a drug sensitizing mutation that may not affect overall Ras signaling.
Figure 14:
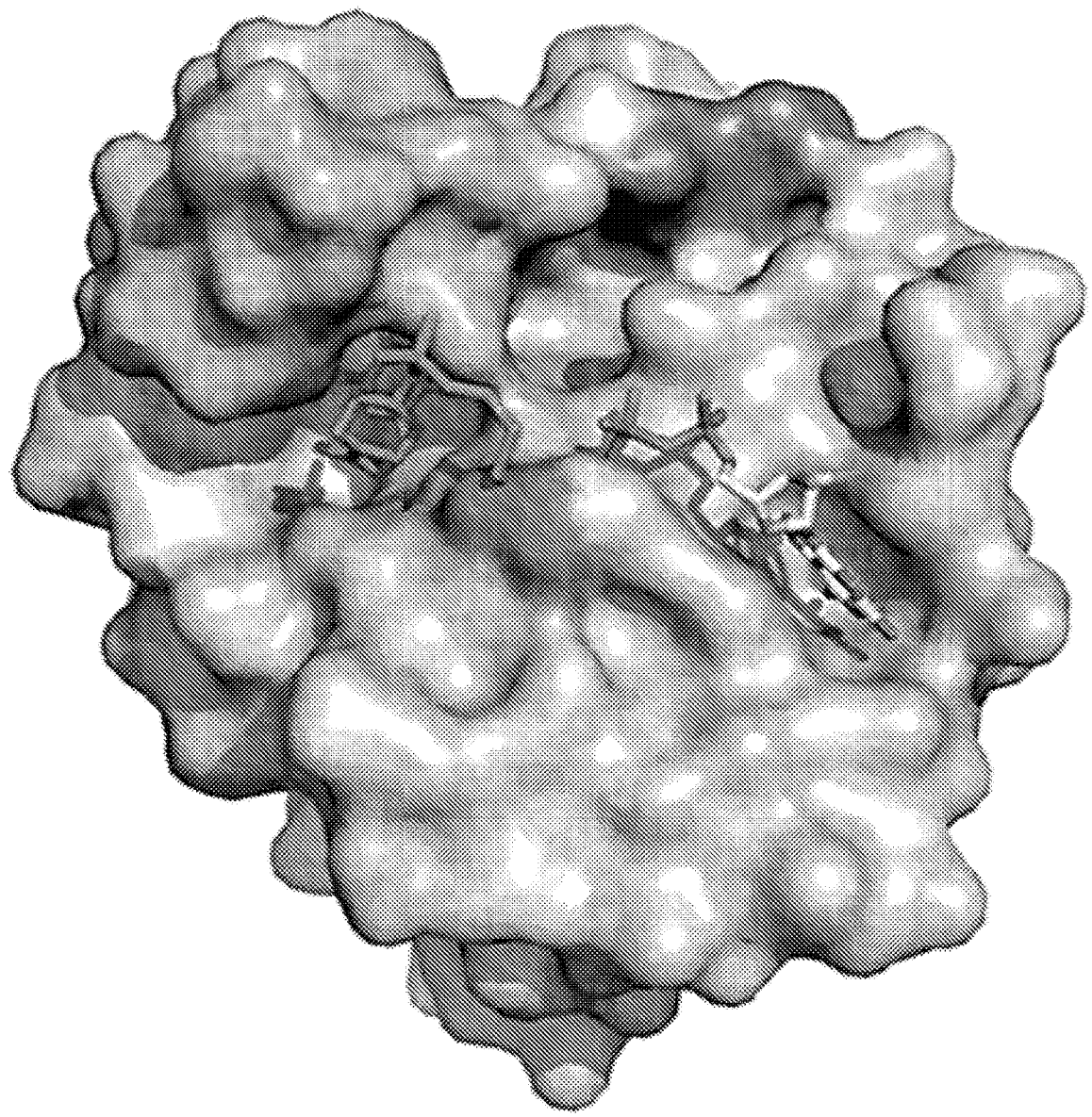
FIG. 14. Crystal structure of the Kras protein.
Figure 15A:
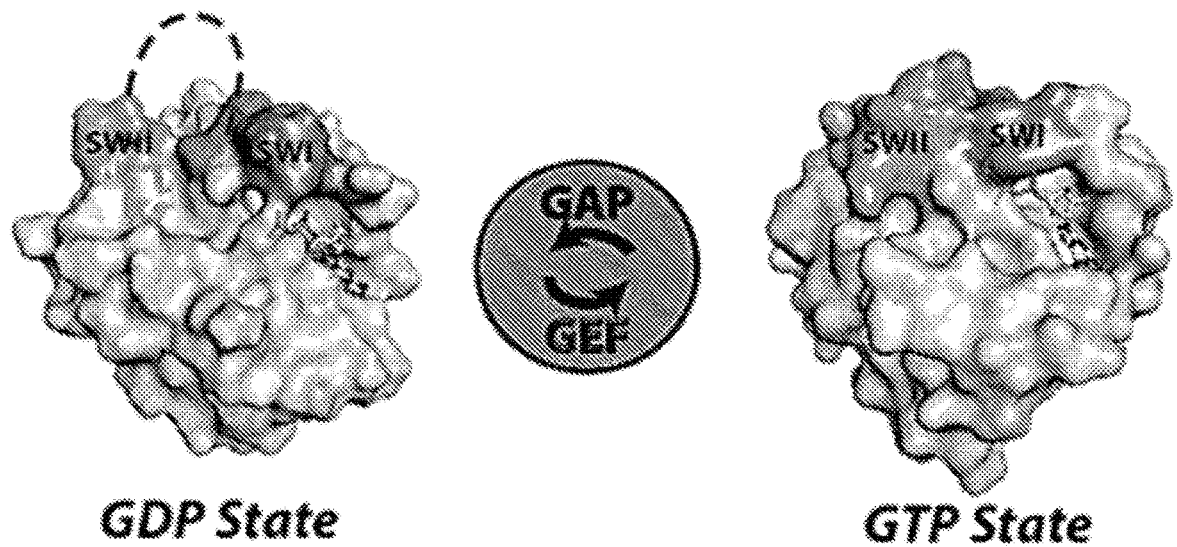
FIGS. 15A-15B. Glutamine 61 is involved in the catalysis of GTP hydrolysis.
Figure 15B:
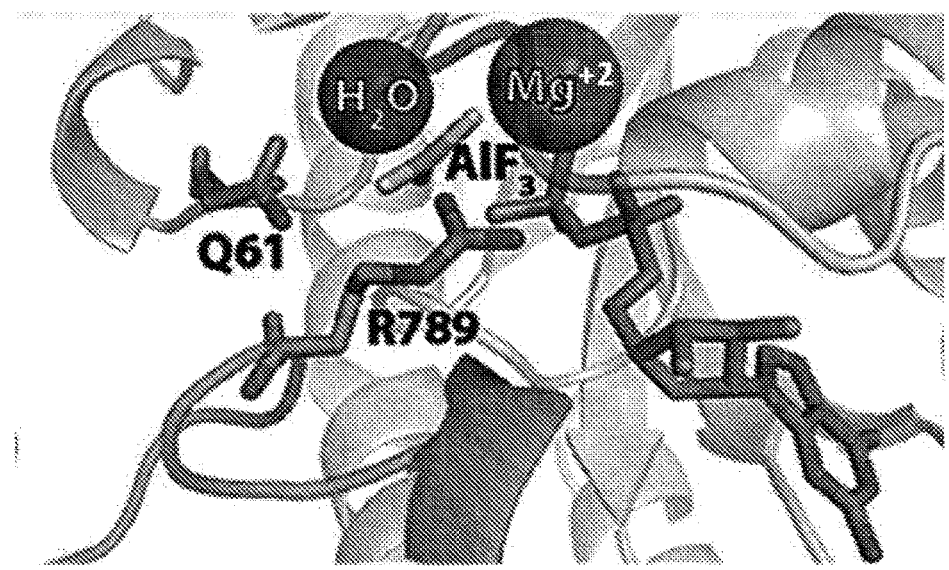
Figure 16:
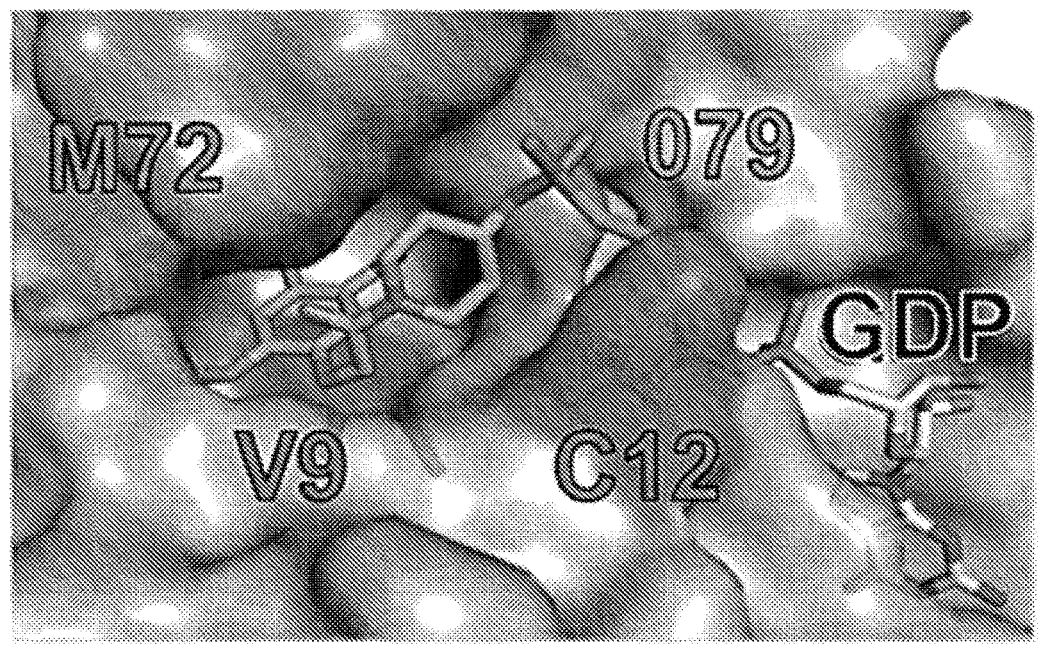
FIG. 16. A zoomed in view of the switch 2 binding pocket. The introduction of an unnatural cysteine in the switch II pocket to develop new probes. Residues M72 and V9 are marked and are proximal to the high affinity region of S-IIP's binding pocket.
Figure 16:
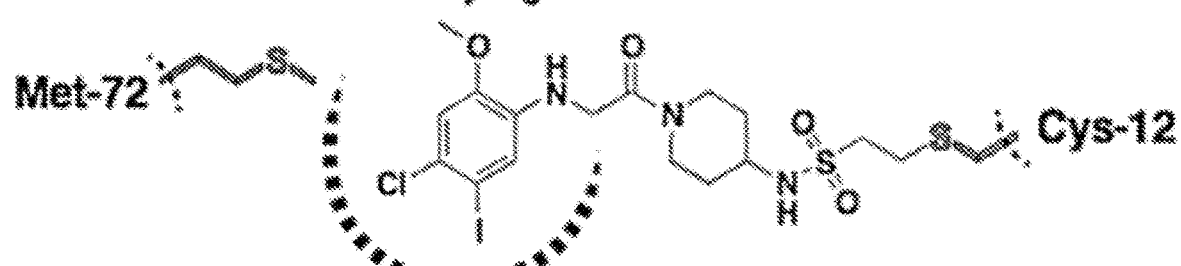

In some embodiments, the compound binds Ras (e.g. K-Ras, H-Ras, N-Ras, mutant Ras, K-Ras G12C, K-Ras G12V, K-Ras G13C, K-Ras G12D, K-Ras G13D) behind Switch II (e.g., behind referring to the cleft behind Switch 2 or the Switch 2—Binding Pocket, or behind referring to the space occupied by iRAS148, as observed in FIG. 6). In embodiments, the compound modulates the conformation of Switch II. In embodiments, the compound modulates the conformation of Switch I. In embodiments, the compound modulates the conformation of Switch I and Switch II. In embodiments, the compound inhibits (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000 fold or more) Ras (e.g. K-Ras, H-Ras, N-Ras, mutant Ras, K-Ras G12C, K-Ras G12V, K-Ras G13C, K-Ras G12D, K-Ras G13D) nucleotide exchange (e.g. GDP for GTP or GTP for GDP) relative to the absence of the compound. In embodiments, the compound inhibits release of GDP from Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound inhibits binding of GDP to Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound inhibits binding of GTP to Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound increases (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000 fold or more) Ras (e.g. K-Ras, H-Ras, N-Ras, mutant Ras, K-Ras G12C, K-Ras G12V, K-Ras G13C, K-Ras G12D, K-Ras G13D) nucleotide exchange (e.g. GDP for GTP or GTP for GDP) relative to the absence of the compound. In embodiments, the compound increases release of GDP from Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound increases release of GTP from Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound increases binding of GDP to Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound inhibits binding of GTP to Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound inhibits binding of a GTP analog (e.g. mant-dGTP) to Ras (e.g. K-Ras, H-Ras, N-Ras, mutant Ras, K-Ras G12C, K-Ras G12V, K-Ras G13C, K-Ras G12D, K-Ras G13D) relative to the absence of the compound. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid that contacts GTP in the absence of the compound. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid that contacts GDP in the absence of the compound. In embodiments, the compound modulates the conformation of a plurality of Ras (e.g. K-Ras, H-Ras, N-Ras, mutant Ras, K-Ras G12C, K-Ras G12V, K-Ras G13C, K-Ras G12D, K-Ras G13D) amino acids that contact GTP in the absence of the compound. In embodiments, the compound modulates the conformation of a plurality of Ras (e.g. K-Ras, H-Ras, N-Ras, mutant Ras, K-Ras G12C, K-Ras G12V, K-Ras G13C, K-Ras G12D, K-Ras G13D) amino acids that contact GDP in the absence of the compound. In embodiments, the compound modulates the binding of GTP and/or GDP to Ras (e.g. K-Ras, H-Ras, N-Ras, mutant Ras, K-Ras G12C, K-Ras G12V, K-Ras G13C, K-Ras G12D, K-Ras G13D) compared to binding in the absence of the compound. In embodiments, the compound modulates the release of GTP and/or GDP from Ras (e.g. K-Ras, H-Ras, N-Ras, mutant Ras, K-Ras G12C, K-Ras G12V, K-Ras G13C, K-Ras G12D, K-Ras G13D) compared to release in the absence of the compound. In embodiments, the compound modulates the ratio of the binding of GTP and GDP to Ras (e.g. K-Ras, H-Ras, N-Ras, mutant Ras, K-Ras G12C, K-Ras G12V, K-Ras G13C, K-Ras G12D, K-Ras G13D) compared to the ratio in the absence of the compound. In embodiments, the compound modulates the ratio of the rate of release of GTP and GDP from Ras (e.g. K-Ras, H-Ras, N-Ras, mutant Ras, K-Ras G12C, K-Ras G12V, K-Ras G13C, K-Ras G12D, K-Ras G13D) compared to the ratio in the absence of the compound. In embodiments, the compound modulates the conformation of a Ras amino acid that contacts the gamma phosphate of GTP when GTP is bound to Ras. In embodiments, the compound inhibits the binding of the gamma phosphate of GTP relative to the binding in the absence of the compound. In embodiments, the compound binds Ras (e.g. K-Ras, H-Ras, N-Ras, mutant Ras, K-Ras G12C, K-Ras G12V, K-Ras G13C, K-Ras G12D, K-Ras G13D) protein bound to GDP and, after release of the GDP, modulates the subsequent binding of GDP or GTP to the Ras bound to the compound. In embodiments, the compound binds Ras (e.g. K-Ras, H-Ras, N-Ras, mutant Ras, K-Ras G12C, K-Ras G12V, K-Ras G13C, K-Ras G12D, K-Ras G13D) protein bound to GDP and, after release of the GDP, modulates the subsequent binding of GDP to the Ras bound to the compound. In embodiments, the compound binds Ras (e.g. K-Ras, H-Ras, N-Ras, mutant Ras, K-Ras G12C, K-Ras G12V, K-Ras G13C, K-Ras G12D, K-Ras G13D) protein bound to GDP and after release of the GDP, modulates the subsequent binding of GTP to the Ras bound to the compound. In embodiments, the compound modulates the hydrolysis of GTP by Ras (e.g. K-Ras, H-Ras, N-Ras, mutant Ras, K-Ras G12C, K-Ras G12V, K-Ras G13C, K-Ras G12D, K-Ras G13D) compared to hydrolysis in the absence of the compound. In embodiments, the compound increases the hydrolysis of GTP by Ras (e.g. K-Ras, H-Ras, N-Ras, mutant Ras, K-Ras G12C, K-Ras G12V, K-Ras G13C, K-Ras G12D, K-Ras G13D) compared to hydrolysis in the absence of the compound. In embodiments, the compound increases the hydrolysis rate of GTP by Ras (e.g. K-Ras, H-Ras, N-Ras, mutant Ras, K-Ras G12C, K-Ras G12V, K-Ras G13C, K-Ras G12D, K-Ras G13D) compared to hydrolysis in the absence of the compound. In embodiments, the compound decreases the hydrolysis of GTP by Ras (e.g. K-Ras, H-Ras, N-Ras, mutant Ras, K-Ras G12C, K-Ras G12V, K-Ras G13C, K-Ras G12D, K-Ras G13D) compared to hydrolysis in the absence of the compound. In embodiments, the compound decreases the hydrolysis rate of GTP by Ras (e.g. K-Ras, H-Ras, N-Ras, mutant Ras, K-Ras G12C, K-Ras G12V, K-Ras G13C, K-Ras G12D, K-Ras G13D) compared to hydrolysis in the absence of the compound. In embodiments, the compound binds Ras (e.g. K-Ras, H-Ras, N-Ras, mutant Ras, K-Ras G12C, K-Ras G12V, K-Ras G13C, K-Ras G12D, K-Ras G13D) protein bound to GTP and, after release of GDP, modulates the subsequent binding of GDP or GTP to the Ras bound to the compound. In embodiments, the compound binds Ras (e.g. K-Ras, H-Ras, N-Ras, mutant Ras, K-Ras G12C, K-Ras G12V, K-Ras G13C, K-Ras G12D, K-Ras G13D) protein bound to GTP and, after release of GDP, modulates the subsequent binding of GTP to the Ras bound to the compound. In embodiments, the compound binds Ras (e.g. K-Ras, H-Ras, N-Ras, mutant Ras, K-Ras G12C, K-Ras G12V, K-Ras G13C, K-Ras G12D, K-Ras G13D) protein bound to GTP and after release of GDP, modulates the subsequent binding of GDP to the Ras bound to the compound.

In embodiments, the compound inhibits proliferation of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under serum deprivation conditions relative to the absence of the compound. In embodiments, the compound inhibits proliferation of cancer cells under serum deprivation conditions relative to the absence of the compound. In embodiments, the compound inhibits growth of cancer cells under conditions (e.g. local cell environment in a patient) mimicking serum deprivation relative to the absence of the compound. In embodiments, the compound inhibits proliferation of cancer cells under conditions (e.g. local cell environment in a patient) mimicking serum deprivation relative to the absence of the compound.

In embodiments, the compound modulates the conformation of the amino acid corresponding to amino acid 60 in human K-Ras in a Ras protein. In embodiments, the compound modulates the distance between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G12V, K-Ras G13C, K-Ras G12D, K-Ras G13D). In embodiments the compound increases the distance between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G12V, K-Ras G13C, K-Ras G12D, K-Ras G13D). In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras K-Ras G12V, G12C, K-Ras G13C, K-Ras G12D, K-Ras G13D) relative to the absence of the compound. In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G12V, K-Ras G13C, K-Ras G12D, K-Ras G13D) when bound to GDP, relative to the absence of the compound. In embodiments the compound increases the distance (e.g. by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, or more angstroms) between the alpha carbon of the amino acid corresponding to amino acid 12 in human K-Ras and the alpha carbon of the amino acid corresponding to amino acid 60 in human K-Ras, in a Ras protein (e.g. K-Ras, H-Ras, N-Ras, mutant Ras, K-Ras G12C, K-Ras G12V, K-Ras G13C, K-Ras G12D, K-Ras G13D) when bound to GTP, compared to the distance in the absence of the compound. In embodiments, upon binding to Ras (e.g. K-Ras, H-Ras, N-Ras, mutant Ras, K-Ras G12C, K-Ras G12V, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G12V, K-Ras G13C, K-Ras G12D, K-Ras G13D) to be about 4.9 angstoms or greater (e.g. about 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G12V, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G12V, K-Ras G13C, K-Ras G12D, K-Ras G13D) to be greater than about 4.9 angstoms (e.g. greater than about 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G12V, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G12V, K-Ras G13C, K-Ras G12D, K-Ras G13D) to be 4.9 angstoms or greater (e.g. 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater). In embodiments, upon binding to Ras (e.g. K-Ras, H-Ras, N-Ras, mutant Ras, K-Ras G12C, K-Ras G12V, K-Ras G13C, K-Ras G12D, K-Ras G13D) the compound (e.g. a compound described herein, including embodiments and including a compound described in a table, example, or figure) modulates the distance between the alpha carbon of the amino acid corresponding to amino acid 12 in human K-Ras and the alpha carbon of the amino acid corresponding to amino acid 60 in human K-Ras, in the Ras protein (e.g. K-Ras, H-Ras, N-Ras, mutant Ras, K-Ras G12C, K-Ras G12V, K-Ras G13C, K-Ras G12D, K-Ras G13D) to be greater than 4.9 angstoms (e.g. greater than 5.0, 5.1, 5.2, 5.3, 5.4, 5.5, 5.6, 5.7, 5.8, 5.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0 angstroms, or greater).

In embodiments, the compound increases the flexibility of Switch I relative to the absence of the compound. In embodiments, the compound increases the disorder of Switch I relative to the absence of the compound. In embodiments, the compound inhibits the binding of Ras (e.g. K-Ras, H-Ras, N-Ras, mutant Ras, K-Ras G12C, K-Ras G12V, K-Ras G13C, K-Ras G12D, K-Ras G13D) to another protein. In embodiments, the compound inhibits the binding of Ras (e.g. K-Ras, H-Ras, N-Ras, mutant Ras, K-Ras G12C, K-Ras G12V, K-Ras G13C, K-Ras G12D, K-Ras G13D) to another protein, wherein the binding is dependent on Ras binding to GTP. In embodiments, the compound inhibits the binding of Ras (e.g. K-Ras, H-Ras, N-Ras, mutant Ras, K-Ras G12C, K-Ras G12V, K-Ras G13C, K-Ras G12D, K-Ras G13D) to another protein, wherein the binding is dependent on Ras binding to GDP. In embodiments, the compound inhibits the binding of Ras (e.g. K-Ras, H-Ras, N-Ras, mutant Ras, K-Ras G12C, K-Ras G12V, K-Ras G13C, K-Ras G12D, K-Ras G13D) to Raf (e.g. Raf1). In embodiments, the compound inhibits the binding of Ras (e.g. K-Ras, H-Ras, N-Ras, mutant Ras, K-Ras G12C, K-Ras G12V, K-Ras G13C, K-Ras G12D, K-Ras G13D) to SOS. In embodiments, the compound inhibits the binding of Ras (e.g. K-Ras, H-Ras, N-Ras, mutant Ras) to a GEF. In embodiments, the compound inhibits the binding of Ras (e.g. K-Ras, H-Ras, N-Ras, mutant Ras, K-Ras G12C, K-Ras G12V, K-Ras G13C, K-Ras G12D, K-Ras G13D) to PI3K. In embodiments, the compound modulates metal binding near the nucleotide binding site. In embodiments, the compound modulates the conformation of the Ras metal binding site near the nucleotide binding site. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid relative to the conformation in the absence of the compound, wherein the Ras amino acid conformation is also modulated by a Ras G60 mutation. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid relative to the conformation in the absence of the compound, wherein the Ras amino acid conformation is also modulated by a Ras G60A mutation. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid relative to the conformation in the absence of the compound, wherein the Ras amino acid conformation is also modulated by a Ras T35 mutation. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid relative to the conformation in the absence of the compound, wherein the Ras amino acid conformation is also modulated by a Ras T35S mutation. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid relative to the conformation in the absence of the compound, wherein the Ras amino acid conformation is also modulated by a mutation of the Ras amino acid corresponding to K-Ras G60. In embodiments, the compound modulates the conformation of a Ras (e.g. K-Ras, H-Ras, N-Ras, mutant Ras, K-Ras G12C, K-Ras G12V, K-Ras G13C, K-Ras G12D, K-Ras G13D) amino acid relative to the conformation in the absence of the compound, wherein the Ras amino acid conformation is also modulated by a mutation of the Ras amino acid corresponding to K-Ras T35.

The crystal structures of Hras and Kras bound to GTP show a contact between the gamma phosphate and the backbone amide of glycine-60 in switch II. This contact is known to be critical for orienting the switches for binding to downstream effectors. This conformation required for binding downstream effectors is called state 2. Mutation of glycine-60 to alanine (G60A) prevents proper rotation of residue-60 upon GTP binding, and induces an alternate conformation called state 1. In this conformation, the gamma phosphate of GTP forms a water-mediated hydrogen bond to alanine-60, which likely acts to maintain GTP affinity. Similarly, direct contacts between the gamma phosphate and switch I are replaced by water-mediated contacts. The complete loss of these contacts to the gamma phosphate would be likely to decrease the affinity of Ras for GTP, having less effect on the affinity for GDP.

The state 1 conformation can also be stabilized by mutating threonine-35 to serine (T35S), and the GTP-bound crystal structure of this mutant is known. A crystal structure of the wild-type protein in state 1 has also been solved. The conformation of Ras (state 1 or state 2) could be predicted by measuring the distance between the alpha carbon of residue-60 and the alpha carbon of residue-12. If this distance is 3.9 Å or less, direct contacts between the gamma phosphate and the switches are possible and the protein adopts state 2. If this distance is 4.9 Å or greater, these direct contacts are no longer possible and the protein adopts state 1.

In embodiments, the compound binds Ras (e.g., K-Ras, H-Ras, human K-Ras, human H-Ras) protein contacting GDP. In embodiments, the compound binds Ras (e.g., K-Ras, H-Ras, human K-Ras, human H-Ras) protein contacting GTP. In embodiments, the compound binds Ras (e.g., K-Ras, H-Ras, human K-Ras, human H-Ras) protein contacting GDP or GTP.

In embodiments, the compound modulates Ras (e.g., K-Ras, H-Ras, human K-Ras, human H-Ras) protein binding to GTP (e.g., modifies protein-GTP interactions compared to control). In embodiments, the compound modulates Ras (e.g., K-Ras, H-Ras, human K-Ras, human H-Ras) protein binding to GDP (e.g., modifies protein-GDP interactions compared to control).

In embodiments, the compound modulates the relative binding affinity of Ras (e.g., K-Ras, H-Ras, human K-Ras, human H-Ras) protein to GDP compared to GTP. In embodiments, the compound reduces the relative binding affinity of Ras (e.g., K-Ras, H-Ras, human K-Ras, human H-Ras) protein to GDP compared to GTP. In embodiments, the compound increases the relative binding affinity of Ras (e.g., K-Ras, H-Ras, human K-Ras, human H-Ras) protein to GDP compared to GTP.

In embodiments, the compound modulates Ras (e.g., K-Ras, H-Ras, human K-Ras, human H-Ras) protein binding to a guanine nucleotide exchange factor (GEF) (e.g., SOS, human SOS1, human SOS2). In embodiments, the compound reduces Ras (e.g., K-Ras, H-Ras, human K-Ras, human H-Ras) protein binding to a guanine nucleotide exchange factor (GEF) (e.g., SOS, human SOS1, human SOS2). In embodiments, the compound inhibits Ras (e.g., K-Ras, H-Ras, human K-Ras, human H-Ras) protein binding to a guanine nucleotide exchange factor (GEF) (e.g., SOS, human SOS1, human SOS2). In embodiments, the compound modulates Ras (e.g., K-Ras, H-Ras, human K-Ras, human H-Ras) protein binding to a PI3K (e.g., PI3K alpha, PI3K beta, PI3K delta, PI3K gamma). In embodiments, the compound reduces Ras (e.g., K-Ras, H-Ras, human K-Ras, human H-Ras) protein binding to a PI3K (e.g., PI3K alpha, PI3K beta, PI3K delta, PI3K gamma). In embodiments, the compound inhibits Ras (e.g., K-Ras, H-Ras, human K-Ras, human H-Ras) protein binding to a PI3K (e.g., PI3K alpha, PI3K beta, PI3K delta, PI3K gamma). In embodiments, the compound modulates Ras (e.g., K-Ras, H-Ras, human K-Ras, human H-Ras) protein binding to Raf protein. In embodiments, the compound does not modulate Ras (e.g., K-Ras, H-Ras, human K-Ras, human H-Ras) protein binding to Raf protein.

In embodiments, the compound modulates Ras (e.g., K-Ras, H-Ras, human K-Ras, human H-Ras) protein nucleotide exchange (e.g., binding of GTP, release of GDP). In embodiments, the compound inhibits Ras (e.g., K-Ras, H-Ras, human K-Ras, human H-Ras) protein nucleotide exchange (e.g., binding of GTP, release of GDP).

In embodiments, the compound modulates contact between Ras (e.g., K-Ras, H-Ras, human K-Ras, human H-Ras) protein and GTP. In embodiments, the compound inhibits contact between Ras (e.g., K-Ras, H-Ras, human K-Ras, human H-Ras) protein and GTP. In embodiments, the compound modulates contact between the Ras (e.g., K-Ras, H-Ras, human K-Ras, human H-Ras) amino acid corresponding to human H-Ras Y32 and GTP. In embodiments, the compound inhibits contact between the Ras (e.g., K-Ras, H-Ras, human K-Ras, human H-Ras) amino acid corresponding to human H-Ras Y32 and GTP. In embodiments, the compound modulates contact between the Ras (e.g., K-Ras, H-Ras, human K-Ras, human H-Ras) amino acid corresponding to human K-Ras Y32 and GTP. In embodiments, the compound inhibits contact between the Ras (e.g., K-Ras, H-Ras, human K-Ras, human H-Ras) amino acid corresponding to human K-Ras Y32 and GTP.

In some embodiments, a compound as described herein may include multiple instances of $R^1$, $R^2$, $R^3$, $R^4$, $R^6$, $R^7$, and/or other variables. In such embodiments, each variable may optional be different and be appropriately labeled to distinguish each group for greater clarity. For example, where each $R^1$, $R^2$, $R^3$, $R^4$, $R^6$, and/or $R^7$, is different, they may be referred to, for example, as $R^{1.1}$, $R^{1.2}$, $R^{1.3}$, $R^{1.4}$, $R^{1.5}$, $R^{2.1}$, $R^{2.2}$, $R^{2.3}$, $R^{3.1}$, $R^{3.2}$, $R^{3.3}$, $R^{3.4}$, $R^{3.5}$, $R^{4.1}$, $R^{4.2}$, $R^{6.1}$, $R^{6.2}$, $R^{6.3}$, $R^{6.4}$, $R^{6.5}$, $R^{6.6}$, $R^{6.7}$, $R^{6.8}$, $R^{7.1}$, $R^{7.2}$, $R^{7.3}$, $R^{7.4}$, respectively, wherein the definition of $R^1$ is assumed by $R^{1.1}$, $R^{1.2}$, $R^{1.3}$, $R^{1.4}$, $R^{15}$, the definition of $R^2$ is assumed by $R^{2.1}$, $R^{2.2}$, $R^{2.3}$, the definition of $R^3$ is assumed by $R^{3.1}$, $R^{3.2}$, $R^{3.3}$, $R^{3.4}$, $R^{3.5}$, the definition of $R^4$ is assumed by $R^{4.1}$, $R^{4.2}$, the definition of $R^6$ is assumed by $R^{6.1}$, $R^{6.2}$, $R^{6.3}$, $R^{6.4}$, $R^{6.5}$, $R^{6.6}$, $R^{6.7}$, $R^{6.8}$, the definition of $R^7$ is assumed by $R^{7.1}$, $R^{7.2}$, $R^{7.3}$, $R^{7.4}$.

The variables used within a definition of $R^1$, $R^2$, $R^3$, $R^4$, $R^6$, $R^7$, and/or other variables that appear at multiple instances and are different may similarly be appropriately labeled to distinguish each group for greater clarity.

III. Pharmaceutical Compositions and Methods

In an aspect, is provided a pharmaceutical composition including a pharmaceutically acceptable excipient and a compound described herein. In embodiments, the compound is in an effective (e.g., therapeutically effective) amount. In embodiments, the pharmaceutical composition includes a second agent (e.g., an anti-cancer agent). In embodiments, the pharmaceutical composition includes a second agent (e.g, an anti-cancer agent) in an effective (e.g., therapeutically effective) amount.

In an aspect is provided a pharmaceutical composition including a pharmaceutically acceptable excipient and a compound as described herein.

In an aspect is provided a method of treating a disease in a patient in need of such treatment, the method including administering a therapeutically effective amount of a compound as described herein to the patient. In embodiments, the disease is cancer. In embodiments, the cancer is lung cancer, colon cancer, colorectal cancer, pancreatic cancer, breast cancer, or leukemia. In embodiments, the cancer is lung cancer. In embodiments, the cancer is colon cancer. In embodiments, the cancer is colorectal cancer. In embodiments, the cancer is pancreatic cancer. In embodiments, the cancer is breast cancer. In embodiments, the cancer is leukemia.

In an aspect is provided a method of modulating the activity of a Ras protein (e.g., K-Ras, H-Ras, N-Ras, human K-Ras, human H-Ras, or human N-Ras), the method including contacting the Ras protein (e.g., K-Ras, H-Ras, N-Ras, human K-Ras, human H-Ras, or human N-Ras) with an effective amount of a compound as described herein. In embodiments, the Ras protein is K-Ras. In embodiments, the Ras protein is H-Ras. In embodiments, the Ras protein is N-Ras. In embodiments, the Ras protein is human K-Ras. In embodiments, the Ras protein is human H-Ras. In embodiments, the Ras protein is human N-Ras.

In embodiments, the activity includes modulating GTPase activity, nucleotide exchange, GDP binding, GTP binding, differential GDP or GTP binding, effector protein binding, K-Ras binding to Raf, effector protein activation, guanine exchange factor (GEF) binding, GEF-facilitated nucleotide exchange, phosphate release, nucleotide release, nucleotide binding, K-Ras subcellular localization, K-Ras post-translational processing, or K-Ras post-translational modifications. In embodiments, the modulating is reducing the activity of the K-Ras protein. In embodiments, the K-Ras protein is a human K-Ras protein. In embodiments, the human K-Ras protein contains a G12C, G12V, G12D, G13C, or G13D mutation. In embodiments, the human K-Ras protein contains a G12C mutation. In embodiments, the human K-Ras protein contains a G12V mutation. In embodiments, the human K-Ras protein contains a G12D mutation. In embodiments, the human K-Ras protein contains a G13C mutation. In embodiments, the human K-Ras protein contains a G13D mutation.

In an aspect is provided a method of modulating a Ras protein (e.g., K-Ras, H-Ras, N-Ras, human K-Ras, human H-Ras, or human N-Ras), the method including contacting the Ras protein (e.g., K-Ras, H-Ras, N-Ras, human K-Ras, human H-Ras, or human N-Ras) with an effective amount of a compound as described herein. In embodiments, the Ras protein is K-Ras. In embodiments, the Ras protein is H-Ras. In embodiments, the Ras protein is N-Ras. In embodiments, the Ras protein is human K-Ras. In embodiments, the Ras protein is human H-Ras. In embodiments, the Ras protein is human N-Ras.

In embodiments, the compound contacts at least one amino acid residue forming a Switch 2 binding pocket of the Ras protein (e.g., K-Ras, H-Ras, N-Ras, human K-Ras, human H-Ras, or human N-Ras), wherein the at least one amino acid residue is V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 of the Ras protein. In embodiments, the compound covalently reacts with an amino acid residue of the Ras protein (e.g., K-Ras, H-Ras, N-Ras, human K-Ras, human H-Ras, or human N-Ras). In embodiments, the compound contacts V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 of the Ras protein. In embodiments, the compound contacts V9, A59, E63, Y64, R68, D69, M72, R73, F78, K88, E91, D92, H94, H95, Y96, R97, Q99, R102, or V103 of the Ras protein. In embodiments, the compound contacts V7, V9, T58, A59, G60, E63, Y64, R68, D69, Y71, M72, R73, F78, K88, E91, D92, H94, H95, Y96, R97, Q99, I100, R102, or V103 of the Ras protein. In embodiments, the compound contacts A59, Y64, D69, R73, F78, K88, E91, D92, H94, H95, R97, R102, or V103 of the Ras protein. In embodiments, the compound contacts V9, E63, Y64, R68, M72, H94, Y96, or Q99 of the Ras protein.

In an aspect is provided a Ras protein (e.g., K-Ras, H-Ras, N-Ras, human K-Ras, human H-Ras, or human N-Ras) covalently bound to a compound as described herein, wherein the compound is covalently bound to a cysteine residue of the Ras protein (e.g., K-Ras, H-Ras, N-Ras, human K-Ras, human H-Ras, or human N-Ras).

In an aspect is provided a Ras protein (e.g., K-Ras, H-Ras, N-Ras, human K-Ras, human H-Ras, or human N-Ras) non-covalently bound to a compound as described herein, wherein the compound is non-covalently bound to the Ras protein (e.g., K-Ras, H-Ras, N-Ras, human K-Ras, human H-Ras, or human N-Ras). Typical non-covalent interactions include electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like.

In an aspect is provided a method of identifying an inhibitor (e.g., a covalent or non-covalent inhibitor) of Ras protein (e.g., K-Ras, H-Ras, N-Ras, human K-Ras, human H-Ras, or human N-Ras) including: contacting a Ras protein (e.g., K-Ras, H-Ras, N-Ras, human K-Ras, human H-Ras, or human N-Ras) with a Ras (e.g., K-Ras, H-Ras, N-Ras, human K-Ras, human H-Ras, or human N-Ras) inhibitor test compound; allowing the Ras (e.g., K-Ras, H-Ras, N-Ras, human K-Ras, human H-Ras, or human N-Ras) inhibitor test compound to inhibit (e.g., covalently or non-covalently) the Ras protein (e.g., K-Ras, H-Ras, N-Ras, human K-Ras, human H-Ras, or human N-Ras); detecting the level of inhibition of the Ras protein (e.g., K-Ras, H-Ras, N-Ras, human K-Ras, human H-Ras, or human N-Ras) thereby identifying an inhibitor (e.g., a covalent or non-covalent inhibitor) of a Ras protein (e.g., K-Ras, H-Ras, N-Ras, human K-Ras, human H-Ras, or human N-Ras).

In embodiments, the method includes, prior to the contacting, determining whether the K-Ras inhibitor test compound contacts an amino acid residue within the Switch 2—Binding Pocket in silico using a computer modeling methodology. In embodiments, the amino acid residue within the Switch 2—Binding Pocket is V7, V9, G10, P34, T58, A59, G60, Q61, E62, E63, Y64, R68, D69, Y71, M72, R73, F78, K88, E91, D92, H94, H95, Y96, R97, Q99, I100, R102, or V103. In embodiments, the amino acid residue within the Switch 2—Binding Pocket is V9, A59, E63, Y64, R68, D69, M72, R73, F78, K88, E91, D92, H94, H95, Y96, R97, Q99, R102, or V103. In embodiments, the amino acid residue within the Switch 2—Binding Pocket is V7, V9, T58, A59, G60, E63, Y64, R68, D69, Y71, M72, R73, F78, K88, E91, D92, H94, H95, Y96, R97, Q99, I100, R102, or V103. In embodiments, the amino acid residue within the Switch 2—Binding Pocket is A59, Y64, D69, R73, F78, K88, E91, D92, H94, H95, R97, R102, or V103. In embodiments, the amino acid residue within the Switch 2—Binding Pocket is V9, E63, Y64, R68, M72, H94, Y96, or Q99. In embodiments, the K-Ras inhibitor test compound is a Switch 2—Binding Pocket covalent inhibitor test compound and said K-Ras protein is a G12C mutant K-Ras protein.

In an aspect is provided a method of selectively modulating a Ras protein (e.g., K-Ras, H-Ras, N-Ras, human K-Ras, human H-Ras, or human N-Ras), the method including contacting the Ras protein (e.g., K-Ras, H-Ras, N-Ras, human K-Ras, human H-Ras, or human N-Ras) with a compound which contacts at least one amino acid residue forming a Switch 2 binding pocket of the Ras protein (e.g., K-Ras, H-Ras, N-Ras, human K-Ras, human H-Ras, or human N-Ras), wherein the at least one amino acid residue is selected from an amino acid corresponding to V9, $C_{72}$, E63, Y64, R68, H94, Y96, and Q99; V9, E63, Y64, R68, M72, H94, Y96, and Q99; amino acids binding or contacting 2C07 in FIG. 18, 21A-B, 23A-B, 24, 26A-E, 27A-D, or 28A-C; V7, V9, G10, P34, T58, A59, G60, Q61, E62, E63, Y64, R68, D69, Y71, M72, R73, F78, K88, E91, D92, H94, H95, Y96, R97, Q99, I100, R102, and V103; V7, V9, T58, A59, G60, E63, Y64, R68, D69, Y71, M72, R73, F78, K88, E91, D92, H94, H95, Y96, R97, Q99, I100, R102, and V103, A59, Y64, D69, R73, F78, K88, E91, D92, H94, H95, R97, R102, and V103, V9, E63, Y64, R68, M72, H94, Y96, and Q99, V9, A59, E63, Y64, R68, D69, M72, R73, F78, K88, E91, D92, H94, H95, Y96, R97, Q99, R102, and V103, (all amino acid number of human K-Ras) and wherein the compound covalently reacts with an amino acid residue of the Ras protein (e.g., K-Ras, H-Ras, N-Ras, human K-Ras, human H-Ras, or human N-Ras).

In an aspect, a method of treating a disease in a patient in need of such treatment is provided. The method including administering a compound described herein to the patient. In embodiments the compound is administered in an effective amount. In embodiments the compound is administered in a therapeutically effective amount. In embodiments the compound is administered in a prophylactically effective amount. In some embodiments, the disease is cancer. In some embodiments, the cancer is lung cancer (e.g., NSCLC), colorectal cancer, colon cancer, pancreatic cancer, breast cancer, or leukemia. In some embodiments, the cancer is lung cancer. In some embodiments, the cancer is non-small cell lung cancer. In some embodiments, the cancer is colon cancer. In some embodiments, the cancer is colorectal cancer. In some embodiments, the cancer is breast cancer. In some embodiments, the cancer is leukemia. In some embodiments, the cancer is pancreatic cancer. In some embodiments, the cancer is a cancer associated with aberrant K-Ras. In some embodiments, the cancer is a cancer associated with a mutant K-Ras. In some embodiments, the cancer is a cancer associated with a mutant H-Ras. In some embodiments, the cancer is a cancer associated with a mutant N-Ras. In some embodiments, the cancer is a cancer associated with K-Ras G12C. In some embodiments, the cancer is a cancer associated with K-Ras G12V. In some embodiments, the cancer is a cancer associated with K-Ras G12D. In some embodiments, the cancer is a cancer associated with K-Ras G13C. In some embodiments, the cancer is a cancer associated with K-Ras G13D. In embodiments, the method includes co-administering a second agent (e.g., in an effective amount, in a therapeutically effective amount, an anti-cancer agent).

In some embodiments, a method of treating a disorder in a subject in need thereof is provided, comprising a) determining the presence or absence of a mutation in a Ras protein (such as in a K-Ras, N-Ras, or H-Ras protein) in a malignant or neoplastic cell isolated from the subject and b) if the mutation is determined to be present in the subject, administering to the subject a therapeutically effective amount of a compound or pharmaceutically acceptable salt of the disclosure. In some embodiments, the disorder is cancer.

Various methods are suitable for determining the presence of absence of a mutation in a Ras protein in a cell isolated from a subject. As used herein, the term "mutation" is used to refer to deletions, insertions and/or substitutions as indicated. For example, assays can be performed to determine the presence of a nucleic acid sequence in the cell, where the nucleic acid sequence or a fragment thereof encodes the Ras protein. In some embodiments, nucleic acid detection comprises the use of a hybridization assay. Generally, a hybridization assay involves hybridization between complimentary sequences of one or more pairs of polynucleotides, such as between an oligonucleotide and an extracted or amplified genomic DNA. Non-limiting examples of hybridization assays for genotyping SNPs include polymerase chain reaction (PCR) assays, blotting assays, TaqMan assays (Life Technologies; Carlsbad, Calif.), mass spectroscopy assays, sequencing assays, gel electrophoresis, ELISA, MALDI-TOF mass spectrometry hybridization, primer extension, fluorescence detection, fluorescence resonance energy transfer (FRET), fluorescence polarization, microchannel electrophoresis, microarray, southern blot, northern blot, slot blot, dot blot, single primer linear nucleic acid amplification, as described in U.S. Pat. No. 6,251,639, SNP-IT, GeneChips (Affymetrix; Santa Clara, Calif.), HuSNP (Affymetrix; Santa Clara, Calif.), BeadArray (Illumina; San Diego, Calif.), Invader assay (Hologic; Bedford, Mass.), MassEXTEND (Sequenom; San Diego Calif.), MassCLEAVE (hMC) method (Sequenom; San Diego Calif.), and others. PCR assays include any assays utilizing a PCR amplification process. In some embodiments, the PCR assay comprises the use of oligonucleotide primers that hybridize only to the variant or wild type allele (e.g., to the region of polymorphism or mutation) of a diallelic SNP. PCR assays may also combine amplification with probe hybridization, such as in a TaqMan assay (see e.g., U.S. Pat. Nos. 5,962,233 and 5,538,848, each of which is herein incorporated by reference) where the assay is performed during a PCR reaction. Alternatively, detection of one or more mutations may utilize a SNP-IT primer extension assay (Orchid Cellmark, Burlington, N.C.; See e.g., U.S. Pat. Nos. 5,952,174 and 5,919,626, each of which is herein incorporated by reference). In other embodiments, a mass spectroscopy-based assay is used, such as a MassARRAY system (Sequenom; San Diego Calif.). See for example U.S. Pat. Nos. 6,043, 031; 5,777,324; and 5,605,798, incorporated herein by reference. Detection of one or more mutations may also utilize an array of probes (also referred to as a "DNA chip" assay, e.g. a GeneChip assay—Affymetrix, Santa Clara, Calif.). See e.g., U.S. Pat. Nos. 6,045,996; 5,925,525; and 5,858, 659; each of which is herein incorporated by reference. In still other embodiments, a DNA microchip containing electronically captured probes is used (see e.g. U.S. Pat. Nos. 6,017,696; 6,068,818; and 6,051,380; each incorporated herein by reference). In yet other embodiments, detection of mutations is performed using a "bead array" (Illumina, San Diego, Calif.; See e.g., PCT Publications WO 99/67641 and WO 00/39587; each incorporated herein by reference). In other embodiments, a sample comprising nucleic acid obtained from a cell is sequenced to determine the presence of a mutation. Any method known in the art may be used, for instance as described in US 2011/0319290 and US 2009/0298075, each incorporated herein by reference. Sequencing may involve, for example, precipitation of the nucleic acid followed by resuspension and sequencing using Maxam-Gilbert sequencing, chain-termination sequencing, pyrosequencing, polony sequencing, or nanopore sequencing.

In an aspect, a method of modulating the activity of a K-Ras protein is provided. The method including contacting the K-Ras protein with an effective amount of a compound described herein. In some embodiments, the activity of the K-Ras protein is it's GTPase activity, nucleotide exchange, differential GDP or GTP binding, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, K-Ras post-translational modifications, or a GTP bound K-Ras signaling pathway. In some embodiments, the activity of the K-Ras protein is its GTPase activity, nucleotide exchange, effector protein binding, effector protein activation, guanine exchange factor (GEF) binding, GEF-facilitated nucleotide exchange, phosphate release, nucleotide release, nucleotide binding, or the activity of a GTP bound K-Ras signaling pathway. In some embodiments, the modulating of the activity of the K-Ras protein includes modulating the binding affinity of K-Ras for GDP. In some embodiments, the modulating of the activity of the K-Ras protein includes the binding affinity of K-Ras for GTP. In some embodiments, the modulating of the activity of the K-Ras protein includes modulating the relative binding affinity of K-Ras for GTP vs. GDP. In some embodiments, the activity of the K-Ras protein is the activity of a signaling pathway activated by GTP bound K-Ras. In some embodiments, the modulating is increasing the activity of said K-Ras protein. In some embodiments, the modulating is reducing the activity of said K-Ras protein. In some embodiments, the K-Ras protein is a human K-Ras protein. In some embodiments, the human K-Ras protein contains a G12C mutation. In some embodiments, the human K-Ras protein contains a G12V mutation. In some embodiments, the human K-Ras protein contains a G12D mutation. In some embodiments, the human K-Ras protein contains a G13C mutation. In some embodiments, the human K-Ras protein contains a G13D mutation. In some embodiments, the K-Ras protein is a human K-Ras4A protein. In some embodiments, the K-Ras protein is a human K-Ras4B protein. In some embodiments, the K-Ras protein is a mutant K-Ras protein. In some embodiments, the K-Ras protein is an activated K-Ras protein. In some embodiments, the K-Ras protein is within a biological cell. In some embodiments, the biological cell forms part of an organism. In some embodiments of the method of modulating the activity of a K-Ras protein including contacting the K-Ras protein with an effective amount of a compound described herein, the compound is less effective at modulating the activity of an H-Ras protein. In some embodiments of the method, the compound modulates the activity of K-Ras at least two-fold more than it modulates the activity of H-Ras. In some embodiments of the method, the compound modulates the activity of K-Ras at least five-fold more than it modulates the activity of H-Ras. In some embodiments of the method, the compound modulates the activity of K-Ras at least ten-fold more than it modulates the activity of H-Ras. In some embodiments of the method, the compound modulates the activity of K-Ras at least fifty-fold more than it modulates the activity of H-Ras. In some embodiments of the method of modulating the activity of a K-Ras protein including contacting the K-Ras protein with an effective amount of a compound described herein, the compound is less effective at modulating the activity of an N-Ras protein. In embodiments of the method, the compound modulates the activity of K-Ras at least two-fold more than it modulates the activity of N-Ras. In some embodiments of the method, the compound modulates the activity of K-Ras at least five-fold more than it modulates the activity of N-Ras. In some embodiments of the method, the compound modulates the activity of K-Ras at least ten-fold more than it modulates the activity of N-Ras. In some embodiments of the method, the compound modulates the activity of K-Ras at least fifty-fold more than it modulates the activity of N-Ras.

In an aspect, a method of modulating a K-Ras protein is provided. The method including contacting the K-Ras protein with an effective amount of a compound described herein. In some embodiments, the K-Ras protein is modulated in K-Ras subcellular localization, K-Ras post-translational processing, K-Ras post-translational modifications, or a GTP bound K-Ras signaling pathway. In some embodiments, the modulating is increasing the post-translational processing or modifications of the K-Ras protein. In some embodiments, the modulating is reducing the post-translational processing or modifications of the K-Ras protein. In some embodiments, the K-Ras protein is a human K-Ras protein. In some embodiments, the human K-Ras protein contains a G12C mutation. In some embodiments, the human K-Ras protein contains a G12V mutation. In some embodiments, the human K-Ras protein contains a G12D mutation. In some embodiments, the human K-Ras protein contains a G13C mutation. In some embodiments, the human K-Ras protein contains a G13D mutation. In some embodiments, the K-Ras protein is a human K-Ras4A protein. In some embodiments, the K-Ras protein is a human K-Ras4B protein. In some embodiments, the K-Ras protein is a mutant K-Ras protein. In some embodiments, the K-Ras protein is an activated K-Ras protein. In some embodiments, the K-Ras protein is within a biological cell. In some embodiments, the biological cell forms part of an organism.

In an aspect, a K-Ras protein covalently bonded to a compound, for example a compound as described herein, is provided. The compound is covalently bonded to a cysteine residue of the K-Ras protein. In some embodiments, the covalently modified K-Ras protein has a modulated activity relative to a control, wherein the activity is selected from GTPase activity, nucleotide exchange, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, and K-Ras post-translational modifications. In some embodiments, the covalently modified K-Ras protein is modulated in K-Ras subcellular localization, K-Ras post-translational processing, or K-Ras post-translational modifications. In some embodiments, the covalently modified K-Ras protein contains a G12C mutation. In some embodiments, the covalently modified K-Ras protein contains a G12V mutation. In some embodiments, the compound is covalently bonded to cysteine residue 12. In some embodiments, the covalently modified K-Ras protein contains a G13C mutation. In some embodiments, the compound is covalently bonded to cysteine residue 13. In some embodiments, the K-Ras protein is bonded to a K-Ras inhibitor, a mutant K-Ras inhibitor, a K-Ras G12C inhibitor, a K-Ras G12V inhibitor, or a K-Ras G13C inhibitor. In some embodiments, the K-Ras protein is bonded to a K-Ras modulator, a mutant K-Ras modulator, a K-Ras G12C modulator, K-Ras G12V modulator, or a K-Ras G13C modulator. In embodiments, the compound is reversibly covalently bound to a cysteine residue of the K-Ras protein. In embodiments, the compound is irreversibly covalently bound to a cysteine residue of the K-Ras protein.

In an aspect, a method of identifying a covalent inhibitor of K-Ras protein is provided. The method including contacting a K-Ras protein with a K-Ras inhibitor test compound, allowing the K-Ras inhibitor test compound to covalently inhibit the K-Ras protein, detecting the level of covalent inhibition of the K-Ras protein, and thereby identifying a covalent inhibitor of K-Ras protein. In some embodiments of the method, the K-Ras inhibitor test compound is a Switch 2—Binding Pocket covalent inhibitor test compound. In some embodiments, the K-Ras protein is a G12C mutant K-Ras protein. In some embodiments, the K-Ras protein is a G12V mutant K-Ras protein. In some embodiments, the K-Ras protein is a G13C mutant K-Ras protein. In some embodiments, the K-Ras protein is a G12D mutant K-Ras protein. In some embodiments, the K-Ras protein is a G13D mutant K-Ras protein. In some embodiments of the method, wherein the K-Ras protein contacting the Switch 2—Binding Pocket covalent inhibitor test compound is a mutant K-Ras (e.g. K-Ras G12C, G12V, G12D, G13C, G13D), the method further includes contacting a wildtype K-Ras protein with the Switch 2—Binding Pocket covalent inhibitor test compound, allowing the Switch 2—Binding Pocket covalent inhibitor test compound to inhibit the wildtype K-Ras protein, detecting the level of inhibition of the wildtype K-Ras protein, comparing the level of inhibition of the wildtype K-Ras protein to the level of covalent inhibition of the mutant K-Ras protein (e.g. K-Ras G12C, G12V, G12D, G13C, G13D), wherein a higher level of covalent inhibition of the mutant K-Ras protein indicates the Switch 2—Binding Pocket covalent inhibitor test compound is specific for the mutant K-Ras protein.

In an aspect is provided a method of selectively modulating a Ras (e.g., K-Ras, human Ras, human K-Ras, H-Ras, human H-Ras, N-Ras, human N-Ras) protein, the method including contacting the Ras protein with a compound which contacts at least one amino acid residue forming a Switch 2 binding pocket of the Ras protein and wherein the compound covalently reacts with an amino acid residue of the Ras protein. In embodiments, the at least one amino acid residue is selected from V9, C72, E63, Y64, R68, H94, Y96, and Q99, or amino acids corresponding thereto, of the Ras protein. In embodiments, the at least one amino acid residue is selected from V7, V9, T58, A59, G60, E63, Y64, R68, D69, Y71, M72, R73, F78, K88, E91, D92, H94, H95, Y96, R97, Q99, I100, R102, and V103, or amino acids corresponding thereto, of the Ras protein. In embodiments, the at least one amino acid residue is selected from V7, V9, G10, P34, T58, A59, G60, Q61, E62, E63, Y64, R68, D69, Y71, M72, R73, F78, K88, E91, D92, H94, H95, Y96, R97, Q99, I100, R102, and V103, or amino acids corresponding thereto, of the Ras protein. In embodiments, the at least one amino acid residue is selected from V9, A59, E63, Y64, R68, D69, M72, R73, F78, K88, E91, D92, H94, H95, Y96, R97, Q99, R102, and V103, or amino acids corresponding thereto, of the Ras protein. In embodiments, the at least one amino acid residue is selected from A59, Y64, D69, R73, F78, K88, E91, D92, H94, H95, R97, R102, or V103 or amino acids corresponding thereto. In embodiments, the at least one amino acid residue is selected from V9, E63, Y64, R68, M72, H94, Y96, or Q99, or amino acids corresponding thereto, of the Ras protein. The amino acid numbering used above is human K-Ras amino acid numbering.

In embodiments, the compound binds Ras (e.g., K-Ras, H-Ras, human K-Ras, human H-Ras) protein contacting GDP. In embodiments, the compound binds Ras (e.g., K-Ras, H-Ras, human K-Ras, human H-Ras) protein contacting GTP. In embodiments, the compound binds Ras (e.g., K-Ras, H-Ras, human K-Ras, human H-Ras) protein contacting GDP or GTP.

In embodiments, the compound modulates Ras (e.g., K-Ras, H-Ras, human K-Ras, human H-Ras) protein binding to GTP (e.g., modifies protein-GTP interactions compared to control). In embodiments, the compound modulates Ras (e.g., K-Ras, H-Ras, human K-Ras, human H-Ras) protein binding to GDP (e.g., modifies protein-GDP interactions compared to control).

In embodiments, the compound modulates the relative binding affinity of Ras (e.g., K-Ras, H-Ras, human K-Ras, human H-Ras) protein to GDP compared to GTP. In embodiments, the compound reduces the relative binding affinity of Ras (e.g., K-Ras, H-Ras, human K-Ras, human H-Ras) protein to GDP compared to GTP. In embodiments, the compound increases the relative binding affinity of Ras (e.g., K-Ras, H-Ras, human K-Ras, human H-Ras) protein to GDP compared to GTP.

In embodiments, the compound modulates Ras (e.g., K-Ras, H-Ras, human K-Ras, human H-Ras) protein binding to a guanine nucleotide exchange factor (GEF) (e.g., SOS, human SOS1, human SOS2). In embodiments, the compound reduces Ras (e.g., K-Ras, H-Ras, human K-Ras, human H-Ras) protein binding to a guanine nucleotide exchange factor (GEF) (e.g., SOS, human SOS1, human SOS2). In embodiments, the compound inhibits Ras (e.g., K-Ras, H-Ras, human K-Ras, human H-Ras) protein binding to a guanine nucleotide exchange factor (GEF) (e.g., SOS, human SOS1, human SOS2). In embodiments, the compound modulates Ras (e.g., K-Ras, H-Ras, human K-Ras, human H-Ras) protein binding to a PI3K (e.g., PI3K alpha, PI3K beta, PI3K delta, PI3K gamma). In embodiments, the compound reduces Ras (e.g., K-Ras, H-Ras, human K-Ras, human H-Ras) protein binding to a PI3K (e.g., PI3K alpha, PI3K beta, PI3K delta, PI3K gamma). In embodiments, the compound inhibits Ras (e.g., K-Ras, H-Ras, human K-Ras, human H-Ras) protein binding to a PI3K (e.g., PI3K alpha, PI3K beta, PI3K delta, PI3K gamma). In embodiments, the compound modulates Ras (e.g., K-Ras, H-Ras, human K-Ras, human H-Ras) protein binding to Raf protein. In embodiments, the compound does not modulate Ras (e.g., K-Ras, H-Ras, human K-Ras, human H-Ras) protein binding to Raf protein.

In embodiments, the compound modulates Ras (e.g., K-Ras, H-Ras, human K-Ras, human H-Ras) protein nucleotide exchange (e.g., binding of GTP, release of GDP). In embodiments, the compound inhibits Ras (e.g., K-Ras, H-Ras, human K-Ras, human H-Ras) protein nucleotide exchange (e.g., binding of GTP, release of GDP).

In embodiments, the compound modulates contact between Ras (e.g., K-Ras, H-Ras, human K-Ras, human H-Ras) protein and GTP. In embodiments, the compound inhibits contact between Ras (e.g., K-Ras, H-Ras, human K-Ras, human H-Ras) protein and GTP. In embodiments, the compound modulates contact between the Ras (e.g., K-Ras, H-Ras, human K-Ras, human H-Ras) amino acid corresponding to human H-Ras Y32 and GTP. In embodiments, the compound inhibits contact between the Ras (e.g., K-Ras, H-Ras, human K-Ras, human H-Ras) amino acid corresponding to human H-Ras Y32 and GTP. In embodiments, the compound modulates contact between the Ras (e.g., K-Ras, H-Ras, human K-Ras, human H-Ras) amino acid corresponding to human K-Ras Y32 and GTP. In embodiments, the compound inhibits contact between the Ras (e.g., K-Ras, H-Ras, human K-Ras, human H-Ras) amino acid corresponding to human K-Ras Y32 and GTP.

IV. Kits/Articles of Manufacture

For use in the methods and/or applications (e.g. therapeutic applications) described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

V. Embodiments

Embodiment P1

A compound having the formula:

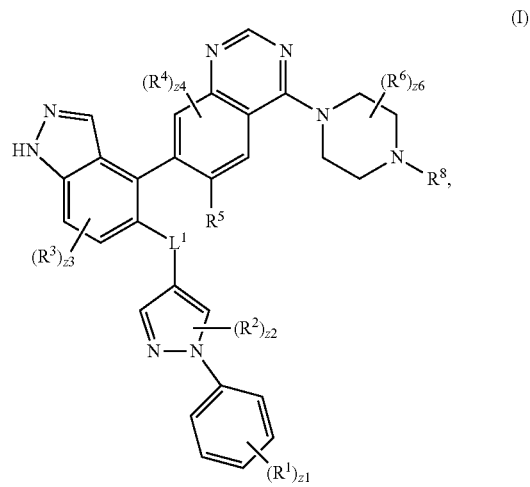

(I)

-continued

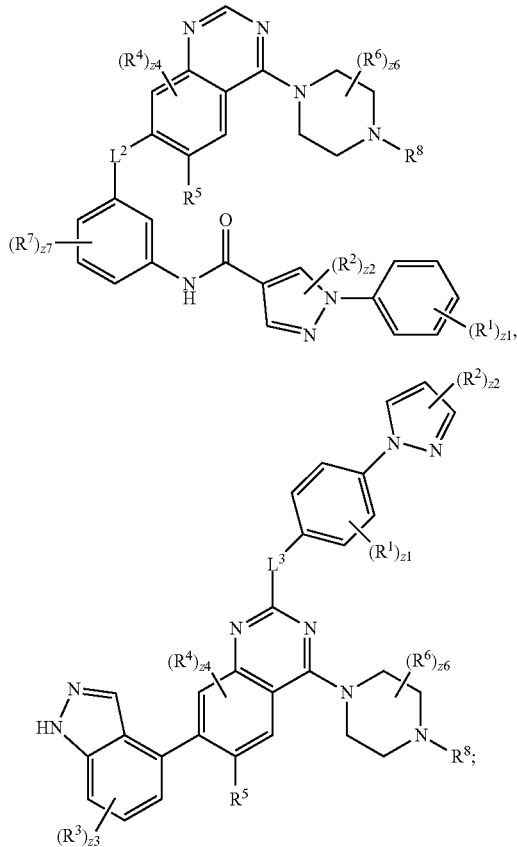

(II)

(III)

wherein,

R¹ is independently halogen, —CX¹₃, —CHX¹₂, —CH₂X¹, —OCX¹₃, —OCH₂X¹, —OCHX¹₂, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is independently halogen, —CX²₃, —CHX²₂, —CH₂X², —OCX²₃, —OCH₂X², —OCHX²₂, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO₂R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R³ is independently halogen, —CX³₃, —CHX³₂, —CH₂X³, —OCX³₃, —OCH₂X³, —OCHX³₂, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO₂R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁴ is independently halogen, —CX⁴₃, —CHX⁴₂, —CH₂X⁴, —OCX⁴₃, —OCH₂X⁴, —OCHX⁴₂, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO₂R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁵ is independently hydrogen, halogen, —CX⁵₃, —CHX⁵₂, —CH₂X⁵, —OCX⁵₃, —OCH₂X⁵, —OCHX⁵₂, —CN, —SO$_{n8}$R$^{5D}$, —SO$_{v8}$NR$^{5A}$R$^{5B}$, —NHC(O)NR$^{5A}$R$^{5B}$, —N(O)$_{m}$s, —NR$^{5A}$R$^{5B}$, —C(O)R$^{8C}$, —C(O)—OR$^{5C}$, —C(O)NR$^{5A}$R$^{5B}$, —OR$^{5D}$, —NR$^{5A}$SO₂R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁶ is independently halogen, —CX⁶₃, —CHX⁶₂, —CH₂X⁶, —OCX⁶₃, —OCH₂X⁶, —OCHX⁶₂, —CN, —SO$_{n6}$R$^{6D}$, —SO$_{v6}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO₂R$^{6D}$, —NR$^{6A}$C(O)R$^{6C}$, —NR$^{6A}$C(O)OR$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁷ is independently halogen, —CX⁷₃, —CHX⁷₂, —CH₂X⁷, —OCX⁷₃, —OCH₂X⁷, —OCHX⁷₂, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO₂R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁸ is independently hydrogen, halogen, —CX⁸₃, —CHX⁸₂, —CH₂X⁸, —CN, —SO$_{n8}$R$^{8D}$, —SO$_{v8}$NR$^{8A}$R$^{8B}$, —C(O)R$^{8C}$, —C(O)OR$^{8C}$, —C(O)NR$^{8A}$R$^{8B}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L¹ is a bond, —N(H)—, —O—, —S—, —C(O)—, —C(O)N(H)—, —N(H)C(O)—, —N(H)C(O)NH—, —NHC(O)N(H)—, —C(O)O—, —OC(O)—, substituted or unsubstituted alkylene, or substituted or unsubstituted heteroalkylene;

L² is a bond, —N(H)—, —O—, —S—, —C(O)—, —C(O)N(H)—, —N(H)C(O)—, —N(H)C(O)NH—, —NHC(O)N(H)—, —C(O)O—, —OC(O)—, substituted or unsubstituted alkylene, or substituted or unsubstituted heteroalkylene;

L³ is a bond, —N(H)—, —O—, —S—, —C(O)—, —C(O)N(H)—, —N(H)C(O)—, —N(H)C(O)NH—, —NHC(O)N(H)—, —C(O)O—, —OC(O)—, substituted or unsubstituted alkylene, or substituted or unsubstituted heteroalkylene;

E is an electrophilic moiety;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, and $R^{8D}$ is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{8A}$ and $R^{8B}$ substituents bonded to the same nitrogen atom may optionally be joined to form a substituted or unsubstituted heterocycloalkyl or substituted or unsubstituted heteroaryl;

z1 is an integer from 0 to 5;

z2 is an integer from 0 to 3;

z3 is an integer from 0 to 5;

z4 is an integer from 0 to 2;

z6 is an integer from 0 to 8;

z7 is an integer from 0 to 4;

each X, $X^1$, $X^2$, $X^3$, $X^4$, $X^5$, $X^6$, $X^7$, and $X^8$ is independently —F, —Cl, —Br, or —I;

n1, n2, n3, n4, n5, n6, n7, and n8 are independently an integer from 0 to 4; and m1, m2, m3, m4, m5, m6, m7, m8, v1, v2, v3, v4, v5, v6, v7, and v8 are independently 1 or 2.

Embodiment P2

The compound of Embodiment P1, wherein E is a covalent cysteine modifier moiety.

Embodiment P3

The compound of Embodiment P1, wherein E is

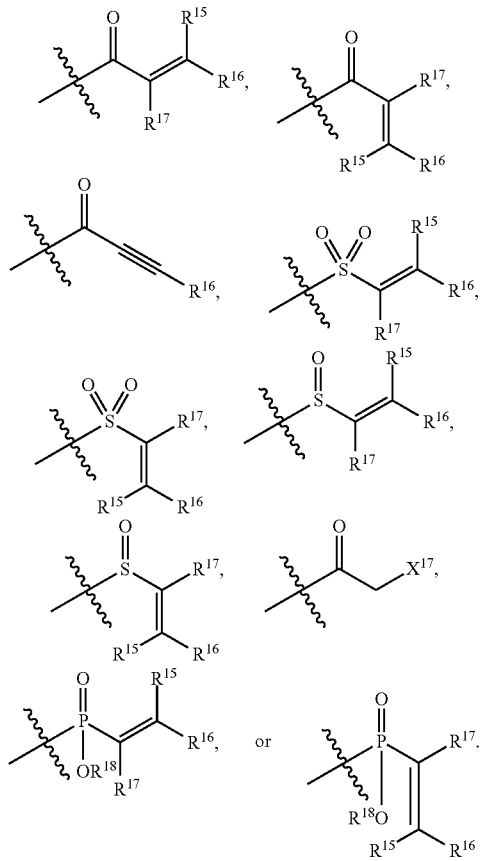

$R^{15}$ is independently hydrogen, halogen, —CX¹⁵₃, —CHX¹⁵₂, —CH₂X¹⁵, —CN, —SO$_{n15}$R$^{15D}$, —SO$_{v15}$NR$^{15A}$R$^{15B}$, —NHNR$^{15A}$R$^{15B}$, —ONR$^{15A}$R$^{15B}$, —NHC═(O)NHNR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO₂R$^{15D}$, —NR$^{15A}$C(O)R$^{15C}$, —NR$^{15A}$C(O)OR$^{15C}$, —NR$^{15A}$OR$^{15C}$, —OCX¹⁵₃, —OCHX¹⁵₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is independently hydrogen, halogen, —CX¹⁶₃, —CHX¹⁶₂, —CH₂X¹⁶, —CN, —SO$_{n16}$R$^{16D}$, —SO$_{v16}$NR$^{16A}$R$^{16B}$, —NHNR$^{16A}$R$^{16B}$, —ONR$^{16A}$R$^{16B}$, —NHC═(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO₂R$^{16D}$, —NR$^{16A}$C(O)R$^{16C}$, —NR$^{16A}$C(O)OR$^{16C}$, —NR$^{16A}$OR$^{16C}$, —OCX¹⁶₃, —OCHX¹⁶₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, —CX¹⁷₃, —CHX¹⁷₂, —CH₂X¹⁷, —CN, —SO$_{n17}$R$^{17D}$, —$SO_{v17}NR^{17A}R^{17B}$, —$NHNR^{17A}R^{17B}$, —$ONR^{17A}R^{17B}$, —$NHC=(O)NHNR^{17A}R^{17B}$, —$NHC(O)NR^{17A}R^{17B}$, —$N(O)_{m7}$, —$NR^{17A}R^{17B}$, —$C(O)R^{17C}$, —$C(O)$—$OR^{17C}$, —$C(O)NR^{17A}R^{17B}$, —$OR^{17D}$, —$NR^{17A}SO_2R^{17D}$, —$NR^{17A}C(O)R^{17C}$, —$NR^{17A}C(O)OR^{17C}$, —$NR^{17A}OR^{17C}$, —$OCX^{17}_3$, —$OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{18}$ is independently hydrogen, —$CX^{18}_3$, —$CHX^{18}_2$, —$CH_2X^{18}$, —$C(O)R^{18C}$, —$C(O)OR^{18C}$, —$C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, are independently hydrogen, —$CX_3$, —$CN$, —$COOH$, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl;

each X, $X^{15}$, $X^{16}$, $X^{17}$ and $X^{18}$ is independently —F, —Cl, —Br, or —I;

n15, n16, n17, v15, v16, and v17, are independently an integer from 0 to 4; and m15, m16, and m17 are independently 1 or 2.

Embodiment P4

The compound of Embodiment P1, wherein E is:

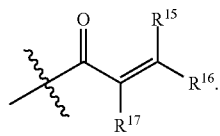

Embodiment P5

The compound of Embodiment P4, wherein
$R^{15}$ is hydrogen;
$R^{16}$ is hydrogen; and
$R^{17}$ is hydrogen.

Embodiment P6

The compound of Embodiment P1 having the formula:

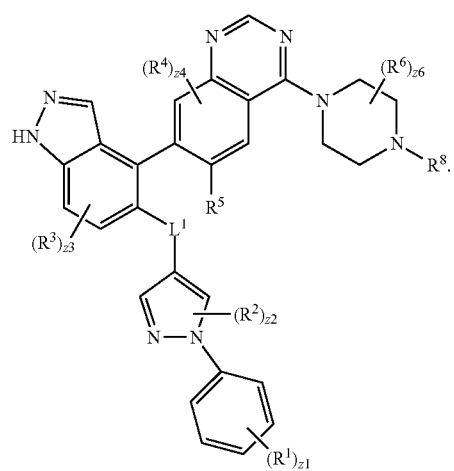

(I)

Embodiment P7

The compound of Embodiment P6, having the formula:

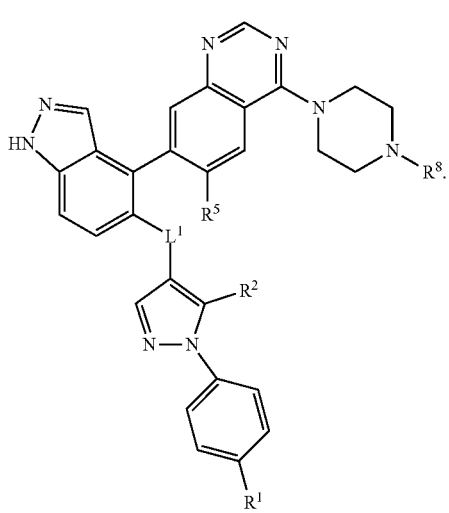

(Ia)

Embodiment P8

The compound of Embodiment P7, wherein
$L^1$ is —N(H)C(O)—, —$OCH_2$—, or —$NHCH_2CH_2CH_2$—;
$R^1$ is unsubstituted $C_1$-$C_4$ alkoxy;
$R^2$ is —$CX^2_3$;
$R^5$ is halogen; and
$R^8$ is independently hydrogen or E.

Embodiment P9
The compound of Embodiment P6 having the formula:
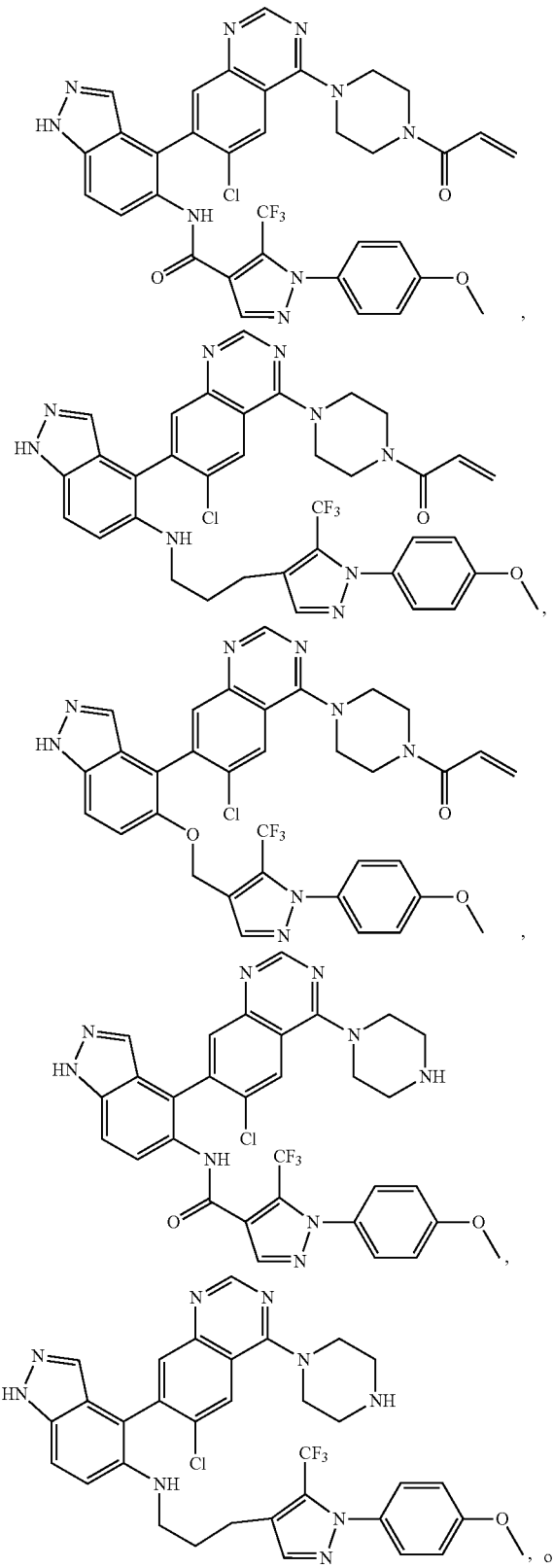
,
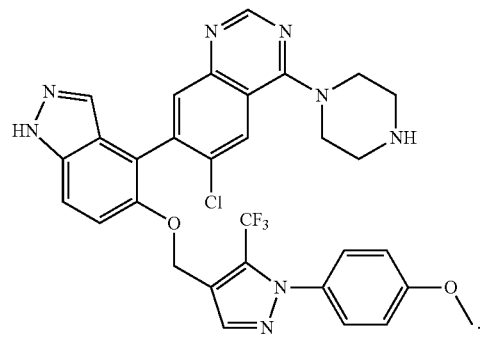
Embodiment P10
The compound of Embodiment P1 having the formula:
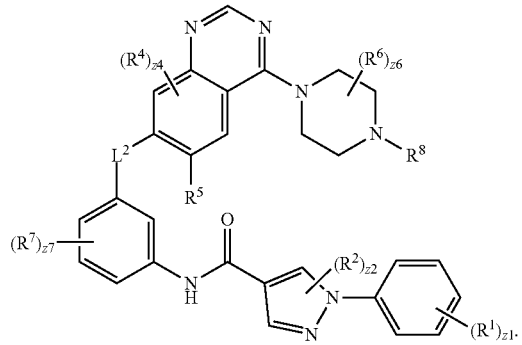
(II)
Embodiment P11
The compound of Embodiment P10 having the formula:
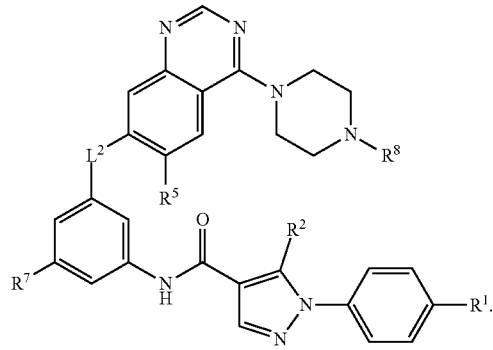
(IIa)

Embodiment P12

The compound of Embodiment P11, wherein
$L^2$ is —O—, —OCH$_2$—, —CH$_2$—, or —CH$_2$CH$_2$—;
$R^1$ is unsubstituted C$_1$-C$_4$ alkoxy;
$R^2$ is —CX$^2{}_3$;
$R^5$ is halogen;
$R^7$ is —NHC(O)CH$_2$CH$_3$; and
$R^8$ is hydrogen or E.

Embodiment P13

The compound of Embodiment P10 having the formula:

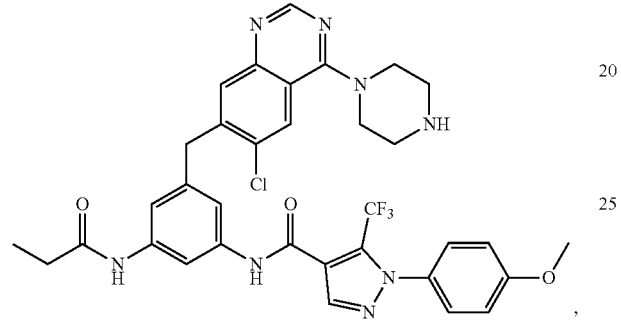

,

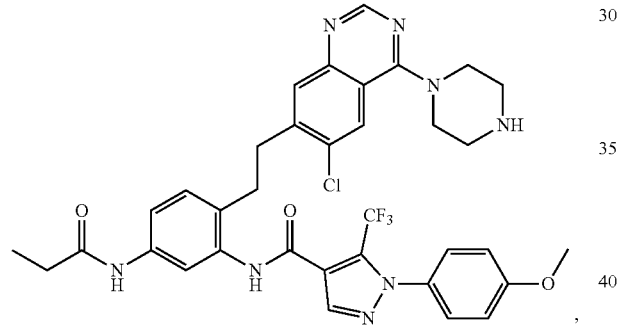

,

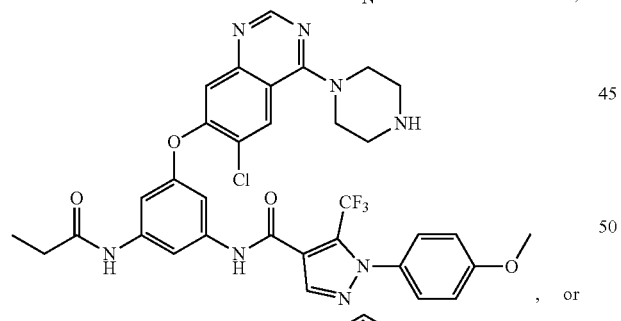

, or

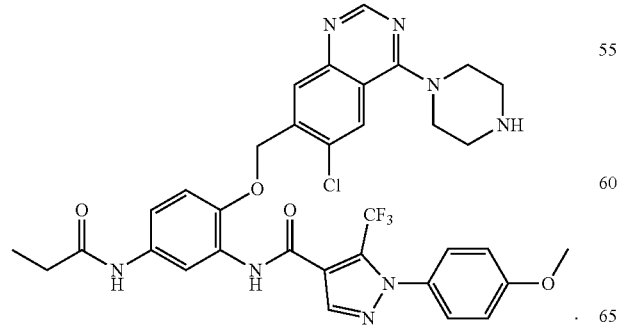

.

Embodiment P14

The compound of Embodiment P1 having the formula:

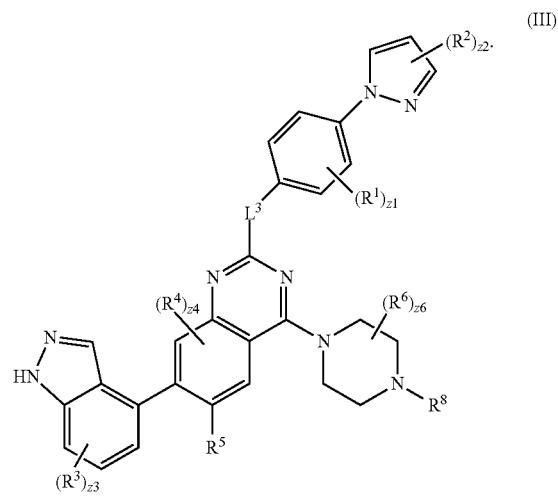

(III)

Embodiment P15

The compound of Embodiment P14 having the formula:

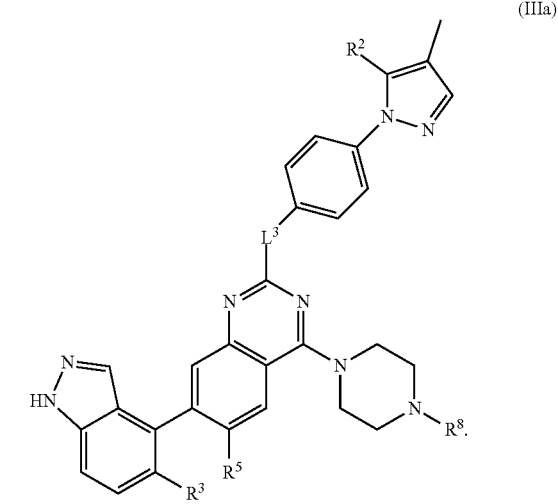

(IIIa)

Embodiment P16

The compound of Embodiment P15, wherein
$L^3$ is —OCH$_2$CH$_2$NH—;
$R^2$ is —CX$^2{}_3$;
$R^3$ is unsubstituted C$_1$-C$_4$ alkyl;
$R^5$ is halogen; and
$R^8$ is hydrogen or E.

Embodiment P17

The compound of Embodiment P14 having the formula:

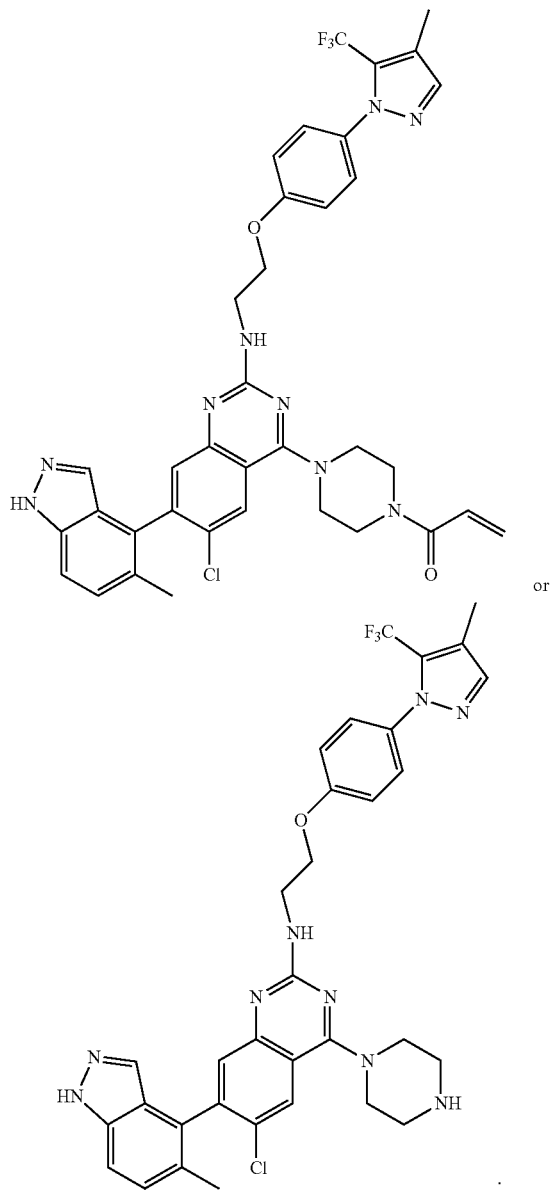

Embodiment P18

A compound having the formula:

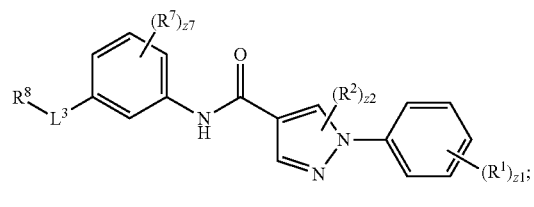

(IV)

wherein, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is independently hydrogen, halogen, $-CX^8_3$, $-CHX^8_2$, $-CH_2X^8$, $-CN$, $-SO_{n8}R^{8D}$, $-SO_{v8}NR^{8A}R^{8B}$, $-C(O)R^{8C}$, $-C(O)OR^{8C}$, $-C(O)NR^{8A}R^{8B}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^3$ is a bond, $-N(H)-$, $-O-$, $-S-$, $-C(O)-$, $-C(O)N(H)-$, $-N(H)C(O)-$, $-N(H)C(O)NH-$, $-NHC(O)N(H)-$, $-C(O)O-$, $-OC(O)-$, substituted or unsubstituted alkylene, or substituted or unsubstituted heteroalkylene;

E is an electrophilic moiety;

Each $R^{1A}$, $R^{1B}$, $R^{1C}$, $R^{1D}$, $R^{2A}$, $R^{2B}$, $R^{2C}$, $R^{2D}$, $R^{7A}$, $R^{7B}$, $R^{7C}$, $R^{7D}$, $R^{8A}$, $R^{8B}$, $R^{8C}$, and $R^{8D}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl;

$R^{8A}$ and $R^{8B}$ substituents bonded to the same nitrogen atom may optionally be joined to form a substituted or unsubstituted heterocycloalkyl or substituted or unsubstituted heteroaryl;

z1 is an integer from 0 to 5;
z2 is an integer from 0 to 3;
z7 is an integer from 0 to 4;
each X, $X^1$, $X^2$, $X^7$, and $X^8$ is independently —F, —Cl, —Br, or —I;
n1, n2, n7, and n8 are independently an integer from 0 to 4; and
m1, m2, m7, m8, v1, v2, v7, and v8 are independently 1 or 2.

Embodiment P19

The compound of Embodiment P18 having the formula:

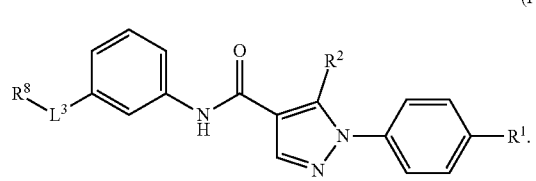

(IVa)

Embodiment P20

The compound of Embodiment P19, wherein
$L^3$ is —NH—;
$R^1$ is unsubstituted $C_1$-$C_4$ alkoxy;
$R^2$ is —$CX^2{}_3$; and
$R^8$ is hydrogen or E Embodiment P21

The compound of Embodiment P18 having the formula:

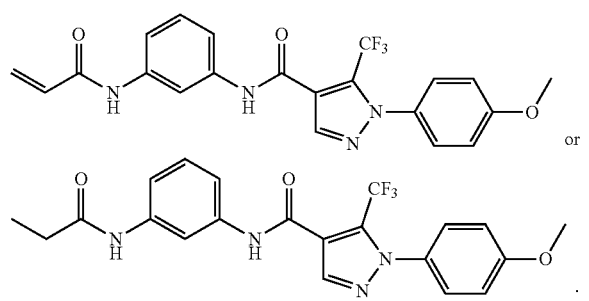

Embodiment P22

A pharmaceutical composition comprising a pharmaceutically acceptable excipient and a compound of any one of Embodiments P1 to P21.

Embodiment P23

A method of treating a disease in a patient in need of such treatment, said method comprising administering a therapeutically effective amount of a compound of any one of Embodiments P1 to P17 to said patient.

Embodiment P24

The method of Embodiment P23, wherein said disease is cancer.

Embodiment P25

The method of Embodiment P24, wherein said cancer is lung cancer, colon cancer, colorectal cancer, pancreatic cancer, breast cancer, or leukemia.

Embodiment P26

A method of modulating the activity of a K-Ras protein, said method comprising contacting said K-Ras protein with an effective amount of a compound of any one of Embodiments P1 to P21.

Embodiment P27

The method of Embodiment P26, wherein said modulating of said activity comprises modulating GTPase activity, nucleotide exchange, GDP binding, GTP binding, differential GDP or GTP binding, effector protein binding, K-Ras binding to Raf, effector protein activation, guanine exchange factor (GEF) binding, GEF-facilitated nucleotide exchange, phosphate release, nucleotide release, nucleotide binding, K-Ras subcellular localization, K-Ras post-translational processing, or K-Ras post-translational modifications.

Embodiment P28

The method of Embodiment P26, wherein said modulating is reducing the activity of said K-Ras protein.

Embodiment P29

The method of Embodiment P26, wherein said K-Ras protein is a human K-Ras protein.

Embodiment P30

The method of Embodiment P29, wherein said human K-Ras protein contains a G12C, G12V, G12D, G13C, or G13D mutation.

Embodiment P31

A method of modulating a K-Ras protein, said method comprising contacting said K-Ras protein with an effective amount of a compound of any one of Embodiments P1 to P21.

Embodiment P32

The method of Embodiment P31, wherein said compound contacts at least one amino acid residue forming a Switch 2 binding pocket of said Ras protein, wherein said at least one amino acid residue is V7, V9, G10, P34, T58, A59, G60, Q61, E62, E63, Y64, R68, D69, Y71, M72, R73, F78, K88, E91, D92, H94, H95, Y96, R97, Q99, I100, R102, or V103 of said Ras protein, and wherein said compound covalently reacts with an amino acid residue of said Ras protein.

Embodiment P33

The method of Embodiment P31, wherein said compound contacts at least one amino acid residue forming a Switch 2 binding pocket of said Ras protein, wherein said at least one amino acid residue is V9, A59, E63, Y64, R68, D69, M72, R73, F78, K88, E91, D92, H94, H95, Y96, R97, Q99, R102, or V103 of said Ras protein, and wherein said compound covalently reacts with an amino acid residue of said Ras protein.

Embodiment P34

The method of Embodiment P31, wherein said compound contacts at least one amino acid residue forming a Switch 2 binding pocket of said Ras protein, wherein said at least one amino acid residue is V7, V9, T58, A59, G60, E63, Y64, R68, D69, Y71, M72, R73, F78, K88, E91, D92, H94, H95, Y96, R97, Q99, I100, R102, or V103 of said Ras protein, and wherein said compound covalently reacts with an amino acid residue of said Ras protein.

Embodiment P35

The method of Embodiment P31, wherein said compound contacts at least one amino acid residue forming a Switch 2 binding pocket of said Ras protein, wherein said at least one amino acid residue is A59, Y64, D69, R73, F78, K88, E91, D92, H94, H95, R97, R102, or V103 of said Ras protein, and wherein said compound covalently reacts with an amino acid residue of said Ras protein.

Embodiment P36

The method of Embodiment P31, wherein said compound contacts at least one amino acid residue forming a Switch 2 binding pocket of said Ras protein, wherein said at least one amino acid residue is V9, E63, Y64, R68, M72, H94, Y96, or Q99 of said Ras protein, and wherein said compound covalently reacts with an amino acid residue of said Ras protein.

Embodiment P37

The method of Embodiment P31, wherein said K-Ras protein is a human K-Ras protein.

Embodiment P38

The method of Embodiment P31, wherein said K-Ras protein is within a biological cell.

Embodiment P39

The method of Embodiment P38, wherein said biological cell forms part of an organism.

Embodiment P40

A K-Ras protein covalently bound to a compound of any one of Embodiments P1 to P21, wherein said compound is covalently bound to a cysteine residue of said K-Ras protein.

Embodiment P41

The covalently modified K-Ras protein of Embodiment P40, wherein said compound is reversibly covalently bound to a cysteine residue of said K-Ras protein.

Embodiment P42

The covalently modified K-Ras protein of Embodiment P40, wherein said compound is irreversibly covalently bound to a cysteine residue of said K-Ras protein.

Embodiment P43

A method of identifying a covalent inhibitor of K-Ras protein comprising:
  contacting a K-Ras protein with a K-Ras inhibitor test compound;
  allowing said K-Ras inhibitor test compound to covalently inhibit said K-Ras protein;
  detecting the level of covalent inhibition of said K-Ras protein thereby identifying a covalent inhibitor of K-Ras protein.

Embodiment P44

The method of Embodiment P43, comprising, prior to said contacting, determining whether said K-Ras inhibitor test compound contacts an amino acid residue within the Switch 2—Binding Pocket in silico using a computer modeling methodology.

Embodiment P45

The method of Embodiment P44, wherein said amino acid acid residue within the Switch 2—Binding Pocket is V7, V9, G10, P34, T58, A59, G60, Q61, E62, E63, Y64, R68, D69, Y71, M72, R73, F78, K88, E91, D92, H94, H95, Y96, R97, Q99, I100, R102, or V103.

Embodiment P46

The method of Embodiment P44, wherein said amino acid acid residue within the Switch 2—Binding Pocket is V9, A59, E63, Y64, R68, D69, M72, R73, F78, K88, E91, D92, H94, H95, Y96, R97, Q99, R102, or V103.

Embodiment P47

The method of Embodiment P44, wherein said amino acid acid residue within the Switch 2—Binding Pocket is V7, V9, T58, A59, G60, E63, Y64, R68, D69, Y71, M72, R73, F78, K88, E91, D92, H94, H95, Y96, R97, Q99, I100, R102, or V103.

Embodiment P48

The method of Embodiment P44, wherein said amino acid acid residue within the Switch 2—Binding Pocket is A59, Y64, D69, R73, F78, K88, E91, D92, H94, H95, R97, R102, or V103.

Embodiment P49

The method of Embodiment P44, wherein said amino acid acid residue within the Switch 2—Binding Pocket is V9, E63, Y64, R68, M72, H94, Y96, or Q99.

Embodiment P50

The method of Embodiment P43, wherein said K-Ras inhibitor test compound is a Switch 2—Binding Pocket

207 covalent inhibitor test compound and said K-Ras protein is a G12C mutant K-Ras protein.

VI. Additional Embodiments

Embodiment 1

A compound having the formula:

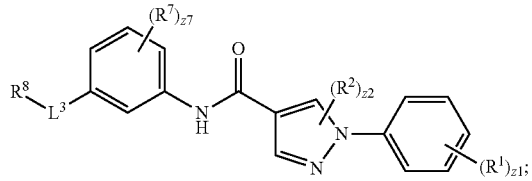

(IV)

wherein, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^7$ substituents may optionally be joined to form a substituted or unsubstituted cycloalkyl, substituted or unsubstituted heterocycloalkyl, substituted or unsubstituted aryl, or substituted or unsubstituted heteroaryl;

$R^8$ is independently hydrogen, halogen, $-CX^8_3$, $-CHX^8_2$, $-CH_2X^8$, $-CN$, $-SO_{n8}R^{8D}$, $-SO_{v8}NR^{8A}R^{8B}$, $-C(O)R^{8C}$, $-C(O)OR^{8C}$, $-C(O)NR^{8A}R^{8B}$, E, substituted or unsubstituted alkyl, substituted or unsubstituted heteroalkyl, substituted or unsub-

208 stituted cycloalkyl, substituted or unsubstituted heterocycloalkyl, substituted or unsubstituted aryl, or substituted or unsubstituted heteroaryl;

$L^3$ is a bond, $-N(H)-$, $-O-$, $-S-$, $-C(O)-$, $-C(O)N(H)-$, $-N(H)C(O)-$, $-NHC(O)N(H)-$, $-C(O)O-$, $-OC(O)-$, substituted or unsubstituted alkylene, or substituted or unsubstituted heteroalkylene;

E is an electrophilic moiety;

Each $R^{1A}$, $R^{1B}$, $R^{1C}$, $R^{1D}$, $R^{2A}$, $R^{2B}$, $R^{2C}$, $R^{2D}$, $R^{7A}$, $R^{7B}$, $R^{7C}$, $R^{7D}$, $R^{8A}$, $R^{8B}$, $R^{8C}$, and $R^{8D}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{8A}$ and $R^{8B}$ substituents bonded to the same nitrogen atom may optionally be joined to form a substituted or unsubstituted heterocycloalkyl or substituted or unsubstituted heteroaryl;

z1 is an integer from 0 to 5;

z2 is an integer from 0 to 3;

z7 is an integer from 0 to 4;

each X, $X^1$, $X^2$, $X^7$, and $X^8$ is independently $-F$, $-Cl$, $-Br$, or $-I$;

n1, n2, n7, and n8 are independently an integer from 0 to 4; and m1, m2, m7, m8, v1, v2, v7, and v8 are independently 1 or 2.

Embodiment 2

The compound of embodiment 1, wherein $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, or substituted or unsubstituted heteroalkyl.

Embodiment 3

The compound of embodiment 1, wherein $R^1$ is independently $-OR^{1D}$, substituted or unsubstituted alkyl, or substituted or unsubstituted heteroalkyl.

Embodiment 4

The compound of embodiment 1, wherein $R^1$ is independently $-OR^{1D}$, wherein $R^{1D}$ is substituted or unsubstituted alkyl.

Embodiment 5

The compound of embodiment 1, wherein $R^1$ is independently $-OR^{1D}$, wherein $R^{1D}$ is substituted or unsubstituted $C_1$-$C_6$ alkyl.

Embodiment 6

The compound of any one of embodiments 1 to 5, wherein $R^2$ is independently halogen, $-CX^2_3$, $-CHX^2_2$, $-CH_2X^2$, $-OCX^2_3$, $-OCH_2X^2$, $-OCHX^2_2$, substituted or unsubstituted alkyl, or substituted or unsubstituted heteroalkyl.

Embodiment 7

The compound of any one of embodiments 1 to 5, wherein $R^2$ is independently halogen, $-CX^2_3$, $-CHX^2_2$, or $-CH_2X^2$.

Embodiment 8

The compound of any one of embodiments 1 to 5, wherein $R^2$ is independently $-CX^2_3$.

Embodiment 9

The compound of any one of embodiments 1 to 8, wherein $R^7$ is independently halogen, $-CX^7_3$, $-CHX^7_2$, $-CH_2X^7$, $-OCX^7_3$, $-OCH_2X^7$, $-OCHX^7_2$, $-CN$, substituted or unsubstituted alkyl, or substituted or unsubstituted heteroalkyl.

Embodiment 10

The compound of any one of embodiments 1 to 8, wherein $R^7$ is independently halogen, $-CX^7_3$, $-CHX^7_2$, $-CH_2X^7$, $-OCX^7_3$, $-OCH_2X^7$, or $-OCHX^7_2$.

Embodiment 11

The compound of any one of embodiments 1 to 8, wherein $R^7$ is independently halogen.

Embodiment 12

The compound of any one of embodiments 1 to 8, wherein $R^7$ is independently $-Cl$.

Embodiment 13

The compound of any one of embodiments 1 to 12, wherein $L^3$ is independently a bond, $-N(H)-$, $-C(O)N(H)-$, $-N(H)C(O)-$, $-N(H)C(O)NH-$, $-C(O)O-$, $-OC(O)-$, substituted or unsubstituted alkylene, or substituted or unsubstituted heteroalkylene.

Embodiment 14

The compound of any one of embodiments 1 to 12, wherein $L^3$ is independently a $-N(H)-$, $-C(O)N(H)-$, or $-N(H)C(O)-$.

Embodiment 15

The compound of any one of embodiments 1 to 14, wherein $R^8$ is independently hydrogen, halogen, $-SO_{n8}R^{8D}$, $-SO_{v8}NR^{8A}R^{8B}$, $-C(O)R^{8C}$, $-C(O)OR^{8C}$, $-C(O)NR^{8A}R^{8B}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 16

The compound of any one of embodiments 1 to 14, wherein $R^8$ is independently hydrogen, $-SO_2R^{8D}$, $-SO_2NR^{8A}R^{8B}$, $-C(O)R^{8C}$, $-C(O)OR^{8C}$, $-C(O)NR^{8A}R^{8B}$, substituted or unsubstituted alkyl, or substituted or unsubstituted heteroalkyl.

Embodiment 17

The compound of any one of embodiments 1 to 14, wherein $R^8$ is independently $-C(O)R^{8C}$ or $-C(O)OR^{8C}$, wherein $R^{8C}$ is substituted or unsubstituted alkyl, substituted or unsubstituted heteroalkyl.

Embodiment 18

The compound of any one of embodiments 1 to 14, wherein $R^8$ is independently $-C(O)R^{8C}$, wherein $R^{8C}$ is substituted or unsubstituted $C_1$-$C_6$ alkyl.

Embodiment 19

The compound of embodiment 1 having the formula:

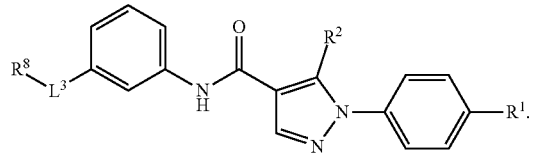

(IVa)

Embodiment 20

The compound of embodiment 1 having the formula:

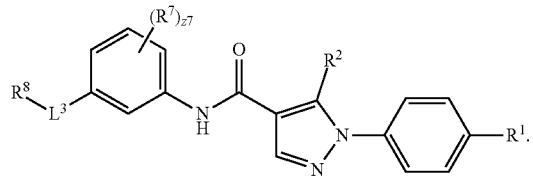

(IVb)

Embodiment 21

The compound of embodiment 19 or 20, wherein
$L^3$ is $-NH-$;
$R^1$ is unsubstituted $C_1$-$C_4$ alkoxy;
$R^2$ is $-CX^2_3$; and
$R^8$ is hydrogen, substituted $C_1$-$C_4$ alkyl, or E.

Embodiment 22

The compound of embodiment 1 having the formula:

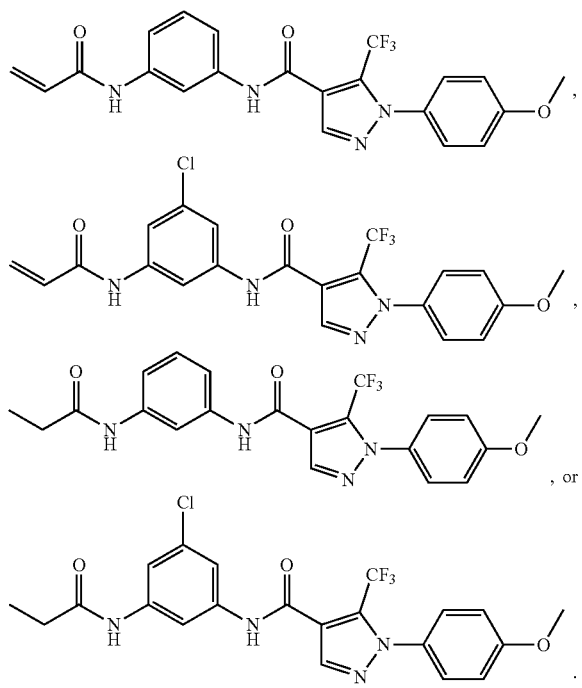

, or

Embodiment 23

A pharmaceutical composition comprising a pharmaceutically acceptable excipient and a compound of any one of embodiments 1 to 22.

Embodiment 24

A method of treating a disease in a patient in need of such treatment, said method comprising administering a therapeutically effective amount of a compound of any one of embodiments 1 to 17 to said patient.

Embodiment 25

The method of embodiment 24, wherein said disease is cancer.

Embodiment 26

The method of embodiment 25, wherein said cancer is lung cancer, colon cancer, colorectal cancer, pancreatic cancer, breast cancer, or leukemia.

Embodiment 27

A method of modulating the activity of a K-Ras protein, said method comprising contacting said K-Ras protein with an effective amount of a compound of any one of embodiments 1 to 22.

Embodiment 28

The method of embodiment 27, wherein said activity comprises GTPase activity, nucleotide exchange, GDP binding, GTP binding, differential GDP or GTP binding, effector protein binding, K-Ras binding to Raf, effector protein activation, guanine exchange factor (GEF) binding, GEF-facilitated nucleotide exchange, phosphate release, nucleotide release, nucleotide binding, K-Ras subcellular localization, K-Ras post-translational processing, or K-Ras post-translational modifications.

Embodiment 29

The method of embodiment 27, wherein said modulating is reducing the activity of said K-Ras protein.

Embodiment 30

The method of embodiment 27, wherein said K-Ras protein is a human K-Ras protein.

Embodiment 31

The method of embodiment 30, wherein said human K-Ras protein contains a G12C, G12V, G12D, G13C, or G13D mutation.

Embodiment 32

A method of modulating a K-Ras protein, said method comprising contacting said K-Ras protein with an effective amount of a compound of any one of embodiments 1 to 22.

Embodiment 33

The method of embodiment 32, wherein said compound contacts at least one amino acid residue of said K-Ras protein selected from V7, V9, G10, P34, T58, A59, G60, Q61, E62, E63, Y64, R68, D69, Y71, M72, R73, F78, K88, E91, D92, H94, H95, Y96, R97, Q99, I100, R102, and V103, and said compound covalently reacts with an amino acid residue of said K-Ras protein.

Embodiment 34

The method of embodiment 32, wherein said compound contacts at least one amino acid residue f of said K-Ras protein selected from V9, A59, E63, Y64, R68, D69, M72, R73, F78, K88, E91, D92, H94, H95, Y96, R97, Q99, R102, and V103, and said compound covalently reacts with an amino acid residue of said K-Ras protein.

Embodiment 35

The method of embodiment 32, wherein said compound contacts at least one amino acid residue of said K-Ras protein, selected from V7, V9, T58, A59, G60, E63, Y64, R68, D69, Y71, M72, R73, F78, K88, E91, D92, H94, H95, Y96, R97, Q99, I100, R102, and V103, and wherein said compound covalently reacts with an amino acid residue of said K-Ras protein.

Embodiment 36

The method of embodiment 32, wherein said compound contacts at least one amino acid residue f of said K-Ras protein selected from A59, Y64, D69, R73, F78, K88, E91, D92, H94, H95, R97, R102, and V103, and wherein said compound covalently reacts with an amino acid residue of said K-Ras protein.

Embodiment 37

The method of embodiment 32, wherein said compound contacts at least one amino acid residue of said K-Ras protein selected from V9, E63, Y64, R68, M72, H94, Y96, and Q99, and said compound covalently reacts with an amino acid residue of said K-Ras protein.

Embodiment 38

The method of embodiment 32, wherein said K-Ras protein is a human K-Ras protein.

Embodiment 39

The method of embodiment 32, wherein said K-Ras protein is within a biological cell.

Embodiment 40

The method of embodiment 39, wherein said biological cell forms part of an organism.

Embodiment 41

A K-Ras protein covalently bound to a compound of any one of embodiments 1 to 22, wherein said compound is covalently bound to a cysteine residue of said K-Ras protein.

Embodiment 42

The covalently modified K-Ras protein of embodiment 41, wherein said compound is reversibly covalently bound to a cysteine residue of said K-Ras protein.

Embodiment 43

The covalently modified K-Ras protein of embodiment 41, wherein said compound is irreversibly covalently bound to a cysteine residue of said K-Ras protein.

Embodiment 44

A method of identifying a covalent inhibitor of K-Ras protein comprising: contacting a K-Ras protein with a K-Ras inhibitor test compound; allowing said K-Ras inhibitor test compound to covalently inhibit said K-Ras protein; detecting the level of covalent inhibition of said K-Ras protein thereby identifying a covalent inhibitor of K-Ras protein.

Embodiment 45

The method of embodiment 44, comprising, prior to said contacting, determining whether said K-Ras inhibitor test compound contacts an amino acid residue within the K-Ras Switch 2—Binding Pocket in silico using a computer modeling methodology.

Embodiment 46

The method of embodiment 45, wherein said amino acid residue is V7, V9, G10, P34, T58, A59, G60, Q61, E62, E63, Y64, R68, D69, Y71, M72, R73, F78, K88, E91, D92, H94, H95, Y96, R97, Q99, I100, R102, or V103.

Embodiment 47

The method of embodiment 45, wherein said amino acid residue is V9, A59, E63, Y64, R68, D69, M72, R73, F78, K88, E91, D92, H94, H95, Y96, R97, Q99, R102, or V103.

Embodiment 48

The method of embodiment 45, wherein said amino acid residue is V7, V9, T58, A59, G60, E63, Y64, R68, D69, Y71, M72, R73, F78, K88, E91, D92, H94, H95, Y96, R97, Q99, I100, R102, or V103.

Embodiment 49

The method of embodiment 45, wherein said amino acid residue is A59, Y64, D69, R73, F78, K88, E91, D92, H94, H95, R97, R102, or V103.

Embodiment 50

The method of embodiment 45, wherein said amino acid residue is V9, E63, Y64, R68, M72, H94, Y96, or Q99.

Embodiment 51

The method of embodiment 44, wherein said K-Ras inhibitor test compound is a Switch 2—Binding Pocket covalent inhibitor test compound and said K-Ras protein is a G12C mutant K-Ras protein.

EXAMPLES

The following examples are meant to illustrate certain embodiments of the invention and not to limit the scope of the invention described herein. Activating mutations in K-Ras are among the most common lesions found in human cancer, and such mutations are generally associated with poor prognosis. Molecules that selectively target mutant K-Ras while sparing the wild type protein are needed. We have used a fragment-based screen to discover inhibitors of K-Ras (e.g., oncogenic mutant-specific). Crystallographic studies with multiple inhibitors in complex with K-Ras reveal that the compounds bind in a novel pocket of Ras. These inhibitors may disrupt the conformations of Switch I and Switch II, domains that are essential for the association and activation of downstream signaling partners. Our discovery of a new druggable pocket in K-Ras, and a set of inhibitors that bind to it in a mutant-specific fashion, provides a promising new avenue for the direct pharmacological inhibition of oncogenic Ras.

A. Compound Binding to K-Ras

In some embodiments of the compounds, several groups have been found to be effective as the reactive portion of the compounds (e.g. E, the electrophilic moiety, thiol reactive, aspartate reactive). In some embodiments, the electrophilic moiety E is selected from vinyl sulfones, acrylamides and epoxides. In some embodiments, the modulation of Switch 1 by compound binding may modulate K-Ras activity or function (e.g. effector binding, for example Raf or PI3K). In some embodiments, the compound binding to K-Ras may modulate K-Ras metal binding by modulating Switch 1 structure or function (e.g. partially disordering Switch-1 relative to the Switch 1 conformation in K-Ras that is not bound to a compound as described herein). In some embodiments, the electrophilic group E contributes to the binding of compound to K-Ras by contacting K-Ras residues. In some embodiments, the electrophilic group E contributes to the binding of compound to K-Ras by covalently bonding to K-Ras through a cysteine or aspartate at residues 12 or 13. The right balance between chemically reactivity, sterical demands and favorable contacts with the protein needs to be achieved for the best reactive group to link the compound to oncogenic cysteine-12.

In some embodiments, the compounds described herein provide contacts with K-Ras through a novel complementary pocket. In some embodiments, E can contribute to K-Ras binding through contacts beyond the covalent bond formation and can modulate Switch-1 conformation and stability. In some embodiments, by utilizing both features with the described compounds, K-Ras G12C or G12V or G12D or G13C or G13D can be selectively targeted.

B. The Switch 2—Binding Pocket

In some embodiments, the S2BP binding moiety or S2BP binding compound contacts one or more of amino acid residues selected from V7, V9, G10, P34, T58, G60, Q61, E62, E63, R68, Y71, M72, Y96, Q99, and I100; V7, V9, G10, P34, T58, G60, Q61, E62, E63, Y64, R68, Y71, M72, H94, Y96, Q99, and I100; V7, V9, G10, P34, T58, A59, G60, Q61, E62, E63, Y64, R68, D69, Y71, M72, R73, F78, K88, E91, D92, H94, H95, Y96, R97, Q99, I100, R102, and V103; V7, V9, T58, A59, G60, E63, Y64, R68, D69, Y71, M72, R73, F78, K88, E91, D92, H94, H95, Y96, R97, Q99, I100, R102, and V103; A59, Y64, D69, R73, F78, K88, E91, D92, H94, H95, R97, R102, and V103; V9, E63, Y64, R68, M72, H94, Y96, and Q99; or V9, A59, E63, Y64, R68, D69, M72, R73, F78, K88, E91, D92, H94, H95, Y96, R97, Q99, R102, and V103, of K-Ras or the equivalent (i.e. corresponding) amino acids present in mutants or homologs of Ras (e.g., human Ras, human K-Ras, human H-Ras, or a mutant of any of the foregoing). In some embodiments, the S2BP binding moiety or S2BP binding compound displace one or more amino acids in Switch 2 of Ras (e.g., K-Ras, human K-Ras, H-Ras, human H-Ras, or human Ras) that contacts, in the GTP bound form, one or more of the amino acids of the Switch 2 Binding Region of Ras (e.g., K-Ras, human K-Ras, H-Ras, human H-Ras, or human Ras), or the equivalent (i.e. corresponding) amino acids present in mutants or homologs of Ras (e.g., K-Ras, human K-Ras, H-Ras, human H-Ras, or human Ras). In some embodiments, the S2BP binding moiety or S2BP binding compound displace one or more amino acids in the Switch 2 Binding Region of Ras (e.g., K-Ras, human K-Ras, H-Ras, human H-Ras, or human Ras) that contacts, in the GTP bound form, one or more of the Switch 2 residues of Ras (e.g., K-Ras, human K-Ras, H-Ras, human H-Ras, or human Ras), or the equivalent (i.e. corresponding) amino acids present in mutants or homologs of Ras (e.g., K-Ras, human K-Ras, H-Ras, human H-Ras, or human Ras).

In some embodiments, the Switch 2—Binding Pocket binding moiety additionally contacts (e.g. bonds) an amino acid that forms part of the Switch 2—Binding Pocket. In some related embodiments, the contacting is a hydrogen bond, van der Waals interaction, ionic bond, covalent bond (e.g. disulfide bond) or hydrophobic contact.

C. Switch 2—Binding Pocket Binding Moieties that Contact the Switch 2—Binding Pocket In some embodiments, to determine whether the Switch 2—Binding Pocket binding moiety or Switch 2—Binding Pocket binding compound contacts and/or fills space within the Switch 2—Binding Pocket, computer modeling techniques are employed (e.g., in silico screening or modeling). In some embodiments, a query Switch 2—Binding Pocket binding compound (i.e. a test or reference compound) is fit into a structural model, such as a computer image, of Ras (e.g., K-Ras, human K-Ras, H-Ras, human H-Ras, or human Ras). In some embodiments, the structural model is derived from one or more of the solved co-crystal structures of Ras (e.g., K-Ras, human K-Ras, H-Ras, human H-Ras, or human Ras) bound to a compound as described herein. The PyMOL Molecular Graphics System may be employed to generate the image.

The computer models are typically analyzed to prevent any gross steric clashes and to satisfy key hydrogen bonds between the query Switch 2—Binding Pocket binding compound and the Ras (e.g., K-Ras, human K-Ras, H-Ras, human H-Ras, or human Ras) protein. In some embodiments, energy minimization calculations are performed to optimize binding energy. Using these techniques, one skilled in the art can easily determine whether a query Switch 2—Binding Pocket binding compound includes a Switch 2—Binding Pocket binding moiety that fills space within the Switch 2—Binding Pocket.

In some embodiments, the query Switch 2—Binding Pocket binding compound is analyzed to determine whether at least one bond (e.g. a hydrogen bond) is formed between the query Switch 2—Binding Pocket binding compound and an amino acid that forms part of the Switch 2—Binding Pocket. In some embodiments, using a computer modeling technique as described above, the distance between one or more amino acids that form part of the Switch 2—Binding Pocket and a potential contact point on the Switch 2—Binding Pocket binding moiety is determined. In some embodiments, based on this distance, one skilled in the art may determine whether at least one bond is formed between one or more amino acids that form part of the Switch 2—Binding Pocket and a Switch 2—Binding Pocket binding moiety.

D. Identification of Covalent K-Ras Inhibitors

Described herein is a method of designing a compound which covalently binds to a Switch 2 binding pocket of a Ras (e.g., K-Ras, human K-Ras, H-Ras, human H-Ras, or human Ras) protein, the method including the steps of: a) providing a structural model of a reference compound bound to the Switch 2 binding pocket of the Ras (e.g., K-Ras, human K-Ras, H-Ras, human H-Ras, or human Ras) protein, wherein the reference compound is covalently or non-covalently bound to said Switch 2 binding pocket; b) identifying a cysteine, aspartate, lysine, tyrosine or glutamate residue located in proximity to said Switch 2 binding pocket when said reference compound is bound to said Switch 2 binding pocket; c) generating at least one additional structural model of a test compound bound to said Switch 2 binding pocket, wherein said test compound comprises an electrophilic moiety; and d) selecting said test compound if said electrophilic moiety is located within bonding distance of said cysteine, aspartate, lysine, tyrosine or glutamate residue when said test compound is bound to said Switch 2 binding pocket.

A structural model of a reference compound bound to a Switch 2 binding pocket of a Ras protein (such as K-Ras, N-Ras, or H-Ras) may be provided as described above. Any suitable structural model of a reference compound bound covalently or non-covalently to the Ras protein can be used. For example, a three-dimensional computer model or a representation thereof (e.g. a computer image) is used. In some embodiments, an X-Ray crystal structure is used. For example, one of the solved co-crystal structures of human K-Ras can be used. In some embodiments, a structural model of a Switch 2 binding pocket of a K-Ras protein is used. Structural models can be obtained from public databases, including but not limited to the RCSB Protein Data Bank, available online at pdb.org and rcsb.orb. Alternatively, structural models can also be obtained and manipulated by computer modeling, including homology modeling and folding studies.

Suitable reactive amino acid residues can be identified by analyzing the sequence of the protein in conjunction with the structural model to which the reference compound is bound. Putative reactive amino acid residues which are cysteine, aspartate, lysine, tyrosine or glutamate may be identified in proximity to the reference compound. For example, cysteine residues in proximity to the reference compound are identified. Once an amino acid residue in the structural model has been identified, the intermolecular distance between the reference compound and the putative reactive amino acid may be noted. In some embodiments, the distance between the putative reactive amino acid and at least one atom of the reactive compound is less than or equal to 15, 12, 10, 8, 6, or 4 angstroms.

Test compounds comprising an electrophilic moiety may subsequently be used to generate additional structural models in which the position of the electrophilic moiety relative to one or more of the identified putative reactive amino acid residues is noted. The bonding distance between the test compound and one of such residues may be calculated based on the structural model, and a determination may be made regarding the potential bonding distance between the test compound (e.g. the electrophilic moiety) and the putative reactive residue. Test compounds which appear to provide a suitable bonding distance likely to result in the formation of a covalent bond may then be chosen for further development. When making such determinations, factors such as steric hindrance and orientation of each chemical moiety may be taken into account. Test compounds which are initially rejected may also be further modified in order to improve the likelihood that they will form a covalent bond with the target protein.

In some embodiments, the compounds described herein target a mutant of K-Ras, glycine-12 to cysteine (G12C). This is the most common Ras mutation in lung cancer (Forbes et al. 2006 *Br J Cancer*) and the only known transforming mutation found in a recent comparative sequencing study of a human lung tumor (Lee et al. 2010 Nature). 100% of K-Ras mutations in MYH-associated polyposis (familial colon cancer syndrome) are K-RasG12C (Jones, S., Lambert, S., Williams, G. T., Best, J. M., Sampson, J. R., & Cheadle, J. P. (2004). Increased frequency of the k-ras G12C mutation in MYH polyposis colorectal adenomas. *British Journal of Cancer*, 90(8), 1591-1593. doi: 10.1038/sj.bjc.6601747) G12C places a nucleophilic sulfhydryl group between the nucleotide-binding site and the allosteric site. Since the regions surrounding both sites are involved in contacts with effectors and GEFs, binding of compounds (e.g. antagonists, inhibitors, small molecules) at either site has the potential to disrupt downstream signaling. In some embodiments, the location and nucleophilicity of this mutant residue allows development of covalent (e.g. reversible, irreversible) inhibitors of oncogenic K-Ras that bind in either the active site or the cleft behind Switch 2 or the Switch 2—Binding Pocket.

In some embodiments, a library of disulfide compounds may be screened against a cysteine-containing protein in the presence of a reducing agent such as β-mercaptoethanol (BME). Compounds with complementary binding contacts with a region of the protein near the cysteine may shift the disulfide exchange equilibrium away from BME modification of the cysteine thiol and enhance the ratio of the hit ligand bound to the cysteine. The resulting mass change of the protein can be readily detected by mass spectrometry, and the percentage of modified protein can be used as a measure of potency. Compounds which exchange with the cysteine without conferring affinity should exchange with reducing agent equally well and will not shift the equilibrium toward protein modification. The potency of various compounds at a given concentration of BME may be compared by calculating the dose-response 50 (DR50), which is the concentration of compound at which the protein becomes 50% modified.

In some embodiments, screening is for inhibitors of K-Ras G12C, a naturally occurring, oncogenic form of the target does not require removal of the mutant cysteine residue.

The Switch 1 and Switch 2 areas of Ras show significant structural differences between the GDP- and GTP-bound states. Moreover, these regions are involved in contacts with all known Ras binding partners, including effectors, GEFs and GAPs. In some embodiments, the compounds described herein covalently modify cysteine-12 thereby altering the conformation of either switch region affecting GEF binding or effector protein binding. Multiple modes of compound (e.g. small molecule, antagonist, or inhibitor) interruption of Ras function can be employed.

In some embodiments, the compounds provided herein effect the Ras binding to Raf or PI3K. In some embodiments, binding of the compounds provided herein to K-Ras modulates K-Ras binding to Raf. In some embodiments, binding of the compounds provided herein to K-Ras modulates K-Ras binding to PI3K. In some embodiments, binding of the compounds provided herein to K-Ras modulates K-Ras binding to PI3K but not K-Ras binding to Raf. In some embodiments, binding of the compounds provided herein to K-Ras reduces K-Ras binding to PI3K but not K-Ras binding to Raf. In some embodiments, binding of the compounds provided herein to K-Ras modulates K-Ras binding to Raf but not K-Ras binding to PI3K. In some embodiments, binding of the compounds provided herein to K-Ras reduces K-Ras binding to Raf but not K-Ras binding to PI3K. In other embodiments, the compounds provided herein alter intrinsic or GEF-enhanced nucleotide exchange. In other embodiments, the compounds provided herein alter Ras binding to SOS. In other embodiments, the compounds provided herein modulate SOS-enhanced nucleotide exchange. In some embodiments, the compounds provided herein increase the intrinsic or GAP-stimulated rate of GTP hydrolysis. In some embodiments, the compounds provided herein decrease the intrinsic affinity of K-Ras for nucleotide. In some embodiments, the compounds provided herein decrease the intrinsic affinity of K-Ras for GTP. In some embodiments, the compounds provided herein decrease the intrinsic affinity of K-Ras for GDP.

Residue 12 of K-Ras lies between the nucleotide-binding site and an allosteric pocket. In some embodiments, the compounds provided herein bind to either site or both sites. In some embodiments, compound binding to the allosteric pocket alters K-Ras-effector contacts. In some embodiments, compound binding to the S2BP alters K-Ras-effector contacts. In some embodiments, compound binding to the nucleotide-binding site alters K-Ras-effector contacts. In some embodiments, simultaneous compound binding to the allosteric pocket and the nucleotide-binding site alters K-Ras-effector contacts. In some embodiments, simultaneous compound binding to the S2BP and the nucleotide-binding site alters K-Ras-effector contacts. In some embodiments, compound binding to the allosteric pocket, S2BP, and/or nucleotide-binding site alters the activity of the K-Ras protein, it's GTPase activity, nucleotide exchange, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, K-Ras post-translational modifications, or GTP bound K-Ras signaling pathway.

In some embodiments, the compounds described herein afford a covalent yet reversible handle. In embodiments, the methods described above may be used to make a non-covalent modulator of Ras (e.g., K-Ras, human K-Ras, H-Ras, human H-Ras, or human Ras) without an electrophilic moiety (e.g., binds Switch 2 amino acids).

E. Determining Intrinsic and GEF Mediated Nucleotide Exchange Rates for Compound-Bound K-RasG12C GEF-mediated nucleotide exchange assays are carried out using full-length recombinant human K-Ras G12C and WT containing an N-terminal hexahistidine tag and the catalytic domain of SOS (residues 566-1049), also containing a hexahistidine tag, in the presence of $\alpha$-$^{32}$P-labeled GTP. K-Ras WT and G12C are treated with 250 µM inhibitor overnight at 4 C in the following buffer: 20 mM HEPES [pH 7.5], 150 mM NaCl, 10 mM EDTA. The percent modification is determined by mass spectrometry (Waters Acquity TQD). The proteins are then run over NAP-5 columns, eluting with Buffer A (20 mM HEPES [pH 7.5], 150 mM NaCl, 20 mM MgCl$_2$), following the manufacturer's instructions. Reaction mixes are prepared containing 4 M K-Ras and 1 µM SOS in Buffer A with 1 mg/mL BSA. Separately, a solution of [$\alpha$-$^{32}$P] GTP (160 pCi/mL, 2 µM total GTP) is prepared. The reactions are initiated by adding 25 µL GTP solution to 25 µL of each reaction mixture. Exchange is measured by blotting the reaction onto nitrocellulose, washing with Buffer A, then visualizing by phosphorimager.

F. Determining Intrinsic GTPase and GAP Mediated Activity of Compound-Bound K-Ras G12C The assays are carried out as described previously (Schubbert et al., Mol. Cell Biol. 2007, 7765-70). 200 nM of each recombinant K-Ras protein (G12C, compound loaded G12C, G12D, WT) that has been preloaded with [$\gamma$-$^{32}$P]GTP is incubated without (intrinsic GTPase activity assay) or with (GAP assays) GAP-related domain (GRD) proteins (neurofibromin or p120 GAP) at room temperature. The hydrolyzed and released radioactive phosphate is extracted and detected by liquid scintillation counting at defined time points. Recombinant K-Ras and GRD proteins are produced in *Escherichia coli*.

G. Initial Stop Flow Experiments

Conditions: 1 micM protein, buffer: 20 mM HEPES pH=7.5, 150 mM NaCl, 1 mM DTT, 2 mM unlabeled GDP if indicated, 1 micM SOS if indicated, 2.5 mM EDTA if indicated, no added free Mg in buffer, protein loaded with mant-dGDP, (1h r.t. incubation with 2 mM EDTA, NAP-5 purification), protein pre-labeled with compounds and frozen, experiment at 20C. Results:fast intrinsic bleaching/exchange, larger drop in fluorescence due to EDTA treatment with compound, acceleration of exchange in presence of SOS.

The small GTPase K-Ras is the most frequently mutated oncogene in cancer, and its high nucleotide affinity and lack of druggable pockets have made direct inhibitors difficult to develop. Previous work in our lab identified covalent inhibitors of K-Ras$^{G12C}$ that bind a novel inhibitory pocket. This pocket can be targeted to allosterically alter nucleotide affinity towards the inactive GDP-bound state and interfere with effector contacts. These inhibitors are specific for the GDP state and rely on covalent attachment to C12. These limitations are problematic since a majority of Ras-driven cancers express non-cysteine mutations at positions 12, 13, or 61, which are predominately GTP bound. Using this novel pocket, we have developed targeted screening methods designed to select compounds free from these limitations. Particularly, tethering against introduced cysteine residues near the initial novel pocket has yielded new scaffolds. Crystal structures of K and H-Ras labeled with these early leads have shown that compounds partially occupy the initially identified novel pocket in both the GDP and GTP states and have novel binding contacts that expand the original initial novel pocket in new and intriguing ways. Preliminary SAR has demonstrated that these leads are tractable for ligand optimization and are readily converted to carbon-based electrophiles. This study demonstrates that the expanded pocket (S-IIP) is widely accessible in both of Ras' nucleotide states and presents a new series of scaffolds that could directly inhibit Ras function through covalent modification. These structures will help guide the development of reversible S-IIP inhibitors that can directly inhibit Ras with alternative binding sites.

TABLE 1

Intrinsic and GAP-simulated GTP hydrolysis rates
$K_{hydrolysis}$ $10^{-5}$ (sec$^{-1}$)

| | Intrinsic | | P120GAP Simulated | |
|---|---|---|---|---|
| WT | 68 | ±3.5 | 4300 | ±100 |
| G12A | 1.3 | ±0.06 | 32 | ±0.8 |
| G12C | 49 | ±1.8 | 20 | ±3 |
| G12D | 19 | ±1 | 89 | ±8 |
| G12R | 1.8 | ±0.07 | 20 | ±0.8 |
| G12V | 4.2 | ±0.2 | 24 | ±1 |
| G13D | 9.6 | ±0.2 | 20 | ±5 |
| Q61L | 0.80 | ±0.05 | 12 | ±0.7 |
| Q61H | 1.3 | ±0.03 | 5 | ±0.6 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

H. Novel Ras Binder Occupies a Modified Switch-II Pocket in GTP- and GDP-States and Allosterically Controls Nucleotide Preference and SOS Activation Covalent inhibitors of K-Ras(G12C) have been reported that exclusively recognize the GDP state. Here, we utilize disulfide tethering of a non-natural cysteine (K-Ras(M72C)) to identify a new Switch-II Pocket (S-IIP) binding ligand (2C07) that engages the active GTP state. Co-crystal structures of 2C07 bound to H-Ras(M72C) reveal binding in a cryptic groove we term S-IIG. In the GppNHp state, 2C07 binding to a modified S-IIP pushes switch-I away from the nucleotide breaking the network of polar contacts essential for adopting the canonical GTP state. Biochemical studies show 2C07 alters nucleotide preference and inhibits SOS binding and exchange, but permits Raf-1-RBD binding. 2C07 was converted to irreversible covalent analogs, which target both nucleotide states and function as occupancy probes to detect reversible engagement in competition assays. 2C07's ability to target both nucleotide states opens the possibility of inhibiting oncogenic mutants of Ras, which exist predominantly in the GTP state in cells.

Oncogenic mutations in Ras are found in over 20% of all cancers and are generally associated with increased mortality (Forbes et al., 2010). Mutations in Ras lead to constitutive activation of Ras signaling by impairing GTP hydrolysis, making signaling dependent on nucleotide affinity and relative nucleotide concentration rather than GAP (GTPase Accelerating Protein) mediated inactivation (Ostrem and Shokat, 2016). The switch-like activation cycle is mediated by switch-I (residues 30-38) and switch-II (residues 59-76), which undergo drastic changes in topology and dynamics upon nucleotide exchange (Ito et al., 1997; Milburn et al., 1990; Muraoka et al., 2012). Oncogenic mutations at G12, G13, and Q61 disturb these structural changes causing constitutive activation (Hunter et al., 2015).

Ras has until recently been deemed "undruggable" due to its picomolar affinity for nucleotide and a lack of other functional binding pockets (John et al., 1990). Our lab and others have begun to re-evaluate the possibility of direct Ras inhibition by employing various methods to detect protein allostery and screen for binding ligands (Lim et al., 2013; Maurer et al., 2012; Muraoka et al., 2012; Ostrem et al., 2013; Patgiri et al., 2011; Shima et al., 2013; Spencer-Smith et al., 2017; Sun et al., 2012; Welsch et al., 2017). From this work, novel pockets have been identified that provide new opportunities for drug discovery. A series of oncogene specific irreversible K-Ras(G12C) inhibitors (eg. ARS-853), which bind to a transient pocket under switch-II (termed S-IIP), have been reported (Ostrem et al., 2013; Lito et al., 2016; Patricelli et al., 2016). Intriguingly, these electrophiles inhibit K-Ras(G12C) signaling by exclusively binding to and stabilizing the GDP form, which is the "inactive state" of the target in cells (Ostrem et al., 2013; Lito et al., 2016; Patricelli et al., 2016). The inability to bind the GTP state of K-Ras(G12C) is compensated by the near wild-type intrinsic GTPase activity of this oncogenic allele (Hunter et al., 2015; Patricelli et al., 2016). Although the G12C binding compounds provide an attractive entry point into drugging K-Ras, their exclusive specificity for the GDP state may limit their application beyond this particular allele. Other prevalent oncogenic K-Ras mutations such as G12V and G12D have significantly lower intrinsic hydrolysis rates and are predominately GTP bound in cells (Hunter et al., 2015).

Figure 36:
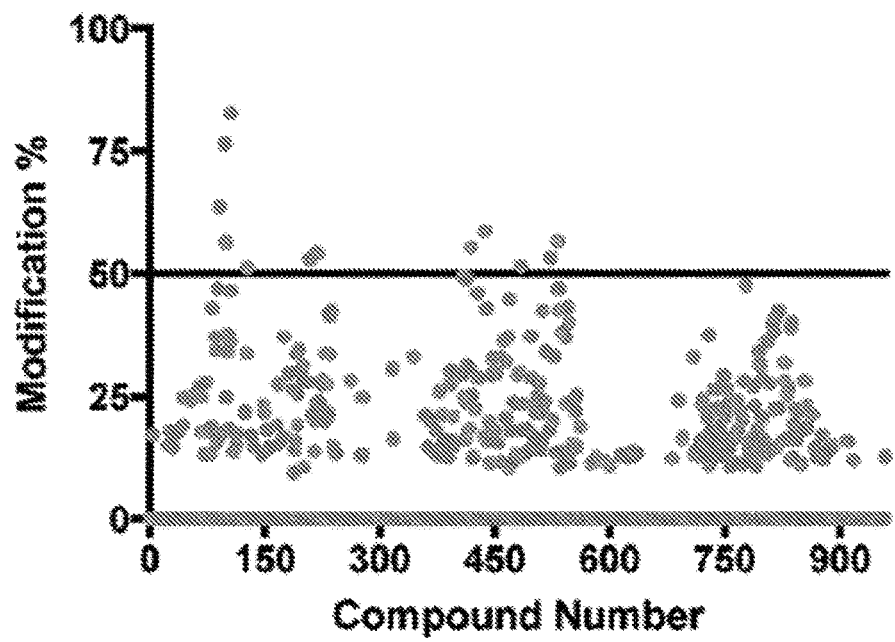
FIG. 36. K-Ras(M72C) Full Tethering Screen Results. Percent modification for each member of the tethering screen library (screened at a βME concentration of 1 mM) is plotted versus compound number. 50% modification was the cut-off for positive hits, and the hit rate was 1.6%.

Analysis of multiple Ras GDP crystal structures revealed residues that comprise the S-IIP are highly mobile in the GDP state but only form a stable pocket upon binding of a S-IIP ligand (Ostrem et al., 2013; Domaille et al., 1994; Ostrem and Shokat, 2016). By contrast, crystal structures of Ras GppNHp (5'-guanylyl imidodiphosphate, a non-hydrolyzable GTP analog) show the residues of switch-II closed over the S-IIP suggesting limited access to the pocket (Ostrem et al., 2013). However, analysis of B-factors for the deposited GppNHp structure of H-Ras(G12C) indicates that the switch-II region is still highly mobile (FIG. 36) (Ostrem et al., 2013). NMR studies also suggest that activated Ras transitions between multiple conformational states to accommodate effector binding and GTPase activities (Kalbitzer et al., 2009; Muraoka et al., 2012). Therefore, we hypothesized it may be possible to find a ligand that takes advantage of switch-II's flexibility in the GTP state for binding. Since the site of covalent attachment (residue 12) is proximal to the γ-phosphate of GTP, we wondered if the opposite end of the S-IIP, distant from position 12 might be accessible in the GTP state. Driven by the hypothesis that S-IIP inhibitors that bind to the GTP state could offer a means to access the most active form of K-Ras in cells, we carried out a fragment-based tethering screen with an engineered cysteine mutant of Ras (M72C) to discover new scaffolds that could expand switch-II inhibition to both nucleotide states and reveal new S-IIP dynamics and structural changes. This screen yielded a fragment that binds to both the GDP and GTP nucleotide states of mutant Ras, revealing unexpected Ras dynamics in the ligand bound GTP state and altering biochemical properties of Ras. 2C07 was then readily converted to a series of carbon-based electrophiles, which irreversibly target both nucleotide states and have detectable reversible binding in competition studies with fully reversible and equivalent scaffolds.

Fragment 2C07 Occupies an Expanded S-IIP in K-Ras (M72C) GDP: The discovery of the S-IIP relied on a disulfide-fragment-based screening approach called tethering to identify weak reversible covalent binders of K-Ras (G12C) (Erlanson et al., 2004; Forbes et al., 2010; Ostrem et al., 2013). Analysis of co-crystal structures of numerous published ligands for K-Ras(G12C) reveal a tripartite Switch-II Pocket: 1) Covalent attachment to G12C near the 3-phosphate of GDP, including a common H-bond of the acrylamide to Lys 16, 2) The "linker region" which connects regions #1 and #3 and lacks obvious H-bond interactions, and 3) Distal to G12C a sub-pocket with several H-bond interactions (Asp 69 and Arg 68) to substituents on the phenol ring found in all reported S-IIP binders (FIG. 31a) (Ostrem et al., 2013; Patricelli et al., 2016). Focusing on the two sub-pockets (#2 & #3) critical for non-covalent recognition, it is clear from extensive SAR analysis of various S-IIP binders that the phenol recognition pocket is critical for compound binding. In contrast, sub-pocket #2 makes limited ligand interactions and analyses of co-crystal structures and SAR across various compounds reveal modest improvements in potency and suggest the linker must be of appropriate length and flexibility to reach sub-pocket #3. To target sub-pocket #3 distal to position 12 and the γ-phosphate of GTP, non-native cysteine residues were introduced near the binding site of the phenol of ARS-853 to serve as a reactive handle for targeted tethering. By placing non-native cysteines far from the nucleotide-binding site, we hoped to select for fragments with higher potency and greater interactions with sub-pocket #3, which could potentially bind either nucleotide state.

We first identified two amino acids, Met 72 and Val 9, that interact with current K-Ras(G12C) binders but do not form critical H-bonding interactions and individually mutated these residues to cysteine for tethering. K-Ras(V9C) was not reactive with various electrophiles such as Ellman's reagent and a small panel of the disulfide tethering library. This lack of reactivity precluded its use for screening purposes. We therefore focused on K-Ras(M72C), which was solvent exposed and readily reacted with disulfide containing fragments.

Figure 37:
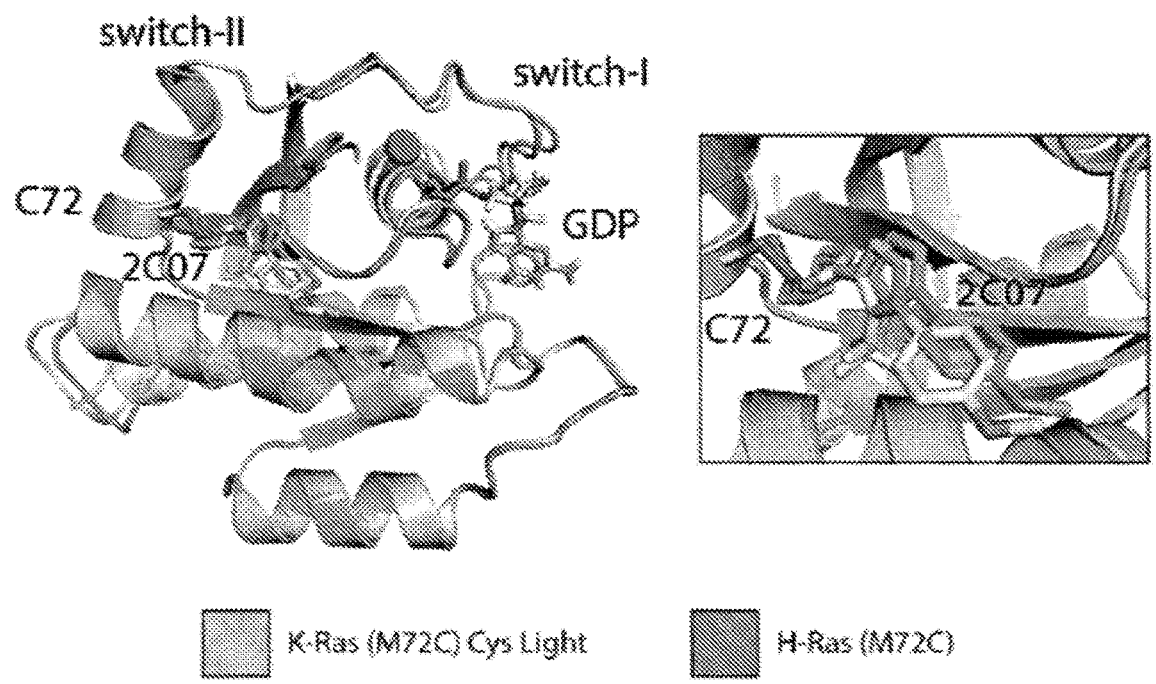
FIG. 37. Structure Comparison Between GDP Bound K and H-Ras 2C07 Co-crystal Structures. Overall secondary structure is identical between 2C07 bound isoforms (Left). 2C07 binding is also consistent between isoforms (right).

A tethering library of 960 disulfides were screened against 1-169 K-Ras(M72C) GDP using intact protein mass spectrometry to monitor percent modification (See Methods, and FIG. 37). Fragments 2C07 (69.7%+3.1%) and 2B02 (52.8%+1.9%) exhibited the highest level of modification. These fragments were selective for Cys 72 as they did not modify full-length wild-type K-Ras (which contains 4 native cysteine residues), formed a single adduct with full-length K-Ras(M72C), and labeled Cys 72 in both truncated K and H-Ras isoforms (FIG. 31B). 2C07 labeling is not significantly different between truncated isoforms, which reflects the near sequence identity between isoforms in the absence of their hypervariable region (Vigil et al., 2010). To better prioritize tethering fragments, a $\beta ME_{50}$ value (the concentration of βME needed to reduce disulfide fragment modification to 50%) was determined for each compound. A higher βME$_{50}$ value corresponds to a better fragment as it can bind with increasing concentrations of competitive thiol (Erlanson et al., 2004; Yang et al., 2009).

We next explored small chemical modifications to 2C07. Increasing the 2C07 linker length (2C07b) lead to a modest loss in binding potency indicated by a small decrease in βME$_{50}$. Removal of the trifluoromethyl group (2C07c) resulted in a drastic decrease in βME$_{50}$ indicative of a substantial role in binding. We chose to investigate 2C07 further since it had a high starting βME$_{50}$, a distinct chemotype from previously reported S-IIP binders, and several analogs suggested elements of 2C07 could be optimized to improve binding.

In order to better understand 2C07 binding, we solved its structure bound to K-Ras(M72C). To ensure uniform labeling specifically at Cys 72, we used a previously validated K-Ras Cys-light construct lacking all native cysteines (Ostrem et al., 2013). Using this construct, we obtained a 1.49 Å co-crystal structure of 2C07 bound to K-Ras(M72C) GDP (PDB: 5VBM) (FIG. 31c). 2C07 binds under switch-II, but does not engage with a fully formed S-IIP as seen in K-Ras(G12C) binders. Instead of projecting back through sub-pockets #1 and #2 as described above, 2C07 engages with sub pocket #3 and diverts down into a new hydrophobic groove away from the nucleotide-binding site. Unexpectedly, 2C07 also expands this sub-pocket further by extending into a new hydrophobic groove. We refer to this S-IIP structural change as the Switch-II Groove (S-IIG) to convey that the ligand projects out of the S-IIP and is not covered by switch-II.

Figure 31:
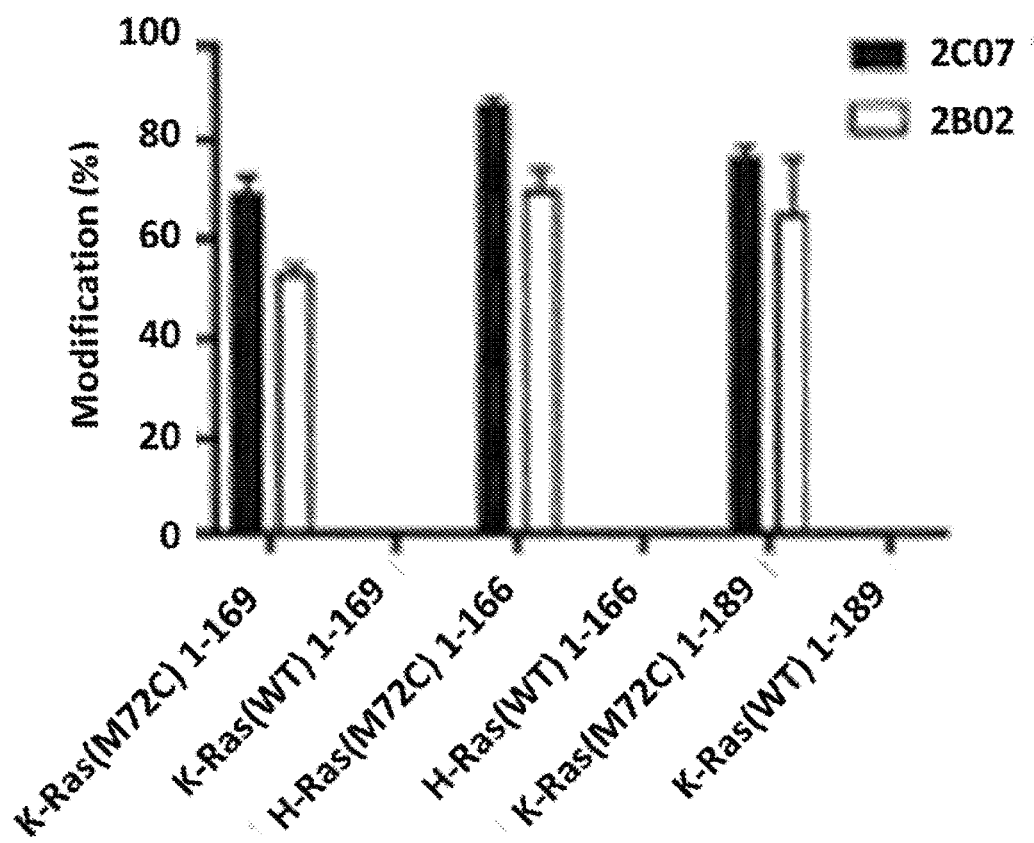
FIG. 31. Tethering at 72 Yields New S-IIP Binder. Top hits from the tethering screen as well as two 2C07 derivatives with βME$_{50}$ values reported. Percent labeling of 2C07 and 2B02 against various Ras constructs at screening βME concentration (1 mM) are graphed.

Like the S-IIP, the S-IIG is located between the central β-sheet and the α2-(switch-II) and α3 helices. However, 2C07 has more extensive interactions with the surface between the central β-sheet and the α3 helix than the original G12C fragment hits. This surface is shown in detail in FIG. 31c (top) with key residues annotated and the defined and complete electron density of 2C07 shown (F$_o$-F$_c$, 2.5σ, bottom). FIG. 31d shows a comparison between 2C07 and ARS-853 binding. 2C07 has a distinct trajectory away from the nucleotide-binding site and the conformation of the α2-(switch-II) helix is higher than the ARS-853 structure where polar contacts hold the helix close to the ligand. From its point of covalent attachment at Cys 12, ARS-853 traverses the mouth of the pocket and displaces Gly 60 reaching sub-pocket #3 underneath switch-II. Overlaying the two ligands (FIG. 31d, right) with the surface of the 2C07 structure suggests overlapping but distinct trajectories occurring with specific switch-II conformations. The 2C07 (cyan sticks) stabilized switch-II surface (blue) clashes and cuts off sub-pocket #2, which ARS-853 (magenta sticks) traverses to form key H-bonding interactions with residues of sub-pocket #3 (FIG. 31c). Since 2C07 possesses a new trajectory away from the nucleotide-binding pocket, we hypothesized that it may also have measurable binding to Ras GTP, in contrast to K-Ras(G12C) binding molecules.

Figure 32:
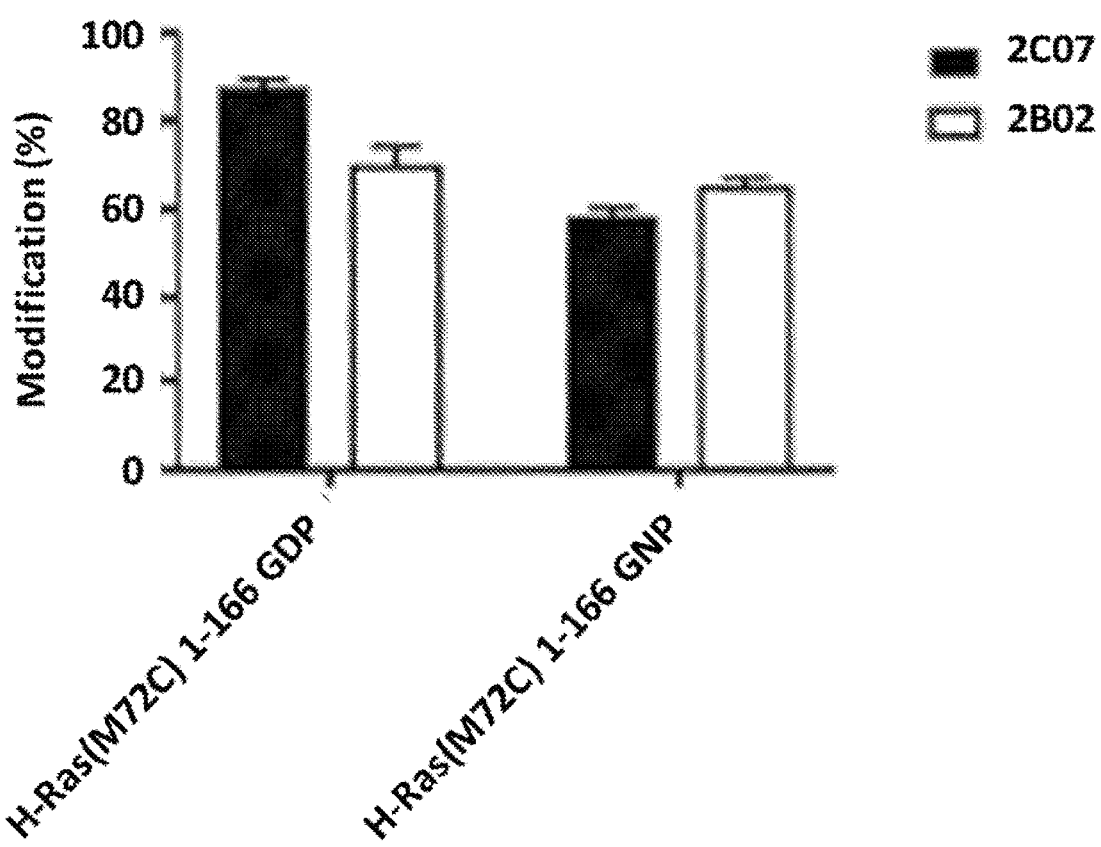
FIG. 32. 2C07 Binds to H-Ras(M72C) GppNHp Causing Alternative Mg$^{2+}$ Coordination. βME50 values of 2C07 and 2B02 binding to the GppNHp state. Percent labeling against H-Ras(M72C) GDP and GppNHp at the screening βME concentration (1 mM) are graphed.

2C07 Binds the GppNHp-state of H-Ras(M72C): The tethering hit, 2C07, readily modifies H-Ras(M72C) GppNHp and retains its ability to label Cys 72 even in the presence of excess competitive thiol βME$_{50}$: 1.10 mM (1.01 mM-1.20 mM)) (FIG. 32a). This is in striking contrast to previous tethering fragments against K-Ras(G12C), which did not label the GppNHp state even at the lowest βME concentrations. We also observed that the second hit (2B02) labeled H-Ras(M72C) GppNHp, but chose to investigate 2C07 further due to its higher labeling efficiency for both nucleotide states and ease of crystallographic analysis.

In order to determine the co-crystal structure of 2C07 bound to the GppNHp bound state, we turned to the 1-166 H-Ras(M72C) construct as more H-Ras GppNHp structures have been reported in the PDB, and there was negligible difference in 2C07 labeling between truncated K and H-Ras isoforms (FIG. 31b) (Burns et al., 2014; Johnson et al., 2016). Using a truncated 1-166 H-Ras(M72C) construct containing all endogenous cysteines, we obtained a 2.2 Å resolution co-crystal structure of 2C07 bound to H-Ras (M72C) GppNHp (PDB: 5VBZ). To our knowledge, this is the first structure of a drug-like fragment bound to active Ras. The unit cell contains three Ras molecules with complete density for 2C07 present in Chain C, which is shown in FIG. 32B. We also obtained a 1.57 Å co-crystal structure of 2C07 bound to H-Ras(M72C) GDP (PDB: 5VBE) and found minimal differences between this structure and the 2C07 K-Ras(M72C) GDP Cys-light structure (FIG. 38), which supports the similar labeling efficiency of 2C07 across different Ras isoforms. FIG. 32c shows the major structural differences between the H-Ras(M72C) 2C07 bound GDP and GppNHp states. The binding pose of 2C07 is not significantly altered except for a slight rotation out of the S-IIG along the axis of the trifluoromethyl group. The switch-II conformation is also similar with a slight disordering and loss of α-helical secondary structure for the α2-(switch-II) helix in the GppNHp structure. It appears that the switch-II structural changes needed to form the S-IIG are relatively conserved in both nucleotide states. Surprisingly, switch-I is significantly altered by 2C07 in the GppNHp crystal structure.

In multiple K- and H-Ras GppNHp crystal structures, both switch regions form essential polar contacts between the GppNHp γ-phosphate mediated by Gly 60 of switch-II and Thr 35, and Tyr 32 of switch-I (Ostrem et al., 2013; Ostrem and Shokat, 2016). These three residues have been implicated in GTP binding and effector signaling in previous mutational studies (Ford et al., 2005; Hall et al., 2001; Spoemer et al., 2001). In the GppNHp state, 2C07 binding to the S-IIG causes a drastic movement of switch-I away from the nucleotide thereby breaking the network of polar contacts important for switch-I adoption of the canonical "GTP state." The critical hydroxyl group of Tyr 32 no longer coordinates the γ-phosphate and the entire residue is distal from the nucleotide (FIG. 32c). Gly 60 could not be modeled, which suggests this region is likely destabilized and highly flexible. Most striking is the change in Thr 35's conformation, which results in alteration of the highly conserved Mg$^{2+}$ coordination in the GTP state.

Two distinct states of Mg$^{2+}$ coordination in the GTP state of Ras have been identified and linked to divergent Ras effector binding interactions (Kalbitzer et al., 2009; Matsumoto et al., 2016; Spoemer et al., 2001; 2004). FIG. 32d shows the changes in Mg$^{2+}$ coordination that occur between the two GppNHp bound states (Muraoka et al., 2012). $^{31}$P NMR and crystallographic studies have demonstrated that activated Ras exists in one of two states (State 1 and State 2) that differ in the alternative coordination of Mg$^{2+}$ through either the hydroxyl of Thr 35 (State 2) or an ordered water molecule (State 1) (Spoemer et al., 2004). This difference leads to a significant reordering of switch-1, which alters the presentation and conformation of the Ras effector region. Previously characterized mutants, G60A and T35S, each bias activated Ras towards State 1, which has been correlated with decreased effector binding to Raf-1 kinase compared to State 2 (Ford et al., 2005; Muraoka et al., 2012). In the 2C07 bound H-Ras(M72C) GppNHp structure, we observe a new $Mg^{2+}$ coordination by Thr 35 where the hydroxyl and carbonyl backbone each displace an ordered water to form contacts with magnesium (FIG. 32d). Alternative coordination of $Mg^{2+}$ by the threonine carbonyl or hydroxyl has also been observed in the GppNHp state of Ras-like GTPase Cdc42 which has significant effects on signaling (Adams and Oswald, 2007). The co-crystal structure of 2C07 H-Ras GppNHp reveals unexpectedly that some ligands have access to switch-II in both nucleotide states and those that bind the GppNHp state can allosterically alter switch-I mediated nucleotide interactions, which are over 13 Å removed from the ligand.

Hydrogen Deuterium Exchange Mass Spectrometry (HDX-MS) Analysis of 2C07 Bound to the GppNHp State of Ras: To rule out the possibility that our crystallographic evidence for 2C07 induced allosteric changes in switch-I in the GppNHp state are the result of crystallographic packing interactions, we next characterized the dynamics of 2C07-bound structures in solution using hydrogen deuterium exchange mass spectrometry (HDX-MS). HDX-MS measures the exchange of amide hydrogens in solution and, as their rate of exchange is mediated by their involvement in secondary structure, it is an excellent probe of protein conformational dynamics. This technique offers a strong complement to our X-ray crystallographic analysis as it is not influenced by crystal packing, and offers time resolved information on protein dynamics (Fowler et al., 2016; Gallagher and Hudgens, 2016; Vadas and Burke, 2015). We therefore utilized HDX-MS to complement our static X-ray structure data and to explore the structural and dynamic differences between both 2C07 bound nucleotide states in solution.

Figure 33A:
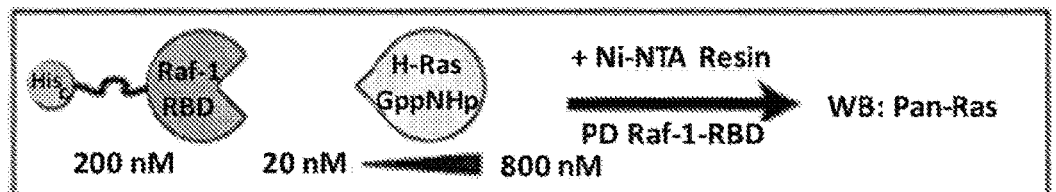
FIGS. 33A-33D. Pull-down Studies Demonstrate 2C07 Preserves H-Ras(M72C) Binding to Raf, Shifts Intrinsic Nucleotide Preference Towards the GDP State, and Prevents SOS Binding and Catalyzed Nucleotide Exchange.
Figure 33A:
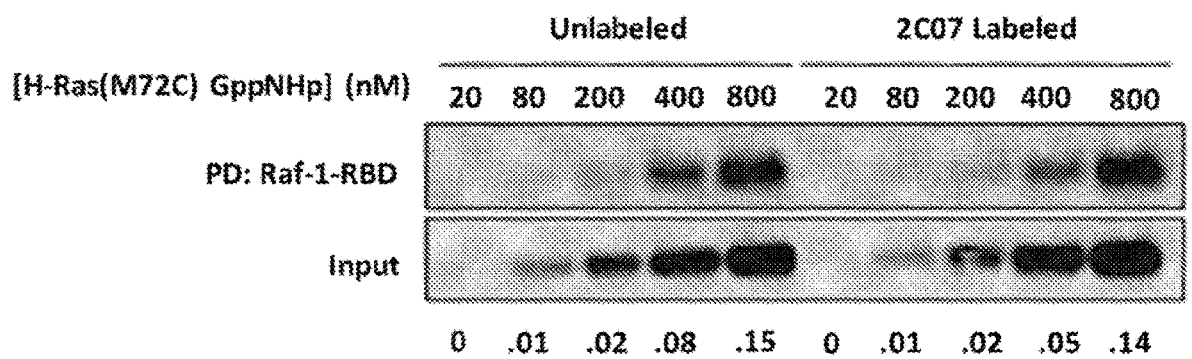

As a point of reference for H/D exchange, we first compared the difference in deuterium incorporation between unlabeled H-Ras(M72C) GDP and GppNHp. Numerous regions in H-Ras(M72C) showed decreases in deuterium exchange in the presence of GppNHp compared to in the presence of GDP (FIG. 33a). Comparing the crystal structures of GppNHp and GDP loaded H-Ras revealed differences in deuterium incorporation decreased significantly for regions that are more structured and less dynamic in the GppNHp state, as expected. The largest decrease in exchange was in switch-II, which has increased alpha helical structure, as well as regions of switch-I that form stabilizing polar contacts with the γ-phosphate. Portions of the central β-sheet, which connect both switch regions, and the α3 helix also had decreased deuterium incorporation. This investigation validated our HDX-MS approach and confirmed the M72C mutation does not significantly disturb the structure or dynamics associated with nucleotide exchange.

Figure 33B:
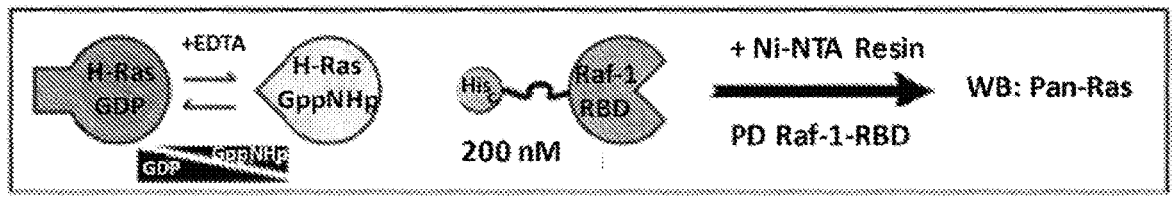
Figure 33B:
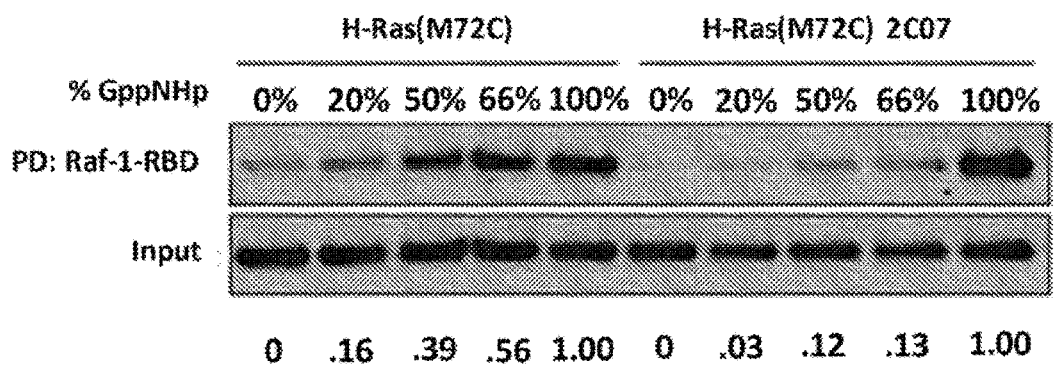

When comparing the change in deuterium incorporation between H-Ras(M72C) GDP and the 2C07 modified protein, we observed both significant increases and decreases in H/D exchange rates (FIG. 33B). The α3 helix directly beneath the ligand as well as portions of the central beta sheet closest to the binding site exhibited decreased deuterium incorporation. Decreased deuterium exchange was also observed for portions of the nucleotide-binding pocket, which suggests 2C07 binding can increase shielding in regions outside of the S-IIG. Additionally, there was a small increase in H/D exchange radiating out from 2C07 in the other direction near the end of the α3 helix and the beginning of the next β-sheet. Overall the HDX-MS results support our crystallographic model of 2C07 binding to the GDP bound state.

Figure 33C:
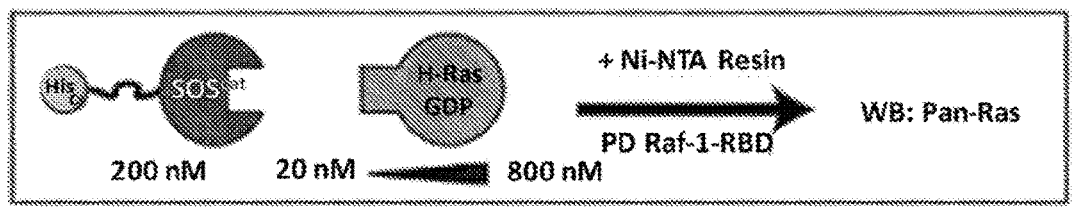
Figure 33C:
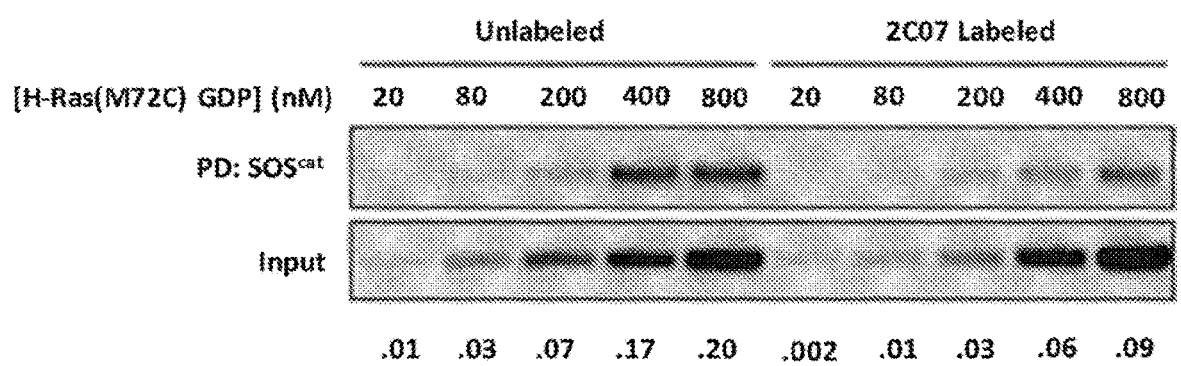
Figure 33D:
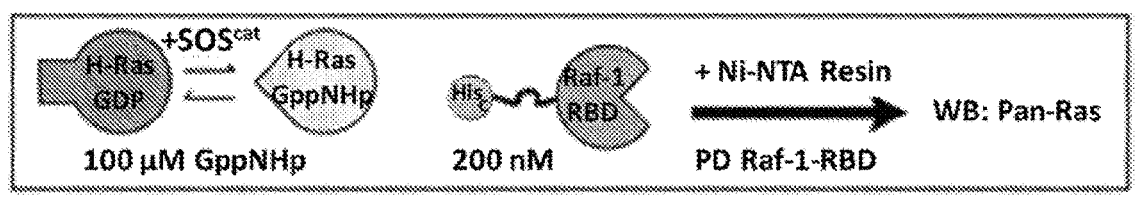
Figure 33D:
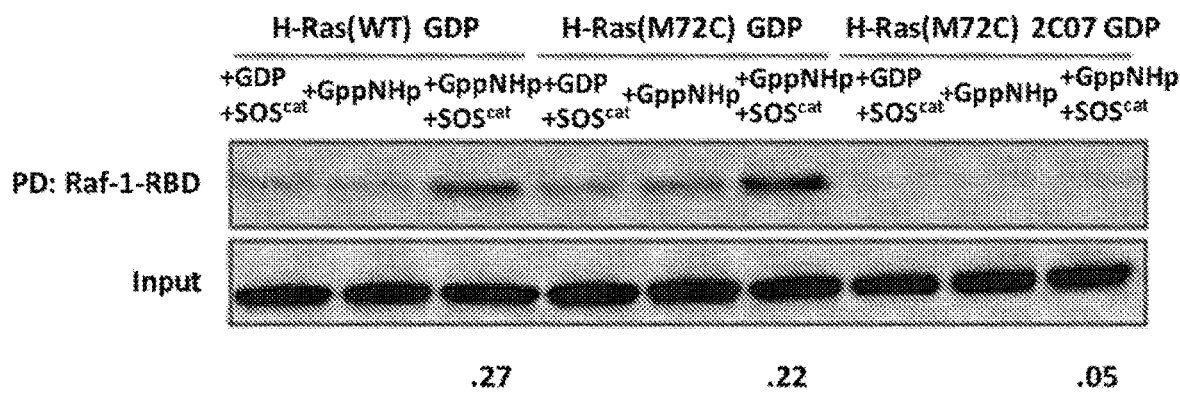

When comparing the change in deuterium incorporation between the H-Ras(M72C) GppNHp and the 2C07 modified state, we see a significant increase in deuterium incorporation in both switch regions. This suggests a large increase in switch dynamics and exposure to solvent after compound binding (FIG. 33C). The largest increases in deuterium exchange occur in portions of switch-I that are responsible for coordinating $Mg^{2+}$ and the γ-phosphate as well as the central beta sheet, which connects to the nucleotide binding pocket. This data supports our crystallographic analysis in which 2C07 binding results in an alternative coordination of $Mg^{2+}$, which induces switch-I to disengage from the nucleotide and move into a less shielded environment. We also detected an increase in deuterium incorporation for the switch-II helix near Cys 72, indicating increased flexibility in the vicinity of 2C07 binding. This is consistent with the x-ray structure showing that 2C07 wedges underneath and pushes the switch outward, which results in a loss of helical character for a large portion of the α2-(switch-II) helix. The increase in deuterium exchange for the central beta sheet indicates that even while 2C07 binds in this region, it still results in destabilization possibly suggesting that it is not an optimal binder to the S-IIG in the GppNHp state. The combination of x-ray co-crystal structures and HDX may aid development of future 2C07 derivatives that better engage the GTP state by prioritizing compounds that destabilize switch-I while not destabilizing the central beta sheet and α3 helix.

Figure 34A:
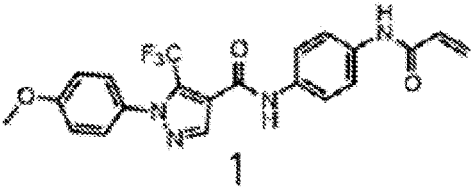
FIGS. 34A-34D. Electrophiles Derived from the 2C07 Scaffold Readily Modify Ras(M72C) in both Nucleotide States.
Figure 34A:
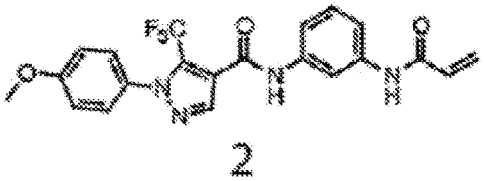
Figure 34A:
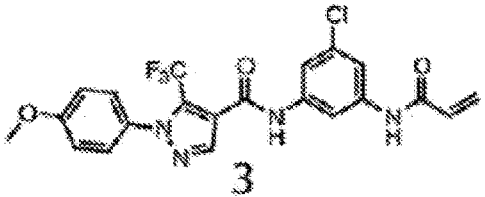
Figure 34A:
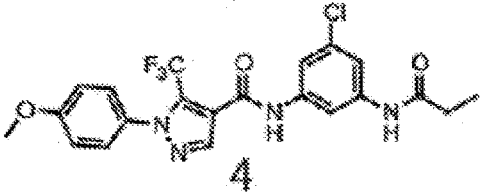

2C07 Binding Alters Nucleotide Preference, Inhibits Ras Binding to SOS and Prevents Catalytic Activation of Ras by SOS in vitro: To determine whether the structural changes we observed might influence Ras activity in vitro, we assessed the influence of 2C07 on Ras binding to a portion (Raf-1-RBD, residues 52-131) of the effector Raf, preference for nucleotide under various GppNHp/GDP concentrations, and the effect of 2C07 on SOS catalyzed nucleotide exchange. Based on the large changes to H-Ras(M72C) GppNHp induced by 2C07, we anticipated a decrease in Raf-1-RBD binding. However, no significant difference in Raf-1-RBD binding was observed between 2C07 labeled and unlabeled protein (FIG. 34a). Co-crystal structures of active Ras bound to the Raf-1-RBD (RBD residues 52-131 and Cysteine Rich Domain (CRD) residues 139-184) show binding interactions occur exclusively between the RBD and switch-I residues with no ordering of the CRD domain (FIG. 42) (Fetics et al., 2015). Perhaps the allosteric disruption of switch-I by 2C07 as seen in our co-crystal structure and HDX-MS analysis is not significant enough of a perturbation to overcome the tight binding between active Ras and the Raf-1-RBD. Previous investigations have reported the $K_d$ of Raf-1-RBD binding to be less than 20 nM (Fetics et al., 2015; Thapar et al., 2004), which may effectively outcompete the 2C07-induced allosteric disruption of switch-I. Modifications to 2C07 may lead to a more stable interaction with the S-IIG, while maintaining a stronger disruption of the active state of switch I, leading to inhibition of Raf effector binding.

We next investigated how 2C07 binding affects intrinsic nucleotide preference and Ras activation. Incubating H-Ras (M72C) GDP with varying ratios of GDP:GppNHp at a constant total nucleotide concentration, we observed dose dependent exchange of GDP for GppNHp by EDTA catalyzed exchange. The total activated (GppNHp bound) Ras was measured indirectly by Raf-1-RBD pull down. FIG. 33B illustrates that H-Ras(M72C) GDP exhibits a dose dependent increase in Raf-1-RBD pull down as the relative ratio of GppNHp to GDP is increased. When we performed the same assay with 2C07 bound Ras, we observed decreased Raf-1-RBD pull down even at high ratios of GppNHp to GDP, although the pull-down efficiency with only GppNHp present remained the same. These results suggest that 2C07 bound Ras has a nucleotide preference for GDP over GppNHp. Therefore, 2C07 retains the GDP trapping mechanism of the original G12C targeting electrophiles while expanding engagement to the active, GTP state (Ostrem et al., 2013; Lito et al., 2016; Patricelli et al., 2016).

Figures 4, 5:
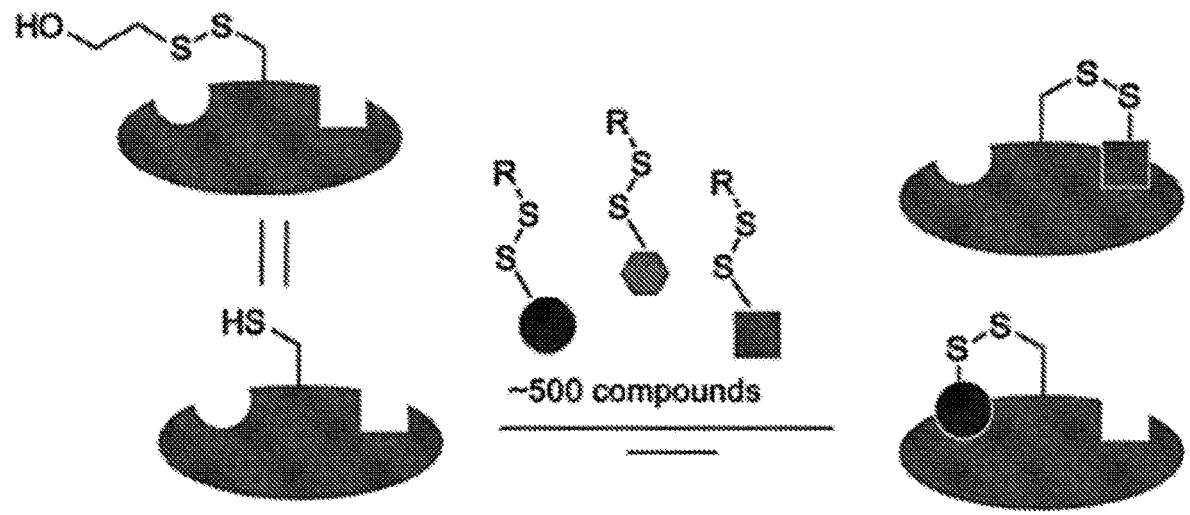
FIG. 4. Schematic overview of the tethering discovery method. The steps include identifying hits using mass spectrometry (% modification); find low affinity fragments, optimize leads using mass spectrometry along with biochemical assays; and finding active site or allosteric binders.
FIG. 5. The figure summarizes the binding interactions of initial tethering hits DG01 and DG02 with H-Ras$^{M72C}$•GDP and the non-hydrolyzable analog GppNHp. $\beta ME_{50}$ (concentration of $\beta ME$ necessary for 50% labeling of protein) and thermofluor $\Delta T_{50}$ (temperature at which 50% of protein is unfolded) values are reported to demonstrate target engagement in vitro.

Tables 33B-33D. S. E. M and Standard T-Test Analysis for FIG. 4 Pull-Down Experiments: This table summarizes the standard error of the mean (S.E.M.) for pull-down experiments done in triplicate with α-values reported for each comparison across unlabeled H-Ras(M72C) and 2C07 labeled H-Ras(M72C) of the same condition. Statistical analysis of normalized pull-down signals with α-values<0.05 are bolded in FIGS. 33A-33D and are significantly different.

TABLE 33B

Quantification of Nucleotide Exchange PD Assay

| | H-Ras(M72C) | | H-Ras(M72C) 2C07 | | |
| --- | --- | --- | --- | --- | --- |
| GTP:GDP | Normalized Average | S.E.M. (n = 5) | Normalized Average | S.E.M. (n = 4) | T-Test (α-value) |
| 0 | 0.00 | N/A | 0.00 | N/A | N/A |
| 0.2 | 0.16 | 0.044 | 0.03 | 0.005 | 0.033 |
| 0.5 | 0.39 | 0.085 | 0.12 | 0.029 | 0.030 |
| 0.67 | 0.56 | 0.097 | 0.13 | 0.018 | 0.006 |
| 1.00 | N/A | | 1.00 | N/A | N/A |

TABLE 33C

Quantification of SOS PD Assay

| | H-Ras(M72C) | | | | H-Ras(M72C) 2C07 | | | | |
| --- | --- | --- | --- | --- | --- | --- | --- | --- | --- |
| [Ras] (nM) | Average Normalized Input | S.E.M. (n = 3) | Normalized Averaged Pull Down | S.E.M. (n = 3) | Average Normalized Input | S.E.M. (n = 3) | Normalized Averaged Pull Down | S.E.M. (n = 3) | T-Test (α-value) |
| 20 | 0.04 | 0.01 | 0.01 | 0.001 | 0.06 | 0.02 | 0.002 | 0.001 | 0.020 |
| 80 | 0.12 | 0.03 | 0.03 | 0.003 | 0.10 | 0.02 | 0.01 | 0.003 | 0.0078 |
| 200 | 0.25 | 0.04 | 0.07 | 0.01 | 0.24 | 0.05 | 0.03 | 0.006 | 0.023 |
| 400 | 0.49 | 0.05 | 0.17 | 0.04 | 0.54 | 0.09 | 0.06 | 0.007 | 0.047 |
| 200 | 1.00 | N/A | 0.20 | 0.04 | 1.00 | N/A | 0.09 | 0.02 | 0.062 |

TABLE 33D

Quantification of SOS Catalyzed Nucleotide Exchange PD Assay

| Condition | Normalized Average Ratio of PD/Input | SEM (N = 3) | T-Test (α-value) |
| --- | --- | --- | --- |
| H-Ras(WT)/ GppNHP/SOS | 0.27 | 0.05 | 0.013 |
| H-Ras(M72C)/ GppNHP/SOS | 0.22 | 0.006 | 0.0005 |
| H-Ras(M72C) 2C07/ GppNHp/SOS | 0.05 | 0.01 | N/A |

We next investigated the effect of 2C07 on the ability of SOS, the Ras cognate guanosine exchange factor (GEF), to catalyze nucleotide exchange. In contrast to Raf-1-RBD, which only contacts switch-I, co-crystal structures of Ras-SOS show contacts with both switch-I and -II, implying that 2C07 might in fact be able to disrupt this interaction. We first asked if 2C07 interferes with Ras/GEF binding by utilizing $His_6$ tagged $SOS^{cat}$ to pull down Ras (Hall et al., 2001). FIG. 33C shows that 2C07 diminishes the efficiency of Ras pull down by SOS. This is consistent with structural analysis of Ras-SOS structures that demonstrate the importance of key contacts in switch-II as essential for SOS binding (Hall et al., 2001). Since 2C07 binds underneath switch-II and raises the α2-(switch-II) helix upward, the switch may be less able to engage with SOS resulting in reduced binding. Since SOS mediated nucleotide exchange may still occur despite reduced binding affinity for Ras-2C07, we asked if SOS catalyzed exchange is directly affected by 2C07 binding. We reconstituted the nucleotide exchange cycle in vitro by utilizing untagged $SOS^{cat}$ and $His_6$ tagged Raf-1-RBD. After incubating constant concentrations of GDP-bound H-Ras (WT, M72C, or M72C-2C07) GDP, $SOS^{cat}$, and GppNHp, the amount of Ras activation was measured indirectly by Raf-1-RBD pull down. Lanes 1-3 and 4-6 in FIG. 33D confirm that SOS and GppNHp are both necessary for H-Ras and H-Ras(M72C) pull down by Raf-1-RBD, respectively. However, 2C07 modified H-Ras(M72C) is significantly compromised in SOS mediated exchange compared to unlabeled H-Ras(M72C).

Figure 34B:
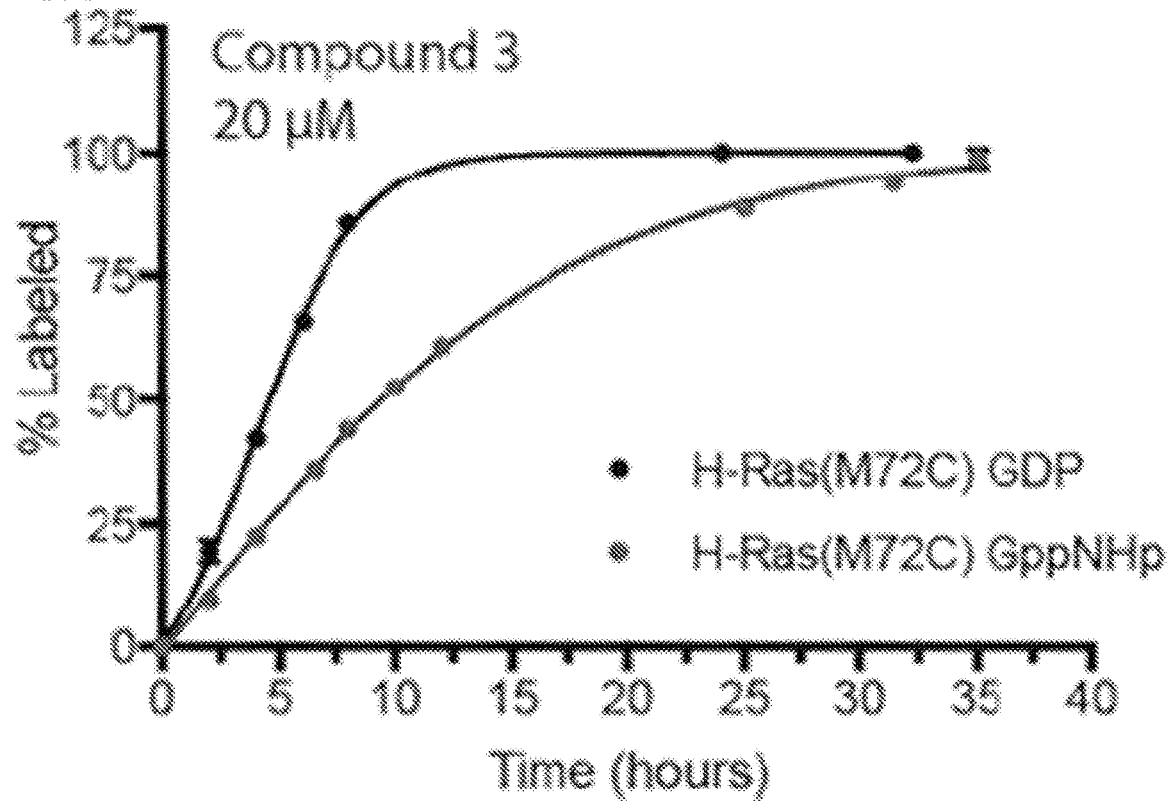
Figure 34B:
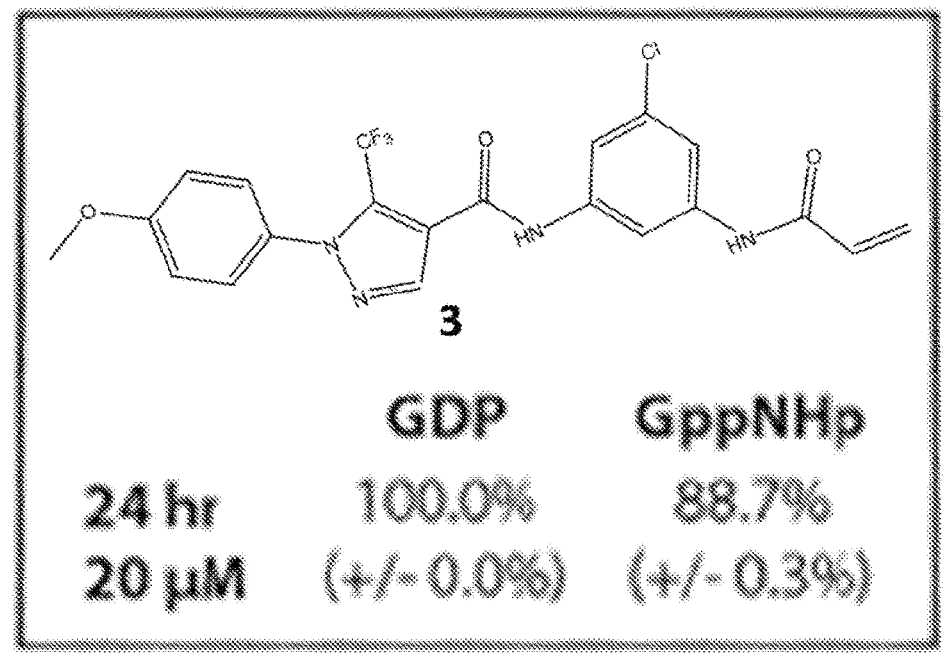

Electrophiles Derived from 2C07 Modify H-Ras(M72C) in Both Nucleotide States and Bind Reversibly in Competition Labeling Studies: An acrylamide analog of 2C07 was developed as an occupancy probe for SII-G, to obviate complications due to the reversible nature of the disulfide 2C07. Our tethering screen relied on the positioning of the engineered cysteine to select fragments that bind distal to the nucleotide-binding site in sub-pocket 3 of the S-IIP. After reviewing both 2C07 crystal structures, it was apparent that improvements to the flexible methylene linker could provide further interactions with sub-pocket 3 and potentially improve binding. The overlay between ARS-853 and 2C07 shows a significant portion of the 2C07 linker overlays with the phenol ring of ARS-853, which is critical for ARS-853 binding. Taking advantage of existing crystallographic data and SAR information from G12C specific electrophiles, we modified 2C07 to contain a phenylenediamine linker to mimic ARS-853's phenol motif. This yielded a series of 2C07-based electrophiles, which are summarized in FIG. 35A. Percent modification was monitored for each derivative by whole protein LC/MS against 4 μM H-Ras(M72C) bound to either GDP or GppNHp with 100 NM electrophile for 24 hours. Placement of the electrophile was extremely important for successful targeting of Cys 72. In particular, acrylamides in a p-phenylenediamine linker had no detectable labeling (Compound 1) while a m-phenylenediamine linker had a significant increase (Compound 2). Furthermore, the introduction of a 5-chloro substitution to 2, also improved covalent binding (Compound 3). Additional labeling kinetics demonstrate 3 also rapidly and fully labels the GDP state while significantly modifying the GppNHp state (88.7% (+/−0.3%)) at a much lower electrophile concentration of 20 µM (ie. 1:5 Ras to Compound 3) (FIG. 34B). Labeling studies were conducted using the 1-166 H-Ras (M72C) construct containing all endogenous cysteines and only one covalent modification was observed for all electrophiles. Trials using full-length Ras constructs also showed no off target labeling. Pull-down experiments were also conducted with H-Ras(M72C) pre-labeled with Compound 2 and, like 2C07, did not inhibit Raf-1-RBD binding.

Figure 34C:
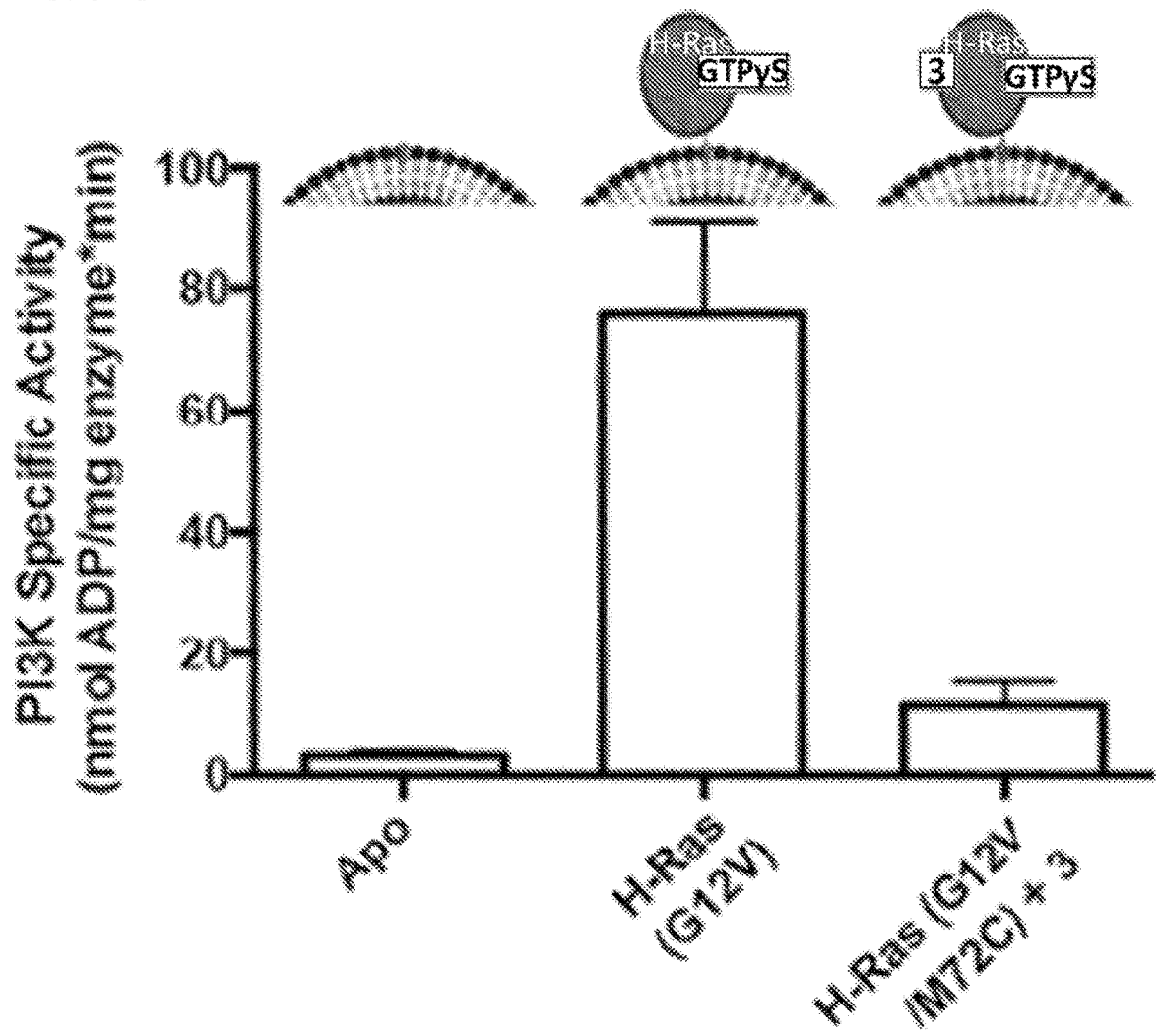
Figure 34D:
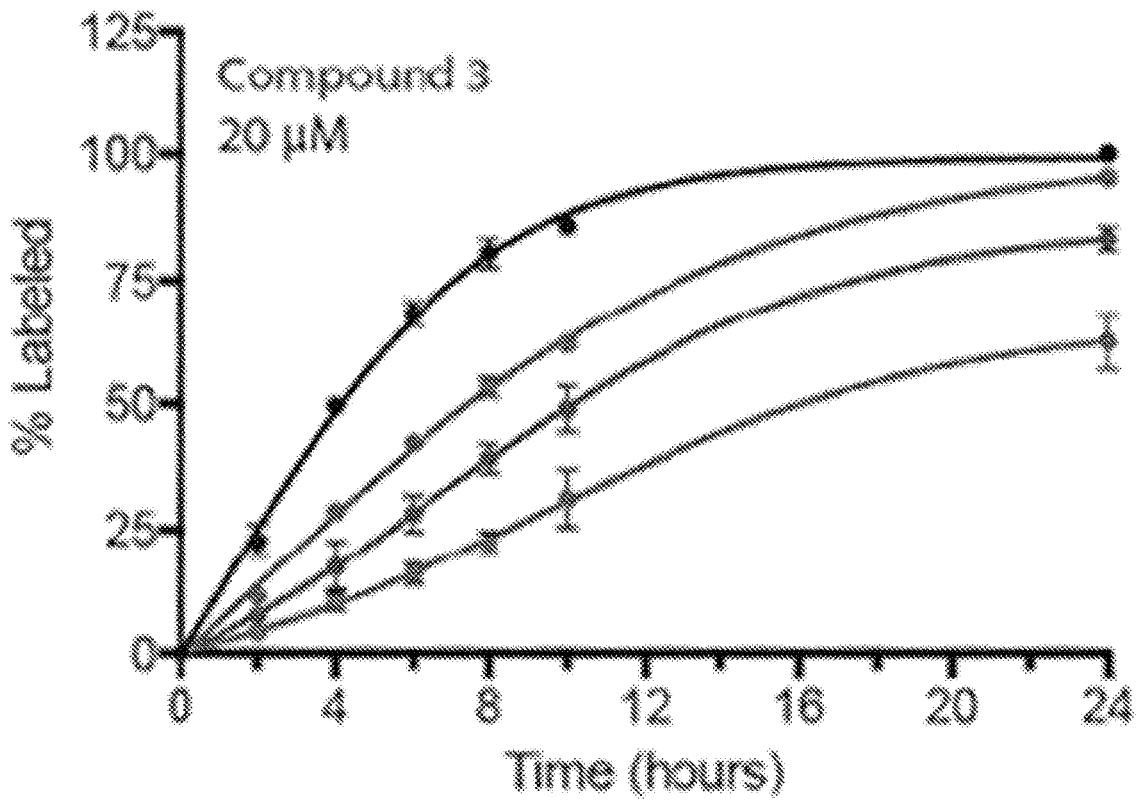
Figure 34D:
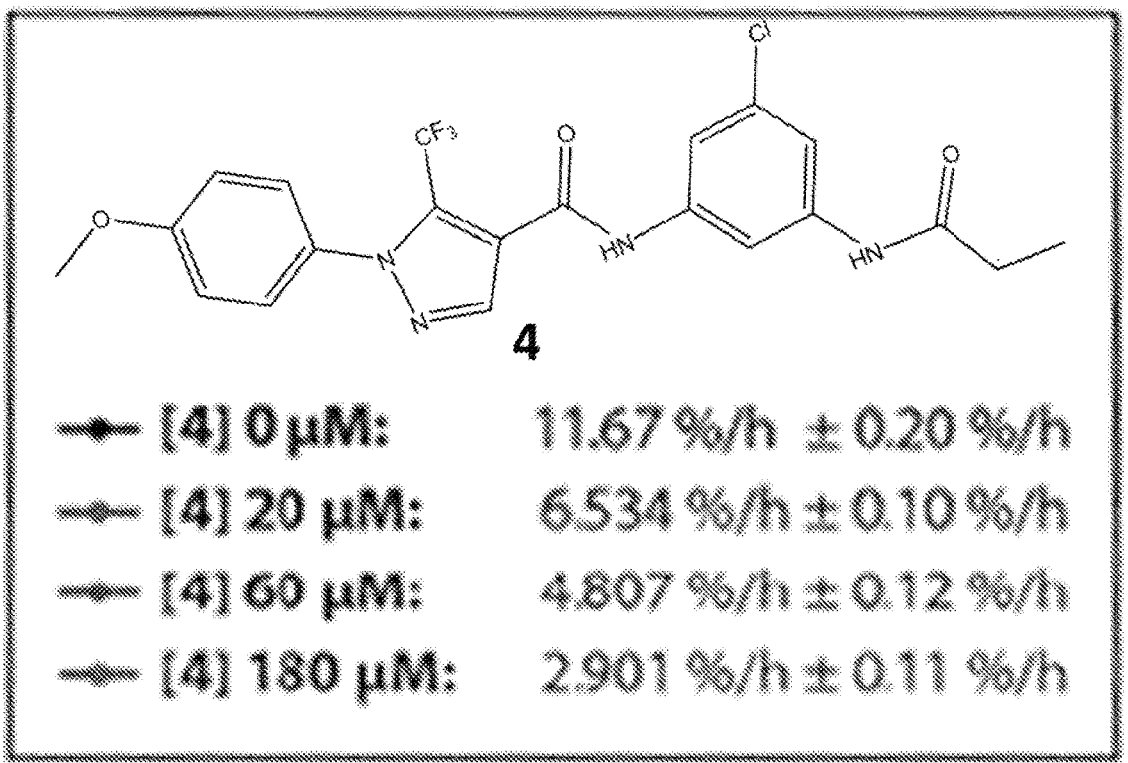

The availability of an irreversible covalent ligand for the SII-G of H-Ras(M72C) provided the opportunity to carry out a competition binding experiment for non-covalent binding to the site. The readout for reversible ligand binding is dependent on competition for covalent attachment of Compound 3 to H-Ras(M72C). A similar screening platform has been exploited using irreversible activity based protein profiling (ABPP) probes in competition with reversible inhibitors against multiple protein families (Adibekian et al., 2012; Bachovchin et al., 2009; Carelli et al., 2015; Zhao et al., 2017). At long time points the irreversible ligand will always predominate, so we measured competition at multiple time points. One caveat of this assay system is its requirement for H-Ras(M72C) rather than native K- or H-Ras. We synthesized a non-electrophilic derivative of 3 (Compound 4). The competition labeling experiment is summarized in FIG. 34C where a constant concentration (20 µM) of 3 was co-incubated with varying concentrations of 4. Labeling kinetics are reported as % labeled per hour against 4 µM H-Ras(M72C) GDP. This experiment shows a dose dependent decrease in the rate of 3 labeling in the presence of higher concentrations of 4. This is the first evidence of a reversible compound competing with an irreversible switch-II binder for Ras engagement (McGregor et al., 2017; Patricelli et al., 2016). These results show 2C07 is a potential starting point for the development of reversible inhibitors of H-Ras.

Figure 35:
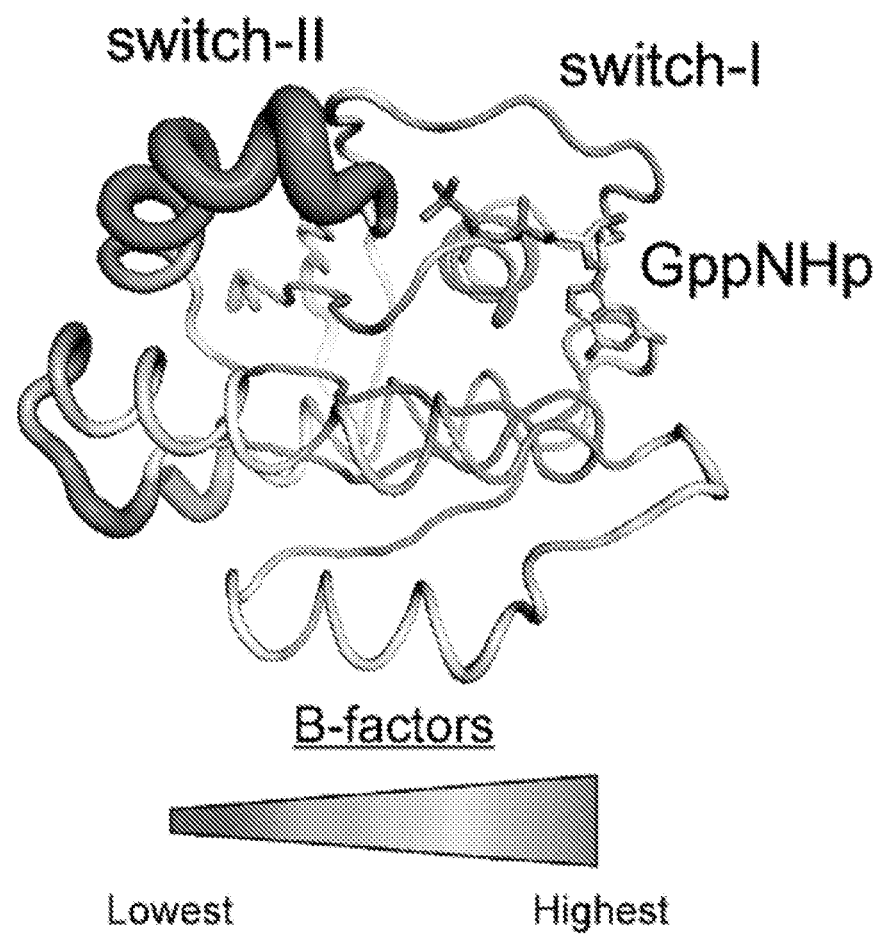
FIG. 35. The figure shows B-Factor Putty Cartoon Representation of H-Ras(G12C) GppNHp (PDB: 4L9W). The region of highest B-factor is still switch-II even in the GppNHp state where both switches form stabilizing polar contacts with the γ-phosphate. The flexibility of switch-II implies the S-IIP should still be accessible even in the GTP state.

Electrophiles Derived from 2C07 Modify H-Ras(M72C) in Both Nucleotide States, Inhibit PI3K Activation, and Bind Reversibly in Competition Labeling Studies. SOS inhibition supports that 2C07-induced switch-II changes are sufficient to inhibit GDP-dependent effector binding. In the 2C07 bound GppNHp state, similar changes to switch II occur as well as additional allosteric disruption of switch I. However, this allosteric change was not sufficient to inhibit Raf-1-RBD binding, which interacts exclusively with switch I. The crystal structure of active Ras bound to phosphoinositide 3-kinase g (PI3K-g) (PDB: 1HE8) suggests that this GTP-dependent effector, unlike Raf-1-RBD, forms essential interactions with both switches for binding and activation (Pacold et al., 2000). We therefore hypothesized that 2C07 would have a larger effect on PI3K activation compared with Raf-1-RBD binding. Until recently, assessment of Ras activation of PI3K has been exceedingly difficult to reconstitute in vitro since membrane localization is required for Ras to be presented to PI3K (Siempelkamp et al., 2017). Membrane attachment of full-length Ras through the reaction of C118 with maleimide-functionalized lipids provided a means to assess whether occupancy of the S-IIG affects PI3K activation. However, the irreversible maleimide chemistry is incompatible with a disulfide attachment of 2C07 to Ras (M72C). Thus, to successfully test PI3K activation, we required an irreversible covalent 2C07 analog to obviate complications arising from the reversible nature of the disulfide in the presence of reductant. Our tethering screen relied on the positioning of the engineered cysteine to select fragments that bind distal to the nucleotide binding site in subpocket #3 of the S-IIP. After reviewing both 2C07 crystal structures, it was apparent that improvements to the flexible methylene linker could provide further interactions with subpocket #3 and potentially improve binding. The overlay between ARS-853 and 2C07 in shows a significant portion of the 2C07 linker overlays with the phenol ring of ARS-853, which is critical for ARS-853 binding. Taking advantage of existing crystallographic data and SAR information from G12C-specific electrophiles, we modified 2C07 to contain a phenylene-diamine linker to mimic ARS-853's phenol motif. This yielded a series of 2C07-based electrophiles, which are summarized in FIG. 35A. Percent modification was monitored for each derivative by whole-protein liquid chromatography-mass spectrometry (LC-MS) against 4 mM H-Ras(M72C) bound to either GDP or GppNHp with 100 mM electrophile for 24 hr. Placement of the electrophile was extremely important for successful targeting of Cys72. In particular, acrylamides in a p-phenylenediamine linker had no detectable labeling (compound 1) while an m-phenylenediamine linker had a significant increase (compound 2). Furthermore, the introduction of a 5-chloro substitution to 2 also improved covalent binding (compound 3). Additional label-ing kinetics demonstrate that 3 also rapidly and fully labels the GDP state while significantly modifying the GppNHp state (88.7%+0.3%) at a much lower electrophile concentration of 20 mM (i.e., 1:5 Ras to compound 3) (FIG. 35B). Labeling studies were conducted using the 1-166 H-Ras(M72C) construct containing all endogenous cysteines, and only one covalent modification was observed for all electrophiles. Trials using full-length Ras constructs also showed no off-target labeling. Pull-down experiments were also conducted with H-Ras(M72C) pre-labeled with compound 2 and, like 2C07, did not inhibit Raf-1-RBD binding as expected.

Compound 3 is a 2C07 derivative that retains selectivity for Cys72 and targets both nucleotide-bound states, making it a suitable irreversible ligand to test in our PI3K activation assay. To interrogate how S-IIG binders affect active Ras signaling, we screened the ability for compound 3 to inhibit PI3K activation. We used a covalently coupled H-Ras PI3K activation assay, with H-Ras coupled through its C-terminal cysteine to maleimide-functionalized lipids present in vesicles mimicking the composition of the plasma membrane. We examined the activation of full-length p110d/p85a (referred to hereafter as PI3K-d) by H-Ras-GTP in the presence of a receptor tyrosine kinase-derived phosphopeptide. Experiments were carried out under three conditions: PI3K-d in the absence of H-Ras, PI3K-d with H-Ras(G12V), and H-Ras(G12V/M72C) coupled to compound 3. The presence of H-Ras(G12V) led to a 20-fold activation of PI3K-d activity, similar to previous results; however, PI3K-d was only weakly activated by H-Ras(G12V/M72C) bound to compound 3 (~3 fold) (Figure #5D) (Siempelkamp et al., 2017). These results demonstrate that H-Ras modified with S-IIG binders are unable to fully activate PI3K-d downstream of Ras. Interrogation of the structure of H-Ras bound to PI3K-g as well as the Raf-1-RBD revealed a potential mechanism for this selectivity (Fetics et al., 2015; Pacold et al., 2000). When comparing both effector structures, it is evident that the 2C07-induced switch-II conformation is well tolerated in the Ras/Raf-1-RBD. In this model, there is sufficient space to accommodate the movement of the α2-(switch-II) helix without disrupting key switch-I binding interactions to Raf-1-RBD. However, in the Ras/PI3K-g structure, movement of the α2-(switch-II) helix would result in significant clashes and loss of key PI3K-g binding interactions. These data support that targeting the S-IIG in active Ras is inhibitory and significantly affects effectors that require direct interactions with switch II for activation. Thus, S-IIG binders retain the GDP-trapping mecha-nism of the original K-Ras(G12C) binders while expanding inhibition to the active GTP state where switch-II-dependent effectors, such as PI3K, are inhibited.

The availability of an irreversible covalent ligand for the S-IIG of H-Ras(M72C) provided the opportunity to carry out a competition binding experiment for non-covalent binding to the site. The readout for reversible ligand binding is dependent on competition for covalent attachment of Compound 3 to H-Ras(M72C). A similar screening platform has been exploited using irreversible activity-based protein profiling probes in competition with reversible inhibitors against multiple protein families (Adibekian et al., 2012; Bachovchin et al., 2009; Carelli et al., 2015; Zhao et al., 2017). At long time points the irreversible ligand will always predominate, so we measured competition at multiple time points. One caveat of this assay system is its requirement for H-Ras(M72C) rather than native K- or H-Ras. We synthesized a non-electrophilic derivative of 3 (compound 4). The competition labeling experiment is summarized in FIG. 35C where a constant concentration (20 mM) of 3 was co-incubated with varying concentrations of 4. Labeling kinetics are re-ported as percent labeled per hour against 4 mM H-Ras(M72C) GDP. This experiment shows a dose-dependent decrease in the rate of 3 labeling in the presence of higher concentrations of 4. This is the first evidence of a reversible compound competing with an irreversible switch-II binder for Ras engagement (McGregor et al., 2017; Patricelli et al., 2016). We also tested compound 4's ability to reversibly bind WT H-Ras by BioLayer interferometry (BLI), but were unable to detect measurable binding. These results show that 2C07 is a potential starting point for the development of reversible inhibitors of H-Ras.

In the past 5 years, significant advances have led to the dis-covery of direct inhibitors of Ras. Several distinct regions of the protein have been proposed as sites for allosteric inhibition (McCormick, 2016; Ostrem and Shokat, 2016; Stephen et al., 2014). The cardinal feature of current K-Ras(G12C)S-IIP binders is their inability to access the GTP-bound state. Our study sug-gests that the dynamics of switch II allows access to fragments, which bind in a new region under switch II, termed the S-IIG. The current covalent S-IIG binding ligands are not able to block Raf-1-RBD binding, thus necessitating further modifications to target this important RAS effector. The current ligands do, however, block SOS-mediated exchange, which is known to be highly sensitive to switch-II loop mutations (Hall et al., 2001). Electrophiles derived from 2C07 target both nucleotide states and demonstrate the first evidence of reversible binding through competition labeling experiments. Furthermore, our S-IIG binders inhibit PI3K activation by directly targeting Ras-GTP, but do not affect Raf-1-RBD binding, which has never before been demonstrated. Perhaps selecting for binders that more drastically alter switch I and potently stabilize the S-IIG could expand effector inhibition to Raf as well. Our work thus expands the diversity of ligands that bind to Ras and, more importantly, demonstrates accessibility and inhibition of the active GTP state, which is most abundant in oncogenic Ras-transformed cells.

In the past five years, significant advances have led to the discovery of direct inhibitors of Ras. Several distinct regions of the protein have been proposed as sites for allosteric inhibition (McCormick, 2016; Ostrem and Shokat, 2016; Stephen et al., 2014). The cardinal feature of current K-Ras (G12C)S-IIP binders is their inability to access the GTP bound state. Our study suggests that the dynamics of switch-II allow access to fragments, which bind in a new region under switch-II, termed the SII-G. The current covalent S-IIG binding ligands are not able to block Raf-1-RBD binding, thus necessitating further modifications to target this important RAS effector. The current ligands do however block SOS mediated exchange, which is known to be highly sensitive to switch-II loop mutations (Hall et al., 2001). Electrophiles derived from 2C07 target both nucleotide states and demonstrate the first evidence of reversible binding through competition labeling experiments. The reversible binding potential of Compound 4 may offer a useful starting point for PROTAC targeted degradation, which has emerged as an efficient way to target proteins even when the binding ligand alone has minimal effects on activated protein function (Lai and Crews, 2017). Our work expands the diversity of ligands that bind to Ras, and most importantly, demonstrate accessibility of the protein in the active GTP state, which is most abundant in oncogenic Ras transformed cells.

Significance: Since the discovery of Ras and its ability to drive tumor growth, Ras continues to inspire efforts to better understand and treat cancer. The small GTPase K-Ras is the most frequently mutated oncogene in cancer, and its high nucleotide affinity and lack of druggable pockets have made direct inhibitors difficult to develop. Recently, covalent inhibitors of K-Ras(G12C) were discovered that are GDP specific and rely on covalent attachment to Cys 12 to bind the switch-II pocket (S-IIP) and inhibit Ras signaling. These limitations are problematic since a majority of Ras-driven cancers express non-cysteine mutations and are predominately GTP bound. Using previously published structures and SAR from various S-IIP binders, we designed a tethering screen to a non-native cysteine to select fragments free from these limitations. This screen yielded fragment 2C07, which binds to both nucleotide states and expands the S-IIP into a new groove away from the nucleotide, which we termed the Switch-II Groove (S-IIG). Herein we provide a complete structural model for the S-IIG in both nucleotide states through the combination of crystallography and hydrogen deuterium exchange mass spectrometry. We present the first active Ras crystal structure bound to an inhibitory molecule, which demonstrates switch-II inhibitory pockets are dynamic and accessible in both nucleotide states. Through in vitro biochemical assays, we confirmed 2C07 allosterically biases nucleotide preference towards GDP and prevents SOS binding and catalyzed exchange. We further validated 2C07 by developing irreversible covalent electrophiles that potently target Cys 72 in both states and serve as occupancy probes for reversible engagement. A reversible derivative of our best occupancy probe provided the first evidence of a reversible compound competing with an irreversible switch-II binder. The use of fragment 2C07 to reveal the S-IIG may guide the development of more potent, fully reversible Ras inhibitors that bind regardless of nucleotide state.

I. Methods

All recombinant proteins herein were expressed and purified from BL21(DE3) *E. coli*. Please refer to the specific protein purification protocols below for growth, induction, and purification procedures.

General Ras Protein Purification Protocol for Crystallography and In Vitro Studies. His6-tagged recombinant bacterial codon optimized human K-Ras (isoform 2, residues 1-169), K-Ras Cys Light (isoform 2, residues 1-169, C51S/C80L/C118S), K-Ras (isoform 2, residues 1-189), and H-Ras (residues 1-166) were transformed into *Escherichia coli* (BL21 (DE3)) for expression. The M72C mutation was introduced into each vector using the standard QuikChange PCR protocol (Li et al., 2008). The plasmids used and the expression/purification protocol for all aforementioned constructs were previously published in the methods section of Ostrem et al., 2013.

Isolation of Fully Modified Ras(M72C) 2C07 for Crystallographic and Hydrogen Deuterium Exchange Mass Spectrometry (HDX-MS). Large-scale labeling reactions were set to isolate enough protein for screening crystal conditions and setting trays for XTAL collection (usually between 8-10 mg of total protein). Labeling reactions were done with 150-200 mM Ras protein and 400 mM 2C07 in gel filtration buffer (20 mM HEPES (pH 7.5), 150 mM NaCl) supplemented with 5 mM $MgCl_2$, 200 mM bME, and a total DMSO of 5% by volume. Reactions were kept at 4° C. and monitored for completion by LC/MS. The percent modification was analyzed by electrospray mass spectrometry using a Waters Acquity UPLC/ESI-TQD with a 2.1×50 mm Acquity UPLC BEH300 C4 column. Once complete, reactions were cleared by ultracentrifugation, concentrated, and purified by gel filtration using gel filtration buffer with added reductant. Pure labeled protein was concentrated (8-12 mg/mL) and immediately used for crystallography or prepped for HDX-MS.

All samples analyzed by HDX-MS were dialyzed overnight into the same preparation of gel filtration buffer using Slide-A-Lyzer MINI Dialysis units. Samples were recovered from the dialysis unit, and sample concentrations were determined by Bradford. Samples were normalized to 1 mg/mL and immediately snap frozen in liquid nitrogen prior to analysis by HDX-MS.

Nucleotide Exchange Protocol.

This procedure was adapted from Ostrem et al., 2013 who created their protocol from prior studies (Ahmadian et al., 1999; John et al., 1990; Maurer et al., 2012). As an example, to make the H-Ras(M72C) GppNHp protein bound to 2C07 for crystallography, 3.0 mL of partially purified protein (anion-exchange only) at 3 mg/mL (9.0 mg total, 0.15 mM) 6 mg of GppNHP (4 mM final) was added along with 25 mM EDTA (Diluted from a 0.5M EDTA pH 8.0 buffered stock). After incubation for 1h at room temperature slowly rotating, the solution was concentrated to less than 2.5 mL and was buffer exchanged using a PD-10 column into phosphatase compatible buffer at 4° C. (32 mM Tris pH=8, 200 mM ammonium sulfate, 0.1 mM zinc chloride). To the 3.5 mL eluted buffer exchanged sample 30 units of calf intestine alkaline phosphatase was added, along with 4 mg more of GppNHp. After slowly rotating for 1 hour at 4° C., 30 mM (final) magnesium chloride was added, the protein was concentrated using an Amicon-4 (10,000 MWCO) concentrator to approximately 1 mL and purified by gel filtration as previously described in the General Ras Protein Purification Protocol.

$SOS^{cat}$ (residues 566-1049) Protein Purification Protocol. The $SOS^{cat}$ purification protocol was previously described and slightly modified to isolate both pure $SOS^{cat}$ and His6-tagged $SOS^{cat}$ for pull down assays (Sondermann et al., 2004). To purify protein containing the His6 tag, a portion was dialyzed after elution from Ni-NTA beads without TEV protease. Due to the tag's effect on the isoelectric point (pI), the ion exchange chromatography step was omitted and the final purification step after batch binding and dialysis was gel filtration using a Superdex 200 column (10/300 GL). All proteins were concentrated to approximately 15-20 mg/mL, aliquoted, snap frozen in liquid nitrogen, and stored at −80° C.

Raf-1-RBDwitt (Residues 52-131) Protein Purification Protocol. Recombinant bacterial codon optimized His6-MBP-TEV-Raf-1-RBDwitt (residues 52-131) was transformed into *Escherichia coli* (BL21 (DE3)) for expression. The same induction protocol used to express Ras in Ostrem et al. (2013) was used for Raf-1-RBDwitt. A similar lysis and purification procedure was used omitting the ion exchange chromatography purification step with the following amended buffers: Lysis Buffer: 20 mM HEPES (pH 7.3), 300 mM NaCl, 35 mM imidazole, 1 mM TCEP, protease inhibitor cocktail (Roche complete EDTA free). Elution Buffer: Lysis Buffer containing 500 mM imidazole, pH 7.3. Dialysis/TEV/Gel Filtration Buffer: 20 mM HEPES (pH 7.3), 300 mM NaCl, 1 mM TCEP. For the Raf-1-RBDwitt pull down assay it was necessary to purify protein containing the His6 tag so a portion was dialyzed without TEV protease and purified by gel filtration using a Superdex 75 column (10/300 GL). All proteins were concentrated to approximately 15-20 mg/mL, aliquoted, snap frozen in liquid nitrogen, and stored at −80° C.

Tethering Screen by LC/MS Whole Protein Mass Spectrometry. This procedure was adapted in full from Ostrem et al. (2013). Untagged recombinant 1-169 K-Ras(M72C) GDP at 4 mM was allowed to react with 100 mM tethering fragment and 1 mM bME in 20 mM HEPES, pH 7.5, 150 mM NaCl, and 10 mM EDTA. The total reaction volume for each tethering reaction was 25 mL and 2% DMSO by volume. Reactions were conducted in 96 well plate format and analyzed individually by LC/MS after equilibrating for 1h shaking at room temperature. The percent modification was analyzed by electrospray mass spectrometry using a Waters Acquity UPLC/ESI-TQD with a 2.1×50 mm Acquity UPLC BEH300 C4 column. Using a threshold of R 50% modification, we achieved a 1.6% hit rate.

Chemical Synthesis and Characterization of 2C07 and Its Derivatives

General Methods for Chemical Synthesis. All solvents and chemical reagents were purchased from commercial sources and used as provided. $^1H$ spectra were obtained on either a Bruker Avance DRX 400 or 500 MHz NMR spectrometer as specified, and all $^{13}C$ NMR were obtained on a Bruker Avance DRX 500 NMR spectrometer. NMR chemical shifts are reported in d (ppm) relative to internal solvent peaks and coupling constants were measured in Hz. $^1H$ splitting patterns are reported as s (singlet), d (dublet), dd (dublet of dublets), t (triplet), q (quartet), and m (multiplet). NMR spectra were processed and analyzed using MNova NMR software. Low resolution LC/MS analysis of purified compounds was performed on a Waters Acquity UPLC/ESI-TQD instrument with a 2.1×50 mm Acquity UPLC BEH C18 column (Product #: 186002350). Silica chromatography was performed on a Teledyne CombiFlash Rf+instrument. All reverse phase high performance liquid chromatography (RP-HPLC) was performed on a Waters 2545 binary gradient module equipped with an XBridge prep $C_{18}$ column using $H2O+0.1\%$ formic acid and $CH_3CN+0.1\%$ formic acid (5-95% gradient) while monitoring peak collection at 254 nm.

Synthesis of S1-4: tert-butyl (3-((2-(dimethylamino)ethyl)disulfanyl)propyl)carbamate

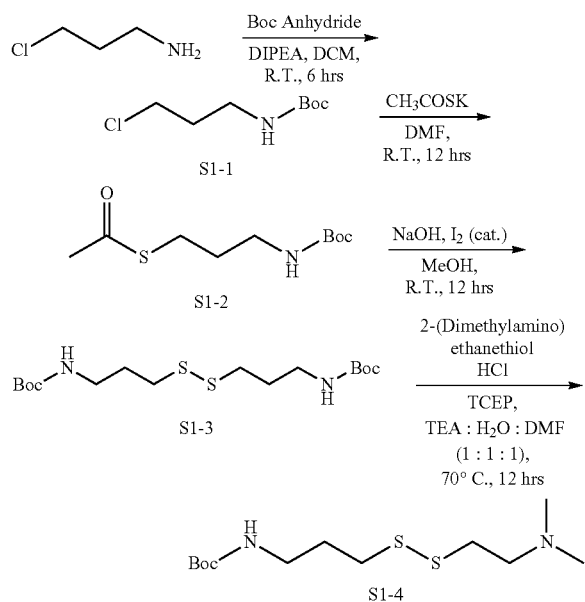

[S1-1]: 3-chloropropylamine-HCL (5 g, 38.46 mmole, 1.0 equiv) was dissolved in 20 mL dry DCM under inert atmosphere. DIPEA (5.47 g, 42.31 mmole, 1.1 equiv) was added via syringe at room temperature to the stirring mixture. When the solution was clear and all reagents solubilized, the reaction mixture was cooled to 0° C. Under inert atmosphere, boc-anhydride (8.4 g, 38.49 mmole, 1.1 equiv) was dissolved in 5 mL dry DCM. This solution was added slowly to the stirring solution of 3-chloropropylamine-HCL at 0° C. After addition, the solution was allowed to warm up to R.T. and mix for 5 hrs while monitoring for completion by TLC and LC/MS. Upon completion, 25 mL of H2O was added to the reaction at ambient atmosphere while mixing. The mixture was then diluted, transferred to a seperatory funnel, and the water layer extracted into DCM (3×20 mL). The organic layer was dried over Na2SO4, filtered, and evaporated to dryness to afford a crude powder. The product was purified by Hex:EtOAc silica chromatography using a CombiFlash purification system. Product eluted at 2:1 Hex:EtOAc and collected fractions were evaporated to dryness to afford S1-1 as a white powder (MW: 193.67 g/mol, 6.08 g, 82% yield). 1H NMR (400 MHz, CDCl3): 3.58 (t, J=6.4 Hz, 2H), 3.27 (m, 2H), 1.96 (m, 2H), 1.43 (s, 9H).

[S1-2]: S1-1 (557 mg, 2.876 mmole, 1 equiv) was dissolved in 2 mL dry DMF under inert atmosphere. To this solution, potassium thioacetate (548 mg, 3.164 mmole, 1.1 equiv) was added as a powder to the stirring reaction mixture. The reaction was allowed to go overnight and monitored for completion by TLC and LC/MS. The reaction mixture was diluted with 20 mL EtOAc and transferred to a seperatory funnel. The organic layer was washed with 3×20 mL saturated NaCl solution. The organic layer was dried over Na2SO4, filtered, and evaporated to dryness to afford a crude yellow oil (MW: 233.33 g/mol, 400 mg, 60% yield), which was of sufficient purity for the next step. 1H NMR (400 MHz, CDCl3): 3.12 (m, 2H), 2.86 (t, J=7.0 Hz, 2H), 2.3 (s, 3H), 1.71 (m, 2H), 1.40 (s, 9H).

[S1-3]: S1-2 (400 mg, 1.71 mmole, 1 equiv) was dissolved in 5 mL of methanolic NaOH (5 g of NaOH powder in 5 mL of MeOH). To the slurry mixture, $I_{2(s)}$ (70.8 mg, 0.56 mmole, 0.3 equiv) was added. The reaction mixture was left at ambient atmosphere at R.T. over-night while monitoring for completion by TLC and LC/MS. Upon completion, 20 mL of H2O was added to the reaction to dissolve any solid NaOH, the mixture was transferred to a seperatory funnel, and the water layer was extracted into EtOAc (3×20 mL). The organic layer was dried over Na2SO4, filtered, and evaporated to dryness to afford a crude oil. The product was purified by Hex:EtOAc silica chromatography using a CombiFlash purification system. Product eluted at 1:1 Hex:EtOAc and collected fractions were evaporated to dryness to afford S1-3 as a light yellow oil (MW: 380.57 g/mol, 182.5 mg, 56% yield). 1H NMR (400 MHz, CDCl3): 3.25 (m, 4H), 2.73 (t, J=7.2 Hz, 4H), 1.90 (m, 4H), 1.46 (s, 18H)

[S1-4]: S1-3 (60.6 mg, 0.159 mmole, 1 equiv) was dissolved in 3 mL of 1:1:1 H2O:TEA:DMF. To this stirring solution, 2-(Dime-thylamino)ethanethiol HCL was added (243.5 mg, 1.27 mmole, 8 equiv) with TCEP (16 mg, 0.064 mmole, 0.4 equiv). The solution was then heated to 70° C. and let react overnight while monitoring for completion by TLC and LC/MS. When complete, the reaction mixture was separated by RP-HPLC (H2O [0.1% TFA]: ACN [0.1% TFA]) and lyophilized to afford the product S1-4 as a clear oil (MW: 294.48 g/mol, 52 mg, 56% yield). 1H NMR (400 MHz, CD3OD): 3.14 (m, 2H), 2.90 (m, 4H), 2.74 (m, 2H), 2.48 (s, 6), 1.86 (m, 2H), 1.44 (s, 9).

Synthesis of S2-2: tert-butyl (4-((2-(dimethylamino)ethyl)disulfanyl)butyl)carbamate

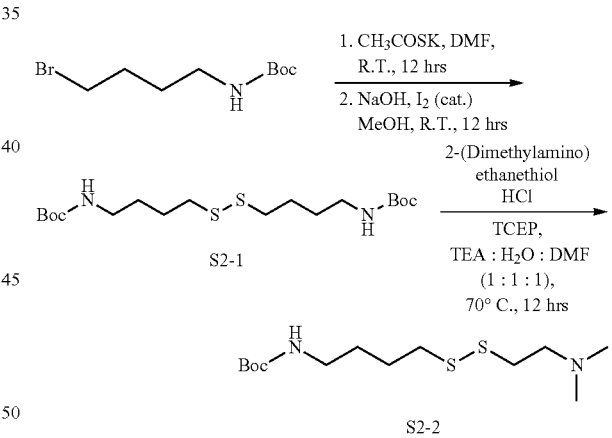

[2-1]: 1. 4-bromobutan-1-amine (420 mg, 1.67 mmole, 1.0 equiv) was dissolved in 2 mL dry DMF under inert atmosphere. To this solution, potassium thioacetate (347 mg, 3.04 mmole, 1.8 equiv) was added as a powder to the stirring reaction mixture. The reaction was allowed to go overnight and monitored for completion by TLC and LC/MS. The reaction mixture was diluted with 10 mL EtOAc and transferred to a seperatory funnel. The organic layer was washed with 3×10 mL sat NaCl solution. The organic layer was dried over Na2SO4, filtered, and evaporated to dryness to afford a crude yellow oil. 2. The crude oil was then dissolved in 5 mL of methanolic NaOH (5 g of NaOH powder in 5 mL of MeOH). To the slurry mixture, $I_{2(s)}$ (70.8 mg, 0.56 mmole, 0.38 equiv) was added. The reaction mixture was left at ambient atmosphere at R.T. overnight while monitoring for completion by TLC and LC/MS. Upon completion, 20 mL of H2O was added to the reaction to dissolve any solid NaOH, the mixture was transferred to a seperatory funnel, and the water layer was extracted into EtOAc (3×20 mL). The organic layer was dried over Na2SO4, filtered, and evaporated to dryness to afford a crude oil. The product was purified by Hex:EtOAc silica chromatography using a CombiFlash purification system. Product eluted at 1:1 Hex:EtOAc and collected fractions were evaporated to dryness to afford S2-1 as a light yellow oil (MW: 408.62 g/mol, 207.2 mg, 61% yield over two steps). 1H NMR (400 MHz, CDCl3): 3.15 (m, 4H), 2.70 (m, 4H), 1.73 (m, 4H), 1.60 (m, 4H), 1.45 (s, 18H).

[S2-2]: S2-1 (207.2 mg, 0.507 mmole, 1 equiv) was dissolved in 3 mL of 1:1:1 H2O:TEA:DMF. To this stirring solution, 2-(Dime-thylamino)ethanethiol HCL was added (998.6 mg, 3.55 mmole, 7 equiv) with TCEP (16 mg, 0.064 mmole, 0.13 equiv). The solution was then heated to 70° C. and allowed to react overnight while monitoring for completion by TLC and LC/MS. When complete, the reaction mixture was separated by RP-HPLC (H2O [0.1% TFA]: ACN [0.1% TFA]) and lyophilized to afford the product S2-2 as a clear oil formic acid salt (MW: 308.5+46.03 (FA) g/mol, 95 mg, 26% yield). 1H NMR (500 MHz, (CD3)₂SO): 8.21 (s, 1H, HCOOH aldehyde proton), 6.85 (m, 1H), 3.31 (m, 2H), 2.84 (m, 2H), 2.72 (m, 2H), 2.58 (m, 2H), 2.21 (s, 6H), 1.60 (m, 2H), 1.45 (m, 2H), 1.38 (s, 9H).

Synthesis of 2C07: N-(3-((2-(dimethylamino)ethyl) disulfanyl)propyl)-1-(4-methoxyphenyl)-5-(trifluoromethyl)-1H-pyrazole-4-carboxamide

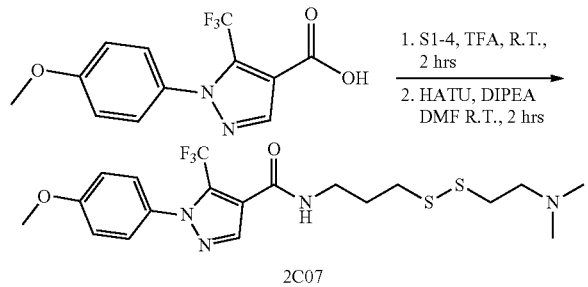

2C07

[2C07]: 1. S1-4 (12 mg, 0.041 mmol, 1 equiv) was dissolved in 1 mL DCM and cooled to 0° C. To this solution, neat TFA (250 mL, 3.3 mmol, 80 equiv) was added drop wise while stirring. Once added, the reaction was allowed to warm up to R.T. over 2 hrs while being monitored by TLC and LC/MS. When complete, the crude mixture was evaporated to dryness. Once dry, the crude oil was resuspended in 5 mL toluene and evaporated to dryness three times to remove by azeotrope in vacuo any excess TFA or H2O. This crude oil was then dissolved in 0.5 mL dry DMF under inert atmosphere. 2. To a separate reaction vessel, 1-(4-Methoxyphenyl)-5-(trifluoromethyl)-1H-pyrazole-4-carboxylic acid (15 mg, 0.052 mmol, 1.3 equiv) was dissolved in 1 mL dry DMF under inert atmosphere with HATU (24 mg, mmol, 1.5 equiv). While stirring, DIPEA (16 mg, 0.12 mmol, 3 equiv) was added drop wise at 0° C. When all the DIPEA was added, it was allowed to sit for 15 minutes. After this, the 1 mL DMF solution containing the crude de-protected S2-2 was added via syringe. This reaction was allowed to warm up to R.T. over the course of 2 hrs and was monitored by TLC and LC/MS. When complete, the reaction mixture was separated by RP-HPLC (H2O [0.1% TFA]: ACN [0.1% TFA]) and lyophilized to afford the product 2C07 as a white powder formic acid salt (462.55+46.04 (FA) g/mol, 14 mg, 67% yield). 1H (500 MHz, (CD3)₂SO) d: 8.60 (m, 1H), 8.18 (s, 1H, HCOOH aldehyde proton), 8.08 (s, 1H), 7.41 (d, J=8.9 Hz, 2H), 7.10. (d, J=8.9 Hz, 2H), 3.83 (s, 3H), 3.31 (m, 2H), 2.85 (m, 2H), 2.77 (m, 2H), 2.56 (m, 2H), 2.19 (s, 6H), 1.86 (m, 2H). 13C (125 MHz, (CD3)2SO) d: 163.55 (HCOOH carbonyl signal), 160.40, 160.04, 139.18, 131.67, 127.43 (2C), 121.18, 120.49, 118.34, 114.36 (2C), 58.03, 55.60, 44.70 (2C), 37.74, 35.80, 35.24, 28.61.

Synthesis of 2C07b: N-(4-((2-(dimethylamino) ethyl)disulfanyl)butyl)-1-(4-methoxyphenyl)-5-(trifluoromethyl)-1H-pyrazole-4-carboxamide

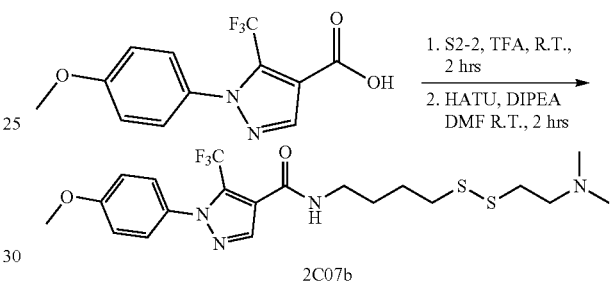

2C07b

[2C07b]: 1. S2-2 (10 mg, 0.032 mmol, 1 equiv) was dissolved in 1 mL DCM and cooled to 0° C. To this solution, neat TFA (250 mL, 3.3 mmol, 97 equiv) was added drop wise while stirring. Once all the TFA was added, the reaction was allowed to warm up to R.T. over 2 hrs while being monitored by TLC and LC/MS. When complete, the crude mixture was evaporated to dryness. Once dry, the crude oil was re-suspended in 5 mL toluene and evaporated to dryness three times to remove by azeotrope in vacuo any excess TFA or H2O. This crude oil was then dissolved in 0.5 mL dry DMF under inert atmosphere. 2. To a separate reaction vessel, 1-(4-Methoxyphenyl)-5-(trifluoromethyl)-1H-pyrazole-4-carboxylic acid (14 mg, 0.049 mmol, 1.5 equiv) was dissolved in 1 mL dry DMF under inert atmosphere with HATU (mg, mmol, equiv). While stirring, DIPEA (6.8 mg, 0.053 mmol, 1.6 equiv) was added drop wise at 0° C. When all the DIPEA was added, it was allowed to sit for 15 minutes. After this, the 1 mL DMF solution containing the crude de-protected S2-2 was added via syringe. This reaction was allowed to warm up to R.T. over the course of 2 hrs and was monitored by TLC and LC/MS. When complete, the reaction mixture was separated by RP-HPLC (H2O [0.1% TFA]: ACN [0.1% TFA]) and lyophilized to afford the product 2C07b as a white powder formic acid salt (476.57+ 46.03 (FA) g/mol, 11 mg, 66% yield). 1H NMR (500 MHz, (CD3)2SO) d: 8.56 (m, 1H), 8.18 (s, 1H, HCOOH aldehyde proton), 8.05 (s, 1H), 7.40 (d, J=8.3 Hz, 2H), 7.09 (d, J=8.3 Hz, 2H), 3.83 (s, 3H), 3.24 (m, 2H), 2.85 (m, 2H), 2.76 (m, 2H), 2.63 (m, 2H), 2.24 (s, 6H), 1.68 (m, 2H), 1.58 (m, 2H), 13C NMR (125 MHz, (CD3)2SO) d: 163.55 (HCOOH carbonyl signal), 160.31, 160.04, 139.12, 131.69, 127.43 (2C), 121.30, 120.51, 118.35, 114.37 (2C), 57.80, 55.60, 44.50 (2C), 38.47, 37.46, 35.37, 27.80, 25.96.

Synthesis of 2C07c: N-(3-((2-(dimethylamino)ethyl) disulfanyl)propyl)-1-(4-methoxyphenyl)-1H-pyrazole-4-carboxamide

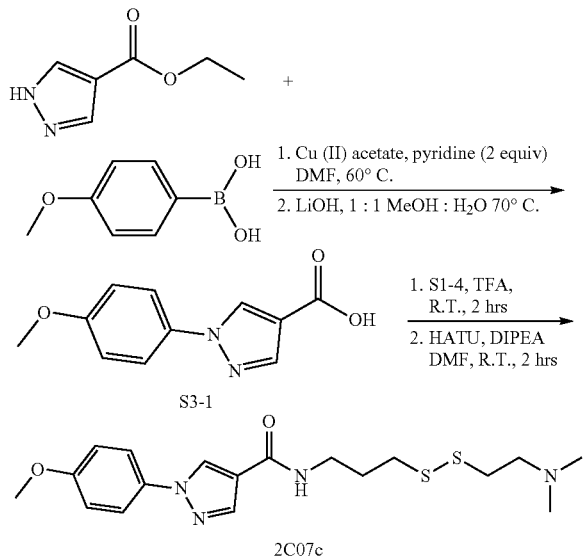

[S3-1]: 1. Ethyl-4-pyrazole carboxylate (100 mg, 0.71 mmol, 1 equiv) and 4-methoxy-phenyl boronic acid (110.6 mg, 0.71 mmol, 11 equiv) were dissolved in 1 mL dry DMF under inert atmosphere and heated to 60° C. Cu(II) acetate (117.4 mg, 0.54 mmol, 0.75 equiv) was dissolved in a mixture of 1:1 dry pyridine and DMF (0.5 mL: 0.5 mL) under inert atmosphere. This mixture was then added via syringe to the DMF solution of the carboxylate and boronic acid and the reaction was monitored for completion by TLC and LC/MS. When complete, the reaction was cooled to R.T. and filtered through cotton to remove insoluble Cu precipitant. The filtered reaction was concentrated in vacuo and the product was purified by Hex:EtOAc silica chromatography using a CombiFlash purification system. Product eluted at 3:1 Hex:EtOAc and collected fractions were evaporated to dryness to afford the product S3-1 as a clear oil (MW: 246.26 g/mol, 110 mg, 63% yield). 2. S3-1 was dissolved (110 mg, 0.45 mmole, 1 equiv) in 2 mL 1:1 MeOH:H2O and LiOH (11 mg, 0.45 mmol, 1 equiv) was added. The mixture was heated to 70° C. and was monitored for completion by TLC and LC/MS. Once complete, the reaction mixture was cooled to R. T. To the cooled mixture, 2 mL of 1N HCl was added until the pH<4. The reaction mixture was then diluted with 5 mL of EtOAc and transferred to a seperatory funnel. The aqueous layer was extracted into EtOAc (5 mL×3). The organic layer was dried over Na2SO4, filtered, and evaporated to dryness to afford a crude white powder, which was of sufficient purity for the next step (MW: 218.21 g/mol, 90 mg, 92% yield).

[2C07c]: 1. S1-4 (10 mg, 0.034 mmol, 1 equiv) was dissolved in 1 mL DCM and cooled to 0° C. To this solution, neat TFA (250 mL, 3.3 mmol, 97 equiv) was added drop wise while stirring. Once all the TFA was added, the reaction was allowed to warm up to R.T. over 2 hrs while being monitored by TLC and LC/MS. When complete, the crude mixture was evaporated to dryness. Once dry, the crude oil was re-suspended in 5 mL toluene and evaporated to dryness three times to remove by azeotrope in vacuo any excess TFA or H2O. This crude oil was then dissolved in 0.5 mL dry DMF under inert atmosphere. 2. To a separate reaction vessel, S3-1 (12 mg, 0.055 mmol, 1.6 equiv) was dissolved in 1 mL dry DMF under inert atmosphere with HATU (26 mg, 0.068 mmol, 2 equiv). While stirring, DIPEA (9 mg, 0.070 mmol, 2 equiv) was added drop wise at 0° C. When all the DIPEA was added, it was allowed to sit for 15 minutes. After this, the 1 mL DMF solution containing the crude de-protected S2-2 was added via syringe. This reaction was allowed to warm up to R.T. over the course of 2 hrs and was monitored by TLC and LC/MS. When complete, 5 mL of H2O and 5 mL of EtOAc were added and the mixture was transferred to a seperatory funnel. The aqueous layer was extracted into EtOAc (5 mL×3). The organic layer was dried over Na2SO4, filtered, and evaporated to dryness. The crude product was purified by Hex:EtOAc silica chromatography using a CombiFlash purification system. Product eluted at 3:1 Hex:EtOAc and collected fractions were evaporated to dryness to afford the product 2C07c as a clear oil (394.55 g/mol, 9 mg, 67% yield). 1H (500 MHz, (CD3)2SO) d: 8.78 (s, 1H), 8.24 (m, 1H), 8.08 (s, 1H), 7.74 (d, J=8.9 Hz), 7.07 (d, J=8.9 Hz), 3.80 (s, 3H), 3.31 (m, 2H), 2.84 (m, 2H), 2.78 (m, 2H), 2.55 (m, 2H), 2.18 (s, 6H), 1.86 (m, 2H). 13C (125 MHz, (CD3)2SO) d: 161.50, 158.10, 139.72, 132.83, 128.60, 120.35, 120.26 (2C), 114.70 (2C), 58.05, 55.47, 44.75 (2C), 37.32, 35.88, 35.34, 28.90.

Synthesis of 2B02: N-(3-((2-(dimethylamino)ethyl) disulfanyl)propyl)-2-(1H-indol-3-yl)-2-oxoacetamide

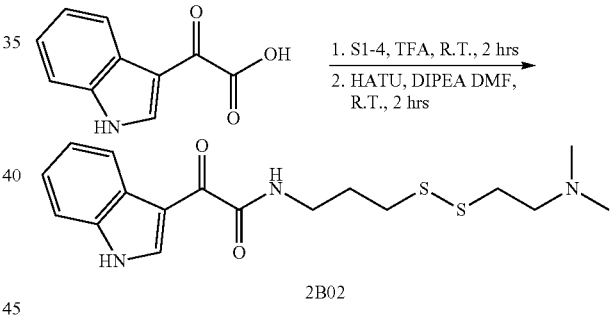

[2B02]: 1. S1-4 (10 mg, 0.034 mmol, 1 equiv) was dissolved in 1 mL DCM and cooled to 0° C. To this solution, neat TFA (250 mL, 3.3 mmol, 97 equiv) was added drop wise while stirring. Once all the TFA was added, the reaction was allowed to warm up to R.T. over 2 hrs while being monitored by TLC and LC/MS. When complete, the crude mixture was evaporated to dryness. Once dry, the crude oil was re-suspended in 5 mL toluene and evaporated to dryness three times to remove by azeotrope in vacuo any excess TFA or H2O. This crude oil was then dissolved in 0.5 mL dry DMF under inert atmosphere. 2. To a separate reaction vessel, 2-(1H-indol-3-yl)-2-oxoacetic acid (9.6 mg, 0.051 mmol, 1.5 equiv) was dissolved in 1 mL dry DMF under inert atmosphere with HATU (21.7 mg, 0.057 mmol, 1.7 equiv). While stirring, DIPEA (7.4 mg, 0.051 mmol, 1.5 equiv) was added drop wise at 0° C. When all the DIPEA was added, it was allowed to sit for 15 minutes. After this, the 1 mL DMF solution containing the crude de-protected S2-2 was added via syringe. This reaction was allowed to warm up to R.T. over the course of 2 hrs and was monitored by TLC and LC/MS. When complete, the reaction mixture was separated by RP-HPLC (H2O [0.1% TFA]: ACN [0.1% TFA]) and lyophilized to afford the product 2B02 as a white powder formic acid salt (365.51+46.03 (FA) g/mol, 7 mg, 50% yield). 1H (500 MHz, (CD3)2SO) d: 8.84 (m, 1H), 8.73 (s, 1H), 8.17 (s, 1H, HCOOH aldehyde proton), 8.22 (m, 1H), 7.26 (m, 2H), 7.26 (m, 1H), 3.31 (m, 2H), 2.86 (m, 2H), 2.76 (m, 2H), 2.61 (m, 2H), 2.22 (m, 6H), 1.88 (m, 2H). 13C (125 MHz, (CD3)2SO) d: 182.28, 163.83, 163.58 (HCOOH carbonyl signal), 138.55, 136.35, 126.27, 123.57, 122.68, 121.34, 112.67, 112.24, 57.89, 44.58 (2C), 37.44, 35.51, 35.49, 28.57.

Synthesis of 1: N-(4-acrylamidophenyl)-1-(4-methoxyphenyl)-5-(trifluoromethyl)-1H-pyrazole-4-carboxamide

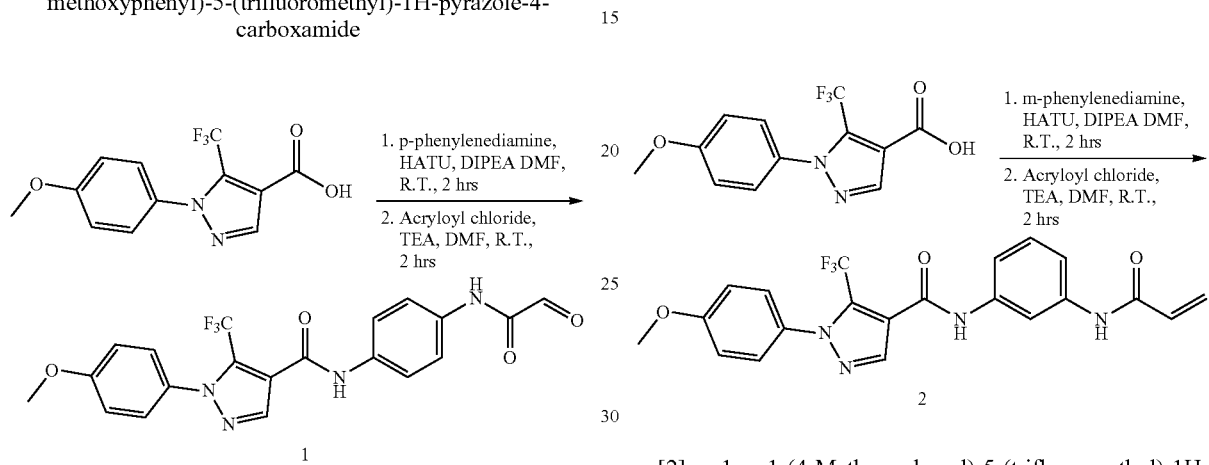

[1]: 1. 1-(4-Methoxyphenyl)-5-(trifluoromethyl)-1H-pyrazole-4-carboxylic acid (50 mg, 0.175 mmol, 1 equiv) was dissolved in 0.5 mL dry DMF under inert atmosphere with HATU (66.5 mg, 0.175 mmol, 1 equiv). While stirring, DIPEA (24.2 mg, 0.192 mmol, 1.1 equiv) was added drop wise at 0° C. When all the DIPEA was added, it was allowed to sit for 15 minutes. After this, p-phenylenediamine (75.7 mg, 0.7 mmol, 4 equiv) was added. The reaction was allowed to warm up to R.T. over the course of 2 hrs and was monitored by TLC and LC/MS. When complete, 5 mL of H2O and 5 mL of EtOAc were added and the mixture transferred to a seperatory funnel. The aqueous layer was extracted into EtOAc (5 mL×3). The organic layer was dried over Na2SO4, filtered, and evaporated to dryness. The crude product was purified by Hex:EtOAc silica chromatography using a CombiFlash purification system. The intermediate eluted at 1:1 Hex:EtOAc and collected fractions were evaporated to dryness to afford the coupled intermediate as a yellow oil (376.41 g/mol, 33.5 mg, 51% yield). 2. A portion of the purified product from step one (15 mg, 0.040 mmol, 1 equiv) was dissolved in 0.5 mL dry DMF under inert atmosphere. Dry TEA (8.1 mg, 0.080 mmole, 2 equiv) was added via syringe at 0° C. In a separate vial under inert atmosphere, 900 mL dry DMF and 100 mL of neat acryloyl chloride were mixed to make a 1:10 dilution of the acryloyl chloride reagent. 32 mL of this dilution as transferred via syringe to the reaction vial (3.6 mg, 0.040 mmol, 1 equiv) at 0° C. The reaction was allowed to warm up to R. T. and was monitored by TLC and LC/MS. Once complete, 1 mL of saturated NaHCO$_3$ solution was added and allowed to mix for 15 minutes to quench the reaction. To this, 5 mL of EtOAc was added and the mixture was transferred to a seperatory funnel. The aqueous layer was extracted into EtOAc (5 mL×3). The organic layer was dried over Na2SO4, filtered, and evaporated to dryness. The crude product was purified by DCM:MeOH silica chromatography using a CombiFlash purification system. The intermediate eluted at 10:1 DCM:MeOH and collected fractions were evaporated to dryness to afford the compound 1 as a clear oil (430.38 g/mol, 9.3 mg, 54% yield). 1H (500 MHz, (CD3)2CO) d: 8.08 (s, 1H), 7.65 (s, 4H), 7.42 (m, 2H), 7.10 (m, 2H), 6.44 (dd, J1=17.0 Hz, J2=9.5 Hz, 1H), 6.36 (dd, J1=17.0 Hz, J2=2.3 Hz, 1H), 5.78 (dd, J1=9.5 Hz, J2=2.3 Hz, 1H), 3.89 (s, 3H).

Synthesis of 2: N-(3-acrylamidophenyl)-1-(4-methoxyphenyl)-5-(trifluoromethyl)-1H-pyrazole-4-carboxamide

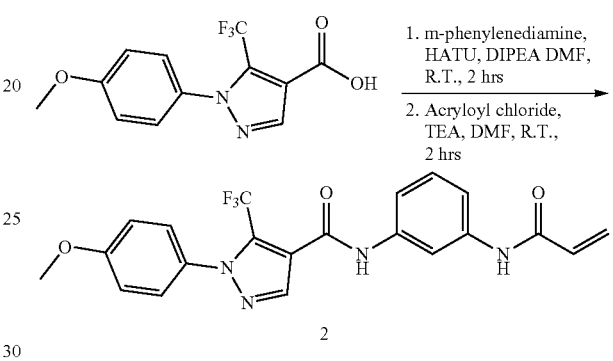

[2]: 1. 1-(4-Methoxyphenyl)-5-(trifluoromethyl)-1H-pyrazole-4-carboxylic acid (50 mg, 0.175 mmol, 1 equiv) was dissolved in 0.5 mL dry DMF under inert atmosphere with HATU (66.5 mg, 0.175 mmol, 1 equiv). While stirring, DIPEA (90.3 mg, 0.700 mmol, 4 equiv) was added drop wise at 0° C. When all the DIPEA was added, it was allowed to sit for 15 minutes. After this, m-phenylenediamine (76 mg, 0.700 mmol, 4 equiv) was added. The reaction was allowed to warm up to R.T. over the course of 2 hrs and was monitored by TLC and LC/MS. When complete, 5 mL of H2O and 5 mL of EtOAc were added and the mixture transferred to a seperatory funnel. The aqueous layer was extracted into EtOAc (5 mL×3). The organic layer was dried over Na2SO4, filtered, and evaporated to dryness. The crude product was purified by DCM:MeOH silica chromatography using a CombiFlash purification system. The intermediate eluted at 10:1 DCM:MeOH and collected fractions were evaporated to dryness to afford the coupled intermediate as a yellow oil (376.41 g/mol, 21 mg, 32% yield). 2. The purified product from step one (21 mg, 0.056 mmol, 1 equiv) was dissolved in 0.5 mL dry DMF under inert atmosphere. Dry TEA (22.7 mg, 0.223 mmole, 4 equiv) was added via syringe at 0° C. In a separate vial under inert atmosphere, 900 mL dry DMF and 100 mL of neat acryloyl chloride were mixed to make a 1:10 dilution of the acryloyl chloride reagent. 50 mL of this dilution as transferred via syringe to the reaction vial (5.5 mg, 0.061 mmol, 1.1 equiv) at 0° C. The reaction was allowed to warm up to R. T. and was monitored by TLC and LC/MS. Once complete, 1 mL of saturated NaHCO$_3$ solution was added and allowed to mix for 15 minutes to quench the reaction. To this, 5 mL of EtOAc was added and the mixture was transferred to a seperatory funnel. The aqueous layer was extracted into EtOAc (5 mL×3). The organic layer was dried over Na2SO4, filtered, and evaporated to dryness. The crude product was purified by DCM:MeOH silica chromatography using a CombiFlash purification system. The intermediate eluted at 10:1 DCM:MeOH and collected fractions were evaporated to dryness to afford compound 2 as a clear oil (430.38 g/mol, 8.2 mg, 34% yield). 1H (500 MHz, CD3OD) d: 8.06 (s, 1H), 7.43 (m, 1H), 7.41 (m, 1H), 7.40 (m, 2H), 7.31 (s, 1H), 7.08 (s, 2H), 6.44 (dd, J1=16.94 Hz, J2=9 Hz, 1H), 6.35 (d, J=16.94 Hz, 1H), 5.76 (d, J=9.7 Hz, 1H)

Synthesis of 3: N-(3-acrylamido-5-chlorophenyl)-1-(4-methoxyphenyl)-5-(trifluoromethyl)-1H-pyrazole-4-carboxamide

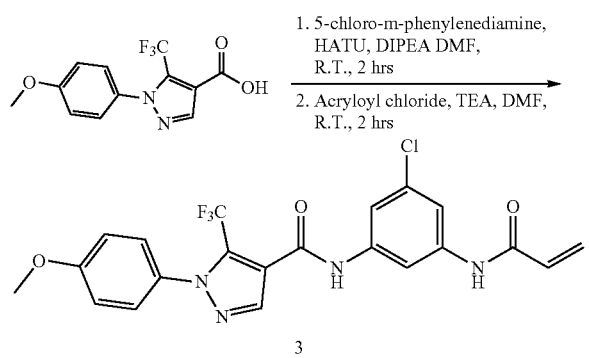

[3]: 1. 1-(4-Methoxyphenyl)-5-(trifluoromethyl)-1H-pyrazole-4-carboxylic acid (500 mg, 1.75 mmol, 1 equiv) was dissolved in 0.5 mL dry DMF under inert atmosphere with HATU (732 mg, 1.93 mmol, 1.1 equiv). While stirring, DIPEA (1.8 g, 14 mmol, 8 equiv) was added drop wise at 0° C. When all the DIPEA was added, it was allowed to sit for 15 minutes. After this, 5-chloro-m-phenylenediamine (996 mg, 7.0 mmol, 4 equiv) was added. The reaction was allowed to warm up to R.T. over the course of 2 hrs and was monitored by TLC and LC/MS. When complete, 5 mL of H2O and 5 mL of EtOAc were added and the mixture transferred to a seperatory funnel. The aqueous layer was extracted into EtOAc (5 mL×3). The crude product was dissolved in 1:1 ACN:H2O, separated by RP-HPLC (H2O [0.1% TFA]: ACN [0.1% TFA]), and lyophilized to afford the coupled intermediate as a clear oil (410.78 g/mol, 245 mg, 34% yield). 2. A portion of the purified product from step one (100 mg, 0.22 mmol, 1 equiv) was dissolved in 0.5 mL dry DMF under inert atmosphere. Dry TEA (90 mg, 0.85 mmole, 4 equiv) was added via syringe at 0° C. 20 mL of acryloyl chloride was transferred via syringe to the reaction vial (22 mg, 0.242 mmol, 1.1 equiv) at 0° C. The reaction was allowed to warm up to R. T. and was monitored by TLC and LC/MS. Once complete, 1 mL of saturated NaHCO3 solution was added and allowed to mix for 15 minutes to quench the reaction. To this, 5 mL of EtOAc was added and the mixture was transferred to a seperatory funnel. The aqueous layer was extracted into EtOAc (5 mL×3). The crude product was dissolved in 1:1 ACN:H2O, separated by RP-HPLC (H2O [0.1% TFA]: ACN [0.1% TFA]), and lyophilized to afford compound 3 as a clear oil (464.78 g/mol, 48 mg, 47% yield). 1H (500 MHz, (CD3)2SO) d: 10.71 (s, 1H), 10.41 (s, 1H), 8.05 (m, 1H), 7.69 (m, 1H), 7.49 (m, 1H), 8.29 (s, 1H), 7.46 (m, 2H), 7.12 (m, 2H), 6.44 (dd, J1=17.00 Hz, J2=10.08 Hz, 1H), 6.30 (dd, J1=17.00 Hz, J2=1.76 Hz, 1H), 5.80 (dd, J1=10.08 Hz, J2=1.76 Hz, 1H), 3.85 (s, 3H). 13C (125 MHz, (CD3)2SO) d: 163.47, 160.15, 159.32, 140.64, 140.25, 139.55, 133.08, 131.51, 131.46, 127.64, 127.47 (2C), 120.74, 120.38, 118.22, 114.40 (2C), 114.28, 114.26, 108.83, 55.60.

Synthesis of 4: N-(3-chloro-5-propionamidophenyl)-1-(4-methoxyphenyl)-5-(trifluoromethyl)-1H-pyrazole-4-carboxamide

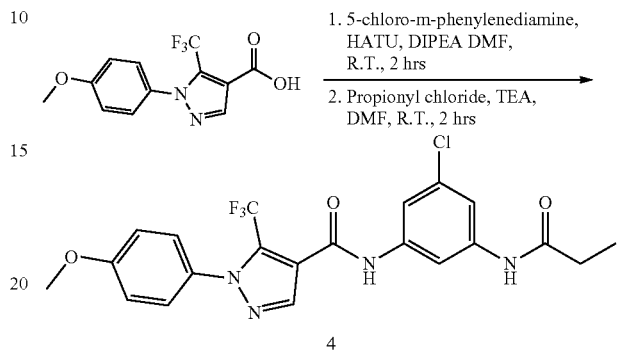

[4]: 1. Please refer to step one of the synthesis of compound 3 above. 2. A portion of the purified coupled intermediate from step one compound 3's synthesis (100 mg, 0.22 mmol, 1 equiv) was dissolved in 0.5 mL dry DMF under inert atmosphere. Dry TEA (90 mg, 0.85 mmole, 4 equiv) was added via syringe at 0° C. 20 mL of propionyl chloride was transferred via syringe to the reaction vial (22 mg, 0.242 mmol, 1.1 equiv) at 0° C. The reaction was allowed to warm up to R. T. and was monitored by TLC and LC/MS. Once complete, 1 mL of saturated NaHCO3 solution was added and allowed to mix for 15 minutes to quench the reaction. To this, 5 mL of EtOAc was added and the mixture was transferred to a seperatory funnel. The aqueous layer was extracted into EtOAc (5 mL×3). The crude product was dissolved in 1:1 ACN:H2O, separated by RP-HPLC (H2O [1% TFA]: ACN [0.1% TFA]), and lyophilized to afford compound 4 as a clear oil (466.8 g/mol, 74 mg, 72% yield). 1H (500 MHz, (CD3)2SO) d: 10.66 (s, 1H), 10.12 (s, 1H), 8.28, (s, 1H), 7.97 (m, 1H), 7.58 (m, 1H), 7.46 (m, 3H), 7.12 (m, 2H), 3.85 (s, 3H), 2.33 (q, J=7.6 Hz, 2H), 1.08 (t, J=7.6 Hz, 3H). 13C (125 MHz, (CD3)2SO) d: 172.47, 160.13, 159.29, 140.96, 140.16, 139.54, 132.96, 131.47, 127.47 (2C), 120.78, 120.39, 118.22, 114.40 (2C), 113.97, 113.73, 108.52, 55.60, 29.56, 9.53.

βME50 Determination of 2C07, 2B02, and 2C07 Derivatives.

Each reaction was 50 mL total volume and conducted in a 96 well plate format for analysis by LC/MS. A base master mix of 4 mM Ras, 1 mM MgCl2, 100 mM tethering compound in Gel Filtration Buffer was made. Another master mix containing the same reagents supplemented with 25 mM βME was also made. 100 mL of the master mix containing 25 mM βME was put in wells in row A. The remaining rows were filled with 50 mL of the master mix with no βME. Using a multi-channel pipette, the solutions were serial diluted 1:1 from row A down to H. This made 8 reactions with βME concentration varying from 25 mM down to 185 mM. Once set, the tray was allowed to equilibrate while mixing at room temperature for 1 h. After equilibration, the percent modification was detected by LC/MS. The percent modification was analyzed by electrospray mass spectrometry using a Waters Acquity UPLC/ESI-TQD with a 2.1×50 mm Acquity UPLC BEH300 C4 column. Percent modifications for each βME concentration were plotted in PRISM and fit using a Boltzman sigmoidal non-linear regression (curve fit) to determine the βME50 value and 95% confidence interval.

Crystallization, Data Collection, and Structure Determination. For all X-Ray crystallography, a similar protocol was followed as outlined in Ostrem et al. (2013). To every protein crystallography prep, 1 mM $MgCl_2$ was added prior to setup. After high-speed centrifugation to remove insoluble protein, a 1:1 volume of protein and precipitation solutions were mixed for hanging drop evaporative diffusion. Protein concentrations varied from 8-12 mg/mL prior to dilution with precipitation solutions. For initial screening, Qiagen screening plates (see Key Resources Table) were used to find the optimal precipitation solution. To set up our 96-well screening trays, we utilized a TTPLabtech Mosquito Nanoliter Dropsetter and let our crystals rest at 20° C. in a climate controlled crystal storagefacility. Each day, trays were monitored for crystal formation. Commonly, several days would elapse (3-5 days) before crystals had sufficiently grown for harvesting. Common successful reservoir conditions contained various PEG precipitants (see table below) and some were improved by the addition of an additive solution. Additive solutions were added 10% (by volume) and screened from commercially available NeXtal DWBlock Opti Salt Suite solutions. For the best precipitation solution hits, hanging drops were set using larger crystal trays and optimized to yield large, singular crystals. Crystals were cryoprotected by adding various amounts of glycerol. Once looped, crystals were frozen and stored in liquid nitrogen prior to obtaining diffraction data. All data-sets were collected at Beamline 8.2.2 (100 K nitrogen stream) at the Berkeley Advanced Light Source. Datasets were integrated with iMosflm and scaled with Aimless and Scala in the CCP4 software suite (Battye et al., 2011; Evans and Murshudov, 2013; Evans, 2006). Phenix MRage molecular replacement program was used to solve the initial structure of 1-169 K-Ras(M72C) Cys Light GDP 2C07 (Collaborative Computational ProjectN.4, 1994; Evans and Murshudov, 2013; Evans, 2006). A previously deposited S-IIP structure by Ostrem et al (PDB: 4LYJ) provided the best solution and starting point for model building. The solution was further refined with manual building in Coot and several rounds of refinement in Phenix, with simulated annealing, ADP (B factor) refinement, TLS (parameters provided by the TLSMD server) (Adams et al., 2011; Painter et al., 2006). Subsequent crystal structure datasets underwent a similar refinement process. Ligand geometrical restraints were generated using Phenix Elbow (Moriarty et al., 2009). The 1-166 H-Ras(M72C) GppNHp 2C07 dataset underwent MRage molecular replacement using several truncated models, and the previously deposited 1-166 H-Ras GppNHp structure (PDB: 3K9L) gave the best starting solution. All figures were made with PyMOL except for electrostatic surfaces, which were generated by CCP4 mg and then rendered in PyMOL. For crystal statistics, please refer to Table 2 described herein.

TABLE 2

Deposited Crystal Structure Statistics: This table summarizes relevant statistics for each uploaded structure to the Protein Database (PDB) along with corresponding ascension codes.

| | K-Ras(M72C) Cys Light 2C07 GDP (PDB: 5VBM) | H-Ras(M72C) 2C07 GDP (PDB: 5VBE) | H-Ras(M72C) 2C07 GppNHp (PDB: 5BVZ) |
|---|---|---|---|
| Data Collection: | | | |
| Space group | P212121 | R32:H | P212121 |
| Cell Dimension: | | | |
| a, b, c, (Å) | 32.6, 41.18, 111.1 | 92.648, 92.648, 120.532 | 61.84, 75.44, 93.63 |
| α, β, γ (°) | 90, 90, 90 | 90, 90, 120 | 90, 90, 90 |
| Resolution (Å) | 55.55-1.49 (1.490-1.510) | 38.06-1.57 (1.626-1.57) | 51.6-2.2 (2.279-2.2) |
| $R_{merge}$ | 0.053 (0.255) | .074 (.837) | 0.150 (.654) |
| Mean I/σI | 15.700 (3.900) | 7.700 (2.000) | 5.800 (1.900) |
| Completeness (%) | 98.70 (91.80) | 99.73 (97.61) | 97.000 (97.000) |
| Multiplicity | 3.7 (2.9) | 10.9 (9.9) | 3.3 (3.3) |
| Refinement: | | | |
| Resolution (Å) | 55.55-1.49 | 38.06-1.57 | 51.6-2.2 |
| No. reflections | 25082 (2405) | 27936 (2323) | 22134 (3169) |
| $R_{work}/R_{free}$ | 0.1722/0.1962 | 0.1782/0.2010 | 0.2103/0.2530 |
| No. Atoms: | | | |
| Protein | 1338 | 1306 | 3825 |
| Ligand/ion | 53 | 54 | 123 |
| Water | 105 | 104 | 62 |
| B-factors: | | | |
| Protein | 21.8 | 31.7 | 37.5 |
| Ligand/ion | 16.8 | 38.92 | 22.1 |
| Water | 27 | 32.3 | 22.3 |
| R.M.S Deviations: | | | |
| Bond lengths (Å) | 0.007 | 0.016 | 0.017 |
| Bond angles (°) | 1.41 | 1.17 | 1.26 |

Crystallography Growth Conditions Summary Table:

| Crystal (PDB Code) | Growth Condition | 10% Additive Solution | Beamline/ Wavelength (Å) |
|---|---|---|---|
| K-Ras(M72C) Cys Light GDP 2C07 (5VBM) | 33% PEG4000, .1M Na Citrate (pH 4.6), .2M Ammonium Acetate | 2.2M KCl | ALS 8.2.2/1.0000 |
| K-Ras(M72C) GDP 2C07 (5VBE) | 22% PEG8000, .1M Tris HCl (PH 7.7), .1M $CaCl_2$ | .1M Tris HCl (pH 8.5), 1.75M Na Formate | ALS 8.2.2/1.0000 |
| H-Ras(M72C) GppNHp 2C07 (5BVZ) | 32% PEG4000, .1M Na Cacodylate (PH 6.6), .2M $CaCl_2$ | N/A | ALS 8.2.2/1.0000 |

Hydrogen Deuterium Exchange Mass Spectrometry Data Collection. HDX reactions were conducted with 40 pmol of protein, and were initiated by the addition of 46 μL of D2O Buffer Solution (10 mM HEPES pH 7.5, 50 mM NaCl, 97% D2O), to give a final concentration of 87% D2O. Exchange was carried out for 0.3s, 3s, 30s, 300s and 3000s, and exchange was terminated by the addition of a quench buffer (final concentration 0.6 M guanidine-HCL, 0.8% formic acid). Samples were rapidly frozen in liquid nitrogen and stored at −80° C. until mass analysis. Protein samples were rapidly thawed and injected onto a UPLC system at 2° C. The protein was run over two immobilized pepsin columns (Applied Biosystems; porosyme, 2-3131-00) at 10° C. and 2° C. at 200 μL/min for 3 minutes, and peptides were collected onto a VanGuard precolumn trap (Waters). The trap was subsequently eluted in line with an Acquity 1.7 μm particle, 100 3 1 mm2 C18 UPLC column (Waters), using a gradient of 5-36% B (buffer A 0.1% formic acid, buffer B 100% acetonitrile) over 16 minutes. Mass spectrometry experiments were performed on an Impact II TOF (Bruker) acquiring over a mass range from 150 to 2200 m/z using an electrospray ionization source operated at a temperature of 200° C. and a spray voltage of 4.5 kV. Peptides were identified using data-dependent acquisition methods following tandem MS/MS experiments (0.5 s precursor scan from 150-2200 m/z; twelve 0.25 s fragment scans from 150-2200 m/z). MS/MS datasets were analyzed using PEAKS7 (PEAKS), and a false discovery rate was set at 1% using a database of purified proteins and known contaminants.

Deuterium incorporation calculations were carried out as described previously (Fowler et al., 2016). HD-Examiner Software (Sierra Analytics) was used to automatically calculate the level of deuterium incorporation into each peptide. All peptides were manually inspected for correct charge state and presence of overlapping peptides. Deuteration levels were calculated using the centroid of the experimental isotope clusters.

Ras GppNHp In Vitro Pull Down Assay by His6-MBP-Raf-1-RBD. For each His6-MBP-Raf-1-RBD in vitro pull down the total volume was 500 μL. Each reaction had the following final composition: Either 20, 80, 200, 400, or 800 nM Ras GppNHp (from 0.2 mg/mL Ras stock), 75 nM BSA (2.5 μg, 5 μL of 0.5 mg/mL BSA stock), 200 nM of His6-MBP-Raf-1-RBD (5.3 μg, 1.2 μL of 4.38 mg/mL stock of His6-MBP-Raf-1-RBDwitt), and Raf Pull Down Buffer to volume (25 mM Tris (pH 7.2), 150 mM NaCl, 5 mM MgCl2, 1% NP-40, 5% glycerol, 20 mM imidazole). Samples were then mixed by gentle rotation at 4° C. for 30 min. While equilibrating, add 50 μL Ni-NTA slurry (Qiagen) to a cellulose acetate spin cup and spin at 5,000 rpm on a tabletop centrifuge for 30 seconds. Wash the beads with 400 μL of Raf Pull Down Buffer to wash away bead storage buffer. Before adding each pull down solution, take 10 μL and save as a loading control sample. To each spin cup filled with washed Ni-NTA beads, add the remaining equilibrated pull down solution, seal the spin cup with parafilm and let rotate at 4° C. for 30 more minutes. After mixing, centrifuge the sample for 30 seconds at 5,000 rpm. Toss flow through. Wash the beads X 5 with 400 μL of Raf Pull Down Buffer. After last wash, centrifuge one last time to remove any excess buffer stuck to the beads. To each cup, add 50 μL of 5×SDS loading buffer and mix by vortexing. Let the buffer sit on the beads for 5 minutes and then elute into a fresh tube by centrifuging at 5000 rpm for 1.5 minutes. Load 10 μL of each loading control sample and 25 μL of each eluted pull down onto a SDS-PAGE gel and transfer to a nitrocellulose blot for Western Blot analysis. Block with 5% BSA TBS buffer and then blot with pan Ras primary antibody at a 1:500 dilution in 5% BSA in TBST (Cell Signaling #3965). Blots were read out using LICOR compatible secondary antibodies. Pull-down signals were reported as ratios relative to input protein signal.

Intrinsic Nucleotide Affinity by EDTA Catalyzed Nucleotide Exchange. For each EDTA catalyzed reaction, the total reaction volume was 500 μL. Each reaction had the following final composition: 100 nM Ras GDP (1 μg, 5 μL of 0.2 mg/mL Ras stock), 75 nM BSA (2.5 μg, 5 μL of 0.5 mg/mL BSA stock), 100 μM total nucleotide concentration (5 μL of various ratios of GDP:GppNHp from 10 mM stock solutions), 10 mM of EDTA (10 μL of 0.5M EDTA pH 8.0), 64 mM of MgCl2 (16 μL of 2M $MgCl_2$ stock), 3 μM of His6-MBP-Raf-1-RBDwitt (80 μg, 18.3 μL of 4.38 mg/mL stock of His6-MBP-Raf-1-RBDwitt), and Raf Pull Down Buffer to volume (25 mM Tris (pH 7.2), 150 mM NaCl, 5 mM MgCl2, 1% NP-40, 5% glycerol, 20 mM imidazole). Prior to initiating the EDTA catalyzed nucleotide exchange, the Ras, BSA, nucleotide, and Raf Pull Down Buffer were mixed by pipette on ice. To each tube, the EDTA was added, sample was inverted X 3, and then placed in a pre-warmed tube rack at 30° C. The exchange was allowed to occur at 30° C. for 15 minutes, inverting each tube X 3 every 5 minutes. Once the 15 minutes of exchange was complete, MgCl2 was added to each tube and inverted X 3 and placed on ice for 15 minutes. During the quenching on ice, add 100 μL Ni-NTA slurry (Qiagen) to a cellulose acetate spin cup and spin at 5,000 rpm on a tabletop centrifuge for 30 seconds. Wash the beads with 400 μL of Raf Pull Down Buffer to wash away bead storage buffer. Before adding the beads and His6-tagged Raf-1-RBDwitt, take a 10 μL sample as a loading control and quench it with 5 μL 5×SDS loading buffer. To each spin cup filled with washed Ni-NTA beads, add the quenched EDTA catalyzed exchange reaction and the His6-tagged Raf-1-RBDwitt. Seal the spin cup with parafilm and let rotate at 4° C. for 1 h. After mixing, centrifuge the sample for 30 seconds at 5,000 rpm. Toss flow through. Wash the beads×5 with 400 μL of Raf Pull Down Buffer. After last wash, centrifuge one last time to remove any excess buffer stuck to the beads. To each cup, add 50 μL of 5×SDS loading buffer and mix by vortexing. Let the buffer sit on the beads for 5 minutes and then elute into a fresh tube by centrifuging at 5000 rpm for 1.5 minutes. Load 10 μL of each loading control sample and 25 μL of each eluted pull down onto a SDS-PAGE gel and transfer to a nitrocellulose blot for Western Blot analysis. Block with 5% BSA TBS buffer and then blot with pan Ras primary antibody at a 1:500 dilution in 5% BSA in TBST (Cell Signaling #3965). Blots were read out using LICOR compatible secondary antibodies and quantified. Signal from each GDP-only (i.e. 0% GppNHp) exchange was subtracted as background from the 20%, 50%, and 66% GppNHp pull-down signals for each protein construct. The signal for the GppNHp only lane (i.e. 100% GppNHp) was normalized to 1 and all other signals were made relative to this band within each protein construct tested.

Ras GDP In Vitro Pull Down Assay by His6 Tagged $SOS^{CAT}$

This experiment was created based on a procedure published in Hall et al., 2001. For each $SOS^{CAT}$ in vitro pull down the total volume was 500 μL. Each reaction had the following final composition: Either 20, 80, 200, 400, or 800 nM Ras GDP (from 0.2 mg/mL Ras stock), 75 nM BSA (2.5 μg, 5 μL of 0.5 mg/mL BSA stock), 200 nM of His6-$SOS^{CAT}$ (6 μg, 3 μL of diluted 0.2 mg/mL stock of His6-$SOS^{CAT}$), and $SOS^{CAT}$ Pull Down Buffer to volume (20 mM Tris (pH 7.6), 50 mM NaCl, 5 mM EDTA, 1% Triton X-100, 20 mM imidazole). Samples were then mixed by gentle rotation at 4° C. for 30 min. While equilibrating, add 50 μL Ni-NTA slurry (Qiagen) to a cellulose acetate spin cup and spin at 5,000 rpm on a tabletop centrifuge for 30 seconds. Wash the beads with 400 μL of $SOS^{CAT}$ Pull Down Buffer to wash away bead storage buffer. Before adding each pull down solution, take 10 μL and save as a loading control sample. To each spin cup filled with washed Ni-NTA beads, add the remaining equilibrated pull down solution, seal the spin cup with parafilm and let rotate at 4° C. for 30 more minutes. After mixing, centrifuge the sample for 30 seconds at 5,000 rpm. Toss flow through. Wash the beads×5 with 400 μL of $SOS^{CAT}$ Pull Down Buffer. After last wash, centrifuge one last time to remove any excess buffer stuck to the beads. To each cup, add 50 µL of 5×SDS loading buffer and mix by vortexing. Let the buffer sit on the beads for 5 minutes and then elute into a fresh tube by centrifuging at 5000 rpm for 1.5 minutes. Load 10 µL of each loading control sample and 25 µL of each eluted pull down onto a SDS-PAGE gel and transfer to a nitrocellulose blot for Western Blot analysis. Block with 5% BSA TBS buffer and then blot with pan Ras primary antibody at a 1:500 dilution in 5% BSA in TBST (Cell Signaling #3965). Blots were read out using LICOR compatible secondary antibodies and quantified. The largest input signal was normalized to one for each protein construct and each pull-down signal (i.e. 20 nM, 80 nM, 200 nM, 400 nM, and 800 nM respectively) was reported relative to that maximum signal. Thus, normalized pull-down signals represent the proportion of Ras pulled down relative to the maximum blot signal detected for that particular protein construct.

$SOS^{CAT}$ Catalyzed Nucleotide Exchange In Vitro Analyzed by Ras GppNHp Pull Down by His6 Tagged Raf-1-RBD. For each $SOS^{CAT}$ in vitro catalyzed nucleotide exchange reaction the total volume was 500 µL. Each reaction had the following final composition: 100 nM Ras GDP (1 µg, 5 µL of 0.2 mg/mL Ras stock), 75 nM BSA (2.5 µg, 5 µL of 0.5 mg/mL BSA stock), 800 nM of $SOS^{CAT}$ (6 µg, 12 µL of diluted 0.2 mg/mL stock of His6-$SOS^{CAT}$), 100 µM total nucleotide concentration (5 µL of 10 mM nucleotide stock solutions), 200 nM of His6-MBP-Raf-1-RBDwitt (5.3 µg, 1.2 µL of 4.38 mg/mL stock of His6-MBP-Raf-1-RBDwitt), and $SOS^{CAT}$ Catalyzed Exchange Buffer to volume (20 mM Tris (pH 7.6), 50 mM NaCl, 5 mM MgCl2, 1% Triton X-100, 20 mM imidazole). Mix the Ras, BSA, $SOS^{CAT}$, nucleotide, and $SOS^{CAT}$ Catalyzed Exchange Buffer in an eppendorf tube and let rotate at 4° C. for 3 h. While equilibrating, add 50 µL Ni-NTA slurry (Qiagen) to a cellulose acetate spin cup and spin at 5,000 rpm on a tabletop centrifuge for 30 seconds. Wash the beads with 400 µL of $SOS^{CAT}$ Catalyzed Exchange Buffer to wash away bead storage buffer. To each exchange reaction, add His6-MBP-Raf-1-RBDwitt. Before adding each pull down solution to the spin cup, take 10 µL and save as a loading control sample. To each spin cup filled with washed Ni-NTA beads, add the remaining exchange reaction, seal the spin cup with parafilm and let rotate at 4° C. for 1 hr. After mixing, centrifuge the sample for 30 seconds at 5,000 rpm. Toss flow through. Wash the beads×5 with 400 µL of $SOS^{CAT}$ Pull Down Buffer. After last wash, centrifuge one last time to remove any excess buffer stuck to the beads. To each cup, add 50 µL of 5×SDS loading buffer and mix by vortexing. Let the buffer sit on the beads for 5 minutes and then elute into a fresh tube by centrifuging at 5000 rpm for 1.5 minutes. Load 10 µL of each loading control sample and 25 µL of each eluted pull down onto a SDS-PAGE gel and transfer to a nitrocellulose blot for Western Blot analysis. Block with 5% BSA TBS buffer and then blot with pan Ras primary antibody at a 1:500 dilution in 5% BSA in TBST (Cell Signaling #3965). Blots were read out using LICOR compatible secondary antibodies and quantified.+GppNHp and +$SOS^{cat}$ pull-down conditions were quantified and re-ported as ratios relative to the input signal for each protein construct.

Electrophile Labeling Experiments.

Each reaction was analyzed in a 96 well plate format for analysis by LC/MS. Total reaction volumes were 25 µL for single time point labeling experiments and 200 uL for full 24-hour time courses. 25 µL reactions were made in the wells of a V-bottom 96 well plate and 200 uL reactions were made in 1.25 mL eppendorf tubes. All labeling reactions were conducted in Gel Filtration Buffer (20 mM HEPES (pH 7.5), 150 mM NaCl) with no added reductant at room temperature. Final reaction mixtures were 4 µM Ras, 1 mM MgCl2, and had a total DMSO concentration of 4% by volume. Electrophile stocks were made in DMSO at 10 mM, aliquoted, and frozen. Labeling reactions were started by the addition of the desired volume of 10 mM electrophile stock and mixed thoroughly by pipette. General screening of new electrophiles was done at 100 µM electrophile in triplicate and sampled as a single time point after 24 hours of incubation. For Compound 3, labeling time courses were conducted at 20 µM compound with sampling done every 2 hours for the first 10 hours of incubation and continued after overnight incubation until the protein was fully modified. Reactions were allowed to sit at room temperature in the dark (either covered in aluminum foil or in a bench drawer) until the desired time point was reached. For 24-hour single point labeling experiments, the reaction was directly sampled from the 96 well plate and analyzed by LC/MS. For experiments with multiple time points, 22.5 µL aliquots of the 200 µL master reaction were sampled and quenched by the addition of 2.5 µL of 2% formic acid (also made in Gel Filtration Buffer). This 25 µL quenched sample was then analyzed by LC/MS and the remaining master reaction was allowed to continue reacting after gentle mixing by pipette. The percent modification was analyzed by electrospray mass spectrometry using a Waters Acquity UPLC/ESI-TQD with a 2.1×50 mm Acquity UPLC BEH300 C4 column.

Competition Labeling Experiments.

200 mL reactions were made in Gel Filtration buffer (20 mM HEPES (pH 7.5), 150 mM NaCl) with no added reductant at room temperature. The final concentrations of each reagent were as follows: 4 mM Ras, 1 mM MgCl2, 20 mM Compound 3, X mM Compound 4, and a total DMSO concentration of 4% by volume. Compound 4 was varied from OX (0 mM), 1× (20 mM), 3× (60 mM), and 9× (180 mM) respectively. Adding the desired volume of Gel Filtration Buffer, MgCl2, DMSO, and 10 mM compound stocks of Compounds 3 and 4 was done first and mixed thoroughly before protein was added. Reactions were started by the addition and gentle mixing by pipette of concentrated Ras stocks diluted into the master reaction down to 4 mM. Each reaction was set in triplicate and allowed to react at room temperature in the dark (either covered in aluminum foil or in a bench drawer) until the desired time point was reached. At each time point, 22.5 mL aliquots of each 200 mL master reaction was sampled and quenched by the addition of 2.5 mL of 2% formic acid (also made in Gel Filtration Buffer). This 25 mL quenched sample was then analyzed by LC/MS and the remaining master reaction was allowed to continue reacting after gentle mixing by pipette. The percent modification was analyzed by electrospray mass spectrometry using a Waters Acquity UPLC/ESI-TQD with a 2.1×50 mm Acquity UPLC BEH300 C4 column.

Purification and Modification of H-Ras Constructs for Lipid Kinase Assays. Plasmids expressing 1-181 H-Ras (G12V/C118S) and H-Ras(G12V/M72C/C118S) were transformed into BL21 DE3 and the culture was induced at OD 0.6-0.9 with 100 mg/mL IPTG. The cultures were then allowed to grow for 4 h at 37° C. after which the cells were pelleted and stored at −80° C. Frozen pellets were resuspended in lysis buffer and lysed by sonication (10s ON; 10s OFF; Power-6.0). Triton-X was added to a final concentration of 0.1% and lysate was centrifuged at 20,000 g for 45 minutes (Beckman Coulter Avanti J-251, JA 25.50 rotor). The supernatant was loaded on a 5 mL HisTrapTm FF column (GE Healthcare) equilibrated with buffer containing 10 mM imidazole pH 8.0 (NiNTA A). Following washes with 20 mL NiNTA A and 20 mL of 6% buffer containing 200 mM imidazole pH 8.0 (NiNTA B), the protein was eluted in 100% NiNTA B. The elution was buffer exchanged with NiNTA A buffer in a 10,000 MWCO Amicon concentrator (Millipore). The sample was concentrated down to <2 mL and TEV protease was added to ~0.3 mg/mL. The cleavage was allowed to proceed overnight at 4° C. To de-enrich the TEV protease, the protein solution was loaded onto a HisTrapTm FF column and eluted with 10 mL of NiNTA A buffer. The elution was concentrated to ~2 mL.

For H-Ras G12V, 2-fold excess GTPgS was added with 25 mM EDTA and incubated for 1 h at room temperature. The solution was buffer exchanged with phosphatase buffer (32 mM Tris pH 8.0, 200 mM ammonium sulphate, 0.1 mM ZnCl2, 2 mM bME) and 1 unit of immobilized calf alkaline phosphatase (Sigma) was added per milligram of H-Ras along with a two-fold excess nucleotide. After incubation for 1 h at room temperature, MgCl2 was added to 30 mM to lock bound nucleotide in place and immobilized phosphatase beads were removed using a 0.22 micron spin filter (EMD Millipore).

For the M72C construct, the protein was incubated with 25 mM EDTA for 1 h at room temperature. Following buffer exchange with phosphatase buffer, immobilized calf alkaline phosphatase was added to 1 unit/mg and incubated for 1 h at room temperature. The phosphatase beads were removed and 5-fold excess GDP was added. After 30 mins at room temperature, MgCl2 was added to a final concentration of 30 mM.

The proteins were buffer exchanged with Ras gel filtration buffer (20 mM HEPES pH 7.0, 150 mM NaCl, 1 mM MgCl2) and concentrated to less than 1 mL. Protein was injected onto a Superdex™ 75 10/300 GL size-exclusion column (GE Healthcare) equilibrated in Ras gel filtration buffer.

Coupling to inhibitor was done in a reaction containing 100 mM of M72C construct, 100 mM TCEP, 1 mM MgCl2 and 200 mM Compound 3. DMSO was adjusted to a final concentration of 5%. After 24 hours, more inhibitor was added to a total final concentration of 250 mM. The coupling was allowed to proceed for ~72 hours at 4° C. Coupling efficiency was ~70%. The coupled protein was exchanged with gel filtration buffer and loaded with GTPgS in the same manner as the H-Ras(G12V) construct. The protein was then run on a Superdex™ 75 10/300 GL size-exclusion column (GE Healthcare) equilibrated in Ras gel filtration buffer to remove excess nucleotide.

Coupling of H-Ras to Maleimide Vesicles.

Coupling to maleimide containing membranes was carried out as described previously (Siempelkamp et al., 2017). In brief, H-Ras constructs were added to 100 mL of 5 mg/mL PM-MCC vesicles (5% porcine brain phosphatidylinositol 4,5-bisphosphate, 10% maleimidomethyl phosphoethanolamine, 30% bovine brain phosphatidylserine, 40% egg yolk phosphatidylethanolamine (PE), and 15% egg yolk phosphatidylcholine) at a molar ratio of 1.25H-Ras per maleimide. The thiol-maleimide conjugation reaction was bubbled under nitrogen for 2 minutes and allowed to proceed at room temperature for 1 h, followed by incubation at 4° C. overnight. A vesicles-only control was treated identically to the H-Ras sample with the exception that buffer was added in place of H-Ras. Reactions were terminated via the addition of 5 mM bME. H-Ras-coupled and non-coupled vesicles were separated from soluble H-Ras by size-exclusion chromatography on a Superdex™ 200 Increase 5/150 GL column (GE Healthcare) equilibrated in Ras gel filtration buffer. Both H-Ras-coupled and non-coupled vesicles were diluted to a final concentration of 1.0 mg/mL. The coupled H-Ras concentration was determined via intensity interpolation (ImageJ) of an SDS-PAGE standard curve using known soluble H-Ras concentrations.

PI3K Lipid Kinase Assays. Lipid kinase assays monitoring hydrolysis of ATP were carried out using the Transcreener ADP$^2$ Fluorescence Intensity (FI) assay (Bellbrook labs). Lipid vesicles with or without coupled H-Ras were used at a final concentration of 0.45 mg/ml, with ATP present at 100 µM. Membrane coupled H-Ras was present at near saturating concentrations for activation of 0.75-1.5 µM H-Ras. Protein solutions containing either pY (PDGFR residues 735-767, with pY740 and pY751, referred to afterwards as pY; final concentration in assay 1 µM) or blank solution in 2×PI3K kinase buffer (100 mM HEPES pH 7.5, 200 mM NaCl, 6 mM MgCl2, 2 mM EDTA, 0.06% CHAPS, 2 mM TCEP) were equilibrated briefly at 25° C. Kinase reactions were started by addition of 2 pL of protein solution to 2 pL of 2× substrate solution (0.9 mg/mL lipid vesicles±H-Ras, 200 µM ATP) in a 384-well black microplate (Corning). The reaction was allowed to proceed at 23° C. for 15 minutes before the addition of 2× Stop and Detect buffer (1× Stop and Detect Buffer, 8 nM ADP Alexa594 Tracer, 93.7 pg/mL ADP$^2$ Antibody-IRDye QC-1). Antibody, tracer, and ADP were equilibrated for 60 minutes. Fluorescence intensity was measured using a Cytation 5 plate reader with Aexcitation=590 nm and Aemission=620 nm (20 nm bandwidth; Molecular Devices). Specific activity was calculated using an ATP/ADP standard curve according to the Transcreener ADP FI protocol.

All crystal structures have been deposited to the Protein Data Bank (PDB) with the following ascension codes: 5VBE, 5VBM, and 5VBZ.

TABLE 38A

Figure 38A:
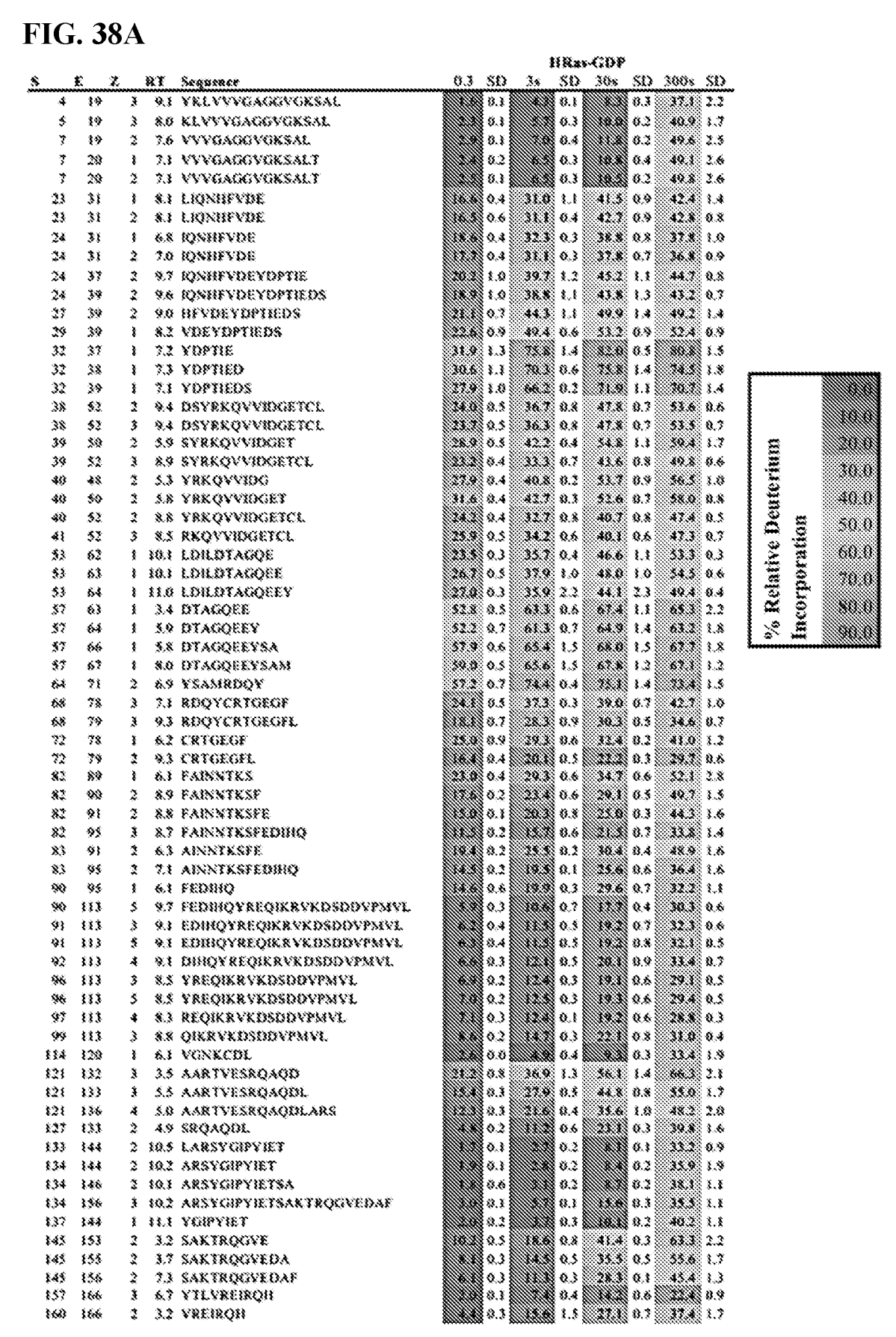

A reproduction of FIG. 38A, without the color legend.

| | | | | | HRas-GDP | | | | | | | |
|---|---|---|---|---|---|---|---|---|---|---|---|---|
| S | E | Z | RT | Sequence | 0.3 | SD | 3 s | SD | 30 s | SD | 300 s | SD |
| 4 | 19 | 3 | 9.1 | YKLVVVGAGGVGKSAL (SEQ ID NO: 7) | 1.6 | 0.1 | 4.3 | 0.1 | 8.3 | 0.3 | 37.1 | 2.2 |
| 5 | 19 | 3 | 8.0 | KLVVVGAGGVGKSAL (SEQ ID NO: 8) | 2.3 | 0.1 | 5.7 | 0.3 | 10.0 | 0.2 | 40.9 | 1.7 |
| 7 | 19 | 2 | 7.6 | VVVGAGGVGKSAL (SEQ ID NO: 9) | 2.9 | 0.1 | 7.0 | 0.4 | 11.8 | 0.2 | 49.6 | 2.5 |

TABLE 38A-continued

A reproduction of FIG. 38A, without the color legend.

| S | E | Z | RT | Sequence | HRas-GDP | | | | | | | |
|---|---|---|---|---|---|---|---|---|---|---|---|---|
| | | | | | 0.3 | SD | 3 s | SD | 30 s | SD | 300 s | SD |
| 7 | 20 | 1 | 7.1 | VVVGAGGVGKSALT (SEQ ID NO: 10) | 2.4 | 0.2 | 6.5 | 0.3 | 10.8 | 0.4 | 49.1 | 2.6 |
| 7 | 20 | 2 | 7.1 | VVVGAGGVGKSALT (SEQ ID NO: 10) | 2.5 | 0.1 | 6.5 | 0.3 | 10.5 | 0.2 | 9.8 | 2.6 |
| 23 | 31 | 1 | 8.1 | LIQNHFVDE (SEQ ID NO: 11) | 16.6 | 0.4 | 31.0 | 1.1 | 41.5 | 0.9 | 42.4 | 1.4 |
| 23 | 31 | 2 | 8.1 | LIQNHFVDE (SEQ ID NO: 11) | 16.5 | 0.6 | 31.1 | 0.4 | 42.7 | 0.9 | 42.8 | 0.8 |
| 24 | 31 | 1 | 6.8 | IQNHFVDE (SEQ ID NO: 12) | 18.6 | 0.4 | 32.3 | 0.3 | 38.8 | 0.8 | 37.8 | 1.0 |
| 24 | 31 | 2 | 7.0 | IQNHFVDE (SEQ ID NO: 12) | 17.7 | 0.4 | 31.1 | 0.3 | 37.8 | 0.7 | 36.8 | 0.9 |
| 24 | 37 | 2 | 9.7 | IQNHFVDEYDPTIE (SEQ ID NO: 13) | 20.2 | 1.0 | 39.7 | 1.2 | 45.2 | 1.1 | 44.7 | 0.8 |
| 24 | 39 | 2 | 9.6 | IQNHFVDEYDPTIEDS (SEQ ID NO: 14) | 18.9 | 1.0 | 38.8 | 1.1 | 43.8 | 1.3 | 43.2 | 0.7 |
| 27 | 39 | 2 | 9.0 | HFVDEYDPTIEDS (SEQ ID NO: 15) | 21.1 | 0.7 | 44.3 | 1.1 | 49.9 | 1.4 | 49.2 | 1.4 |
| 29 | 39 | 1 | 8.2 | VDEYDPTIEDS (SEQ ID NO: 16) | 22.3 | 0.9 | 49.4 | 0.6 | 53.2 | 0.9 | 52.4 | 0.9 |
| 32 | 37 | 1 | 7.2 | YDPTIE (SEQ ID NO: 17) | 31.9 | 1.3 | 75.8 | 1.4 | 82.0 | 0.5 | 80.8 | 1.5 |
| 32 | 38 | 1 | 7.3 | YDPTIED (SEQ ID NO: 18) | 30.6 | 1.1 | 70.3 | 0.6 | 75.8 | 1.4 | 74.5 | 1.8 |
| 32 | 39 | 1 | 7.1 | YDPTIEDS (SEQ ID NO: 19) | 27.9 | 1.0 | 66.2 | 0.2 | 71.9 | 1.1 | 70.7 | 1.4 |
| 38 | 52 | 2 | 9.4 | DSYRQVVIDGETCL (SEQ ID NO: 20) | 24.0 | 0.5 | 36.7 | 0.8 | 47.8 | 0.7 | 53.6 | 0.6 |
| 38 | 52 | 3 | 9.4 | DSYRQVVIDGETCL (SEQ ID NO: 20) | 23.7 | 0.5 | 36.3 | 0.8 | 47.8 | 0.7 | 53.5 | 0.7 |
| 39 | 50 | 2 | 5.9 | SYRQVVIDGET (SEQ ID NO: 21) | 28.9 | 0.5 | 42.2 | 0.4 | 54.8 | 1.1 | 59.4 | 1.7 |
| 39 | 52 | 3 | 8.9 | SYRQVVIDGETCL (SEQ ID NO: 22) | 23.2 | 0.4 | 33.3 | 0.7 | 43.6 | 0.8 | 49.8 | 0.6 |
| 40 | 48 | 2 | 5.3 | YRQVVIDG (SEQ ID NO: 23) | 27.9 | 0.4 | 40.8 | 0.2 | 53.7 | 0.9 | 56.5 | 1.0 |
| 40 | 50 | 2 | 5.8 | YRQVVIDGET (SEQ ID NO: 24) | 31.6 | 0.4 | 42.7 | 0.3 | 52.6 | 0.7 | 58.0 | 0.8 |
| 40 | 52 | 2 | 8.8 | YRQVVIDGETCL (SEQ ID NO: 25) | 24.2 | 0.4 | 32.7 | 0.8 | 40.7 | 0.8 | 47.4 | 0.5 |
| 41 | 52 | 3 | 8.5 | RQVVIDGETCL (SEQ ID NO: 26) | 25.9 | 0.5 | 34.2 | 0.6 | 40.1 | 0.6 | 47.3 | 0.7 |
| 53 | 62 | 1 | 10.1 | LDILDTAGQE (SEQ ID NO: 27) | 23.5 | 0.3 | 35.7 | 0.4 | 46.6 | 1.1 | 53.3 | 0.3 |
| 53 | 63 | 1 | 10.1 | LDILDTAGQEE (SEQ ID NO: 28) | 26.7 | 0.5 | 37.9 | 1.0 | 48.0 | 1.0 | 54.5 | 0.6 |
| 53 | 64 | 1 | 11.0 | LDILDTAGQEEY (SEQ ID NO: 29) | 27.0 | 0.3 | 35.9 | 2.2 | 44.1 | 2.3 | 49.4 | 0.4 |
| 57 | 63 | 1 | 3.4 | DTAGQEE (SEQ ID NO: 30) | 52.8 | 0.5 | 63.3 | 0.6 | 67.4 | 1.1 | 65.3 | 2.2 |

TABLE 38A-continued

A reproduction of FIG. 38A, without the color legend.

| S | E | Z | RT | Sequence | HRas-GDP | | | | | | | |
|---|---|---|---|---|---|---|---|---|---|---|---|---|
| | | | | | 0.3 | SD | 3 s | SD | 30 s | SD | 300 s | SD |
| 57 | 64 | 1 | 5.9 | DTAGQEEY (SEQ ID NO: 31) | 52.2 | 0.7 | 61.3 | 0.7 | 64.9 | 1.4 | 63.2 | 1.8 |
| 57 | 66 | 1 | 5.8 | DTAGQEEYSA (SEQ ID NO: 32) | 57.9 | 0.6 | 65.4 | 1.5 | 68.0 | 1.5 | 67.7 | 1.8 |
| 57 | 67 | 1 | 8.0 | DTAGQEEYSAM (SEQ ID NO: 33) | 59.0 | 0.5 | 65.6 | 1.5 | 67.8 | 1.2 | 67.1 | 1.2 |
| 64 | 71 | 2 | 6.9 | YSAMRDQY (SEQ ID NO: 34) | 57.2 | 0.7 | 74.4 | 0.4 | 75.1 | 1.4 | 73.4 | 1.5 |
| 68 | 78 | 3 | 7.1 | RDQYCRTGEGF (SEQ ID NO: 35) | 24.1 | 0.5 | 37.3 | 0.3 | 39.0 | 0.7 | 42.7 | 1.0 |
| 68 | 79 | 3 | 9.3 | RDQYCRTGEGFL (SEQ ID NO: 36) | 18.1 | 0.7 | 28.3 | 0.9 | 30.3 | 0.5 | 34.6 | 0.7 |
| 72 | 78 | 1 | 6.2 | CRTGEGF (SEQ ID NO: 37) | 25.0 | 0.9 | 29.3 | 0.6 | 32.4 | 0.2 | 41.0 | 1.2 |
| 72 | 79 | 2 | 9.3 | CRTGEGFL (SEQ ID NO: 38) | 16.4 | 0.4 | 20.1 | 0.5 | 22.2 | 0.3 | 29.7 | 0.6 |
| 82 | 89 | 1 | 6.1 | FAINNTKS (SEQ ID NO: 39) | 23.0 | 0.4 | 29.3 | 0.6 | 34.7 | 0.6 | 52.1 | 2.8 |
| 82 | 90 | 2 | 8.9 | FAINNTKSF (SEQ ID NO: 40) | 17.6 | 0.2 | 23.4 | 0.6 | 29.1 | 0.5 | 49.7 | 1.5 |
| 82 | 91 | 2 | 8.8 | FAINNTKSFE (SEQ ID NO: 41) | 15.0 | 0.1 | 20.3 | 0.8 | 25.0 | 0.3 | 44.3 | 1.6 |
| 82 | 95 | 3 | 8.7 | FAINNTKSFEDIHQ (SEQ ID NO: 42) | 11.5 | 0.2 | 15.7 | 0.6 | 21.5 | 0.7 | 33.8 | 1.4 |
| 83 | 91 | 2 | 6.3 | AINNTKSFE (SEQ ID NO: 43) | 19.4 | 0.2 | 25.5 | 0.2 | 30.4 | 0.4 | 48.9 | 1.6 |
| 83 | 95 | 2 | 7.1 | AINNTKSFEDIHQ (SEQ ID NO: 44) | 14.5 | 0.2 | 19.5 | 0.1 | 25.6 | 0.6 | 36.4 | 1.6 |
| 90 | 95 | 1 | 6.1 | FEDIHQ (SEQ ID NO: 45) | 14.6 | 0.6 | 19.9 | 0.3 | 29.6 | 0.7 | 32.2 | 1.1 |
| 90 | 113 | 5 | 9.7 | FEDIHQYREQIKRVKDSDDVPMVL (SEQ ID NO: 46) | 5.9 | 0.3 | 10.6 | 0.7 | 17.7 | 0.4 | 30.3 | 0.6 |
| 91 | 113 | 3 | 9.1 | EDIHQYREQIKRVKDSDDVPMVL (SEQ ID NO: 47) | 6.2 | 0.4 | 11.5 | 0.5 | 19.2 | 0.7 | 32.3 | 0.6 |
| 91 | 113 | 5 | 9.1 | EDIHQYREQIKRVKDSDDVPMVL (SEQ ID NO: 47) | 6.3 | 0.4 | 11.5 | 0.5 | 19.2 | 0.8 | 32.1 | 0.5 |
| 92 | 113 | 4 | 9.1 | DIHQYREQIKRVKDSDDVPMVL (SEQ ID NO: 48) | 6.6 | 0.3 | 12.1 | 0.5 | 20.1 | 0.9 | 33.4 | 0.7 |
| 96 | 113 | 3 | 8.5 | YREQIKRVKDSDDVPMVL (SEQ ID NO: 49) | 6.9 | 0.2 | 12.4 | 0.3 | 19.1 | 0.6 | 29.1 | 0.5 |
| 96 | 113 | 5 | 8.5 | YREQIKRVKDSDDVPMVL (SEQ ID NO: 49) | 7.0 | 0.2 | 12.5 | 0.3 | 19.3 | 0.6 | 29.4 | 0.5 |
| 97 | 113 | 4 | 8.3 | REQIKRVKDSDDVPMVL (SEQ ID NO: 50) | 7.1 | 0.3 | 12.4 | 0.1 | 19.2 | 0.6 | 28.8 | 0.3 |
| 99 | 113 | 3 | 8.8 | QIKRVKDSDDVPMVL (SEQ ID NO: 51) | 8.6 | 0.2 | 14.7 | 0.3 | 22.1 | 0.8 | 31.0 | 0.4 |
| 114 | 120 | 1 | 6.1 | VGNKCDL (SEQ ID NO: 52) | 2.6 | 0.0 | 4.9 | 0.4 | 9.3 | 0.3 | 33.4 | 1.9 |

TABLE 38A-continued

A reproduction of FIG. 38A, without the color legend.

| | | | | | HRas-GDP | | | | | | | |
|---|---|---|---|---|---|---|---|---|---|---|---|---|
| S | E | Z | RT | Sequence | 0.3 | SD | 3 s | SD | 30 s | SD | 300 s | SD |
| 121 | 132 | 3 | 3.5 | AARTVESRQAQD (SEQ ID NO: 53) | 21.2 | 0.8 | 36.9 | 1.3 | 56.1 | 1.4 | 66.3 | 2.1 |
| 121 | 133 | 3 | 5.5 | AARTVESRQAQDL (SEQ ID NO: 54) | 15.4 | 0.3 | 27.9 | 0.5 | 44.8 | 0.8 | 55.0 | 1.7 |
| 121 | 136 | 4 | 5.0 | AARTVESRQAQDLARS (SEQ ID NO: 55) | 12.3 | 0.3 | 21.6 | 0.4 | 35.6 | 1.0 | 48.2 | 2.0 |
| 127 | 133 | 2 | 4.9 | SRQAQDL (SEQ ID NO: 56) | 4.8 | 0.2 | 11.2 | 0.6 | 23.1 | 0.3 | 39.8 | 1.6 |
| 133 | 144 | 2 | 10.5 | LARSYGIPYIET (SEQ ID NO: 57) | 1.7 | 0.1 | 2.7 | 0.2 | 8.1 | 0.1 | 33.2 | 0.9 |
| 134 | 144 | 2 | 10.2 | ARSYGIPYIET (SEQ ID NO: 58) | 1.9 | 0.1 | 2.8 | 0.2 | 8.4 | 0.2 | 35.9 | 1.9 |
| 134 | 146 | 2 | 10.1 | ARSYGIPYIETSA (SEQ ID NO: 59) | 1.8 | 0.6 | 3.1 | 0.2 | 8.7 | 0.2 | 38.1 | 1.1 |
| 134 | 156 | 3 | 10.2 | ARSYGIPYIETSAKTRQGVEDAF (SEQ ID NO: 60) | 3.0 | 0.1 | 5.7 | 0.1 | 15.6 | 0.3 | 35.5 | 1.1 |
| 137 | 144 | 1 | 11.1 | YGIPYIET (SEQ ID NO: 61) | 2.0 | 0.2 | 3.7 | 0.3 | 10.1 | 0.2 | 40.2 | 1.1 |
| 145 | 153 | 2 | 3.2 | SAKTRQGVE (SEQ ID NO: 62) | 10.2 | 0.5 | 18.6 | 0.8 | 41.4 | 0.3 | 63.3 | 2.2 |
| 145 | 155 | 2 | 3.7 | SAKTRQGVEDA (SEQ ID NO: 63) | 8.1 | 0.3 | 14.5 | 0.5 | 35.5 | 0.5 | 55.6 | 1.7 |
| 145 | 156 | 2 | 7.3 | SAKTRQGVEDAF (SEQ ID NO: 64) | 6.1 | 0.3 | 11.3 | 0.3 | 28.3 | 0.1 | 45.4 | 1.3 |
| 157 | 166 | 3 | 6.7 | YTLVREIRQH (SEQ ID NO: 65) | 2.0 | 0.1 | 7.4 | 0.4 | 14.2 | 0.6 | 22.4 | 0.9 |
| 160 | 166 | 2 | 3.2 | VREIRQH (SEQ ID NO: 66) | 4.4 | 0.3 | 15.6 | 1.5 | 27.1 | 0.7 | 37.4 | 1.7 |

TABLE 38B

A reproduction of FIG. 38B, without the color legend.

| | | | | | HRas-GppNHp | | | | | | | |
|---|---|---|---|---|---|---|---|---|---|---|---|---|
| S | E | Z | RT | Sequence | 0.3 | SD | 3 s | SD | 30 s | SD | 300 s | SD |
| 4 | 19 | 3 | 9.1 | YKLVVVGAGGVGKSAL (SEQ ID NO: 7) | 3.3 | 0.2 | 6.3 | 0.2 | 9.6 | 0.3 | 37.5 | 0.8 |
| 5 | 19 | 3 | 8.0 | KLVVVGAGGVGKSAL (SEQ ID NO: 8) | 4.6 | 0.2 | 8.1 | 0.4 | 11.8 | 0.5 | 41.1 | 1.4 |
| 7 | 19 | 2 | 7.6 | VVVGAGGVGKSAL (SEQ ID NO: 9) | 5.4 | 0.3 | 10.0 | 0.5 | 14.4 | 0.8 | 50.2 | 1.3 |
| 7 | 20 | 1 | 7.1 | VVVGAGGVGKSALT (SEQ ID NO: 10) | 4.8 | 0.2 | 9.1 | 0.2 | 13.3 | 0.7 | 49.3 | 1.7 |
| 7 | 20 | 2 | 7.1 | VVVGAGGVGKSALT (SEQ ID NO: 10) | 4.9 | 0.3 | 9.1 | 0.3 | 13.3 | 0.8 | 50.2 | 1.1 |
| 23 | 31 | 1 | 8.1 | LIQNHFVDE (SEQ ID NO: 11) | 13.9 | 0.4 | 25.2 | 0.8 | 38.7 | 0.3 | 41.8 | 1.6 |
| 23 | 31 | 2 | 8.1 | LIQNHFVDE (SEQ ID NO: 11) | 13.9 | 0.4 | 26.3 | 0.7 | 40.1 | 0.8 | 42.8 | 1.5 |

TABLE 38B-continued

A reproduction of FIG. 38B, without the color legend.

| S | E | Z | RT | Sequence | HRas-GppNHp | | | | | | | |
|---|---|---|----|----------|-----|-----|-----|-----|-----|-----|-----|-----|
| | | | | | 0.3 | SD | 3 s | SD | 30 s | SD | 300 s | SD |
| 24 | 31 | 1 | 6.8 | IQNHFVDE (SEQ ID NO: 12) | 15.5 | 0.9 | 28.2 | 1.0 | 37.9 | 0.5 | 38.0 | 1.3 |
| 24 | 31 | 2 | 7.0 | IQNHFVDE (SEQ ID NO: 12) | 14.7 | 0.4 | 27.1 | 0.9 | 36.9 | 0.5 | 37.0 | 1.1 |
| 24 | 37 | 2 | 9.7 | IQNHFVDEYDPTIE (SEQ ID NO: 13) | 17.9 | 1.2 | 37.4 | 0.6 | 44.0 | 0.5 | 44.6 | 1.1 |
| 24 | 39 | 2 | 9.6 | IQNHFVDEYDPTIEDS (SEQ ID NO: 14) | 16.5 | 1.0 | 35.8 | 0.7 | 42.6 | 0.6 | 42.9 | 1.5 |
| 27 | 39 | 2 | 9.0 | HFVDEYDPTIEDS (SEQ ID NO: 15) | 19.6 | 0.9 | 42.3 | 0.6 | 48.6 | 0.6 | 49.4 | 2.0 |
| 29 | 39 | 1 | 8.2 | VDEYDPTIEDS (SEQ ID NO: 16) | 20.9 | 1.0 | 48.4 | 0.9 | 52.8 | 0.6 | 52.6 | 1.2 |
| 32 | 37 | 1 | 7.2 | YDPTIE (SEQ ID NO: 17) | 27.8 | 2.0 | 76.5 | 1.8 | 81.4 | 0.6 | 81.1 | 0.9 |
| 32 | 38 | 1 | 7.3 | YDPTIED (SEQ ID NO: 18) | 26.1 | 1.5 | 70.4 | 1.4 | 75.0 | 0.7 | 74.5 | 1.6 |
| 32 | 39 | 1 | 7.1 | YDPTIEDS (SEQ ID NO: 19) | 22.5 | 1.4 | 64.4 | 1.6 | 71.6 | 0.8 | 71.0 | 1.3 |
| 38 | 52 | 2 | 9.4 | DSYRKQVVIDGETCL (SEQ ID NO: 20) | 25.4 | 0.2 | 36.6 | 0.6 | 42.2 | 0.8 | 49.4 | 1.0 |
| 38 | 52 | 3 | 9.4 | DSYRKQVVIDGETCL (SEQ ID NO: 20) | 25.1 | 0.4 | 36.2 | 0.4 | 41.8 | 0.7 | 49.1 | 1.1 |
| 39 | 50 | 2 | 5.9 | SYRKQVVIDGET (SEQ ID NO: 21) | 30.3 | 0.3 | 43.6 | 1.3 | 48.6 | 0.8 | 56.5 | 1.7 |
| 39 | 52 | 3 | 8.9 | SYRKQVVIDGETCL (SEQ ID NO: 22) | 24.6 | 0.3 | 33.8 | 0.4 | 38.0 | 0.6 | 45.3 | 1.1 |
| 40 | 48 | 2 | 5.3 | YRKQVVIDG (SEQ ID NO: 23) | 29.0 | 0.4 | 40.8 | 1.5 | 45.7 | 0.6 | 52.4 | 0.9 |
| 40 | 50 | 2 | 5.8 | YRKQVVIDGET (SEQ ID NO: 24) | 33.0 | 0.1 | 42.9 | 0.5 | 47.4 | 0.9 | 55.2 | 1.2 |
| 40 | 52 | 2 | 8.8 | YRKQVVIDGETCL (SEQ ID NO: 25) | 25.2 | 0.3 | 32.6 | 0.4 | 36.3 | 0.6 | 43.1 | 0.9 |
| 41 | 52 | 3 | 8.5 | RKQVVIDGETCL (SEQ ID NO: 26) | 27.3 | 0.1 | 35.1 | 0.6 | 38.8 | 1.1 | 43.8 | 1.0 |
| 53 | 62 | 1 | 10.1 | LDILDTAGQE (SEQ ID NO: 27) | 12.8 | 0.7 | 24.3 | 1.1 | 35.8 | 1.4 | 46.1 | 0.9 |
| 53 | 63 | 1 | 10.1 | LDILDTAGQEE (SEQ ID NO: 28) | 16.7 | 0.4 | 27.1 | 0.9 | 37.4 | 0.4 | 47.3 | 1.4 |
| 53 | 64 | 1 | 11.0 | LDILDTAGQEEY (SEQ ID NO: 29) | 18.4 | 0.7 | 27.3 | 0.8 | 36.1 | 0.9 | 44.0 | 1.6 |
| 57 | 63 | 1 | 3.4 | DTAGQEE (SEQ ID NO: 30) | 33.7 | 0.8 | 53.9 | 2.5 | 66.7 | 0.7 | 66.1 | 1.2 |
| 57 | 64 | 1 | 5.9 | DTAGQEEY (SEQ ID NO: 31) | 37.4 | 0.7 | 54.2 | 1.7 | 64.2 | 0.8 | 63.5 | 2.1 |
| 57 | 66 | 1 | 5.8 | DTAGQEEYSA (SEQ ID NO: 32) | 46.7 | 0.0 | 59.1 | 1.3 | 68.3 | 0.6 | 66.6 | 2.8 |
| 57 | 67 | 1 | 8.0 | DTAGQEEYSAM (SEQ ID NO: 33) | 49.6 | 1.2 | 59.2 | 0.5 | 67.3 | 0.9 | 66.7 | 1.8 |

TABLE 38B-continued

A reproduction of FIG. 38B, without the color legend.

| S | E | Z | RT | Sequence | HRas-GppNHp | | | | | | | |
|---|---|---|---|---|---|---|---|---|---|---|---|---|
| | | | | | 0.3 | SD | 3 s | SD | 30 s | SD | 300 s | SD |
| 64 | 71 | 2 | 6.9 | YSAMRDQY (SEQ ID NO: 34) | 52.5 | 1.3 | 72.6 | 0.7 | 74.6 | 0.6 | 73.5 | 1.8 |
| 68 | 78 | 3 | 7.1 | RDQYCRTGEGF (SEQ ID NO: 35) | 22.1 | 0.5 | 35.7 | 0.6 | 37.5 | 0.6 | 40.3 | 1.3 |
| 68 | 79 | 3 | 9.3 | RDQYCRTGEGFL (SEQ ID NO: 36) | 17.1 | 0.4 | 27.3 | 0.6 | 28.9 | 0.7 | 32.5 | 1.0 |
| 72 | 78 | 1 | 6.2 | CRTGEGF (SEQ ID NO: 37) | 26.5 | 0.1 | 29.3 | 0.7 | 30.3 | 1.1 | 36.9 | 1.3 |
| 72 | 79 | 2 | 9.3 | CRTGEGFL (SEQ ID NO: 38) | 18.3 | 0.2 | 19.7 | 0.5 | 20.6 | 0.5 | 26.5 | 0.9 |
| 82 | 89 | 1 | 6.1 | FAINNTKS (SEQ ID NO: 39) | 22.9 | 0.9 | 30.0 | 0.6 | 34.2 | 0.9 | 52.5 | 1.1 |
| 82 | 90 | 2 | 8.9 | FAINNTKSF (SEQ ID NO: 40) | 17.9 | 0.5 | 23.5 | 0.4 | 27.8 | 0.7 | 50.8 | 0.9 |
| 82 | 91 | 2 | 8.8 | FAINNTKSFE (SEQ ID NO: 41) | 15.4 | 0.4 | 20.4 | 0.7 | 23.8 | 0.8 | 45.5 | 1.0 |
| 82 | 95 | 3 | 8.7 | FAINNTKSFEDIHQ (SEQ ID NO: 42) | 11.8 | 0.3 | 15.7 | 0.3 | 20.3 | 0.6 | 34.3 | 1.3 |
| 83 | 91 | 2 | 6.3 | AINNTKSFE (SEQ ID NO: 43) | 19.4 | 0.3 | 25.8 | 0.2 | 29.1 | 0.8 | 49.8 | 1.6 |
| 83 | 95 | 2 | 7.1 | AINNTKSFEDIHQ (SEQ ID NO: 44) | 14.4 | 0.5 | 19.5 | 0.4 | 24.5 | 0.6 | 36.9 | 1.1 |
| 90 | 95 | 1 | 6.1 | FEDIHQ (SEQ ID NO: 45) | 14.9 | 0.4 | 21.1 | 0.4 | 29.1 | 0.6 | 31.7 | 2.2 |
| 90 | 113 | 5 | 9.7 | FEDIHQYREQIKRVKDSDDVPMVL (SEQ ID NO: 46) | 6.0 | 0.1 | 10.1 | 0.5 | 14.0 | 0.6 | 23.7 | 1.3 |
| 91 | 113 | 3 | 9.1 | EDIHQYREQIKRVKDSDDVPMVL (SEQ ID NO: 47) | 6.3 | 0.2 | 10.8 | 0.3 | 15.0 | 0.5 | 25.4 | 1.0 |
| 91 | 113 | 5 | 9.1 | EDIHQYREQIKRVKDSDDVPMVL (SEQ ID NO: 47) | 6.4 | 0.2 | 10.8 | 0.4 | 15.1 | 0.5 | 25.3 | 1.0 |
| 92 | 113 | 4 | 9.1 | DIHQYREQIKRVKDSDDVPMVL (SEQ ID NO: 48) | 6.7 | 0.2 | 11.4 | 0.4 | 15.9 | 0.7 | 26.5 | 1.0 |
| 96 | 113 | 3 | 8.5 | YREQIKRVKDSDDVPMVL (SEQ ID NO: 49) | 6.9 | 0.2 | 11.4 | 0.4 | 15.0 | 0.4 | 23.5 | 0.8 |
| 96 | 113 | 5 | 8.5 | YREQIKRVKDSDDVPMVL (SEQ ID NO: 49) | 7.0 | 0.2 | 11.5 | 0.3 | 15.2 | 0.6 | 24.1 | 1.0 |
| 97 | 113 | 4 | 8.3 | REQIKRVKDSDDVPMVL (SEQ ID NO: 50) | 7.1 | 0.0 | 11.9 | 0.2 | 15.0 | 0.7 | 23.7 | 1.2 |
| 99 | 113 | 3 | 8.8 | QIKRVKDSDDVPMVL (SEQ ID NO: 51) | 8.2 | 0.2 | 13.6 | 0.3 | 17.4 | 0.6 | 26.3 | 1.0 |
| 114 | 120 | 1 | 6.1 | VGNKCDL (SEQ ID NO: 52) | 2.7 | 0.1 | 5.0 | 0.4 | 7.2 | 1.1 | 32.2 | 1.6 |
| 121 | 132 | 3 | 3.5 | AARTVESRQAQD (SEQ ID NO: 53) | 21.1 | 0.6 | 39.8 | 1.6 | 54.7 | 1.3 | 67.6 | 1.9 |
| 121 | 133 | 3 | 5.5 | AARTVESRQAQDL (SEQ ID NO: 54) | 15.8 | 0.4 | 30.1 | 1.2 | 43.5 | 0.8 | 56.3 | 2.0 |
| 121 | 136 | 4 | 5.0 | AARTVESRQAQDLARS (SEQ ID NO: 55) | 12.5 | 0.5 | 23.3 | 1.1 | 34.5 | 0.4 | 49.6 | 2.0 |

TABLE 38B-continued

A reproduction of FIG. 38B, without the color legend.

| | | | | | HRas-GppNHp | | | | | | | |
|---|---|---|---|---|---|---|---|---|---|---|---|---|
| S | E | Z | RT | Sequence | 0.3 | SD | 3 s | SD | 30 s | SD | 300 s | SD |
| 127 | 133 | 2 | 4.9 | SRQAQDL (SEQ ID NO: 56) | 4.8 | 0.1 | 13.3 | 0.3 | 22.2 | 0.9 | 41.8 | 1.5 |
| 133 | 144 | 2 | 10.5 | LARSYGIPYIET (SEQ ID NO: 57) | 1.8 | 0.1 | 3.2 | 0.2 | 7.8 | 0.4 | 35.1 | 1.0 |
| 134 | 144 | 2 | 10.2 | ARSYGIPYIET (SEQ ID NO: 58) | 2.1 | 0.0 | 3.4 | 0.1 | 8.2 | 0.5 | 37.6 | 1.1 |
| 134 | 146 | 2 | 10.1 | ARSYGIPYIETSA (SEQ ID NO: 59) | 2.1 | 0.1 | 3.5 | 0.4 | 8.4 | 1.0 | 38.6 | 0.9 |
| 134 | 156 | 3 | 10.2 | ARSYGIPYIETSAKTRQGVEDAF (SEQ ID NO: 60) | 3.4 | 0.2 | 6.1 | 0.2 | 14.5 | 0.3 | 35.8 | 0.9 |
| 137 | 144 | 1 | 11.1 | YGIPYIET (SEQ ID NO: 61) | 2.1 | 0.1 | 4.1 | 0.0 | 9.3 | 0.5 | 41.6 | 1.0 |
| 145 | 153 | 2 | 3.2 | SAKTRQGVE (SEQ ID NO: 62) | 10.9 | 0.9 | 19.8 | 0.6 | 38.4 | 1.2 | 62.9 | 1.7 |
| 145 | 155 | 2 | 3.7 | SAKTRQGVEDA (SEQ ID NO: 63) | 8.3 | 0.5 | 15.7 | 0.6 | 32.9 | 1.1 | 55.3 | 2.0 |
| 145 | 156 | 2 | 7.3 | SAKTRQGVEDAF (SEQ ID NO: 64) | 6.6 | 0.2 | 11.9 | 0.2 | 25.9 | 0.9 | 45.3 | 1.3 |
| 157 | 166 | 3 | 6.7 | YTLVREIRQH (SEQ ID NO: 65) | 2.0 | 0.2 | 8.3 | 0.5 | 13.6 | 0.3 | 22.4 | 1.0 |
| 160 | 166 | 2 | 3.2 | VREIRQH (SEQ ID NO: 66) | 4.4 | 0.4 | 17.4 | 1.4 | 26.4 | 1.0 | 37.6 | 1.7 |

TABLE 38C

Figure 38C:
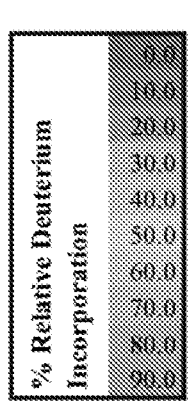
Figure 39A:
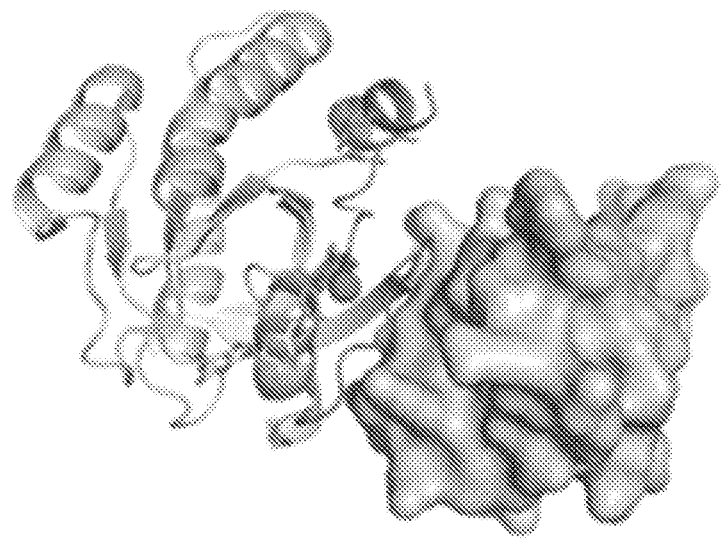
FIGS. 39A-39D. Comparison of Ras/Raf-1-RBD (4G0N) and Ras/PI3K-γ (1HE8) Crystal Structures, Related to FIGS. 33A-33D and FIGS. 34A-34D: All structures shown depict Ras in cartoon with switch-I and II each colored dark gray. Effectors are shown as surface representations corresponding to Raf-1-RBD and PI3K-γ respectively. Black arrows represent the swinging out of switch-II that occurs upon binding the S-IIG.
Figure 39B:
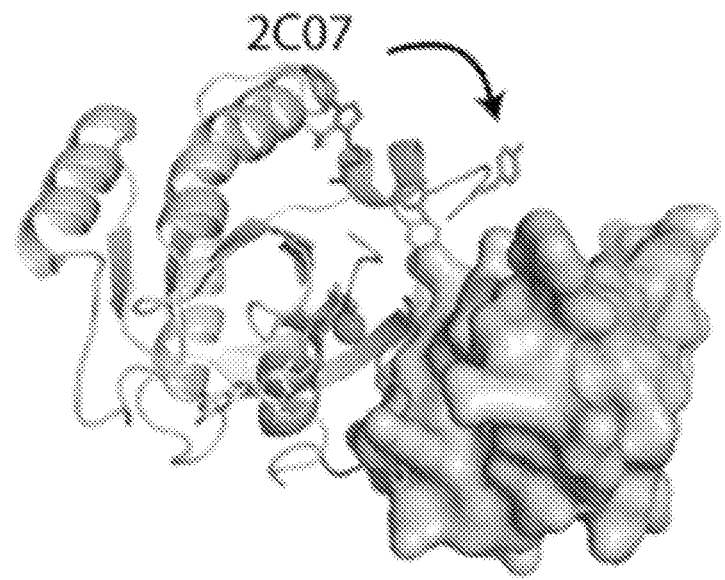
Figure 39C:
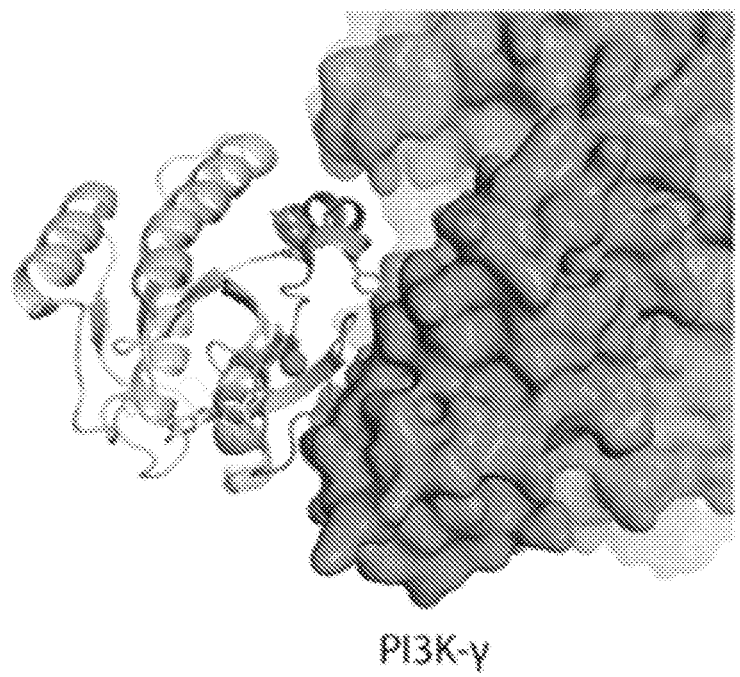
Figure 39D:
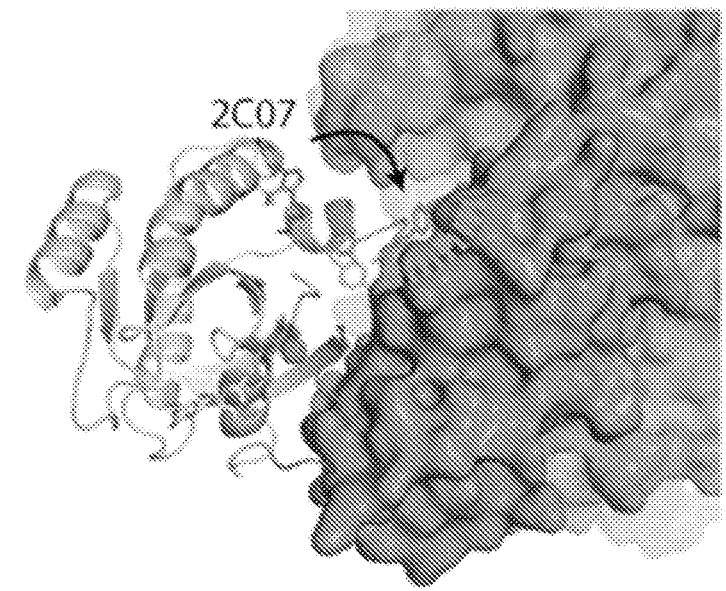
Figure 40:
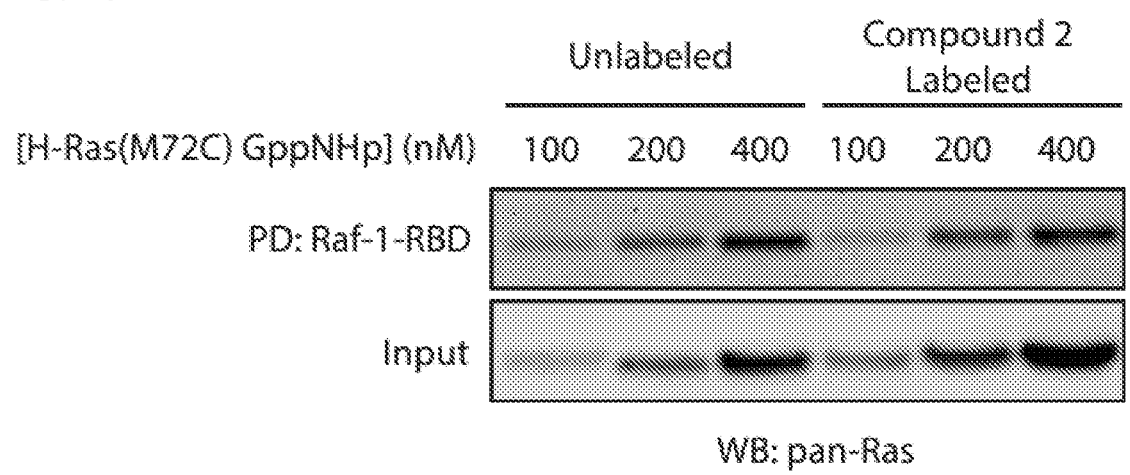
FIG. 40. Raf RBD Pull Down by H-Ras(M72C) GppNHp Pre-labeled With Compound 2, Related to FIGS. 34A-34D: Like 2C07, electrophile compounds based off the 2C07 fragment do not inhibit Raf RBD binding to activated Ras.

A reproduction of FIG. 38C, without the color legend.

| | | | | | Hras-2C07-GDP | | | | | | | |
|---|---|---|---|---|---|---|---|---|---|---|---|---|
| S | E | Z | RT | Sequence | 0.3 | SD | 3 s | SD | 30 s | SD | 300 s | SD |
| 4 | 19 | 3 | 9.1 | YKLVVVGAGGVGKSAL (SEQ ID NO: 7) | 2.9 | 0.2 | 5.2 | 0.3 | 8.9 | 0.5 | 30.4 | 0.8 |
| 5 | 19 | 3 | 8.0 | KLVVVGAGGVGKSAL (SEQ ID NO: 8) | 4.2 | 0.6 | 6.5 | 0.0 | 10.6 | 0.3 | 34.0 | 0.5 |
| 7 | 19 | 2 | 7.6 | VVVGAGGVGKSAL (SEQ ID NO: 9) | 4.9 | 0.5 | 7.9 | 0.2 | 12.1 | 0.1 | 42.3 | 0.7 |
| 7 | 20 | 1 | 7.1 | VVVGAGGVGKSALT (SEQ ID NO: 10) | 4.5 | 0.7 | 7.4 | 0.1 | 11.1 | 0.1 | 41.8 | 0.7 |
| 7 | 20 | 2 | 7.1 | VVVGAGGVGKSALT (SEQ ID NO: 10) | 4.6 | 0.6 | 7.5 | 0.1 | 11.3 | 0.3 | 42.4 | 0.7 |
| 23 | 31 | 1 | 8.1 | LIQNHFVDE (SEQ ID NO: 11) | 21.8 | 0.6 | 30.2 | 1.4 | 41.4 | 0.6 | 41.4 | 1.6 |
| 23 | 31 | 2 | 8.1 | LIQNHFVDE (SEQ ID NO: 11) | 22.3 | 1.0 | 30.9 | 1.4 | 41.9 | 0.5 | 42.1 | 1.4 |
| 24 | 31 | 1 | 6.8 | IQNHFVDE (SEQ ID NO: 12) | 21.1 | 0.2 | 30.0 | 0.8 | 38.2 | 0.3 | 37.8 | 1.2 |
| 24 | 31 | 2 | 7.0 | IQNHFVDE (SEQ ID NO: 12) | 20.2 | 0.2 | 28.9 | 1.0 | 36.9 | 0.1 | 36.7 | 1.2 |
| 24 | 37 | 2 | 9.7 | IQNHFVDEYDPTIE (SEQ ID NO: 13) | 22.1 | 0.3 | 36.9 | 0.1 | 45.3 | 0.5 | 44.3 | 1.4 |

TABLE 38C-continued

A reproduction of FIG. 38C, without the color legend.

| | | | | | Hras-2C07-GDP | | | | | | | |
|---|---|---|---|---|---|---|---|---|---|---|---|---|
| S | E | Z | RT | Sequence | 0.3 | SD | 3 s | SD | 30 s | SD | 300 s | SD |
| 24 | 39 | 2 | 9.6 | IQNHFVDEYDPTIEDS (SEQ ID NO: 14) | 20.6 | 0.4 | 35.4 | 0.1 | 43.9 | 0.7 | 43.0 | 1.7 |
| 27 | 39 | 2 | 9.0 | HFVDEYDPTIEDS (SEQ ID NO: 15) | 27.1 | 1.0 | 42.5 | 0.8 | 49.6 | 0.2 | 49.3 | 1.5 |
| 29 | 39 | 1 | 8.2 | VDEYDPTIEDS (SEQ ID NO: 16) | 26.8 | 0.4 | 46.1 | 0.6 | 53.6 | 0.3 | 52.8 | 0.9 |
| 32 | 37 | 1 | 7.2 | YDPTIE (SEQ ID NO: 17) | 37.9 | 0.4 | 70.6 | 1.1 | 81.6 | 1.1 | 81.1 | 0.6 |
| 32 | 38 | 1 | 7.3 | YDPTIED (SEQ ID NO: 18) | 35.9 | 0.4 | 65.1 | 1.0 | 75.4 | 0.0 | 75.2 | 1.6 |
| 32 | 39 | 1 | 7.1 | YDPTIEDS (SEQ ID NO: 19) | 33.0 | 0.2 | 60.3 | 1.0 | 72.0 | 0.2 | 71.7 | 1.0 |
| 38 | 52 | 2 | 9.4 | DSYRKQVVIDGETCL (SEQ ID NO: 20) | 25.8 | 0.2 | 34.6 | 0.4 | 46.6 | 0.4 | 50.9 | 1.1 |
| 38 | 52 | 3 | 9.4 | DSYRKQVVIDGETCL (SEQ ID NO: 20) | 25.7 | 0.2 | 34.5 | 0.5 | 46.5 | 0.5 | 50.8 | 1.1 |
| 39 | 50 | 2 | 5.9 | SYRKQVVIDGET (SEQ ID NO: 21) | 32.2 | 0.5 | 40.9 | 1.2 | 53.8 | 0.9 | 59.5 | 0.6 |
| 39 | 52 | 3 | 8.9 | SYRKQVVIDGETCL (SEQ ID NO: 22) | 25.2 | 0.2 | 32.4 | 0.7 | 42.3 | 0.7 | 47.0 | 1.2 |
| 40 | 48 | 2 | 5.3 | YRKQVVIDG (SEQ ID NO: 23) | 31.4 | 0.2 | 41.6 | 1.3 | 52.6 | 0.7 | 56.8 | 0.2 |
| 40 | 50 | 2 | 5.8 | YRKQVVIDGET (SEQ ID NO: 24) | 34.9 | 0.5 | 42.3 | 0.6 | 51.2 | 0.6 | 57.6 | 0.5 |
| 40 | 52 | 2 | 8.8 | YRKQVVIDGETCL (SEQ ID NO: 25) | 26.0 | 0.1 | 32.3 | 0.4 | 39.5 | 0.6 | 44.5 | 0.8 |
| 41 | 52 | 3 | 8.5 | RKQVVIDGETCL (SEQ ID NO: 26) | 28.2 | 0.1 | 34.7 | 0.7 | 40.1 | 0.6 | 45.1 | 1.2 |
| 53 | 62 | 1 | 10.1 | LDILDTAGQE (SEQ ID NO: 27) | 25.1 | 0.3 | 34.3 | 0.9 | 47.0 | 0.5 | 51.8 | 1.4 |
| 53 | 63 | 1 | 10.1 | LDILDTAGQEE (SEQ ID NO: 28) | 27.5 | 0.3 | 36.2 | 0.1 | 48.2 | 0.7 | 53.0 | 1.3 |
| 53 | 64 | 1 | 11.0 | LDILDTAGQEEY (SEQ ID NO: 29) | 27.6 | 0.4 | 35.3 | 0.2 | 45.6 | 0.7 | 49.8 | 1.2 |
| 57 | 63 | 1 | 3.4 | DTAGQEE (SEQ ID NO: 30) | 54.3 | 0.8 | 60.0 | 0.2 | 66.7 | 0.3 | 67.7 | 0.2 |
| 57 | 64 | 1 | 5.9 | DTAGQEEY (SEQ ID NO: 31) | 52.7 | 1.0 | 58.1 | 0.4 | 64.4 | 0.6 | 64.9 | 0.9 |
| 57 | 66 | 1 | 5.8 | DTAGQEEYSA (SEQ ID NO: 32) | 59.9 | 0.4 | 63.1 | 0.5 | 67.2 | 0.2 | 68.2 | 0.1 |
| 57 | 67 | 1 | 8.0 | DTAGQEEYSAM (SEQ ID NO: 33) | 58.7 | 0.8 | 63.6 | 0.1 | 67.7 | 0.8 | 67.1 | 1.8 |
| 64 | 71 | 2 | 6.9 | YSAMRDQY (SEQ ID NO: 34) | 52.1 | 0.5 | 71.2 | 0.6 | 74.6 | 0.5 | 73.9 | 1.5 |
| 68 | 78 | 3 | 7.1 | RDQYCRTGEGF (SEQ ID NO: 35) | 23.1 | 1.5 | 34.3 | 1.6 | 37.4 | 3.3 | 42.7 | 1.2 |
| 68 | 79 | 3 | 9.3 | RDQYCRTGEGFL (SEQ ID NO: 36) | 17.3 | 0.3 | 27.9 | 1.8 | 30.3 | 2.6 | 36.3 | 1.7 |

TABLE 38C-continued

A reproduction of FIG. 38C, without the color legend.

| S | E | Z | RT | Sequence | Hras-2C07-GDP | | | | | | | |
|---|---|---|----|----------|------|-----|------|-----|------|-----|-------|-----|
| | | | | | 0.3 | SD | 3 s | SD | 30 s | SD | 300 s | SD |
| 72 | 78 | 1 | 6.2 | CRTGEGF (SEQ ID NO: 37) | 25.5 | 0.6 | 31.4 | 1.3 | 33.4 | 3.9 | 46.6 | 1.5 |
| 72 | 79 | 2 | 9.3 | CRTGEGFL (SEQ ID NO: 38) | 15.9 | 0.8 | 23.1 | 2.0 | 24.9 | 3.0 | 35.6 | 1.1 |
| 82 | 89 | 1 | 6.1 | FAINNTKS (SEQ ID NO: 39) | 26.7 | 0.4 | 31.5 | 0.6 | 35.0 | 0.6 | 50.9 | 0.5 |
| 82 | 90 | 2 | 8.9 | FAINNTKSF (SEQ ID NO: 40) | 20.8 | 0.2 | 25.4 | 0.9 | 29.1 | 0.7 | 45.6 | 0.5 |
| 82 | 91 | 2 | 8.8 | FAINNTKSFE (SEQ ID NO: 41) | 18.0 | 0.2 | 21.6 | 0.3 | 24.8 | 0.5 | 40.1 | 0.5 |
| 82 | 95 | 3 | 8.7 | FAINNTKSFEDIHQ (SEQ ID NO: 42) | 13.7 | 0.1 | 16.4 | 0.1 | 20.9 | 0.8 | 31.4 | 1.0 |
| 83 | 91 | 2 | 6.3 | AINNTKSFE (SEQ ID NO: 43) | 22.8 | 0.4 | 26.4 | 0.9 | 29.8 | 0.5 | 45.7 | 0.7 |
| 83 | 95 | 2 | 7.1 | AINNTKSFEDIHQ (SEQ ID NO: 44) | 17.1 | 0.4 | 19.3 | 0.5 | 23.9 | 0.6 | 34.3 | 1.2 |
| 90 | 95 | 1 | 6.1 | FEDIHQ (SEQ ID NO: 45) | 17.5 | 0.6 | 20.3 | 1.3 | 26.4 | 0.7 | 32.3 | 0.9 |
| 90 | 113 | 5 | 9.7 | FEDIHQYREQIKRVKDSDDVPMVL (SEQ ID NO: 46) | 6.8 | 0.2 | 9.7 | 0.2 | 13.6 | 0.5 | 22.0 | 1.5 |
| 91 | 113 | 3 | 9.1 | EDIHQYREQIKRVKDSDDVPMVL (SEQ ID NO: 47) | 7.4 | 0.1 | 10.6 | 0.2 | 14.7 | 0.9 | 24.2 | 1.4 |
| 91 | 113 | 5 | 9.1 | EDIHQYREQIKRVKDSDDVPMVL (SEQ ID NO: 47) | 7.4 | 0.2 | 10.5 | 0.2 | 14.5 | 0.9 | 23.8 | 1.9 |
| 92 | 113 | 4 | 9.1 | DIHQYREQIKRVKDSDDVPMVL (SEQ ID NO: 48) | 7.7 | 0.2 | 10.9 | 0.3 | 15.1 | 0.7 | 24.7 | 1.5 |
| 96 | 113 | 3 | 8.5 | YREQIKRVKDSDDVPMVL (SEQ ID NO: 49) | 8.5 | 0.1 | 11.8 | 0.2 | 15.2 | 0.5 | 22.4 | 0.9 |
| 96 | 113 | 5 | 8.5 | YREQIKRVKDSDDVPMVL (SEQ ID NO: 49) | 8.6 | 0.2 | 11.6 | 0.4 | 15.2 | 0.6 | 22.8 | 1.1 |
| 97 | 113 | 4 | 8.3 | REQIKRVKDSDDVPMVL (SEQ ID NO: 50) | 11.8 | 0.9 | 14.0 | 0.9 | 21.0 | 2.4 | 28.7 | 1.2 |
| 99 | 113 | 3 | 8.8 | QIKRVKDSDDVPMVL (SEQ ID NO: 51) | 18.7 | 1.5 | 22.1 | 2.8 | 25.1 | 0.8 | 30.6 | 1.3 |
| 114 | 120 | 1 | 6.1 | VGNKCDL (SEQ ID NO: 52) | 4.1 | 0.6 | 5.6 | 0.7 | 8.1 | 0.5 | 27.1 | 0.5 |
| 121 | 132 | 3 | 3.5 | AARTVESRQAQD (SEQ ID NO: 53) | 24.5 | 0.3 | 35.7 | 0.1 | 54.6 | 0.3 | 65.8 | 0.1 |
| 121 | 133 | 3 | 5.5 | AARTVESRQAQDL (SEQ ID NO: 54) | 17.7 | 0.4 | 27.0 | 0.6 | 42.8 | 0.8 | 53.0 | 0.5 |
| 121 | 136 | 4 | 5.0 | AARTVESRQAQDLARS (SEQ ID NO: 55) | 14.0 | 0.4 | 21.0 | 0.3 | 34.6 | 1.1 | 47.0 | 0.7 |
| 127 | 133 | 2 | 4.9 | SRQAQDL (SEQ ID NO: 56) | 6.9 | 0.4 | 12.6 | 0.2 | 23.3 | 0.6 | 37.1 | 0.7 |
| 133 | 144 | 2 | 10.5 | LARSYGIPYIET (SEQ ID NO: 57) | 2.1 | 0.2 | 2.7 | 0.2 | 7.0 | 0.4 | 25.4 | 0.4 |
| 134 | 144 | 2 | 10.2 | ARSYGIPYIET (SEQ ID NO: 58) | 2.3 | 0.2 | 2.9 | 0.3 | 7.1 | 0.5 | 26.3 | 0.2 |

TABLE 38C-continued

A reproduction of FIG. 38C, without the color legend.

| | | | | | Hras-2C07-GDP | | | | | | | |
|---|---|---|---|---|---|---|---|---|---|---|---|---|
| S | E | Z | RT | Sequence | 0.3 | SD | 3 s | SD | 30 s | SD | 300 s | SD |
| 134 | 146 | 2 | 10.1 | ARSYGIPYIETSA (SEQ ID NO: 59) | 2.8 | 0.3 | 3.4 | 0.1 | 7.6 | 0.1 | 30.4 | 0.9 |
| 134 | 156 | 3 | 10.2 | ARSYGIPYIETSAKTRQGVEDAF (SEQ ID NO: 60) | 3.8 | 0.1 | 5.8 | 0.2 | 15.3 | 0.9 | 31.1 | 1.0 |
| 137 | 144 | 1 | 11.1 | YGIPYIET (SEQ ID NO: 61) | 3.2 | 0.2 | 4.1 | 0.7 | 8.9 | 0.5 | 31.6 | 1.4 |
| 145 | 153 | 2 | 3.2 | SAKTRQGVE (SEQ ID NO: 62) | 13.4 | 0.1 | 18.8 | 0.3 | 40.8 | 0.5 | 64.3 | 0.2 |
| 145 | 155 | 2 | 3.7 | SAKTRQGVEDA (SEQ ID NO: 63) | 10.5 | 0.3 | 14.6 | 0.3 | 34.9 | 0.7 | 56.2 | 0.0 |
| 145 | 156 | 2 | 7.3 | SAKTRQGVEDAF (SEQ ID NO: 64) | 8.1 | 0.2 | 11.7 | 0.3 | 27.6 | 0.9 | 43.6 | 1.4 |
| 157 | 166 | 3 | 6.7 | YTLVREIRQH (SEQ ID NO: 65) | 2.4 | 0.1 | 6.7 | 0.4 | 13.5 | 0.5 | 21.2 | 0.8 |
| 160 | 166 | 2 | 3.2 | VREIRQH (SEQ ID NO: 66) | 6.5 | 0.2 | 15.4 | 0.6 | 26.8 | 0.2 | 39.1 | 0.1 |

TABLE 38D

A reproduction of FIG. 38D, without the color legend.

| | | | | | Hras-2C07-GppNHp | | | | | | | |
|---|---|---|---|---|---|---|---|---|---|---|---|---|
| S | E | Z | RT | Sequence | 0.3 | SD | 3 s | SD | 30 s | SD | 300 s | SD |
| 4 | 19 | 3 | 9.1 | YKLVVVGAGGVGKSAL (SEQ ID NO: 7) | 3.5 | 0.1 | 6.5 | 0.5 | 11.1 | 0.2 | 41.5 | 1.0 |
| 5 | 19 | 3 | 8.0 | KLVVVGAGGVGKSAL (SEQ ID NO: 8) | 5.1 | 0.3 | 8.2 | 0.4 | 14.1 | 0.3 | 47.7 | 0.8 |
| 7 | 19 | 2 | 7.6 | VVVGAGGVGKSAL (SEQ ID NO: 9) | 6.4 | 0.4 | 10.2 | 0.2 | 16.3 | 0.2 | 64.7 | 0.9 |
| 7 | 20 | 1 | 7.1 | VVVGAGGVGKSALT (SEQ ID NO: 10) | 5.9 | 0.4 | 9.2 | 0.3 | 15.1 | 0.2 | 65.2 | 3.2 |
| 7 | 20 | 2 | 7.1 | VVVGAGGVGKSALT (SEQ ID NO: 10) | 5.8 | 0.3 | 9.3 | 0.2 | 14.9 | 0.2 | 65.2 | 0.8 |
| 23 | 31 | 1 | 8.1 | LIQNHFVDE (SEQ ID NO: 11) | 20.4 | 1.8 | 30.2 | 2.5 | 41.2 | 0.4 | 43.6 | 0.4 |
| 23 | 31 | 2 | 8.1 | LIQNHFVDE (SEQ ID NO: 11) | 20.8 | 0.4 | 31.0 | 1.0 | 41.4 | 0.3 | 43.4 | 0.1 |
| 24 | 31 | 1 | 6.8 | IQNHFVDE (SEQ ID NO: 12) | 20.2 | 1.1 | 30.6 | 0.9 | 38.3 | 0.2 | 49.0 | 0.2 |
| 24 | 31 | 2 | 7.0 | IQNHFVDE (SEQ ID NO: 12) | 19.3 | 1.0 | 29.2 | 0.8 | 36.9 | 0.2 | 37.5 | 0.2 |
| 24 | 37 | 2 | 9.7 | IQNHFVDEYDPTIE (SEQ ID NO: 13) | 24.6 | 2.2 | 38.3 | 2.7 | 42.2 | 0.3 | 43.7 | 1.1 |
| 24 | 39 | 2 | 9.6 | IQNHFVDEYDPTIEDS (SEQ ID NO: 14) | 23.0 | 1.9 | 37.1 | 2.6 | 41.3 | 0.3 | 42.2 | 0.7 |
| 27 | 39 | 2 | 9.0 | HFVDEYDPTIEDS (SEQ ID NO: 15) | 32.2 | 1.6 | 45.5 | 1.1 | 48.7 | 0.7 | 50.4 | 1.1 |
| 29 | 39 | 1 | 8.2 | VDEYDPTIEDS (SEQ ID NO: 16) | 33.0 | 1.9 | 50.6 | 1.1 | 52.0 | 0.1 | 52.8 | 0.4 |

TABLE 38D-continued

A reproduction of FIG. 38D, without the color legend.

| | | | | | Hras-2C07-GppNHp | | | | | | | |
|---|---|---|---|---|---|---|---|---|---|---|---|---|
| S | E | Z | RT | Sequence | 0.3 | SD | 3 s | SD | 30 s | SD | 300 s | SD |
| 32 | 37 | 1 | 7.2 | YDPTIE (SEQ ID NO: 17) | 53.2 | 3.4 | 78.4 | 2.5 | 80.3 | 0.2 | 81.0 | 0.1 |
| 32 | 38 | 1 | 7.3 | YDPTIED (SEQ ID NO: 18) | 47.6 | 3.3 | 72.6 | 1.1 | 74.0 | 0.4 | 75.0 | 0.9 |
| 32 | 39 | 1 | 7.1 | YDPTIEDS (SEQ ID NO: 19) | 42.3 | 2.9 | 68.0 | 1.2 | 71.0 | 0.2 | 71.9 | 0.7 |
| 38 | 52 | 2 | 9.4 | DSYRKQVVIDGETCL (SEQ ID NO: 20) | 25.4 | 0.8 | 35.6 | 0.9 | 42.1 | 0.4 | 50.7 | 0.4 |
| 38 | 52 | 3 | 9.4 | DSYRKQVVIDGETCL (SEQ ID NO: 20) | 25.2 | 0.8 | 35.5 | 0.9 | 42.0 | 0.2 | 50.7 | 0.4 |
| 39 | 50 | 2 | 5.9 | SYRKQVVIDGET (SEQ ID NO: 21) | 31.4 | 1.2 | 41.3 | 1.1 | 48.8 | 0.2 | 59.1 | 1.2 |
| 39 | 52 | 3 | 8.9 | SYRKQVVIDGETCL (SEQ ID NO: 22) | 24.3 | 0.7 | 32.8 | 0.8 | 37.8 | 0.4 | 46.8 | 0.1 |
| 40 | 48 | 2 | 5.3 | YRKQVVIDG (SEQ ID NO: 23) | 30.2 | 0.7 | 40.6 | 1.5 | 46.5 | 1.0 | 55.9 | 1.3 |
| 40 | 50 | 2 | 5.8 | YRKQVVIDGET (SEQ ID NO: 24) | 34.1 | 1.2 | 42.9 | 0.7 | 47.8 | 0.4 | 57.6 | 0.1 |
| 40 | 52 | 2 | 8.8 | YRKQVVIDGETCL (SEQ ID NO: 25) | 25.3 | 0.7 | 32.8 | 0.7 | 36.1 | 0.3 | 44.5 | 0.2 |
| 41 | 52 | 3 | 8.5 | RKQVVIDGETCL (SEQ ID NO: 26) | 27.0 | 0.7 | 35.5 | 0.9 | 38.3 | 0.2 | 45.3 | 0.3 |
| 53 | 62 | 1 | 10.1 | LDILDTAGQE (SEQ ID NO: 27) | 15.8 | 1.1 | 29.5 | 1.8 | 39.3 | 0.3 | 48.7 | 0.4 |
| 53 | 63 | 1 | 10.1 | LDILDTAGQEE (SEQ ID NO: 28) | 18.4 | 1.3 | 31.4 | 1.8 | 40.4 | 0.6 | 49.7 | 0.4 |
| 53 | 64 | 1 | 11.0 | LDILDTAGQEEY (SEQ ID NO: 29) | 19.4 | 1.1 | 34.2 | 2.0 | 41.8 | 0.5 | 49.9 | 1.4 |
| 57 | 63 | 1 | 3.4 | DTAGQEE (SEQ ID NO: 30) | 40.5 | 2.0 | 58.6 | 2.0 | 65.6 | 0.9 | 66.1 | 1.7 |
| 57 | 64 | 1 | 5.9 | DTAGQEEY (SEQ ID NO: 31) | 41.3 | 1.8 | 56.0 | 1.1 | 64.2 | 0.8 | 65.0 | 1.3 |
| 57 | 66 | 1 | 5.8 | DTAGQEEYSA (SEQ ID NO: 32) | 48.2 | 2.8 | 62.1 | 2.3 | 65.9 | 1.9 | 68.6 | 0.1 |
| 57 | 67 | 1 | 8.0 | DTAGQEEYSAM (SEQ ID NO: 33) | 49.5 | 2.9 | 63.1 | 1.8 | 65.9 | 0.4 | 67.2 | 0.4 |
| 64 | 71 | 2 | 6.9 | YSAMRDQY (SEQ ID NO: 34) | 55.3 | 3.5 | 73.1 | 0.7 | 73.5 | 0.4 | 74.5 | 0.5 |
| 68 | 78 | 3 | 7.1 | RDQYCRTGEGF (SEQ ID NO: 35) | 21.1 | 2.2 | 36.3 | 2.3 | 36.3 | 0.6 | 46.1 | 0.1 |
| 68 | 79 | 3 | 9.3 | RDQYCRTGEGFL (SEQ ID NO: 36) | 15.7 | 1.2 | 30.1 | 2.0 | 29.2 | 0.6 | 41.4 | 0.7 |
| 72 | 78 | 1 | 6.2 | CRTGEGF (SEQ ID NO: 37) | 25.9 | 1.2 | 34.7 | 1.2 | 35.2 | 1.9 | 56.5 | 1.6 |
| 72 | 79 | 2 | 9.3 | CRTGEGFL (SEQ ID NO: 38) | 16.9 | 0.8 | 27.8 | 1.4 | 25.1 | 1.2 | 42.7 | 1.6 |
| 82 | 89 | 1 | 6.1 | FAINNTKS (SEQ ID NO: 39) | 24.7 | 0.6 | 30.4 | 0.6 | 35.2 | 0.9 | 57.1 | 1.2 |

TABLE 38D-continued

A reproduction of FIG. 38D, without the color legend.

| S | E | Z | RT | Sequence | Hras-2C07-GppNHp | | | | | | | |
|---|---|---|---|---|---|---|---|---|---|---|---|---|
| | | | | | 0.3 | SD | 3 s | SD | 30 s | SD | 300 s | SD |
| 82 | 90 | 2 | 8.9 | FAINNTKSF (SEQ ID NO: 40) | 18.9 | 0.2 | 24.6 | 0.6 | 29.2 | 0.5 | 54.6 | 0.9 |
| 82 | 91 | 2 | 8.8 | FAINNTKSFE (SEQ ID NO: 41) | 16.4 | 0.1 | 21.2 | 0.4 | 24.9 | 0.3 | 49.8 | 0.7 |
| 82 | 95 | 3 | 8.7 | FAINNTKSFEDIHQ (SEQ ID NO: 42) | 11.7 | 0.5 | 15.0 | 0.7 | 19.3 | 0.5 | 37.4 | 0.2 |
| 83 | 91 | 2 | 6.3 | AINNTKSFE (SEQ ID NO: 43) | 21.4 | 0.8 | 4.0 | 0.4 | 30.7 | 0.2 | 54.4 | 1.1 |
| 83 | 95 | 2 | 7.1 | AINNTKSFEDIHQ (SEQ ID NO: 44) | 15.4 | 0.7 | 26.5 | 0.5 | 23.5 | 0.4 | 40.1 | 1.0 |
| 90 | 95 | 1 | 6.1 | FEDIHQ (SEQ ID NO: 45) | 17.0 | 1.1 | 19.0 | 0.8 | 23.9 | 0.3 | 34.4 | 0.2 |
| 90 | 113 | 5 | 9.7 | FEDIHQYREQIKRVKDSDDVPMVL (SEQ ID NO: 46) | 6.3 | 0.2 | 20.3 | 0.6 | 12.2 | 0.4 | 22.9 | 0.2 |
| 91 | 113 | 3 | 9.1 | EDIHQYREQIKRVKDSDDVPMVL (SEQ ID NO: 47) | 6.8 | 0.1 | 9.5 | 0.5 | 13.3 | 0.5 | 25.0 | 0.7 |
| 91 | 113 | 5 | 9.1 | EDIHQYREQIKRVKDSDDVPMVL (SEQ ID NO: 47) | 6.9 | 0.1 | 10.2 | 0.5 | 13.3 | 0.4 | 25.3 | 0.2 |
| 92 | 113 | 4 | 9.1 | DIHQYREQIKRVKDSDDVPMVL (SEQ ID NO: 48) | 7.4 | 0.2 | 11.0 | 0.3 | 13.9 | 0.5 | 26.8 | 0.1 |
| 96 | 113 | 3 | 8.5 | YREQIKRVKDSDDVPMVL (SEQ ID NO: 49) | 7.5 | 0.1 | 11.2 | 0.2 | 13.5 | 0.3 | 24.1 | 0.1 |
| 96 | 113 | 5 | 8.5 | YREQIKRVKDSDDVPMVL (SEQ ID NO: 49) | 7.6 | 0.1 | 11.3 | 0.3 | 13.7 | 0.2 | 24.5 | 0.4 |
| 97 | 113 | 4 | 8.3 | REQIKRVKDSDDVPMVL (SEQ ID NO: 50) | 8.9 | 0.0 | 12.2 | 0.5 | 14.4 | 1.0 | 26.3 | 0.0 |
| 99 | 113 | 3 | 8.8 | QIKRVKDSDDVPMVL (SEQ ID NO: 51) | 9.4 | 0.2 | 14.0 | 0.3 | 16.0 | 0.7 | 27.6 | 0.1 |
| 114 | 120 | 1 | 6.1 | VGNKCDL (SEQ ID NO: 52) | 2.8 | 0.5 | 5.4 | 0.5 | 10.6 | 0.5 | 38.1 | 1.0 |
| 121 | 132 | 3 | 3.5 | AARTVESRQAQD (SEQ ID NO: 53) | 22.9 | 1.7 | 37.5 | 1.8 | 54.3 | 0.6 | 68.7 | 2.6 |
| 121 | 133 | 3 | 5.5 | AARTVESRQAQDL (SEQ ID NO: 54) | 16.8 | 1.1 | 28.4 | 1.0 | 42.8 | 0.3 | 57.0 | 0.6 |
| 121 | 136 | 4 | 5.0 | AARTVESRQAQDLARS (SEQ ID NO: 55) | 12.8 | 1.3 | 21.4 | 1.2 | 33.7 | 0.1 | 49.6 | 1.8 |
| 127 | 133 | 2 | 4.9 | SRQAQDL (SEQ ID NO: 56) | 5.6 | 0.5 | 12.4 | 0.5 | 22.0 | 0.2 | 43.0 | 2.0 |
| 133 | 144 | 2 | 10.5 | LARSYGIPYIET (SEQ ID NO: 57) | 1.8 | 0.3 | 2.8 | 0.1 | 7.3 | 0.3 | 33.1 | 0.8 |
| 134 | 144 | 2 | 10.2 | ARSYGIPYIET (SEQ ID NO: 58) | 2.1 | 0.3 | 3.1 | 0.1 | 7.5 | 0.7 | 35.5 | 1.8 |
| 134 | 146 | 2 | 10.1 | ARSYGIPYIETSA (SEQ ID NO: 59) | 2.5 | 0.3 | 3.7 | 0.1 | 9.1 | 0.6 | 38.5 | 0.7 |
| 134 | 156 | 3 | 10.2 | ARSYGIPYIETSAKTRQGVEDAF (SEQ ID NO: 60) | 3.5 | 0.1 | 5.5 | 0.2 | 14.7 | 0.5 | 35.3 | 0.4 |
| 137 | 144 | 1 | 11.1 | YGIPYIET (SEQ ID NO: 61) | 2.0 | 0.4 | 3.9 | 0.1 | 8.8 | 0.5 | 40.3 | 0.8 |

TABLE 38D-continued

A reproduction of FIG. 38D, without the color legend.

| S | E | Z | RT | Sequence | Hras-2C07-GppNHp | | | | | | | |
|---|---|---|---|---|---|---|---|---|---|---|---|---|
| | | | | | 0.3 | SD | 3 s | SD | 30 s | SD | 300 s | SD |
| 145 | 153 | 2 | 3.2 | SAKTRQGVE (SEQ ID NO: 62) | 12.8 | 1.0 | 18.8 | 0.4 | 41.3 | 0.5 | 68.1 | 2.8 |
| 145 | 155 | 2 | 3.7 | SAKTRQGVEDA (SEQ ID NO: 63) | 9.8 | 0.7 | 15.0 | 0.5 | 34.6 | 0.6 | 59.8 | 2.3 |
| 145 | 156 | 2 | 7.3 | SAKTRQGVEDAF (SEQ ID NO: 64) | 7.4 | 0.3 | 11.5 | 0.2 | 27.4 | 0.9 | 48.8 | 0.7 |
| 157 | 166 | 3 | 6.7 | YTLVREIRQH (SEQ ID NO: 65) | 2.2 | 0.2 | 7.1 | 0.7 | 12.5 | 0.4 | 21.9 | 0.5 |
| 160 | 166 | 2 | 3.2 | VREIRQH (SEQ ID NO: 66) | 5.9 | 0.6 | 16.5 | 0.7 | 26.0 | 0.5 | 39.6 | 2.5 |

REFERENCES

Adams, P. D., and Oswald, R. E. (2007). NMR assignment of Cdc42(T35A), an active Switch I mutant of Cdc42. Biomol NMR Assign 1, 225-227. Adibekian, A., Martin, B. R., Chang, J. W., Hsu, K.-L., Tsuboi, K., Bachovchin, D. A., Speers, A. E., Brown, S. J., Spicer, T., Fernandez-Vega, V., et al. (2012). Confirming Target Engagement for Reversible Inhibitors in Vivo by Kinetically Tuned Activity-Based Probes. J. Am. Chem. Soc. 134, 10345-10348. Bachovchin, D. A., Brown, S. J., Rosen, H., and Cravatt, B. F. (2009). Identification of selective inhibitors of uncharacterized enzymes by high-throughput screening with fluorescent activity-based probes. Nature Biotechnology 27, 387-394. Burns, M. C., Sun, Q., Daniels, R. N., Camper, D., Kennedy, J. P., Phan, J., Olejniczak, E. T., Lee, T., Waterson, A. G., Rossanese, O. W., et al. (2014). Approach for targeting Ras with small molecules that activate SOS-mediated nucleotide exchange. Proc Natl Acad Sci USA 111, 3401-3406. Carelli, J. D., Sethofer, S. G., Smith, G. A., Miller, H. R., Simard, J. L., Merrick, W. C., Jain, R. K., Ross, N. T., and Taunton, J. (2015). Ternatin and improved synthetic variants kill cancer cells by targeting the elongation factor-1A ternary complex. eLife 4, e10222. Domaille, P. J., Campbell-Burk, S. L., Kraulis, P. J., Van Aken, T., and Laue, E. D. (1994). Solution Structure and Dynamics of Ras p21. cntdot. GDP Determined by Heteronuclear Three- and Four-Dimensional NMR Spectroscopy. Biochemistry 33, 3515-3531. Erlanson, D. A., Wells, J. A., and Braisted, A. C. (2004). Tethering: Fragment-Based Drug Discovery. Annu. Rev. Biophys. Biomol. Struct. 33, 199-223. Fetics, S. K., Guterres, H., Kearney, B. M., Buhrman, G., Ma, B., Nussinov, R., and Mattos, C. (2015). Allosteric effects of the oncogenic RasQ61L mutant on Raf-RBD. Structure 23, 505-516. Forbes, S. A., Forbes, S. A., Bindal, N., Bindal, N., Bamford, S., Bamford, S., Kok, C. Y., Cole, C., Cole, C., Kok, C. Y., et al. (2010). COSMIC: mining complete cancer genomes in the Catalogue of Somatic Mutations in Cancer. Nucleic Acids Research 39, D945-D950. Ford, B., Skowronek, K., Boykevisch, S., Bar-Sagi, D., and Nassar, N. (2005). Structure of the G60A mutant of Ras: implications for the dominant negative effect. J. Biol. Chem. 280, 25697-25705. Fowler, M. L., McPhail, J. A., Jenkins, M. L., Masson, G. R., Rutaganira, F. U., Shokat, K. M., Williams, R. L., and Burke, J. E. (2016). Using hydrogen deuterium exchange mass spectrometry to engineer optimized constructs for crystallization of protein complexes: Case study of PI4KIIIβ with Rab11. Protein Science 25, 826-839. Gallagher, E. S., and Hudgens, J. W. (2016). Mapping Protein-Ligand Interactions with Proteolytic Fragmentation, Hydrogen/Deuterium Exchange-Mass Spectrometry (Elsevier Inc.). Hall, B. E., Yang, S. S., Boriack-Sjodin, P. A., Kuriyan, J., and Bar-Sagi, D. (2001). Structure-based mutagenesis reveals distinct functions for Ras switch 1 and switch 2 in Sos-catalyzed guanine nucleotide exchange. J. Biol. Chem. 276, 27629-27637. Hunter, J. C., Manandhar, A., Carrasco, M. A., Gurbani, D., Gondi, S., and Westover, K. D. (2015). Biochemical and Structural Analysis of Common Cancer-Associated KRAS Mutations. Molecular Cancer Research 13, 1325-1335. Ito, Y., Ito, Y., Yamasaki, K., Kamiya, A., Yamasaki, K., Shirouzu, M., Iwahara, J., Iwahara, J., Yokoyama, S., Terada, T., et al. (1997). Regional Polysterism in the GTP-Bound Form of the Human c-Ha-Ras Protein †,‡. Biochemistry 36, 9109-9119. John, J., Sohmen, R., Feuerstein, J., Linke, R., Wittinghofer, A., and Goody, R. S. (1990). Kinetics of interaction of nucleotides with nucleotide-free H-ras p21. Biochemistry 29, 6058-6065. Johnson, C. W., Buhrman, G., Ting, P. Y., Colicelli, J., and Mattos, C. (2016). Expression, purification, crystallization and X-ray data collection for RAS and its mutants. Data Brief 6, 423-427. Kalbitzer, H. R., Spoerner, M., Ganser, P., Hozsa, C., and Kremer, W. (2009). Fundamental Link between Folding States and Functional States of Proteins. J. Am. Chem. Soc. 131, 16714-16719. Lai, A. C., and Crews, C. M. (2017). Induced protein degradation: an emerging drug discovery paradigm. Nature Publishing Group 16, 101-114. Lim, S. M., Westover, K. D., Ficarro, S. B., Harrison, R. A., Choi, H. G., Pacold, M. E., Carrasco, M., Hunter, J., Kim, N. D., Xie, T., et al. (2013). Therapeutic Targeting of Oncogenic K-Ras by a Covalent Catalytic Site Inhibitor. Angew. Chem. Int. Ed. 53, 199-204. Lito, P., Solomon, M., Li, L., Hansen, R., and Rosen, N. (2016). Allele-specific inhibitors inactivate mutant KRAS G12C by a trapping mechanism. Science 351, 604-608. Matsumoto, S., Miyano, N., Baba, S., Liao, J., Kawamura, T., Tsuda, C., Takeda, A., Yamamoto, M., Kumasaka, T., Kataoka, T., et al. (2016). Molecular Mechanism for Conformational Dynamics of Ras-GTP Elucidated from In-Situ Structural Transition in Crystal. Scientific Reports 6, 517. Maurer, T., Maurer, T., Garrenton, L. S., Garrenton, L. S., Oh, A., Oh, A., Pitts, K., Pitts, K., Anderson, D. J., Anderson, D. J., et al. (2012). Small-molecule ligands bind to a distinct pocket in Ras and inhibit SOS-mediated nucleotide exchange activity. Proc Natl Acad Sci USA 109, 5299-5304. McCormick, F. (2016). K-Ras protein as a drug target. J Mol Med 1-6. McGregor, L. M., Jenkins, M. L., Kerwin, C., Burke, J. E., and Shokat, K. M. (2017). Expanding the Scope of Electrophiles Capable of Targeting K-Ras Oncogenes. Biochemistry 56, 3178-3183. Milburn, M. V., Tong, L., deVos, A. M., Brunger, A., Yamaizumi, Z., Nishimura, S., and Kim, S. H. (1990). Molecular switch for signal transduction: structural differences between active and inactive forms of protooncogenic ras proteins. Science 247, 939-945. Muraoka, S., Shima, F., Araki, M., Inoue, T., Yoshimoto, A., Ijiri, Y., Seki, N., Tamura, A., Kumasaka, T., Yamamoto, M., et al. (2012). Crystal structures of the state 1 conformations of the GTP-bound H-Ras protein and its oncogenic G12V and Q61L mutants. FEBS Letters 586, 1715-1718. Ostrem, J. M. L., and Shokat, K. M. (2016). Direct small-molecule inhibitors of KRAS: from structural insights to mechanism-based design. Nature Publishing Group 15, 771-785. Ostrem, J. M., Peters, U., Sos, M. L., Wells, J. A., and Shokat, K. M. (2013). K-Ras(G12C) inhibitors allosterically control GTP affinity and effector interactions. Nature 503, 548-551. Patgiri, A., Yadav, K. K., Arora, P. S., and Bar-Sagi, D. (2011). An orthosteric inhibitor of the Ras-Sos interaction. Nat Chem Biol 7, 585-587. Patricelli, M. P., Janes, M. R., Li, L. S., Hansen, R., Peters, U., Kessler, L. V., Chen, Y., Kucharski, J. M., Feng, J., Ely, T., et al. (2016). Selective Inhibition of Oncogenic KRAS Output with Small Molecules Targeting the Inactive State. Cancer Discovery 6, 316-329. Shima, F., Shima, F., Yoshikawa, Y., Yoshikawa, Y., Ye, M., Ye, M., Araki, M., Araki, M., Matsumoto, S., Matsumoto, S., et al. (2013). In silico discovery of small-molecule Ras inhibitors that display antitumor activity by blocking the Ras-effector interaction. Proc Natl Acad Sci USA 110, 8182-8187. Spencer-Smith, R., Koide, A., Zhou, Y., Eguchi, R. R., Sha, F., Gajwani, P., Santana, D., Gupta, A., Jacobs, M., Herrero-Garcia, E., et al. (2017). Inhibition of RAS function through targeting an allosteric regulatory site. Nat Chem Biol 13, 62-68. Spoemer, M., Herrmann, C., Vetter, I. R., Kalbitzer, H. R., and Wittinghofer, A. (2001). Dynamic properties of the Ras switch I region and its importance for binding to effectors. Proc Natl Acad Sci USA 98, 4944-4949. Spoemer, M., Wittinghofer, A., and Kalbitzer, H. R. (2004). Perturbation of the conformational equilibria in Ras by selective mutations as studied by 31P NMR spectroscopy. FEBS Letters 578, 305-310. Stephen, A. G., Esposito, D., Bagni, R. K., and McCormick, F. (2014). Dragging Ras Back in the Ring. Cancer Cell 25, 272-281. Sun, Q., Burke, J. P., Phan, J., Burns, M. C., Olejniczak, E. T., Waterson, A. G., Lee, T., Rossanese, O. W., and Fesik, S. W. (2012). Discovery of Small Molecules that Bind to K-Ras and Inhibit Sos-Mediated Activation. Angew. Chem. 124, 6244-6247. Thapar, R., Williams, J. G., and Campbell, S. L. (2004). NMR Characterization of Full-length Farnesylated and Non-farnesylated H-Ras and its Implications for Raf Activation. Journal of Molecular Biology 343, 1391-1408. Vadas, O., and Burke, J. E. (2015). Probing the dynamic regulation of peripheral membrane proteins using hydrogen deuterium exchange-MS (HDX-MS). Biochm. Soc. Trans. 43, 773-786. Vigil, D., Cherfils, J., Rossman, K. L., and Der, C. J. (2010). Ras superfamily GEFs and GAPs: validated and tractable targets for cancer therapy?Nat. Rev. Cancer 10, 842-857. Welsch, M. E., Kaplan, A., Chambers, J. M., Stokes, M. E., Bos, P. H., Zask, A., Zhang, Y., Sanchez-Martin, M., Badgley, M. A., Huang, C. S., et al. (2017). Multivalent Small-Molecule Pan-RAS Inhibitors. Cell 168, 878-889.e29. Yang, W., Fucini, R. V., Fahr, B. T., Lam, M. B., Lu, Y., Randal, M., Lind, K. E., Cary, D. R., Colussi, D., Lu, W., et al. (2009). Fragment-Based Discovery of Nonpeptidic BACE-1 Inhibitors Using Tethering. Biochemistry 48, 4488-4496. Zhao, Q., Ouyang, X., Wan, X., Gajiwala, K. S., Kath, J. C., Jones, L. H., Burlingame, A. L., and Taunton, J. (2017). Broad-Spectrum Kinase Profiling in Live Cells with Lysine-Targeted Sulfonyl Fluoride Probes. J. Am. Chem. Soc. 139, 680-685.

---

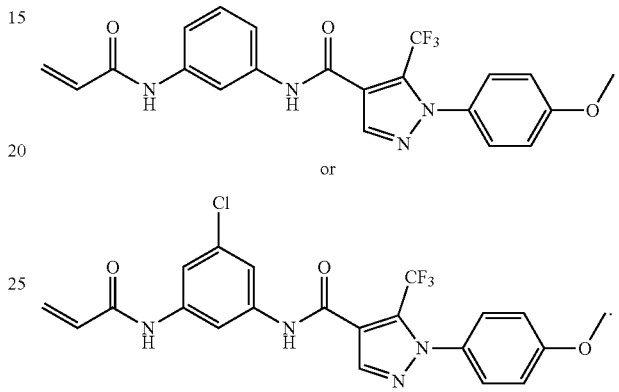

What is claimed is:

1. A compound having the formula:

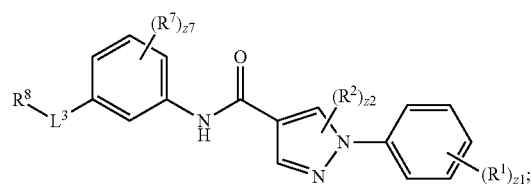

(IV)

wherein, $R^1$ is independently —$OR^{1D}$, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently —$CX^2_3$, halogen, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —$C(O)$—$OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^7$ substituents may optionally be joined to form a substituted or unsubstituted cycloalkyl, substituted or unsubstituted heterocycloalkyl, substituted or unsubstituted aryl, or substituted or unsubstituted heteroaryl;

$R^8$ is E;

$L^3$ is —N(H)C(O)—, a bond, —N(H)—, —O—, —S—, —C(O)—, —C(O)N(H)—, —NHC(O)N(H)—, —C(O)O—, —OC(O)—, substituted or unsubstituted alkylene, or substituted or unsubstituted heteroalkylene;

E is

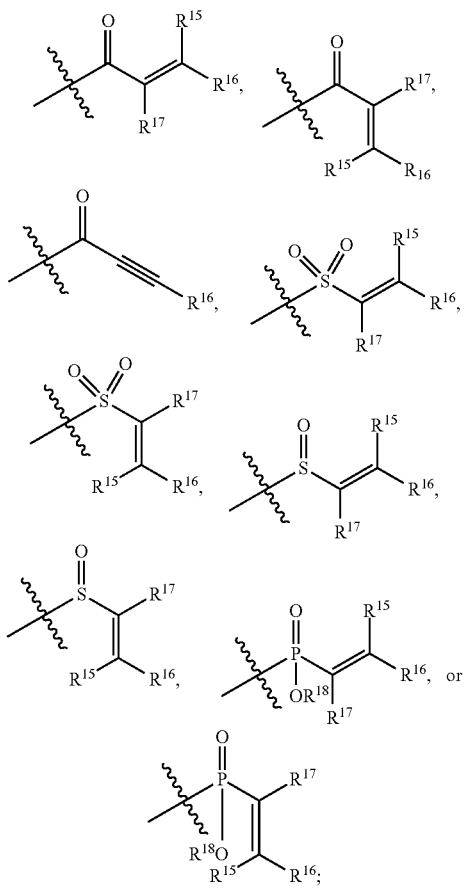

$R^{15}$ is independently hydrogen, halogen, —$CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —NHC=(O)$NHNR^{15A}R^{15B}$, —NHC(O)$NR^{15A}R^{15B}$, —$N(O)_{m15}$, —$NR^{15A}R^{15B}$, —$C(O)R^{15C}$, —$C(O)$—$OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$OCX^{15}_3$, —$OCHX^{15}_2$, —OCH₂X¹⁵, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is independently hydrogen, halogen, —CX$^{16}$₃, —CHX$^{16}$₂, —CH₂X$^{16}$, —CN, —SO$_{n16}$R$^{16D}$, —SO$_{v16}$NR$^{16A}$R$^{16B}$, —NHNR$^{16A}$R$^{16B}$, —ONR$^{16A}$R$^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO₂R$^{16D}$, —NR$^{16A}$C(O)R$^{16C}$, —NR$^{16A}$C(O)OR$^{16C}$, —NR$^{16A}$OR$^{16C}$, —OCX$^{16}$₃, —OCHX$^{16}$₂, —OCH₂X$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is independently hydrogen, halogen, —CX$^{17}$₃, —CHX$^{17}$₂, —CH₂X$^{17}$, —CN, —SO$_{n17}$R$^{17D}$, —SO$_{v17}$NR$^{17A}$R$^{17B}$, —NHNR$^{17A}$R$^{17B}$, —ONR$^{17A}$R$^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO₂R$^{17D}$, —NR$^{17A}$C(O)R$^{17C}$, —NR$^{17A}$C(O)OR$^{17C}$, —NR$^{17A}$OR$^{17C}$, —OCX$^{17}$₃, —OCHX$^{17}$₂, —OCH₂X$^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is independently hydrogen, —CX$^{18}$₃, —CHX$^{18}$₂, —CH₂X$^{18}$, —C(O)R$^{18C}$, —C(O)OR$^{18C}$, —C(O)NR$^{18A}$R$^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each $R^{1A}$, $R^{1B}$, $R^{1C}$, $R^{1D}$, $R^{2A}$, $R^{2B}$, $R^{2C}$, $R^{2D}$, $R^{7A}$, $R^{7B}$, $R^{7C}$, and $R^{7D}$, is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl;

each $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, and $R^{18C}$ is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl;

z1 is an integer from 0 to 5;
z2 is an integer from 0 to 2;
z7 is an integer from 0 to 4;
each X, X¹, X², X⁷, X¹⁵, X¹⁶, X¹⁷ and X¹⁸ is independently —F, —Cl, —Br, or —I;
n1, n2, n7, n15, n16, and n17 are independently an integer from 0 to 4; and
m1, m2, m7, m15, m16, m17, v1, v2, v7, v15, v16, and v17 are independently 1 or 2.

2. The compound of claim 1 having the formula:

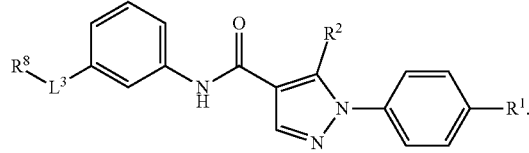

(IVa)

3. The compound of claim 1 having the formula:

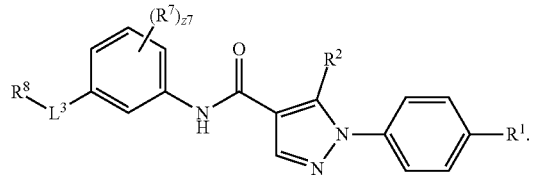

(IVb)

4. A pharmaceutical composition comprising a pharmaceutically acceptable excipient and a compound of any one of claims 1, 2, or 3.

5. The compound of claim 1, wherein $R^1$ is independently halogen, —CX$^1$₃, —CHX$^1$₂, —CH₂X$^1$, —OCX$^1$₃, —OCH₂X$^1$, —OCHX$^1$₂, —CN, —SO$_{n10}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, or substituted or unsubstituted heteroalkyl.

6. The compound of claim 1, wherein $R^1$ is independently —OR$^{1D}$, substituted or unsubstituted alkyl, or substituted or unsubstituted heteroalkyl.

7. The compound of claim 1, wherein $R^1$ is independently —OR$^{1D}$, wherein $R^{1D}$ is substituted or unsubstituted alkyl.

8. The compound of claim 1, wherein $R^1$ is independently —OR$^{1D}$, wherein $R^{1D}$ is substituted or unsubstituted $C_1$-$C_6$ alkyl.

9. The compound of claim 1, wherein $R^2$ is independently halogen, —CX$^2$₃, —CHX$^2$₂, —CH₂X$^2$, —OCX$^2$₃, —OCH$_2$X$^2$, —OCHX$^2_2$, substituted or unsubstituted alkyl, or substituted or unsubstituted heteroalkyl.

10. The compound of claim 1, wherein R$^2$ is independently halogen, —CX$^2_3$, —CHX$^2_2$, or —CH$_2$X$^2$.

11. The compound of claim 1, wherein R$^7$ is independently halogen, —CX$^7_3$, —CHX$^7_2$, —CH$_2$X$^7$, —OCX$^7_3$, —OCH$_2$X$^7$, —OCHX$^7_2$, —CN, substituted or unsubstituted alkyl, or substituted or unsubstituted heteroalkyl.

12. The compound of claim 1, wherein R$^7$ is independently halogen.

13. The compound of claim 1, wherein L$^3$ is independently a bond, —N(H)—, —C(O)N(H)—, —N(H)C(O)—, —N(H)C(O)NH—, —C(O)O—, —OC(O)—, substituted or unsubstituted alkylene, or substituted or unsubstituted heteroalkylene.

14. The compound of claim 1, wherein L$^3$ is independently a —N(H)—, —C(O)N(H)—, or —N(H)C(O)—.

15. The compound of claim 1, wherein E is independently

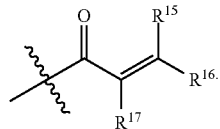

16. The compound of claim 1, wherein R$^{15}$ is independently hydrogen or substituted or unsubstituted alkyl, R$^{16}$ independently hydrogen or substituted or unsubstituted alkyl, and R$^{17}$ is independently hydrogen or substituted or unsubstituted alkyl.

17. The compound of claim 1, wherein R$^{15}$ is independently hydrogen or unsubstituted C$_1$-C$_4$ alkyl, R$^{16}$ independently hydrogen or unsubstituted C$_1$-C$_4$, and R$^{17}$ is independently hydrogen or unsubstituted C$_1$-C$_4$ alkyl.

18. The compound of claim 1, wherein R$^{15}$ is hydrogen; R$^{16}$ is hydrogen; and R$^{17}$ is hydrogen.

19. The compound of claim 2, wherein
L$^3$ is —NH—;
R$^1$ is unsubstituted C$_1$-C$_4$ alkoxy;
R$^2$ is —CX$^2_3$; and
R$^8$ is E.

20. The compound of claim 1 having the formula:

SEQUENCE LISTING

<160> NUMBER OF SEQ ID NOS: 66

<210> SEQ ID NO 1
<211> LENGTH: 169
<212> TYPE: PRT
<213> ORGANISM: Artificial sequence
<220> FEATURE:
<223> OTHER INFORMATION: Synthetic polypeptide

<400> SEQUENCE: 1

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
```

```
            100                 105                 110
Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys
                165

<210> SEQ ID NO 2
<211> LENGTH: 188
<212> TYPE: PRT
<213> ORGANISM: Artificial sequence
<220> FEATURE:
<223> OTHER INFORMATION: Synthetic polypeptide

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 3
<211> LENGTH: 188
<212> TYPE: PRT
<213> ORGANISM: Artificial sequence
<220> FEATURE:
<223> OTHER INFORMATION: Synthetic polypeptide

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45
```

```
Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 4
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 4

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His
                165

<210> SEQ ID NO 5
<211> LENGTH: 189
<212> TYPE: PRT
<213> ORGANISM: Artificial sequence
<220> FEATURE:
<223> OTHER INFORMATION: Synthetic polypeptide

<400> SEQUENCE: 5
```

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 6
<211> LENGTH: 189
<212> TYPE: PRT
<213> ORGANISM: Artificial sequence
<220> FEATURE:
<223> OTHER INFORMATION: Synthetic polypeptide

<400> SEQUENCE: 6

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

```
Ser Gly Pro Gly Cys Met Ser Cys Lys Cys Val Leu Ser
            180                 185

<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 7

Tyr Lys Leu Val Val Val Gly Ala Gly Gly Val Gly Lys Ser Ala Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 8

Lys Leu Val Val Val Gly Ala Gly Gly Val Gly Lys Ser Ala Leu
1               5                   10                  15

<210> SEQ ID NO 9
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 9

Val Val Val Gly Ala Gly Gly Val Gly Lys Ser Ala Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 10

Val Val Val Gly Ala Gly Gly Val Gly Lys Ser Ala Leu Thr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Leu Ile Gln Asn His Phe Val Asp Glu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12
```

```
Ile Gln Asn His Phe Val Asp Glu
1               5

<210> SEQ ID NO 13
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 13

Ile Gln Asn His Phe Val Asp Glu Tyr Asp Pro Thr Ile Glu
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 14

Ile Gln Asn His Phe Val Asp Glu Tyr Asp Pro Thr Ile Glu Asp Ser
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 15

His Phe Val Asp Glu Tyr Asp Pro Thr Ile Glu Asp Ser
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 16

Val Asp Glu Tyr Asp Pro Thr Ile Glu Asp Ser
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 17

Tyr Asp Pro Thr Ile Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 18

Tyr Asp Pro Thr Ile Glu Asp
```

```
1               5
```

<210> SEQ ID NO 19
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 19

```
Tyr Asp Pro Thr Ile Glu Asp Ser
1               5
```

<210> SEQ ID NO 20
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 20

```
Asp Ser Tyr Arg Lys Gln Val Val Ile Asp Gly Glu Thr Cys Leu
1               5                   10                  15
```

<210> SEQ ID NO 21
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 21

```
Ser Tyr Arg Lys Gln Val Val Ile Asp Gly Glu Thr
1               5                   10
```

<210> SEQ ID NO 22
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 22

```
Ser Tyr Arg Lys Gln Val Val Ile Asp Gly Glu Thr Cys Leu
1               5                   10
```

<210> SEQ ID NO 23
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 23

```
Tyr Arg Lys Gln Val Val Ile Asp Gly
1               5
```

<210> SEQ ID NO 24
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 24

```
Tyr Arg Lys Gln Val Val Ile Asp Gly Glu Thr
1               5                   10
```

```
<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 25

Tyr Arg Lys Gln Val Val Ile Asp Gly Glu Thr Cys Leu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 26

Arg Lys Gln Val Val Ile Asp Gly Glu Thr Cys Leu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 27

Leu Asp Ile Leu Asp Thr Ala Gly Gln Glu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 28

Leu Asp Ile Leu Asp Thr Ala Gly Gln Glu Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 29

Leu Asp Ile Leu Asp Thr Ala Gly Gln Glu Glu Tyr
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 30

Asp Thr Ala Gly Gln Glu Glu
1               5
```

<210> SEQ ID NO 31
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 31

Asp Thr Ala Gly Gln Glu Glu Tyr
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 32

Asp Thr Ala Gly Gln Glu Glu Tyr Ser Ala
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 33

Asp Thr Ala Gly Gln Glu Glu Tyr Ser Ala Met
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 34

Tyr Ser Ala Met Arg Asp Gln Tyr
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 35

Arg Asp Gln Tyr Cys Arg Thr Gly Glu Gly Phe
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 36

Arg Asp Gln Tyr Cys Arg Thr Gly Glu Gly Phe Leu
1               5                   10

```
<210> SEQ ID NO 37
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 37

Cys Arg Thr Gly Glu Gly Phe
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 38

Cys Arg Thr Gly Glu Gly Phe Leu
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 39

Phe Ala Ile Asn Asn Thr Lys Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 40

Phe Ala Ile Asn Asn Thr Lys Ser Phe
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 41

Phe Ala Ile Asn Asn Thr Lys Ser Phe Glu
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 42

Phe Ala Ile Asn Asn Thr Lys Ser Phe Glu Asp Ile His Gln
1               5                   10

<210> SEQ ID NO 43
```

```
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 43

Ala Ile Asn Asn Thr Lys Ser Phe Glu
1               5

<210> SEQ ID NO 44
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 44

Ala Ile Asn Asn Thr Lys Ser Phe Glu Asp Ile His Gln
1               5                   10

<210> SEQ ID NO 45
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 45

Phe Glu Asp Ile His Gln
1               5

<210> SEQ ID NO 46
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 46

Phe Glu Asp Ile His Gln Tyr Arg Glu Gln Ile Lys Arg Val Lys Asp
1               5                   10                  15

Ser Asp Asp Val Pro Met Val Leu
            20

<210> SEQ ID NO 47
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 47

Glu Asp Ile His Gln Tyr Arg Glu Gln Ile Lys Arg Val Lys Asp Ser
1               5                   10                  15

Asp Asp Val Pro Met Val Leu
            20

<210> SEQ ID NO 48
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 48
```

```
Asp Ile His Gln Tyr Arg Glu Gln Ile Lys Arg Val Lys Asp Ser Asp
1               5                   10                  15

Asp Val Pro Met Val Leu
            20

<210> SEQ ID NO 49
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 49

Tyr Arg Glu Gln Ile Lys Arg Val Lys Asp Ser Asp Asp Val Pro Met
1               5                   10                  15

Val Leu

<210> SEQ ID NO 50
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 50

Arg Glu Gln Ile Lys Arg Val Lys Asp Ser Asp Asp Val Pro Met Val
1               5                   10                  15

Leu

<210> SEQ ID NO 51
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 51

Gln Ile Lys Arg Val Lys Asp Ser Asp Asp Val Pro Met Val Leu
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 52

Val Gly Asn Lys Cys Asp Leu
1               5

<210> SEQ ID NO 53
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 53

Ala Ala Arg Thr Val Glu Ser Arg Gln Ala Gln Asp
1               5                   10

<210> SEQ ID NO 54
<211> LENGTH: 13
<212> TYPE: PRT
```

<213> ORGANISM: Artificial Sequence
<220> FEATURE:
<223> OTHER INFORMATION: Synthetic polypeptide

<400> SEQUENCE: 54

Ala Ala Arg Thr Val Glu Ser Arg Gln Ala Gln Asp Leu
1               5                   10

<210> SEQ ID NO 55
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 55

Ala Ala Arg Thr Val Glu Ser Arg Gln Ala Gln Asp Leu Ala Arg Ser
1               5                   10                  15

<210> SEQ ID NO 56
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 56

Ser Arg Gln Ala Gln Asp Leu
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 57

Leu Ala Arg Ser Tyr Gly Ile Pro Tyr Ile Glu Thr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 58

Ala Arg Ser Tyr Gly Ile Pro Tyr Ile Glu Thr
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 59

Ala Arg Ser Tyr Gly Ile Pro Tyr Ile Glu Thr Ser Ala
1               5                   10

<210> SEQ ID NO 60
<211> LENGTH: 23
<212> TYPE: PRT
<213> ORGANISM: Artificial Sequence

```
<220> FEATURE:
<223> OTHER INFORMATION: Synthetic polypeptide

<400> SEQUENCE: 60

Ala Arg Ser Tyr Gly Ile Pro Tyr Ile Glu Thr Ser Ala Lys Thr Arg
1               5                   10                  15

Gln Gly Val Glu Asp Ala Phe
            20

<210> SEQ ID NO 61
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 61

Tyr Gly Ile Pro Tyr Ile Glu Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 62

Ser Ala Lys Thr Arg Gln Gly Val Glu
1               5

<210> SEQ ID NO 63
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 63

Ser Ala Lys Thr Arg Gln Gly Val Glu Asp Ala
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 64

Ser Ala Lys Thr Arg Gln Gly Val Glu Asp Ala Phe
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 65

Tyr Thr Leu Val Arg Glu Ile Arg Gln His
1               5                   10

<210> SEQ ID NO 66
<211> LENGTH: 7
```

```
<212> TYPE: PRT
<213> ORGANISM: Artificial Sequence
<220> FEATURE:
<223> OTHER INFORMATION: Synthetic polypeptide

<400> SEQUENCE: 66

Val Arg Glu Ile Arg Gln His
1               5
```